US012767957B2

(12) United States Patent
Sabeti et al.

(10) Patent No.: US 12,767,957 B2
(45) **Date of Patent: *Oct. 20, 2026**

(54) ENGINEERED MUSCLE TARGETING COMPOSITIONS

(71) Applicants: The Broad Institute, Inc., Cambridge, MA (US); President and Fellows of Harvard College, Cambridge, MA (US); Massachusetts Institute of Technology, Cambridge, MA (US)

(72) Inventors: Pardis Sabeti, Cambridge, MA (US); Mohammadsharif Tabebordbar, Cambridge, MA (US); Simon Ye, Cambridge, MA (US)

(73) Assignees: The Broad Institute, Inc., Cambridge, MA (US); President and Fellows of Harvard College, Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/390,070

(22) Filed: Nov. 14, 2025

(65) Prior Publication Data

US 2026/0071236 A1 Mar. 12, 2026

Related U.S. Application Data

(63) Continuation of application No. 17/764,509, filed as application No. PCT/US2020/056133 on Oct. 16, 2020.

(60) Provisional application No. 63/055,252, filed on Jul. 22, 2020, provisional application No. 63/018,454, filed on Apr. 30, 2020, provisional application No. 62/916,207, filed on Oct. 16, 2019, provisional application No. 62/916,221, filed on Oct. 16, 2019.

(51) Int. Cl.

| | |
|---|---|
| ***C12N 15/86*** | (2006.01) |
| ***A61K 31/7088*** | (2006.01) |
| ***A61K 38/17*** | (2006.01) |
| ***A61K 47/64*** | (2017.01) |
| ***A61K 48/00*** | (2006.01) |
| ***A61P 21/00*** | (2006.01) |
| ***C07K 7/06*** | (2006.01) |
| ***C07K 14/005*** | (2006.01) |
| ***C07K 14/47*** | (2006.01) |
| ***C12N 9/22*** | (2006.01) |
| ***C12N 15/11*** | (2006.01) |

(52) U.S. Cl.

CPC .......... *C12N 15/86* (2013.01); *A61K 31/7088* (2013.01); *A61K 47/6435* (2017.08); *A61K 48/0066* (2013.01); *C07K 7/06* (2013.01); *C07K 14/005* (2013.01); *C07K 14/47* (2013.01); *C12N 9/22* (2013.01); *C12N 15/11* (2013.01); *C07K 2319/01* (2013.01); *C12N 2310/20* (2017.05); *C12N 2750/14122* (2013.01); *C12N 2750/14123* (2013.01); *C12N 2750/14143* (2013.01); *C12N 2750/14145* (2013.01); *C12N 2800/80* (2013.01); *C12N 2810/405* (2013.01); *C12N 2810/6027* (2013.01); *C12N 2830/008* (2013.01)

(58) Field of Classification Search

CPC .. C07K 14/005; C07K 14/4716; C12N 15/86; C12N 2830/008; C12N 2810/405

See application file for complete search history.

(56) References Cited

U.S. PATENT DOCUMENTS

| | | | |
|---|---|---|---|
| 4,797,368 | A | 1/1989 | Carter et al. |
| 5,173,414 | A | 12/1992 | Lebkowski et al. |
| 5,846,946 | A | 12/1998 | Huebner et al. |
| 6,911,199 | B2 | 6/2005 | Vigne et al. |
| 6,962,815 | B2 | 11/2005 | Bartlett |
| 7,285,381 | B1 | 10/2007 | Hallek et al. |
| 7,745,391 | B2 | 6/2010 | Mintz et al. |
| 7,749,492 | B2 | 7/2010 | Bartlett |
| 8,404,658 | B2 | 3/2013 | Hajjar et al. |
| 8,454,972 | B2 | 6/2013 | Nabel et al. |
| 8,476,418 | B2 | 7/2013 | Mueller et al. |
| 8,703,735 | B2 | 4/2014 | Iversen et al. |
| 8,771,945 | B1 | 7/2014 | Zhang |
| 8,895,308 | B1 | 11/2014 | Zhang et al. |
| 10,066,228 | B2 | 9/2018 | Linsley et al. |

(Continued)

FOREIGN PATENT DOCUMENTS

| | | |
|---|---|---|
| CN | 103561774 A | 2/2014 |
| CN | 107532177 A | 1/2018 |

(Continued)

OTHER PUBLICATIONS

Salva et al., "Design of tissue-specific regulatory cassettes for high-level rAAV-mediated expression in skeletal and cardiac muscle", Molecular Therapy, 2007, 15(2):320-329.*

(Continued)

*Primary Examiner* — Barry A Chestnut
(74) *Attorney, Agent, or Firm* — F. Brent Nix, Esq.; Johnson, Marcou, Isaacs & Nix, LLC; Ming Zhang

(57) ABSTRACT

Described herein are targeting moieties that can be capable of specifically targeting muscle cells and can include an n-mer motif. In some embodiments, the n-mer motif contains an RGD motif. Also described herein are vector systems, particles, polypeptides that can encode and/or contain one or more targeting moieties. Also described herein are methods of delivering a cargo to a cell, such as a muscle cell, using one or more of the targeting moieties described herein.

29 Claims, 36 Drawing Sheets

Specification includes a Sequence Listing.

(56) References Cited

U.S. PATENT DOCUMENTS

| | | | |
|---|---|---|---|
| 10,076,536 B2 | 9/2018 | Kole et al. |
| 11,920,150 B2 | 3/2024 | Sabeti et al. |
| 2005/0287122 A1 | 12/2005 | Bartlett et al. |
| 2009/0222937 A1 | 9/2009 | Arnould et al. |
| 2009/0271881 A1 | 10/2009 | Arnould et al. |
| 2010/0229252 A1 | 9/2010 | Perez-Michaut |
| 2011/0016540 A1 | 1/2011 | Weinstein et al. |
| 2011/0023145 A1 | 1/2011 | Weinstein et al. |
| 2011/0091441 A1 | 4/2011 | Gouble et al. |
| 2011/0182867 A1 | 7/2011 | Orkin et al. |
| 2011/0225664 A1 | 9/2011 | Smith |
| 2012/0204282 A1 | 8/2012 | Zhang |
| 2013/0145487 A1 | 6/2013 | Cedrone |
| 2014/0287983 A1 | 9/2014 | Mourich et al. |
| 2014/0315977 A1 | 10/2014 | Bestwick et al. |
| 2015/0079038 A1 | 3/2015 | Deverman et al. |
| 2015/0267202 A1 | 9/2015 | Iversen et al. |
| 2016/0251398 A1 | 9/2016 | Weller et al. |
| 2017/0051278 A1 | 2/2017 | Kole et al. |
| 2017/0130245 A1 | 5/2017 | Kotin et al. |
| 2018/0161359 A1 | 6/2018 | Mourich et al. |
| 2018/0169130 A1 | 6/2018 | Lorain et al. |
| 2018/0189244 A1 | 7/2018 | Ghafourifar et al. |
| 2018/0216111 A1 | 8/2018 | Wilton et al. |
| 2018/0271893 A1 | 9/2018 | Kole et al. |
| 2019/0015440 A1 | 1/2019 | Passini et al. |
| 2019/0054113 A1 | 2/2019 | Kaye |
| 2019/0100755 A1 | 4/2019 | Linsley et al. |
| 2019/0127424 A1 | 5/2019 | Srivastava et al. |
| 2019/0177723 A1 | 6/2019 | Dickson |
| 2019/0284555 A1 | 9/2019 | Schnell |
| 2020/0325456 A1 | 10/2020 | Li et al. |
| 2021/0380969 A1 | 12/2021 | Nonnenmacher et al. |

FOREIGN PATENT DOCUMENTS

| | | |
|---|---|---|
| CN | 109476707 A | 3/2019 |
| CN | 109897831 A | 6/2019 |
| CN | 114729384 A | 7/2022 |
| CN | 114787179 A | 7/2022 |
| WO | WO 93/24641 A2 | 12/1993 |
| WO | 00/12738 A1 | 3/2000 |
| WO | WO 0170955 A2 | 9/2001 |
| WO | 2007118245 A2 | 10/2007 |
| WO | WO 2013126794 A1 | 7/2013 |
| WO | WO 2013130824 A1 | 9/2013 |
| WO | WO 2013163628 A2 | 10/2013 |
| WO | WO 2015048577 A2 | 4/2014 |
| WO | WO 2014093622 A2 | 6/2014 |
| WO | WO 2015089354 A1 | 6/2015 |
| WO | 2015116568 A2 | 8/2015 |
| WO | WO 2015134812 A1 | 9/2015 |
| WO | WO 2015148670 A1 | 10/2015 |
| WO | WO 2015148860 A1 | 10/2015 |
| WO | WO 2015148863 A2 | 10/2015 |
| WO | WO 2015153789 A1 | 10/2015 |
| WO | WO 2015153791 A1 | 10/2015 |
| WO | WO 2016115543 A2 | 7/2016 |
| WO | WO 2017006283 A1 | 1/2017 |
| WO | 2017096164 A1 | 6/2017 |
| WO | WO 2017106304 A1 | 6/2017 |
| WO | WO 2017165862 A1 | 9/2017 |
| WO | WO 2018119330 A2 | 6/2018 |
| WO | 2018189244 A1 | 10/2018 |
| WO | 2019060454 A2 | 3/2019 |
| WO | WO 2019059973 A1 | 3/2019 |
| WO | WO 2019118806 A1 | 6/2019 |
| WO | 2019193119 A1 | 10/2019 |
| WO | 2019207132 A1 | 10/2019 |
| WO | WO 2019217911 A1 | 11/2019 |
| WO | WO 2020160183 A1 | 8/2020 |
| WO | 2019/050974 A1 | 3/2021 |
| WO | 2021/072197 A1 | 4/2021 |

OTHER PUBLICATIONS

The Broad Institute, Inc., Non-Final Office Action for U.S. Appl. No. 17/707,951, Nov. 18, 2025, 18 pages.

The Broad Institute, Inc., Decision of Rejection for Japanese Patent Application No. 2022-515996, Dec. 2, 2025, 17 pages.

Chan, S., et al. "Branched fibers in dystrophic mdx muscle are associated with a loss of force following lengthening contractions". Am J Physiol Cell Physiol vol. 293,Jun. 13, 2007, pp. C985-C992.

S. Childers et al. "Gene therapy prolongs survival and restores function in murine and canine models of myotubular myopathy". Sci Transl Med vol. 6, No. 220ra210. Jan. 1, 2014, pp. 1-31.

D. Dalkara et al. "In vivo-directed evolution of a new adeno-associated virus for therapeutic outer retinal gene delivery from the vitreous". Sci Transl Med vol. 5, No. 189, 189ra176, Jun. 12, 2013, pp. 1-12.

R. C. Challis et al. "Widespread and targeted gene expression by systemic AAV vectors: Production, purification, and administration" bioRxiv, Jan. 19, 2018. doi: https://doi.org/10.1101/246405, pp. 1-66.

M. Davidsson et al. "A systematic capsid evolution approach performed in vivo for the design of AAV vectors with tailored properties and tropism". Proc Natl Acad Sci U S A, vol. 116, No. 52, Dec. 26, 2019, pp. 27053-27062.

B.E. Deverman Cre-dependent selection yields AAV variants for widespread gene transfer to the adult brain. Nat Biotechnol vol. 34, No. 2, Feb. 2016, pp. 1-21.

W. Ding et al. "Intracellular trafficking of adeno-associated viral vectors". Gene Ther vo. 12, No. 11, Jun. 2005, pp. 873-880.

Duan,, D. "Micro-Dystrophin Gene Therapy Goes Systemic in Duchenne Muscular Dystrophy Patients". Hum Gene Ther vol. 29, No. 7, Apr. 5, 2018, pp. 733-736.

Duan, D., "Systemic AAV Micro-dystrophin Gene Therapy for Duchenne Muscular Dystrophy". Mol Ther vol. 26, No. 10 Oct. 2018, pp. 2337-2356.

A.M. Dudek et al. An Alternate Route for Adeno-associated Virus (AAV) Entry Independent of AAV Receptor. J Virol vol. 92, No. 7, e02213-17, Apr. 1, 2018, pp. 1-15.

M. Elverman et al. "Long-term effects of systemic gene therapy in a canine model of myotubular myopathy". Muscle Nerve vol. 56, No. 5, May 22, 2017, pp. 943-953.

K.D. Farris et al. "Improved splicing of adeno-associated viral (AAV) capsid protein-supplying pre-mRNAs leads to increased recombinant AAV vector production". Hum Gene Ther vol. 19, No. 12, Dec. 19, 2008, pp. 1421-1427.

G. Gao et al. "Biology of AAV serotype vectors in liver-directed gene transfer to nonhuman primates". Mol Ther vol. 13, No. 1, Oct. 10, 2005, pp. 77-87.

J.M. Goldstein, et al. "In Situ Modification of Tissue Stem and Progenitor Cell Genomes". Cell Rep vo. 27, No. 4, Apr. 23, 2019, pp. 1254-1264 e1257.

C.H. Hakim et al. "A Five-Repeat Micro-Dystrophin Gene Ameliorated Dystrophic Phenotype in the Severe DBA/2J-mdx Model of Duchenne Muscular Dystrophy". Mol Ther Methods Clin Dev, vol. 27, No. 3, Mar. 6, 2019, pp. 216-230.

K.S. Hanlon et al. "Selection of an Efficient AAV Vector for Robust CNS Transgene Expression". Mol Ther Methods Clin Dev, vol. 15, Oct. 23, 2019, pp. 320-332.

C. Hinderer et al. "Severe Toxicity in Nonhuman Primates and Piglets Following High-Dose Intravenous Administration of an Adeno-Associated Virus Vector Expressing Human SMN". Hum Gene Ther. vol. 29, No. 3 Feb. 12, 2018, pp. 285-298.

J. Hordeaux et al. "The Neurotropic Properties of AAV-PHP.B Are Limited to C57BL/6J Mice". Mol Ther, vol. 26, No. 3, Mar. 7, 2018, pp. 664-668.

Hynes R.O. "Integrins: bidirectional, allosteric signaling machines". Cell, vol. 110, No. 6, Sep. 20, 2002, pp. 673-687.

Korbelin, J., et al. Pulmonary Targeting of Adeno-associated Viral Vectors by Next-generation Sequencing-guided Screening of Random Capsid Displayed Peptide Libraries. Mol Ther vol. 24, No. 6, Jun. 2016, pp. 1050-1061.

N. Levitt et al. "Definition of an efficient synthetic poly(A) site". Genes Dev, vol. 3, Jul. 1989, 1019-1025.

(56) References Cited

OTHER PUBLICATIONS

C. Li and R. J. Samulski. Engineering adeno-associated virus vectors for gene therapy. Nat Rev Genet, vol. 21, No. 4, Feb. 10, 2020, pp. 255-272.
C. Li et al. "Development of Patient-specific AAV Vectors After Neutralizing Antibody Selection for Enhanced Muscle Gene Transfer", Mol. Ther. vol. 24, No. 6, Jan. 2016, pp. 53-65.
D. L. Mack, "Systemic AAV8-Mediated Gene Therapy Drives Whole-Body Correction of Myotubular Myopathy in Dogs". Mol Ther, vol. 25, No. 4, Apr. 5, 2017, pp. 839-854.
J.R. Mendell et al. "Assessment of Systemic Delivery of rAAVrh74. MHCK7.micro-dystrophin in Children With Duchenne Muscular Dystrophy", JAMA Neurology, vo. 77 No. 9, Jun. 15, 2020, pp. 1-10.
L. Morales et al. "Broader Implications of Progressive Liver Dysfunction and Lethal Sepsis in Two Boys following Systemic High-Dose AAV". Mol Ther, vol. 28, No. 8, Aug. 5, 2020, pp. 1753-1755.
D.A. Murrey et al., "Feasibility and safety of systemic rAAV9-hNAGLU delivery for treating mucopolysaccharidosis IIIB: toxicology, biodistribution, and immunological assessments in primates". Hum Gene Ther Clin Dev, vol. 25, No. 2, Jun. 2014, pp. 72-84.
C.E. Nelson et al. "In vivo genome editing improves muscle function in a mouse model of Duchenne muscular dystrophy". Science vol. 351, No. 6271, Jan. 22, 2016, pp. 403-407 (included as pp. 1-12).
M.D. Pierschbacher and E. Ruoslahti, "Cell attachment activity of fibronectin can be duplicated by small synthetic fragments of the molecule". Nature 309, 30-33.
S. Pillay et al. "An essential receptor for adeno-associated virus infection". Nature vol. 530, No. 7588, Feb. 4, 2016, pp. 108-112.
N. Pulicherla et al. Engineering liver-detargeted AAV9 vectors for cardiac and musculoskeletal gene transfer. Mol Ther, vol. 19,No. 6, Jun. 2011, pp. 1070-1078.
E. Ruoslahti. "RGD and other recognition sequences for integrins" Annu Rev Cell Dev Biol, vol. 12, 1996, pp. 697-715.
C. Summerford et al. "AlphaVbeta5 integrin: a co-receptor for adeno-associated virus type 2 infection". Nat Med vol. 5, No. 1, Jan. 1999, pp. 78-82.
M. Tabebordbar et al. "In vivo gene editing in dystrophic mouse muscle and muscle stem cells". Science vol. 351, No. 6271,Jan. 26, 2016, pp. 407-411.
L. V. Tse et al. "Structure-guided evolution of antigenically distinct adeno-associated virus variants for immune evasion". Proc Natl Acad Sci U S A vol. 114, May 30, 2017, pp. E4812-E4821.
J. Weinmann et al. "Identification of a myotropic AAV by massively parallel in vivo evaluation of barcoded capsid variants". Nat Commun vol. 11, No. 1, article 5432, Oct. 28, 2020, pp. 1-12.
Z. Wu et al. Single amino acid changes can influence titer, heparin binding, and tissue tropism in different adeno-associated virus serotypes. J Virol, vol. 80, No. 22, Nov. 2006, pp. 11393-11397.
L. Yang et al. "A myocardium tropic adeno-associated virus (AAV)evolved by DNA shuffling and in vivo selection", Proc Natl Acad Sci U S A vol. 106, No. 10, Mar. 10, 2009, pp. 3946-3951.
L. Yang and X. Xiao. "Creation of a cardiotropic adeno-associated virus: the story of viral directed evolution" Virology Journal. vol. 10, article 50, 2013, pp. 1-8.
C. Zincarelli et al. "Analysis of AAV serotypes 1-9 mediated gene expression and tropism in mice after systemic injection". Mol Ther, vol. 16, No. 6, Jun. 2008, pp. 1073-1080.
UniProt Acession No. A0A1P8U1E3, UniProtKB—A0A1P8U1E3 (A0A1PU1E3_9ACTN), Apr. 12, 2017 [online]. pp. 1-3.
The Broad Institute, Inc., "International Search Report and Written Opinion for PCT/US2021/0042812", issued by The United States Patent Office, as International Searching Authority on Dec. 28, 2021, 25 pages.
The Broad Institute, Inc., "Invitation to Pay Additional Fees", issued by the U.S. Patent Office as International Searching Authority for PCT/US2021/042812 on Oct. 19, 2021, 2 pages.
The Broad Institute, Inc., "Chapter I International Preliminary Report on Patentability", mailed by the International Bureau for PCT/US2021/042812 on Feb. 2, 2023, 8 pages.
The Broad Institute, Inc., "Restriction Requirement", issued by the U.S. Patent Office U.S. Appl. No. 17/707,944, on Aug. 2, 2022.
"Third-Party Pre-issuance Submission under 37 C.F.R. §1.290", filed in U.S. Appl. No. 17/707,944, on Nov. 6, 2022. pages 1-29.
The Broad Institute, Inc., "Non-Final Office Action", issued by the U.S. Patent Office in U.S. Appl. No. 17/707,944, on Nov. 7, 2022.
Büning, H. and A. Srivastava. "Capsid Modifications for Targeting and Improving the Efficacy of AAV Vectors." Molecular Therapy: Methods & Clinical Development, vol. 12, Mar. 2019, pp. 248-265.
The Broad Institute, Inc., "Chapter I International Preliminary Report on Patentability", mailed by the International Bureau for PCT/US2020/050534 on Mar. 24, 2022, 11 pages.
The Broad Institute, Inc., "Chapter I International Preliminary Report on Patentability", mailed by the International Bureau for PCT/US2020/056133 on Apr. 28, 2022, 12 pages.
"International Search Report and Written Opinion", issued by the U.S. Patent Office, as International Searching Authority for PCT/US2020/056133 on Mar. 26, 2021.
"Invitation to Pay Additional Fees", issued by the U.S. Patent and Trademark Office, as International Searching Authority on Jan. 11, 2021.
The Broad Institute, Inc., Notice of Rejection for Japanese Patent Application No. 2022-522782, Jan. 7, 2025, 8 pages.
The Broad Institute, Inc., Notification of Fourth Office Action for Chinese Patent Application No. 2020800849233, Feb. 10, 2025, 25 pages.
The Broad Institute, Inc., Notice of Rejection for Japanese Patent Application No. 2022-515996, Mar. 5, 2025, 14 pages.
The Broad Institute, Inc., Final Office Action for U.S. Appl. No. 17/707,951, filed Jun. 18, 2025, 28 pages.
The Broad Institute, Inc., Rejection Decision for Chinese Patent Application No. 202080084923.3, Jul. 21, 2025, 25 pages.
The Broad Institute, Inc., International Preliminary Report on Patentability for PCT/US2020/056133, issued by The International Bureau of WIPO on Apr. 28, 2022, 12 pges.
The Broad Institute, Inc.,"third Office Action and Search Report for Chinese Patent Application No. 2020800849233", Sep. 5, 2024, 58 pages.
The Broad Institute, Inc., "Extended European Search Report for EP 20877004.0", Oct. 19, 2023, 10 pages.
Adachi et al., "Creation of Liver-Detargeting AAV2-Derived Mutants Based on the Knowledge of AAV9 Capsid Functions", Molecular Therapy vol. 21, Supplement 1, S51, May 2013.
Büning et al., "Capsid Modifications for Targeting and Improving the Efficacy of AAV Vectors", Molecular Therapy: Methods & Clinical Development, vol. 12, pp. 248-265, Mar. 2019.
Choudhury et al., "In Vivo Selection Yields AAV-B1 Capsid for Central Nervous System and Muscle Gene Therapy", MolecularTherapy, vol. 24, No. 7, pp. 1247-1257, Jul. 2016.
Michelfelder et al., "Successful Expansion but Not Complete Restriction of Tropism of Adeno-Associated Virus by In Vivo Biopanning of Random Virus Display Peptide Libraries", PLoS One, vol. 4, Issue 4, e5122-e5122, Apr. 2009.
Perabo et al., "In Vitro Selection of Viral Vectors with Modified Tropism: The Adeno-associated Virus Display", Molecular Therapy, vol. 8, No. 1, pp. 151-157, Jul. 2003.
Tang et al., "AAV-directed muscular dystrophy gene therapy", Expert Opinion on Biological Therapy, vol. 10, Issue 3, pp. 395-408, Published online: Feb. 4, 2010.
Varadi et al., "Novel random peptide libraries displayed on AAV serotype 9 for selection of endothelial cell-directed gene transfer vectors", Gene Therapy vol. 19, pp. 800-809; Published Online: Sep. 29, 2011.
Wang et al., "The potential of adeno-associated viral vectors for gene delivery to muscle tissue", Expert Opin Drug Deliv., vol. 11, No. 3, pp. 345-364, Mar. 2014.
Yang et al., "A myocardium tropic adeno-associated virus (AAV) evolved by DNA shuffling and in vivo selection", PNAS, vol. 106, No. 10, pp. 3946-3951, Mar. 10, 2009.

(56) References Cited

OTHER PUBLICATIONS

Yu et al., "A muscle-targeting peptide displayed on AAV2 improves muscle tropism upon systemic delivery", Gene Ther., vol. 16, No. 8, pp. 953-962, Aug. 2009.
Unknown et al., "Third-Party Submission filed under 37 § C.F.R. 1.290 in U.S. Appl. No. 17/764,509" Jun. 27, 2023, pp. 1-133.
Tabebordbar et al., "Directed evolution of a family of AAV capsid variants enabling potent muscle-directed gene delivery across species," Cell, vol. 184, No. 19, pp. 4919-4938, Sep. 2021.
The Broad Institute, Inc., "Office Action for Canadian Patent Application No. 3,153,902", Dec. 23, 2024, 4 pages.
Stutika et al. (2016) J. Viral., vol. 90(3), 1278-1289.
Farris et al. (2008) Human Gene Ther., vol. 19, 14221-1427.
Pan et al., "Development and application of DNA shuffling in the directed evolution of adeno-associated virus", Chinese Science Bulletin , vol. 58, Issue 5-6: 411-418, 2013—English abstract.
Michelfelder et al. (2011) PLoS One, vol. 6(8), e23101.doi:10.1371/journal.pone.002310, 11 pages.
Wu et al. Journal of Virology (2000) vol. 7 4, No. 18, pp. 8635-8647.
The Broad Institute, Inc., "Office Action for Canadian Patent Application No. 3,148,356", Dec. 19, 2024, 4 pages.
K. Varadi et al. "Novel random peptide libraries displayed on AAV serotype 9 for selection of endothelial cell-directed gene transfer vectors", Gene Therapy. vol. 19, No. 8, Aug. 1, 2012, pp. 800-809.
Mgne, et al., "RGD Inclusion in the Hexon Monomer Provides Adenovirus Type 5-Based Vectors with a Fiber Knob-Independent Pathway for Infection." Journal of Virology. vol. 73, No. 6, Jun. 1999, pp. 5165-5161.
Dan Wang et al. "The potential of adeno-associated viral vectors for gene delivery to muscle tissue", Expert Opinion on Drug Delivery, vol. 11, No. 3., Mar. 1, 2014, pp. 345-364.
Sourav R. Choudhury et al. "In Vivo Selection Yields AAV-B1 Capsid for Central Nervous System and Muscle Gene Therapy", Molecular Therapy, vol. 24, No. 7, Jun. 7, 2016, pp. 1247-1257.
L. Yang et al., "A myocardium tropic adeno-associated virus (AAV) evolved by DNA shuffling and in vivo selection", Proceeding sof the National Academy of Sciences, vol. 106, No. 10, Mar. 10, 2009, pp. 3946-3951.
Perabo L. et al., "In vitro selection of viral vectors with modified tropism: The Adeno-Associated virus display", Mol. Ther. vol. 8, No. 1, Jul. 2003, pp. 151-157.
Stefan Michelfelder et al., Successful Expansion but Not Complete Restriction of Tropism of Adeno-Associated Virus by In vivo Biopanning of Random Virus Display Peptide Libraries. PLOS One, vol. 4, No. 4, Apr. 9, 2009, e5122, pp. 1-13.
Adachi K. et al. "Creation of a liver-detargeting AAV2-derived mutant based on the knowledge of AAV9 capsid function." Mol. Ther., vol. 21, No. S1, abstract No. 124 May 2013, p. 1.
Tang Ying et al. "AAV-directed muscular dystrophy gene therapy", Expert Opinion on Biological Therapy vol. 10, No. 3. Mar. 1, 2010 pp. 395-408.
Dimattia et al. Structural Insight into the Unique Properties of Adeno-Associated Virus Serotype 9. J. Virology. vol. 86, No. 12, Apr. 11, 2012. pp. 6947-6958.
M. D. Weitzman and R. M. Linden. "Adeno-Associated Virus Biology". Chapter in Methods in Molecular Biology. R. O. Snyder and P. Moullier (eds.) Humana Press. Totowa NJ, USA. Jan. 1, 2011. pp. 1-23.
K. Adachi et al. "Drawing a high-resolution functional map of adeno-associated virus capsid by massively parallel sequencing". Nature Communications, vol. 5. No. 3075. Jan. 17, 2014, pp. 1-14.
S. Teramato et al. "Crisis of adenoviruses in human gene therapy." The Lancet, vol. 355, May 27, 2000, pp. 1911-1912.
C. M. Lai et al. "Adenovirus and Adeno-Associated Virus Vectors". DNA Cell Biol.vol. 21, No. 12, Jul. 6, 2004, pp. 895-913.
A.V. Cideciyan. "Vision 1 Year after Gene Therapy for Leber's Congenital Amaurosis" N. Engl J Med. Aug. 13, 2009, pp. 725-727.
F. Simonelli et al. "Gene Therapy for Leber's Congenital Amaurosis is Safe and Effective Through 1.5 Years After Vector Administration", Molecular Therapy, vol. 18, No. 3, Mar. 2010 pp. 643-650.
M.A. Croyle et al. "PEGylated helper-dependent adenoviral vectors: highly efficient vectors with an enhanced safety profile", Gene Therapy vol. 12, Jan. 13, 2005, pp. 579-587.
A. Amalfitano et al. "Production and Characterization of Improved Adenovirus Vectors with the E1, E2b, and E3 Genes Deleted", Gene Therapy, vol. 72, No. 2, Feb. 1, 1998, pp. 923-933.
N. Morral et al. "Administration of helper-dependent adenoviral vectors and sequential delivery of different vector serotype for long-term liver-directed gene transfer in baboons", PNAS, vol. 26, No. 22, Oct. 26, 1999, pp. 12816-12821.
A. Rosewell et al. "Helper-Dependent Adenoviral Vectors", J Genet Syndr Gene Ther., Suppl. 5, No. 001, Oct. 29, 2011, pp. 1-34.
Balague, C. et al. "Sustained high-level expression of full-length human factor VIII and restoration of clotting activity in hemophilic mice using a minimal adenovirus vector". Blood, vol. 95, No. 3, Feb. 1, 2000, pp. 820-828.
S. Kubo and K. Mitani et al. "A New Hybrid System Capable of Efficient Lentiviral Vector Production and Stable Gene Transfer Mediated by a Single Helper-Dependent Adenoviral Vector", Journal of Virology, vol. 77, Mar. 2003, pp. 2964-2971.
W. Zhang et al. "Hybrid Adeno-Associated Viral Vectors Utilizing Transposase-Mediated Somatic Integration for Stable Transgene Expression in Human Cells", PLOS One, vol. 8, No. 10, e76771, Oct. 2013, pp. 1-17.
A. L. Cooney et al. "Hybrid Nonviral/Viral Vector Systems for Improved piggyBac DNA Transposon In Vivo Delivery", Molecular Therapy, vol. 23, No. 4, Apr. 2015, pp. 667-674.
Kubo, S. et al "Adenovirus-retrovirus hybrid vectors achieve highly enhanced tumor transduction and antitumor efficacy in vivo". Mol Ther, vol. 19., No. 1, Jan. 2011. pp. 76-82.
A. Ehrhardt et al. "Somatic integration from an adenoviral hybrid vector into a hot spot in mouse liver results in persistent transgene expression levels in vivo", Mol. Ther. vol. 15, No. 1, Jan. 2007, pp. 146-156.
W. Liu et al. "Recombinant Human Foamy VirMus, a Novel Vector for Neurological Disorders Gene Therapy, Drives Production of GAD in Cultured Astrocytes", Mol. Ther. vol. 15, No. 10, Oct. 2007, pp. 1834-1841.
R. M. Kotin. "Prosepects for the Use of Adeon-Associated Virus as a Vector for Human Gene Therapy", Human Gene Therapy, vol. 5, No. 7, Jul. 1994, pp. 793-801.
N. Muzyczka. "Adeno-associated Virus (AAV) Vectors: Will they work?" J. Clin Invest. vol. 94, Oct. 1994, p. 1351.
A. Srivastava. "In vivo tissue-tropism of adeno-associated viral vectors". Curr Opin Virol. vol. 21., Dec. 2016, pp. 1-12.
D. Grimm et al. "In Vitro and In Vivo Gene Therapy Vector Evolution via Multispecies Interbreeding and Retargeting of Adeno-Associated Viruses", J. Virololgy. vol. 82, No. 12, Jun. 2008, pp. 5887-5911.
J. Tratschin et al. "Adeno-Associated Virus Vector for High-Frequency Integration, Expression, and Rescue of Genes in Mammalian Cells", Molecular and Cellular Biology, vol. 5, No. 11, Nov. 1985, pp. 3251-3260.
J. Tratschin et al. "A human parvovirus, adeno-associated virus, as a eucaryotic vector: transient expression and encapsidation of the procaryotic gene for chloramphenicol acetyltransferase.", Mol Cell Biol. vol. 4, No. 10, Oct. 1984, pp. 2072-2081.
P. L. Hermonat et al. Use of adeno-associated virus as a mammalian DNA cloning vector: Transduction of neomycin resistance into mammalian tissue culture cells Proc. Natl. Acad. Sci. USA, vol. 81, Oct. 1984, pp. 6466-6470.
R. J. Samulski et al. "Helper-free stocks of recombinant adeno-associated viruses: normal integration does not require viral gene expression", J. Virology, vol. 63, No. 9, Sep. 1989, pp. 3822-3828.
S. Q. Harper, et al. "Modular flexibility of dystrophin: Implications for gene therapy of Duchenne muscular dystrophy" Nat. Medicine. vol. 8, No. 3, Mar. 2002, pp. 253-261.
S.B. England et al. "Very mild muscular dystrophy associated with the deletion of 46% of dystrophin", Nature. vol. 343, Jan. 11, 1990, pp. 180-182.

(56) References Cited

OTHER PUBLICATIONS

D. J. Wells et al., "Expression of human full-length and minidystrophin in transgenic mdx mice: implications for gene therapy of Duchenne muscular dystrophy", Human Molecular Genetics, vol. 4, No. 8, Aug. 1995, pp. 1245-1250.
Salva, M.Z., et al. "Design of Tissue-specific Regulatory Cassettes for High-Level rAAV-mediated Expression in Skeletal and Cardiac Muscle" Molecular Therapy, vol. 15, No. 2, Feb. 2007, pp. 320-329.
J.R. Mendell, et al. "Gene therapy for muscular dystrophy: Lessons learned and path forward", Neuorscience Letters, vol. 527, No. 2, Oct. 11, 2012, pp. 90-99.
L. R. Rodino-Klapac et al. "Micro-dystrophin and follistatin co-delivery restores muscle function in aged DMD model" Human Molecular Genetics, vol. 22, No. 24, Dec. 15, 2013, pp. 4929-4937.
V. M. Velazquez, et al. "Effective Depletion of Pre-existing Anti-AAV Antibodies Requires Broad Immune Targeting" Molecular Therapy: Methods & Clinical Development. vol. 4, Mar. 2017, pp. 159-168.
D. M. Nelson et al. "Variable rescue of microtubule and physiological phenotypes in mdx muscle expressing different miniaturized dystrophins", Human Molecular Genetics, vol. 27, No. 12, Jun. 15, 2018, pp. 2090-2100.
Asokan, A. et al. Adeno-associated virus type 2 contains an integrin alpha5beta1 binding domain essential for viral cell entry. J Virol, vol. 80, Sep. 2006, pp. 8961-8969.
Bengtsson, N. E., et al. "Muscle-specific CRISPR/Cas9 dystrophin gene editing ameliorates pathophysiology in a mouse model for Duchenne muscular dystrophy", Nat Commun vol. 8, 14454 Feb. 14, 2017, pp. 1-10.
G. Berry and A. Asokan, "Cellular transduction mechanisms of adeno-associated viral vectors", Curr Opin Virol vol. 21, Dec. 2016 pp. 1-12.
C.L. Bell et al. "The AAV9 receptor and its modification to improve in vivo lung gene transfer in mice", J Clin Invest vol. 121, No. 6 Jun. 2011 pp. 2427-2435.
Börner, K., et al., "Pre-arrayed Pan-AAV Peptide Display Libraries for Rapid Single-Round Screening". Mol Ther 28, 1016-1032. Molecular Therapy. vol. 28, No. 4, Feb. 12, 2020, pp. 1016-1032.
M. Cerletti et al. "Highly efficient, functional engraftment of skeletal muscle stem cells in dystrophic muscles". Cell vol. 134 No. 1, Jul. 11, 2008, pp. 37-47.
K. Y. Chan et al. "Engineered AAVs for efficient noninvasive gene delivery to the central and peripheral nervous systems". Nat Neurosci vol. 20, No. 8, Jun. 26, 2017, pp. 1172-1179.
Alba, R., et al., "Gutless adenovirus: last-generation adenovirus for gee therapy." Gene Therapy, vol. 12, 2005, pp. S18-S27.
The Broad Institute, Inc., "Invitation to Pay Additional Fees", issued by the U.S. Patent Office as International Searching Authority for PCT/US2020/056133 on Jan. 11, 2021, 3 pages.
The Broad Institute, Inc., "International Search Report and Written Opinion for PCT/US2020/056133", issued by The United States Patent Office, as International Searching Authority on Mar. 26, 2021, 17 pages.
The Broad Institute, Inc., "Restriction Requirement", issued by the U.S. Patent Office U.S. Appl. No. 17/707,940, on Jun. 30, 2022, 17 pages.
The Broad Institute, Inc., "Non-Final Office Action", issued by the U.S. Patent Office in U.S. Appl. No. 17/707,940, on Oct. 20, 2022, 21 pages.
The Broad Institute, Inc., "Notice of Allowability", issued by the U.S. Patent Office in U.S. Appl. No. 17/707,940, on Feb. 6, 2023, 4 pages.
Flotte, et al. "A Phase I Study of an Adeno-Associated Virus-CFTR Gene Vector in Adult CF Patients with Mild Lung Disease." Human Gene Therapy. vol. 7, Jun. 10, 1996, pp. 1145-1159.
Kay, M.A., et al. "Evidence of gene transfer and expression of factor IX in haemophilia B patients treated with an AAV vector." Nature. vol. 24, Mar. 2000, pp. 257-261.
Thrasher, A.J., et al. "X-SCID transgene leukaemogenicity." Nature. vol. 44, Sep. 21, 2006, pp. E5-E6.
Woods, N., et al. "Woods et al., Reply." Nature. vol. 44, Sep. 21, 2006, pp. E6-E7.
Crane, B., et al. "Rescue administration of a helper-dependent adenovirus vector with long-term efficacy in dogs with glycogen storage disease type 1a." Gene Therapy, vol. 19, 2012, pp. 443-452.
West, M. H. P., et al. "Gene Expression in Adeno-Associated Virus Vectors: The Effects of Chimeric mRNA Structure, Helper Virus, and Adenovirus VAI, RNA." Virology. vol. 160, 1987, pp. 38-47.
The Broad Institute, Inc., "International Search Report and Written Opinion for PCT/US2022/076117", issued by The United States Patent Office, as International Searching Authority on Jan. 31, 2023, 14 pages.
The Broad Institute, Inc., "Invitation to Pay Additional Fees", issued by the U.S. Patent Office as International Searching Authority for PCT/US2022/076117 on Nov. 29, 2022, 2 pages.
The Broad Institute, Inc., "Invitation to Pay Additional Fees", issued by the U.S. Patent Office as International Searching Authority for PCT/US2022/076127 on Nov. 28, 2022, 3 pages.
The Broad Institute, Inc., "International Search Report and Written Opinion for PCT/US2022/076127", issued by The United States Patent Office, as International Searching Authority on Feb. 14, 2023, 51 pages.
The Broad Institute, Inc., "Invitation to Pay Additional Fees", issued by the U.S. Patent Office as International Searching Authority for PCT/US2022/074611 on Oct. 26, 2022, 3 pages.
The Broad Institute, Inc., "International Search Report and Written Opinion for PCT/US2022/074611", issued by The United States Patent Office, as International Searching Authority on Jan. 12, 2023, 16 pages.
Wang, M., et al. "Evaluation of Amphiphilic Peptide Modified Antisense Morpholino Oligonucleotides In Vitro and in Dystrophic mdx Mice." Polymers, vol. 9, 2017, pp. 1-14.
Geisler, A., and H. Fechner. "MicroRNA-regulated viral vectors for gene therapy." World J Exp Med, vol. 6, No. 2, May 20, 2016, pp. 37-54.
The Broad Institute, Inc., "Invitation to Pay Additional Fees", issued by the U.S. Patent Office as International Searching Authority for PCT/US2022/077628 on Jan. 9, 2023, 2 pages.
Morral, N., et al., "High Doses of a Helper-Dependent Adenoviral Vector Yield Supraphysiological Levels of alpha1-Antitrypsin with Negligible Toxicity." Human Gene Therapy, vol. 9, Dec. 10, 1998, pp. 2709-2716.
Afione, S. A., et al., "In vivo Model of Adeno-Associated Virus Vector Persistence and Rescue." Journal of Virology , vo. 70, No. 5, May 1996, pp. 3235-3241.
Mendell, J. R., et al., "Single-Dose Gene-Replacement Therapy for Spinal Muscular Atrophy." New England Journal of Medicine, vol. 377, No. 18, Nov. 2, 2017, pp. 1713-1722.
Naso, M. F., et al., "Adeno-Associated Virus (AAV) as a Vector for Gene Therapy." BioDrugs, vol. 31 (2017), pp. 317-334.
Wu, Z., et al., "Adeno-associated Virus Serotypes: Vector Toolkit for Human Gene Therapy." Molecular Therapy, vol. 14, No. 3, Sep. 2006, pp. 316-327.
Faust, S. M., et al., "CpG-depleted adeno-associated virus vectors evade immune detection." Journal of Clinical Investigation, vol. 123, Jul. 2013, pp. 2994-3001.
Hocquemiller, M., et al., "Adeno-Associated Virus-Based Gene Therapy for CNS Diseases." Human Gene Therapy, vol. 27, No. 7, pp. 478-496.
Qiao, C., et al., "Liver-specific microRNA-122 target sequences incorporated in AAV vectors efficiently inhibits transgene expression in the liver." Gene Therapy, vol. 18, No. 4, Apr. 2011, pp. 1-19.
Xiang, Z., et al., "The Effect of CpG Sequences on Capsid-Specific CD8+TCellResponses toAAVVectorGene Transfer." Molecular Therapy, vol. 28, No. 3 Mar. 2020, pp. 771-783.
Xie, J., et al., "MicroRNA-regulated, Systemically Delivered rAAV9: A Step Closer to CNS-restricted Transgene Expression." Molecular Therapy, vol. 19, No. 3, Mar. 2011, pp. 526-535.
Zincarelli, C., et al., "Analysis of AAV Serotypes 1-9 Mediated Gene Expression and Tropism in Mice After Systemic Injection." Molecular Therapy, vol. 16, No. 6, Jun. 2008, pp. 1073-1080.

(56) References Cited

OTHER PUBLICATIONS

Domenger and Grimm "Next-generation AAV vectors—do not judge a virus (only) by its cover." Human Molecular genetics, vo. 28, No. R1, Oct. 1, 2019, pp. R3-R14.
The Broad Institute, Inc., "International Search Report and Written Opinion", issued by the European Patent Office (EPO), as International Searching Authority for PCT/US2020/050534 on Feb. 3, 2021, 20 pages.
The Broad Institute, Inc., "Invitation to Pay Additional Fees", issued by the European Patent Office for PCT/US2020/050534 on Dec. 2, 2020, 15 pages.
Adachi, et al., "A New Recombinant Adeno-Associated Virus (AAV)-Based Random Peptide Display Library System: Infection-Defective AAVI.9-3 as a Novel Detargeted Platform for Vector Evolution", Gene Therapy and Regulation, vol. 5, No. 1, pp. 31-55, Sep. 11, 2010.
Jang, et al., "An Evolved Adeno-assciciated Viral Variant Enhances Gene Delivery and Gene Targeting in Neural Stem Cells", Molecular Therapy, vol. 19, No. 4, pp. 667-675, Apr. 4, 2011.
Wang, et al., "A Rationally Engineered Capsid Variant of AAV9 for Systemic CNS-Directed and Peripheral Tissue-Detargeted Gene Delivery in Neonates", Molecular Therapy, Methods & Clinical Development, vol. 9, pp. 234-246, Jun. 1, 2018.
Yu, et al., "A muscle-targeting peptide displayed on AA V2 improves muscle tropism on systemic delivery", Gene Therapy, vol. 16, pp. 953-962, May 28, 2009.
Zhang, et al., "Addition of Six-His-Tagged Peptide to the CTerminus of Adeno-Associated Virus VPS Does Not Affect Viral Tropism or Production", Journal of Virology, vol. 76, No. 23, pp. 12023-12031, Aug. 14, 2002.
The Broad Institute, Inc., "Patent Search Report for CN 2020800759364", Aug. 9, 2023, 8 pages.
The Broad Institute, Inc., "Notification of the First Office Action for CN 2020800759364", Aug. 9, 2023, 10 pages.
Sayroo et al., "Development of novel AAV serotype 6 based vectors with selective tropism for human cancer cells", Gene Therapy, 23, pp. 18-25, 2016.
Lee et al., "Adeno-Associated Virus (AAV) Vectors: Rational Design Strategies for Capsid Engineering", Curr Opin Biomed Eng. 7, pp. 58-63, 2018.
The Broad Institute, Inc., "Notice of Rejection for Japanese Patent Application No. 2022-515996", Aug. 9, 2024, 15 pages.
Eichoff et al., 2019, Mol. Ther. Methods Clin. Devl. 15, 211-220.
Zedechlik et al., 2020, Bioconjugate Chem. 31, 1093-1106.
Michels et al., Mol. Ther. Methods Clin. Dev. 23, 334-347, 2021.
Judd et al., Mol. Ther. Nucleic Acids 1, e54, 10 pages, 2012.
Wagner et al., 2021, Adv. Sci. 8, 2004018, 22 pages.
Aguti et al., The Progress of AAV-Mediated Gene Therapy in Neuromuscular Disorders, Exp. Opin. Biol. Ther., vol. 18(6), 681-693, 2018.
Shi et al., RGD Inclusion in VP3 Provides Adeno-Associated Virus Type 2 (AAV2)-Based Vectors with a Heparan Sulfate-Independent Cell Entry Mechanism, Mol. Ther., vol. 7(4), 515-525, 2023.
Sinanan et al, $\alpha v\beta 3$ and $\alpha v\beta 5$ integrins and their role in muscle precursor cell adhesion, Bio. Cell, vol. 100, 465-477, 2008.
The Broad Institute, Inc., Non-Final Office Action for U.S. Appl. No. 19/390,128, Mar. 11, 2026, 20 pages.
The Broad Institute, Inc., Non-Final Office Action for U.S. Appl. No. 17/642,541, Apr. 9, 2026, 33 pages.
Ying et al., Heart-targeted adeno-associated viral vectors selected by in vivo biopanning of a random viral display peptide library, 2010, Gene Therapy, vol. 17, 980-990.
Becerra et al., Synthesis of adeno-associated virus structural proteins requires both alternative mRNA splicing and alternative initiations from a single transcript, 1988, J. Virol., vol. 62(8), 2745-2754.
The Broad Institute, Inc., Examination Report No. 1 for Standard Patent Application for Patent Application No. AU 2020347276, Apr. 15, 2026, 4 pages.

* cited by examiner

| Mouse strain | Tissue type | First 3 amino acids | Rank |
|---|---|---|---|
| C57BL/6J | Diaphragm | RGD | 2 |
| C57BL/6J | Gastrocnemius | RGD | 2 |
| C57BL/6J | Quadriceps | RGD | 1 |
| C57BL/6J | Tibialis Anterior | RGD | 3 |
| C57BL/6J | Triceps | RGD | 12 |
| C57BL/6J | Heart | RGD | 8 |
| C57BL/6J | Liver | RGD | 245 |
| C57BL/6J | Brain | RGD | 2312 |

FIG. 20A

| Mouse strain | Tissue type | First 3 amino acids | Rank |
|---|---|---|---|
| BALB/cJ | Diaphragm | RGD | 9 |
| BALB/cJ | Gastrocnemius | RGD | 2 |
| BALB/cJ | Quadriceps | RGD | 18 |
| BALB/cJ | Tibialis Anterior | RGD | 10 |
| BALB/cJ | Triceps | RGD | 4 |
| BALB/cJ | Heart | RGD | 4 |
| BALB/cJ | Liver | RGD | 883 |
| BALB/cJ | Brain | RGD | 1266 |

FIG. 20B

| Mouse strain | Tissue type | First 3 amino acids | Rank |
|---|---|---|---|
| mdx | Diaphragm | RGD | 6 |
| mdx | Gastrocnemius | RGD | 1 |
| mdx | Quadriceps | RGD | 1 |
| mdx | Tibialis Anterior | RGD | 1 |
| mdx | Triceps | RGD | 1 |
| mdx | Heart | RGD | 25 |
| mdx | Liver | RGD | 166 |
| mdx | Brain | RGD | 1584 |

FIG. 20C

ENGINEERED MUSCLE TARGETING COMPOSITIONS

CROSS-REFERENCE TO RELATED APPLICATIONS

This application is a continuation of U.S. patent application Ser. No. 17/764,509, filed on Mar. 28, 2022, which is the U.S. National Stage Application under 35 U.S.C. § 371 of Patent Cooperation Treaty Application No.: PCT/US2020/056133, filed on Oct. 16, 2020. Patent Cooperation Treaty Application No.: PCT/US2020/056133 claims the benefit of and priority to U.S. Provisional Patent Application Nos. 62/916,207, filed on Oct. 16, 2019; entitled "Engineered Adeno-Associated Virus Capsids"; 62/916,221, filed on Oct. 16, 2019, entitled "Engineered Adeno-Associated Virus Capsids"; 63/018,454, filed on Apr. 30, 2020, entitled "Engineered Adeno-Associated Virus Capsids"; and 63/055,252, filed on Jul. 22, 2020, entitled "Engineered Muscle Targeting Compositions". The contents of the above-identified applications are hereby fully incorporated herein by reference in their entireties.

SEQUENCE LISTING

The contents of the electronic sequence listing ("BROD-5005US-CON4_ST26.xml"; size is 11,165,381 bytes and it was created on Nov. 14, 2025) is herein incorporated by reference in its entirety.

TECHNICAL FIELD

The subject matter disclosed herein is generally directed to muscle targeting compositions including, but not limited to, recombinant adeno-associated virus (AAV) vectors and systems thereof, compositions, and uses thereof.

BACKGROUND

Recombinant AAVs (rAAVs) are the most commonly used delivery vehicles for gene therapy and gene editing. Nonetheless, rAAVs that contain natural capsid variants have limited cell tropism. Indeed, rAAVs used today mainly infect the liver after systemic delivery. Further, the transduction efficiency of conventional rAAVs in other cell-types, tissues, and organs by these conventional rAAVs with natural capsid variants is limited. Therefore, AAV-mediated polynucleotide delivery for diseased that affect cells, tissues, and organs other than the liver (e.g. nervous system, skeletal muscle, and cardiac muscle) typically requires an injection of a large dose of virus (typically about $1\times10^{14}$ vg/kg), which often results in liver toxicity. Furthermore, because large doses are required when using conventional rAAVs, manufacturing sufficient amounts of a therapeutic rAAV needed to dose adult patients is extremely challenging. Additionally, due to differences in gene expression and physiology, mouse and primate models respond differently to viral capsids. Transduction efficiency of different virus particles varies between different species, and as a result, preclinical studies in mice often do not accurately reflect results in primates, including humans. As such, there exists a need for improved rAAVs for use in the treatment of various genetic diseases.

SUMMARY

Described in certain example embodiments herein are compositions comprising a targeting moiety effective to target a muscle cell, wherein the targeting moiety comprises an n-mer motif; and a cargo, wherein the cargo is coupled to or is otherwise associated with the targeting moiety.

In certain example embodiments, the n-mer motif comprises an RGD motif or a non-RGD n-mer motif.

In certain example embodiments, the RGD motif has a formula of XmRGDXn, wherein m is 0-4 amino acids, wherein n is 0-15 amino acids, wherein X is any amino acid, and wherein each X amino acid present is independently selected from the others from the group consisting of: any amino acid.

In certain example embodiments, the RGD motif has the formula RGDXn, wherein n is 4 or 5, wherein X is any amino acid, and wherein each X amino acid present is independently selected from the others from the group consisting of: any amino acid.

In certain example embodiments, the n-mer motif is any one of SEQ ID NO: 13-50, 1277-2493, 3737-4979, 6647-8313, 8314-8502, or 8692-8889.

In certain example embodiments, the targeting moiety comprises a polypeptide, a polynucleotide, a lipid, a polymer, a sugar, or a combination thereof.

In certain example embodiments, the targeting moiety comprises a viral protein.

In certain example embodiments, the viral protein is a capsid protein.

In certain example embodiments, the viral protein is an adeno associated virus (AAV) protein.

In certain example embodiments, the n-mer motif is located between two amino acids of the viral protein such that the n-mer motif is external to a viral capsid of which the viral capsid protein is part.

In certain example embodiments, the n-mer motif is inserted between any two contiguous amino acids between amino acids 262-269, 327-332, 382-386, 452-460, 488-505, 527-539, 545-558, 581-593, 704-714, or any combination thereof in an AAV9 capsid polypeptide or in an analogous position in an AAV1, AAV2, AAV3, AAV4, AAV5, AAV6, AAV7, AAV8, AAV rh.74, or AAV rh.10 capsid polypeptide.

In certain example embodiments, the n-mer motif is inserted between amino acids 588 and 589 in an AAV9 capsid polypeptide or in an analogous position in an AAV1, AAV2, AAV3, AAV4, AAV5, AAV6, AAV7, AAV8, AAV rh.74, or AAV rh.10 capsid polypeptide.

In certain example embodiments, the composition is an engineered viral particle.

In certain example embodiments, the engineered viral particle is an engineered AAV viral particle.

In certain example embodiments, the AAV viral particle is an engineered AAV1, AAV2, AAV3, AAV4, AAV5, AAV6, AAV7, AAV8, AAV9, AAV rh.74, or AAV rh.10 viral particle.

In certain example embodiments, the cargo is capable of treating or preventing a muscle disease or disorder.

In certain example embodiments, the muscle disease or disorder is a. an auto immune disease;
b. a cancer;
c. a muscular dystrophy;
d. a neuro-muscular disease;
e. a sugar or glycogen storage disease;
f. an expanded repeat disease;
g. a dominant negative disease;
h. a cardiomyopathy;
i. a viral disease;
j. a progeroid disease; or
k. any combination thereof.

In certain example embodiments, the cargo is a. a morpholino;

b. a peptide-linked morpholino;

c. an antisense oligonucleotide;

d. a PMO, a therapeutic transgene;

e. a polynucleotide encoding a therapeutic polypeptide or peptide;

f. a PPMO;

g. one or more peptides or polypeptides;

h. one or more polynucleotides encoding a CRISPR-Cas protein, a guide RNA, or both;

i. a ribonucleoprotein, wherein the ribonucleoprotein comprises a CRISPR-Cas system molecule;

j. a therapeutic transgene RNA, or other gene modifying or therapeutic RNA and/or protein; or k. any combination thereof.

In certain example embodiments, the cargo is capable of inducing exon skipping in a gene.

In certain example embodiments, the cargo is capable of inducing exon skipping in a dystrophin gene.

In certain example embodiments, the cargo is a mini- or micro-dystrophin gene.

In certain example embodiments, the mini- or micro-dystrophin gene comprises spectrin-like repeats 1, 1', 2, 3, 16, 17, 20, 21, 22, 23, 24, or any combination thereof, and optionally an nNOS domain, an actin binding domain, one or more hinge regions, a dystroglycan binding domain, or any combination thereof.

In certain example embodiments, the cargo is operably coupled to a muscle specific promoter.

In certain example embodiments, the expanded repeat disease is Huntington's disease, a Myotonic Dystrophy, or Facioscapulohumeral muscular dystrophy (FSHD).

In certain example embodiments, the muscular dystrophy is Duchene muscular dystrophy, Becker Muscular dystrophy, a Limb-Girdle muscular dystrophy, an Emery Dreifuss muscular dystrophy, a myotonic dystrophy, or FSHD.

In certain example embodiments, the myotonic dystrophy is a Type 1 or a Type 2 myotonic dystrophy.

In certain example embodiments, the cardiomyopathy is dilated cardiomyopathy, hypertrophic cardiomyopathy, Duchene muscular dystrophy-associated cardiomyopathy, or Dannon disease.

In certain example embodiments, the sugar or glycogen storage disease is a MPS type III disease or Pompe disease.

In certain example embodiments, the MPS type III disease, is MPS Type IIIA, IIIB, IIIC, or IIID.

In certain example embodiments, the neuro-muscular disease is Charcot-Marie-Tooth disease or Friedreich's Ataxia.

In certain example embodiments, the composition has increased muscle cell potency, muscle cell specificity, reduced immunogenicity, or any combination thereof.

Described in certain example embodiments herein are vector systems comprising a vector comprising: one or more polynucleotides each encoding all or part of one or more targeting moieties effective to target a muscle cell, wherein each targeting moiety comprises one or more n-mer motifs, wherein each n-mer motif an RGD motif or a non-RGD n-mer motif, and wherein each polynucleotide at least encodes one or more of the one or more n-mer motifs; and optionally, a regulatory element operatively coupled to one or more of the one or more polynucleotides.

In certain example embodiments, the RGD motif has a formula of $X_mRGDX_n$, wherein m is 0-4 amino acids, wherein n is 0-15 amino acids, wherein X is any amino acid, and wherein each X amino acid present is independently selected from the others from the group consisting of: any amino acid.

In certain example embodiments, the RGD motif has the formula RGDXn, wherein n is 4 or 5, wherein X is any amino acid, and wherein each X amino acid present is independently selected from the others from the group consisting of: any amino acid.

In certain example embodiments, the n-mer motif is any one of SEQ ID NO: 13-50, 1277-2493, 3737-4979, 6647-8313, 8314-8502, or 8692-8889.

In certain example embodiments, the vector system further comprises a cargo.

In certain example embodiments, the cargo is a cargo polynucleotide and is optionally coupled to one or more of the one or more polynucleotides encoding the targeting moiety, the regulatory element, or both.

In certain example embodiments, the cargo polynucleotide is present on the same vector or a different vector as the one or more polynucleotides encoding the targeting moiety.

In certain example embodiments, the vector system is capable of producing virus particles that contain the cargo.

In certain example embodiments, the vector system is capable of producing a viral capsid polypeptide comprising one or more of the targeting moieties.

In certain example embodiments, the vector system is capable of producing AAV virus particles.

In certain example embodiments, AAV viral particles are engineered AAV1, AAV2, AAV3, AAV4, AAV5, AAV6, AAV7, AAV8, AAV9, AAV rh.74, or AAV rh.10 viral particle.

In certain example embodiments, the capsid polypeptide is an engineered AAV1, AAV2, AAV3, AAV4, AAV5, AAV6, AAV7, AAV8, AAV9, AAV rh.74, AAV rh.10 capsid polypeptide.

In certain example embodiments, wherein at least one of the one or more polynucleotides encoding the n-mer motif(s) is inserted between two codons corresponding to two amino acids of the viral protein such that at least one of the n-mer motifs is external to the viral capsid.

In certain example embodiments, the two codons correspond to any two contiguous amino acids between amino acids 262-269, 327-332, 382-386, 452-460, 488-505, 527-539, 545-558, 581-593, 704-714, or any combination thereof in an AAV9 capsid polypeptide or in an analogous position in an AAV1, AAV2, AAV3, AAV4, AAV5, AAV6, AAV7, AAV8, AAV rh.74, or AAV rh.10 capsid polypeptide.

In certain example embodiments, the two codons correspond to amino acid 588 and 589 in the AAV9 capsid polynucleotide or in an analogous position in an AAV1, AAV2, AAV3, AAV4, AAV5, AAV6, AAV7, AAV8, AAV rh.74, or AAV rh.10 capsid polypeptide.

In certain example embodiments, the vector comprising the one or more polynucleotides each encoding all or part of one or more targeting moieties does not comprise splice regulatory elements.

In certain example embodiments, the vector system further comprises a polynucleotide encoding a viral rep protein.

In certain example embodiments, the viral rep protein is an AAV rep protein.

In certain example embodiments, the polynucleotide encoding the viral rep protein is on the same vector or different vector as the one or more polynucleotides each encoding all or part of one or more targeting moieties.

In certain example embodiments, the viral rep protein is operatively coupled to a regulatory element.

Described in certain example embodiments herein are polypeptides produced by expressing a vector system as described herein.

In certain example embodiments, the polypeptide is a viral polypeptide.

In certain example embodiments, the viral polypeptide is an AAV polypeptide.

Described in certain example embodiments herein are particles produced by expressing a vector system as described herein.

In certain example embodiments, the particle is a viral particle.

In certain example embodiments, the viral particle is an adeno-associated virus (AAV) particle.

In certain example embodiments, the viral particle has a muscle-specific tropism.

Described in certain example embodiments, a vector system as described herein, a polypeptide as described herein, or a particle as described herein, wherein the cargo is capable of treating or preventing a muscle disease or disorder.

In certain example embodiments, the muscle disease or disorder is a. an auto immune disease;
b. a cancer;
c. a muscular dystrophy;
d. a neuro-muscular disease;
e. a sugar or glycogen storage disease;
f. an expanded repeat disease;
g. a dominant negative disease;
h. a cardiomyopathy;
i. a viral disease;
j. a progeroid disease; or
k. any combination thereof.

In certain example embodiments, the cargo is a. a morpholino;
b. a peptide-linked morpholino;
c. an antisense oligonucleotide;
d. a PMO, a therapeutic transgene;
e. a polynucleotide encoding a therapeutic polypeptide or peptide;
f. a PPMO;
g. one or more peptides or polypeptides;
h. one or more polynucleotides encoding a CRISPR-Cas protein, a guide RNA, or both;
i. a ribonucleoprotein, wherein the ribonucleoprotein comprises a CRISPR-Cas system molecule;
j. a therapeutic transgene RNA, or other gene modifying or therapeutic RNA and/or protein; or
k. any combination thereof.

In certain example embodiments, the cargo is capable of inducing exon skipping in a gene.

In certain example embodiments, the cargo is capable of inducing exon skipping in a dystrophin gene.

In certain example embodiments, the cargo is a mini- or micro-dystrophin gene.

In certain example embodiments, the mini- or micro-dystrophin gene comprises spectrin-like repeats 1, 1', 2, 3, 16, 17, 20, 21, 22, 23, 24, or any combination thereof, and optionally an nNOS domain, an actin binding domain, one or more hinge regions, a dystroglycan binding domain, or any combination thereof.

In certain example embodiments, the expanded repeat disease is Huntington's disease, a Myotonic Dystrophy, or Facioscapulohumeral muscular dystrophy (FSHD).

In certain example embodiments, the muscular dystrophy is Duchene muscular dystrophy, Becker Muscular dystrophy, a Limb-Girdle muscular dystrophy, an Emery Dreifuss muscular dystrophy, a myotonic dystrophy, or FSHD.

In certain example embodiments, the myotonic dystrophy is Type 1 or Type 2.

In certain example embodiments, the cardiomyopathy is dilated cardiomyopathy, hypertrophic cardiomyopathy, DMD-associated cardiomyopathy, or Dannon disease.

In certain example embodiments, the sugar or glycogen storage disease is a MPS type III disease or Pompe disease.

In certain example embodiments, the MPS type III disease, is MPS Type IIIA, IIIB, IIIC, or IIID.

In certain example embodiments, the neuro-muscular disease is Charcot-Marie-Tooth disease or Friedreich's Ataxia.

In certain example embodiments, the polypeptide, the particle, or both have increased muscle cell potency, muscle cell specificity, reduced immunogenicity, or any combination thereof.

A cell comprising:

a. a composition as described herein;
b. a vector system as described herein;
c. a polypeptide as described herein;
d. a particle as described herein; or
e. a combination thereof.

In certain example embodiments, wherein the cell is prokaryotic.

In certain example embodiments, wherein the cell is eukaryotic.

A pharmaceutical formulation comprising:

a. a composition as described herein;
b. a vector system as described herein;
c. a polypeptide as described herein;
d. a particle as described herein;
e. a cell as described herein; or
f. a combination thereof; and a pharmaceutically acceptable carrier.

A method comprising:

administering, to a subject in need thereof, a a. a composition as described herein;
b. a vector system as described herein;
c. a polypeptide as described herein;
d. a particle as described herein;
e. a cell as described herein;
f. a pharmaceutical formulation as described herein; or
g. a combination thereof.

In certain example embodiments, the subject in need thereof has a muscle disease or disorder.

In certain example embodiments, the muscle disease or disorder is a. an auto immune disease;
b. a cancer;
c. a muscular dystrophy;
d. a neuro-muscular disease;
e. a sugar or glycogen storage disease;
f. an expanded repeat disease;
g. a dominant negative disease;
h. a cardiomyopathy;
i. a viral disease;
j. a progeroid disease; or
k. any combination thereof.

In certain example embodiments, the expanded repeat disease is Huntington's disease, a Myotonic Dystrophy, or Facioscapulohumeral muscular dystrophy (FSHD).

In certain example embodiments, the muscular dystrophy is Duchene muscular dystrophy, Becker Muscular dystrophy, a Limb-Girdle muscular dystrophy, an Emery Dreifuss muscular dystrophy, a myotonic dystrophy, or FSHD.

In certain example embodiments, the myotonic dystrophy is Type 1 or Type 2.

In certain example embodiments, the cardiomyopathy is dilated cardiomyopathy, hypertrophic cardiomyopathy, DMD-associated cardiomyopathy, or Dannon disease.

In certain example embodiments, the sugar or glycogen storage disease is a MPS type III disease or Pompe disease.

In certain example embodiments, the MPS type III disease, is MPS Type IIIA, IIIB, IIIC, or IIID.

In certain example embodiments, the neuro-muscular disease is Charcot-Marie-Tooth disease or Friedreich's Ataxia.

These and other embodiments, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 8) that can be used in an AAV vector system to generate an AAV capsid variant library.

FIGS. 20A-20C show tables that can demonstrate selection in different strains of mice identifies the same variants as the top muscle-tropic hits.

Figure 1:
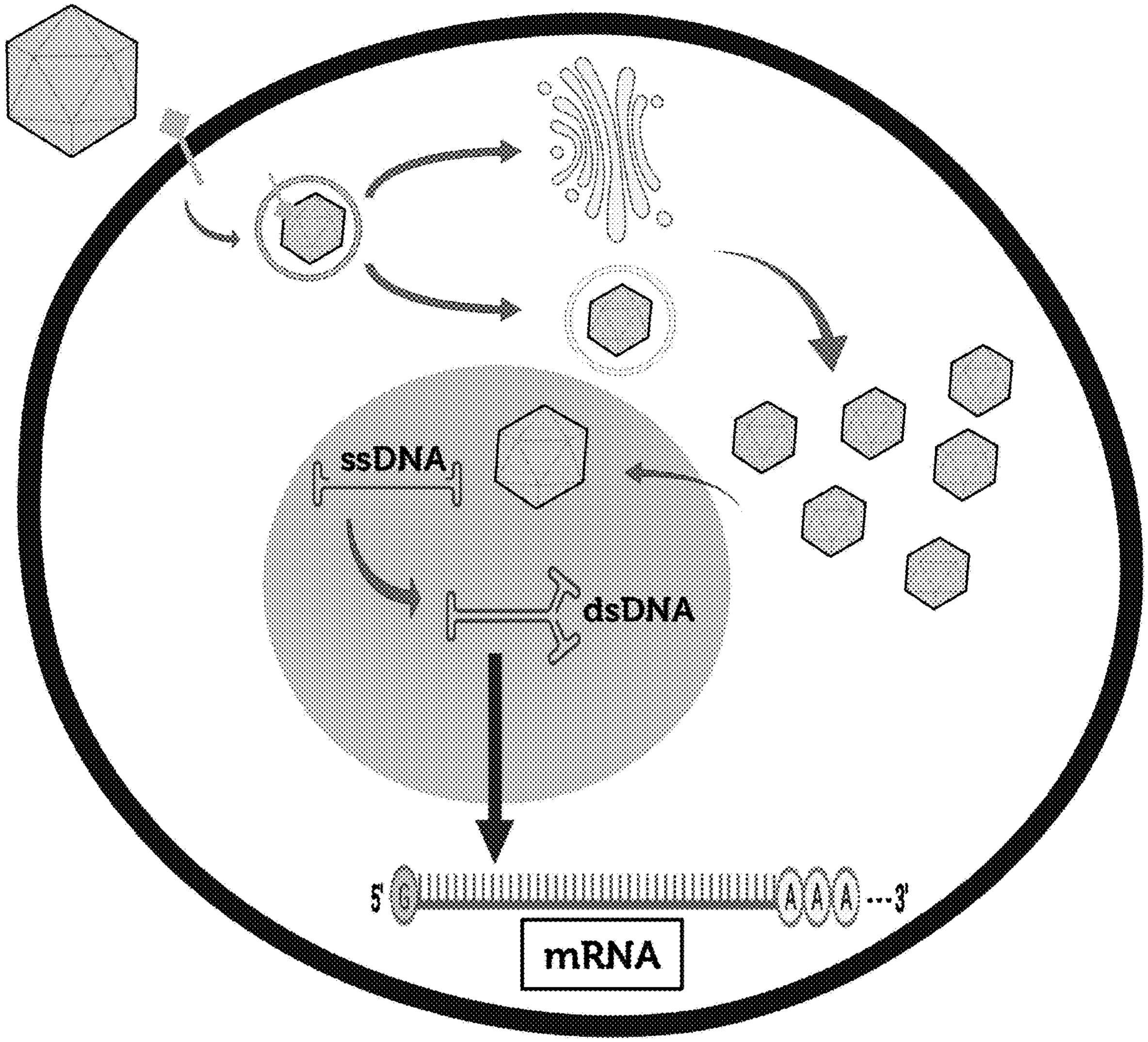
FIG. 1 demonstrates the adeno-associated virus (AAV) transduction mechanism, which results in production of mRNA from the transgene.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further embodiment. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range. Where a range is expressed, a further embodiment includes from the one particular value and/or to the other particular value.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', 'less than y', and 'less than z'. Likewise, the phrase 'about x, y, z, or greater' should be interpreted to include the specific ranges of 'about x', 'about y', and 'about z' as well as the ranges of 'greater than x', 'greater than y', and 'greater than z'. In addition, the phrase "about 'x' to 'y'", where 'x' and 'y' are numerical values, includes "about 'x' to about 'y'".

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader embodiments discussed herein. One embodiment described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to U.S. Provisional Application No. 62/899,453 and International Application No. PCT/US20/50534.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide muscle-specific targeting moieties that can be coupled to or otherwise associated with a cargo. Embodiments disclosed herein provide polypeptides and particles that can incorporate one or more of the muscle-specific targeting moieties. The polypeptides and/or particles can be coupled to, attached to, encapsulate, or otherwise incorporate a cargo, thereby associating the cargo with the targeting moiety(ies).

Embodiments disclosed herein provide muscle-specific targeting moieties that can contain one or more of an n-mer motif as further described herein, an RGD motif as further described herein, or both. In some embodiments, the n-mer motif and/or the RGD motif can confer muscle-specificity of the targeting moiety.

Embodiments disclosed herein provide engineered adeno-associated virus (AAV) capsids that can be engineered to confer cell-specific and/or species-specific tropism to an engineered AAV particle.

Embodiments disclosed herein also provide methods of generating the rAAVs having engineered capsids that can involve systematically directing the generation of diverse libraries of variants of modified surface structures, such as variant capsid proteins. Embodiments of the method of generating rAAVs having engineered capsids can also include stringent selection of capsid variants capable of targeting a specific cell, tissue, and/or organ type. Embodiments of the method of generating rAAVs having engineered capsids can include stringent selection of capsid variants capable of efficient and/or homogenous transduction in at least two or more species.

Embodiments disclosed herein provide vectors and systems thereof capable of producing an engineered AAV described herein.

Embodiments disclosed herein provide cells that can be capable of producing the engineered AAV particles described herein. In some embodiments, the cells include one or more vectors or system thereof described herein.

Embodiments disclosed herein provide engineered AAVs that can include an engineered capsid described herein. In some embodiments, the engineered AAV can include a cargo polynucleotide to be delivered to a cell. In some embodiments, the cargo polynucleotide is a gene modification polynucleotide.

Embodiments disclosed herein provide formulations that can contain an engineered AAV vector or system thereof, an engineered AAV capsid, engineered AAV particles including an engineered AAV capsid described herein, and/or an engineered cell described herein that contains an engineered AAV capsid, and/or an engineered AAV vector or system thereof. In some embodiments, the formulation can also include a pharmaceutically acceptable carrier. The formulations described herein can be delivered to a subject in need thereof or a cell.

Embodiments disclosed herein also provide kits that contain one or more of the one or more of the polypeptides, polynucleotides, vectors, engineered AAV capsids, engineered AAV particles, cells, or other components described herein and combinations thereof and pharmaceutical formulations described herein. In embodiments, one or more of the polypeptides, polynucleotides, vectors, engineered AAV capsids, engineered AAV particles cells, and combinations thereof described herein can be presented as a combination kit.

Embodiments disclosed herein provide methods of using the engineered AAVs having a cell-specific tropism described herein to deliver, for example, a therapeutic polynucleotide to a cell. In this way, the engineered AAVs described herein can be used to treat and/or prevent a disease in a subject in need thereof. Embodiments disclosed herein also provide methods of delivering the engineered AAV capsids, engineered AAV virus particles, engineered AAV vectors or systems thereof and/or formulations thereof to a cell. Also provided herein are methods of treating a subject in need thereof by delivering an engineered AAV particle, engineered AAV capsid, engineered AAV capsid vector or system thereof, an engineered cell, and/or formulation thereof to the subject.

Additional features and advantages of the embodiments engineered AAVs and methods of making and using the engineered AAVs are further described herein.

Muscle-Specific Targeting Moieties and Compositions Thereof

Described herein are targeting moieties that are capable of specifically targeting, binding, associating with, or otherwise interact specifically with a muscle cell. N-mer motifs are short peptide motifs that can confer cell and/or tissue type-targeting capabilities to another molecule, such as a cargo, to which it is incorporated, coupled to, attached, or otherwise associated with. In one example embodiment, the n-mer motif is incorporated into a viral capsid such that it is expressed on the capsid surface and confers tissue-specific targeting capability to the viral particle to facilitate tissue-specific delivery of viral particle and any optional cargo contained therein. In certain example embodiments, the n-mer motif is about 1-20 amino acids, such as 1, 2, 3, 4, 5, 6, 7, 8, 9, 10, 11, 12, 13, 14, 15, 16, 17, 18, 19, or 20 amino acids long. The term n-mer motif encompasses both n-mer motifs that have an RGD motif and those that do not (referred to herein as "non-RGD n-mer motifs"). In some example embodiments, the n-mer motif confers muscle cell/tissue specificity. In some example embodiments, the n-mer motif that confers muscle cell/tissue specificity is an RGD motif. In some example embodiments, the n-mer motif that confers muscle cell/tissue specificity is a non-RGD n-mer motif.

In some embodiments, the targeting moiety is or includes one or more n-mer motifs, where each of the one or more n-mer motifs is independently selected from an RGD motif or a non-RGD n-mer motif. N-mer motifs, RGD motifs and non-RGD n-mer motifs are described in greater detail elsewhere herein. In some embodiments, the targeting moiety includes more than one n-mer motifs, where each of the more than one n-mer motifs is independently selected from an RGD motif or a non-RGD n-mer motif. In some embodiments, the targeting moiety can include 1, 2, 3, 4, 5, 6, 7, 8, 9 10 or more n-mer motifs, where each n-mer motif is independently selected from an RGD motif or a non-RGD n-mer motif. In some embodiments, all the n-mer motifs included in the targeting moiety can be the same (i.e. have the same amino acid sequence). In some embodiments where more than one n-mer motif is included, at least two of the n-mer motifs are different from each other (i.e. have a different amino acid sequence). In some embodiments where more than one n-mer motif is included, all the n-mer motifs are different from each other. In some embodiments, each n-mer motif included in the targeting moiety can be any one of those set forth in any of Tables 1-6 and 8-9, which correspond to SEQ ID NOs: 13-50, 1277-2493, 3737-4979, 6647-8313, 8314-8502, or 8692-8889.

TABLE 1

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 1 | AGGGGTGATCTTTCTACGCCT | 60 | RGDLSTP | 1277 | 715.366 |
| 2 | AGGGGCGACCTGAACCAATAC | 61 | RGDLNQY | 1278 | 712.149 |
| 3 | CGGGGTGATCTTACTACGCCT | 62 | RGDLTTP | 1279 | 461.536 |
| 4 | AGGGGGGATGCGACGGAGCTT | 63 | RGDATEL | 1280 | 452.77 |
| 5 | CGGGGTGATCAGCTTTATCAT | 64 | RGDQLYH | 1281 | 444.505 |
| 6 | AGAGGCGACTTATCCACACCC | 65 | RGDLSTP | 1282 | 411.692 |
| 7 | CGTGGTGATGTGGCGGCTAAG | 66 | RGDVAAK | 1283 | 371.7 |
| 8 | AGAGGAGACTTGACAACCCCA | 67 | RGDLTTP | 1284 | 361.486 |
| 9 | CGGGGTGATCTTAATCAGTAT | 68 | RGDLNQY | 1285 | 342.712 |
| 10 | CGAGGAGACACCATGAGCAAA | 69 | RGDTMSK | 1286 | 325.632 |
| 11 | CGCGGAGACGTAGCCGCCAAA | 70 | RGDVAAK | 1287 | 315.01 |
| 12 | CGGGGGGATACTATGTCTAAG | 71 | RGDTMSK | 1288 | 309.567 |
| 13 | CGGGGTGACGCAACAGAATTG | 72 | RGDATEL | 1289 | 306.99 |
| 14 | GCACGGTCAAACGACTCGGTC | 73 | ARSNDSV | 1290 | 293.22 |
| 15 | CGGGGTGACATGAACAACTCA | 74 | RGDMNNS | 1291 | 268.677 |
| 16 | ACGATGGGTGCTAATGGTACT | 75 | TMGANGT | 1292 | 260.853 |
| 17 | CCTAATGTTACGCAGTCTTAT | 76 | PNVTQSY | 1293 | 259.718 |
| 18 | CGTTTGGACCTGCAAGTCCAC | 77 | RLDLQVH | 1294 | 257.65 |
| 19 | GGGCTTTCTAAGGCGTCTGAT | 78 | GLSKASD | 1295 | 255.938 |
| 20 | GATCCTGGTCGGACGGGTACG | 79 | DPGRTGT | 1296 | 253.325 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 21 | TATCGGGGTAGGGAGGATTGG | 80 | YRGREDW | 1297 | 244.83 |
| 22 | AGATACGGAGAATCCATCGAA | 81 | RYGESIE | 1298 | 231.696 |
| 23 | AGTCTGAACAACATGGGATCG | 82 | SLNNMGS | 1299 | 229.6044 |
| 24 | AATAGTGATCAGCGGAATTGG | 83 | NSDQRNW | 1300 | 229.031 |
| 25 | CGTGGTGATATGTCTCGTGAG | 84 | RGDMSRE | 1301 | 227.081 |
| 26 | ATGACTGATGCGAATAGGATT | 85 | MTDANRI | 1302 | 226.194 |
| 27 | GTCTACAACGGCAACGTAGTA | 86 | VYNGNVV | 1303 | 223.663 |
| 28 | CGTGGGGATATGATTAATACG | 87 | RGDMINT | 1304 | 223.46 |
| 29 | AGTGGTCTTTCGCATGGTCAG | 88 | SGLSHGQ | 1305 | 221.726 |
| 30 | ACTGGCCAATTAGTAGGAACC | 89 | TGQLVGT | 1306 | 221.181 |
| 31 | GCTAATTCTATTGGGGGTCCG | 90 | ANSIGGP | 1307 | 220.304 |
| 32 | TACAGTCAATCGCTGTCTGAA | 91 | YSQSLSE | 1308 | 220.02 |
| 33 | TATCATAAGTATAGTACGGAT | 92 | YHKYSTD | 1309 | 217.64 |
| 34 | GCTCGTCATGATGAGCATGTG | 93 | ARHDEHV | 1310 | 217 |
| 35 | GCCATAGACTCTATCAAACAA | 94 | AIDSIKQ | 1311 | 216.071 |
| 36 | CGTTTGGACCTGCAAGTCAAC | 95 | RLDLQVN | 1312 | 215 |
| 37 | CGCGGCGACATGATAAACACC | 96 | RGDMINT | 1313 | 214.271 |
| 38 | AGTGTGTTGTCTCAGGCTAAT | 97 | SVLSQAN | 1314 | 213.907 |
| 39 | TTTACGGTGAATCAGGATCTT | 98 | FTVNQDL | 1315 | 213.78 |
| 40 | ACGGATAATGGTCTTCTTGTG | 99 | TDNGLLV | 1316 | 211.787 |
| 41 | TATCAGCAGACTTCTAGTACG | 100 | YQQTSST | 1317 | 211.386 |
| 42 | ACAGAACAATCTTACTCACGA | 101 | TEQSYSR | 1318 | 210.762 |
| 43 | ATTATGGGGCTTAGTCAGGCT | 102 | IMGLSQA | 1319 | 208.157 |
| 44 | GCTACTGCGCATCAGGATGGT | 103 | ATAHQDG | 1320 | 207.212 |
| 45 | TATAATGCTACTCCTTCGCAG | 104 | YNATPSQ | 1321 | 206.964 |
| 46 | TATACGCAGGGTATTATGAAT | 105 | YTQGIMN | 1322 | 206.672 |
| 47 | GAATCCCTCCCAATCTCTAAA | 106 | ESLPISK | 1323 | 206.576 |
| 48 | GGCACCGTCGTTCCGGGCTCC | 107 | GTVVPGS | 1324 | 206.111 |
| 49 | GGATTAGCTAGTCTACACCTG | 108 | GLASLHL | 1325 | 204.394 |
| 50 | TATATTGCTGCGGGTGAGCAG | 109 | YIAAGEQ | 1326 | 204.24 |
| 51 | AACACCTACCCCTTCAACGCC | 110 | NTYPFNA | 1327 | 203.931 |
| 52 | GTTGGTGCGAGTACGGCTTCG | 111 | VGASTAS | 1328 | 202.92 |
| 53 | GGATCCAACTACTTAGCAAAC | 112 | GSNYLAN | 1329 | 202.857 |
| 54 | GATACTGGTCGGACGGGTACG | 113 | DTGRTGT | 1330 | 202.83 |
| 55 | AAGCCGAATACGATGAGTGAT | 114 | KPNTMSD | 1331 | 202.7282 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 56 | GTAGACAAATCTAGCCCAGTG | 115 | VDKSSPV | 1332 | 201.849 |
| 57 | AGTTCGGACCCAAAAGGTCAA | 116 | SSDPKGQ | 1333 | 201.825 |
| 58 | TGGCAGACGAATGGTATGCAG | 117 | WQTNGMQ | 1334 | 201.6943 |
| 59 | ACCGGTAGCTTGAACTCTATG | 118 | TGSLNSM | 1335 | 201.671 |
| 60 | CATTCTAATTCGAGTCAGAAT | 119 | HSNSSQN | 1336 | 200.954 |
| 61 | GGCCGTGACGACCTCACAAAC | 120 | GRDDLTN | 1337 | 200.911 |
| 62 | GATACTTATAAGGGTAAGTGG | 121 | DTYKGKW | 1338 | 200.7787 |
| 63 | TATACGGCGCAGACCGGCTGG | 122 | YTAQTGW | 1339 | 200 |
| 64 | AATCAGGTGGGTGCGTCTGCG | 123 | NQVGASA | 1340 | 200 |
| 65 | ATCGACGTACTGAACGGAAGT | 124 | IDVLNGS | 1341 | 200 |
| 66 | TTTCGGACGGTGTATACTGGT | 125 | FRTVYTG | 1342 | 200 |
| 67 | GGAAACATGGTGACTCCAAAC | 126 | GNMVTPN | 1343 | 200 |
| 68 | GATACTTATAACGGTAAGTGG | 127 | DTYNGKW | 1344 | 200 |
| 69 | ACCATCCAAGACCACATAAAA | 128 | TIQDHIK | 1345 | 200 |
| 70 | GGAGCAAAAGGAACCATGGGC | 129 | GAKGTMG | 1346 | 200 |
| 71 | ACGAGGAGCAACTCCGACGAA | 130 | TRSNSDE | 1347 | 200 |
| 72 | GCTACTACTCTTACTGGTGAT | 131 | ATTLTGD | 1348 | 200 |
| 73 | TCATACGGAGGATCTGGCCCC | 132 | SYGGSGP | 1349 | 198.715 |
| 74 | GAAAAATCCGTCGAATCCAAA | 133 | EKSVESK | 1350 | 196.418 |
| 75 | CGAGGCGACACAATGAACTAC | 134 | RGDTMNY | 1351 | 195.3082 |
| 76 | CGGGATCTGGGGCAGACCGGC | 135 | RDLGQTG | 1352 | 194.34 |
| 77 | AGTCCGCAGCTGAGTGTGATG | 136 | SPQLSVM | 1353 | 194.21 |
| 78 | CGAGGAGACAACAGCACACCG | 137 | RGDNSTP | 1354 | 193.05 |
| 79 | CCTATGGCAGGACACCCCCCG | 138 | PMAGHPP | 1355 | 192.726 |
| 80 | ACGGCGTATCAGGCTGGTCTG | 139 | TAYQAGL | 1356 | 191.778 |
| 81 | GTGGTAAACCAAGGAAACCAA | 140 | VVNQGNQ | 1357 | 191.737 |
| 82 | GATAAGACTGAGATGCTGCAG | 141 | DKTEMLQ | 1358 | 191.13 |
| 83 | ACTGTGATGATGAGTACGAGG | 142 | TVMMSTR | 1359 | 191.063 |
| 84 | CAGCAGAATACGCGTTTGCCG | 143 | QQNTRLP | 1360 | 190.1825 |
| 85 | TACCAACACAACCAAGCCCAC | 144 | YQHNQAH | 1361 | 189.595 |
| 86 | AATCAGAGTATTAATAATATT | 145 | NQSINNI | 1362 | 188.654 |
| 87 | CGAGGAGACCACAGCACACCG | 146 | RGDHSTP | 1363 | 187.365 |
| 88 | GACTCTACACTTCACTTAAGT | 147 | DSTLHLS | 1364 | 187.36 |
| 89 | GCGAACATAGAAAACACGTCA | 148 | ANIENTS | 1365 | 187.03 |
| 90 | ACAAACGCTGCTCTAGTACCA | 149 | TNAALVP | 1366 | 185.9743 |
| 91 | GGGCAGAAGGAGACTACTGCG | 150 | GQKETTA | 1367 | 184.457 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 92 | GAACTTAACACCGCACACGCA | 151 | ELNTAHA | 1368 | 184.059 |
| 93 | GGTGTTAGTAGTAATTCTGCG | 152 | GVSSNSA | 1369 | 183.964 |
| 94 | AGCACAAACGCGGGACAAAGG | 153 | STNAGQR | 1370 | 183.571 |
| 95 | GAACAACAAAAAACAGACAAC | 154 | EQQKTDN | 1371 | 182.331 |
| 96 | GCTGTTGTGAATGAGAATATG | 155 | AVVNENM | 1372 | 182.3 |
| 97 | GGCAGCGTCAGCACCAGCGCA | 156 | GSVSTSA | 1373 | 181.451 |
| 98 | GAGTTGGGTAGTCAGCGTATG | 157 | ELGSQRM | 1374 | 181.36 |
| 99 | AGAGGCGACTTATCCACACAC | 158 | RGDLSTH | 1375 | 181.15 |
| 100 | GACCACCAACAAGCCCTAGCT | 159 | DHQQALA | 1376 | 180.295 |
| 101 | AACAGATCTGACGCTCACGAA | 160 | NRSDAHE | 1377 | 180.265 |
| 102 | AATGTTAATGCGCAGAGTAGG | 161 | NVNAQSR | 1378 | 179.918 |
| 103 | ACCCAAGGGAACAACATGGTA | 162 | TQGNNMV | 1379 | 179.575 |
| 104 | ACGGCGCTGAATACGTATCCT | 163 | TALNTYP | 1380 | 179.568 |
| 105 | GTCTCTACATACCTCCTGGCA | 164 | VSTYLLA | 1381 | 179.172 |
| 106 | GGCGGCAACTACAACACAACT | 165 | GGNYNTT | 1382 | 178.62 |
| 107 | AGTAATATTAAGCCGGAGATT | 166 | SNIKPEI | 1383 | 178.567 |
| 108 | CCGAGGGTGCATGGTCAGGTT | 167 | PRVHGQV | 1384 | 178.479 |
| 109 | TCTAATTCTAATACTGCTGCT | 168 | SNSNTAA | 1385 | 178.119 |
| 110 | CTTGAGGTGGCGACGAGTCCG | 169 | LEVATSP | 1386 | 177.75 |
| 111 | CACGACGCCGACAAATTAGCT | 170 | HDADKLA | 1387 | 177.05 |
| 112 | GGTGTGTATATTGATGGTCGG | 171 | GVYIDGR | 1388 | 176.229 |
| 113 | TCGATGCAGTCGTATACGATG | 172 | SMQSYTM | 1389 | 175.538 |
| 114 | TCTAAAGGAAACGAACAAATG | 173 | SKGNEQM | 1390 | 175.311 |
| 115 | GGTCGGGATTATGCTATGAGT | 174 | GRDYAMS | 1391 | 174.17 |
| 116 | ACTGATGGTATTTTTCAGCCT | 175 | TDGIFQP | 1392 | 174.014 |
| 117 | GGGAGCCCAGTGATAGTAAAC | 176 | GSPVIVN | 1393 | 173.652 |
| 118 | ACATTAACAGACGTTCACCGA | 177 | TLTDVHR | 1394 | 172.837 |
| 119 | AAAAGCGAAGTACCCGCCCGA | 178 | KSEVPAR | 1395 | 172.72 |
| 120 | GTCAACACTGGCGCACTCTTG | 179 | VNTGALL | 1396 | 172.648 |
| 121 | AGTCAGCAGGGTTTTACTCTG | 180 | SQQGFTL | 1397 | 172.124 |
| 122 | AATAATAAGTCTGTGCCGGAT | 181 | NNKSVPD | 1398 | 172.0753 |
| 123 | AGTGTGATGGTGGGTACGAAT | 182 | SVMVGTN | 1399 | 171.86 |
| 124 | CGAAACGAAAACACTTACAAC | 183 | RNENTYN | 1400 | 170.674 |
| 125 | CAAGCTAACTTATCAATAATC | 184 | QANLSII | 1401 | 170.5862 |
| 126 | CCCGGACGGGACAGCAGAACG | 185 | PGRDSRT | 1402 | 169.875 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 127 | TTTCCGGCTAATGGTGGTGCT | 186 | FPANGGA | 1403 | 169.639 |
| 128 | GCTGGTAAGGATCTTAGTAAT | 187 | AGKDLSN | 1404 | 169.592 |
| 129 | GCACAATTCGAATCAGGCCGA | 188 | AQFESGR | 1405 | 169.281 |
| 130 | GGATACGGCAGTTACAGCAAC | 189 | GYGSYSN | 1406 | 169.247 |
| 131 | ACAATCGTTTCCGCTTACGCC | 190 | TIVSAYA | 1407 | 168.87 |
| 132 | AATGTGAGTCCTAATTTGACT | 191 | NVSPNLT | 1408 | 168.739 |
| 133 | AGAGGCGACTTATCAACACCC | 192 | RGDLSTP | 1409 | 167.66 |
| 134 | TTCTTAGAAGGAGTCGCTCAA | 193 | FLEGVAQ | 1410 | 167.647 |
| 135 | GGCTCCGAACGAGGAGAACGA | 194 | GSERGER | 1411 | 167.585 |
| 136 | TTGAATGTTGGTTCGAGTCTT | 195 | LNVGSSL | 1412 | 167.104 |
| 137 | CGTATTGTGGCTAATGAGCAG | 196 | RIVANEQ | 1413 | 166.96 |
| 138 | CAATCTATCGGCCACCCCGTT | 197 | QSIGHPV | 1414 | 166.7759 |
| 139 | GGTGGTATGTCGGCGCATTCG | 198 | GGMSAHS | 1415 | 166.775 |
| 140 | CATTCTACGACGTCTATGACG | 199 | HSTTSMT | 1416 | 166.711 |
| 141 | ACTGTAAACGGTACGAACGTA | 200 | TVNGTNV | 1417 | 166.64 |
| 142 | CTTGCGCCTGATAATATTGGG | 201 | LAPDNIG | 1418 | 166.005 |
| 143 | CAAACAGCGACTCTCGTGGCA | 202 | QTATLVA | 1419 | 165.921 |
| 144 | GCATCAGCACCGTCTGAATTC | 203 | ASAPSEF | 1420 | 165.64 |
| 145 | TCGATGGAGGGTCAGCAGCAT | 204 | SMEGQQH | 1421 | 165.62 |
| 146 | CAAGACGTAGGACGCACGAAC | 205 | QDVGRTN | 1422 | 164.147 |
| 147 | GTCTACAACGGCAACGAAGTA | 206 | VYNGNEV | 1423 | 164.11 |
| 148 | GCACAGGCGCAGACAGGCTGG | 207 | AQAQTGW | 1424 | 163.93 |
| 149 | CGGCTGGATCTGACGCATACG | 208 | RLDLTHT | 1425 | 163.75 |
| 150 | GCTGCACACGGCCGCGAACAA | 209 | AAHGREQ | 1426 | 163.577 |
| 151 | AGAGGCGACTTATACACACCC | 210 | RGDLYTP | 1427 | 163.43 |
| 152 | GGTATGCAGCAGAGGGAGAAG | 211 | GMQQREK | 1428 | 163.075 |
| 153 | CAGACTCAGGCGAGTACTAAT | 212 | QTQASTN | 1429 | 161.336 |
| 154 | CGGGACACCAACGCCCTCGGA | 213 | RDTNALG | 1430 | 161.225 |
| 155 | TCGAGTCAGATTTCTAATAGT | 214 | SSQISNS | 1431 | 161.063 |
| 156 | CAGTCGGTTAATAGTACGAGT | 215 | QSVNSTS | 1432 | 160.873 |
| 157 | GCTCTGGAGAGGGCTCAGTAT | 216 | ALERAQY | 1433 | 160.837 |
| 158 | CATACTGGGCATAGTTCTGTG | 217 | HTGHSSV | 1434 | 160.068 |
| 159 | CGGGGAGACATGACCCGAGCA | 218 | RGDMTRA | 1435 | 159.605 |
| 160 | TTTCAGCGTGATCTTGGGCAT | 219 | FQRDLGH | 1436 | 159.442 |
| 161 | ACAACCGGCGACATAATACGC | 220 | TTGDIIR | 1437 | 159.11 |
| 162 | TCTTTTCAGACGGATCGTGCG | 221 | SFQTDRA | 1438 | 159.04 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 163 | CAATCCAGCGACGGCCGAGTG | 222 | QSSDGRV | 1439 | 158.634 |
| 164 | ACTTCTGGGGCTTTGACCCGG | 223 | TSGALTR | 1440 | 158.32 |
| 165 | AATTCGAATACTGTGAATACG | 224 | NSNTVNT | 1441 | 157.71 |
| 166 | ATCTCCGGTAGTAGCAGTCTA | 225 | ISGSSSL | 1442 | 157.64 |
| 167 | AACGACAAATCAACCAACGTA | 226 | NDKSTNV | 1443 | 157.594 |
| 168 | ATCGTACTTGCTCCCACATCG | 227 | IVLAPTS | 1444 | 157.48 |
| 169 | TCAGGCGTCAACTACGGTGTC | 228 | SGVNYGV | 1445 | 157.321 |
| 170 | GTCGGCGCCCAACGGGACCCC | 229 | VGAQRDP | 1446 | 157.055 |
| 171 | ACGGGTATGAATAGTAATAAG | 230 | TGMNSNK | 1447 | 156.85 |
| 172 | ATCGAAGCCTACTCACGAGAC | 231 | IEAYSRD | 1448 | 156.774 |
| 173 | TTACACACAACACTAATGCCC | 232 | LHTTLMF | 1449 | 156.364 |
| 174 | TCTGATAATCATCTGAAGACT | 233 | SDNHLKT | 1450 | 156.334 |
| 175 | CGAAACGAAGACAAAGGAGGA | 234 | RNEDKGG | 1451 | 156.027 |
| 176 | ACGAAGGGTGCTAATGGTACT | 235 | TKGANGT | 1452 | 155.56 |
| 177 | GTCTACAACGGCAACGTAGAA | 236 | VYNGNVE | 1453 | 155.56 |
| 178 | TCAAACAGCGGAGGCAACCAC | 237 | SNSGGNH | 1454 | 155.294 |
| 179 | GTAGCCGCGGGACCAGAAGCG | 238 | VAAGPEA | 1455 | 154.25 |
| 180 | ACGTCTCTTAGTGGTAGTGCG | 239 | TSLSGSA | 1456 | 153.988 |
| 181 | GTTGGGCTGCAGAGTAATACT | 240 | VGLQSNT | 1457 | 153.453 |
| 182 | CACACCGCCCACAGCGTGGAC | 241 | HTAHSVD | 1458 | 153.3866 |
| 183 | AACGTGGGAATGAGCTCAACC | 242 | NVGMSST | 1459 | 153.212 |
| 184 | CATGCGGATGTGAATGCTGGG | 243 | HADVNAG | 1460 | 153.21 |
| 185 | AAAGCGGGACAACTAGTGGAA | 244 | KAGQLVE | 1461 | 153.178 |
| 186 | AGTACTTTTAGTGTGCTGCCT | 245 | STFSVLP | 1462 | 153.09 |
| 187 | CCTCAGTCTCCGAGTCGGGTT | 246 | PQSPSRV | 1463 | 152.823 |
| 188 | CACACCGCCACCCTTAGCAGC | 247 | HTATLSS | 1464 | 152.8 |
| 189 | CTTCCGCGTCATGATCAGTAT | 248 | LPRHDQY | 1465 | 152.412 |
| 190 | CAAGTGAACAACCCACTCACA | 249 | QVNNPLT | 1466 | 151.574 |
| 191 | ACAACAGAAACCGCACGAGGT | 250 | TTETARG | 1467 | 151.4255 |
| 192 | GTTCATGGGACGTTGACTTAT | 251 | VHGTLTY | 1468 | 150.654 |
| 193 | TATAGTACTGATCTTAGGATG | 252 | YSTDLRM | 1469 | 150.626 |
| 194 | GCACACGCTACCTCAAGCACT | 253 | AHATSST | 1470 | 150.587 |
| 195 | AGGGAGAGTGCTGCTCTGGCG | 254 | RESAALA | 1471 | 150.506 |
| 196 | AAGGATACTAATCAGCAGATT | 255 | KDTNQQI | 1472 | 150.189 |
| 197 | AGTATGCAATCATACACCATG | 256 | SMQSYTM | 1473 | 148.994 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 198 | ACAGCCTACTCGCCCACAGTC | 257 | TAYSPTV | 1474 | 148.946 |
| 199 | GAATCTGCCCACCAAAGAATA | 258 | ESAHQRI | 1475 | 148.867 |
| 200 | AGATACACAACAGCACAACAA | 259 | RYTTAQQ | 1476 | 148.802 |
| 201 | ACGTCTGTGGCGAATGTGAGT | 260 | TSVANVS | 1477 | 148.731 |
| 202 | AGGGATCAGCATACTTCTATT | 261 | RDQHTSI | 1478 | 148.687 |
| 203 | TCTGTTACGTCTTCTGGTCCG | 262 | SVTSSGP | 1479 | 148.574 |
| 204 | GCGGTTGTTCTGAATAGTAAT | 263 | AVVLNSN | 1480 | 148.476 |
| 205 | CCTGGGAATCCGTCTAGTAAT | 264 | PGNPSSN | 1481 | 147.792 |
| 206 | ACGGGGTCTACTACTCAGCTT | 265 | TGSTTQL | 1482 | 147.767 |
| 207 | GCTAATGAGCATAATGTGGGT | 266 | ANEHNVG | 1483 | 147.569 |
| 208 | ATGCAAAGAGAAGCAGCCAAC | 267 | MQREAAN | 1484 | 147.562 |
| 209 | TTAACCGACACAAACACCCGG | 268 | LTDTNTR | 1485 | 147.306 |
| 210 | CGAATGACCGAAATATCATAC | 269 | RMTEISY | 1486 | 146.933 |
| 211 | AAAGTGGACATGACCTCCAAA | 270 | KVDMTSK | 1487 | 146.392 |
| 212 | AGAGGAGACTTATCCACACCC | 271 | RGDLSTP | 1488 | 146.3 |
| 213 | CAAGCAAAAGCTAGCACAACT | 272 | QAKASTT | 1489 | 146.214 |
| 214 | CTACCCTCAACAGAAACTTTG | 273 | LPSTETL | 1490 | 145.892 |
| 215 | AGTAGTGCGCTTAATGCGTAT | 274 | SSALNAY | 1491 | 145.667 |
| 216 | TCGTCTGATCCTAAGGGGCAG | 275 | SSDPKGQ | 1492 | 145.644 |
| 217 | TTAGACGTGACGAGAATGAGA | 276 | LDVTRMR | 1493 | 145.51 |
| 218 | GCGGATGGTGGTGATAAGGGG | 277 | ADGGDKG | 1494 | 145.45 |
| 219 | ATGCTGTCTCAGGTTACGTTG | 278 | MLSQVTL | 1495 | 145.32 |
| 220 | AGTGTTAGTTCTGTGGTGTTG | 279 | SVSSVVL | 1496 | 145.202 |
| 221 | ACCGAATCGCAAACCATGAGG | 280 | TESQTMR | 1497 | 145.0149 |
| 222 | TTCGGATCCCAAGAAAAACTC | 281 | FGSQEKL | 1498 | 144.467 |
| 223 | ACAGCCGGCGGCGAACGCGCC | 282 | TAGGERA | 1499 | 144.445 |
| 224 | GATCATAGTAAGCAGAGTTCG | 283 | DHSKQSS | 1500 | 144.0179 |
| 225 | ATTGATAGTACTTGGAATACG | 284 | IDSTWNT | 1501 | 143.92 |
| 226 | TCGCCTCGCCCCGAACTCCGA | 285 | SPRPELR | 1502 | 143.362 |
| 227 | AGTATTGCGACTGCTACTAGT | 286 | SIATATS | 1503 | 143.312 |
| 228 | GTAATAGGCGGACACGGGACT | 287 | VIGGHGT | 1504 | 143.136 |
| 229 | AGCACCGCCATGTACCCCCAC | 288 | STAMYPH | 1505 | 142.798 |
| 230 | CGGGACTTGAGACCCGTGACG | 289 | RDLRPVT | 1506 | 142.461 |
| 231 | GCTCATCTGACTGATCTTCCG | 290 | AHLTDLP | 1507 | 142.37 |
| 232 | TTTCTGAATAGTACGCAGCTT | 291 | FLNSTQL | 1508 | 142.276 |
| 233 | TTAAACAACAGTGCCACAGTC | 292 | LNNSATV | 1509 | 142.021 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 234 | GATCGTCCGAATAATATGACG | 293 | DRPNNMT | 1510 | 141.945 |
| 235 | TCATCGTCAGACTCACCCAGA | 294 | SSSDSPR | 1511 | 141.849 |
| 236 | CGCTTGGACGTTGGAAGCCCG | 295 | RLDVGSP | 1512 | 141.82 |
| 237 | GCGCAGCAGAGTCTTCATGGT | 296 | AQQSLHG | 1513 | 141.401 |
| 238 | ATGGGGAAGCATGAGGGTCTT | 297 | MGKHEGL | 1514 | 141.2916 |
| 239 | GAGAATGCTCGTGAGGGTGTG | 298 | ENAREGV | 1515 | 140.87 |
| 240 | ACCGTATCTCTCTCGGAAGGC | 299 | TVSLSEG | 1516 | 140.529 |
| 241 | CTTAACACACTAATCGACCGG | 300 | LNTLIDR | 1517 | 140.256 |
| 242 | GAACTCTCCGTTCCGAAACCA | 301 | ELSVPKP | 1518 | 140.203 |
| 243 | AAAGACAAAAACGTATACATA | 302 | KDKNVYI | 1519 | 140.171 |
| 244 | AATGCGAATGGGCCTGTGAGT | 303 | NANGPVS | 1520 | 140.158 |
| 245 | CTTACTACGAATGGTATGCTG | 304 | LTTNGML | 1521 | 140.147 |
| 246 | GCCGGCGAATCTTCACCCACA | 305 | AGESSPT | 1522 | 139.95 |
| 247 | AGTGGGATTGGTACTTATTCT | 306 | SGIGTYS | 1523 | 139.76 |
| 248 | GTCAGATCTATGGACGAATTG | 307 | VRSMDEL | 1524 | 139.74 |
| 249 | ATGAACACCGGCTCTTCGAGT | 308 | MNTGSSS | 1525 | 139.328 |
| 250 | GGGGTGACTGTTAGGGAGCTT | 309 | GVTVREL | 1526 | 139.099 |
| 251 | CAGATTTTGAATTATAGTGTG | 310 | QILNYSV | 1527 | 138.991 |
| 252 | ATGGCGGGTGAGTATAGGGTT | 311 | MAGEYRV | 1528 | 138.933 |
| 253 | TGGTCGCATGATCGGCCTACT | 312 | WSHDRPT | 1529 | 138.703 |
| 254 | TGCAAAAACAACTCAGAATGC | 313 | CKNNSEC | 1530 | 138.668 |
| 255 | TTGACGACGAATAGTCATTAT | 314 | LTTNSHY | 1531 | 138.525 |
| 256 | ATGCTTGTTCAGAATACTCCT | 315 | MLVQNTP | 1532 | 138.3 |
| 257 | CGTGGTGCGACTGAGCATGCG | 316 | RGATEHA | 1533 | 138.186 |
| 258 | GCTTCGAATGGGAGTATGGGT | 317 | ASNGSMG | 1534 | 138.1181 |
| 259 | AATAGTTATACTGCTGGGAAG | 318 | NSYTAGK | 1535 | 137.4033 |
| 260 | TCCACCCAAGGAGCCATCCTC | 319 | STQGAIL | 1536 | 137.294 |
| 261 | TGGAATACGAATATGGCGATT | 320 | WNTNMAI | 1537 | 137.17 |
| 262 | GTCTCATCGTACGAAAAAATA | 321 | VSSYEKI | 1538 | 137.055 |
| 263 | GTGCTGAGTACGGGGCAGCGG | 322 | VLSTGQR | 1539 | 136.9001 |
| 264 | CCTATACCCCACGGTTCATCC | 323 | PIPHGSS | 1540 | 136.523 |
| 265 | AACGTGTCACTAACGCAAACG | 324 | NVSLTQT | 1541 | 136.4003 |
| 266 | TCTACCATCGGCAACAGCACG | 325 | STIGNST | 1542 | 136.393 |
| 267 | TCTGAGAAGCTGACTGATAAG | 326 | SEKLTDK | 1543 | 136.36 |
| 268 | TCCAAAGACTCGAACATAAGT | 327 | SKDSNIS | 1544 | 136.166 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 269 | GCGAATAGTAATCATGAGCGT | 328 | ANSNHER | 1545 | 136.102 |
| 270 | AGGGATACGGGTGATAAGGCT | 329 | RDTGDKA | 1546 | 135.913 |
| 271 | AGAACAGACACGCCGTCAACC | 330 | RTDTPST | 1547 | 135.583 |
| 272 | CCTACTATGTCGAGTCTGAAT | 331 | PTMSSLN | 1548 | 135.539 |
| 273 | GATATTACTAATCAGTCGTAT | 332 | DITNQSY | 1549 | 135.473 |
| 274 | CTTGTAAAACCGGAAACTTGG | 333 | LVKPETW | 1550 | 134.988 |
| 275 | GGGACTTCCTTGGAAAACCGA | 334 | GTSLENR | 1551 | 134.981 |
| 276 | GCTGCTGGTAATCCTACTCGT | 335 | AAGNPTR | 1552 | 134.779 |
| 277 | CACAACGTCGGCCTAGGACAC | 336 | HNVGLGH | 1553 | 134.677 |
| 278 | GTATCAACGACAACGGACCGG | 337 | VSTTTDR | 1554 | 134.639 |
| 279 | TATTTGTCGTCTGGTAAGATG | 338 | YLSSGKM | 1555 | 134.553 |
| 280 | GATAGTCGGAATGCTGCTTTG | 339 | DSRNAAL | 1556 | 134.213 |
| 281 | GTGGAGCGGAATACTGATATG | 340 | VERNTDM | 1557 | 133.962 |
| 282 | ACTGTTGGGAGTAATTCTATT | 341 | TVGSNSI | 1558 | 133.95 |
| 283 | GTGCGGTCTGGTAATAAGCCG | 342 | VRSGNKP | 1559 | 133.87 |
| 284 | GGCAGTTCGGGGAACAGCGGA | 343 | GSSGNSG | 1560 | 133.776 |
| 285 | TCTACTTCAATAGGAGTGGTA | 344 | STSIGVV | 1561 | 133.69 |
| 286 | CCGAGTCAGAGTAGGTCGCTT | 345 | PSQSRSL | 1562 | 133.6751 |
| 287 | CGGAATGAGAATCTTAATAAT | 346 | RNENLNN | 1563 | 133.26 |
| 288 | TCGTTGGGTAAGAGGGAGGAG | 347 | SLGKREE | 1564 | 133.032 |
| 289 | TCACGCTTGGACTCGAGCTCC | 348 | SRLDSSS | 1565 | 132.783 |
| 290 | GATTCGACGTATGTTTTGGCT | 349 | DSTYVLA | 1566 | 132.54 |
| 291 | GAGCGTAATCCTATTTCTGAT | 350 | ERNPISD | 1567 | 132.49 |
| 292 | GTTAGCTCCGGCCACACGAAA | 351 | VSSGHTK | 1568 | 132.466 |
| 293 | AAGTATACGGAGTCGAATGCG | 352 | KYTESNA | 1569 | 132.305 |
| 294 | AACCGCAACTCAGTTGGGACT | 353 | NRNSVGT | 1570 | 132.2576 |
| 295 | CACGAAAGCCACTACGTGTCA | 354 | HESHYVS | 1571 | 132.014 |
| 296 | ACGACTGGGGGGACGGGGATG | 355 | TTGGTGM | 1572 | 131.954 |
| 297 | GCGACTGATAAGATGACTCCT | 356 | ATDKMTP | 1573 | 131.931 |
| 298 | TCCGCGTCTAGCGGCGCTACA | 357 | SASSGAT | 1574 | 131.886 |
| 299 | TCAACCACTACTGGCCACATG | 358 | STTTGHM | 1575 | 131.581 |
| 300 | ATAATAGCATCCTCTACCACG | 359 | IIASSTT | 1576 | 131.506 |
| 301 | GATACTGGGTCTAGGATTGCG | 360 | DTGSRIA | 1577 | 131.486 |
| 302 | TGGGCTGATGATTCGCAGCGG | 361 | WADDSQR | 1578 | 131.47 |
| 303 | AGGGGTAACACTCTCGAAATG | 362 | RGNTLEM | 1579 | 131.381 |
| 304 | AATCTGCAGGTGAATGCGAAT | 363 | NLQVNAN | 1580 | 131.172 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 305 | GCGACGACTCAGCTGATGACT | 364 | ATTQLMT | 1581 | 130.96 |
| 306 | GCTGATACGAATATTATTGTG | 365 | ADTNIIV | 1582 | 130.47 |
| 307 | GCCATAACAATCACTCAAAAA | 366 | AITITQK | 1583 | 130.225 |
| 308 | GACTCCAACAAAGGAGCGACG | 367 | DSNKGAT | 1584 | 130.1749 |
| 309 | GGCAACGCTTCCGGAAACCCA | 368 | GNASGNP | 1585 | 129.97 |
| 310 | ACGATGGGTGCTAAAGGTACT | 369 | TMGAKGT | 1586 | 129.92 |
| 311 | TATCTGCAGACGGGTACTCTG | 370 | YLQTGTL | 1587 | 129.907 |
| 312 | GCATTACACACCAAAGACCTA | 371 | ALHTKDL | 1588 | 129.846 |
| 313 | GTCGACAAAAGCGAAGCCGTC | 372 | VDKSEAV | 1589 | 129.734 |
| 314 | GGGAGGACGGATCTTATGGCG | 373 | GRTDLMA | 1590 | 129.651 |
| 315 | GGCACGGAACCGCGCACTGCA | 374 | GTEPRTA | 1591 | 129.37 |
| 316 | AGAGGCGACATGTCACGAGAA | 375 | RGDMSRE | 1592 | 129.137 |
| 317 | CGGGGGGATACTAAGTCTAAG | 376 | RGDTKSK | 1593 | 128.94 |
| 318 | GGGACATTAGCCTCAATGTCC | 377 | GTLASMS | 1594 | 128.734 |
| 319 | CAGAAGTCTGTGACGTATTCG | 378 | QKSVTYS | 1595 | 128.602 |
| 320 | AGTACGGGGCAGACTCTTGTT | 379 | STGQTLV | 1596 | 128.1669 |
| 321 | TCGCACATAAACATGGGGTCG | 380 | SHINMGS | 1597 | 128.101 |
| 322 | GCGTTGAATGGTACTGGTAAT | 381 | ALNGTGN | 1598 | 128.045 |
| 323 | ACTACGAGTTCGAATCAGCAT | 382 | TTSSNQH | 1599 | 128.003 |
| 324 | AAAAACTACGCAAGCACCGAC | 383 | KNYASTD | 1600 | 127.84 |
| 325 | GAATCCACAAGCAGGACGTAC | 384 | ESTSRTY | 1601 | 127.765 |
| 326 | CCGCGTTCTATTACGGAGTTG | 385 | PRSITEL | 1602 | 127.623 |
| 327 | TACATAGCCGGAGGAGAAAAA | 386 | YIAGGEK | 1603 | 127.544 |
| 328 | ACTAGTAATTATATGCATGAG | 387 | TSNYMBE | 1604 | 127.522 |
| 329 | TTGGATCCTAATAGTACTCGG | 388 | LDPNSTR | 1605 | 127.175 |
| 330 | CACAGTGACATGGGCTCAAGC | 389 | HSDMGSS | 1606 | 127.01 |
| 331 | GACACCGCCAACCGATCCACA | 390 | DTANRST | 1607 | 127.01 |
| 332 | AACGCCGGACACAGCGGTCAA | 391 | NAGHSGQ | 1608 | 126.611 |
| 333 | AGTTTGGGGTCGGATCGTATG | 392 | SLGSDRM | 1609 | 126.579 |
| 334 | GACAACCAACAAGCCCTAGCT | 393 | DNQQALA | 1610 | 126.49 |
| 335 | CCATCCTCAGCGGGTAGCACA | 394 | PSSAGST | 1611 | 126.201 |
| 336 | GACAGGAAAGGGTACGACGCA | 395 | DRKGYDA | 1612 | 126.06 |
| 337 | GGAGGAAACCAAAACCTTACT | 396 | GGNQNLT | 1613 | 125.7806 |
| 338 | GTGAATCTGAATGAGACGGAG | 397 | VNLNETE | 1614 | 125.719 |
| 339 | TCCCCCGGCAACGGGTTGCTA | 398 | SPGNGLL | 1615 | 125.687 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 340 | TCTGTCGGGGACCTCACAAAA | 399 | SVGDLTK | 1616 | 125.627 |
| 341 | CGATACGAATCCGTCGGACTC | 400 | RYESVGL | 1617 | 125.54 |
| 342 | ACGAGAGAATTGACAAAAAAC | 401 | TRELTKN | 1618 | 125.47 |
| 343 | ACTCCAACTAACGGGAACCCT | 402 | TPTNGNP | 1619 | 125.37 |
| 344 | GCGACTGATCAGCGTTCGAGG | 403 | ATDQRSR | 1620 | 125.26 |
| 345 | GGAACATCGGCAGAATCACGC | 404 | GTSAESR | 1621 | 125.214 |
| 346 | AGGATGCTCTCTACTTTGCCT | 405 | RMLSTLP | 1622 | 125.088 |
| 347 | GGTATCAACTCCTCACACTTC | 406 | GINSSHF | 1623 | 125.044 |
| 348 | AGTAGCTCAACTGAAGGGCAA | 407 | SSSTEGQ | 1624 | 124.971 |
| 349 | GACAAACAACAAACCGGACAA | 408 | DKQQTGQ | 1625 | 124.923 |
| 350 | ACCCAACACCTACCATCCACA | 409 | TQHLPST | 1626 | 124.773 |
| 351 | GGTCTGGGGCAGCCTCAGTTG | 410 | GLGQPQL | 1627 | 124.752 |
| 352 | GTGACTAATGAGAGTCGTGCT | 411 | VTNESRA | 1628 | 124.728 |
| 353 | GGCAACTCGAACTACCGAGAA | 412 | GNSNYRE | 1629 | 124.482 |
| 354 | TGGAATGCTGAGAATAGTAAG | 413 | WNAENSK | 1630 | 124.373 |
| 355 | CCTGGGAGTCAGCGTCAGGAT | 414 | PGSQRQD | 1631 | 124.325 |
| 356 | CATACGTATTCGCAGGCTGAT | 415 | HTYSQAD | 1632 | 124.3 |
| 357 | ACTGCCGGCAACCTAAGAAGT | 416 | TAGNLRS | 1633 | 124.203 |
| 358 | GGCAGACACCTTCAATCGGAC | 417 | GRHLQSD | 1634 | 124.19 |
| 359 | AACAACGCACACACCGCCACT | 418 | NNAHTAT | 1635 | 124.118 |
| 360 | AGTACGAGTCAGGAGAATAGG | 419 | STSQENR | 1636 | 124.0658 |
| 361 | AGGGGTGATACTATGAATTAT | 420 | RGDTMNY | 1637 | 124.04 |
| 362 | CCGGTTGCTACTCAGCATGCG | 421 | PVATQHA | 1638 | 123.9189 |
| 363 | GGGCATTTGAATGCTCCGACT | 422 | GHLNAPT | 1639 | 123.495 |
| 364 | CAAATATTAAACTACTCAGTC | 423 | QILNYSV | 1640 | 123.4 |
| 365 | CAAAACCACGCGTCTGGTGAA | 424 | QNHASGE | 1641 | 123.372 |
| 366 | GGTTTAACAGGGCGGGAACTA | 425 | GLTGREL | 1642 | 123.32 |
| 367 | GACGTAGCCGTGACTCAACAC | 426 | DVAVTQH | 1643 | 123.31 |
| 368 | GCAACTTACACCGGGCGAACA | 427 | ATYTGRT | 1644 | 123.292 |
| 369 | AAAGAACTACAATGGCAACGA | 428 | KELQWQR | 1645 | 123.251 |
| 370 | GCTAGTTATAGTAGTATGGTG | 429 | ASYSSMV | 1646 | 123.193 |
| 371 | GTTATTAGTCATGGGGCGCTG | 430 | VISHGAL | 1647 | 123.094 |
| 372 | CCTATACACCACGGTTCATCC | 431 | PIHHGSS | 1648 | 123.09 |
| 373 | GTGGATAAGAATCATCCTTTG | 432 | VDKNHPL | 1649 | 123.04 |
| 374 | ACCTCGGGTGACCGGTACACG | 433 | TSGDRYT | 1650 | 122.844 |
| 375 | GGGACAAAAAGCTGGCCTGTC | 434 | GTKSWPV | 1651 | 122.8432 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 376 | TACAACGCCCACGAATCATTC | 435 | YNAHESF | 1652 | 122.813 |
| 377 | AGAGTCCACGACACTCCTTCA | 436 | RVHDTPS | 1653 | 122.7503 |
| 378 | GCACAAATCGAATCAGGCCGA | 437 | AQIESGR | 1654 | 122.66 |
| 379 | TGGAAGGATAATATGCGGATG | 438 | WKDNMRM | 1655 | 122.624 |
| 380 | ATGCCTAGTGAACCACCAGGG | 439 | MPSEPPG | 1656 | 122.51 |
| 381 | CGTGGTGATTATCCGACGTCG | 440 | RGDYPTS | 1657 | 122.487 |
| 382 | TTTCATAATGAGTCTTATGGG | 441 | FHNESYG | 1658 | 122.36 |
| 383 | TTGAATACGATGATTGATAAG | 442 | LNTMIDK | 1659 | 122.272 |
| 384 | TCCACACTAAGCCAAGGAGCA | 443 | STLSQGA | 1660 | 122.2662 |
| 385 | CCTTTGCACAACATACCTCCT | 444 | PLHNIPP | 1661 | 122.24 |
| 386 | GCTTCGTCTACGTTTTTGCCT | 445 | ASSTFLP | 1662 | 122.24 |
| 387 | ATGGAAGGAATGGGACTCGGA | 446 | MEGMGLG | 1663 | 122.04 |
| 388 | AAGGATTATAAGCCGTATGCT | 447 | KDYKPYA | 1664 | 121.95 |
| 389 | AATTTGCAGTCTGGTGTTCAG | 448 | NLQSGVQ | 1665 | 121.91 |
| 390 | ACAACTCTTAGCCAACAAAGC | 449 | TTLSQQS | 1666 | 121.82 |
| 391 | CTTATGTCGTCTACTTCCTCA | 450 | LMSSTSS | 1667 | 121.536 |
| 392 | ACTGGCCAAGGATTCTCGGCA | 451 | TGQGFSA | 1668 | 121.45 |
| 393 | TCTACAATCGGCAACAGCACG | 452 | STIGNST | 1669 | 121.27 |
| 394 | CTGAGGGCGAGTGAGGCTCCG | 453 | LRASEAP | 1670 | 121.2297 |
| 395 | CAGCCTAATAATGGTAATCAT | 454 | QPNNGNH | 1671 | 121.02 |
| 396 | TCGTCAGACGTTACCAGACAA | 455 | SSDVTRQ | 1672 | 120.98 |
| 397 | CGGGGTGACGCAACAGAAATG | 456 | RGDATEM | 1673 | 120.74 |
| 398 | TATAGGGGTAGGGAGGATTGG | 457 | YRGREDW | 1674 | 120.58 |
| 399 | AGCTTGCAACAATCACAATTG | 458 | SLQQSQL | 1675 | 120.491 |
| 400 | AAGCCGACTGCGAATGATTGG | 459 | KPTANDW | 1676 | 120.3784 |
| 401 | CGTCTGACTGATACTATGCAT | 460 | RLTDTMH | 1677 | 120.35 |
| 402 | CTTCATGGGAATTATAGTCCG | 461 | LHGNYSP | 1678 | 120.346 |
| 403 | ATTCCGGTTGGGGCGATGGCT | 462 | IPVGAMA | 1679 | 120.248 |
| 404 | CCGAACACCGCCTCAAACTTC | 463 | PNTASNF | 1680 | 120.24 |
| 405 | ACGAGTAGAGAAGTCAAAGGG | 464 | TSREVKG | 1681 | 120.171 |
| 406 | GACACGTCCTCCGGCAACAGG | 465 | DTSSGNR | 1682 | 119.94 |
| 407 | GAAGCAGTAACAAGTAAATGG | 466 | EAVTSKW | 1683 | 119.919 |
| 408 | CTAATCACAGCCACCACTAAC | 467 | LITATTN | 1684 | 119.872 |
| 409 | GATGGGGGTCGTTCGGGTATT | 468 | DGGRSGI | 1685 | 119.847 |
| 410 | TTCATGGAAGTCATGAAAAAC | 469 | FMEVMKN | 1686 | 119.82 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 411 | TCCTACCAAAACCCACCACCA | 470 | SYQNPPP | 1687 | 119.701 |
| 412 | ACTAATGTGACGTTTAAGCTT | 471 | TNVTFKL | 1688 | 119.681 |
| 413 | ATTTCTACGCATACGATGACG | 472 | ISTHTMT | 1689 | 119.64 |
| 414 | GAAACCCAAGGAGCAAGATAC | 473 | ETQGARY | 1690 | 119.591 |
| 415 | GCGGCTTATGAGCATGCGCCT | 474 | AAYEHAP | 1691 | 119.588 |
| 416 | TCAACGAACGACCGTGCGTTA | 475 | STNDRAL | 1692 | 119.57 |
| 417 | TTCACCGAACGCGCACTCCAA | 476 | FTERALQ | 1693 | 119.423 |
| 418 | GTAGCGGGCTTAGTCGACATA | 477 | VAGLVDI | 1694 | 119.41 |
| 419 | AGCTCGGTAACTAACCTTGCA | 478 | SSVTNLA | 1695 | 119.38 |
| 420 | GATACTACTACTGGTCATCTT | 479 | DTTTGHL | 1696 | 119.27 |
| 421 | ACGCGTAATTTGTCTGAGAGT | 480 | TRNLSES | 1697 | 118.919 |
| 422 | CAGGTGAATGTTGGGCCTGGT | 481 | QVNVGPG | 1698 | 118.831 |
| 423 | AAACAAACGATGTCCGACACA | 482 | KQTMSDT | 1699 | 118.829 |
| 424 | ATGTCGACAACCAGCAAAACT | 483 | MSTTSKT | 1700 | 118.7215 |
| 425 | ACTACAATAGGGACAAACCAA | 484 | TTIGTNQ | 1701 | 118.676 |
| 426 | GGGACTCTGACGCCGAATCTT | 485 | GTLTPNL | 1702 | 118.622 |
| 427 | TTTGATAGTTATAATATTGTG | 486 | FDSYNIV | 1703 | 118.51 |
| 428 | CGTGGTGCGCCTGAGCAAGCG | 487 | RGAPEQA | 1704 | 118.47 |
| 429 | ATCGAAAACGTAAACCACTTG | 488 | IENVNHL | 1705 | 118.42 |
| 430 | AGGTCTCTGGAGAGTCAGGCT | 489 | RSLESQA | 1706 | 118.231 |
| 431 | CAGTATACGAGTCTGAGTCCG | 490 | QYTSLSP | 1707 | 118.006 |
| 432 | ACGAAGGGTTATAATGATCTT | 491 | TKGYNDL | 1708 | 117.876 |
| 433 | GTCGCCTCGATGGTACACAAC | 492 | VASMVHN | 1709 | 117.874 |
| 434 | TCCACAACCCACACCTCAGCA | 493 | STTHTSA | 1710 | 117.821 |
| 435 | CTTGCGCACCCACAACCAAAC | 494 | LAHPQPN | 1711 | 117.542 |
| 436 | TCGATAAACAACATAGGCGCA | 495 | SINNIGA | 1712 | 117.538 |
| 437 | GCTATAGACTCCATCAAAATG | 496 | AIDSIKM | 1713 | 117.472 |
| 438 | TCTATGTATGGGCAGGCTGGG | 497 | SMYGQAG | 1714 | 117.362 |
| 439 | GAGTATGCTAATGCTAAGACT | 498 | EYANAKT | 1715 | 117.351 |
| 440 | TATCGGGCTTCGGATGTGGCG | 499 | YRASDVA | 1716 | 117.348 |
| 441 | GTTAGTTTGGAGAGTCGGTTG | 500 | VSLESRL | 1717 | 117.332 |
| 442 | ATTGAGACTAGTTCGCGTTCG | 501 | IETSSRS | 1718 | 117.176 |
| 443 | ATGGGAGTGAAACCCGAACAA | 502 | MGVKPEQ | 1719 | 116.975 |
| 444 | GCGCTTCCGTCTCGTGAGCGG | 503 | ALPSRER | 1720 | 116.914 |
| 445 | GGCACCGGATCTTCAGCGCAC | 504 | GTGSSAH | 1721 | 116.896 |
| 446 | CAAACGAACACCAACGACAGA | 505 | QTNTNDR | 1722 | 116.664 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 447 | GTATTACACTCTGTATCAGCA | 506 | VLHSVSA | 1723 | 116.583 |
| 448 | CCTTATTCTGCTACTGATCGG | 507 | PYSATDR | 1724 | 116.577 |
| 449 | GCAAACTCCGGATTACACAAC | 508 | ANSGLHN | 1725 | 116.505 |
| 450 | TATGAGAGTACTCATGTTAAT | 509 | YESTHVN | 1726 | 116.418 |
| 451 | AACAACGCACTAGTAGGAAGT | 510 | NNALVGS | 1727 | 116.34 |
| 452 | GGTATCAACTCCTCACACATC | 511 | GINSSHI | 1728 | 116.28 |
| 453 | AGTATTTCTGATAAGAATCAG | 512 | SISDKNQ | 1729 | 116.141 |
| 454 | GACCACCAACAAGCCCTAGCA | 513 | DHQQALA | 1730 | 116.13 |
| 455 | GACTCTACCAAAGCCATGCAA | 514 | DSTKAMQ | 1731 | 116.116 |
| 456 | ACTATTACTAGTCAGTCGGTG | 515 | TITSQSV | 1732 | 115.95 |
| 457 | GGCGCCCGTACAATCTTAGAC | 516 | GARTILD | 1733 | 115.938 |
| 458 | GAGCATAGTCCTACGACTGGT | 517 | EHSPTTG | 1734 | 115.8995 |
| 459 | GGGCTCACAGGATACCCAATG | 518 | GLTGYPM | 1735 | 115.844 |
| 460 | ACGATGGAATCCGGCCGCCAC | 519 | TMESGRH | 1736 | 115.82 |
| 461 | TCTGCGTCGAAAGTGGAATAC | 520 | SASKVEY | 1737 | 115.719 |
| 462 | GATAAGTCTAATTATAGTATT | 521 | DKSNYSI | 1738 | 115.714 |
| 463 | TTCAACGAAACTGCCGGGCGA | 522 | FNETAGR | 1739 | 115.65 |
| 464 | CAAAAATCGGAAACCTACACT | 523 | QKSETYT | 1740 | 115.528 |
| 465 | GCACTTACCCGTATGCCTAAC | 524 | ALTRMPN | 1741 | 115.476 |
| 466 | CGTAACGGCTCCGCCCAAAGC | 525 | RNGSAQS | 1742 | 115.465 |
| 467 | GCGAGGGATACGCCTGGGATT | 526 | ARDTPGI | 1743 | 115.432 |
| 468 | ATTGTTAATGCTGAGATTTAT | 527 | IVNAEIY | 1744 | 115.31 |
| 469 | CGACAAGGCGACTTAAAAGAA | 528 | RQGDLKE | 1745 | 115.3059 |
| 470 | CGAAACAACCCATCGCACGAC | 529 | RNNPSHD | 1746 | 115.224 |
| 471 | CTCGCCCACAACTACTTAAGC | 530 | LAHNYLS | 1747 | 115.195 |
| 472 | AACACCCACAACCTACAAATG | 531 | NTHNLQM | 1748 | 115.171 |
| 473 | CGAGGAGACCACAGCACACAG | 532 | RGDHSTQ | 1749 | 115.12 |
| 474 | CTCCACGGAGTCAGCAGTATA | 533 | LHGVSSI | 1750 | 115.105 |
| 475 | GGTATTAATCATGTGGCGTCT | 534 | GINHVAS | 1751 | 115.102 |
| 476 | ACTGATAAGCTTCAGGGTGTG | 535 | TDKLQGV | 1752 | 115.062 |
| 477 | GGAACCTCCATAGACTACGTA | 536 | GTSIDYV | 1753 | 115.053 |
| 478 | TCGAACACTGCCCCCCCCCCC | 537 | SNTAPPP | 1754 | 115.034 |
| 479 | ACTGCTAAGAGTTATGGGCCT | 538 | TAKSYGP | 1755 | 115.006 |
| 480 | GACCACCAACAAGCACTAGCT | 539 | DHQQALA | 1756 | 114.98 |
| 481 | ACACAAGTAGTCGCAAGAACA | 540 | TQVVART | 1757 | 114.9299 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 482 | AGTCCTCCTAGTACGTCGGGT | 541 | SPPSTSG | 1758 | 114.816 |
| 483 | CCTATGCGAACACCACCGTAC | 542 | PMRTPPY | 1759 | 114.806 |
| 484 | GCTGCTGGTAATACTACTCGT | 543 | AAGNTTR | 1760 | 114.78 |
| 485 | AGAGGCGACTAATCCACACCC | 544 | RGD*STP | 1761 | 114.78 |
| 486 | CTAGCGAAAACTGTCGCTATC | 545 | LAKTVAI | 1762 | 114.722 |
| 487 | TCTAAATCTGAAAACCTGCAA | 546 | SKSENLQ | 1763 | 114.59 |
| 488 | ACTCAGACGTCGTATGCTACG | 547 | TQTSYAT | 1764 | 114.505 |
| 489 | ACTGGGGATAGGACTTCGGTG | 548 | TGDRTSV | 1765 | 114.4766 |
| 490 | ATATCGCAAGGCTCGAGCCTC | 549 | ISQGSSL | 1766 | 114.305 |
| 491 | CTTGTTCAGATGGGGAGTGTG | 550 | LVQMGSV | 1767 | 114.256 |
| 492 | TTATCCGCAACATCTACGATG | 551 | LSATSTM | 1768 | 114.245 |
| 493 | CAAAACCACAACGAACTAAAA | 552 | QNHNELK | 1769 | 114.217 |
| 494 | CGTGGTGCGCCTGAGCATGCG | 553 | RGAPEHA | 1770 | 114.09 |
| 495 | TCTTCTTTCGGAAAAGACAAC | 554 | SSFGKDN | 1771 | 113.982 |
| 496 | AACGCTAACGCCGGTGGAAAC | 555 | NANAGGN | 1772 | 113.958 |
| 497 | GATCATCATCCTCAGAGTCGT | 556 | DHHPQSR | 1773 | 113.83 |
| 498 | ATGAGGCATGAGGCTCCTCTT | 557 | MRHEAPL | 1774 | 113.819 |
| 499 | AAGGGGGATGGTGCTTATGAG | 558 | KGDGAYE | 1775 | 113.742 |
| 500 | CCTATGAATGGTATTCTGTTG | 559 | PMNGILL | 1776 | 113.722 |
| 501 | AGTAGTGGGGGTATGAAGGCG | 560 | SSGGMKA | 1777 | 113.69 |
| 502 | GTGCTGGTTACTCAGAATCAT | 561 | VLVTQNH | 1778 | 113.631 |
| 503 | GAGATTAATAATCGGACTGGT | 562 | EINNRTG | 1779 | 113.588 |
| 504 | TTACCAACAGGCGTCCTGCCC | 563 | LPTGVLP | 1780 | 113.561 |
| 505 | GCCTACGGTATCAGAGAAGTG | 564 | AYGIREV | 1781 | 113.547 |
| 506 | TCGACAAACTCTATAGGCGCC | 565 | STNSIGA | 1782 | 113.471 |
| 507 | GTGCAGTTGACGCATAATGGG | 566 | VQLTHNG | 1783 | 113.43 |
| 508 | GTTCAGTTGGAGAATGCGAAT | 567 | VQLENAN | 1784 | 113.43 |
| 509 | GGAAAAGCCAACGACGGTTCT | 568 | GKANDGS | 1785 | 113.427 |
| 510 | ACCGGGGTTCGAGAAACCATA | 569 | TGVRETI | 1786 | 113.41 |
| 511 | GGCCTGAACCAGATCACATCG | 570 | GLNQITS | 1787 | 113.4 |
| 512 | ACGGAGAAGGCGAGTCCTCTG | 571 | TEKASPL | 1788 | 113.381 |
| 513 | TTTCTGGAGGGTGTTGCGCAG | 572 | FLEGVAQ | 1789 | 113.333 |
| 514 | ACGAATTATAATATTGGTCCG | 573 | TNYNIGP | 1790 | 113.318 |
| 515 | AGAGGAGACTTGACAACCACA | 574 | RGDLTTT | 1791 | 113.29 |
| 516 | ATGATGAATGTGAGTGGTCAT | 575 | MMNVSGH | 1792 | 113.09 |
| 517 | TCTCAGTCGATTAATGGGCTT | 576 | SQSINGL | 1793 | 113.084 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 518 | CTCACGACTTTAACTAACCAC | 577 | LTTLTNH | 1794 | 113.033 |
| 519 | AACTCTGTTCAATCCACCCCA | 578 | NSVQSTP | 1795 | 113.021 |
| 520 | TATAATACGGATCGGACTAAT | 579 | YNTDRTN | 1796 | 113.001 |
| 521 | GAGAAGCCTCAGCATAATAGT | 580 | EKPQHNS | 1797 | 112.98 |
| 522 | ACGATGGCTACAAACTTAAGT | 581 | TMATNLS | 1798 | 112.937 |
| 523 | GTGGGGACGCATTTGCATTCG | 582 | VGTHLHS | 1799 | 112.918 |
| 524 | GACGCCCACCACTCAAGCAGC | 583 | DAHHSSS | 1800 | 112.88 |
| 525 | CTTGTGGGGACTTTGGTGTAT | 584 | LVGTLVY | 1801 | 112.853 |
| 526 | TATGGTGTGCAGGCGAATAGT | 585 | YGVQANS | 1802 | 112.806 |
| 527 | GTTTTGTCTGATAAGGCGTAT | 586 | VLSDKAY | 1803 | 112.787 |
| 528 | CTTGAGGGTCAGAATAAGACG | 587 | LEGQNKT | 1804 | 112.731 |
| 529 | GAGGTTAGTAATAATAATTAT | 588 | EVSNNNY | 1805 | 112.69 |
| 530 | GCCCACCAACAAGCCCTAGCT | 589 | AHQQALA | 1806 | 112.67 |
| 531 | CTTCCGACCACACTCAACCAC | 590 | LPTTLNH | 1807 | 112.667 |
| 532 | TACATAGCAGGTGGTGAACAA | 591 | YIAGGEQ | 1808 | 112.6513 |
| 533 | AATTCTGGTACTCTTTATCAG | 592 | NSGTLYQ | 1809 | 112.609 |
| 534 | CGGGGTCTGCCTGATGTTAAT | 593 | RGLPDVN | 1810 | 112.43 |
| 535 | AACCAACAACTATCCCACTCA | 594 | NQQLSHS | 1811 | 112.375 |
| 536 | AATCCTAGTTATGATCATCGG | 595 | NPSYDHR | 1812 | 112.363 |
| 537 | ATAGACAGCGACACCTTCGTA | 596 | IDSDTFV | 1813 | 112.355 |
| 538 | ACCGCTTACCTTGCGGGATTA | 597 | TAYLAGL | 1814 | 112.17 |
| 539 | CATAGTAATGTTAGTCTTGAG | 598 | HSNVSLE | 1815 | 112.162 |
| 540 | GGTAATAATTTGAGTTTGTCT | 599 | GNNLSLS | 1816 | 112.16 |
| 541 | GTTATGGATACGCATGGGATG | 600 | VMDTHGM | 1817 | 112.145 |
| 542 | GCGTATAATATGTCGTCTGTT | 601 | AYNMSSV | 1818 | 112.14 |
| 543 | ACTAACGCCATCTCTCAAACG | 602 | TNAISQT | 1819 | 112.063 |
| 544 | GCAACACACGCCATGCGCCCA | 603 | ATHAMRP | 1820 | 112.016 |
| 545 | ATGTTAAACAACACAATGATG | 604 | MLNNTMM | 1821 | 111.939 |
| 546 | ATTAGTTCGGGGATTTTGTCG | 605 | ISSGILS | 1822 | 111.907 |
| 547 | CGCCAAGGCAGCTTGATGATA | 606 | RQGSLMI | 1823 | 111.83 |
| 548 | ACGACTGATAAGGGTATTAAT | 607 | TTDKGIN | 1824 | 111.818 |
| 549 | CACAACTTAATGACCCAAATA | 608 | HNLMTQI | 1825 | 111.77 |
| 550 | AACCAAAACACCTACGAACTG | 609 | NQNTYEL | 1826 | 111.756 |
| 551 | GCTAACACCGTCACAGAACGA | 610 | ANTVTER | 1827 | 111.7323 |
| 552 | TCTACGCTGCAGACTAATGGT | 611 | STLQTNG | 1828 | 111.683 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 553 | CCCAACGAATACAAAGCACCG | 612 | PNEYKAP | 1829 | 111.646 |
| 554 | ATGCAAACACGCTCGGACACA | 613 | MQTRSDT | 1830 | 111.629 |
| 555 | GGAACAGGGTACGCTGGATCA | 614 | GTGYAGS | 1831 | 111.6183 |
| 556 | ATGGGTATGCAGAATACGCAT | 615 | MGMQNTH | 1832 | 111.599 |
| 557 | TCTAGTAAGGAGCGTACATCG | 616 | SSKERTS | 1833 | 111.57 |
| 558 | CGAACGGACACCCCCTACACC | 617 | RTDTPYT | 1834 | 111.562 |
| 559 | ACTGCGCTGCGGGATAATAAG | 618 | TALRDNK | 1835 | 111.51 |
| 560 | AGGATGTCTGAGAGTTCGGAT | 619 | RMSESSD | 1836 | 111.51 |
| 561 | AACCAATCTATAAGCATGGAC | 620 | NQSISMD | 1837 | 111.491 |
| 562 | TCGCTTGGGCATAGTAATAAT | 621 | SLGHSNN | 1838 | 111.432 |
| 563 | CTTAATAGTGGTGGTGCGATG | 622 | LNSGGAM | 1839 | 111.361 |
| 564 | AACGAACAATTCGAAAAAGTC | 623 | NEQFEKV | 1840 | 111.341 |
| 565 | ATGATGGCGAATAATATGCAG | 624 | MMANNMQ | 1841 | 111.28 |
| 566 | AGTCGGCGCGAAGAACAACCA | 625 | SRREEQP | 1842 | 111.2512 |
| 567 | GCGACTATGACTTCGTCGACG | 626 | ATMTSST | 1843 | 111.238 |
| 568 | CGTGGTTCAGACGGAGGATTG | 627 | RGSDGGL | 1844 | 111.172 |
| 569 | AGTTTGACGCCTAATAATCTT | 628 | SLTPNNL | 1845 | 111.152 |
| 570 | GCTACTCTTTCTCCGCATGCT | 629 | ATLSPHA | 1846 | 111.132 |
| 571 | TATCTGCAGGAGAAGTTTCCT | 630 | YLQEKFP | 1847 | 111.112 |
| 572 | GGCACCGGGTACCCAAACCAA | 631 | GTGYPNQ | 1848 | 111.111 |
| 573 | AATTATCCTTCGGTTCAGGAG | 632 | NYPSVQE | 1849 | 111.07 |
| 574 | ACTGACGCATCGGGTAGATCA | 633 | TDASGRS | 1850 | 111.017 |
| 575 | CGTGTGATTACTGCGGGTGAT | 634 | RVITAGD | 1851 | 111.009 |
| 576 | GTGACTGTGAGTAATAGTCTG | 635 | VTVSNSL | 1852 | 110.95 |
| 577 | TTGTTGACGGCTCCGCATAGG | 636 | LLTAPHR | 1853 | 110.908 |
| 578 | TCAATCGCAAACCACATGATA | 637 | SIANHMI | 1854 | 110.861 |
| 579 | ATGCCTTCGAAAGGCGAAGTA | 638 | MPSKGEV | 1855 | 110.816 |
| 580 | AACATGACCAACGAACGGCTC | 639 | NMTNERL | 1856 | 110.801 |
| 581 | TCATTCTCTTCAGGCATAATG | 640 | SFSSGIM | 1857 | 110.771 |
| 582 | CGCGACCGTCAAGACTCGGTA | 641 | RDRQDSV | 1858 | 110.754 |
| 583 | CACGGTGACCGAACAGCTTTA | 642 | HGDRTAL | 1859 | 110.748 |
| 584 | GAAGTACGGGGCAGCGTGCCA | 643 | EVRGSVP | 1860 | 110.747 |
| 585 | CTGATTTCGACTGGTAATAAT | 644 | LISTGNN | 1861 | 110.735 |
| 586 | CCAACATCTGGGGACAAACCG | 645 | PTSGDKP | 1862 | 110.735 |
| 587 | AAAGCGGACCACAGTGGGGCA | 646 | KADHSGA | 1863 | 110.73 |
| 588 | CTAAACGACGTCTACCGTAAA | 647 | LNDVYRK | 1864 | 110.724 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 589 | AACAGTTTGCAAGCAAGTGCA | 648 | NSLQASA | 1865 | 110.72 |
| 590 | TATCATAATGAGATTATGACG | 649 | YHNEIMT | 1866 | 110.708 |
| 591 | AACAACACCCTAAACATCCTA | 650 | NNTLNIL | 1867 | 110.69 |
| 592 | TCTTATGGGCAGGGTCTGGAG | 651 | SYGQGLE | 1868 | 110.684 |
| 593 | ATGATAAAAACCAACATGTTG | 652 | MIKTNML | 1869 | 110.668 |
| 594 | ACCGAAGCGGGCCGCCCCCAA | 653 | TEAGRPQ | 1870 | 110.663 |
| 595 | AGGATTGATCAGACTAATGTG | 654 | RIDQTNV | 1871 | 110.624 |
| 596 | GAGGGGCATAATCGTGGTATT | 655 | EGHNRGI | 1872 | 110.559 |
| 597 | ATGGGGACTGAGTATCGTATG | 656 | MGTEYRM | 1873 | 110.524 |
| 598 | TCGGGTATGAATAGTAATAAG | 657 | SGMNSNK | 1874 | 110.499 |
| 599 | TTGACTAATGATAATAAGTTG | 658 | LTNDNKL | 1875 | 110.479 |
| 600 | TTACACAACTACCAAGACCGT | 659 | LHNYQDR | 1876 | 110.438 |
| 601 | AAGTCTAATTTGGAGGGTAAG | 660 | KSNLEGK | 1877 | 110.438 |
| 602 | CTTACTGGTCAGAATGCGATT | 661 | LTGQNAI | 1878 | 110.416 |
| 603 | CATACTGTGGGGGCTATGCAT | 662 | HTVGAMH | 1879 | 110.41 |
| 604 | CTCCAACTGGCTACATCCCAC | 663 | LQLATSH | 1880 | 110.384 |
| 605 | AGTCTGAATGGGGTGTTGGTT | 664 | SLNGVLV | 1881 | 110.359 |
| 606 | AGTCACAACCAAGTAAACGTA | 665 | SHNQVNV | 1882 | 110.349 |
| 607 | AGTTTGAGTACTGATGTGTTT | 666 | SLSTDVF | 1883 | 110.261 |
| 608 | ATGGTAGGTCGTGCCGAAATC | 667 | MVGRAEI | 1884 | 110.224 |
| 609 | TTGTCTAGTATGAGTACGGAT | 668 | LSSMSTD | 1885 | 110.204 |
| 610 | TCCTACAGTACTTCAACACCG | 669 | SYSTSTP | 1886 | 110.189 |
| 611 | TCCGAATTAATGGTCAGACCC | 670 | SELMVRP | 1887 | 110.0813 |
| 612 | TGGAACGGAAACGCCACACAA | 671 | WNGNATQ | 1888 | 110.039 |
| 613 | ATGGATACTGAGCTTTATAGG | 672 | MDTELYR | 1889 | 109.985 |
| 614 | AGGACGAGTCCTGATACGAAT | 673 | RTSPDTN | 1890 | 109.977 |
| 615 | TTCTCAACGCAAGACATAAGC | 674 | FSTQDIS | 1891 | 109.948 |
| 616 | ACGACTGTGCTGGGGAATAAT | 675 | TTVLGNN | 1892 | 109.94 |
| 617 | CAGCGTGATGCTGCGTATGCT | 676 | QRDAAYA | 1893 | 109.927 |
| 618 | CACCAAACCGTGGTCCCTACT | 677 | HQTVVPT | 1894 | 109.8948 |
| 619 | TCTAATCCGGGTAATCATAAT | 678 | SNPGNHN | 1895 | 109.853 |
| 620 | TGGGAGACTATGGCTAAGCCT | 679 | WETMAKP | 1896 | 109.818 |
| 621 | GGTCTTTATCAGAATCCTACG | 680 | GLYQNPT | 1897 | 109.73 |
| 622 | CTTAATCTTACTAATCATAAT | 681 | LNLTNHN | 1898 | 109.727 |
| 623 | ATGAGTCTCGCCTCCACCCAA | 682 | MSLASTQ | 1899 | 109.672 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 624 | ACGTCCCAAACCGTCCGAGTA | 683 | TSQTVRV | 1900 | 109.654 |
| 625 | GGAGCAACGGTCAACACGCGA | 684 | GATVNTR | 1901 | 109.64 |
| 626 | AAAGGGGGAAACCTCACCGCA | 685 | KGGNLTA | 1902 | 109.632 |
| 627 | GCGTGGTCTCAAGTCCTGACG | 686 | AWSQVLT | 1903 | 109.587 |
| 628 | GTAGAACACGTAGCCCACCAA | 687 | VEHVAHQ | 1904 | 109.552 |
| 629 | CTAATGTCGTCCTACTCATCA | 688 | LMSSYSS | 1905 | 109.546 |
| 630 | TCTCTGGGTGGGAATCCGCCT | 689 | SLGGNPP | 1906 | 109.511 |
| 631 | AAGAATGAGAATACGAATTAT | 690 | KNENTNY | 1907 | 109.5055 |
| 632 | ATATTGGACAACCACCGTTTC | 691 | ILDNHRF | 1908 | 109.489 |
| 633 | AATTCGTCGCATGTTAATTCT | 692 | NSSHVNS | 1909 | 109.473 |
| 634 | CAGGTGCAGCATGAGAGGGTG | 693 | QVQHERV | 1910 | 109.47 |
| 635 | TTGGGAGGAACCCTGGGAATA | 694 | LGGTLGI | 1911 | 109.46 |
| 636 | ACTCAAGAACGACCACTAATC | 695 | TQERPLI | 1912 | 109.455 |
| 637 | CGTAAGACTGAGGATAGGATG | 696 | RKTEDRM | 1913 | 109.429 |
| 638 | ACCGAACTCACAGCGCGGAAC | 697 | TELTARN | 1914 | 109.398 |
| 639 | CGCGGCGACAACACTTACTCC | 698 | RGDNTYS | 1915 | 109.387 |
| 640 | CAGTCTAATACTAATAATAGT | 699 | QSNTNNS | 1916 | 109.372 |
| 641 | GCTTCTTATAGTATTTCTGAT | 700 | ASYSISD | 1917 | 109.309 |
| 642 | AGCGAACACCACGCCGGAATA | 701 | SEHHAGI | 1918 | 109.281 |
| 643 | CGTGGTGCGCCAGAGCATGCG | 702 | RGAPEHA | 1919 | 109.237 |
| 644 | AATTTTAGTAGTGGTGATGTT | 703 | NFSSGDV | 1920 | 109.229 |
| 645 | AGTGGCATCAACGCCACCGAC | 704 | SGINATD | 1921 | 109.22 |
| 646 | CGGGCTGATGTTTCTTGGTCT | 705 | RADVSWS | 1922 | 109.213 |
| 647 | TGTATGGATGTTGGTAAGGCG | 706 | CMDVGKA | 1923 | 109.203 |
| 648 | GGGGTCGGAGCCACTTCGGTA | 707 | GVGATSV | 1924 | 109.193 |
| 649 | AAAAACAACAACTCAGACAGT | 708 | KNNNSDS | 1925 | 109.177 |
| 650 | AATGTTGCGAGTATTGATAGG | 709 | NVASIDR | 1926 | 109.174 |
| 651 | AATAGTGTGAATGGTCTTCTG | 710 | NSVNGLL | 1927 | 109.154 |
| 652 | ACACTAGACCGAAACCAAACC | 711 | TLDRNQT | 1928 | 109.132 |
| 653 | GACCAAAACTTCGAACGTAGA | 712 | DQNFERR | 1929 | 109.108 |
| 654 | GTCGGTGACAGGAACTTGGTC | 713 | VGDRNLV | 1930 | 109.062 |
| 655 | TTAGAAGTAAACCTGCAAACG | 714 | LEVNLQT | 1931 | 109.057 |
| 656 | ACTAATGGGGGGTCGCTTAAT | 715 | TNGGSLN | 1932 | 109.049 |
| 657 | TTCACGCGCACACCAGTAACC | 716 | FTRTPVT | 1933 | 109.033 |
| 658 | ACACCGGCGGAAAGCAAAGTT | 717 | TPAESKV | 1934 | 108.991 |
| 659 | TTTCCTTCGCATAATGGGGCG | 718 | FPSHNGA | 1935 | 108.959 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 660 | GCCAGGAACGTAATGCTGGGG | 719 | ARNVMLG | 1936 | 108.958 |
| 661 | ACGATTCAGGATCATATTAAG | 720 | TIQDHIK | 1937 | 108.942 |
| 662 | ATTAATTCGTATTTGCATGAG | 721 | INSYLHE | 1938 | 108.918 |
| 663 | GCGCATGATGTTACTGTGAAT | 722 | AHDVTVN | 1939 | 108.918 |
| 664 | ACTGTGGGGGTTCAGCAGACG | 723 | TVGVQQT | 1940 | 108.8891 |
| 665 | ACAGGTAGTTCAGACAGATTA | 724 | TGSSDRL | 1941 | 108.887 |
| 666 | AATCATGATACTGCTCATGCT | 725 | NHDTAHA | 1942 | 108.884 |
| 667 | GCCGAATCCCAACTAGCTAGC | 726 | AESQLAS | 1943 | 108.8752 |
| 668 | GGTAATGCGTATAATACGACT | 727 | GNAYNTT | 1944 | 108.818 |
| 669 | AATCATCAGGCTGGTACTACT | 728 | NHQAGTT | 1945 | 108.807 |
| 670 | ACGGTAGGAGAAAACCACCGA | 729 | TVGENHR | 1946 | 108.779 |
| 671 | CTAACTACTAAAATACCCCTC | 730 | LTTKIPL | 1947 | 108.773 |
| 672 | ACTAATTATCCTGAGGCGAAT | 731 | TNYPEAN | 1948 | 108.748 |
| 673 | AATACTGCTCCGCCGAATCAT | 732 | NTAPPNH | 1949 | 108.733 |
| 674 | GTGCTGAGTACGGGGCTGCGG | 733 | VLSTGLR | 1950 | 108.677 |
| 675 | CTCACGTCCCACTCTGCGGGC | 734 | LTSHSAG | 1951 | 108.648 |
| 676 | ATGAATAAGCATGGTGTGCTT | 735 | MNKHGVL | 1952 | 108.5736 |
| 677 | GACCTGACCAGAGCTGCAATA | 736 | DLTRAAI | 1953 | 108.552 |
| 678 | TATATTGTGGATCATGCGAAT | 737 | YIVDHAN | 1954 | 108.526 |
| 679 | AGTGGGCCTGAGAATACGTTG | 738 | SGPENTL | 1955 | 108.526 |
| 680 | CGTTATGGTGATACGGGTATG | 739 | RYGDTGM | 1956 | 108.512 |
| 681 | GATGGTAAGAATAGTTATGCG | 740 | DGKNSYA | 1957 | 108.451 |
| 682 | GAGGCGCATAATCGTGTTATT | 741 | EAHNRVI | 1958 | 108.451 |
| 683 | AGTTTGCAGGCTGGTAGGATG | 742 | SLQAGRM | 1959 | 108.3681 |
| 684 | GATGCGAAGGCTCTTACGACT | 743 | DAKALTT | 1960 | 108.368 |
| 685 | ACCGACACCCGAAAAAACGAC | 744 | TDTRKND | 1961 | 108.357 |
| 686 | GACTCTTCACACTACTCGACA | 745 | DSSHYST | 1962 | 108.219 |
| 687 | ACAATGCACCTTCCCAACCTG | 746 | TMHLPNL | 1963 | 108.214 |
| 688 | CGAGACGGCTCTACTAAAGTT | 747 | RDGSTKV | 1964 | 108.207 |
| 689 | TCAGGGTACCAAATGACAGAA | 748 | SGYQMTE | 1965 | 108.16 |
| 690 | TGCGACTTGTCACAATCATGC | 749 | CDLSQSC | 1966 | 108.133 |
| 691 | AGAAACGCGTCAAACGGCGTA | 750 | RNASNGV | 1967 | 108.044 |
| 692 | CAGTCGCAGAATGTGACTCAG | 751 | QSQNVTQ | 1968 | 108.033 |
| 693 | GATTCTGCTCCGAGTACTATT | 752 | DSAPSTI | 1969 | 108.003 |
| 694 | AGGTCCGTACCATCACCACAC | 753 | RSVPSPH | 1970 | 108.001 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 695 | ATGACGTCTGCGTCTCGTGGT | 754 | MTSASRG | 1971 | 107.974 |
| 696 | GCTCTTGCTAGTCGTCCTATG | 755 | ALASRPM | 1972 | 107.907 |
| 697 | CTAAACCTCTCCAACGACTGG | 756 | LNLSNDW | 1973 | 107.899 |
| 698 | GTTTCTACGGCGCAGAGGCAG | 757 | VSTAQRQ | 1974 | 107.896 |
| 699 | CACGCCGACGTTGGCATGAGC | 758 | HADVGMS | 1975 | 107.888 |
| 700 | GCGGGGGGTTTGCTGTCGCGG | 759 | AGGLLSR | 1976 | 107.878 |
| 701 | CATCTTAGTCAGGCTAATCAT | 760 | HLSQANH | 1977 | 107.848 |
| 702 | GTGCATAATCCTACTACTACG | 761 | VHNPTTT | 1978 | 107.8152 |
| 703 | TCTCAGCGGAATCCGGATGAT | 762 | SQRNPDD | 1979 | 107.784 |
| 704 | AGGGAGACTAATAATTTTGCG | 763 | RETNNFA | 1980 | 107.771 |
| 705 | AATGCGGGGGCTCTTATGGGT | 764 | NAGALMG | 1981 | 107.764 |
| 706 | TTGCCGAAGACTGTGAATATG | 765 | LPKTVNM | 1982 | 107.738 |
| 707 | GCAAGTGACCTACAAATGACG | 766 | ASDLQMT | 1983 | 107.723 |
| 708 | CAAGCCCTGGCCACCACAAAC | 767 | QALATTN | 1984 | 107.716 |
| 709 | CATGAGTCGTCTGGTTATCAT | 768 | HESSGYH | 1985 | 107.696 |
| 710 | GGGGTGAATGATCGTGCTAGG | 769 | GVNDRAR | 1986 | 107.69 |
| 711 | CCTCGGGATGCTCTTCGTACT | 770 | PRDALRT | 1987 | 107.673 |
| 712 | AACGACTCCTCGTCAATGTCC | 771 | NDSSSMS | 1988 | 107.641 |
| 713 | GAATACAACACGCGCCACGAC | 772 | EYNTRHD | 1989 | 107.611 |
| 714 | GCGTCTCCGGCGCATACGTCT | 773 | ASPAHTS | 1990 | 107.598 |
| 715 | CAAAACAGCAACACTCCCTCA | 774 | QNSNTPS | 1991 | 107.546 |
| 716 | TTGGCAAAACTAGGGAACTAC | 775 | LAKLGNY | 1992 | 107.541 |
| 717 | GCTAGTGATAGGCAGTCTGGT | 776 | ASDRQSG | 1993 | 107.527 |
| 718 | TATCAGAATGGTGTGCTTCCT | 777 | YQNGVLP | 1994 | 107.5199 |
| 719 | AATAAGTTTGGTTATAATCCT | 778 | NKFGYNP | 1995 | 107.513 |
| 720 | AAAAAAACCAACGGAATCCCC | 779 | KKTNGIP | 1996 | 107.5 |
| 721 | GTTAACGACAACCGAGGAAAC | 780 | VNDNRGN | 1997 | 107.4937 |
| 722 | ATGCACACCATAACGGGATCC | 781 | MHTITGS | 1998 | 107.491 |
| 723 | ATTGATGGTGTTCAGAAGCTT | 782 | IDGVQKL | 1999 | 107.489 |
| 724 | GCGCAGGTTAATAATCATGAT | 783 | AQVNNHD | 2000 | 107.489 |
| 725 | GTTTCTTCGCCTAATGGTACG | 784 | VSSPNGT | 2001 | 107.487 |
| 726 | GATTCTGCTCCGAGGGCTATT | 785 | DSAPRAI | 2002 | 107.455 |
| 727 | TCTGCGAGTGATAGTCAGCAT | 786 | SASDSQH | 2003 | 107.455 |
| 728 | TCGGCTCATCAGACGCCGACG | 787 | SAHQTPT | 2004 | 107.427 |
| 729 | GCGACGCTGAATAATAGTTAT | 788 | ATLNNSY | 2005 | 107.411 |
| 730 | GAAGACAGTATGAGATTCTCT | 789 | EDSMRFS | 2006 | 107.407 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 731 | GAACGAAACGGACTAATAGAA | 790 | ERNGLIE | 2007 | 107.405 |
| 732 | TTAGTACTTGACTCACGGAAC | 791 | LVLDSRN | 2008 | 107.382 |
| 733 | ACCGTCGAACAAATAAACTCG | 792 | TVEQINS | 2009 | 107.349 |
| 734 | GGGACAGGTACCGTTGGATGG | 793 | GTGTVGW | 2010 | 107.203 |
| 735 | AATCAGCAGCGTATTGATAAT | 794 | NQQRIDN | 2011 | 107.185 |
| 736 | ATCCAAAACGGGGTCCTGCCA | 795 | IQNGVLP | 2012 | 107.184 |
| 737 | GGAGACATCTCAAGCAGAAAC | 796 | GDISSRN | 2013 | 107.1386 |
| 738 | GTCACTGGCACTACCCCGGGA | 797 | VTGTTPG | 2014 | 107.137 |
| 739 | ACAAGGGAATCAATGTCCATC | 798 | TRESMSI | 2015 | 107.071 |
| 740 | CACACTTACTCACAAGCAGAC | 799 | HTYSQAD | 2016 | 107.012 |
| 741 | TCCAACATGGGCGTAGCCTCT | 800 | SNMGVAS | 2017 | 106.985 |
| 742 | CACGACTTGAACCACGGAAAA | 801 | HDLNHGK | 2018 | 106.942 |
| 743 | CTGTACGGGGGAGCACACCAA | 802 | LYGGAHQ | 2019 | 106.904 |
| 744 | AACGTGTACGGAGACGGAATA | 803 | NVYGDGI | 2020 | 106.87 |
| 745 | TCTACTATTAATATGCGTGCG | 804 | STINMRA | 2021 | 106.868 |
| 746 | AAGATGGGGAGTATTGAGGTT | 805 | KMGSIEV | 2022 | 106.864 |
| 747 | TCCGAAACGCGCGCTGGATAC | 806 | SETRAGY | 2023 | 106.85 |
| 748 | AATGTGGGTAATACTCTTGGG | 807 | NVGNTLG | 2024 | 106.842 |
| 749 | ATTGGTGGGACTGATACGCGG | 808 | IGGTDTR | 2025 | 106.786 |
| 750 | GCCGACAAAGGATTCGGCCAC | 809 | ADKGFGH | 2026 | 106.73 |
| 751 | TGGCAGGATCATAATAAGGTG | 810 | WQDHNKV | 2027 | 106.719 |
| 752 | AACTACGGTTCCGGACGAATC | 811 | NYGSGRI | 2028 | 106.701 |
| 753 | ACTCATAAGCAGGTGGATCTT | 812 | THKQVDL | 2029 | 106.695 |
| 754 | CGGCAGAATGATAAGGGTAAT | 813 | RQNDKGN | 2030 | 106.658 |
| 755 | GGTAGGAATGAGAGTCCGGAG | 814 | GRNESPE | 2031 | 106.658 |
| 756 | GTTTTTACTGGGCAGACGGAG | 815 | VFTGQTE | 2032 | 106.632 |
| 757 | TATGTTGATCGTAAGGATAAT | 816 | YVDRKDN | 2033 | 106.631 |
| 758 | AATAATACTTTGAATATTTTG | 817 | NNTLNIL | 2034 | 106.63 |
| 759 | TTGAGCTACAGCATCCAACAC | 818 | LSYSIQH | 2035 | 106.621 |
| 760 | GCTACCAACAGATCGCCCCTA | 819 | ATNRSPL | 2036 | 106.5898 |
| 761 | GTTCACACCGCAGACACAATA | 820 | VHTADTI | 2037 | 106.564 |
| 762 | GGGCATTTGGTTAATATGTCT | 821 | GHLVNMS | 2038 | 106.56 |
| 763 | TTAGACTACACCCCTCAAAAC | 822 | LDYTPQN | 2039 | 106.519 |
| 764 | TCCGCCTCTTACTCCAGGATG | 823 | SASYSRM | 2040 | 106.501 |
| 765 | TCCGGAGCGGCACAAAACCCA | 824 | SGAAQNP | 2041 | 106.499 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 766 | AGAAACACACTTGCTGACCTT | 825 | RNTLADL | 2042 | 106.496 |
| 767 | GGTTCTACGGTGTCGGCGCAG | 826 | GSTVSAQ | 2043 | 106.491 |
| 768 | TCTAAGGATAGTACTATGTAT | 827 | SKDSTMY | 2044 | 106.48 |
| 769 | GTGGTGGTTCACACTATCCCA | 828 | VVVHTIP | 2045 | 106.45 |
| 770 | CCACGTACTGTCTCATTGGAC | 829 | PRTVSLD | 2046 | 106.4434 |
| 771 | ATGATGAAGAGTGAGGAGAAT | 830 | MMKSEEN | 2047 | 106.425 |
| 772 | ACCACCGACCGGCCAAACGGA | 831 | TTDRPNG | 2048 | 106.406 |
| 773 | CATAGTCCTCCTACGACTATG | 832 | HSPPTTM | 2049 | 106.376 |
| 774 | GGCCAATGGACAACAGGGACA | 833 | GQWTTGT | 2050 | 106.357 |
| 775 | GACGGTATGAACGGAGTGGGT | 834 | DGMNGVG | 2051 | 106.317 |
| 776 | CTTCATACTGTTGCGAATGAG | 835 | LHTVANE | 2052 | 106.312 |
| 777 | TATACGTCGCAGACGTCTACG | 836 | YTSQTST | 2053 | 106.2842 |
| 778 | AACTTCTCCGAAATGTCCACA | 837 | NFSEMST | 2054 | 106.27 |
| 779 | ATTAATATTCGTAGTGATTTG | 838 | INIRSDL | 2055 | 106.266 |
| 780 | CCCTCCAACAGTGAAAGATTC | 839 | PSNSERF | 2056 | 106.249 |
| 781 | TATACGAATTATGGGGATCTT | 840 | YTNYGDL | 2057 | 106.241 |
| 782 | GATAAGAGTACGGCGCAGGCG | 841 | DKSTAQA | 2058 | 106.238 |
| 783 | CACACCGACATGGTATCCTCT | 842 | HTDMVSS | 2059 | 106.222 |
| 784 | AACAAAAGTCTGTCAATGGAC | 843 | NKSLSMD | 2060 | 106.196 |
| 785 | GGGCACTACGCTACAAACACA | 844 | GHYATNT | 2061 | 106.158 |
| 786 | GTCATCGTATCTACAAAATCA | 845 | VIVSTKS | 2062 | 106.124 |
| 787 | ACTCATAGTCTTATGAATGAT | 846 | THSLMND | 2063 | 106.116 |
| 788 | AACTACCACGGAGACAACGTT | 847 | NYHGDNV | 2064 | 106.106 |
| 789 | CGTGATGATCAGCAGCTTGAT | 848 | RDDQQLD | 2065 | 106.064 |
| 790 | GATGATAAGACTGGTCGGTAT | 849 | DDKTGRY | 2066 | 106.055 |
| 791 | GGGTCGAGCCAACACCACGAA | 850 | GSSQHHE | 2067 | 106.042 |
| 792 | CGTGTTACAGGTGTCTCAACA | 851 | RVTGVST | 2068 | 106.017 |
| 793 | AGTACTGCGTCGGGGCATACT | 852 | STASGHT | 2069 | 106.007 |
| 794 | ACTAACAACCTCTCATACGAA | 853 | TNNLSYE | 2070 | 105.998 |
| 795 | CAGCATAATAGTGCGTCGGCG | 854 | QHNSASA | 2071 | 105.987 |
| 796 | CCGGCTAAGGGTTTTGGTCAT | 855 | PAKGFGH | 2072 | 105.9781 |
| 797 | TGGTACGAAACAATCAGCCCG | 856 | WYETISP | 2073 | 105.959 |
| 798 | ACGGATGCTACGGGGAGGCAT | 857 | TDATGRH | 2074 | 105.942 |
| 799 | ATTCAGGCGAAGAATTCTGAG | 858 | IQAKNSE | 2075 | 105.939 |
| 800 | AGTACTGAGACTAGGGGTGGG | 859 | STETRGG | 2076 | 105.926 |
| 801 | TTCTCAACAAACTCTGTAATC | 860 | FSTNSVI | 2077 | 105.918 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 802 | TCTAACCTTCGAAACACAATA | 861 | SNLRNTI | 2078 | 105.854 |
| 803 | GGGATGATCGGGCACAACGCA | 862 | GMIGHNA | 2079 | 105.832 |
| 804 | TCTGGCCAAGGATTCTCGGCA | 863 | SGQGFSA | 2080 | 105.831 |
| 805 | ACCCACAACTCTACAGGCCTT | 864 | THNSTGL | 2081 | 105.802 |
| 806 | AGGATTGATAGTGCTATGGTG | 865 | RIDSAMV | 2082 | 105.8 |
| 807 | GTCGCTATGGGAGGCGGTCCC | 866 | VAMGGGP | 2083 | 105.795 |
| 808 | GGCTCTCACAACGGCCCAGCC | 867 | GSHNGPA | 2084 | 105.763 |
| 809 | CACTCCGCAGCGGGTGACGGT | 868 | HSAAGDG | 2085 | 105.73 |
| 810 | GCACAAGGCATAACCCACGCT | 869 | AQGITHA | 2086 | 105.711 |
| 811 | TCTGCGCTTTTGCGGATGGAT | 870 | SALLRMD | 2087 | 105.707 |
| 812 | TGGCAAATGGGGGCCGGGAGC | 871 | WQMGAGS | 2088 | 105.698 |
| 813 | ATAGACTCGCACGCCAGCATA | 872 | IDSHASI | 2089 | 105.695 |
| 814 | AGCCTAGACCACGCCCCTCTA | 873 | SLDHAPL | 2090 | 105.661 |
| 815 | GAAAACAACATGCAACACGGC | 874 | ENNMQHG | 2091 | 105.651 |
| 816 | AAGGGTGCGCAGGGTGTTCAG | 875 | KGAQGVQ | 2092 | 105.646 |
| 817 | GTCGCTGTATCGAACACTCCA | 876 | VAVSNTP | 2093 | 105.643 |
| 818 | GTTGAGTCTTCTTATTCTCGG | 877 | VESSYSR | 2094 | 105.633 |
| 819 | CATAATACGGAGTCTAAGACT | 878 | HNTESKT | 2095 | 105.625 |
| 820 | AATGAGAGTACGAAGGAGAGT | 879 | NESTKES | 2096 | 105.599 |
| 821 | GATGTTTATCTTAAGAGTCCG | 880 | DVYLKSP | 2097 | 105.586 |
| 822 | CAGTCGGGGGCTAGGACTCTG | 881 | QSGARTL | 2098 | 105.5854 |
| 823 | TCGAACAGTCAAGTACACAAC | 882 | SNSQVHN | 2099 | 105.573 |
| 824 | GTAGTCTCATCGGGCGGCTGG | 883 | VVSSGGW | 2100 | 105.551 |
| 825 | CCATCAAGTTTCAACAGCGCC | 884 | PSSFNSA | 2101 | 105.542 |
| 826 | AAGCAGACTGATAGTAGGGGT | 885 | KQTDSRG | 2102 | 105.5 |
| 827 | AACACAACGCCACCTAACCAC | 886 | NTTPPNH | 2103 | 105.483 |
| 828 | CAAAACGGAACCTCGTCTATA | 887 | QNGTSSI | 2104 | 105.483 |
| 829 | CTCATGAAAGACATGGAATCC | 888 | LMKDMES | 2105 | 105.458 |
| 830 | ACTCAGACTGGTCATGTTTCT | 889 | TQTGHVS | 2106 | 105.4558 |
| 831 | GAAATACACACGACCACAGGC | 890 | EIHTTTG | 2107 | 105.449 |
| 832 | ATACAAACTACTACAAAATGC | 891 | IQTTTKC | 2108 | 105.442 |
| 833 | CCCGCTGAAGGAAACAACCGT | 892 | PAEGNNR | 2109 | 105.442 |
| 834 | TACATCGCCGGAGGGGAACAA | 893 | YIAGGEQ | 2110 | 105.415 |
| 835 | GAAGTACGCGACCAAAAAACA | 894 | EVRDQKT | 2111 | 105.375 |
| 836 | TACGCCGTCGCGATAGGCACA | 895 | YAVAIGT | 2112 | 105.366 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 837 | TCCGCTAACGAACACAACCAC | 896 | SANEHNH | 2113 | 105.337 |
| 838 | GGGATGAGGGATACGCCGCCG | 897 | GMRDTPP | 2114 | 105.322 |
| 839 | GCTCAGCAGATTGTTAATGGG | 898 | AQQIVNG | 2115 | 105.321 |
| 840 | TCAAGTTCCCAAACGGTTTTG | 899 | SSSQTVL | 2116 | 105.321 |
| 841 | GTTATTCAGTCTGATAATACG | 900 | VIQSDNT | 2117 | 105.32 |
| 842 | GTTCCGGCGCATTCTCGGGGT | 901 | VPAHSRG | 2118 | 105.305 |
| 843 | TCGAATACGGGGTCGTTGGGT | 902 | SNTGSLG | 2119 | 105.2779 |
| 844 | TGGGCCAAAGACGTCAACGTC | 903 | WAKDVNV | 2120 | 105.273 |
| 845 | AATGTGTTGGGTGCTTCGAGT | 904 | NVLGASS | 2121 | 105.187 |
| 846 | ACTCCGGAGGCTAGTGCGCGT | 905 | TPEASAR | 2122 | 105.173 |
| 847 | AATTATAATGGGGTTAATGTG | 906 | NYNGVNV | 2123 | 105.152 |
| 848 | AACACAACCGGTAGCTCGGGC | 907 | NTTGSSG | 2124 | 105.145 |
| 849 | TCCAGCGGCCAACCGCTCGTC | 908 | SSGQPLV | 2125 | 105.136 |
| 850 | CAGGCGGGGGGTGTGGCGAGT | 909 | QAGGVAS | 2126 | 105.133 |
| 851 | CCGCTTCAATCCCAATCGGGA | 910 | PLQSQSG | 2127 | 105.133 |
| 852 | CAACGTACCTCGGAAGCGCCA | 911 | QRTSEAP | 2128 | 105.128 |
| 853 | TTGGCTAAGACGGTTGCGATT | 912 | LAKTVAI | 2129 | 105.1155 |
| 854 | ACCCACACCCTTGGGGGAACA | 913 | THTLGGT | 2130 | 105.08 |
| 855 | CACGACTACAGTATGAACGCG | 914 | HDYSMNA | 2131 | 105.079 |
| 856 | GGGAAACCTGCGGAAGCGCCG | 915 | GKPAEAP | 2132 | 105.055 |
| 857 | AGAAACGAAAACGTAAACGCT | 916 | RNENVNA | 2133 | 105.051 |
| 858 | AGTTCTCGGGAGGCGAAGTTT | 917 | SSREAKF | 2134 | 105.0379 |
| 859 | TCTTCTTCTGATAGTCCGCGT | 918 | SSSDSPR | 2135 | 105.035 |
| 860 | ATGAATACGACTTATAATGAG | 919 | MNTTYNE | 2136 | 105.031 |
| 861 | GTAAGGAGTGGAATAAAACCA | 920 | VRSGIKP | 2137 | 105.008 |
| 862 | CAGGAGAATCCTATGAAGATG | 921 | QENPMKM | 2138 | 104.926 |
| 863 | ACTGAGCCGCTTCCGATGTCT | 922 | TEPLPMS | 2139 | 104.869 |
| 864 | CGCCACGGGGACACACCGATG | 923 | RHGDTPM | 2140 | 104.844 |
| 865 | GCGGTGAATACGTATAATAGT | 924 | AVNTYNS | 2141 | 104.82 |
| 866 | GCGTCGACTGAGTCTCATGTG | 925 | ASTESHV | 2142 | 104.816 |
| 867 | ACAAACCTAAGTCAATCGGCC | 926 | TNLSQSA | 2143 | 104.791 |
| 868 | GAGCTGTCTACTCCTATGGTT | 927 | ELSTPMV | 2144 | 104.783 |
| 869 | TATGCGCATCCTGTGACTCAT | 928 | YAHPVTH | 2145 | 104.76 |
| 870 | CGGGGGTCTACTGGTACGCAG | 929 | RGSTGTQ | 2146 | 104.749 |
| 871 | TGTGTTGGTTCGTGTGGTGTG | 930 | CVGSCGV | 2147 | 104.738 |
| 872 | TCGGTTGCTAAGGATCAGACG | 931 | SVAKDQT | 2148 | 104.736 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 873 | ACGAATCTTTCTCCTAAGACG | 932 | TNLSPKT | 2149 | 104.6855 |
| 874 | CTAGGTTTCACACCCCAACCG | 933 | LGFTPQP | 2150 | 104.677 |
| 875 | AATATTAGTAGTATTAATCAG | 934 | NISSINQ | 2151 | 104.657 |
| 876 | GTTTACGACAACGTTTCTTCT | 935 | VYDNVSS | 2152 | 104.657 |
| 877 | AGTGGAAAACAAGACAAATAC | 936 | SGKQDKY | 2153 | 104.654 |
| 878 | AGACTTACAGAACTGGTCATA | 937 | RLTELVI | 2154 | 104.651 |
| 879 | CATAAGAGTGAGAGTCATAAT | 938 | HKSESHN | 2155 | 104.626 |
| 880 | GAGGCGACTCATGGTTCTTAT | 939 | EATHGSY | 2156 | 104.613 |
| 881 | AACCTACTTGTCGACCAACGT | 940 | NLLVDQR | 2157 | 104.579 |
| 882 | AATATTAATGATACTAAGAAT | 941 | NINDTKN | 2158 | 104.522 |
| 883 | CTTGCGGTTACGAATGTGCGG | 942 | LAVTNVR | 2159 | 104.498 |
| 884 | CCGTCGACACTCGCTGAAACA | 943 | PSTLAET | 2160 | 104.449 |
| 885 | CCGAAGCCTGGGACGGGGGAG | 944 | PKPGTGE | 2161 | 104.427 |
| 886 | GTGCTGTTGCAGAATTCTCAT | 945 | VLLQNSH | 2162 | 104.416 |
| 887 | TACGGTAACGCGAACACCGTA | 946 | YGNANTV | 2163 | 104.386 |
| 888 | ACATCTGGAGTTCTGACACGC | 947 | TSGVLTR | 2164 | 104.375 |
| 889 | AAAATAACGGAAACCAACCTC | 948 | KITETNL | 2165 | 104.359 |
| 890 | GTTCGCAGAGACGAAACACCT | 949 | VRRDETP | 2166 | 104.359 |
| 891 | TCTAAAATGTCAAACCCAGTG | 950 | SKMSNPV | 2167 | 104.352 |
| 892 | TGGGAATCCCTCTCCAACGCA | 951 | WESLSNA | 2168 | 104.349 |
| 893 | GCCAACGGAGGAGGATACCCC | 952 | ANGGGYP | 2169 | 104.34 |
| 894 | ATGTTGGCTTCTCGGGTGCCT | 953 | MLASRVP | 2170 | 104.336 |
| 895 | TGCGGCCTGAACTGCGGTAAA | 954 | CGLNCGK | 2171 | 104.331 |
| 896 | ACTATTACTAGTCCGTCGGTG | 955 | TITSPSV | 2172 | 104.3055 |
| 897 | TGGTCGAATGCTCAGAGTCCG | 956 | WSNAQSP | 2173 | 104.288 |
| 898 | ACAGAAAGCCCCAAACTACTA | 957 | TESPKLL | 2174 | 104.283 |
| 899 | CATTTGGTTACTAGTGGTATT | 958 | HLVTSGI | 2175 | 104.273 |
| 900 | CCTCCTAAGTCGGATTCGAAT | 959 | PPKSDSN | 2176 | 104.265 |
| 901 | ATTGCGGTGCATGTGCTGAGT | 960 | IAVHVLS | 2177 | 104.254 |
| 902 | ACTGGTACTGCGACTTTGCCT | 961 | TGTATLP | 2178 | 104.254 |
| 903 | AATACTACTCCGCCTAATCAT | 962 | NTTPPNH | 2179 | 104.232 |
| 904 | TGCACCGCCACAAAATGCTCA | 963 | CTATKCS | 2180 | 104.23 |
| 905 | CACAGTGACATGGTCAGCGGC | 964 | HSDMVSG | 2181 | 104.208 |
| 906 | CCAAACGCACACCACCTGCCC | 965 | PNAHHLP | 2182 | 104.2 |
| 907 | TCTAATAATATGAATCAGGCG | 966 | SNNMNQA | 2183 | 104.187 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 908 | AGTGATAATAATAGGGCTAAT | 967 | SDNNRAN | 2184 | 104.1865 |
| 909 | TTGCAGACGCCTGGGACGACG | 968 | LQTPGTT | 2185 | 104.169 |
| 910 | GTGCGCGGCGTTCAAGACGCC | 969 | VRGVQDA | 2186 | 104.167 |
| 911 | TCTCTAGACTCGCGCTCCTCG | 970 | SLDSRSS | 2187 | 104.14 |
| 912 | GTTTGTGTTACTACTTGTGCT | 971 | VCVTTCA | 2188 | 104.137 |
| 913 | CCGAATACTAATCATCTTGTG | 972 | PNTNHLV | 2189 | 104.121 |
| 914 | CTCATGTCAGGGAAAGAAAAC | 973 | LMSGKEN | 2190 | 104.109 |
| 915 | ACTTCTGCTAGTGAGAATTGG | 974 | TSASENW | 2191 | 104.108 |
| 916 | TTTTTGCCGCAGCTGGGGCAG | 975 | FLPQLGQ | 2192 | 104.094 |
| 917 | CCTTTTAATCCTGGGAATGTG | 976 | PFNPGNV | 2193 | 104.0922 |
| 918 | GGGACACCTGGTCAAAGTATA | 977 | GTPGQSI | 2194 | 104.092 |
| 919 | TATAATAATGGTGGGCATGTT | 978 | YNNGGHV | 2195 | 104.085 |
| 920 | CTCGGAAACCACTACACACCC | 979 | LGNHYTP | 2196 | 104.064 |
| 921 | CAAGTCAACCAACCGAGAATA | 980 | QVNQPRI | 2197 | 104.061 |
| 922 | TTAGGAAACAACCGGCCACTA | 981 | LGNNRPL | 2198 | 104.06 |
| 923 | CCTCCGGAAAGTGCCAGGGGC | 982 | PPESARG | 2199 | 104.023 |
| 924 | AAATCTGTAGGCGACGGGAGA | 983 | KSVGDGR | 2200 | 104.0009 |
| 925 | TCACTTCGGACGGACGAATTC | 984 | SLRTDEF | 2201 | 103.997 |
| 926 | AGTACTACTAATGTTGCGTAT | 985 | STTNVAY | 2202 | 103.987 |
| 927 | AGGATGTCGGATCCTAGTGAT | 986 | RMSDPSD | 2203 | 103.981 |
| 928 | AGTCTGTCTATTACTTCGGCG | 987 | SLSITSA | 2204 | 103.963 |
| 929 | GAAAGTGCCACATCTCTAAAA | 988 | ESATSLK | 2205 | 103.954 |
| 930 | TACACTGACGGAAGAAACACC | 989 | YTDGRNT | 2206 | 103.949 |
| 931 | TCCATATCCAACCTGCGTACC | 990 | SISNLRT | 2207 | 103.935 |
| 932 | CAAAACGACAAATCTGACAAC | 991 | QNDKSDN | 2208 | 103.9165 |
| 933 | GGTGGAACAGGTCTTTCCAAA | 992 | GGTGLSK | 2209 | 103.916 |
| 934 | AGTCAGGCTCAGATTCGTGTT | 993 | SQAQIRV | 2210 | 103.915 |
| 935 | GGTTTGATGGCGCATGTGACT | 994 | GLMAHVT | 2211 | 103.877 |
| 936 | CTGGTTGTTTCGAATAGTCTG | 995 | LVVSNSL | 2212 | 103.865 |
| 937 | CATGATTCTGTGAATACGGCG | 996 | HDSVNTA | 2213 | 103.8588 |
| 938 | ACTCTTGCGAAGGATGGGAAT | 997 | TLAKDGN | 2214 | 103.842 |
| 939 | TCCGACGGATCGAAACTACTA | 998 | SDGSKLL | 2215 | 103.829 |
| 940 | ATAGACAAAACGTTCTCGGTC | 999 | IDKTFSV | 2216 | 103.812 |
| 941 | CGGCTGGTTAACATCGACCAC | 1000 | RLVNIDH | 2217 | 103.8026 |
| 942 | AAAAACTACGACAGTGACTCA | 1001 | KNYDSDS | 2218 | 103.794 |
| 943 | AGTACGCAGAGTACTAATCCG | 1002 | STQSTNP | 2219 | 103.7868 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 944 | CAAATATCACTACAACTCGGC | 1003 | QISLQLG | 2220 | 103.77 |
| 945 | TCCGAACCCCTTAGAGTTGGA | 1004 | SEPLRVG | 2221 | 103.749 |
| 946 | AGTCGTCTGCAGACTCAGCAG | 1005 | SRLQTQQ | 2222 | 103.7406 |
| 947 | GAAGGTTCACAAGGAAACCAC | 1006 | EGSQGNH | 2223 | 103.739 |
| 948 | CGTTCTGACCTTACTGAAAGT | 1007 | RSDLTES | 2224 | 103.736 |
| 949 | CATACTGGTGTTCAGACTAAT | 1008 | HTGVQTN | 2225 | 103.724 |
| 950 | GAGTTGGATCATCTTTCGCAT | 1009 | ELDHLSH | 2226 | 103.714 |
| 951 | GTTACTGGTGTTGATTATGCG | 1010 | VTGVDYA | 2227 | 103.713 |
| 952 | GGCGGCGCACACACTCGTGTA | 1011 | GGAHTRV | 2228 | 103.676 |
| 953 | GCCTACGGTATACACGAAGTG | 1012 | AYGIHEV | 2229 | 103.653 |
| 954 | GCGATGCTGCGTATGGAGCAG | 1013 | AMLRMEQ | 2230 | 103.652 |
| 955 | AGGCAGGCGAATCAGACGTAT | 1014 | RQANQTY | 2231 | 103.652 |
| 956 | TTTTCTGGTCAGGCGTTGGCT | 1015 | FSGQALA | 2232 | 103.646 |
| 957 | GATAATGTGAATTCTCAGCCT | 1016 | DNVNSQP | 2233 | 103.646 |
| 958 | GGGTTGCATGGGACGAGTAAT | 1017 | GLHGTSN | 2234 | 103.633 |
| 959 | GAGAGGGAGCCTCCTAAGAAT | 1018 | EREPPKN | 2235 | 103.621 |
| 960 | GTGGTGACGCTTGGGATGCTG | 1019 | VVTLGML | 2236 | 103.619 |
| 961 | CATAATAATAATTTGCTGAAT | 1020 | HNNNLLN | 2237 | 103.612 |
| 962 | TTGATTAATATGAGTCAGAAT | 1021 | LINMSQN | 2238 | 103.6 |
| 963 | AATACTAATGCGTCGTATTCT | 1022 | NTNASYS | 2239 | 103.599 |
| 964 | AGGCTTAATGCGGGTGAGCAT | 1023 | RLNAGEH | 2240 | 103.594 |
| 965 | GCTGTTATTCTGAATCCTGTT | 1024 | AVILNPV | 2241 | 103.576 |
| 966 | CCGAGTACTCATGGGTATGTT | 1025 | PSTHGYV | 2242 | 103.571 |
| 967 | CTTAGGGCGTCTGTGTCGGAG | 1026 | LRASVSE | 2243 | 103.564 |
| 968 | ATGATGACCTCTATGACGTTA | 1027 | MMTSMTL | 2244 | 103.561 |
| 969 | TCGGCACACAACATAGTATAC | 1028 | SAHNIVY | 2245 | 103.556 |
| 970 | CACGACAGCACAACCCGCCCA | 1029 | HDSTTRP | 2246 | 103.545 |
| 971 | ATCAAAGACTCGTACCTTACT | 1030 | IKDSYLT | 2247 | 103.542 |
| 972 | TATACGCCTGGGCTTACTGAG | 1031 | YTPGLTE | 2248 | 103.541 |
| 973 | AAGATGGGTGGTTCTCAGAGT | 1032 | KMGGSQS | 2249 | 103.477 |
| 974 | TCACGTCAAACAGCGCTAACA | 1033 | SRQTALT | 2250 | 103.4599 |
| 975 | GTAGAAACCAGCAGATTGTAC | 1034 | VETSRLY | 2251 | 103.45 |
| 976 | AAATCCAACAACGGGGAATAC | 1035 | KSNNGEY | 2252 | 103.424 |
| 977 | TCGGGTGTTCATAGTGCGCGT | 1036 | SGVHSAR | 2253 | 103.3881 |
| 978 | CCTAACAACGAAAAAAACCCG | 1037 | PNNEKNP | 2254 | 103.326 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 979 | ACTATTGGTGAGGGGTATCAT | 1038 | TIGEGYH | 2255 | 103.325 |
| 980 | CTGCAGACTTCTGTTGCTACT | 1039 | LQTSVAT | 2256 | 103.316 |
| 981 | CTATTGGGAAACGCACCCACA | 1040 | LLGNAPT | 2257 | 103.308 |
| 982 | ATTTCGGGGTCTCATTTGAAT | 1041 | ISGSHLN | 2258 | 103.297 |
| 983 | AAGTCTCTTAGTAGTGATGAT | 1042 | KSLSSDD | 2259 | 103.285 |
| 984 | ACGAGGACTCAGGGGACGTCT | 1043 | TRTQGTS | 2260 | 103.2635 |
| 985 | GTTAGTAGGTCTGGGAGTACT | 1044 | VSRSGST | 2261 | 103.257 |
| 986 | AGCGCCGACACCCGGTCCCCC | 1045 | SADTRSP | 2262 | 103.242 |
| 987 | CGTGATACTGCTAATGGGCCG | 1046 | RDTANGP | 2263 | 103.2389 |
| 988 | ATGATGTCTAACAGCCTCGCG | 1047 | MMSNSLA | 2264 | 103.232 |
| 989 | ACTGGGAGGATTGAGCTTAGG | 1048 | TGRIELR | 2265 | 103.214 |
| 990 | GCTAATAATGCGGCTGCGTCG | 1049 | ANNAAAS | 2266 | 103.209 |
| 991 | CAGTTGAATATTAATGATAAG | 1050 | QLNINDK | 2267 | 103.208 |
| 992 | ATGGACGGGGCTCACACGTCA | 1051 | MDGAHTS | 2268 | 103.202 |
| 993 | ACTAGTGCGACTGATTCGATG | 1052 | TSATDSM | 2269 | 103.197 |
| 994 | GCCGCCAGCTTGTCGCAAAGC | 1053 | AASLSQS | 2270 | 103.152 |
| 995 | TCTCAGGCGGGTCTGCTTGTG | 1054 | SQAGLLV | 2271 | 103.116 |
| 996 | ACGACTTATTCGGATCTGAGT | 1055 | TTYSDLS | 2272 | 103.104 |
| 997 | TTCTCCTCCGGAACAACCATA | 1056 | FSSGTTI | 2273 | 103.102 |
| 998 | GTCTTCACAGAAATAGAATCG | 1057 | VFTEIES | 2274 | 103.101 |
| 999 | GCAGACCCCGCTAAAGGCAAA | 1058 | ADPAKGK | 2275 | 103.083 |
| 1000 | AAAGAATCTGAATACAGAGTT | 1059 | KESEYRV | 2276 | 103.07 |
| 1001 | GGGATGGTGTCTCTTAATAGG | 1060 | GMVSLNR | 2277 | 103.06 |
| 1002 | ACCGTTATCGAACGCAAAGAC | 1061 | TVIERKD | 2278 | 103.0575 |
| 1003 | AGGATTGATACGTTGTTGGTG | 1062 | RIDTLLV | 2279 | 103.055 |
| 1004 | GGATCCACAGGCCTACCCCCG | 1063 | GSTGLPP | 2280 | 103.047 |
| 1005 | ATGGAGTTGACTTCTACTAGT | 1064 | MELTSTS | 2281 | 103.026 |
| 1006 | CAACCAGGAGCCCCCCAAACC | 1065 | QPGAPQT | 2282 | 103.014 |
| 1007 | AATTCGATGGGTAATGGGGGT | 1066 | NSMGNGG | 2283 | 103.009 |
| 1008 | GGTAGTACTAAGTCTGGGCAG | 1067 | GSTKSGQ | 2284 | 103.0049 |
| 1009 | ACTTTTTTGCCTCAGCTTGGG | 1068 | TFLPQLG | 2285 | 102.994 |
| 1010 | ATGGGAATAAACGTACTGAGC | 1069 | MGINVLS | 2286 | 102.986 |
| 1011 | GTGAATCTTGGTATTTCGGGG | 1070 | VNLGISG | 2287 | 102.985 |
| 1012 | AGTGAGAATCGGGCTGGTAAT | 1071 | SENRAGN | 2288 | 102.945 |
| 1013 | CACTCCAACGCGACTACGATA | 1072 | HSNATTI | 2289 | 102.916 |
| 1014 | CCGGGGTCGTCCGCTTCCATC | 1073 | PGSSASI | 2290 | 102.914 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 1015 | ATTACGTCGTTGAATGGGATG | 1074 | ITSLNGM | 2291 | 102.909 |
| 1016 | TATCTGGAGGGTGCTCATCGT | 1075 | YLEGAHR | 2292 | 102.896 |
| 1017 | AGGCAGGTTGAGCAGTCTGAT | 1076 | RQVEQSD | 2293 | 102.889 |
| 1018 | AGCTCTCAAAGTTCCGGGTCG | 1077 | SSQSSGS | 2294 | 102.8836 |
| 1019 | CAGCTTACTGTTGGGAAGCCG | 1078 | QLTVGKP | 2295 | 102.8762 |
| 1020 | GTTGTGCATTCGAGTATTACT | 1079 | VVHSSIT | 2296 | 102.8257 |
| 1021 | CTAGAACAACTACGGGTCCCA | 1080 | LEQLRVP | 2297 | 102.815 |
| 1022 | CAGCATTCTCCGAAGCCGGTT | 1081 | QHSPKPV | 2298 | 102.81 |
| 1023 | GCGGGCAGTTCGCCATCACGC | 1082 | AGSSPSR | 2299 | 102.8035 |
| 1024 | GGAGTAACAATCGGTAGCAGG | 1083 | GVTIGSR | 2300 | 102.7752 |
| 1025 | TACATCGCGGGAGGCGACCAA | 1084 | YIAGGDQ | 2301 | 102.75 |
| 1026 | ATTAGTAGTGAGAGGTTTTCT | 1085 | ISSERFS | 2302 | 102.729 |
| 1027 | AGGAGTGAGGGTAATCATGCT | 1086 | RSEGNHA | 2303 | 102.719 |
| 1028 | GAGAAGGGGAATAGTGGGGTT | 1087 | EKGNSGV | 2304 | 102.71 |
| 1029 | TACATAGTTGACCACGCTAAC | 1088 | YIVDHAN | 2305 | 102.71 |
| 1030 | CGTCGGTTGAGTACGGATCTT | 1089 | RRLSTDL | 2306 | 102.702 |
| 1031 | GCGAATAGTAGGCTTGGGGCG | 1090 | ANSRLGA | 2307 | 102.6979 |
| 1032 | GGTACTGCTGAGAATACGAGT | 1091 | GTAENTS | 2308 | 102.696 |
| 1033 | GTGAGGGATGTTGCTAAGGAG | 1092 | VRDVAKE | 2309 | 102.691 |
| 1034 | GGAGGCCTTACCAACGGTCTA | 1093 | GGLTNGL | 2310 | 102.67 |
| 1035 | CCTTCGATTCCGTCGTTTTCG | 1094 | PSIPSFS | 2311 | 102.657 |
| 1036 | AACGCTCTCCTCAACGCACCT | 1095 | NALLNAP | 2312 | 102.628 |
| 1037 | GACGACATGGTCAAAAACTCA | 1096 | DDMVKNS | 2313 | 102.623 |
| 1038 | ACTGCGAATACGCATGCTCTG | 1097 | TANTHAL | 2314 | 102.613 |
| 1039 | GTATACGCCACCGCACTCGCA | 1098 | VYATALA | 2315 | 102.611 |
| 1040 | GGTATATACCCGGCATCCACC | 1099 | GIYPAST | 2316 | 102.61 |
| 1041 | GGTTTTGATGGTAAGCAGCTT | 1100 | GFDGKQL | 2317 | 102.606 |
| 1042 | CACTCTATGTCCGCAAACACC | 1101 | HSMSANT | 2318 | 102.605 |
| 1043 | TGGAGCATCAAAAACCAAACA | 1102 | WSIKNQT | 2319 | 102.586 |
| 1044 | ACCCTCCACACCAAAGACCTA | 1103 | TLHTKDL | 2320 | 102.57 |
| 1045 | TCTTATGGTAATACTCATGAT | 1104 | SYGNTHD | 2321 | 102.566 |
| 1046 | CAGTCGGGGTCTCTGGTGCCG | 1105 | QSGSLVP | 2322 | 102.552 |
| 1047 | AATACTTTGCAGAATAGTCAT | 1106 | NTLQNSH | 2323 | 102.5506 |
| 1048 | ACGGCTGAGTCTAGTCATCCG | 1107 | TAESSHP | 2324 | 102.548 |
| 1049 | GCCTCTACAGTCTCACTCTAC | 1108 | ASTVSLY | 2325 | 102.547 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 1050 | CTGACTGCTGTTGCGATTAGT | 1109 | LTAVAIS | 2326 | 102.542 |
| 1051 | GTCTCGGGACAAAGTGCGTAC | 1110 | VSGQSAY | 2327 | 102.541 |
| 1052 | GGTGAAACTAACTTCCCAACT | 1111 | GETNFPT | 2328 | 102.532 |
| 1053 | AATGATAATAGGTCGATGAAT | 1112 | NDNRSMN | 2329 | 102.526 |
| 1054 | CGATCAGGCGACCCTAAAAAC | 1113 | RSGDPKN | 2330 | 102.519 |
| 1055 | TGGGAGAGTGATAAGTTTCGT | 1114 | WESDKFR | 2331 | 102.514 |
| 1056 | CAGGTTAATCATAATACTAGT | 1115 | QVNHNTS | 2332 | 102.514 |
| 1057 | GGGTGGTCGAACAACGAACTA | 1116 | GWSNNEL | 2333 | 102.507 |
| 1058 | CGGGCTGTGCTTGCGACTAAT | 1117 | RAVLATN | 2334 | 102.49 |
| 1059 | CATATGGGTTTGAATGAGCTT | 1118 | HMGLNEL | 2335 | 102.484 |
| 1060 | GGAGAAAGCTCCTCAATAAGC | 1119 | GESSSIS | 2336 | 102.477 |
| 1061 | ATACACAAATCTAGCGTCGAA | 1120 | IHKSSVE | 2337 | 102.473 |
| 1062 | ATGTCCGGATCCATGATATCA | 1121 | MSGSMIS | 2338 | 102.463 |
| 1063 | TTGAGTCTGGCTGGGAATAGG | 1122 | LSLAGNR | 2339 | 102.448 |
| 1064 | TCTGCAACAACGAACCACGGA | 1123 | SATTNHG | 2340 | 102.441 |
| 1065 | TCTACGGAGTCTAATGCTAGT | 1124 | STESNAS | 2341 | 102.43 |
| 1066 | CCGATTGCTGAGAGGCCTTCT | 1125 | PIAERPS | 2342 | 102.428 |
| 1067 | TTACTTCCAAACAACACCCAC | 1126 | LLPNNTH | 2343 | 102.424 |
| 1068 | GGGACTCTTAAGAAGGATGCG | 1127 | GTLKKDA | 2344 | 102.412 |
| 1069 | GCTCTTGAGAATCGGAGTCTG | 1128 | ALENRSL | 2345 | 102.408 |
| 1070 | ACCACCGGGAACTCCACGATG | 1129 | TTGNSTM | 2346 | 102.383 |
| 1071 | GTGTATGATAGTGCGCCTAAT | 1130 | VYDSAPN | 2347 | 102.366 |
| 1072 | CTACTATCTAAAGGGGACTCC | 1131 | LLSKGDS | 2348 | 102.346 |
| 1073 | TCTTACGCCATAAACCAATCA | 1132 | SYAINQS | 2349 | 102.335 |
| 1074 | GGAGGAGGGGAACGTTCCACG | 1133 | GGGERST | 2350 | 102.323 |
| 1075 | ATTCAGGTTAGTGGTAGTCAG | 1134 | IQVSGSQ | 2351 | 102.315 |
| 1076 | TATCCTGTTTCGCTTTCGCCG | 1135 | YPVSLSP | 2352 | 102.312 |
| 1077 | GAGTTGGGTAATAAGACGGCT | 1136 | ELGNKTA | 2353 | 102.311 |
| 1078 | TCGGGGGTAAACTTCGGAGTA | 1137 | SGVNFGV | 2354 | 102.287 |
| 1079 | GCGTGGAGTTCGCCGAGTGGG | 1138 | AWSSPSG | 2355 | 102.285 |
| 1080 | GGTGTGAATTATCATACTACG | 1139 | GVNYHTT | 2356 | 102.261 |
| 1081 | CTGATTGGGGAGCTTAAGATG | 1140 | LIGELKM | 2357 | 102.255 |
| 1082 | TATCTGAATAGTAAGCAGCTT | 1141 | YLNSKQL | 2358 | 102.212 |
| 1083 | ACTGTTGATAGGCCGATTGTG | 1142 | TVDRPIV | 2359 | 102.191 |
| 1084 | GTCAGCAAAACCAAAGACTCG | 1143 | VSKTKDS | 2360 | 102.184 |
| 1085 | CAAGCTGGGAACGCGCCAAGG | 1144 | QAGNAPR | 2361 | 102.1806 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 1086 | CAAGACCAAACGAGCAACCGT | 1145 | QDQTSNR | 2362 | 102.177 |
| 1087 | GATACTACGTATCGGAATACT | 1146 | DTTYRNT | 2363 | 102.173 |
| 1088 | GGGACAACCGAAGTTAACAAA | 1147 | GTTEVNK | 2364 | 102.17 |
| 1089 | GGGTTTACTAATACGAGTAAG | 1148 | GFTNTSK | 2365 | 102.152 |
| 1090 | GTGCAGAAGAATGATGTGCTT | 1149 | VQKNDVL | 2366 | 102.14 |
| 1091 | AGCGTCAACAACATGCGACTC | 1150 | SVNNMRL | 2367 | 102.1324 |
| 1092 | TTCAGTGCCGCCTTACCGTTA | 1151 | FSAALPL | 2368 | 102.13 |
| 1093 | GACGTCCCAAACAACAAAAGG | 1152 | DVPNNKR | 2369 | 102.126 |
| 1094 | GGTGAGACTATGCGTCATAAT | 1153 | GETMRHN | 2370 | 102.119 |
| 1095 | ATTCGGACTTCTGTGATTAAT | 1154 | IRTSVIN | 2371 | 102.103 |
| 1096 | CCGCGTGCTCCTGGTCATAAT | 1155 | PRAPGHN | 2372 | 102.101 |
| 1097 | AGTGTTGCGCATCCTTTGTCT | 1156 | SVAHPLS | 2373 | 102.101 |
| 1098 | ATGACAATAACCGTCGAACCG | 1157 | MTITVEP | 2374 | 102.096 |
| 1099 | CCATTAAACGCGAACGGCTCC | 1158 | PLNANGS | 2375 | 102.094 |
| 1100 | AATAGGCAGCGGGATTTTGAG | 1159 | NRQRDFE | 2376 | 102.073 |
| 1101 | GATATTCATAATCCGCGTACG | 1160 | DIHNPRT | 2377 | 102.073 |
| 1102 | TGGATAGCAGGAAACCACTCC | 1161 | WIAGNHS | 2378 | 102.07 |
| 1103 | TCTACTCATCATGCTGATCGT | 1162 | STHHADR | 2379 | 102.069 |
| 1104 | CCGGAATCCGCCGCCAAAAGC | 1163 | PESAAKS | 2380 | 102.058 |
| 1105 | CACTCCGACAAAGTCTCCTCA | 1164 | HSDKVSS | 2381 | 102.051 |
| 1106 | TCAAACAGCGCCGACGCGGGG | 1165 | SNSADAG | 2382 | 102.047 |
| 1107 | GAGTTTCAGAGGATTCGTGAG | 1166 | EFQRIRE | 2383 | 102.039 |
| 1108 | TCCGCGGGGATGACATTGGAC | 1167 | SAGMTLD | 2384 | 102.016 |
| 1109 | ACTCAAACTTCTACCTGGACC | 1168 | TQTSTWT | 2385 | 102.009 |
| 1110 | ACGACACTAACGCAAACGGAC | 1169 | TTLTQTD | 2386 | 102.003 |
| 1111 | GCCTCGAAAGGCTTCGGCCAC | 1170 | ASKGFGH | 2387 | 101.991 |
| 1112 | CCGGCTACGATGATTAGTGAG | 1171 | PATMISE | 2388 | 101.985 |
| 1113 | ACTGACTCATCTGCAGACTCC | 1172 | TDSSADS | 2389 | 101.981 |
| 1114 | TCAACCAGAAAAGAACACGAC | 1173 | STRKEHD | 2390 | 101.98 |
| 1115 | GGTGATATTTCTTATAGGGTT | 1174 | GDISYRV | 2391 | 101.977 |
| 1116 | ATGGGGTATGTTGATAGTCTG | 1175 | MGYVDSL | 2392 | 101.953 |
| 1117 | CAAACCATCACCTCACAAATG | 1176 | QTITSQM | 2393 | 101.941 |
| 1118 | TCGATTGGGTATTCGCCTCCG | 1177 | SIGYSPP | 2394 | 101.939 |
| 1119 | TCATCCCCAGACTCGTACAGA | 1178 | SSPDSYR | 2395 | 101.921 |
| 1120 | ATTAGTCCGAGTGCTTCTAAT | 1179 | ISPSASN | 2396 | 101.855 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 1121 | TATCCGGCTGATCATCGGACT | 1180 | YPADHRT | 2397 | 101.85 |
| 1122 | CACACCGGCCAAACACCATCA | 1181 | HTGQTPS | 2398 | 101.837 |
| 1123 | CAGACGACTATTCTGGCTGCT | 1182 | QTTILAA | 2399 | 101.837 |
| 1124 | GATGGTACGAGGCAGGTTCAT | 1183 | DGTRQVH | 2400 | 101.836 |
| 1125 | AGGAGTAGTCCTGCGACGAAT | 1184 | RSSPATN | 2401 | 101.829 |
| 1126 | GCGATGAGTCATACGTATAAG | 1185 | AMSHTYK | 2402 | 101.813 |
| 1127 | ATGGCGGCTCCGCCGGAGCAT | 1186 | MAAPPEH | 2403 | 101.802 |
| 1128 | GGTCCTAGTACTTCGGAGGCG | 1187 | GPSTSEA | 2404 | 101.794 |
| 1129 | CATAATCATGATAGGTCGTCT | 1188 | HNHDRSS | 2405 | 101.7829 |
| 1130 | GTGGTCCCATCGACCCAAGCA | 1189 | VVPSTQA | 2406 | 101.781 |
| 1131 | ATTCCTGTGACTACTCGTAAT | 1190 | IPVTTRN | 2407 | 101.722 |
| 1132 | AACCAACTCGTACGCGGGACA | 1191 | NQLVRGT | 2408 | 101.717 |
| 1133 | GGGTTTGCGCTTACGGGTACG | 1192 | GFALTGT | 2409 | 101.696 |
| 1134 | TCTAAGGGTGGTGATATGGTG | 1193 | SKGGDMV | 2410 | 101.666 |
| 1135 | GCTCGACCAGGCCAATCTATG | 1194 | ARPGQSM | 2411 | 101.6287 |
| 1136 | AAAGCAGACTACGAATCCTCC | 1195 | KADYESS | 2412 | 101.626 |
| 1137 | GGACCAAGTTCGCACATCGTT | 1196 | GPSSHIV | 2413 | 101.616 |
| 1138 | GAAGTTGTCAAAACCACGCAC | 1197 | EVVKTTH | 2414 | 101.61 |
| 1139 | ACTTTGGATAATAATCATTCT | 1198 | TLDNNHS | 2415 | 101.604 |
| 1140 | ACGATTTATAATATGGGTCCG | 1199 | TIYNMGP | 2416 | 101.599 |
| 1141 | TCTACCATGAACACGATCACG | 1200 | STMNTIT | 2417 | 101.597 |
| 1142 | ACGCTGGCGCGGACTACTGAG | 1201 | TLARTTE | 2418 | 101.581 |
| 1143 | TTGATTTCTTCGCAGACTTCT | 1202 | LISSQTS | 2419 | 101.553 |
| 1144 | CAGACTGCGTCTGGTGATACT | 1203 | QTASGDT | 2420 | 101.497 |
| 1145 | GCGCATGGTGCTTTTCCGGTT | 1204 | AHGAFPV | 2421 | 101.495 |
| 1146 | GGGGAGACGCGGTCGACTGCT | 1205 | GETRSTA | 2422 | 101.494 |
| 1147 | AACAACTACGCCTACTCCGCT | 1206 | NNYAYSA | 2423 | 101.493 |
| 1148 | GAGGCTTATCAGACTGAGAAG | 1207 | EAYQTEK | 2424 | 101.49 |
| 1149 | TCTCTAGCACACGCCGTAAGC | 1208 | SLAHAVS | 2425 | 101.485 |
| 1150 | ACGTATCAGTTGAGTGGGAAT | 1209 | TYQLSGN | 2426 | 101.452 |
| 1151 | ATGAGCGAAAGGTTGCGGATA | 1210 | MSERLRI | 2427 | 101.431 |
| 1152 | GGGTCGGGGAAAGACCCAGGG | 1211 | GSGKDPG | 2428 | 101.43 |
| 1153 | TACAACAGCAACGCTTCTGTA | 1212 | YNSNASV | 2429 | 101.428 |
| 1154 | ACGAGGGGTGATATGGAGTTT | 1213 | TRGDMEF | 2430 | 101.424 |
| 1155 | GGAATCACCGGAAGCCCCGGC | 1214 | GITGSPG | 2431 | 101.42 |
| 1156 | CAACACACCGCCCACCCCATG | 1215 | QHTAHPM | 2432 | 101.416 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 1157 | GATACGGCGAATCGTTCGACT | 1216 | DTANRST | 2433 | 101.407 |
| 1158 | TCGGCACACGACGCAAGACTA | 1217 | SAHDARL | 2434 | 101.387 |
| 1159 | CTTAATCATACTCTGGGGCAT | 1218 | LNHTLGH | 2435 | 101.385 |
| 1160 | GGGTTTGAGACGAGTAGTCCT | 1219 | GFETSSP | 2436 | 101.369 |
| 1161 | GGTACGAGTGCGGAGAGTCGG | 1220 | GTSAESR | 2437 | 101.366 |
| 1162 | CATGCTAATTATGTTGAGGTG | 1221 | HANYVEV | 2438 | 101.345 |
| 1163 | ACAACGAAACCGGTCGCGGAA | 1222 | TTKPVAE | 2439 | 101.338 |
| 1164 | TCGACCGCCGTTACTAACTCA | 1223 | STAVTNS | 2440 | 101.304 |
| 1165 | CTGGGGCTTGCTGGTCAGGTT | 1224 | LGLAGQV | 2441 | 101.304 |
| 1166 | GTGCTTAAGGGTACGTTTCCG | 1225 | VLKGTFP | 2442 | 101.298 |
| 1167 | ATGAATGAGCCTGGTAGGACG | 1226 | MNEPGRT | 2443 | 101.283 |
| 1168 | ACTTCTGATCCTTTGAGGAAT | 1227 | TSDPLRN | 2444 | 101.252 |
| 1169 | CGTGATACTAATACGGATAAG | 1228 | RDTNTDK | 2445 | 101.234 |
| 1170 | GAGTCTGATTTGCGTCAGCGG | 1229 | ESDLRQR | 2446 | 101.225 |
| 1171 | TCCGGAATGGCCGGCCTTTCC | 1230 | SGMAGLS | 2447 | 101.211 |
| 1172 | ATAGCAACAACGTCTGGGCGG | 1231 | IATTSGR | 2448 | 101.21 |
| 1173 | ACGATTAGGAGTGAGGGTTTT | 1232 | TIRSEGF | 2449 | 101.202 |
| 1174 | GGTCTGTCTATTACTATTGCG | 1233 | GLSITIA | 2450 | 101.176 |
| 1175 | CCGCCTACTAATGGGCGTATG | 1234 | PPTNGRM | 2451 | 101.17 |
| 1176 | CTACAAGACCGGGCAACGAAC | 1235 | LQDRATN | 2452 | 101.165 |
| 1177 | CTTAAATCGACCGGTGACCAC | 1236 | LKSTGDH | 2453 | 101.132 |
| 1178 | GATAATAATAATCAGGTTTAT | 1237 | DNNNQVY | 2454 | 101.13 |
| 1179 | GTGCATATGGAGTCGTATGCG | 1238 | VHMESYA | 2455 | 101.111 |
| 1180 | GACCAAATAGGGCACGGAACA | 1239 | DQIGHGT | 2456 | 101.106 |
| 1181 | GGGACGGGGCCGCATGGTACT | 1240 | GTGPHGT | 2457 | 101.0712 |
| 1182 | ATTGGGAATAATACTGGTCTT | 1241 | IGNNTGL | 2458 | 101.0529 |
| 1183 | TTAAACGCAGAATACACCAAC | 1242 | LNAEYTN | 2459 | 101.047 |
| 1184 | GTGACGTCGTCTGCTAGTGGT | 1243 | VTSSASG | 2460 | 101.027 |
| 1185 | ACGCATGTTGCTAAGCCTGAT | 1244 | THVAKPD | 2461 | 101.017 |
| 1186 | CCGATGAACAAAGACATACTG | 1245 | PMNKDIL | 2462 | 100.9906 |
| 1187 | CTTAGTTTGAATATGAATGAG | 1246 | LSLNMNE | 2463 | 100.99 |
| 1188 | GTCGGCAACTCAAGCACTCAC | 1247 | VGNSSTH | 2464 | 100.99 |
| 1189 | GGCCACGGAAGTGACTTGACC | 1248 | GHGSDLT | 2465 | 100.9576 |
| 1190 | CTTACACAAAACCCAACGAAC | 1249 | LTQNPTN | 2466 | 100.934 |
| 1191 | CCGAGTGATCATATGCGGACT | 1250 | PSDHMRT | 2467 | 100.8849 |

TABLE 1-continued

CK8 Results mRNA Second Round of Capsid Variant Selection in C57BL6 mice-score capped at 100

| Variant ID | Nucleotide Sequence | SEQ ID NO: | Amino Acid Sequence | SEQ ID NO: | Sum of muscle mRNA score_capped at 100 |
|---|---|---|---|---|---|
| 1192 | CCTGATAGTCGTTTGGCGGCT | 1251 | PDSRLAA | 2468 | 100.843 |
| 1193 | TGGGGTAGTGAGGGGACGATT | 1252 | WGSEGTI | 2469 | 100.84 |
| 1194 | AAACCGACAAACGACTCGTAC | 1253 | KPTNDSY | 2470 | 100.821 |
| 1195 | AACCGCGGAACAGAAGTTTAC | 1254 | NRGTEVY | 2471 | 100.8147 |
| 1196 | CACGTGATCACAACAAAAGAC | 1255 | HVITTKD | 2472 | 100.7896 |
| 1197 | ATTGTGTCTAATCCGCCGGCG | 1256 | IVSNPPA | 2473 | 100.76 |
| 1198 | ATGCGTAACGACCAACAACTT | 1257 | MRNDQQL | 2474 | 100.7503 |
| 1199 | TTTCAGCGTGATGTTGGTCAT | 1258 | FQRDVGH | 2475 | 100.7392 |
| 1200 | GCCAACGACAACACCAAACAA | 1259 | ANDNTKQ | 2476 | 100.7364 |
| 1201 | TCTGTTCCGCATGCGGGGGAT | 1260 | SVPHAGD | 2477 | 100.7276 |
| 1202 | AATGCTACTCCGCCGAATCAT | 1261 | NATPPNH | 2478 | 100.6678 |
| 1203 | TCAGAACACACATCAGTTCTA | 1262 | SEHTSVL | 2479 | 100.64 |
| 1204 | GCCATGTCCCAAACGGACATC | 1263 | AMSQTDI | 2480 | 100.628 |
| 1205 | CCTAAGGCTCCGCTTAATAAT | 1264 | PKAPLNN | 2481 | 100.627 |
| 1206 | ACCAACAACTTACTCGCACAA | 1265 | TNNLLAQ | 2482 | 100.55 |
| 1207 | CAGCGTCAGGGTTCGGGGGTT | 1266 | QRQGSGV | 2483 | 100.5318 |
| 1208 | CGCAGTGACACCACTAACGCC | 1267 | RSDTTNA | 2484 | 100.51 |
| 1209 | GAGGCTGATAAGAATGGTGTT | 1268 | EADKNGV | 2485 | 100.386 |
| 1210 | ATGCTGGGGGGTTTTGCGCAG | 1269 | MLGGFAQ | 2486 | 100.3622 |
| 1211 | ATGACACACCTCAGCACAGAC | 1270 | MTHLSTD | 2487 | 100.267 |
| 1212 | GTTTTGTCTGATAAGGCGTTT | 1271 | VLSDKAF | 2488 | 100.231 |
| 1213 | ACACCCTCCGGTACCATAAAA | 1272 | TPSGTIK | 2489 | 100.22 |
| 1214 | ATTATTCTTATGGGTCAGAGT | 1273 | IILMGQS | 2490 | 100.213 |
| 1215 | CTTTCGGGGGGTGAGACTCTT | 1274 | LSGGETL | 2491 | 100.154 |
| 1216 | ACCGACGGCGCCCTGGGTTAC | 1275 | TDGALGY | 2492 | 100.129 |
| 1217 | GGGAATAAGGCTGCGCTGACG | 1276 | GNKAALT | 2493 | 100.066 |

TABLE 2

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 1 | AGAGGAGACTTGACAACCCCA | 2494 | RGDLTTP | 3737 | 576.12 |
| 2 | CGGGGTGATCTTAATCAGTAT | 2495 | RGDLNQY | 3738 | 496.41 |
| 3 | AGGGGTGATCTTTCTACGCCT | 2496 | RGDLSTP | 3739 | 475.909 |
| 4 | CGGGGTGATCAGCTTTATCAT | 2497 | RGDQLYH | 3740 | 460.578 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 5 | CGAGGAGACACCATGAGCAAA | 2498 | RGDTMSK | 3741 | 439.771 |
| 6 | AGGGGGGATGCGACGGAGCTT | 2499 | RGDATEL | 3742 | 429.74 |
| 7 | AGAGGCGACTTATCCACACCC | 2500 | RGDLSTP | 3743 | 429.182 |
| 8 | CGCGGCGACATGATAAACACC | 2501 | RGDMINT | 3744 | 397.62 |
| 9 | AGGGGCGACCTGAACCAATAC | 2502 | RGDLNQY | 3745 | 388.417 |
| 10 | CGGGGGGATACTATGTCTAAG | 2503 | RGDTMSK | 3746 | 352.268 |
| 11 | CGGGGTGATCTTACTACGCCT | 2504 | RGDLTTP | 3747 | 320.042 |
| 12 | AGGGGCGACCTCAACGACAGC | 2505 | RGDLNDS | 3748 | 315.615 |
| 13 | GCAAACCCCAACATACTAGAC | 2506 | ANPNILD | 3749 | 302.02 |
| 14 | CGAGGCGACACAATGAACTAC | 2507 | RGDTMNY | 3750 | 285.332 |
| 15 | ATGAGTAATTTGGGGTATGAG | 2508 | MSNLGYE | 3751 | 270.74 |
| 16 | TACACCTCTCAAACCAGCACT | 2509 | YTSQTST | 3752 | 256.544 |
| 17 | CTCGGAGGAAACAGCAGGTTC | 2510 | LGGNSRF | 3753 | 255.425 |
| 18 | CAAAGCCAAGCGATACAACTA | 2511 | QSQAIQL | 3754 | 254.191 |
| 19 | AACACGTACACACCGGGAAAA | 2512 | NTYTPGK | 3755 | 239.565 |
| 20 | GGGGCGGAAGCGGGCCGCCAA | 2513 | GAEAGRQ | 3756 | 237.2829 |
| 21 | GAACACGCTACAGCAAAACAA | 2514 | EHATAKQ | 3757 | 236.826 |
| 22 | GCGGCACAACTCGTCAGTCCA | 2515 | AAQLVSP | 3758 | 225.034 |
| 23 | GATCAGACGGCTAGTATTGTT | 2516 | DQTASIV | 3759 | 224.832 |
| 24 | GTTCAAACCCACATAGGAGTC | 2517 | VQTHIGV | 3760 | 224.306 |
| 25 | TCTTATGGTAATACTCATGAT | 2518 | SYGNTHD | 3761 | 224.26 |
| 26 | ACCTCCACGGCTTCAAAACAA | 2519 | TSTASKQ | 3762 | 221.617 |
| 27 | TTGGTGACTCATGAGCGGATT | 2520 | LVTHERI | 3763 | 219.227 |
| 28 | ATGGATAAGTCTAATAATTCT | 2521 | MDKSNNS | 3764 | 216.638 |
| 29 | CGTGGTGATATGTCTCGTGAG | 2522 | RGDMSRE | 3765 | 214.708 |
| 30 | CGCGGTGACGTGGCAGAAATA | 2523 | RGDVAEI | 3766 | 212.967 |
| 31 | GGTGGCGAAAACAGAACCCCA | 2524 | GGENRTP | 3767 | 210.4 |
| 32 | GCTGGGCATCAGCAGCTTGCT | 2525 | AGHQQLA | 3768 | 210.1746 |
| 33 | CGTCTTAATAGTAGTATGAAT | 2526 | RLNSSMN | 3769 | 209.449 |
| 34 | TATTATGAGAAGCTTAGTGCG | 2527 | YYEKLSA | 3770 | 209.263 |
| 35 | GAAGCGTCCAACTACGAACGA | 2528 | EASNYER | 3771 | 209.09 |
| 36 | TTCCAAACTGACACGCACCGA | 2529 | FQTDTHR | 3772 | 208.95 |
| 37 | AACAGTTCCCAATGGCCCAAC | 2530 | NSSQWPN | 3773 | 208.638 |
| 38 | GATGGTAAGACTACGTCTAAT | 2531 | DGKTTSN | 3774 | 207.638 |
| 39 | GCTGTGCATGCGACTAGTAGT | 2532 | AVHATSS | 3775 | 205.952 |
| 40 | AAAACACTCCCCGGCAGGGAA | 2533 | KTLPGRE | 3776 | 205.926 |
| 41 | ATACTGAAATCCGACGCACCA | 2534 | ILKSDAP | 3777 | 204.523 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 42 | AGTACGAATGAGGCTCCTAAG | 2535 | STNEAPK | 3778 | 204.522 |
| 43 | TTTGATAGTGCGAATGGTCGG | 2536 | FDSANGR | 3779 | 203.996 |
| 44 | ATGGACGCTGCGTACGGTAGT | 2537 | MDAAYGS | 3780 | 203.401 |
| 45 | AACAAAGACCACAACCACCTG | 2538 | NKDHNHL | 3781 | 202.878 |
| 46 | GGTCAGTATAGTCAGACGCTT | 2539 | GQYSQTL | 3782 | 202.553 |
| 47 | GAAGCATTCCCGCGAGCGGGC | 2540 | EAFPRAG | 3783 | 202.275 |
| 48 | GAACACACTCACTTAAACCCG | 2541 | EHTHLNP | 3784 | 201.959 |
| 49 | ATGCAACGCGAAGACGCGAAC | 2542 | MQREDAN | 3785 | 201.523 |
| 50 | CTAACCGGCTCTGACATGAAA | 2543 | LTGSDMK | 3786 | 200.376 |
| 51 | CGAGTAAACAACGACGCAATA | 2544 | RVNNDAI | 3787 | 200 |
| 52 | CGTGGTGACCAAGGCACACAC | 2545 | RGDQGTH | 3788 | 200 |
| 53 | ATTAATATTAGTAGTGATTTT | 2546 | INISSDF | 3789 | 200 |
| 54 | AATAATGATAATGGTTTTGTT | 2547 | NNDNGFV | 3790 | 200 |
| 55 | TTCATCGCTAACACTAACCCA | 2548 | FIANTNP | 3791 | 200 |
| 56 | GGACTGCACGGCACCAACGCA | 2549 | GLHGTNA | 3792 | 200 |
| 57 | AAAACCATCGACATAGCACAA | 2550 | KTIDIAQ | 3793 | 200 |
| 58 | TCGAGTGATTCTCGTATTCCG | 2551 | SSDSRIP | 3794 | 200 |
| 59 | TCTACATCTCCGGTTAACAGC | 2552 | STSPVNS | 3795 | 200 |
| 60 | GCCAGCATGCCCTCTGTAGAC | 2553 | ASMPSVD | 3796 | 200 |
| 61 | GGTCATAATATGGCACAGGCG | 2554 | GHNMAQA | 3797 | 200 |
| 62 | CACAACAAACCAAACGGAGAC | 2555 | HNKPNGD | 3798 | 197.851 |
| 63 | TACAGGATGGAAACGAACCCA | 2556 | YRMETNP | 3799 | 197.46 |
| 64 | CTTGGGAATGTGGTTCATCCG | 2557 | LGNVVHP | 3800 | 197.383 |
| 65 | GTAACGGCACACCAATTATCC | 2558 | VTAHQLS | 3801 | 196.095 |
| 66 | ACTATGGTAGAAGTACTGCCA | 2559 | TMVEVLP | 3802 | 195.586 |
| 67 | ATCAAAGGGTCTGGGTCGCAA | 2560 | IKGSGSQ | 3803 | 195.296 |
| 68 | ACTAATGGGGGGTCGCTTAAT | 2561 | TNGGSLN | 3804 | 193.959 |
| 69 | CTCGGAGGAAACAGCAGGATC | 2562 | LGGNSRI | 3805 | 193.21 |
| 70 | AGGGGTGATGCGGCGAATAAG | 2563 | RGDAANK | 3806 | 193.16 |
| 71 | GCGTTAAACGCCCAAGGGATC | 2564 | ALNAQGI | 3807 | 192.986 |
| 72 | GCTGAGCATGCGACTAGTAGT | 2565 | AEHATSS | 3808 | 192.59 |
| 73 | TACTTGACCACCGGTACTGCC | 2566 | YLTTGTA | 3809 | 191.521 |
| 74 | GCGGAGGCTCAGACGCGTGTG | 2567 | AEAQTRV | 3810 | 189.899 |
| 75 | GCTGAGCAGGGGCTGTCTTCG | 2568 | AEQGLSS | 3811 | 188.94 |
| 76 | CTGATTGTTACTCAGCATGTG | 2569 | LIVTQHV | 3812 | 188.588 |
| 77 | TCTAGTTATCAGTCTGGGCTG | 2570 | SSYQSGL | 3813 | 188.4 |
| 78 | GCTACGGTTTATAATGAGTTG | 2571 | ATVYNEL | 3814 | 188.18 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 79 | CATGATACGGTTGGGGAGAGG | 2572 | HDTVGER | 3815 | 187.269 |
| 80 | CGTGGGGATTTGAATGATTCT | 2573 | RGDLNDS | 3816 | 187.25 |
| 81 | CATGATATTAGTCTGGATCGT | 2574 | HDISLDR | 3817 | 186.65 |
| 82 | ACAGAACAATCTTACTCACGA | 2575 | TEQSYSR | 3818 | 186.237 |
| 83 | TGGTGAGGGGCTGAGTTTGCC | 2576 | W*GAEFA | 3819 | 186.1 |
| 84 | GCTGTGCATGCGACTAGTAGA | 2577 | AVHATSR | 3820 | 185.9 |
| 85 | ATTGAGAGTAAGACTGTGCAG | 2578 | IESKTVQ | 3821 | 185.818 |
| 86 | ACGAATGTTAGTACGCTTTTG | 2579 | TNVSTLL | 3822 | 184.365 |
| 87 | CCACCCAACGGCAGCAGTAGA | 2580 | PPNGSSR | 3823 | 183.258 |
| 88 | CCCTCTACACACGGCTACGTA | 2581 | PSTHGYV | 3824 | 183.235 |
| 89 | ACTGCGGCTAGTACTGCGAGG | 2582 | TAASTAR | 3825 | 182.452 |
| 90 | TACAACGCAGGCGGAGAACAA | 2583 | YNAGGEQ | 3826 | 182.14 |
| 91 | ACCCACAACCAACGTGAACTG | 2584 | THNQREL | 3827 | 181.989 |
| 92 | ACCTTCACGGTCGACGGTAGA | 2585 | TFTVDGR | 3828 | 181.724 |
| 93 | CACTCCAGCCCCGGGTCGTCA | 2586 | HSSPGSS | 3829 | 181.331 |
| 94 | AGTACGAGTGGTTATAATACT | 2587 | STSGYNT | 3830 | 180.372 |
| 95 | TCTGAGAAGCTGACTGATAAG | 2588 | SEKLTDK | 3831 | 180.174 |
| 96 | GGGAGGAACACAAGTAACTTG | 2589 | GRNTSNL | 3832 | 180.156 |
| 97 | ACCGGAACAGCGATCTCCCGA | 2590 | TGTAISR | 3833 | 180.148 |
| 98 | TCTATGCAGGATCCTTCTTTG | 2591 | SMQDPSL | 3834 | 179.222 |
| 99 | ACTCGGAGTGATATTGGTGTG | 2592 | TRSDIGV | 3835 | 178.75 |
| 100 | ACGCAGAATCATCAGTTGTCT | 2593 | TQNHQLS | 3836 | 178.39 |
| 101 | TTTGTTGATAATAGGCAGCCT | 2594 | FVDNRQP | 3837 | 178.388 |
| 102 | AGTTTGAATTCTTCGAGTACT | 2595 | SLNSSST | 3838 | 177.704 |
| 103 | AAGGCGGTTTCGGAGATTATT | 2596 | KAVSEII | 3839 | 177.335 |
| 104 | GGTACGAGTGATAATTATAGG | 2597 | GTSDNYR | 3840 | 176.93 |
| 105 | ATGTCTAGCCACACCGTCCAA | 2598 | MSSHTVQ | 3841 | 176.741 |
| 106 | AGTATCACCCACAGCAACACC | 2599 | SITHSNT | 3842 | 176.571 |
| 107 | GTTCAGACTAGTACTGGTGCT | 2600 | VQTSTGA | 3843 | 176.399 |
| 108 | CGTGGTGATATGACTCGTGCG | 2601 | RGDMTRA | 3844 | 176.36 |
| 109 | ATTGGTCTGCAGAATTCTACT | 2602 | IGLQNST | 3845 | 176.164 |
| 110 | AGTGCGGATCGTGATAATAAG | 2603 | SADRDNK | 3846 | 173.544 |
| 111 | TACTCTCAATCCATAAAAAAC | 2604 | YSQSIKN | 3847 | 172.725 |
| 112 | CGCTCGTTGGACAGCGGGATG | 2605 | RSLDSGM | 3848 | 172.632 |
| 113 | GCTGTGCCTCAGTCTCTGCCT | 2606 | AVPQSLP | 3849 | 172.274 |
| 114 | GCGAATGATAGTATTAAGCTG | 2607 | ANDSIKL | 3850 | 172.18 |
| 115 | AATGGTAATATTTATCCGTCT | 2608 | NGNIYPS | 3851 | 171.981 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 116 | GGGCAAACAAACGCAGTACAC | 2609 | GQTNAVH | 3852 | 171.5364 |
| 117 | CAAGGAGACCTACGTGGCTCG | 2610 | QGDLRGS | 3853 | 171.042 |
| 118 | GTTAAGGCGAGTGCTGGGGTT | 2611 | VKASAGV | 3854 | 170.5608 |
| 119 | ATCGCGTCAACGTGGAACATG | 2612 | IASTWNM | 3855 | 170.52 |
| 120 | AACTCGGCTGAATCCTCGAGA | 2613 | NSAESSR | 3856 | 170.31 |
| 121 | GTCTTCACGGGCCAAACTGAA | 2614 | VFTGQTE | 3857 | 170.216 |
| 122 | TTTGGTACTTCTTATACGACT | 2615 | FGTSYTT | 3858 | 169.719 |
| 123 | GCGGTTAATGAGACTAGGCTT | 2616 | AVNETRL | 3859 | 168.767 |
| 124 | GGTCGGACGGATACTCCTAAT | 2617 | GRTDTPN | 3860 | 168.735 |
| 125 | AACGACCGACCGCTTGCCAGC | 2618 | NDRPLAS | 3861 | 168.71 |
| 126 | GCTTATCAGCTGACTCCGGCT | 2619 | AYQLTPA | 3862 | 168.579 |
| 127 | ATGGGTGAGATGGGTAATATT | 2620 | MGEMGNI | 3863 | 168.24 |
| 128 | GCGGACATGCAACACACCGTA | 2621 | ADMQHTV | 3864 | 168.055 |
| 129 | GCGGTTGTTCTGAATAGTAAT | 2622 | AVVLNSN | 3865 | 168.021 |
| 130 | TTTCGTGATGGTCAGGGTATG | 2623 | FRDGQGM | 3866 | 167.193 |
| 131 | AAATCGACATCAAACATCGAA | 2624 | KSTSNIE | 3867 | 166.8294 |
| 132 | ACCCAAGCCTTCTCCCTAGGC | 2625 | TQAFSLG | 3868 | 166.751 |
| 133 | TGGTCGAGAACTGGAAACACC | 2626 | WSRTGNT | 3869 | 166.483 |
| 134 | AGCACAAACACCGAACCTAGG | 2627 | STNTEPR | 3870 | 165.304 |
| 135 | GAGAATAGTGATTTGTCTTAT | 2628 | ENSDLSY | 3871 | 165.08 |
| 136 | ATAGACGAACGTTCCTCGATA | 2629 | IDERSSI | 3872 | 165.02 |
| 137 | GATGTGCATTCGAGTATTCCT | 2630 | DVHSSIP | 3873 | 164.85 |
| 138 | ATAAGCGGTTCCACTACACAC | 2631 | ISGSTTH | 3874 | 164.788 |
| 139 | TGGCAAACCCAAGTCACTACA | 2632 | WQTQVTT | 3875 | 164.759 |
| 140 | AACATGGGTCCAATGGGCCGG | 2633 | NMGPMGR | 3876 | 164.41 |
| 141 | GTTACCCAATCGTCCACGCTA | 2634 | VTQSSTL | 3877 | 164.175 |
| 142 | ATTGATCGTAGTGCTAGTTTG | 2635 | IDRSASL | 3878 | 164.016 |
| 143 | TCTCATAGTATTACGGGTCTT | 2636 | SHSITGL | 3879 | 163.92 |
| 144 | AAAGCGGGACAACTAGTGGAA | 2637 | KAGQLVE | 3880 | 163.845 |
| 145 | AGCGGTGTATCAGAAGGAAAC | 2638 | SGVSEGN | 3881 | 163.413 |
| 146 | ACGCTTACATTATCTACCCTC | 2639 | TLTLSTL | 3882 | 163.242 |
| 147 | GCCCACAACAAACACGAAAGT | 2640 | AHNKHES | 3883 | 162.975 |
| 148 | CACAACAACAACCTGCAAAAC | 2641 | HNNNLQN | 3884 | 162.633 |
| 149 | TATAATGAGTCTTCGAATGCG | 2642 | YNESSNA | 3885 | 161.92 |
| 150 | CGTGAGCAGGCTGCGGAGAGG | 2643 | REQAAER | 3886 | 161.523 |
| 151 | ACTCAGTATGGTACTCTGCCG | 2644 | TQYGTLP | 3887 | 161.32 |
| 152 | CATCCTGGGAATAGTTCTGTG | 2645 | HPGNSSV | 3888 | 161.2 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 153 | AGTTCTAGGGAGGTGAGTCCG | 2646 | SSREVSP | 3889 | 161.091 |
| 154 | GCAAACTCCACAAGCCAATGG | 2647 | ANSTSQW | 3890 | 160.842 |
| 155 | CGCGACATGATCAACTCATCA | 2648 | RDMINSS | 3891 | 160.83 |
| 156 | GCATTGCCCAGCGGCGCACGA | 2649 | ALPSGAR | 3892 | 160.765 |
| 157 | CCTGGCACCAGTGGATCCCGA | 2650 | PGTSGSR | 3893 | 159.7012 |
| 158 | TGGAACGGAAACGCCACACAA | 2651 | WNGNATQ | 3894 | 158.413 |
| 159 | GGTAAAGCAACCTTAGTCCTC | 2652 | GKATLVL | 3895 | 158.386 |
| 160 | TACACCAACGGGGGCCACCTA | 2653 | YTNGGHL | 3896 | 158.346 |
| 161 | TCACAATACAACGGAACGCAA | 2654 | SQYNGTQ | 3897 | 157.872 |
| 162 | TATTCTAGTGAGAGTGCTTAT | 2655 | YSSESAY | 3898 | 157.56 |
| 163 | GTTAAGGCGGGGGTGGCTGAT | 2656 | VKAGVAD | 3899 | 157.534 |
| 164 | ACGATGGGGACGGTGCAGATT | 2657 | TMGTVQI | 3900 | 157.384 |
| 165 | GGTGTGGCTGGTGCGGTGGTG | 2658 | GVAGAVV | 3901 | 156.882 |
| 166 | TATGATAAGACTTTGAGTGTT | 2659 | YDKTLSV | 3902 | 156.791 |
| 167 | CATGGGAGTGCGTATTCGCAG | 2660 | HGSAYSQ | 3903 | 156.45 |
| 168 | ACGGCTAATATTATGAGTAAG | 2661 | TANIMSK | 3904 | 155.935 |
| 169 | TTTTCGCGGGAGACGCTGGCG | 2662 | FSRETLA | 3905 | 155.888 |
| 170 | TTGAGTGGTGCTGGTAGTCAG | 2663 | LSGAGSQ | 3906 | 155.554 |
| 171 | AGTAATGCGAATCAGATGAGT | 2664 | SNANQMS | 3907 | 155.28 |
| 172 | TCGGTCCTTTCGCCTTCGAAC | 2665 | SVLSPSN | 3908 | 154.987 |
| 173 | GATAATGTGCATGGGCAGGTG | 2666 | DNVHGQV | 3909 | 154.72 |
| 174 | GACGGACGAGAATACGCCTCG | 2667 | DGREYAS | 3910 | 154.33 |
| 175 | ATTTCGAATCAGATTAAGATG | 2668 | ISNQIKM | 3911 | 154.262 |
| 176 | GGTCGAGACAACCAACACGTA | 2669 | GRDNQHV | 3912 | 154.136 |
| 177 | CGTAATCATGAGACTGGGGCT | 2670 | RNHETGA | 3913 | 153.8093 |
| 178 | AGTGGGAGTGGTGCGAATATT | 2671 | SGSGANI | 3914 | 153.55 |
| 179 | TCTATGTCTGATGGGCTTCGG | 2672 | SMSDGLR | 3915 | 153.296 |
| 180 | AAGGAGAGTAGTGCTATGGAG | 2673 | KESSAME | 3916 | 153.04 |
| 181 | GCTAATGCTAGTACTAGTCTG | 2674 | ANASTSL | 3917 | 152.807 |
| 182 | AGTGCTTCTGGTTATTTGGTT | 2675 | SASGYLV | 3918 | 152.79 |
| 183 | GATACTACTCAGAAGCCTCAT | 2676 | DTTQKPH | 3919 | 152.687 |
| 184 | CTAATACGAGGTTCCATGGAA | 2677 | LIRGSME | 3920 | 152.55 |
| 185 | GACCGCACCTACTCAAACACA | 2678 | DRTYSNT | 3921 | 152.447 |
| 186 | GCTCTTGGGCATCAGGGGAAT | 2679 | ALGHQGN | 3922 | 152.38 |
| 187 | GCTAATCATACGTCGCAGGAG | 2680 | ANHTSQE | 3923 | 152.056 |
| 188 | GAGAGGGGTTTGAATACTAAT | 2681 | ERGLNTN | 3924 | 151.4 |
| 189 | ACTGTTGGTGGTAATCATCAT | 2682 | TVGGNHH | 3925 | 151.384 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 190 | CCGAGTGATAGGACTACTTAT | 2683 | PSDRTTY | 3926 | 151.365 |
| 191 | TCCAGGCAAGAAAACTTCTCC | 2684 | SRQENFS | 3927 | 151.22 |
| 192 | AATAAGACGACGATGGAGTTT | 2685 | NKTTMEF | 3928 | 151.16 |
| 193 | AAACACACAGAAAACGGGACC | 2686 | KHTENGT | 3929 | 150.985 |
| 194 | GAAACCGGAGCTATGACCTCT | 2687 | ETGAMTS | 3930 | 150.803 |
| 195 | GGTCATAGGGATTCGGGTGGT | 2688 | GHRDSGG | 3931 | 149.991 |
| 196 | AGAAACGCCGAAGGCGGATTG | 2689 | RNAEGGL | 3932 | 149.919 |
| 197 | GGGCAGCGTACGACGAATGAT | 2690 | GQRTTND | 3933 | 149.903 |
| 198 | TATAATGATGCTCTTAGGCCG | 2691 | YNDALRP | 3934 | 149.88 |
| 199 | GGGTATGCGACTACGGTTCAG | 2692 | GYATTVQ | 3935 | 149.694 |
| 200 | ATAGGGGGAGGCATAGGAAAC | 2693 | IGGGIGN | 3936 | 149.622 |
| 201 | GTGGCGGTGTCTAATACGCCT | 2694 | VAVSNTP | 3937 | 148.5637 |
| 202 | CTTGCGAATGGTATGACGGCT | 2695 | LANGMTA | 3938 | 148.449 |
| 203 | ATTTCTGGGTCGTCGTCTCTT | 2696 | ISGSSSL | 3939 | 148.328 |
| 204 | TCTAATGTTCATGTTGTTAAT | 2697 | SNVHVVN | 3940 | 148.32 |
| 205 | GTGGAGACTTCGCGTCTGTAT | 2698 | VETSRLY | 3941 | 148.302 |
| 206 | TCGAACGCAGACATCCTCGCC | 2699 | SNADILA | 3942 | 148.08 |
| 207 | AACAACGTAAACCCGTACTCG | 2700 | NNVNPYS | 3943 | 148.016 |
| 208 | ATAAGTGTAGGTGTGTCCGTA | 2701 | ISVGVSV | 3944 | 147.84 |
| 209 | TCCGCAAACAACATAGCCCCC | 2702 | SANNIAP | 3945 | 147.813 |
| 210 | GGTGTTCAGATGACTGCGGGG | 2703 | GVQMTAG | 3946 | 147.527 |
| 211 | CGTTACATCGCCAACCAAACA | 2704 | RYIANQT | 3947 | 147.305 |
| 212 | ACCACCGAAAGTCTACACCTT | 2705 | TTESLHL | 3948 | 146.899 |
| 213 | GGCTACCAAGACAAAACACGA | 2706 | GYQDKTR | 3949 | 146.705 |
| 214 | GCTTCGCGGCCTGCGGCTCAG | 2707 | ASRPAAQ | 3950 | 146.364 |
| 215 | TCTATTCAGGAGCTGTTGAGG | 2708 | SIQELLR | 3951 | 146.287 |
| 216 | ACTGTGCGTTCGCCTCAGCAG | 2709 | TVRSPQQ | 3952 | 145.74 |
| 217 | GCGGTTCTTGGTGGTAGTAAT | 2710 | AVLGGSN | 3953 | 145.633 |
| 218 | ATGAGTACGGTTCTTCGGGAG | 2711 | MSTVLRE | 3954 | 144.928 |
| 219 | ACTTATGGTATTACTCATGAT | 2712 | TYGITHD | 3955 | 144.751 |
| 220 | GATGCGAATGCGGGTACGAGG | 2713 | DANAGTR | 3956 | 144.597 |
| 221 | TTCAACGGGTACGTCATGGCA | 2714 | FNGYVMA | 3957 | 144.536 |
| 222 | ATTAATAATTTTAATACTCTG | 2715 | INNFNTL | 3958 | 144.08 |
| 223 | GTAGCCAACGAACGCCTACCG | 2716 | VANERLP | 3959 | 143.64 |
| 224 | ACTAATTCTAATCAGGGTTCG | 2717 | TNSNQGS | 3960 | 143.617 |
| 225 | GCGACGCTGAATAATAGTTAT | 2718 | ATLNNSY | 3961 | 143.512 |
| 226 | AAAAACGCTCAAATAGACCTA | 2719 | KNAQIDL | 3962 | 142.66 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 227 | CCTGCTACGCTACACCTGACA | 2720 | PATLHLT | 3963 | 142.552 |
| 228 | TTAGGATCGAGCACAGTATCG | 2721 | LGSSTVS | 3964 | 142.325 |
| 229 | AATTGGAATTCTGAGGGTACG | 2722 | NWNSEGT | 3965 | 142.257 |
| 230 | CCAACAAACAACTTAAGTATG | 2723 | PTNNLSM | 3966 | 141.91 |
| 231 | GCGCTTAAGCCGAATTCTACG | 2724 | ALKPNST | 3967 | 141.737 |
| 232 | ATGGTGAATTCGGAGAATACT | 2725 | MVNSENT | 3968 | 141.624 |
| 233 | AGTATGGATGCTCGGTTGACG | 2726 | SMDARLT | 3969 | 141.6 |
| 234 | AATAATGTTGTTAGGGATGAT | 2727 | NNVVRDD | 3970 | 141.597 |
| 235 | ACAAGGGACCAAAGGTCTACA | 2728 | TRDQRST | 3971 | 141.592 |
| 236 | GCTGACATCCGGAACGACAAA | 2729 | ADIRNDK | 3972 | 141.468 |
| 237 | ATGCGGGATAAGATTAATCCG | 2730 | MRDKINP | 3973 | 141.468 |
| 238 | CCGACTCCTAATGAGCATATG | 2731 | PTPNEHM | 3974 | 141.465 |
| 239 | GGATACTCACACAACTCCGAC | 2732 | GYSHNSD | 3975 | 141.448 |
| 240 | CTTCGGGATGGGATTGCTTCT | 2733 | LRDGIAS | 3976 | 141.105 |
| 241 | ATGAACCAAATGGGCGGCCTG | 2734 | MNQMGGL | 3977 | 141.089 |
| 242 | TCTTCGCCTACTAAGGGTACT | 2735 | SSPTKGT | 3978 | 140.803 |
| 243 | TATTTGGATAATCCGTTGACG | 2736 | YLDNPLT | 3979 | 140.516 |
| 244 | GTCATGCAACGATCTGCACAA | 2737 | VMQRSAQ | 3980 | 140.2 |
| 245 | TCTCTGCAACTCACAGCGGGT | 2738 | SLQLTAG | 3981 | 140.161 |
| 246 | GTGGGGTCTGGGGGTTATAAT | 2739 | VGSGGYN | 3982 | 140.139 |
| 247 | GATCGTCCGAATAATGTGTCG | 2740 | DRPNNVS | 3983 | 140.036 |
| 248 | TTGACTGAGAAGGCTTCTATT | 2741 | LTEKASI | 3984 | 139.945 |
| 249 | ACCACAAAAACGACATCTATG | 2742 | TTKTTSM | 3985 | 139.556 |
| 250 | CGTTTGGACCTGCAAGTCCAC | 2743 | RLDLQVH | 3986 | 139.528 |
| 251 | ACTCATGTGATTGGGGCTGTG | 2744 | THVIGAV | 3987 | 139.34 |
| 252 | ACCCTGACACACCTAAACCCA | 2745 | TLTHLNP | 3988 | 139.142 |
| 253 | ACCTCAATATCGTCGCAAAGC | 2746 | TSISSQS | 3989 | 138.884 |
| 254 | TACCACACCCACCAAGTCGCA | 2747 | YHTHQVA | 3990 | 138.871 |
| 255 | ATGCAAGGGCTTAACAACATG | 2748 | MQGLNNM | 3991 | 138.848 |
| 256 | GGTAGTGCGAGTAATAGTGGT | 2749 | GSASNSG | 3992 | 138.841 |
| 257 | GCGAATACTACGGGGCAGGTG | 2750 | ANTTGQV | 3993 | 138.7122 |
| 258 | AGCGTTGTCAACACCAACATC | 2751 | SVVNTNI | 3994 | 138.699 |
| 259 | TCTAATAATCTGAATCAGGAG | 2752 | SNNLNQE | 3995 | 138.543 |
| 260 | ATGAATGGGAGTGGGATGCAG | 2753 | MNGSGMQ | 3996 | 138.484 |
| 261 | ATAAGTCACGACCTTAAATAC | 2754 | ISHDLKY | 3997 | 138.458 |
| 262 | ACGGTTAATGCGGATGGGTCG | 2755 | TVNADGS | 3998 | 138.21 |
| 263 | AATCATATTAGGAATCCTATG | 2756 | NHIRNPM | 3999 | 138.143 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 264 | AGTACGCGGGTTACTCTGGAT | 2757 | STRVTLD | 4000 | 137.85 |
| 265 | GCTATGGGAGCACTCGTGCAC | 2758 | AMGALVH | 4001 | 137.838 |
| 266 | GCGCAAGCCATGTCAAACAGC | 2759 | AQAMSNS | 4002 | 137.76 |
| 267 | AATGCTAATGGTATGAATACT | 2760 | NANGMNT | 4003 | 137.343 |
| 268 | TTGACGCTTCCTAGTGCTAAT | 2761 | LTLPSAN | 4004 | 137.264 |
| 269 | TACCAAACGGGAGACAAAGAC | 2762 | YQTGDKD | 4005 | 137.017 |
| 270 | AGACGGGAAGAAAACGTCAAC | 2763 | RREENVN | 4006 | 136.962 |
| 271 | GGAACTACCACGGCAGTCGCG | 2764 | GTTTAVA | 4007 | 136.8811 |
| 272 | ACGGCTGGTGGGGAGCGTGCG | 2765 | TAGGERA | 4008 | 136.6 |
| 273 | GCCGGTAACGAACCTAGACCC | 2766 | AGNEPRP | 4009 | 136.593 |
| 274 | GCAAACAACACAGCCAACAGT | 2767 | ANNTANS | 4010 | 136.498 |
| 275 | CATGTGAATAGTAGGGATCTT | 2768 | HVNSRDL | 4011 | 136.187 |
| 276 | ACATACCAACTTTCCGGCAAC | 2769 | TYQLSGN | 4012 | 136.059 |
| 277 | CGGGGTGATTCGATGGCTCGG | 2770 | RGDSMAR | 4013 | 135.8517 |
| 278 | TTGAATAATTCTGCGACTGTT | 2771 | LNNSATV | 4014 | 135.76 |
| 279 | CTACACGCTAACAACGAACGG | 2772 | LHANNER | 4015 | 135.723 |
| 280 | ATGGGTTCTACGACTGGTGTG | 2773 | MGSTTGV | 4016 | 135.16 |
| 281 | GTAGTTGCAGGGCACGCAATG | 2774 | VVAGHAM | 4017 | 135.1261 |
| 282 | GGCAACGAAAAACCATCAGGG | 2775 | GNEKPSG | 4018 | 135.016 |
| 283 | CGTGGTACGGAGGGGACGCCG | 2776 | RGTEGTP | 4019 | 134.8972 |
| 284 | TGGTCCCCCGGACCCGAAGCC | 2777 | WSPGPEA | 4020 | 134.66 |
| 285 | ATTAATGTGAATCAGATGGCG | 2778 | INVNQMA | 4021 | 134.472 |
| 286 | CGGTCGGACGTTATGCAAAGT | 2779 | RSDVMQS | 4022 | 134.362 |
| 287 | AGGGACGTAAGTACAAAAGAA | 2780 | RDVSTKE | 4023 | 134.36 |
| 288 | AAAAAGTCACCCAGACTTGAA | 2781 | KKSPRLE | 4024 | 134.35 |
| 289 | ACGAGCAACACAATGTCAGAC | 2782 | TSNTMSD | 4025 | 134.345 |
| 290 | TCTAAAGGAAACGAACAAATG | 2783 | SKGNEQM | 4026 | 134.224 |
| 291 | GGTTACGCTACGACCGTGCAA | 2784 | GYATTVQ | 4027 | 134.185 |
| 292 | GGATACATGTCTAACGTCATA | 2785 | GYMSNVI | 4028 | 133.922 |
| 293 | GTGACTGTTAGTCTGGATGGG | 2786 | VTVSLDG | 4029 | 133.879 |
| 294 | ACGAATAATTTGCTGGCTCAG | 2787 | TNNLLAQ | 4030 | 133.517 |
| 295 | GCGCAGACGACGGGGTATACG | 2788 | AQTTGYT | 4031 | 133.295 |
| 296 | AGTAAGTCGACTGAGATTATG | 2789 | SKSTEIM | 4032 | 133.249 |
| 297 | TCTGCGATGCACACATTAGTC | 2790 | SAMHTLV | 4033 | 133.226 |
| 298 | GCTGGGGTGCGTGAGTCGTTT | 2791 | AGVRESF | 4034 | 133.15 |
| 299 | CAAGGCAACTCAATGGCGTCC | 2792 | QGNSMAS | 4035 | 132.82 |
| 300 | AAAAACCCGAGTGTCCAAGAA | 2793 | KNPSVQE | 4036 | 132.519 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 301 | CCCATAACACGGGAATCGGGA | 2794 | PITRESG | 4037 | 132.424 |
| 302 | AGCCGCTCGGCAGAAATATCG | 2795 | SRSAEIS | 4038 | 131.747 |
| 303 | AACGACATCCCCACACGAGCC | 2796 | NDIPTRA | 4039 | 131.424 |
| 304 | GCATACGGATCGTCCGGAAGA | 2797 | AYGSSGR | 4040 | 131.375 |
| 305 | CTTCATGGGAATTTTAGTCAG | 2798 | LHGNFSQ | 4041 | 131.002 |
| 306 | GCATCCAACGGGCAAGTTAAC | 2799 | ASNGQVN | 4042 | 130.736 |
| 307 | CAGAAGGGGACGGTTACTCTG | 2800 | QKGTVTL | 4043 | 130.375 |
| 308 | AACTCTAGTAACACTGGTTGG | 2801 | NSSNTGW | 4044 | 130.26 |
| 309 | ACGTATCAGCATCAGGGTCCG | 2802 | TYQHQGP | 4045 | 130.231 |
| 310 | GACGGGGTCGCACACCGCTCA | 2803 | DGVAHRS | 4046 | 130.216 |
| 311 | GACGGGCTCACGCTGGAACGC | 2804 | DGLTLER | 4047 | 130.09 |
| 312 | AGGGGTGATCTATCTACGCCT | 2805 | RGDLSTP | 4048 | 130.02 |
| 313 | ATTAATGAGATTGGTAGGATG | 2806 | INEIGRM | 4049 | 129.944 |
| 314 | CCCCAATGGGGAACTGACCCG | 2807 | PQWGTDP | 4050 | 129.94 |
| 315 | AAGCAGGTGGCGCATATTGAT | 2808 | KQVAHID | 4051 | 129.831 |
| 316 | AATACTTTGCAGAATAGTCAT | 2809 | NTLQNSH | 4052 | 129.563 |
| 317 | TGGAGCCAAGGGAACACAGCG | 2810 | WSQGNTA | 4053 | 129.438 |
| 318 | AACGAAACGCACGTACCTAAA | 2811 | NETHVPK | 4054 | 129.35 |
| 319 | GTAACGAACGAATCCCGCGCC | 2812 | VTNESRA | 4055 | 129.059 |
| 320 | CCCGAAGGCCACATGCAAGAC | 2813 | PEGHMQD | 4056 | 129 |
| 321 | TTGGATTCGACTAATTCTAGG | 2814 | LDSTNSR | 4057 | 128.63 |
| 322 | CAGTCGATTGGGCATCCGGTG | 2815 | QSIGHPV | 4058 | 128.17 |
| 323 | GTCCTGGTTAACGTACACAAC | 2816 | VLVNVHN | 4059 | 128.078 |
| 324 | GTGCATAATCCTACTACTACG | 2817 | VHNPTTT | 4060 | 127.727 |
| 325 | GGGGATAAGGCGAGTTTGGCG | 2818 | GDKASLA | 4061 | 127.698 |
| 326 | CTAAACGAATCCCGAGCGTCG | 2819 | LNESRAS | 4062 | 127.597 |
| 327 | GGTTTTCATATTAATGGTGAG | 2820 | GFHINGE | 4063 | 127.526 |
| 328 | AGTGTTAGTTCTGTGGTGTTG | 2821 | SVSSVVL | 4064 | 127.19 |
| 329 | CTTTCGACTACTTCGACGAAG | 2822 | LSTTSTK | 4065 | 127.153 |
| 330 | ACTAATACGCAGAATAATCCG | 2823 | TNTQNNP | 4066 | 127.089 |
| 331 | ACTAATCTTGCTGTTACGCTG | 2824 | TNLAVTL | 4067 | 127.0208 |
| 332 | ATGTCGGATCGTACTTCTGAT | 2825 | MSDRTSD | 4068 | 126.91 |
| 333 | TCCGCGCAATCTTTCGTAGTT | 2826 | SAQSFVV | 4069 | 126.906 |
| 334 | ATGCACACAAGTAGACCCCCA | 2827 | MHTSAPP | 4070 | 126.861 |
| 335 | ATGTCTAGCCACACAGTCCAA | 2828 | MSSHTVQ | 4071 | 126.79 |
| 336 | AGGGATACGGCTAAGGGGGTG | 2829 | RDTAKGV | 4072 | 126.773 |
| 337 | GCGTTAAAATCCGACAGCGCC | 2830 | ALKSDSA | 4073 | 126.73 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 338 | CAATACGACGCCAGCCGACAA | 2831 | QYDASRQ | 4074 | 126.66 |
| 339 | TTAGCCGACTCAAACAGCAAA | 2832 | LADSNSK | 4075 | 126.48 |
| 340 | TTTCAGTTGGCTAGTAATCCG | 2833 | FQLASNP | 4076 | 126.372 |
| 341 | AACTCTGTCGTAGGGAACATC | 2834 | NSVVGNI | 4077 | 126.308 |
| 342 | AGGTATGAGAGTACTAGTGCT | 2835 | RYESTSA | 4078 | 126.21 |
| 343 | GCGGATCATAATCATATTGCT | 2836 | ADHNHIA | 4079 | 126.21 |
| 344 | GTAGGCGACCAATCCCGCCCG | 2837 | VGDQSRP | 4080 | 126.106 |
| 345 | TTCAACGAAACTGCCGGGCGA | 2838 | FNETAGR | 4081 | 125.693 |
| 346 | AGCAACTCGTACTTACTCAAC | 2839 | SNSYLLN | 4082 | 125.52 |
| 347 | CGAGGCGACACAAAGAACTAC | 2840 | RGDTKNY | 4083 | 125.09 |
| 348 | ACGACTACTACTATGGCATAC | 2841 | TTTTMAY | 4084 | 125.064 |
| 349 | CGACCCCCGAACGAAAACAGA | 2842 | RPPNENR | 4085 | 124.7157 |
| 350 | TGCGCCAACATGACCAACGGC | 2843 | CANMTNG | 4086 | 124.6 |
| 351 | AATCGGTCGGATAGTTTTGCG | 2844 | NRSDSFA | 4087 | 124.567 |
| 352 | AATCTTTTGACTTCGTCGCCT | 2845 | NLLTSSP | 4088 | 124.54 |
| 353 | AACTCCAGGGAAATGGGTGTA | 2846 | NSREMGV | 4089 | 124.539 |
| 354 | ATGGGGAATCAGAGTGGTGCG | 2847 | MGNQSGA | 4090 | 124.506 |
| 355 | ATGCTCACAGAAACCAAAGCA | 2848 | MLTETKA | 4091 | 124.3 |
| 356 | CAAAACATCAAAAACATGACA | 2849 | QNIKNMT | 4092 | 124.1 |
| 357 | ATGAGTACGGTTCTTCGCGAG | 2850 | MSTVLRE | 4093 | 124.05 |
| 358 | GACCGTGCCCAAAACAACGAA | 2851 | DRAQNNE | 4094 | 123.95 |
| 359 | CATACGCAGTCGACGGGTTAT | 2852 | HTQSTGY | 4095 | 123.943 |
| 360 | ATGAGTGTGGGGAAGGTTTAT | 2853 | MSVGKVY | 4096 | 123.919 |
| 361 | GCCGGAAACTACCAATCATCA | 2854 | AGNYQSS | 4097 | 123.855 |
| 362 | AGAAACGAAAACGTAAACGCT | 2855 | RNENVNA | 4098 | 123.777 |
| 363 | GACACCCACCACACATCCAGT | 2856 | DTHHTSS | 4099 | 123.766 |
| 364 | ACTAGCTCCCCTGTTCTACAA | 2857 | TSSPVLQ | 4100 | 123.762 |
| 365 | GTGGGCCGTGACGCAGAAGCT | 2858 | VGRDAEA | 4101 | 123.74 |
| 366 | AACATGGAAAGAGGATCGCAA | 2859 | NMERGSQ | 4102 | 123.646 |
| 367 | GACAGACAAACAGGCCAAAAA | 2860 | DRQTGQK | 4103 | 123.6413 |
| 368 | GTCTTCCGGGAAGGCATCGTG | 2861 | VFREGIV | 4104 | 123.54 |
| 369 | TCCGCAAACAACATAGCCACC | 2862 | SANNIAT | 4105 | 123.32 |
| 370 | GTATCAGAAGGACAACGAATC | 2863 | VSEGQRI | 4106 | 123.005 |
| 371 | CACTACGGTAACAAAGACATA | 2864 | HYGNKDI | 4107 | 122.894 |
| 372 | GATGTTTTGCTTAAGAATTTT | 2865 | DVLLKNF | 4108 | 122.89 |
| 373 | CACACGGTTCAAATACGCGAA | 2866 | HTVQIRE | 4109 | 122.8082 |
| 374 | ACATCAGCACTAGCACACCAA | 2867 | TSALAHQ | 4110 | 122.78 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 375 | ATCCCAACCGGCCAAACTAGC | 2868 | IPTGQTS | 4111 | 122.752 |
| 376 | CGCAGCGACAAAGGAACGTTG | 2869 | RSDKGTL | 4112 | 122.7439 |
| 377 | AATGGTCTTACGGTTCAGCGG | 2870 | NGLTVQR | 4113 | 122.718 |
| 378 | ACGGTTGAGGGTTCTTATCCG | 2871 | TVEGSYP | 4114 | 122.67 |
| 379 | ACTAGCCACTTAGTACTTGCA | 2872 | TSHLVLA | 4115 | 122.653 |
| 380 | AATCATAGTCTGTCGGAGCAT | 2873 | NHSLSEH | 4116 | 122.5 |
| 381 | TTAACAGGCATGAACAGAGAC | 2874 | LTGMNRD | 4117 | 122.335 |
| 382 | AGTCACAACGCTGGGGTCGCC | 2875 | SHNAGVA | 4118 | 122.285 |
| 383 | GCGCACCAAACCGCCGGGCCA | 2876 | AHQTAGP | 4119 | 122.22 |
| 384 | AATTCTCATGATTTGAAGTAT | 2877 | NSHDLKY | 4120 | 121.99 |
| 385 | ACTACAATGAGTACCGGTCAA | 2878 | TTMSTGQ | 4121 | 121.98 |
| 386 | GGGTTCGGGCACGTGCCCGAA | 2879 | GFGHVPE | 4122 | 121.974 |
| 387 | ATCACCGCCGCGTCACCGCAA | 2880 | ITAASPQ | 4123 | 121.868 |
| 388 | GTTAAGGCGAGTGCTGGGGAT | 2881 | VKASAGD | 4124 | 121.75 |
| 389 | AGTATCACACACAGCAACACC | 2882 | SITHSNT | 4125 | 121.75 |
| 390 | CATAATAATAATATGCTGAAT | 2883 | HNNNMLN | 4126 | 121.659 |
| 391 | CCCAAAACTCTAACTTCGACA | 2884 | PKTLTST | 4127 | 121.479 |
| 392 | ATAACCGGCAACACCGTCGGA | 2885 | ITGNTVG | 4128 | 121.385 |
| 393 | CTCGGAAACCACTACACACCC | 2886 | LGNHYTP | 4129 | 121.38 |
| 394 | TCGTTTACTAATACGAATCCT | 2887 | SFTNTNP | 4130 | 121.294 |
| 395 | ACGTTGGATCGGAATCAGACT | 2888 | TLDRNQT | 4131 | 121.25 |
| 396 | ATCTCTACGCAAAGACCGCAC | 2889 | ISTQRPH | 4132 | 121.2071 |
| 397 | ACATTCACTACTCTGGGCAAA | 2890 | TFTTLGK | 4133 | 121.179 |
| 398 | GAGAAGCCTTCTCTTGTGATG | 2891 | EKPSLVM | 4134 | 120.927 |
| 399 | CACATCGAAACCAACACTTCG | 2892 | HIETNTS | 4135 | 120.834 |
| 400 | GGTACGAAGGATATTCTGATT | 2893 | GTKDILI | 4136 | 120.792 |
| 401 | GCGACTTTTAGTCATGCTGGT | 2894 | ATFSHAG | 4137 | 120.788 |
| 402 | GCCAACGGCATATTCCAACCG | 2895 | ANGIFQP | 4138 | 120.646 |
| 403 | CTTAATGTGAATACGCTTAAT | 2896 | LNVNTLN | 4139 | 120.55 |
| 404 | ACTTCTGCTAGTGAGAATTGG | 2897 | TSASENW | 4140 | 120.5 |
| 405 | CTTCTTCAGGGTGCGACTAAG | 2898 | LLQGATK | 4141 | 120.358 |
| 406 | GCTCTTGAGACTACTCGTGCT | 2899 | ALETTRA | 4142 | 120.26 |
| 407 | TTAACGGGACAAAACGAATTC | 2900 | LTGQNEF | 4143 | 120.24 |
| 408 | ATTTCTCATGATTTGAAGAAT | 2901 | ISHDLKN | 4144 | 120.191 |
| 409 | GCACAATACAACAACGGCGTA | 2902 | AQYNNGV | 4145 | 120.19 |
| 410 | ACGACGTCTGTGGAGAAGACT | 2903 | TTSVEKT | 4146 | 120.106 |
| 411 | GGTACGTCGGCTATTATGCCT | 2904 | GTSAIMP | 4147 | 120.093 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 412 | CAGCTGCAGGGGACTGAGGCG | 2905 | QLQGTEA | 4148 | 120.02 |
| 413 | GCCTTAAAATCCCAAGAACCA | 2906 | ALKSQEP | 4149 | 120.007 |
| 414 | TCTAACAGCAGTGTTGCGGTA | 2907 | SNSSVAV | 4150 | 119.89 |
| 415 | AATCATGGTCGTGCTATTGAT | 2908 | NHGRAID | 4151 | 119.776 |
| 416 | GATACGTATAATAGTAATACT | 2909 | DTYNSNT | 4152 | 119.6 |
| 417 | ACATTCCACCAAGCGGTCAAA | 2910 | TFHQAVK | 4153 | 119.54 |
| 418 | TGGCATACTGGTGTGTTTCAG | 2911 | WHTGVFQ | 4154 | 119.48 |
| 419 | AGGGGTGATCTTTCTACGCCA | 2912 | RGDLSTP | 4155 | 119.47 |
| 420 | ATGCTTAGTCAGGTTCTGACG | 2913 | MLSQVLT | 4156 | 119.414 |
| 421 | GAAAACGAAAAACGAGAAAGC | 2914 | ENEKRES | 4157 | 119.391 |
| 422 | ATTTCGAGTTATGATGGTAAT | 2915 | ISSYDGN | 4158 | 119.38 |
| 423 | ACTCGTGGCGACATGGAATTC | 2916 | TRGDMEF | 4159 | 119.36 |
| 424 | AATGTGCAGAATGTGCCTGGG | 2917 | NVQNVPG | 4160 | 119.3363 |
| 425 | TCTTTCACGAACACAAACCCA | 2918 | SFTNTNP | 4161 | 119.24 |
| 426 | TCGAACGCTGGCTACCACTCG | 2919 | SNAGYHS | 4162 | 119.169 |
| 427 | GACTACAAAAACAGCGCGCCA | 2920 | DYKNSAP | 4163 | 119.136 |
| 428 | GTCGGGAAAAACTCGTACGAA | 2921 | VGKNSYE | 4164 | 119.129 |
| 429 | GCTTACGCAGGTGTACTTGGG | 2922 | AYAGVLG | 4165 | 119.123 |
| 430 | ACGACGTCTGAGCGTGTGAAT | 2923 | TTSERVN | 4166 | 119.105 |
| 431 | GACACCGGAATCAAAAACGTT | 2924 | DTGIKNV | 4167 | 119.05 |
| 432 | TCGACCAGCTCTCTGGTTCCC | 2925 | STSSLVP | 4168 | 119.006 |
| 433 | TGGAGCGCCGGCGAACGGGTG | 2926 | WSAGERV | 4169 | 118.995 |
| 434 | AGTTCGGGGAGTTTGATTACT | 2927 | SSGSLIT | 4170 | 118.945 |
| 435 | TGGATTTCTACTGAGATGAGG | 2928 | WISTEMR | 4171 | 118.93 |
| 436 | TTTGCGGCTGGGGCGCATGGT | 2929 | FAAGAHG | 4172 | 118.92 |
| 437 | ATAGGCGACCGCGACCAACGT | 2930 | IGDRDQR | 4173 | 118.886 |
| 438 | AGTACGATTGGTAATTCTACT | 2931 | STIGNST | 4174 | 118.8619 |
| 439 | GGAAGTGGCACCGTCGGTCGA | 2932 | GSGTVGR | 4175 | 118.714 |
| 440 | CATGTTACGGCGGTGGTTGAT | 2933 | HVTAVVD | 4176 | 118.706 |
| 441 | GATAAGGCGGGGGTGGCTAAT | 2934 | DKAGVAN | 4177 | 118.67 |
| 442 | CGTCTGACTGATACTATGCAT | 2935 | RLTDTMH | 4178 | 118.589 |
| 443 | CTGAACACTCTAATCCACAAA | 2936 | LNTLIHK | 4179 | 118.565 |
| 444 | AGTTATCAGAATCCTCCGCCT | 2937 | SYQNPPP | 4180 | 118.512 |
| 445 | TTGACAGGATTAAACGCTTTC | 2938 | LTGLNAF | 4181 | 118.45 |
| 446 | AGTCCTGTGCTTTCTCCTTCG | 2939 | SPVLSPS | 4182 | 118.377 |
| 447 | GTTCAAACACACATAGGAGTC | 2940 | VQTHIGV | 4183 | 118.36 |
| 448 | CATATGTCTTCTGTTGCGACT | 2941 | HMSSVAT | 4184 | 118.34 |

TABLE 2-continued

| Variant ID | Nucleotide Sequence | SEQ ID NO: | aa | SEQ ID NO: | Sum of muscle mRNA score_capped at 100 |
|---|---|---|---|---|---|
| MHCK7 Results mRNA Second Round of Capsid Variant Selection in C57BL6 mice-score capped at 100 | | | | | |
| 449 | GGAAAAGCCAACGACGGTTCT | 2942 | GKANDGS | 4185 | 118.333 |
| 450 | AGTACTAACGACGAACGCAAA | 2943 | STNDERK | 4186 | 118.28 |
| 451 | CAGGGGGGGAATAGTCGGTTT | 2944 | QGGNSRF | 4187 | 118.236 |
| 452 | CCTAACAACGAAAAAAACCCG | 2945 | PNNEKNP | 4188 | 118.22 |
| 453 | GTGGCTGCGACGGGTGGTACT | 2946 | VAATGGT | 4189 | 118.173 |
| 454 | GCGATTGTGGATAGGGGGAGT | 2947 | AIVDRGS | 4190 | 118.167 |
| 455 | TCCCAACACCACACGCCACTG | 2948 | SQHHTPL | 4191 | 118.137 |
| 456 | TTACAAAGCTCGATGAACGTA | 2949 | LQSSMNV | 4192 | 118.073 |
| 457 | CGAGAAACCAACCCGTCTGAA | 2950 | RETNPSE | 4193 | 117.941 |
| 458 | GGGTTCGGGCACCTGCCCGAA | 2951 | GFGHLPE | 4194 | 117.86 |
| 459 | CGGAATGCTACTGTGACTGTT | 2952 | RNATVTV | 4195 | 117.852 |
| 460 | GTTTCAAACGCTTCGGGCTTA | 2953 | VSNASGL | 4196 | 117.707 |
| 461 | GATCGTCCGAATAATGAGTCG | 2954 | DRPNNES | 4197 | 117.7 |
| 462 | CAGGTTAGTCTGGTGAAGTTG | 2955 | QVSLVKL | 4198 | 117.643 |
| 463 | AGTAATATGCGTGAGGAGATT | 2956 | SNMREEI | 4199 | 117.629 |
| 464 | GATATTGGGCGTTCGAATAGT | 2957 | DIGRSNS | 4200 | 117.45 |
| 465 | GATCATATGAATTTGAGGTCT | 2958 | DHMNLRS | 4201 | 117.365 |
| 466 | ATTGAGCGTAGTAGTGATCGT | 2959 | IERSSDR | 4202 | 117.358 |
| 467 | TTGTCTCAGAATTTTAATCCT | 2960 | LSQNFNP | 4203 | 117.3026 |
| 468 | TATTCTATGGGTCAGCAGCCG | 2961 | YSMGQQP | 4204 | 117.283 |
| 469 | TACACACAAGGGATAATGAAC | 2962 | YTQGIMN | 4205 | 117.22 |
| 470 | ATGCTGTCTCATGGTGCGCTT | 2963 | MLSHGAL | 4206 | 117.165 |
| 471 | GCTTATAATGCTCGTCTGCCT | 2964 | AYNARLP | 4207 | 116.957 |
| 472 | AGACACTACTCCGACAACGCC | 2965 | RHYSDNA | 4208 | 116.945 |
| 473 | GCACACACAGCCATGACCTAC | 2966 | AHTAMTY | 4209 | 116.935 |
| 474 | CTAACAGGCTCTGACATGAAA | 2967 | LTGSDMK | 4210 | 116.89 |
| 475 | ACCTTACACACGAAAGACTTG | 2968 | TLHTKDL | 4211 | 116.879 |
| 476 | TCGGGTCAAAACGGTACATCA | 2969 | SGQNGTS | 4212 | 116.851 |
| 477 | CGTGGGGACGTCCACACCAAC | 2970 | RGDVHTN | 4213 | 116.829 |
| 478 | ACCGGAACGGCTACACTCCCA | 2971 | TGTATLP | 4214 | 116.72 |
| 479 | CTGGGTACGCTGCTTAGTCAG | 2972 | LGTLLSQ | 4215 | 116.72 |
| 480 | GTCCTCTCCTCCAACCTGTAC | 2973 | VLSSNLY | 4216 | 116.707 |
| 481 | AGTTTGGGGTCGGATCGTATG | 2974 | SLGSDRM | 4217 | 116.61 |
| 482 | AGGGGAGATCTTTCTACGCCT | 2975 | RGDLSTP | 4218 | 116.59 |
| 483 | AGGATGTCGGAGAGTTCTGAT | 2976 | RMSESSD | 4219 | 116.585 |
| 484 | ATGACTGAGAAGGCTTCTATT | 2977 | MTEKASI | 4220 | 116.54 |
| 485 | ACAGAACAATCTTACTAACGA | 2978 | TEQSY*R | 4221 | 116.54 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 486 | GTTGAATCTAAATCCGAACCA | 2979 | VESKSEP | 4222 | 116.536 |
| 487 | ATGAATCTTGTGAGGGATTCG | 2980 | MNLVRDS | 4223 | 116.526 |
| 488 | CAAAACCACTCTATAACAACA | 2981 | QNHSITT | 4224 | 116.51 |
| 489 | ACGCTGGACAACAACCACAGC | 2982 | TLDNNHS | 4225 | 116.42 |
| 490 | ACGAAGAGTTTTAATGATCTT | 2983 | TKSFNDL | 4226 | 116.38 |
| 491 | GCCACAGAACACTCAGGGCGC | 2984 | ATEHSGR | 4227 | 116.34 |
| 492 | CAAGGGACTCTCTTGTCTCCA | 2985 | QGTLLSP | 4228 | 116.293 |
| 493 | ACATTCCACCAAGGGGTCAAA | 2986 | TFHQGVK | 4229 | 116.175 |
| 494 | TGTCAGCGGGCTGATTGTGCG | 2987 | CQRADCA | 4230 | 116.17 |
| 495 | CGGTATGATGGTACTCTTAAT | 2988 | RYDGTLN | 4231 | 115.929 |
| 496 | CAAGGCGGTACAAACAACCCC | 2989 | QGGTNNP | 4232 | 115.853 |
| 497 | GGGGGTAACTACCACACCACT | 2990 | GGNYHTT | 4233 | 115.838 |
| 498 | CTGGTTGTTCAGAGTGCGCAG | 2991 | LVVQSAQ | 4234 | 115.7942 |
| 499 | TATCCTCATGAGAGTAAGAAT | 2992 | YPHESKN | 4235 | 115.731 |
| 500 | GAGATTGTTAGGCATACGCAT | 2993 | EIVRHTH | 4236 | 115.724 |
| 501 | GACCGGACAAACAACATGAGC | 2994 | DRTNNMS | 4237 | 115.705 |
| 502 | TCCGTAACCAACGGAGCGGAA | 2995 | SVTNGAE | 4238 | 115.66 |
| 503 | AGCGGACAAAAAAACTCAGAA | 2996 | SGQKNSE | 4239 | 115.653 |
| 504 | GAGCAGAAGAAGACTGATCAT | 2997 | EQKKTDH | 4240 | 115.565 |
| 505 | AATATTAATGGTGGGGGGAAT | 2998 | NINGGGN | 4241 | 115.563 |
| 506 | AAGCTGCATACTAAGGATCTT | 2999 | KLHTKDL | 4242 | 115.54 |
| 507 | AGCTTCTTGGTAGCCCACCCA | 3000 | SFLVAHP | 4243 | 115.4 |
| 508 | TACCAACAAAACATAGAAATC | 3001 | YQQNIEI | 4244 | 115.388 |
| 509 | AGGGGTGATCTTTCTACGACT | 3002 | RGDLSTT | 4245 | 115.31 |
| 510 | GCGAACCTCAACTTGACCAGT | 3003 | ANLNLTS | 4246 | 115.305 |
| 511 | ACGGTGCAGCATGCGGCGACG | 3004 | TVQHAAT | 4247 | 115.231 |
| 512 | ACCGTAAACCTCCTAGCGGCA | 3005 | TVNLLAA | 4248 | 115.223 |
| 513 | AACCAAAGAGTTGAACAAAAA | 3006 | NQRVEQK | 4249 | 115.222 |
| 514 | AATACTTATACTGCTGCGAAG | 3007 | NTYTAAK | 4250 | 115.189 |
| 515 | ATCCAAAGAGACGTGGGCCAC | 3008 | IQRDVGH | 4251 | 115.098 |
| 516 | ATCTCAGAAATGACTAGGTAC | 3009 | ISEMTRY | 4252 | 115.098 |
| 517 | ATTGCTACTAATGTGATTTAT | 3010 | IATNVIY | 4253 | 115.089 |
| 518 | AACGGCAACCACTCCATAGAC | 3011 | NGNHSID | 4254 | 115.062 |
| 519 | ACGAGTATTGGTAGTGCTAAG | 3012 | TSIGSAK | 4255 | 115.036 |
| 520 | AACGTACACTCTGTTGACAAA | 3013 | NVHSVDK | 4256 | 114.987 |
| 521 | GAACTCTCCGTTCCGAAACCA | 3014 | ELSVPKP | 4257 | 114.93 |
| 522 | TTCCTCGACAAATACAACTAC | 3015 | FLDKYNY | 4258 | 114.888 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 523 | TACATCCCGAACAACTCAGGA | 3016 | YIPNNSG | 4259 | 114.881 |
| 524 | GGGCTAGGACAACCCCAACTC | 3017 | GLGQPQL | 4260 | 114.817 |
| 525 | GAGGGGAGTCAGGGGAATCAT | 3018 | EGSQGNH | 4261 | 114.66 |
| 526 | AATATTTATATGGCGAGTGGT | 3019 | NIYMASG | 4262 | 114.66 |
| 527 | AATTTGCAGACTGGTGTTCAG | 3020 | NLQTGVQ | 4263 | 114.65 |
| 528 | ACCGTCGCTCCCTACAGTAGC | 3021 | TVAPYSS | 4264 | 114.65 |
| 529 | TCAAACTACTCTGACGGAATA | 3022 | SNYSDGI | 4265 | 114.649 |
| 530 | GCTACTTACGTTGTCGGAACA | 3023 | ATYVVGT | 4266 | 114.64 |
| 531 | TCAAGGGAAGCGGGTTCAACT | 3024 | SREAGST | 4267 | 114.622 |
| 532 | GCCGGAAAAACCCACGCCGAC | 3025 | AGKTHAD | 4268 | 114.6 |
| 533 | CCGCTTTCTCTTCATAATAGT | 3026 | PLSLHNS | 4269 | 114.589 |
| 534 | CTTCGAGACCTAAACGGAGGA | 3027 | LRDLNGG | 4270 | 114.553 |
| 535 | GATAGGACGTATTCGAATACG | 3028 | DRTYSNT | 4271 | 114.548 |
| 536 | TCGGTCACCAGTGGAACACAA | 3029 | SVTSGTQ | 4272 | 114.541 |
| 537 | AATATGACTTCGGCTTATCAT | 3030 | NMTSAYH | 4273 | 114.52 |
| 538 | GTTATGGGTGGTCCTGGGATT | 3031 | VMGGPGI | 4274 | 114.491 |
| 539 | GCTGGGACTCATACTGATAAG | 3032 | AGTHTDK | 4275 | 114.444 |
| 540 | GGTACTATGAATATTGGTATT | 3033 | GTMNIGI | 4276 | 114.356 |
| 541 | ACAGCCGGCGGCGAACGCGCC | 3034 | TAGGERA | 4277 | 114.34 |
| 542 | GGTATGACTTCTAATCAGGTT | 3035 | GMTSNQV | 4278 | 114.298 |
| 543 | CATTTTTCGCAGATTACTAAT | 3036 | HFSQITN | 4279 | 114.278 |
| 544 | AGCAGGATAGAAAACAACAAC | 3037 | SRIENNN | 4280 | 114.055 |
| 545 | GATACGGCGAGTTATAATAAT | 3038 | DTASYNN | 4281 | 114 |
| 546 | GTGAATCAGAGTCCTGGGGCT | 3039 | VNQSPGA | 4282 | 113.85 |
| 547 | AATAATATGGGTCATGGTCAT | 3040 | NNMGHGH | 4283 | 113.837 |
| 548 | TCGCGGCTATCACAAGACCCC | 3041 | SRLSQDP | 4284 | 113.832 |
| 549 | TCTACGTCTCAGGCTGTGCAG | 3042 | STSQAVQ | 4285 | 113.802 |
| 550 | CGATGGCAAGGACTGAGCGCG | 3043 | RWQGLSA | 4286 | 113.76 |
| 551 | GCGCATATGCATTCGGAGTTG | 3044 | AHMHSEL | 4287 | 113.74 |
| 552 | AATAATCTTACGAATTCGACG | 3045 | NNLTNST | 4288 | 113.736 |
| 553 | CAGCCTAGTGCGAGTGAGCTT | 3046 | QPSASEL | 4289 | 113.731 |
| 554 | GGGACTTCCTTGGAAAACCGA | 3047 | GTSLENR | 4290 | 113.709 |
| 555 | CTGTCTAATTCGATTACGCCT | 3048 | LSNSITP | 4291 | 113.683 |
| 556 | ACCATAGTGTCCACTTCTTAC | 3049 | TIVSTSY | 4292 | 113.628 |
| 557 | ACCCTAGGCTACCCAGACAAA | 3050 | TLGYPDK | 4293 | 113.563 |
| 558 | TCAAGACACGACGTCCGAAAC | 3051 | SRHDVRN | 4294 | 113.559 |
| 559 | AATGGTAGTGTGGCTAATCCT | 3052 | NGSVANP | 4295 | 113.48 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 560 | GCGATGGATGGGTATAGGGTT | 3053 | AMDGYRV | 4296 | 113.462 |
| 561 | TGGACGGGCGCACAACCTTCT | 3054 | WTGAQPS | 4297 | 113.3493 |
| 562 | AAAAACGGCGCCATAGGAACA | 3055 | KNGAIGT | 4298 | 113.335 |
| 563 | GTACTTCCAAGTCGGATCGCG | 3056 | VLPSRIA | 4299 | 113.3 |
| 564 | GATAATGTGAATTCTCAGCCT | 3057 | DNVNSQP | 4300 | 113.207 |
| 565 | GGCGTAAACGCTAGCTACAGC | 3058 | GVNASYS | 4301 | 113.174 |
| 566 | CTGTCTCACGCCATGGACCGG | 3059 | LSHAMDR | 4302 | 113.127 |
| 567 | AGGGCTCATGGGGATAATCAG | 3060 | RAHGDNQ | 4303 | 113.036 |
| 568 | TTGCAGACGCCTGGGACGACG | 3061 | LQTPGTT | 4304 | 113.01 |
| 569 | ACTCAGGTTGTTAGTATTTAT | 3062 | TQVVSIY | 4305 | 113.001 |
| 570 | CAGGTTCAGGGGACTCTGGGG | 3063 | QVQGTLG | 4306 | 112.9928 |
| 571 | GTGGGCAACCAAAACTTACCC | 3064 | VGNQNLP | 4307 | 112.889 |
| 572 | TATGTTGATTATAGTAAGTCG | 3065 | YVDYSKS | 4308 | 112.872 |
| 573 | CTGCTTAATTCTTCGGGTGTG | 3066 | LLNSSGV | 4309 | 112.857 |
| 574 | AATCAGTCGCTTACTATGGAT | 3067 | NQSLTMD | 4310 | 112.793 |
| 575 | GCTGGTAAGGATCTTAGTAAT | 3068 | AGKDLSN | 4311 | 112.792 |
| 576 | TCTTACGTTAGCGTCCCCGCC | 3069 | SYVSVPA | 4312 | 112.668 |
| 577 | AATGAGGGGCGTGTGCAGACT | 3070 | NEGRVQT | 4313 | 112.6219 |
| 578 | ACTTTGACGCAGACTGGGATG | 3071 | TLTQTGM | 4314 | 112.588 |
| 579 | GGCTTCGCATTAACTGGCACC | 3072 | GFALTGT | 4315 | 112.564 |
| 580 | CAGTCGACGCTGAATAGGCCT | 3073 | QSTLNRP | 4316 | 112.5575 |
| 581 | ACAACAACACACTCCATCTCC | 3074 | TTTHSIS | 4317 | 112.547 |
| 582 | AACACACACAGACAAGAATAC | 3075 | NTHRQEY | 4318 | 112.522 |
| 583 | TCCCAAATAGTCAACACCACA | 3076 | SQIVNTT | 4319 | 112.519 |
| 584 | CTGGTGCTTGAGATGCAGACG | 3077 | LVLEMQT | 4320 | 112.492 |
| 585 | AACGACATCTCCACCCAACGG | 3078 | NDISTQR | 4321 | 112.444 |
| 586 | TACACCGCCGACAAAAAACAA | 3079 | YTADKKQ | 4322 | 112.402 |
| 587 | TTCGGAGCAACCACCACAGCA | 3080 | FGATTTA | 4323 | 112.399 |
| 588 | GTTCAGATTTCTATGAATAAT | 3081 | VQISMNN | 4324 | 112.364 |
| 589 | ATGCATGCGCAGGAGTCTCGT | 3082 | MHAQESR | 4325 | 112.324 |
| 590 | CATGTGAATACTGCTGATCGG | 3083 | HVNTADR | 4326 | 112.313 |
| 591 | TACAGTACAGACTCCACCAAA | 3084 | YSTDSTK | 4327 | 112.271 |
| 592 | GGACACGACCGAACACCAAAC | 3085 | GHDRTPN | 4328 | 112.213 |
| 593 | ACGAGTGGTGTGCTTACGCGG | 3086 | TSGVLTR | 4329 | 112.212 |
| 594 | AATATTGCTATGTCTAAGATT | 3087 | NIAMSKI | 4330 | 112.204 |
| 595 | ATGGGGACTGAGTATCGTATG | 3088 | MGTEYRM | 4331 | 112.185 |
| 596 | CCTTATGCGAATAGGCTTGAG | 3089 | PYANRLE | 4332 | 112.174 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 597 | CCGCTTCAGAATAATAAGACG | 3090 | PLQNNKT | 4333 | 112.172 |
| 598 | TCCTTGACGGAAAAAGCGCCG | 3091 | SLTEKAP | 4334 | 112.15 |
| 599 | AATATGGTGTATACGAATGTG | 3092 | NMVYTNV | 4335 | 112.077 |
| 600 | ATGTTAAGTGCCACCCAAGGG | 3093 | MLSATQG | 4336 | 112.047 |
| 601 | AACATGACTCACTCAACCGTA | 3094 | NMTHSTV | 4337 | 112.0108 |
| 602 | ATTTATACGAATAGTCATGTT | 3095 | IYTNSHV | 4338 | 111.93 |
| 603 | TGGTCGCATGATCGGCCTACT | 3096 | WSHDRPT | 4339 | 111.926 |
| 604 | GAAAAAGGCACACCAAGTAGC | 3097 | EKGTPSS | 4340 | 111.922 |
| 605 | CATCATTCTACTGAGTCGTTG | 3098 | HHSTESL | 4341 | 111.911 |
| 606 | CCAAAAAGCACCCAAGTAATG | 3099 | PKSTQVM | 4342 | 111.846 |
| 607 | AGTGATAGGACTGCTCAGCAG | 3100 | SDRTAQQ | 4343 | 111.845 |
| 608 | GCTACCCTCGCACGGACCTCA | 3101 | ATLARTS | 4344 | 111.8417 |
| 609 | ATTTCTCAGGTGTCTTTTAAT | 3102 | ISQVSFN | 4345 | 111.81 |
| 610 | CATTATGGGAATAAGGATATT | 3103 | HYGNKDI | 4346 | 111.805 |
| 611 | AATGATGGGACTGATCGTAGG | 3104 | NDGTDRR | 4347 | 111.574 |
| 612 | ACCAACCACATAACCGGTCCA | 3105 | TNHITGP | 4348 | 111.551 |
| 613 | ACTAATTCTAATCAGAGTTCG | 3106 | TNSNQSS | 4349 | 111.532 |
| 614 | GTGGCGACTCATTATAATGAG | 3107 | VATHYNE | 4350 | 111.52 |
| 615 | GACCTCGGTACGGCTAGAACC | 3108 | DLGTART | 4351 | 111.516 |
| 616 | GCTCTTAGTCAGAGTGCGGGT | 3109 | ALSQSAG | 4352 | 111.4957 |
| 617 | AAAACCACCCTACACCAAGCA | 3110 | KTTLHQA | 4353 | 111.46 |
| 618 | ATGATAAACGCCATAACTCCA | 3111 | MINAITP | 4354 | 111.432 |
| 619 | GGGTCTACGCCGGGGGCGAGT | 3112 | GSTPGAS | 4355 | 111.327 |
| 620 | AATGAGAAGCCGCAGTCGACG | 3113 | NEKPQST | 4356 | 111.309 |
| 621 | TCATTGATGGGCAGTGCAGGA | 3114 | SLMGSAG | 4357 | 111.287 |
| 622 | ACCGACACGCTCAGCGAAAGA | 3115 | TDTLSER | 4358 | 111.25 |
| 623 | GCCTCGCAATCAGAAAAAAAC | 3116 | ASQSEKN | 4359 | 111.223 |
| 624 | GCTGTTAGAACACCGGCAATG | 3117 | AVRTPAM | 4360 | 111.215 |
| 625 | CCTAATGCTAGTTTTGGTCCG | 3118 | PNASFGP | 4361 | 111.172 |
| 626 | AAAGCCCACGTTGTAGAAATA | 3119 | KAHVVEI | 4362 | 111.166 |
| 627 | TATATTTCGGCGCCTCCGATG | 3120 | YISAPPM | 4363 | 111.15 |
| 628 | CCAATCCAAAACGAATCGTCC | 3121 | PIQNESS | 4364 | 111.128 |
| 629 | GGCGTAACCAACGCTTCCAAA | 3122 | GVTNASK | 4365 | 111.107 |
| 630 | GTAAACGGGGGAAAACCAGTC | 3123 | VNGGKPV | 4366 | 111.096 |
| 631 | AGTGTTCTGAGTAGTTCGACT | 3124 | SVLSSST | 4367 | 111.07 |
| 632 | TTAGCACAAGGCACGGACCGG | 3125 | LAQGTDR | 4368 | 111.032 |
| 633 | CAGTCTGTGTCGACTGGGGCG | 3126 | QSVSTGA | 4369 | 110.982 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 634 | TTGACGCAGGTTTATCATGAG | 3127 | LTQVYHE | 4370 | 110.91 |
| 635 | AGAGAAATGAGCAGCCTATCT | 3128 | REMSSLS | 4371 | 110.891 |
| 636 | ACGAGTACGATGACTGCGCGT | 3129 | TSTMTAR | 4372 | 110.835 |
| 637 | ACTATTCAGCAGGTTAGTAAT | 3130 | TIQQVSN | 4373 | 110.832 |
| 638 | AGGACGCAAGCAGGGGACTCA | 3131 | RTQAGDS | 4374 | 110.83 |
| 639 | AATACTTATACTGCTGGGAAG | 3132 | NTYTAGK | 4375 | 110.816 |
| 640 | AATGAGCAGAATACGCCGAGT | 3133 | NEQNTPS | 4376 | 110.79 |
| 641 | GGATTCGCCCAACAAGAAGCG | 3134 | GFAQQEA | 4377 | 110.775 |
| 642 | AGTCCGCAGCATGGTGTTATT | 3135 | SPQHGVI | 4378 | 110.7 |
| 643 | GCAGTCCACGCAACATCATCA | 3136 | AVHATSS | 4379 | 110.653 |
| 644 | GGAGACACCCGTGGTGCACAC | 3137 | GDTRGAH | 4380 | 110.63 |
| 645 | GTAAGAGAAACCACACACCTC | 3138 | VRETTHL | 4381 | 110.627 |
| 646 | CTTTCTCAACAACGCGACTAC | 3139 | LSQQRDY | 4382 | 110.6 |
| 647 | GCGACTAGGGGTGAGTCGTCT | 3140 | ATRGESS | 4383 | 110.56 |
| 648 | ACTAATGATTCTGTGGGTAGT | 3141 | TNDSVGS | 4384 | 110.545 |
| 649 | CTTACTAATAATTTTAAGGAT | 3142 | LTNNFKD | 4385 | 110.519 |
| 650 | GTGAATGGGACTCAGATTTTT | 3143 | VNGTQIF | 4386 | 110.47 |
| 651 | GGTAATACTGGGAGTCCGGGG | 3144 | GNTGSPG | 4387 | 110.431 |
| 652 | TGGACAGCTAACCAAGGCTTA | 3145 | WTANQGL | 4388 | 110.43 |
| 653 | AATACTACTCCGACGAATCAT | 3146 | NTTPTNH | 4389 | 110.42 |
| 654 | GAACGAGTCAACGGGATGGCA | 3147 | ERVNGMA | 4390 | 110.405 |
| 655 | AAAGTCACAAACAACGCATAC | 3148 | KVTNNAY | 4391 | 110.363 |
| 656 | TTATCCTCCGAATCACCCAGG | 3149 | LSSESPR | 4392 | 110.346 |
| 657 | CATACGGCGGCGGTTGCTACT | 3150 | HTAAVAT | 4393 | 110.27 |
| 658 | TACGACAGCCGACTCTACGCG | 3151 | YDSRLYA | 4394 | 110.263 |
| 659 | ATAGAACACATGCTTAGACCC | 3152 | IEHMLRP | 4395 | 110.221 |
| 660 | TACCTAGAATCCAACTACACC | 3153 | YLESNYT | 4396 | 110.18 |
| 661 | GCGTACTCATCTACCGGGCAC | 3154 | AYSSTGH | 4397 | 110.176 |
| 662 | ATCGACATATCGACGCAAAGC | 3155 | IDISTQS | 4398 | 110.14 |
| 663 | ACAACAAACTCAGGCGCGACG | 3156 | TTNSGAT | 4399 | 110.139 |
| 664 | AACGTGCTAACCACGGTTGTC | 3157 | NVLTTVV | 4400 | 110.107 |
| 665 | ACAACCGGAATCGAACGTTCC | 3158 | TTGIERS | 4401 | 110.106 |
| 666 | GCACGAGTGGACACCAACCAA | 3159 | ARVDTNQ | 4402 | 110.09 |
| 667 | CAGAGTGTGAAGGAGGCGATT | 3160 | QSVKEAI | 4403 | 110.069 |
| 668 | GCGTTGCTTAGTGTGAATGAG | 3161 | ALLSVNE | 4404 | 110.013 |
| 669 | GGGCGTGATAATCATCATGCG | 3162 | GRDNHHA | 4405 | 109.959 |
| 670 | ATTCAGTCGCAGTCGCAGTTG | 3163 | IQSQSQL | 4406 | 109.941 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 671 | AGTGAGGGTAGTTCGCGGTCG | 3164 | SEGSSRS | 4407 | 109.9403 |
| 672 | GACGTCCAAAACATACGCGAA | 3165 | DVQNIRE | 4408 | 109.921 |
| 673 | AAAGGCCACGCCTACGAAGCC | 3166 | KGHAYEA | 4409 | 109.897 |
| 674 | TATGTTAGGGCGCAGGATCAG | 3167 | YVRAQDQ | 4410 | 109.876 |
| 675 | GTCGACGAATACCGAAGCCGC | 3168 | VDEYRSR | 4411 | 109.853 |
| 676 | ACTCTCTCAGGCTACATGAGA | 3169 | TLSGYMR | 4412 | 109.808 |
| 677 | CCTAGTGTCCGTTTGCCCTTA | 3170 | PSVRLPL | 4413 | 109.742 |
| 678 | AACATAGCAGGCGGAGAACAA | 3171 | NIAGGEQ | 4414 | 109.702 |
| 679 | CTGCTCCAATCGACCTACTTG | 3172 | LLQSTYL | 4415 | 109.672 |
| 680 | CAGTCGGATACGACTTCGATT | 3173 | QSDTTSI | 4416 | 109.605 |
| 681 | ATTAGGTCTGGGAATGCGATG | 3174 | IRSGNAM | 4417 | 109.554 |
| 682 | ATGCTGTCTCAAGTCTTAACA | 3175 | MLSQVLT | 4418 | 109.536 |
| 683 | ACAGAACGCCAAATCGAATTA | 3176 | TERQIEL | 4419 | 109.488 |
| 684 | GGAACCCACGCCTCAGCATAC | 3177 | GTHASAY | 4420 | 109.477 |
| 685 | GTTGAGTCTTCTTATTCTCGG | 3178 | VESSYSR | 4421 | 109.457 |
| 686 | GGTGGGAATTATCATACTAAG | 3179 | GGNYHTK | 4422 | 109.445 |
| 687 | CCCACCAGTCACCAAGAACCC | 3180 | PTSHQEP | 4423 | 109.418 |
| 688 | ACCATAATCGGTGTCTTACCC | 3181 | TIIGVLP | 4424 | 109.381 |
| 689 | TCTAACAGCGGTTCTACCCTC | 3182 | SNSGSTL | 4425 | 109.379 |
| 690 | TCGATAACGACCGTAGCGAAC | 3183 | SITTVAN | 4426 | 109.347 |
| 691 | GCGTCTCCGGCGCAGACCGGC | 3184 | ASPAQTG | 4427 | 109.331 |
| 692 | TCGTTGCCGAGTCATAGTAAT | 3185 | SLPSHSN | 4428 | 109.3106 |
| 693 | CTACACAACGCCGTCGGACCC | 3186 | LHNAVGP | 4429 | 109.307 |
| 694 | CAAGCCCCGCCAACAGCACAA | 3187 | QAPPTAQ | 4430 | 109.294 |
| 695 | CCTAATACTGCTAGTAATTTT | 3188 | PNTASNF | 4431 | 109.249 |
| 696 | CCCTCCAACAGTGAAAGATTC | 3189 | PSNSERF | 4432 | 109.227 |
| 697 | GAACTCCACGCACAACAACCA | 3190 | ELHAQQP | 4433 | 109.194 |
| 698 | GGTTCTTATTCTGATGGTAGT | 3191 | GSYSDGS | 4434 | 109.162 |
| 699 | TATGGTGTGCAGGCGAATAGT | 3192 | YGVQANS | 4435 | 109.152 |
| 700 | GAAGTAGGTAAAACCACCCAC | 3193 | EVGKTTH | 4436 | 109.116 |
| 701 | ACTTCGCAGGGTAGGAGTCCT | 3194 | TSQGRSP | 4437 | 109.097 |
| 702 | GTAGAACACGTAGCCCACCAA | 3195 | VEHVAHQ | 4438 | 109.092 |
| 703 | ATCCAAAGCAGCTACAACCGC | 3196 | IQSSYNR | 4439 | 109.073 |
| 704 | ACGCTATCGGTTACCCTGGGT | 3197 | TLSVTLG | 4440 | 109.046 |
| 705 | CGGAATGAGCCGGTTAGTACT | 3198 | RNEPVST | 4441 | 108.981 |
| 706 | GTGATTGTGGGGAGTAATGAG | 3199 | VIVGSNE | 4442 | 108.955 |
| 707 | GAGCTGTCTACTCCTATGGTT | 3200 | ELSTPMV | 4443 | 108.948 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 708 | GCTTACAACGACCTACGATCA | 3201 | AYNDLRS | 4444 | 108.942 |
| 709 | AACGCGAACTCCGGTGAACGA | 3202 | NANSGER | 4445 | 108.906 |
| 710 | TTGTCATCACAATGGACACAA | 3203 | LSSQWTQ | 4446 | 108.9 |
| 711 | ATCAACGCCGGCAACTACCGA | 3204 | INAGNYR | 4447 | 108.883 |
| 712 | CTGAGGTCGAGTGAGGCTCCG | 3205 | LRSSEAP | 4448 | 108.866 |
| 713 | ACGTCTGATACGAATGCTAGG | 3206 | TSDTNAR | 4449 | 108.858 |
| 714 | CCGAATTCTCCGCATGGTTCT | 3207 | PNSPHGS | 4450 | 108.84 |
| 715 | ACCCAACACCTACCATCCACA | 3208 | TQHLPST | 4451 | 108.803 |
| 716 | GTGCATGGGAATGCTCCGGCT | 3209 | VHGNAPA | 4452 | 108.783 |
| 717 | TCTTCTCAGCGTGATTCTGTT | 3210 | SSQRDSV | 4453 | 108.754 |
| 718 | CCCCCCTCAGTTGACCGAAAA | 3211 | PPSVDRK | 4454 | 108.751 |
| 719 | GAGACTCTGCCGTATAAGAGT | 3212 | ETLPYKS | 4455 | 108.728 |
| 720 | CATCTTAGTCAGGCTAATCAT | 3213 | HLSQANH | 4456 | 108.727 |
| 721 | AAACCGCTAAACGGTACCAAC | 3214 | KPLNGTN | 4457 | 108.683 |
| 722 | TGGCAAACCAACGGCATGCAA | 3215 | WQTNGMQ | 4458 | 108.68 |
| 723 | ACCGTGAACGTCCACTCCGAC | 3216 | TVNVHSD | 4459 | 108.659 |
| 724 | ACCCAATACGTCGTTGCCCCT | 3217 | TQYVVAP | 4460 | 108.64 |
| 725 | AACGTCGACTCCTCTAACGTG | 3218 | NVDSSNV | 4461 | 108.62 |
| 726 | AACGGATACCAACTACAAATC | 3219 | NGYQLQI | 4462 | 108.573 |
| 727 | GAAGAAACACGGACCAGAATG | 3220 | EETRTRM | 4463 | 108.571 |
| 728 | ACCTCTCCAGCCTCTGACCGG | 3221 | TSPASDR | 4464 | 108.552 |
| 729 | CATAGTGGTGCTGGGGTTCTG | 3222 | HSGAGVL | 4465 | 108.539 |
| 730 | GCTGCTAATCCTAGTACGGAG | 3223 | AANPSTE | 4466 | 108.527 |
| 731 | ATGTTGGTACAAAACACACCC | 3224 | MLVQNTP | 4467 | 108.482 |
| 732 | GTGCAGCAGAATAATATTAAT | 3225 | VQQNNIN | 4468 | 108.473 |
| 733 | CATGATGGTTATGTTCCTAAT | 3226 | HDGYVPN | 4469 | 108.469 |
| 734 | AACTCAGGTAACAACCCCATC | 3227 | NSGNNPI | 4470 | 108.467 |
| 735 | ACGGACAACCCGTCCTACAAA | 3228 | TDNPSYK | 4471 | 108.453 |
| 736 | GGAGGCTTAAGTTTATCCTCG | 3229 | GGLSLSS | 4472 | 108.431 |
| 737 | AATAATGAGAATACGCGTAAT | 3230 | NNENTRN | 4473 | 108.418 |
| 738 | AAGAATAATAATTCTGATTCT | 3231 | KNNNSDS | 4474 | 108.367 |
| 739 | AAGGATGAGCATCTTCATTAT | 3232 | KDEHLHY | 4475 | 108.358 |
| 740 | AATTTTACTATTACGGAGGCG | 3233 | NFTITEA | 4476 | 108.32 |
| 741 | TTGAACCAAAACAGTGTCTCC | 3234 | LNQNSVS | 4477 | 108.304 |
| 742 | AATTCTCATGTTCCTAATAAT | 3235 | NSHVPNN | 4478 | 108.289 |
| 743 | AATTCTACGCATATTAATTCG | 3236 | NSTHINS | 4479 | 108.2563 |
| 744 | CATATGTCTAGTTATTCGTCG | 3237 | HMSSYSS | 4480 | 108.253 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 745 | AACGTACCCAACGGACAAGGA | 3238 | NVPNGQG | 4481 | 108.25 |
| 746 | AACGGTCCGACCGGATCCGCC | 3239 | NGPTGSA | 4482 | 108.245 |
| 747 | AAAAGCAACGCGGGATTCGGT | 3240 | KSNAGFG | 4483 | 108.23 |
| 748 | GCGGCCGCACTAGAAACAATA | 3241 | AAALETI | 4484 | 108.223 |
| 749 | AACCGTCAAAGGGACTTCGAA | 3242 | NRQRDFE | 4485 | 108.196 |
| 750 | GGGTCAGGGAACGAACCCGGG | 3243 | GSGNEPG | 4486 | 108.192 |
| 751 | GTTAGTGTGGCTGTGCCTGCG | 3244 | VSVAVPA | 4487 | 108.11 |
| 752 | CACTCTAACACACACTACGAA | 3245 | HSNTHYE | 4488 | 108.11 |
| 753 | CCTGACAGAGCGAACGACAAA | 3246 | PDRANDK | 4489 | 108.058 |
| 754 | CAAGTTGGGGCTCTAATGGTT | 3247 | QVGALMV | 4490 | 108.037 |
| 755 | TTAACACCCCAAGGGACTAGT | 3248 | LTPQGTS | 4491 | 108.028 |
| 756 | CTATACGACGGAAAACACGTC | 3249 | LYDGKHV | 4492 | 107.972 |
| 757 | CTAACCGAATCTGTGAGAAAC | 3250 | LTESVRN | 4493 | 107.93 |
| 758 | AGTACTTATGGGAATACTTAT | 3251 | STYGNTY | 4494 | 107.929 |
| 759 | AATGCTATTTCTACTAATAAT | 3252 | NAISTNN | 4495 | 107.907 |
| 760 | ATTGCTCATGTGTCTACTAAT | 3253 | IAHVSTN | 4496 | 107.849 |
| 761 | AGTGAGGAGAGGACGCGTGCG | 3254 | SEERTRA | 4497 | 107.833 |
| 762 | CGTTGGTCTGAAAACAACTCC | 3255 | RWSENNS | 4498 | 107.83 |
| 763 | GATGGTAATAATACGACTTAT | 3256 | DGNNTTY | 4499 | 107.748 |
| 764 | GTGACGACTGTTGATAGTGCT | 3257 | VTTVDSA | 4500 | 107.738 |
| 765 | ACCGTAAAACAAACAAGTCCG | 3258 | TVKQTSP | 4501 | 107.7213 |
| 766 | TCTATCTACCTCGCGTCCACT | 3259 | SIYLAST | 4502 | 107.712 |
| 767 | ACGACCCGAAACGAACACTCG | 3260 | TTRNEHS | 4503 | 107.707 |
| 768 | TCGTATGATATGCATACGAAT | 3261 | SYDMHTN | 4504 | 107.705 |
| 769 | GTCTCTACATACCTCCTGGCA | 3262 | VSTYLLA | 4505 | 107.687 |
| 770 | GGAGAACAAAGCCACAACCAA | 3263 | GEQSHNQ | 4506 | 107.684 |
| 771 | ACTGCCAACAACCACTCTCCG | 3264 | TANNHSP | 4507 | 107.671 |
| 772 | CAATTCCACGGGACATCTGAA | 3265 | QFHGTSE | 4508 | 107.652 |
| 773 | AACGTTCTGGGAGCGTCTAGC | 3266 | NVLGASS | 4509 | 107.64 |
| 774 | AGGGATAGTACTATTAGTCGG | 3267 | RDSTISR | 4510 | 107.635 |
| 775 | GTTATTGGGACTTCTAGGGAT | 3268 | VIGTSRD | 4511 | 107.5934 |
| 776 | AATTATGAGAAGGAGTTTGTT | 3269 | NYEKEFV | 4512 | 107.592 |
| 777 | ATGGACCAAAGCCACTCCCGA | 3270 | MDQSHSR | 4513 | 107.563 |
| 778 | AATTCTCAGAATCCTCAGGGT | 3271 | NSQNPQG | 4514 | 107.562 |
| 779 | CACACGGGCACGGACAACCGA | 3272 | HTGTDNR | 4515 | 107.5323 |
| 780 | TATAATACTGTTGATCAGCGG | 3273 | YNTVDQR | 4516 | 107.523 |
| 781 | AAAGAAAGCCTCGAAGACGTC | 3274 | KESLEDV | 4517 | 107.49 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 782 | ACTGCGAATAGTACGTATGTG | 3275 | TANSTYV | 4518 | 107.479 |
| 783 | TATCTGAATAGTACGCAGATT | 3276 | YLNSTQI | 4519 | 107.436 |
| 784 | CGTGTTGAAGACACCAACTCC | 3277 | RVEDTNS | 4520 | 107.416 |
| 785 | AACGACGCACGCAACCGTGCA | 3278 | NDARNRA | 4521 | 107.37 |
| 786 | AATACTAATAATCAGGAGCAG | 3279 | NTNNQEQ | 4522 | 107.332 |
| 787 | ACCGTCGGATCGAACAGTATA | 3280 | TVGSNSI | 4523 | 107.3 |
| 788 | TATGGGGAGCGTGCTAGGACG | 3281 | YGERART | 4524 | 107.297 |
| 789 | CCGACCGGAGGCTCACCACCA | 3282 | PTGGSPP | 4525 | 107.265 |
| 790 | CTTGGGCAGGTTAATTCTACG | 3283 | LGQVNST | 4526 | 107.229 |
| 791 | GTCTCGGGTCCGGTATCGGTC | 3284 | VSGPVSV | 4527 | 107.222 |
| 792 | GGTACTAATCATGATTTTTCG | 3285 | GTNHDFS | 4528 | 107.169 |
| 793 | AAGACGCTTGATAATAATGCT | 3286 | KTLDNNA | 4529 | 107.165 |
| 794 | CACAGTGAACTACGTCAAAAC | 3287 | HSELRQN | 4530 | 107.157 |
| 795 | GAGAAGAATCTGACTAATGCT | 3288 | EKNLTNA | 4531 | 107.131 |
| 796 | ACCGGACTCGGAGGCAACAGT | 3289 | TGLGGNS | 4532 | 107.113 |
| 797 | AAAGACCACATCCTCAGCCTC | 3290 | KDHILSL | 4533 | 107.108 |
| 798 | ATAACTACTGGCGGAGTGCTA | 3291 | ITTGGVL | 4534 | 107.108 |
| 799 | CTGGCTGATTCGAATTCTAAG | 3292 | LADSNSK | 4535 | 107.1 |
| 800 | AGTATTTCTGATAAGAATCAG | 3293 | SISDKNQ | 4536 | 107.08 |
| 801 | TATATTGCTGGGGGGGAGCAG | 3294 | YIAGGEQ | 4537 | 107.069 |
| 802 | TTGCCGGATAAGGGGCGGATT | 3295 | LPDKGRI | 4538 | 107.06 |
| 803 | TTGATCCAAACGCAAGGCACG | 3296 | LIQTQGT | 4539 | 107.042 |
| 804 | TACTCCGGAGAACTAAACAAA | 3297 | YSGELNK | 4540 | 107.037 |
| 805 | TGCGCATCAGAAGTTTGCCAA | 3298 | CASEVCQ | 4541 | 107.035 |
| 806 | CTTATGGCTGCTAATACTGCG | 3299 | LMAANTA | 4542 | 107.032 |
| 807 | CATCAGTCTTTTGATGCTGGT | 3300 | HQSFDAG | 4543 | 107.001 |
| 808 | GGGGAGACGCTGAGGTCTCAG | 3301 | GETLRSQ | 4544 | 106.999 |
| 809 | CAGACTGATGGTCCTAATTTT | 3302 | QTDGPNF | 4545 | 106.978 |
| 810 | ACGACGACTAATGTGAATTTT | 3303 | TTTNVNF | 4546 | 106.969 |
| 811 | AACATGACCAACGAAAACGGA | 3304 | NMTNENG | 4547 | 106.938 |
| 812 | GGGTATAGTCCTTCGACGCCG | 3305 | GYSPSTP | 4548 | 106.892 |
| 813 | TTGCAGGTTACGGTTCATAAT | 3306 | LQVTVHN | 4549 | 106.879 |
| 814 | GATCTGACGCATGTTCATCGT | 3307 | DLTHVHR | 4550 | 106.874 |
| 815 | ACGGAGCTTAGTGAGTATACT | 3308 | TELSEYT | 4551 | 106.852 |
| 816 | ATGACAGTCGCCAGTACTAGC | 3309 | MTVASTS | 4552 | 106.843 |
| 817 | AGCAGTCAAGCCCACGGCCCA | 3310 | SSQAHGP | 4553 | 106.822 |
| 818 | ACCAGAAGCCCGAACGAAGAC | 3311 | TRSPNED | 4554 | 106.81 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 819 | GATAATAATAAGCATGGTACT | 3312 | DNNKHGT | 4555 | 106.806 |
| 820 | AGGGAGATTGTTCATAGTAAT | 3313 | REIVHSN | 4556 | 106.802 |
| 821 | CGGAAACTTGAACTCGACCTA | 3314 | RKLELDL | 4557 | 106.801 |
| 822 | ATCTACGAAACCGTAACCTTG | 3315 | IYETVTL | 4558 | 106.801 |
| 823 | AATAGTGGTAGTACGAGTTTT | 3316 | NSGSTSF | 4559 | 106.783 |
| 824 | CCAAGTACGAACGAAAGCCGC | 3317 | PSTNESR | 4560 | 106.782 |
| 825 | CAAGCCGACCTCAGGTACAAA | 3318 | QADLRYK | 4561 | 106.773 |
| 826 | GATCAGCCGGGGTATGTGCGT | 3319 | DQPGYVR | 4562 | 106.7387 |
| 827 | GATGCTATGCTTGCTCATCCG | 3320 | DAMLAHP | 4563 | 106.735 |
| 828 | ACACGTCACGACGGCAGTACG | 3321 | TRHDGST | 4564 | 106.675 |
| 829 | CTGGCGAATATGAGTGCGCCG | 3322 | LANMSAP | 4565 | 106.664 |
| 830 | ACTGGTCATCCGCCGGCGGCG | 3323 | TGHPPAA | 4566 | 106.654 |
| 831 | TCGAGTATTAGTCTGCGGTAT | 3324 | SSISLRY | 4567 | 106.645 |
| 832 | ATGCACGTCGACAAAACGAGT | 3325 | MHVDKTS | 4568 | 106.639 |
| 833 | GGGAGTGATTCTAAGCATCCT | 3326 | GSDSKHP | 4569 | 106.5782 |
| 834 | GGAGAAAGCTCCTCAATAAGC | 3327 | GESSSIS | 4570 | 106.551 |
| 835 | GTCGTCCACTCACACAGTGAA | 3328 | VVHSHSE | 4571 | 106.496 |
| 836 | AGTGTGCGGGCGCATGTTTTG | 3329 | SVRAHVL | 4572 | 106.487 |
| 837 | GCGGATGGGGCTAAGTCTGCT | 3330 | ADGAKSA | 4573 | 106.485 |
| 838 | GGGGAAGCACGCCGAGAAGCC | 3331 | GEARREA | 4574 | 106.442 |
| 839 | TTTAATGCTACGGTGGTGCAT | 3332 | FNATVVH | 4575 | 106.437 |
| 840 | TGGACGGAAGGGGGCTCAGGA | 3333 | WTEGGSG | 4576 | 106.423 |
| 841 | GATTCTTCTTATACGCATCCG | 3334 | DSSYTHP | 4577 | 106.422 |
| 842 | TTCCCAAGTAGGGACAACGTA | 3335 | FPSRDNV | 4578 | 106.39 |
| 843 | GCCATCACGCACATCGGTACA | 3336 | AITHIGT | 4579 | 106.365 |
| 844 | GCTTTTAAGTCGGGTAGTATT | 3337 | AFKSGSI | 4580 | 106.334 |
| 845 | ATGTCAAACGCCTCCTACATA | 3338 | MSNASYI | 4581 | 106.319 |
| 846 | GCGGAGAGGAATGATAGGACG | 3339 | AERNDRT | 4582 | 106.305 |
| 847 | ACATTAGAAACAACCCGCAGC | 3340 | TLETTRS | 4583 | 106.244 |
| 848 | CGCTTACACGGCTCAGACTCG | 3341 | RLHGSDS | 4584 | 106.237 |
| 849 | TATGAGGGGCATATGAATACT | 3342 | YEGHMNT | 4585 | 106.2354 |
| 850 | TCTGTGACGACTAATCTGATG | 3343 | SVTTNLM | 4586 | 106.217 |
| 851 | TTGCGTGATCAGACTAGTATG | 3344 | LRDQTSM | 4587 | 106.167 |
| 852 | CCCGCCAGTCACAGCGCGGGA | 3345 | PASHSAG | 4588 | 106.151 |
| 853 | GTGGTTGAGAATTTGAGGCAG | 3346 | VVENLRQ | 4589 | 106.147 |
| 854 | CAACAATCACAAAACTCTATA | 3347 | QQSQNSI | 4590 | 106.115 |
| 855 | CTTGTTGATACGGATAGGAAT | 3348 | LVDTDRN | 4591 | 106.108 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 856 | AACGAAATGGGAAACTACGTC | 3349 | NEMGNYV | 4592 | 106.104 |
| 857 | TCCACCGACCCCCGATACTCA | 3350 | STDPRYS | 4593 | 106.097 |
| 858 | ACTAATGGTATTTATCAGCCT | 3351 | TNGIYQP | 4594 | 106.095 |
| 859 | TGGGTAAACAGTGTGGGCAAC | 3352 | WVNSVGN | 4595 | 106.084 |
| 860 | GGGGTATCTAACAACTCTAGC | 3353 | GVSNNSS | 4596 | 106.079 |
| 861 | AATGTTAATGCGCAGAGTAGG | 3354 | NVNAQSR | 4597 | 106.064 |
| 862 | ACGACGCCGCCTTTTTCTAAT | 3355 | TTPPFSN | 4598 | 106.044 |
| 863 | ACAGGCAGCTCCCACACCAAC | 3356 | TGSSHTN | 4599 | 106.0345 |
| 864 | TACGTCGACAAATCAATGACA | 3357 | YVDKSMT | 4600 | 106.009 |
| 865 | CTAATCAAAAACAACATGCTC | 3358 | LIKNNML | 4601 | 105.9827 |
| 866 | GGGGGTACGGGGTTGTCGAAG | 3359 | GGTGLSK | 4602 | 105.98 |
| 867 | GCTCTTCATAATCTGATGAAT | 3360 | ALHNLMN | 4603 | 105.977 |
| 868 | GTGCATGTGACTAATGTGTTG | 3361 | VHVTNVL | 4604 | 105.924 |
| 869 | TCGACGACGCACCCTTCCGAA | 3362 | STTHPSE | 4605 | 105.898 |
| 870 | AGCGTAGGTAGTCCAACACAC | 3363 | SVGSPTH | 4606 | 105.8936 |
| 871 | ATGAGTAATGATTTGCCTGGG | 3364 | MSNDLPG | 4607 | 105.877 |
| 872 | TTCTCGTCAACCGAAGCCAGA | 3365 | FSSTEAR | 4608 | 105.858 |
| 873 | GCCGGTCACCAACAACTGGCC | 3366 | AGHQQLA | 4609 | 105.846 |
| 874 | GGTACCATATTACCAAACCAA | 3367 | GTILPNQ | 4610 | 105.829 |
| 875 | AGCGCGGTTTCTGGTAGCAGC | 3368 | SAVSGSS | 4611 | 105.825 |
| 876 | GAGGTGTCTAGGGATGGTCTG | 3369 | EVSRDGL | 4612 | 105.814 |
| 877 | CAATCACTCAAAGACGGCACT | 3370 | QSLKDGT | 4613 | 105.804 |
| 878 | ACGCGTGAGGGTAATCATGCT | 3371 | TREGNHA | 4614 | 105.8 |
| 879 | GTGGCGACCCAAAACCTTCTT | 3372 | VATQNLL | 4615 | 105.795 |
| 880 | GCCGAAATGACGCACCGCCTC | 3373 | AEMTHRL | 4616 | 105.771 |
| 881 | CAACGGCCAGACCCGCTTAAA | 3374 | QRPDPLK | 4617 | 105.764 |
| 882 | GAACACATCTCTAGCTACGGA | 3375 | EHISSYG | 4618 | 105.752 |
| 883 | CAAAAAAGCAACGACCAAAAC | 3376 | QKSNDQN | 4619 | 105.744 |
| 884 | AATCTTGTGATGAGTGGGACG | 3377 | NLVMSGT | 4620 | 105.742 |
| 885 | GGAGCGGGACAATCTCACGTG | 3378 | GAGQSHV | 4621 | 105.721 |
| 886 | CTCAACCACACAATGCCCCTC | 3379 | LNHTMPL | 4622 | 105.713 |
| 887 | GTATCACAATCACACGACGTG | 3380 | VSQSHDV | 4623 | 105.687 |
| 888 | GCTAATTCTGCTACTAATCAG | 3381 | ANSATNQ | 4624 | 105.679 |
| 889 | GGCACAGGAGGTAACCGAGAA | 3382 | GTGGNRE | 4625 | 105.671 |
| 890 | GCGAAGTCGTCGATTATTTTG | 3383 | AKSSIIL | 4626 | 105.661 |
| 891 | GGAGGAACAGCCCTTGGGAGC | 3384 | GGTALGS | 4627 | 105.613 |
| 892 | AACAAAGTAGAATCTGACCCA | 3385 | NKVESDP | 4628 | 105.59 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 893 | AACTCGAAACAACCCGACGTC | 3386 | NSKQPDV | 4629 | 105.572 |
| 894 | AGTTATGCTGATCGTCGGCTG | 3387 | SYADRRL | 4630 | 105.567 |
| 895 | AATGTGAATCCGAATGGGCCG | 3388 | NVNPNGP | 4631 | 105.53 |
| 896 | GAACACAACTCAAAAACTTAC | 3389 | EHNSKTY | 4632 | 105.496 |
| 897 | ACCCAAGGATCTAACACCACA | 3390 | TQGSNTT | 4633 | 105.489 |
| 898 | AGCAACGTATCAGCTTACGCA | 3391 | SNVSAYA | 4634 | 105.48 |
| 899 | GCGTACAGTGACAGCGCCCGC | 3392 | AYSDSAR | 4635 | 105.457 |
| 900 | GGGTCGCAATACGCGAACCGC | 3393 | GSQYANR | 4636 | 105.402 |
| 901 | ACAATGAGCGTAACTCTGGAA | 3394 | TMSVTLE | 4637 | 105.393 |
| 902 | CAGACGACTATTCTGGCTGCT | 3395 | QTTILAA | 4638 | 105.386 |
| 903 | TTGCTCCAATCCATAGTGGTA | 3396 | LLQSIVV | 4639 | 105.381 |
| 904 | GTTCACGCTAACGCTACATTA | 3397 | VHANATL | 4640 | 105.38 |
| 905 | AACAAAACAAACGCCGACTAC | 3398 | NKTNADY | 4641 | 105.38 |
| 906 | AACTACGACACCGGCGCCAAA | 3399 | NYDTGAK | 4642 | 105.378 |
| 907 | GTCTACCACAACCGCGACGTT | 3400 | VYHNRDV | 4643 | 105.358 |
| 908 | GATTCTGCTCCGAGGTCTATT | 3401 | DSAPRSI | 4644 | 105.351 |
| 909 | TTGATTGCGAATCTGAGTAAT | 3402 | LIANLSN | 4645 | 105.341 |
| 910 | CCGCAAGACGTCCGCCAAACA | 3403 | PQDVRQT | 4646 | 105.331 |
| 911 | ACAATGACAGCAATAGCAATG | 3404 | TMTAIAM | 4647 | 105.327 |
| 912 | ACATACGCCTCTACTGAAGCG | 3405 | TYASTEA | 4648 | 105.324 |
| 913 | CCTCACGCCAACGGAGTGACA | 3406 | PHANGVT | 4649 | 105.298 |
| 914 | CGGGCTGATGTTTCTTGGTCT | 3407 | RADVSWS | 4650 | 105.286 |
| 915 | CTGACGCACATGACCGGAACC | 3408 | LTHMTGT | 4651 | 105.272 |
| 916 | GCAAACGACTCTGCCAAAACA | 3409 | ANDSAKT | 4652 | 105.269 |
| 917 | GCTAATTCTGGGTTGCATAAT | 3410 | ANSGLHN | 4653 | 105.246 |
| 918 | AACGTGGGCACCGACAGAGAC | 3411 | NVGTDRD | 4654 | 105.231 |
| 919 | GTCGGAACAACCTCGAACGGC | 3412 | VGTTSNG | 4655 | 105.226 |
| 920 | GGAGTTCTTGGGATACTGGTC | 3413 | GVLGILV | 4656 | 105.184 |
| 921 | CGAATCAACGCAGCAATCGAC | 3414 | RINAAID | 4657 | 105.1475 |
| 922 | CCCGACACTCGCCCATCCATA | 3415 | PDTRPSI | 4658 | 105.135 |
| 923 | GGTGAATCACGTACAAACATG | 3416 | GESRTNM | 4659 | 105.119 |
| 924 | ATTTTGCTTGCTCAGTCTGCT | 3417 | ILLAQSA | 4660 | 105.117 |
| 925 | TATAATAGGGATAATGGTTCT | 3418 | YNRDNGS | 4661 | 105.083 |
| 926 | TGGAATAGTCCGGGTGAGGCG | 3419 | WNSPGEA | 4662 | 105.053 |
| 927 | CTGTTGGGGGCTCATCAGCCG | 3420 | LLGAHQP | 4663 | 105.052 |
| 928 | ATTGGTAAGGATAGTGTTCCG | 3421 | IGKDSVP | 4664 | 105.044 |
| 929 | ACGCGGGAGAGTCTGGTGGAT | 3422 | TRESLVD | 4665 | 105.022 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 930 | GCCTCTAACCACCTACAAGCC | 3423 | ASNHLQA | 4666 | 105.013 |
| 931 | AATCTTCAGACGGGTAAGGCT | 3424 | NLQTGKA | 4667 | 104.976 |
| 932 | ACTGTAGGATCCTCATACGCT | 3425 | TVGSSYA | 4668 | 104.9737 |
| 933 | GACACTAACGGAATAAAATCA | 3426 | DTNGIKS | 4669 | 104.968 |
| 934 | AGTCTGCGGATGGAGAATAGT | 3427 | SLRMENS | 4670 | 104.957 |
| 935 | ACTAAGGGTAATAATCTGGTT | 3428 | TKGNNLV | 4671 | 104.92 |
| 936 | CATACGAATCAGATGCAGCCT | 3429 | HTNQMQP | 4672 | 104.919 |
| 937 | AACGGCAACTACGACGGCGCG | 3430 | NGNYDGA | 4673 | 104.912 |
| 938 | GAGGCGCATAATCGTGGTAAT | 3431 | EAHNRGN | 4674 | 104.898 |
| 939 | GGGACGGTTAACTCAAGTGCA | 3432 | GTVNSSA | 4675 | 104.861 |
| 940 | GGGCCGACGATGAATCATAAT | 3433 | GPTMNHN | 4676 | 104.854 |
| 941 | GTACCCAACAACAACACTTCG | 3434 | VPNNNTS | 4677 | 104.834 |
| 942 | GTTTCTAACAAATCTGGAAGT | 3435 | VSNKSGS | 4678 | 104.818 |
| 943 | TGGGGAGTCAGTAACTCAGCA | 3436 | WGVSNSA | 4679 | 104.795 |
| 944 | GTCTCTAACGTCCTCTACAGC | 3437 | VSNVLYS | 4680 | 104.772 |
| 945 | GCCGGCCAAAACAGTGTGGGC | 3438 | AGQNSVG | 4681 | 104.77 |
| 946 | GGTACGAGTCTGGAGAATAGG | 3439 | GTSLENR | 4682 | 104.754 |
| 947 | CAGATGAATATTCATGATAAG | 3440 | QMNIHDK | 4683 | 104.736 |
| 948 | CCTCAACTAAGCGGCACAGCG | 3441 | PQLSGTA | 4684 | 104.733 |
| 949 | AGTTCGACTCCGCAGGATACT | 3442 | SSTPQDT | 4685 | 104.713 |
| 950 | GTGCAGGGGCAGACCGGCTGG | 3443 | VQGQTGW | 4686 | 104.688 |
| 951 | GGTCTGACGGGTGATTTGGTT | 3444 | GLTGDLV | 4687 | 104.682 |
| 952 | AACCACCCCGCACCAAGCTCA | 3445 | NHPAPSS | 4688 | 104.679 |
| 953 | AAAGAAAAAACCACCCGCGAA | 3446 | KEKTTRE | 4689 | 104.665 |
| 954 | ACTACTAATCCGCAGACGCAG | 3447 | TTNPQTQ | 4690 | 104.663 |
| 955 | GGAGGTGAACACGCAAGAAAC | 3448 | GGEHARN | 4691 | 104.66 |
| 956 | ACGACCGAAGCTGTTGTAGCA | 3449 | TTEAVVA | 4692 | 104.656 |
| 957 | CAAAACAGTGACCTCGCCAGC | 3450 | QNSDLAS | 4693 | 104.638 |
| 958 | TACTCTACAGAAGCACGAGTC | 3451 | YSTEARV | 4694 | 104.609 |
| 959 | ACCGGACAAGCGGGCGGATCG | 3452 | TGQAGGS | 4695 | 104.571 |
| 960 | ACTTCGTCTAATCTTTATGTG | 3453 | TSSNLYV | 4696 | 104.559 |
| 961 | ACGGCTCGTGCGATTGATATG | 3454 | TARAIDM | 4697 | 104.551 |
| 962 | CAGGAGTCTAATAGGGGGGTG | 3455 | QESNRGV | 4698 | 104.547 |
| 963 | AGTATCGGATTCTCAGTAGGC | 3456 | SIGFSVG | 4699 | 104.529 |
| 964 | GAGCGGAGTACGCATAATGTT | 3457 | ERSTHNV | 4700 | 104.513 |
| 965 | GCAAACCACGACAACATCGTG | 3458 | ANHDNIV | 4701 | 104.501 |
| 966 | TGGGCTATGAATAATGTGCCG | 3459 | WAMNNVP | 4702 | 104.498 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 967 | TATATTGCTGCGGGTGAGCAG | 3460 | YIAAGEQ | 4703 | 104.498 |
| 968 | AGTTCGAATACTTCTGGTAGT | 3461 | SSNTSGS | 4704 | 104.4928 |
| 969 | ATGGGGAAGCATGAGGGTCTT | 3462 | MGKHEGL | 4705 | 104.481 |
| 970 | GTGCTTACTCATCTGCCGACG | 3463 | VLTHLPT | 4706 | 104.4786 |
| 971 | GAAATGGGTAACCAATACCCA | 3464 | EMGNQYP | 4707 | 104.453 |
| 972 | AGTCTGCGTCCAACCCTACCT | 3465 | SLAPTLP | 4708 | 104.448 |
| 973 | TCGGCTAACTTATACAAACAA | 3466 | SANLYKQ | 4709 | 104.394 |
| 974 | CAAAACGACAGAAAACCGGAC | 3467 | QNDRKPD | 4710 | 104.391 |
| 975 | ATTATTTCGGGTATTACGGTG | 3468 | IISGITV | 4711 | 104.365 |
| 976 | CCATCCGAAATGAGGGCCGTA | 3469 | PSEMRAV | 4712 | 104.361 |
| 977 | TTGGTTACGCAGACGCCGAAT | 3470 | LVTQTPN | 4713 | 104.337 |
| 978 | ATTGCGCAGAATGAGACGTAT | 3471 | IAQNETY | 4714 | 104.336 |
| 979 | CCATACTTAAGAAACATGGCG | 3472 | PYLRNMA | 4715 | 104.321 |
| 980 | GGCGTGAACACAAAAATCGAA | 3473 | GVNTKIE | 4716 | 104.311 |
| 981 | TACTCTTCTGAAATGAGCGAA | 3474 | YSSEMSE | 4717 | 104.31 |
| 982 | TTAGAAAACCCAACACCAGCA | 3475 | LENPTPA | 4718 | 104.305 |
| 983 | GGTGTTATGTCTAATGCTACT | 3476 | GVMSNAT | 4719 | 104.289 |
| 984 | GCCCACACTGCATTAGCGGGG | 3477 | AHTALAG | 4720 | 104.27 |
| 985 | CCTGTTGTGAGGGATCGTTCT | 3478 | PVVRDRS | 4721 | 104.2336 |
| 986 | TCTGCGGGTATGGTGAGTCTG | 3479 | SAGMVSL | 4722 | 104.229 |
| 987 | TCGGGTGTTAATAGTGAGCGT | 3480 | SGVNSER | 4723 | 104.2093 |
| 988 | AATGGGGATGTTACTAATATG | 3481 | NGDVTNM | 4724 | 104.179 |
| 989 | TCTGTTGTGCCTACGGATAAG | 3482 | SVVPTDK | 4725 | 104.174 |
| 990 | AGTAAGGGTGATCAGCTTAAT | 3483 | SKGDQLN | 4726 | 104.166 |
| 991 | GACGGAGAATCCCGATTATCA | 3484 | DGESRLS | 4727 | 104.158 |
| 992 | GGTAATATGAATCATAGTATT | 3485 | GNMNHSI | 4728 | 104.15 |
| 993 | AGTGGGCATGCTTCTCAGGGT | 3486 | SGHASQG | 4729 | 104.148 |
| 994 | GGTTGGAGTAATAATGAGTTG | 3487 | GWSNNEL | 4730 | 104.145 |
| 995 | GGTGTGCATACTCATACTGTT | 3488 | GVHTHTV | 4731 | 104.139 |
| 996 | CACGTGACAGTAACGTTAAAC | 3489 | HVTVTLN | 4732 | 104.124 |
| 997 | ACCCGTGGCAACGACATATCA | 3490 | TRGNDIS | 4733 | 104.058 |
| 998 | AGCAAAGGCGGCGACATGGTT | 3491 | SKGGDMV | 4734 | 104.043 |
| 999 | ACGCATGGTGATCATATTCAG | 3492 | THGDHIQ | 4735 | 104.032 |
| 1000 | ACTACGAATTCTCATGCGATT | 3493 | TTNSHAI | 4736 | 104.021 |
| 1001 | GTCAGAACAGTCCTTCAACAA | 3494 | VRTVLQQ | 4737 | 104.017 |
| 1002 | ACTGTGCGTTCGCCTCAGCCG | 3495 | TVRSPQP | 4738 | 104.015 |
| 1003 | AATACTTATACTGCTGGTAAG | 3496 | NTYTAGK | 4739 | 104.005 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 1004 | ATTAGTAATCCGGAGAATACG | 3497 | ISNPENT | 4740 | 103.998 |
| 1005 | ATCGGGTCGCCGTTGGCCAAC | 3498 | IGSPLAN | 4741 | 103.928 |
| 1006 | TATACGGGTACTCTTGTTGTT | 3499 | YTGTLVV | 4742 | 103.911 |
| 1007 | GGGCGGCACACATTAGCGGAC | 3500 | GRHTLAD | 4743 | 103.908 |
| 1008 | ACTGATGGGCCGCGTCTGGCT | 3501 | TDGPRLA | 4744 | 103.881 |
| 1009 | GGGGCAGGAAACCTGGGTACC | 3502 | GAGNLGT | 4745 | 103.873 |
| 1010 | CTGATGAATCGTAATGCTCCT | 3503 | LMNRNAP | 4746 | 103.8648 |
| 1011 | AATGCTATGGCTTCTAGTAGG | 3504 | NAMASSR | 4747 | 103.826 |
| 1012 | CAGCATCGTGCGCAGGATGTG | 3505 | QHRAQDV | 4748 | 103.8248 |
| 1013 | AAAATAGAAAGCGGAACCATA | 3506 | KIESGTI | 4749 | 103.822 |
| 1014 | ACTAATTATCCTGAGGCGAAT | 3507 | TNYPEAN | 4750 | 103.806 |
| 1015 | GTATACCACGGGGTAGCCAGC | 3508 | VYHGVAS | 4751 | 103.803 |
| 1016 | TCCAACGTCCACGTAGTAAAC | 3509 | SNVHVVN | 4752 | 103.791 |
| 1017 | ACATACACCGACGGGAACCCC | 3510 | TYTDGNP | 4753 | 103.788 |
| 1018 | TTTATTGCGAATACGAATCCT | 3511 | FIANTNP | 4754 | 103.787 |
| 1019 | GACGCCGGGTACGGCCACGAC | 3512 | DAGYGHD | 4755 | 103.785 |
| 1020 | GGTCTTAGTCGGAATGATGGT | 3513 | GLSRNDG | 4756 | 103.783 |
| 1021 | ATGATGGGCGCGACAACGAAA | 3514 | MMGATTK | 4757 | 103.779 |
| 1022 | CCCATCAACGTACTCACGACA | 3515 | PINVLTT | 4758 | 103.771 |
| 1023 | GCCGTAGACCAATCACGTTTG | 3516 | AVDQSRL | 4759 | 103.765 |
| 1024 | AACGCTTCTACCTACATGGAC | 3517 | NASTYMD | 4760 | 103.728 |
| 1025 | ACACAAGCAGGTCTTGCGTCA | 3518 | TQAGLAS | 4761 | 103.696 |
| 1026 | GCACAATTCGAATCAGGCCGA | 3519 | AQFESGR | 4762 | 103.693 |
| 1027 | CGGAATGGTGGTACTACGGAT | 3520 | RNGGTTD | 4763 | 103.669 |
| 1028 | GCTAATACGTATAATGTTCAG | 3521 | ANTYNVQ | 4764 | 103.64 |
| 1029 | TCGGGTGTTCATAGTGAGCGT | 3522 | SGVHSER | 4765 | 103.636 |
| 1030 | AACACCGGCACCACGAGTGTC | 3523 | NTGTTSV | 4766 | 103.635 |
| 1031 | AGTACGAGTAATAGTCATATG | 3524 | STSNSHM | 4767 | 103.632 |
| 1032 | GGTGAACAACACAACGCCCCC | 3525 | GEQHNAP | 4768 | 103.629 |
| 1033 | GCTCATCATATGACGACGGAG | 3526 | AHHMTTE | 4769 | 103.614 |
| 1034 | TTGATGACTGGTACTGCGTCG | 3527 | LMTGTAS | 4770 | 103.575 |
| 1035 | GCTGCCGGAGCCGACTCTCCA | 3528 | AAGADSP | 4771 | 103.568 |
| 1036 | GTGTCTCTGAGTTCGCCTCCG | 3529 | VSLSSPP | 4772 | 103.563 |
| 1037 | CGTGTTGTAGCCGGTCCCAAC | 3530 | RVVAGPN | 4773 | 103.534 |
| 1038 | GATAAGACTGAGATGCTGCAG | 3531 | DKTEMLQ | 4774 | 103.525 |
| 1039 | GCACGAGACGACACGATACAA | 3532 | ARDDTIQ | 4775 | 103.523 |
| 1040 | TTACACCTTGGGTTATCATCT | 3533 | LHLGLSS | 4776 | 103.513 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 1041 | CTCGAAGGACAACGGGACGTC | 3534 | LEGQRDV | 4777 | 103.505 |
| 1042 | GCGTCGTTGTCGGCTCCGGCG | 3535 | ASLSAPA | 4778 | 103.5036 |
| 1043 | AGCAACCCTGGGAACCACAAC | 3536 | SNPGNHN | 4779 | 103.502 |
| 1044 | GGGCTGAATTCTAAGGGGACT | 3537 | GLNSKGT | 4780 | 103.471 |
| 1045 | AAAACACCCTCAGCTTCAGAA | 3538 | KTPSASE | 4781 | 103.47 |
| 1046 | GTGCTGGCGTCGACTGAGAAG | 3539 | VLASTEK | 4782 | 103.451 |
| 1047 | TCGGTATTGAACAAACCAACA | 3540 | SVLNKPT | 4783 | 103.441 |
| 1048 | CCCGGTAACGGACAAAGTCCG | 3541 | PGNGQSP | 4784 | 103.396 |
| 1049 | ATCTTGATGGGCGCTAGGACA | 3542 | ILMGART | 4785 | 103.385 |
| 1050 | GCACTACCATCCCACTCCTCC | 3543 | ALPSHSS | 4786 | 103.382 |
| 1051 | AGGGATCAGACTCATCCGAAT | 3544 | RDQTHPN | 4787 | 103.378 |
| 1052 | TCTGGTCCGATTCCTGCTGTT | 3545 | SGPIPAV | 4788 | 103.376 |
| 1053 | TACGTGGACGACAACAGTCGC | 3546 | YVDDNSR | 4789 | 103.35 |
| 1054 | TTGACTCGGGGGGTCGCCGCA | 3547 | LTRGVAA | 4790 | 103.334 |
| 1055 | TCTGAGAAGGAGGCTCGGCTG | 3548 | SEKEARL | 4791 | 103.326 |
| 1056 | TCCACAACGCCTCCCTTCAAA | 3549 | STTPPFK | 4792 | 103.308 |
| 1057 | TACTCGACAACCATGCTTAAC | 3550 | YSTTMLN | 4793 | 103.299 |
| 1058 | AAAAACGGTGTTATAAACGAC | 3551 | KNGVIND | 4794 | 103.292 |
| 1059 | TTCGGTATAGGGCACGGAACA | 3552 | FGIGHGT | 4795 | 103.278 |
| 1060 | CCTCTTCATGTTGCTTCTCCT | 3553 | PLHVASP | 4796 | 103.245 |
| 1061 | TTGGGTAATGGTAGTTCTTTG | 3554 | LGNGSSL | 4797 | 103.239 |
| 1062 | AGTGGCAACGCGAACATAGTA | 3555 | SGNANIV | 4798 | 103.225 |
| 1063 | GGGATTAATCGTACTAGTGAG | 3556 | GINRTSE | 4799 | 103.19 |
| 1064 | TCGGATAATAGGAATACTGCG | 3557 | SDNRNTA | 4800 | 103.19 |
| 1065 | CGATTAGGAACCGTCACCAAC | 3558 | RLGTVTN | 4801 | 103.189 |
| 1066 | GTGGAGCATGTTGCTCATCAG | 3559 | VEHVAHQ | 4802 | 103.185 |
| 1067 | TATACTAAGCATCCTGTTGAG | 3560 | YTKHPVE | 4803 | 103.172 |
| 1068 | TCCCGAATCACGGTGAACGCA | 3561 | SRITVNA | 4804 | 103.154 |
| 1069 | ACAGTATCGTCATACGTACAA | 3562 | TVSSYVQ | 4805 | 103.134 |
| 1070 | CGCGCCGAAGGGAGCTCTGGC | 3563 | RAEGSSG | 4806 | 103.127 |
| 1071 | GCTGTGGGGCGGTCGGATGAT | 3564 | AVGRSDD | 4807 | 103.119 |
| 1072 | CGCATAGGCGTTGGAGCACCA | 3565 | RIGVGAP | 4808 | 103.113 |
| 1073 | TACTCAAACCTCGTACTTTCC | 3566 | YSNLVLS | 4809 | 103.095 |
| 1074 | TCGACGAATTCTGAGGCGGTT | 3567 | STNSEAV | 4810 | 103.068 |
| 1075 | GCAATGTCAACCCACATGATA | 3568 | AMSTHMI | 4811 | 103.067 |
| 1076 | AGGGTTGATATTTCGCATTTT | 3569 | RVDISHF | 4812 | 103.049 |
| 1077 | ATTCTTACGCCTTTGGATAAG | 3570 | ILTPLDK | 4813 | 103.039 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 1078 | GTTGCGAGTACGACGCAGACT | 3571 | VASTTQT | 4814 | 103.033 |
| 1079 | GACCGTAGCTCCGCGACGCTC | 3572 | DRSSATL | 4815 | 103.014 |
| 1080 | GATCATAGTGAGCAGAATTCG | 3573 | DHSEQNS | 4816 | 102.995 |
| 1081 | ATACGCAGCGAATTGGAAGTA | 3574 | IRSELEV | 4817 | 102.969 |
| 1082 | GCGAATCTGGGTGATGTTGAG | 3575 | ANLGDVE | 4818 | 102.969 |
| 1083 | GAGCTTAAGGAGAGTCAGAAG | 3576 | ELKESQK | 4819 | 102.956 |
| 1084 | TCATACACAGCAGGAAGACCC | 3577 | SYTAGRP | 4820 | 102.953 |
| 1085 | GGACCAGCCTACAACCAAAGC | 3578 | GPAYNQS | 4821 | 102.924 |
| 1086 | CATGAGAGTCATTATGTTAGT | 3579 | HESHYVS | 4822 | 102.921 |
| 1087 | AATGGTAAGCTGGGTACGACT | 3580 | NGKLGTT | 4823 | 102.921 |
| 1088 | CTTCCGCCTGCGTCGGCGGGT | 3581 | LPPASAG | 4824 | 102.917 |
| 1089 | TTGTCGTATCAGACTGGTCAT | 3582 | LSYQTGH | 4825 | 102.916 |
| 1090 | GACAGCCAAATCACAAGACTA | 3583 | DSQITRL | 4826 | 102.909 |
| 1091 | AACGTATACGAAGGGCACCGC | 3584 | NVYEGHR | 4827 | 102.909 |
| 1092 | TTGTTTACTGCTGGGAGTACT | 3585 | LFTAGST | 4828 | 102.863 |
| 1093 | CTTGTGAATAATGATGGGACT | 3586 | LVNNDGT | 4829 | 102.861 |
| 1094 | GCGATGAATGTGCGGAGTGAT | 3587 | AMNVRSD | 4830 | 102.858 |
| 1095 | GCCAGCCTTGACCGCCTTCCA | 3588 | ASLDRLP | 4831 | 102.857 |
| 1096 | GGCTCTCGGAACGGACCCACA | 3589 | GSRNGPT | 4832 | 102.8532 |
| 1097 | ATGAGTGATGGGCATTCGAAG | 3590 | MSDGHSK | 4833 | 102.833 |
| 1098 | TCTAACCGTACGGAAATGCCA | 3591 | SNRTEMF | 4834 | 102.815 |
| 1099 | AACGTGGTGAAAAACAACACA | 3592 | NVVKNNT | 4835 | 102.801 |
| 1100 | GTGGTCGACTCAACATACCCG | 3593 | VVDSTYP | 4836 | 102.793 |
| 1101 | GTGGCTGGGGGGACTTCGGAG | 3594 | VAGGTSE | 4837 | 102.789 |
| 1102 | CGGGCAGACATGACTCCCTTA | 3595 | RADMTPL | 4838 | 102.77 |
| 1103 | GGACACGAACAAACTGACGCA | 3596 | GHEQTDA | 4839 | 102.764 |
| 1104 | AGTGCTTTGATTAGTGTGGTT | 3597 | SALISVV | 4840 | 102.756 |
| 1105 | AACTCGACAACGGCACAATCA | 3598 | NSTTAQS | 4841 | 102.75 |
| 1106 | TACGGCGACCTAACTACAGTC | 3599 | YGDLTTV | 4842 | 102.737 |
| 1107 | GCACGCAACGACGGACAAGGA | 3600 | ARNDGQG | 4843 | 102.734 |
| 1108 | CTGAACGTTAGTTCATCCAAA | 3601 | LNVSSSK | 4844 | 102.693 |
| 1109 | TCTGGCGTCTCGAAAGAACGG | 3602 | SGVSKER | 4845 | 102.692 |
| 1110 | AACATGGAACACACCATGGCG | 3603 | NMEHTMA | 4846 | 102.687 |
| 1111 | GCTCGTCCGGCTTCGTCTGAT | 3604 | ARPASSD | 4847 | 102.6705 |
| 1112 | CTTAGGGAAGAATCTGCACGT | 3605 | LREESAR | 4848 | 102.639 |
| 1113 | TTGGCCAACATGTCCGCACCA | 3606 | LANMSAP | 4849 | 102.61 |
| 1114 | AACCACACGGTAGAAGGACGC | 3607 | NHTVEGR | 4850 | 102.598 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 1115 | CCTCAGCATCAGCATGAGCAT | 3608 | PQHQHEH | 4851 | 102.582 |
| 1116 | AATTCTTCGGAGCTGAAGACG | 3609 | NSSELKT | 4852 | 102.564 |
| 1117 | CTTGTTGCTGAGCGTTTGCCG | 3610 | LVAERLP | 4853 | 102.552 |
| 1118 | AACGTTATGCACTCTTCCTCC | 3611 | NVMHSSS | 4854 | 102.525 |
| 1119 | GCGAGTGATAAGGGGGCGAAT | 3612 | ASDKGAN | 4855 | 102.509 |
| 1120 | AGTCTGGATCGGAAGCCTCCG | 3613 | SLDRKPP | 4856 | 102.5032 |
| 1121 | ACAGAACACGAAAAATCCACT | 3614 | TEHEKST | 4857 | 102.459 |
| 1122 | CCTCATAATCAGGAGATGGGT | 3615 | PHNQEMG | 4858 | 102.449 |
| 1123 | GAGTCTAAGACTGTGGTTATT | 3616 | ESKTVVI | 4859 | 102.442 |
| 1124 | TCGACGGGCCAAAACTTAAAA | 3617 | STGQNLK | 4860 | 102.442 |
| 1125 | GTTCTTCATGTTTCTGATGTT | 3618 | VLHVSDV | 4861 | 102.441 |
| 1126 | CCTGACGCAGCGCGTAGCCCG | 3619 | PDAARSP | 4862 | 102.421 |
| 1127 | GCTCCTCGGCATGCTCATCCT | 3620 | APRHAHP | 4863 | 102.414 |
| 1128 | CATGTGAATCCTACGCCGGCG | 3621 | HVNPTPA | 4864 | 102.401 |
| 1129 | TTGCCTAATGAGCGTCCGGGT | 3622 | LPNERPG | 4865 | 102.397 |
| 1130 | GAGGCTAAGGGTTTTGGTCAT | 3623 | EAKGFGH | 4866 | 102.395 |
| 1131 | TCAGAAAACACCTCTGTACCC | 3624 | SENTSVP | 4867 | 102.388 |
| 1132 | GGTCCCGGAGAAAACTACCGA | 3625 | GPGENYR | 4868 | 102.375 |
| 1133 | TCTCATGAGATGAATAATGGT | 3626 | SHEMNNG | 4869 | 102.366 |
| 1134 | GTAGACACCTACAGCGGTCTG | 3627 | VDTYSGL | 4870 | 102.35 |
| 1135 | GGAGTCCTAGGAAACATGGTA | 3628 | GVLGNMV | 4871 | 102.325 |
| 1136 | GCGCTGGATAATAGTAGTCGG | 3629 | ALDNSSR | 4872 | 102.322 |
| 1137 | TTTCTGGGTTCTAGTAATCAT | 3630 | FLGSSNH | 4873 | 102.321 |
| 1138 | CCTGTGGTTCATGGTGAGCCT | 3631 | PVVHGEP | 4874 | 102.3142 |
| 1139 | CGCAGGGAAGGTATCCTAATG | 3632 | RREGILM | 4875 | 102.305 |
| 1140 | CAGCAGGGGGCGCCTACTTCT | 3633 | QQGAPTS | 4876 | 102.303 |
| 1141 | AAGGTTAGTGGTGGGGAGACG | 3634 | KVSGGET | 4877 | 102.275 |
| 1142 | GCGAAACACGAAAGCTCGTCT | 3635 | AKHESSS | 4878 | 102.272 |
| 1143 | ATTCTTATGGGTGCGCGTACT | 3636 | ILMGART | 4879 | 102.235 |
| 1144 | ACGCTAGGCAGCAGCAGCACC | 3637 | TLGSSST | 4880 | 102.222 |
| 1145 | CTAAGATCTGAACCGACACAA | 3638 | LRSEPTQ | 4881 | 102.218 |
| 1146 | CGCTCGGAACAAAAAACTCCG | 3639 | RSEQKTP | 4882 | 102.207 |
| 1147 | CACGCTCCAAGCGGCGCCATA | 3640 | HAPSGAI | 4883 | 102.2 |
| 1148 | AGTAGTGTTACTTCGAGGGAG | 3641 | SSVTSRE | 4884 | 102.197 |
| 1149 | GTGAATCCGCATCCTGCGCAG | 3642 | VNPHPAQ | 4885 | 102.185 |
| 1150 | CAATACTCGATGGACACGCGC | 3643 | QYSMDTR | 4886 | 102.173 |
| 1151 | ACTCCTGGTGTTACTAGGACG | 3644 | TPGVTRT | 4887 | 102.172 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 1152 | CTTTATGAGGTTGGTACTCCT | 3645 | LYEVGTP | 4888 | 102.165 |
| 1153 | ACGATGACGAGTGAGCTTTCG | 3646 | TMTSELS | 4889 | 102.16 |
| 1154 | TCAGGTTCGGAATACCGTACC | 3647 | SGSEYRT | 4890 | 102.153 |
| 1155 | GAAATGCAAACCAAAAACGCC | 3648 | EMQTKNA | 4891 | 102.144 |
| 1156 | GGCCACGAAAACATGGGCGTG | 3649 | GHENMGV | 4892 | 102.135 |
| 1157 | GGGGCGCATACGTCGGCTTCG | 3650 | GAHTSAS | 4893 | 102.116 |
| 1158 | GCTGATACGCTGCTGCGTAGG | 3651 | ADTLLRR | 4894 | 102.095 |
| 1159 | GACAACAGCAACAACGTCCCA | 3652 | DNSNNVP | 4895 | 102.092 |
| 1160 | ATGACTGCTAACTTGGTGGAA | 3653 | MTANLVE | 4896 | 102.076 |
| 1161 | GAAGCGGGACGCACGCTTCAA | 3654 | EAGRTLQ | 4897 | 102.07 |
| 1162 | AGACACGTCGTCCCCGACTCC | 3655 | RHVVPDS | 4898 | 102.039 |
| 1163 | GTGAGTTCTGAGCAGTATAGG | 3656 | VSSEQYR | 4899 | 102.03 |
| 1164 | GGTATCGAAGCAAGTCGCGGA | 3657 | GIEASRG | 4900 | 102.008 |
| 1165 | AGACAAGGCGTGAACGGAGTA | 3658 | RQGVNGV | 4901 | 101.991 |
| 1166 | ACTGTGATGATGAGTACGAGG | 3659 | TVMMSTR | 4902 | 101.976 |
| 1167 | TGGCAAGACCACAACAAAGTC | 3660 | WQDHNKV | 4903 | 101.948 |
| 1168 | GGAATCACAGGATCAACAGGA | 3661 | GITGSTG | 4904 | 101.943 |
| 1169 | AATTATGCTCAGAGGGATGGT | 3662 | NYAQRDG | 4905 | 101.936 |
| 1170 | AAACAAGAAGCTCTGTCCTCA | 3663 | KQEALSS | 4906 | 101.872 |
| 1171 | TCAACTTTAGACCGAAGCGAA | 3664 | STLDRSE | 4907 | 101.8665 |
| 1172 | GCGATTACGAATACGCAGCAG | 3665 | AITNTQQ | 4908 | 101.8615 |
| 1173 | AGGCTGGCGACTCAGAGTGCT | 3666 | RLATQSA | 4909 | 101.847 |
| 1174 | TGGCAGCTTACGACGAGTCAT | 3667 | WQLTTSH | 4910 | 101.775 |
| 1175 | GGTGGTAGTGGTTCTAATACT | 3668 | GGSGSNT | 4911 | 101.759 |
| 1176 | AACTTAGTAGCGTACACGAAA | 3669 | NLVAYTK | 4912 | 101.732 |
| 1177 | AAGGCTTCGCATGATACTAGT | 3670 | KASHDTS | 4913 | 101.721 |
| 1178 | GCCATAACGATAATAGGCACT | 3671 | AITIIGT | 4914 | 101.711 |
| 1179 | AACGCATCGTCGGACCGCTTC | 3672 | NASSDRF | 4915 | 101.686 |
| 1180 | GAAACGCAACGTATCGAACTG | 3673 | ETQRIEL | 4916 | 101.636 |
| 1181 | GTGATTGAGGTTAATTCGCGT | 3674 | VIEVNSR | 4917 | 101.614 |
| 1182 | GATAGGGATATGGAGGGTGTT | 3675 | DRDMEGV | 4918 | 101.609 |
| 1183 | ATTTCGGAGATGACGCGGTAT | 3676 | ISEMTRY | 4919 | 101.59 |
| 1184 | GAGCATGATGTGAGTACGCGT | 3677 | EHDVSTR | 4920 | 101.539 |
| 1185 | CGTATGGAGGAGACTGCTTAT | 3678 | RMEETAY | 4921 | 101.533 |
| 1186 | TATAGTACTGATCTTAGGATG | 3679 | YSTDLRM | 4922 | 101.52 |
| 1187 | GTGCCTGAGCCTAAGAAGGCG | 3680 | VPEPKKA | 4923 | 101.495 |
| 1188 | ACTTATGCGCCTAGGTCGCCT | 3681 | TYAPRSP | 4924 | 101.484 |

TABLE 2-continued

MHCK7 Results mRNA Second Round of Capsid Variant Selection in C57BL6 mice-score capped at 100

| Variant ID | Nucleotide Sequence | SEQ ID NO: | aa | SEQ ID NO: | Sum of muscle mRNA score_capped at 100 |
|---|---|---|---|---|---|
| 1189 | GCTGCGGCTTCGCCTTTGGCT | 3682 | AAASPLA | 4925 | 101.484 |
| 1190 | AGTGGGACGTATGCTAGTCGT | 3683 | SGTYASR | 4926 | 101.456 |
| 1191 | ACTGAAGCATCAATCGCGGCG | 3684 | TEASIAA | 4927 | 101.456 |
| 1192 | CGCATCGTAGACACGTTGGGA | 3685 | RIVDTLG | 4928 | 101.447 |
| 1193 | TATCTGCAGGAGAAGTTTCCT | 3686 | YLQEKFP | 4929 | 101.437 |
| 1194 | GTTCATGATCAGGGGGCTGGG | 3687 | VHDQGAG | 4930 | 101.436 |
| 1195 | CCCCAAGCCACTCTCAACAAC | 3688 | PQATLNN | 4931 | 101.432 |
| 1196 | TGCGGAATGTCCGAATGCTCG | 3689 | CGMSECS | 4932 | 101.429 |
| 1197 | GGTTCGCACAACGGGCCGACA | 3690 | GSHNGPT | 4933 | 101.429 |
| 1198 | TTTGGGTCTGGGCCGAATCTT | 3691 | FGSGPNL | 4934 | 101.413 |
| 1199 | ATGGATACGAATACGCATCGT | 3692 | MDTNTHR | 4935 | 101.411 |
| 1200 | AAGAATAATCCTGAGGATGGT | 3693 | KNNPEDG | 4936 | 101.41 |
| 1201 | CTGCCTACGGCTACTGGTCAG | 3694 | LPTATGQ | 4937 | 101.406 |
| 1202 | ACGGCTGAGCGTACTGAGTAT | 3695 | TAERTEY | 4938 | 101.383 |
| 1203 | AACTACAGGGACATCACAATG | 3696 | NYRDITM | 4939 | 101.375 |
| 1204 | CCCGCGAGAAGCGACGCCCTT | 3697 | PARSDAL | 4940 | 101.359 |
| 1205 | TCCGTTGTAACTCTTGGGGTG | 3698 | SVVTLGV | 4941 | 101.324 |
| 1206 | GTTGTTAAGGAGATTAAGCTG | 3699 | VVKEIKL | 4942 | 101.324 |
| 1207 | GACCACTCGAAACAAAACTCT | 3700 | DHSKQNS | 4943 | 101.293 |
| 1208 | CAGTCTAATTTGGTTATTAAT | 3701 | QSNLVIN | 4944 | 101.292 |
| 1209 | ATTCCGGTTGGGGCGATGGCT | 3702 | IPVGAMA | 4945 | 101.286 |
| 1210 | ACGTCGGAGATGCGTACTGCT | 3703 | TSEMRTA | 4946 | 101.255 |
| 1211 | GGTAGTCAGCGTGCTATGAAT | 3704 | GSQRAMN | 4947 | 101.251 |
| 1212 | CACCTGTCACAAGCAAACCAC | 3705 | HLSQANH | 4948 | 101.24 |
| 1213 | GGAGGGAACTCCCACGGGGTA | 3706 | GGNSHGV | 4949 | 101.219 |
| 1214 | GTGACTCGTAGTACGAAGGAG | 3707 | VTRSTKE | 4950 | 101.178 |
| 1215 | ATGCTCAGAGCAAGCACCGCC | 3708 | MLRASTA | 4951 | 101.171 |
| 1216 | GGCAGGCAAATACCAGAACAA | 3709 | GRQIPEQ | 4952 | 101.146 |
| 1217 | TGGAATCAGAATGTGTCTCAT | 3710 | WNQNVSH | 4953 | 101.125 |
| 1218 | CAGCGGGGGGAGCTTCCTGCG | 3711 | QRGELPA | 4954 | 101.114 |
| 1219 | GCGAATGATAGTTTGCGTTCT | 3712 | ANDSLRS | 4955 | 101.079 |
| 1220 | AACATGCCACCGGAATCGCAC | 3713 | NMPPESH | 4956 | 101.037 |
| 1221 | AATTTGAGTCTTCAGAGTCTG | 3714 | NLSLQSL | 4957 | 101.03 |
| 1222 | ACATCAGACGGTCTACTAAGT | 3715 | TSDGLLS | 4958 | 101.028 |
| 1223 | GCGGGCCAAGCGTACCAATCC | 3716 | AGQAYQS | 4959 | 101.016 |
| 1224 | CTGAGTGTGAAGGAGGAGATT | 3717 | LSVKEEI | 4960 | 101.007 |
| 1225 | GATAATAGTCCTGCTAATCAT | 3718 | DNSPANH | 4961 | 100.9812 |

TABLE 2-continued

| MHCK7 Results mRNA Second Round of Capsid Variant Selection in C57BL6 mice-score capped at 100 | | | | | |
|---|---|---|---|---|---|
| Variant ID | Nucleotide Sequence | SEQ ID NO: | aa | SEQ ID NO: | Sum of muscle mRNA score_capped at 100 |
| 1226 | ATGCACAACCTACCCTCATAC | 3719 | MHNLPSY | 4962 | 100.9629 |
| 1227 | TACCAAGCCTCAAACAACAGT | 3720 | YQASNNS | 4963 | 100.9594 |
| 1228 | GCGCGGGCAGAAGGGGTCTTC | 3721 | ARAEGVF | 4964 | 100.9325 |
| 1229 | GGCCGAGAAGGAAACCTACCA | 3722 | GREGNLP | 4965 | 100.913 |
| 1230 | CAAGCTGCAGAAAGGGACAGA | 3723 | QAAERDR | 4966 | 100.8877 |
| 1231 | GTTGAGAATAATCGTATGAGT | 3724 | VENNRMS | 4967 | 100.8183 |
| 1232 | AATATGTCGCATAGTACTCTG | 3725 | NMSHSTL | 4968 | 100.7704 |
| 1233 | TCTTCGTTGGGTCTTGCTCCG | 3726 | SSLGLAP | 4969 | 100.7249 |
| 1234 | AACGTCGCTCCCTACAGTAGC | 3727 | NVAPYSS | 4970 | 100.7069 |
| 1235 | AGGCCTGCGCAGCTGCCTGAG | 3728 | RPAQLPE | 4971 | 100.615 |
| 1236 | ATGTCGGGTTCTGGGAACGCA | 3729 | MSGSGNA | 4972 | 100.597 |
| 1237 | CACGGGGGGGAACACCGGAAC | 3730 | HGGEHRN | 4973 | 100.5793 |
| 1238 | GCATCCGGCGCACGCTACGTC | 3731 | ASGARYV | 4974 | 100.5302 |
| 1239 | CAAAACCACGCGTCTGGTGAA | 3732 | QNHASGE | 4975 | 100.499 |
| 1240 | GCACACCAAAAAGACCTACGC | 3733 | AHQKDLR | 4976 | 100.4529 |
| 1241 | TTTGGGAAGGTTGGTACTGCT | 3734 | FGKVGTA | 4977 | 100.433 |
| 1242 | CTGCAGAAGTCGACTCTGGCT | 3735 | LQKSTLA | 4978 | 100.3439 |
| 1243 | ATTCATAATGAGTCTTATGGT | 3736 | IHNESYG | 4979 | 100.15 |

TABLE 3

| MHCK7/CK8 Combined Results mRNA Second Round of Capsid Variant Selection in C57BL6 mice-score capped at 100 | | | | | |
|---|---|---|---|---|---|
| Variant ID for Table | Nucleotide Sequence | SEQ ID NO: | Amino Acid seq. | SEQ ID NO: | Sum of muscle mRNA score_capped at 100 |
| 1 | AGGGGTGATCTTTCTACGCCT | 4980 | RGDLSTP | 6647 | 856.3525 |
| 2 | AGAGGCGACTTATCCACACCC | 4981 | RGDLSTP | 6648 | 732.672 |
| 3 | AGAGGAGACTTGACAACCCCA | 4982 | RGDLTTP | 6649 | 683.373 |
| 4 | AGGGGCGACCTGAACCAATAC | 4983 | RGDLNQY | 6650 | 680.6265 |
| 5 | CGGGGTGATCAGCTTTATCAT | 4984 | RGDQLYH | 6651 | 624.3915 |
| 6 | AGGGGGGATGCGACGGAGCTT | 4985 | RGDATEL | 6652 | 620.5 |
| 7 | CGAGGAGACACCATGAGCAAA | 4986 | RGDTMSK | 6653 | 599.497 |
| 8 | CGGGGTGATCTTAATCAGTAT | 4987 | RGDLNQY | 6654 | 579.731 |
| 9 | CGGGGTGATCTTACTACGCCT | 4988 | RGDLTTP | 6655 | 531.1525 |
| 10 | CGCGGCGACATGATAAACACC | 4989 | RGDMINT | 6656 | 528.2405 |
| 11 | CGGGGGGATACTATGTCTAAG | 4990 | RGDTMSK | 6657 | 469.5075 |
| 12 | CGAGGCGACACAATGAACTAC | 4991 | RGDTMNY | 6658 | 412.3247 |
| 13 | CGGGGTGACGCAACAGAATTG | 4992 | RGDATEL | 6659 | 408.0865 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 14 | CGTTTGGACCTGCAAGTCCAC | 4993 | RLDLQVH | 6660 | 397.178 |
| 15 | CGTGGTGATGTGGCGGCTAAG | 4994 | RGDVAAK | 6661 | 395.174 |
| 16 | AGGGGCGACCTCAACGACAGC | 4995 | RGDLNDS | 6662 | 360.4535 |
| 17 | CGTGGGGATTTGAATGATTCT | 4996 | RGDLNDS | 6663 | 349.6835 |
| 18 | TCTTATGGTAATACTCATGAT | 4997 | SYGNTHD | 6664 | 326.826 |
| 19 | CGTTTGGACCTGCAAGTCAAC | 4998 | RLDLQVN | 6665 | 317.78 |
| 20 | AAAGCGGGACAACTAGTGGAA | 4999 | KAGQLVE | 6666 | 317.023 |
| 21 | GATCAGACGGCTAGTATTGTT | 5000 | DQTASIV | 6667 | 313.224 |
| 22 | TATATTGCTGCGGGTGAGCAG | 5001 | YIAAGEQ | 6668 | 308.738 |
| 23 | GCGGTTGTTCTGAATAGTAAT | 5002 | AVVLNSN | 6669 | 307.8445 |
| 24 | TCTAAAGGAAACGAACAAATG | 5003 | SKGNEQM | 6670 | 305.016 |
| 25 | GCAAACCCCAACATACTAGAC | 5004 | ANPNILD | 6671 | 302.02 |
| 26 | CACAACAAACCAAACGGAGAC | 5005 | HNKPNGD | 6672 | 297.851 |
| 27 | GATAAGACTGAGATGCTGCAG | 5006 | DKTEMLQ | 6673 | 294.655 |
| 28 | ACAGAACAATCTTACTCACGA | 5007 | TEQSYSR | 6674 | 290.3555 |
| 29 | ACTGTGATGATGAGTACGAGG | 5008 | TVMMSTR | 6675 | 289.3945 |
| 30 | GTCTCTACATACCTCCTGGCA | 5009 | VSTYLLA | 6676 | 286.859 |
| 31 | CCTAATGTTACGCAGTCTTAT | 5010 | PNVTQSY | 6677 | 285.178 |
| 32 | ATGAGTAATTTGGGGTATGAG | 5011 | MSNLGYE | 6678 | 284 |
| 33 | ACGATGGGTGCTAATGGTACT | 5012 | TMGANGT | 6679 | 278.291 |
| 34 | AATGTTAATGCGCAGAGTAGG | 5013 | NVNAQSR | 6680 | 275.45 |
| 35 | GACCAAAACTTCGAACGTAGA | 5014 | DQNFERR | 6681 | 274.6045 |
| 36 | AACACGTACACACCGGGAAAA | 5015 | NTYTPGK | 6682 | 273.83545 |
| 37 | CGTGGGGATATGATTAATACG | 5016 | RGDMINT | 6683 | 270.333 |
| 38 | GCACAATTCGAATCAGGCCGA | 5017 | AQFESGR | 6684 | 267.7345 |
| 39 | ACGGCGTATCAGGCTGGTCTG | 5018 | TAYQAGL | 6685 | 267.054 |
| 40 | AGTGTTAGTTCTGTGGTGTTG | 5019 | SVSSVVL | 6686 | 266.91 |
| 41 | GGGCTTTCTAAGGCGTCTGAT | 5020 | GLSKASD | 6687 | 266.825 |
| 42 | TGGAACGGAAACGCCACACAA | 5021 | WNGNATQ | 6688 | 265.11 |
| 43 | ACAGCCGGCGGCGAACGCGCC | 5022 | TAGGERA | 6689 | 258.785 |
| 44 | TACACCTCTCAAACCAGCACT | 5023 | YTSQTST | 6690 | 258.1818 |
| 45 | GCGAACATAGAAAACACGTCA | 5024 | ANIENTS | 6691 | 257.015 |
| 46 | GAACTCTCCGTTCCGAAACCA | 5025 | ELSVPKP | 6692 | 255.133 |
| 47 | GATCCTGGTCGGACGGGTACG | 5026 | DPGRTGT | 6693 | 254.7 |
| 48 | GATCGTCCGAATAATATGACG | 5027 | DRPNNMT | 6694 | 254.383 |
| 49 | TATAGTACTGATCTTAGGATG | 5028 | YSTDLRM | 6695 | 252.146 |
| 50 | CAGTCGGTTAATAGTACGAGT | 5029 | QSVNSTS | 6696 | 251.508 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 51 | GCGGCACAACTCGTCAGTCCA | 5030 | AAQLVSP | 6697 | 250.413 |
| 52 | CTCGGAGGAAACAGCAGGTTC | 5031 | LGGNSRF | 6698 | 247.9775 |
| 53 | GCGACGCTGAATAATAGTTAT | 5032 | ATLNNSY | 6699 | 247.2955 |
| 54 | CGCTTGGACGTTGGAAGCCCG | 5033 | RLDVGSP | 6700 | 245.839 |
| 55 | TATCGGGGTAGGGAGGATTGG | 5034 | YRGREDW | 6701 | 244.83 |
| 56 | AGGGGAGATCTTTCTACGCCT | 5035 | RGDLSTP | 6702 | 243.25 |
| 57 | AGTGGTCTTTCGCATGGTCAG | 5036 | SGLSHGQ | 6703 | 242.486 |
| 58 | GAACACGCTACAGCAAAACAA | 5037 | EHATAKQ | 6704 | 241.816 |
| 59 | GGGGCGGAAGCGGGCCGCCAA | 5038 | GAEAGRQ | 6705 | 241.46345 |
| 60 | ATAAGCGGTTCCACTACACAC | 5039 | ISGSTTH | 6706 | 240.8811 |
| 61 | GGCACCGTCGTTCCGGGCTCC | 5040 | GTVVPGS | 6707 | 240.8455 |
| 62 | CATAATAATAATATGCTGAAT | 5041 | HNNNMLN | 6708 | 239.0755 |
| 63 | CGTCTGACTGATACTATGCAT | 5042 | RLTDTMH | 6709 | 238.939 |
| 64 | AACACCTACCCCTTCAACGCC | 5043 | NTYPFNA | 6710 | 235.89 |
| 65 | TCAACCACTACTGGCCACATG | 5044 | STTTGHM | 6711 | 231.581 |
| 66 | GTGCATAATCCTACTACTACG | 5045 | VHNPTTT | 6712 | 231.5537 |
| 67 | AATCTGCAGGTGAATGCGAAT | 5046 | NLQVNAN | 6713 | 231.172 |
| 68 | AGATACGGAGAATCCATCGAA | 5047 | RYGESIE | 6714 | 230.66 |
| 69 | AATACTACTCCGCCTAATCAT | 5048 | NTTPPNH | 6715 | 230.225 |
| 70 | AATACTTTGCAGAATAGTCAT | 5049 | NTLQNSH | 6716 | 229.0666 |
| 71 | AGTCTGAACAACATGGGATCG | 5050 | SLNNMGS | 6717 | 228.9154 |
| 72 | AGAAACGAAAACGTAAACGCT | 5051 | RNENVNA | 6718 | 228.828 |
| 73 | GCTGTGCATGCGACTAGTAGT | 5052 | AVHATSS | 6719 | 227.882 |
| 74 | ACCCAACACCTACCATCCACA | 5053 | TQHLPST | 6720 | 227.0845 |
| 75 | AGTGTGTTGTCTCAGGCTAAT | 5054 | SVLSQAN | 6721 | 225.4035 |
| 76 | AGTAGCTCAACTGAAGGGCAA | 5055 | SSSTEGQ | 6722 | 224.971 |
| 77 | GGTCGGACGGATACTCCTAAT | 5056 | GRTDTPN | 6723 | 224.945 |
| 78 | GTTCAAACCCACATAGGAGTC | 5057 | VQTHIGV | 6724 | 224.616 |
| 79 | ACTTCTGCTAGTGAGAATTGG | 5058 | TSASENW | 6725 | 224.608 |
| 80 | GGAAAAGCCAACGACGGTTCT | 5059 | GKANDGS | 6726 | 224.5935 |
| 81 | GTGGAGCGGAATACTGATATG | 5060 | VERNTDM | 6727 | 223.9975 |
| 82 | CAAAACCACGCGTCTGGTGAA | 5061 | QNHASGE | 6728 | 223.871 |
| 83 | TATTATGAGAAGCTTAGTGCG | 5062 | YYEKLSA | 6729 | 222.1725 |
| 84 | TTCATCGCTAACACTAACCCA | 5063 | FIANTNP | 6730 | 221.76 |
| 85 | ACCTCCACGGCTTCAAAACAA | 5064 | TSTASKQ | 6731 | 221.617 |
| 86 | AATAATGATAATGGTTTTGTT | 5065 | NNDNGFV | 6732 | 220.61 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 87 | GCTAATTCTATTGGGGGTCCG | 5066 | ANSIGGP | 6733 | 220.304 |
| 88 | ACTGGCCAATTAGTAGGAACC | 5067 | TGQLVGT | 6734 | 220.262 |
| 89 | TACAGTCAATCGCTGTCTGAA | 5068 | YSQSLSE | 6735 | 220.02 |
| 90 | GTCTACAACGGCAACGTAGTA | 5069 | VYNGNVV | 6736 | 219.824 |
| 91 | AACTCGGCTGAATCCTCGAGA | 5070 | NSAESSR | 6737 | 219.5415 |
| 92 | ACGCGTAATTTGTCTGAGAGT | 5071 | TRNLSES | 6738 | 218.919 |
| 93 | TCTATGTCTGATGGGCTTCGG | 5072 | SMSDGLR | 6739 | 218.868 |
| 94 | GTAGGCGACCAATCCCGCCCG | 5073 | VGDQSRP | 6740 | 218.8565 |
| 95 | TTTACGGTGAATCAGGATCTT | 5074 | FTVNQDL | 6741 | 218.069 |
| 96 | TATCATAAGTATAGTACGGAT | 5075 | YHKYSTD | 6742 | 217.64 |
| 97 | TATGGTGTGCAGGCGAATAGT | 5076 | YGVQANS | 6743 | 217.293 |
| 98 | TTGCAGACGCCTGGGACGACG | 5077 | LQTPGTT | 6744 | 217.179 |
| 99 | TATCAGCAGACTTCTAGTACG | 5078 | YQQTSST | 6745 | 216.8135 |
| 100 | CAAACGAACACCAACGACAGA | 5079 | QTNTNDR | 6746 | 216.664 |
| 101 | ATGGATAAGTCTAATAATTCT | 5080 | MDKSNNS | 6747 | 216.638 |
| 102 | CATCTTAGTCAGGCTAATCAT | 5081 | HLSQANH | 6748 | 216.575 |
| 103 | GTTGGTGCGAGTACGGCTTCG | 5082 | VGASTAS | 6749 | 215.9195 |
| 104 | CACAACAACAACCTGCAAAAC | 5083 | HNNNLQN | 6750 | 215.084 |
| 105 | AGTACTTATGGGAATACTTAT | 5084 | STYGNTY | 6751 | 214.971 |
| 106 | CGGGCTGATGTTTCTTGGTCT | 5085 | RADVSWS | 6752 | 214.499 |
| 107 | CGAGGAGACAACAGCACACCG | 5086 | RGDNSTP | 6753 | 214.29 |
| 108 | GGTCGGGATTATGCTATGAGT | 5087 | GRDYAMS | 6754 | 214.166 |
| 109 | CCTAACAACGAAAAAAACCCG | 5088 | PNNEKNP | 6755 | 214.048 |
| 110 | GATAATGTGAATTCTCAGCCT | 5089 | DNVNSQP | 6756 | 213.6615 |
| 111 | ATGGGGACTGAGTATCGTATG | 5090 | MGTEYRM | 6757 | 213.606 |
| 112 | AATCAGAGTATTAATAATATT | 5091 | NQSINNI | 6758 | 213.36 |
| 113 | GCCATAGACTCTATCAAACAA | 5092 | AIDSIKQ | 6759 | 213.304 |
| 114 | GTTGAGTCTTCTTATTCTCGG | 5093 | VESSYSR | 6760 | 212.9405 |
| 115 | GGTCAGTATAGTCAGACGCTT | 5094 | GQYSQTL | 6761 | 212.242 |
| 116 | ACCATCCAAGACCACATAAAA | 5095 | TIQDHIK | 6762 | 212.116 |
| 117 | AACAGTTCCCAATGGCCCAAC | 5096 | NSSQWPN | 6763 | 211.938 |
| 118 | ACGGATAATGGTCTTCTTGTG | 5097 | TDNGLLV | 6764 | 211.787 |
| 119 | GTAAGAGAAACCACACACCTC | 5098 | VRETTHL | 6765 | 211.44 |
| 120 | CGTGGTGATATGACTCGTGCG | 5099 | RGDMTRA | 6766 | 211.181 |
| 121 | ACTTATGGTATTACTCATGAT | 5100 | TYGITHD | 6767 | 210.641 |
| 122 | ACGGCGCTGAATACGTATCCT | 5101 | TALNTYP | 6768 | 210.568 |
| 123 | GGTGGCGAAAACAGAACCCCA | 5102 | GGENRTP | 6769 | 210.4 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 124 | TATCTGCAGGAGAAGTTTCCT | 5103 | YLQEKFP | 6770 | 210.3715 |
| 125 | CTTAATCTTACTAATCATAAT | 5104 | LNLTNHN | 6771 | 209.727 |
| 126 | GGATTAGCTAGTCTACACCTG | 5105 | GLASLHL | 6772 | 209.3585 |
| 127 | GTAGAACACGTAGCCCACCAA | 5106 | VEHVAHQ | 6773 | 209.322 |
| 128 | AGCGAACACCACGCCGGAATA | 5107 | SEHHAGI | 6774 | 209.188 |
| 129 | GAAGCGTCCAACTACGAACGA | 5108 | EASNYER | 6775 | 208.926 |
| 130 | CCCTCCAACAGTGAAAGATTC | 5109 | PSNSERF | 6776 | 208.6635 |
| 131 | TCCCCCGGCAACGGGTTGCTA | 5110 | SPGNGLL | 6777 | 208.4985 |
| 132 | ATACTGAAATCCGACGCACCA | 5111 | ILKSDAP | 6778 | 208.297 |
| 133 | TTTGATAGTGCGAATGGTCGG | 5112 | FDSANGR | 6779 | 208.26 |
| 134 | GATGGTAAGACTACGTCTAAT | 5113 | DGKTTSN | 6780 | 207.768 |
| 135 | ACTAATTATCCTGAGGCGAAT | 5114 | TNYPEAN | 6781 | 207.706 |
| 136 | CGAGGAGACCACAGCACACCG | 5115 | RGDHSTP | 6782 | 207.4315 |
| 137 | CAGACGACTATTCTGGCTGCT | 5116 | QTTILAA | 6783 | 207.223 |
| 138 | GCTACTGCGCATCAGGATGGT | 5117 | ATAHQDG | 6784 | 207.212 |
| 139 | CAAGCCCTGGCCACCACAAAC | 5118 | QALATTN | 6785 | 207.096 |
| 140 | TATAATGCTACTCCTTCGCAG | 5119 | YNATPSQ | 6786 | 206.964 |
| 141 | GAGCTGTCTACTCCTATGGTT | 5120 | ELSTPMV | 6787 | 206.8655 |
| 142 | ATTAATATTAGTAGTGATTTT | 5121 | INISSDF | 6788 | 206.753 |
| 143 | GTAACGGCACACCAATTATCC | 5122 | VTAHQLS | 6789 | 206.7385 |
| 144 | GGAGAAAGCTCCTCAATAAGC | 5123 | GESSSIS | 6790 | 206.656 |
| 145 | GAATCCCTCCCAATCTCTAAA | 5124 | ESLPISK | 6791 | 206.576 |
| 146 | ACGAATGTTAGTACGCTTTTG | 5125 | TNVSTLL | 6792 | 206.455 |
| 147 | TGGCAGACGAATGGTATGCAG | 5126 | WQTNGMQ | 6793 | 206.4378 |
| 148 | TACAGGATGGAAACGAACCCA | 5127 | YRMETNP | 6794 | 206.121 |
| 149 | ATAACCGGCAACACCGTCGGA | 5128 | ITGNTVG | 6795 | 205.9135 |
| 150 | CTGAACACTCTAATCCACAAA | 5129 | LNTLIHK | 6796 | 205.873 |
| 151 | GGGACTTCCTTGGAAAACCGA | 5130 | GTSLENR | 6797 | 205.8535 |
| 152 | TACCAACACAACCAAGCCCAC | 5131 | YQHNQAH | 6798 | 205.473 |
| 153 | ATTGAGAGTAAGACTGTGCAG | 5132 | IESKTVQ | 6799 | 205.0365 |
| 154 | TATACGCAGGGTATTATGAAT | 5133 | YTQGIMN | 6800 | 204.5275 |
| 155 | AGTACGAATGAGGCTCCTAAG | 5134 | STNEAPK | 6801 | 204.522 |
| 156 | TTGTCTCAGAATTTTAATCCT | 5135 | LSQNFNP | 6802 | 204.3926 |
| 157 | TACTCTTCTGAAATGAGCGAA | 5136 | YSSEMSE | 6803 | 204.31 |
| 158 | TCATACGGAGGATCTGGCCCC | 5137 | SYGGSGP | 6804 | 204.28 |
| 159 | ATGGACGCTGCGTACGGTAGT | 5138 | MDAAYGS | 6805 | 203.959 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 160 | CCTTTTAATCCTGGGAATGTG | 5139 | PFNPGNV | 6806 | 203.2041 |
| 161 | CAAAAATCGGAAACCTACACT | 5140 | QKSETYT | 6807 | 203.1248 |
| 162 | AACAAAGACCACAACCACCTG | 5141 | NKDHNHL | 6808 | 202.8605 |
| 163 | CTAACCGGCTCTGACATGAAA | 5142 | LTGSDMK | 6809 | 202.379 |
| 164 | TCTAAGGATAGTACTATGTAT | 5143 | SKDSTMY | 6810 | 202.335 |
| 165 | GAAGCATTCCCGCGAGCGGGC | 5144 | EAFPRAG | 6811 | 202.275 |
| 166 | GAACACACTCACTTAAACCCG | 5145 | EHTHLNP | 6812 | 201.959 |
| 167 | AGTTCGGACCCAAAAGGTCAA | 5146 | SSDPKGQ | 6813 | 201.825 |
| 168 | AAAACCATCGACATAGCACAA | 5147 | KTIDIAQ | 6814 | 201.699 |
| 169 | ACCGGTAGCTTGAACTCTATG | 5148 | TGSLNSM | 6815 | 201.671 |
| 170 | ATGCAACGCGAAGACGCGAAC | 5149 | MQREDAN | 6816 | 201.523 |
| 171 | GCCTCTACAGTCTCACTCTAC | 5150 | ASTVSLY | 6817 | 201.407 |
| 172 | GGCCGTGACGACCTCACAAAC | 5151 | GRDDLTN | 6818 | 200.911 |
| 173 | TCTAATCCGGGTAATCATAAT | 5152 | SNPGNHN | 6819 | 200.872 |
| 174 | GATACTTATAAGGGTAAGTGG | 5153 | DTYKGKW | 6820 | 200.7787 |
| 175 | CCACCCAACGGCAGCAGTAGA | 5154 | PPNGSSR | 6821 | 200.32615 |
| 176 | GCTTCTTATAGTATTTCTGAT | 5155 | ASYSISD | 6822 | 200.269 |
| 177 | GTGACTGTTAGTCTGGATGGG | 5156 | VTVSLDG | 6823 | 200.021 |
| 178 | ATGGCCATAGGCCACTCCCCA | 5157 | MAIGHSP | 6824 | 200 |
| 179 | TTTCGGACGGTGTATACTGGT | 5158 | FRTVYTG | 6825 | 200 |
| 180 | AAAAAACGGCAGCCCATCGCC | 5159 | KKRQPIA | 6826 | 200 |
| 181 | AAAAATAAGCTCTACTATGGC | 5160 | KNKLYYG | 6827 | 200 |
| 182 | TCTACATCTCCGGTTAACAGC | 5161 | STSPVNS | 6828 | 200 |
| 183 | GGGTCTGGGATTGCGGGGACT | 5162 | GSGIAGT | 6829 | 200 |
| 184 | ATCGACGTACTGAACGGAAGT | 5163 | IDVLNGS | 6830 | 200 |
| 185 | GGTCATAATATGGCACAGGCG | 5164 | GHNMAQA | 6831 | 200 |
| 186 | ACGAGGAGCAACTCCGACGAA | 5165 | TRSNSDE | 6832 | 200 |
| 187 | GGAGCAAAAGGAACCATGGGC | 5166 | GAKGTMG | 6833 | 200 |
| 188 | GCTACTACTCTTACTGGTGAT | 5167 | ATTLTGD | 6834 | 200 |
| 189 | TTCAACACATCGTCGGAATTC | 5168 | FNTSSEF | 6835 | 200 |
| 190 | TATACGGCGCAGACCGGCTGG | 5169 | YTAQTGW | 6836 | 200 |
| 191 | CGAGTAAACAACGACGCAATA | 5170 | RVNNDAI | 6837 | 200 |
| 192 | ACTATTCAGCTTACTGATACT | 5171 | TIQLTDT | 6838 | 200 |
| 193 | GCCAGCATGCCCTCTGTAGAC | 5172 | ASMPSVD | 6839 | 200 |
| 194 | AATCAGGTGGGTGCGTCTGCG | 5173 | NQVGASA | 6840 | 200 |
| 195 | GGAAACATGGTGACTCCAAAC | 5174 | GNMVTPN | 6841 | 200 |
| 196 | CGTGGTGACCAAGGCACACAC | 5175 | RGDQGTH | 6842 | 200 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 197 | TCGAGTGATTCTCGTATTCCG | 5176 | SSDSRIP | 6843 | 200 |
| 198 | GGACTGCACGGCACCAACGCA | 5177 | GLHGTNA | 6844 | 200 |
| 199 | TCTAGTTATCAGTCTGGGCTG | 5178 | SSYQSGL | 6845 | 199.609 |
| 200 | ACAGCCTACTCGCCCACAGTC | 5179 | TAYSPTV | 6846 | 199.236 |
| 201 | CGCAGTGACACCACTAACGCC | 5180 | RSDTTNA | 6847 | 198.59 |
| 202 | CGTATTGTGGCTAATGAGCAG | 5181 | RIVANEQ | 6848 | 197.795 |
| 203 | ATCCACAACGAATCATACGTC | 5182 | IHNESYV | 6849 | 197.72 |
| 204 | CAGCAGAATACGCGTTTGCCG | 5183 | QQNTRLP | 6850 | 197.4665 |
| 205 | GGTATCAACTCCTCACACTTC | 5184 | GINSSHF | 6851 | 197.224 |
| 206 | GGTATGACTTCTAATCAGGTT | 5185 | GMTSNQV | 6852 | 196.916 |
| 207 | AGGGAGATTGTTCATAGTAAT | 5186 | REIVHSN | 6853 | 196.5775 |
| 208 | GCAGAACACACGTACACGGTC | 5187 | AEHTYTV | 6854 | 196.501 |
| 209 | CCTGCTACGCTACACCTGACA | 5188 | PATLHLT | 6855 | 196.1975 |
| 210 | AAGCAGACTGATAGTAGGGGT | 5189 | KQTDSRG | 6856 | 196.15 |
| 211 | ACTATGGTAGAAGTACTGCCA | 5190 | TMVEVLP | 6857 | 195.586 |
| 212 | ATCCCAACCGGCCAAACTAGC | 5191 | IPTGQTS | 6858 | 195.499 |
| 213 | ATGATAAAAACCAACATGTTG | 5192 | MIKTNML | 6859 | 195.198 |
| 214 | GCGGAACGACCCACTAGAGAC | 5193 | AERPTRD | 6860 | 194.842 |
| 215 | CGGGATCTGGGGCAGACCGGC | 5194 | RDLGQTG | 6861 | 194.34 |
| 216 | AATGAGGGGCGTGTGCAGACT | 5195 | NEGRVQT | 6862 | 194.00545 |
| 217 | ACTGCGGCTAGTACTGCGAGG | 5196 | TAASTAR | 6863 | 193.5855 |
| 218 | ACCCAAGGGAACAACATGGTA | 5197 | TQGNNMV | 6864 | 193.362 |
| 219 | CATAGTACTTTTCCTACGACT | 5198 | HSTFPTT | 6865 | 193.274 |
| 220 | CAATCTATCGGCCACCCCGTT | 5199 | QSIGHPV | 6866 | 191.64595 |
| 221 | TCGGGTGTTAATAGTGAGCGT | 5200 | SGVNSER | 6867 | 191.3763 |
| 222 | CCTCACGCCAACGGAGTGACA | 5201 | PHANGVT | 6868 | 191.349 |
| 223 | GACCACCAACAAGCCCTAGCT | 5202 | DHQQALA | 6869 | 191.305 |
| 224 | AGTCAGCAGGGTTTTACTCTG | 5203 | SQQGFTL | 6870 | 191.2955 |
| 225 | ACAAACGCTGCTCTAGTACCA | 5204 | TNAALVP | 6871 | 191.1973 |
| 226 | GGTGTTAGTAGTAATTCTGCG | 5205 | GVSSNSA | 6872 | 190.1595 |
| 227 | CATGATACGGTTGGGGAGAGG | 5206 | HDTVGER | 6873 | 189.859 |
| 228 | GCGTTAAACGCCCAAGGGATC | 5207 | ALNAQGI | 6874 | 189.3825 |
| 229 | CATGATAGTATGTGTTGTGCG | 5208 | HDSMCCA | 6875 | 189.35 |
| 230 | TACATCGCGGCAGGGGAACAA | 5209 | YIAAGEQ | 6876 | 189.046 |
| 231 | GAGAATGCTCGTGAGGGTGTG | 5210 | ENAREGV | 6877 | 188.331 |
| 232 | GCTACGGTTTATAATGAGTTG | 5211 | ATVYNEL | 6878 | 188.18 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 233 | GACACTAACGGAATAAAATCA | 5212 | DTNGIKS | 6879 | 187.628 |
| 234 | AAGCCGACTGCGAATGATTGG | 5213 | KPTANDW | 6880 | 187.4884 |
| 235 | TATGAGAGTACTCATGTTAAT | 5214 | YESTHVN | 6881 | 187.1195 |
| 236 | TACACCAACGGGGGCCACCTA | 5215 | YTNGGHL | 6882 | 187.0304 |
| 237 | GTAGACAAATCTAGCCCAGTG | 5216 | VDKSSPV | 6883 | 186.9365 |
| 238 | CCAATCCAAAACGAATCGTCC | 5217 | PIQNESS | 6884 | 186.748 |
| 239 | ATACACAAATCTAGCGTCGAA | 5218 | IHKSSVE | 6885 | 186.654 |
| 240 | CATGATATTAGTCTGGATCGT | 5219 | HDISLDR | 6886 | 186.65 |
| 241 | TGGTGAGGGGCTGAGTTTGCC | 5220 | W*GAEFA | 6887 | 186.1 |
| 242 | TACTCTCAATCCATAAAAAAC | 5221 | YSQSIKN | 6888 | 186.0095 |
| 243 | GCCCAAGACAACAACCACGAC | 5222 | AQDNNHD | 6889 | 185.6231 |
| 244 | GGGCAGAAGGAGACTACTGCG | 5223 | GQKETTA | 6890 | 184.948 |
| 245 | AAAAGCGAAGTACCCGCCCGA | 5224 | KSEVPAR | 6891 | 184.116 |
| 246 | GAACTTAACACCGCACACGCA | 5225 | ELNTAHA | 6892 | 184.059 |
| 247 | AGCACAAACGCGGGACAAAGG | 5226 | STNAGQR | 6893 | 183.7145 |
| 248 | AAGGCGGTTTCGGAGATTATT | 5227 | KAVSEII | 6894 | 183.539 |
| 249 | ACCTTCACGGTCGACGGTAGA | 5228 | TFTVDGR | 6895 | 183.2535 |
| 250 | AGTACGAGTGGTTATAATACT | 5229 | STSGYNT | 6896 | 182.703 |
| 251 | AATCATAGTCTGTCGGAGCAT | 5230 | NHSLSEH | 6897 | 182.427 |
| 252 | TCTATGCAGGATCCTTCTTTG | 5231 | SMQDPSL | 6898 | 182.375 |
| 253 | GAACAACAAAAAACAGACAAC | 5232 | EQQKTDN | 6899 | 182.331 |
| 254 | GCTGTTGTGAATGAGAATATG | 5233 | AVVNENM | 6900 | 182.3 |
| 255 | GGTCCCGGAGAAAACTACCGA | 5234 | GPGENYR | 6901 | 182.165 |
| 256 | TACAACGCAGGCGGAGAACAA | 5235 | YNAGGEQ | 6902 | 182.14 |
| 257 | GTCCTCTCCTCCAACCTGTAC | 5236 | VLSSNLY | 6903 | 181.3605 |
| 258 | GGTCTTTATCAGAATCCTACG | 5237 | GLYQNPT | 6904 | 181.2475 |
| 259 | AGTTCGGGGAGTTTGATTACT | 5238 | SSGSLIT | 6905 | 180.8125 |
| 260 | TATAATACGGATCGGACTAAT | 5239 | YNTDRTN | 6906 | 180.0485 |
| 261 | GAGAAGCCTCAGCATAATAGT | 5240 | EKPQHNS | 6907 | 179.9715 |
| 262 | GCGGCTTATGAGCATGCGCCT | 5241 | AAYEHAP | 6908 | 178.7065 |
| 263 | GGCGGCAACTACAACACAACT | 5242 | GGNYNTT | 6909 | 178.62 |
| 264 | TATCTGAATAGTACGCAGATT | 5243 | YLNSTQI | 6910 | 178.4905 |
| 265 | TCTAATTCTAATACTGCTGCT | 5244 | SNSNTAA | 6911 | 178.119 |
| 266 | TCGGATAATAGGAATACTGCG | 5245 | SDNRNTA | 6912 | 178.09355 |
| 267 | CGCTCGTTGGACAGCGGGATG | 5246 | RSLDSGM | 6913 | 177.6395 |
| 268 | GTTATGGATACGCATGGGATG | 5247 | VMDTHGM | 6914 | 177.54 |
| 269 | CATGTTACGGCGGTGGTTGAT | 5248 | HVTAVVD | 6915 | 177.447 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 270 | AGTATCACCCACAGCAACACC | 5249 | SITHSNT | 6916 | 177.4093 |
| 271 | GGATACGGCAGTTACAGCAAC | 5250 | GYGSYSN | 6917 | 177.0995 |
| 272 | CGTTGGTCTGAAAACAACTCC | 5251 | RWSENNS | 6918 | 176.788 |
| 273 | ATGTCTAGCCACACCGTCCAA | 5252 | MSSHTVQ | 6919 | 176.741 |
| 274 | TATGTTAGGGCGCAGGATCAG | 5253 | YVRAQDQ | 6920 | 176.713 |
| 275 | TTTGAGGGTGATAAGACTTAT | 5254 | FEGDKTY | 6921 | 176.655 |
| 276 | GTTAGCTCCGGCCACACGAAA | 5255 | VSSGHTK | 6922 | 176.4715 |
| 277 | TCGATGAACCTGCCAACTTCA | 5256 | SMNLPTS | 6923 | 176.425 |
| 278 | CTGAATCCTCAGCATGAGTTG | 5257 | LNPQHEL | 6924 | 176.19 |
| 279 | CTTCCGCCTGCGTCGGCGGGT | 5258 | LPPASAG | 6925 | 176.057 |
| 280 | GGAGGGAACTCCCACGGGGTA | 5259 | GGNSHGV | 6926 | 175.7625 |
| 281 | GGGGGTACGGGGTTGTCGAAG | 5260 | GGTGLSK | 6927 | 175.714 |
| 282 | AGTTTGAATTCTTCGAGTACT | 5261 | SLNSSST | 6928 | 175.4585 |
| 283 | ATGCCTAGTGAACCACCAGGG | 5262 | MPSEPPG | 6929 | 175.45 |
| 284 | GTTGTGCATTCGAGTATTACT | 5263 | VVHSSIT | 6930 | 175.18685 |
| 285 | TTGAGTCTGGCTGGGAATAGG | 5264 | LSLAGNR | 6931 | 175.0985 |
| 286 | GCGGACATGCAACACACCGTA | 5265 | ADMQHTV | 6932 | 175.003 |
| 287 | TTTCGTGATGGTCAGGGTATG | 5266 | FRDGQGM | 6933 | 174.983 |
| 288 | ACCGGAACAGCGATCTCCCGA | 5267 | TGTAISR | 6934 | 174.5465 |
| 289 | ATGGGGAAGCATGAGGGTCTT | 5268 | MGKHEGL | 6935 | 174.3418 |
| 290 | CCGGAATCCGCCGCCAAAAGC | 5269 | PESAAKS | 6936 | 174.268 |
| 291 | ACCCAAGCCTTCTCCCTAGGC | 5270 | TQAFSLG | 6937 | 174.2365 |
| 292 | ACTGATGGTATTTTTCAGCCT | 5271 | TDGIFQP | 6938 | 174.014 |
| 293 | GGGAGCCCAGTGATAGTAAAC | 5272 | GSPVIVN | 6939 | 173.652 |
| 294 | GGGCGTGATAATCATCATGCG | 5273 | GRDNHHA | 6940 | 173.4132 |
| 295 | CCGCGTTCTATTACGGAGTTG | 5274 | PRSITEL | 6941 | 173.403 |
| 296 | TGGGTAAACAGTGTGGGCAAC | 5275 | WVNSVGN | 6942 | 173.244 |
| 297 | GTTCATGGGACGTTGACTTAT | 5276 | VHGTLTY | 6943 | 173.1685 |
| 298 | GGTGTGTATATTGATGGTCGG | 5277 | GVYIDGR | 6944 | 173.081 |
| 299 | ATGAGTAATGATTTGCCTGGG | 5278 | MSNDLPG | 6945 | 172.671 |
| 300 | AATCGGTCGGATAGTTTTGCG | 5279 | NRSDSFA | 6946 | 172.6595 |
| 301 | GGGCAAACAAACGCAGTACAC | 5280 | GQTNAVH | 6947 | 172.4582 |
| 302 | TACGTCGACAAATCAATGACA | 5281 | YVDKSMT | 6948 | 172.1735 |
| 303 | AGTGTGATGGTGGGTACGAAT | 5282 | SVMVGTN | 6949 | 171.86 |
| 304 | ATTGGTCTGCAGAATTCTACT | 5283 | IGLQNST | 6950 | 171.84715 |
| 305 | AACGACCGACCGCTTGCCAGC | 5284 | NDRPLAS | 6951 | 171.464 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 306 | CTCATGGGCAGTCCAGGCGCG | 5285 | LMGSPGA | 6952 | 171.27 |
| 307 | ATTGATCGTAGTGCTAGTTTG | 5286 | IDRSASL | 6953 | 171.009 |
| 308 | ATTCAGGCGAAGAATTCTGAG | 5287 | IQAKNSE | 6954 | 170.983 |
| 309 | CATCAGTCTTTTGATGCTGGT | 5288 | HQSFDAG | 6955 | 170.699 |
| 310 | GCGGTTAATGAGACTAGGCTT | 5289 | AVNETRL | 6956 | 170.564 |
| 311 | ATCGCGTCAACGTGGAACATG | 5290 | IASTWNM | 6957 | 170.52 |
| 312 | AAAGTGGACATGACCTCCAAA | 5291 | KVDMTSK | 6958 | 170.4035 |
| 313 | TCTCATAGTATTACGGGTCTT | 5292 | SHSITGL | 6959 | 170.333 |
| 314 | ACTATTACTAGTCCGTCGGTG | 5293 | TITSPSV | 6960 | 170.18 |
| 315 | GAACACATCTCTAGCTACGGA | 5294 | EHISSYG | 6961 | 169.832 |
| 316 | TTCTCAACAAACTCTGTAATC | 5295 | FSTNSVI | 6962 | 169.7245 |
| 317 | TCGATGGAGGGTCAGCAGCAT | 5296 | SMEGQQH | 6963 | 169.71 |
| 318 | GTCGACAAAAGCGAAGCCGTC | 5297 | VDKSEAV | 6964 | 169.6265 |
| 319 | CAAGCTAACTTATCAATAATC | 5298 | QANLSII | 6965 | 169.3842 |
| 320 | GTTAAGGCGAGTGCTGGGGTT | 5299 | VKASAGV | 6966 | 169.1112 |
| 321 | TTTGGTACTTCTTATACGACT | 5300 | FGTSYTT | 6967 | 168.915 |
| 322 | GGGCTCACAGGATACCCAATG | 5301 | GLTGYPM | 6968 | 168.8625 |
| 323 | GCTATGGGAGCACTCGTGCAC | 5302 | AMGALVH | 6969 | 168.807 |
| 324 | GTATACGCCACCGCACTCGCA | 5303 | VYATALA | 6970 | 168.7005 |
| 325 | ACATTAACAGACGTTCACCGA | 5304 | TLTDVHR | 6971 | 168.7 |
| 326 | CCATCCTCAGCGGGTAGCACA | 5305 | PSSAGST | 6972 | 168.601 |
| 327 | AAAAAACGAAAACACTAACTA | 5306 | KKRKH*L | 6973 | 168.58 |
| 328 | GCTTATCAGCTGACTCCGGCT | 5307 | AYQLTPA | 6974 | 168.579 |
| 329 | CTTGCGCCTGATAATATTGGG | 5308 | LAPDNIG | 6975 | 168.515 |
| 330 | ACAATCGTTTCCGCTTACGCC | 5309 | TIVSAYA | 6976 | 168.3875 |
| 331 | GGTAATAATTTGAGTTTGTCT | 5310 | GNNLSLS | 6977 | 168.1503 |
| 332 | AGCACAAACACCGAACCTAGG | 5311 | STNTEPR | 6978 | 168.122 |
| 333 | TCTTTTCAGACGGATCGTGCG | 5312 | SFQTDRA | 6979 | 167.793 |
| 334 | TTCTTAGAAGGAGTCGCTCAA | 5313 | FLEGVAQ | 6980 | 167.647 |
| 335 | CAAGACGTAGGACGCACGAAC | 5314 | QDVGRTN | 6981 | 167.4595 |
| 336 | ACGCATGGTGATCATATTCAG | 5315 | THGDHIQ | 6982 | 167.197 |
| 337 | GTATCAGAAGGACAACGAATC | 5316 | VSEGQRI | 6983 | 167.049 |
| 338 | AACATGGGTCCAATGGGCCGG | 5317 | NMGPMGR | 6984 | 166.961 |
| 339 | CTACCCTCAACAGAAACTTTG | 5318 | LPSTETL | 6985 | 166.942 |
| 340 | GGTGGTATGTCGGCGCATTCG | 5319 | GGMSAHS | 6986 | 166.775 |
| 341 | GGGATGATCGGGCACAACGCA | 5320 | GMIGHNA | 6987 | 166.716 |
| 342 | ATAGACGAACGTTCCTCGATA | 5321 | IDERSSI | 6988 | 166.601 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 343 | CATGTGAATCCTACGCCGGCG | 5322 | HVNPTPA | 6989 | 166.586 |
| 344 | TGGTCGAGAACTGGAAACACC | 5323 | WSRTGNT | 6990 | 166.483 |
| 345 | ATCAAAGACTCGTACCTTACT | 5324 | IKDSYLT | 6991 | 166.205 |
| 346 | TTGAACCAAAACAGTGTCTCC | 5325 | LNQNSVS | 6992 | 166.174 |
| 347 | TCTGGTCCGATTCCTGCTGTT | 5326 | SGPIPAV | 6993 | 166.146 |
| 348 | ATGCAAGGGCTTAACAACATG | 5327 | MQGLNNM | 6994 | 165.268 |
| 349 | TCAAACAGCGGAGGCAACCAC | 5328 | SNSGGNH | 6995 | 165.1895 |
| 350 | ACGAGTACGATGACTGCGCGT | 5329 | TSTMTAR | 6996 | 165.115 |
| 351 | GAGAATAGTGATTTGTCTTAT | 5330 | ENSDLSY | 6997 | 165.08 |
| 352 | CATCCTGGGAATAGTTCTGTG | 5331 | HPGNSSV | 6998 | 165.062 |
| 353 | TTAACACCCCAAGGGACTAGT | 5332 | LTPQGTS | 6999 | 165.0315 |
| 354 | ACCGACACCCGAAAAAACGAC | 5333 | TDTRKND | 7000 | 164.843 |
| 355 | GGGGAGACGCTGAGGTCTCAG | 5334 | GETLRSQ | 7001 | 164.72165 |
| 356 | AGCGGTGTATCAGAAGGAAAC | 5335 | SGVSEGN | 7002 | 164.715 |
| 357 | ACTCAGTATGGTACTCTGCCG | 5336 | TQYGTLP | 7003 | 164.526 |
| 358 | GGGACGGTTAACTCAAGTGCA | 5337 | GTVNSSA | 7004 | 164.3765 |
| 359 | GGTAAAGCAACCTTAGTCCTC | 5338 | GKATLVL | 7005 | 164.3755 |
| 360 | GGTATATACCCGGCATCCACC | 5339 | GIYPAST | 7006 | 164.34 |
| 361 | GGTGTTATGTCTAATGCTACT | 5340 | GVMSNAT | 7007 | 164.06 |
| 362 | ACTCATGTGATTGGGGCTGTG | 5341 | THVIGAV | 7008 | 163.918 |
| 363 | ACTCGGAGTGATATTGGTGTG | 5342 | TRSDIGV | 7009 | 163.7255 |
| 364 | ACGCTTACATTATCTACCCTC | 5343 | TLTLSTL | 7010 | 163.5555 |
| 365 | TATAATGAGTCTTCGAATGCG | 5344 | YNESSNA | 7011 | 163.314 |
| 366 | TCGACGCAGGCGCAGACCGGC | 5345 | STQAQTG | 7012 | 163.15 |
| 367 | CGCGACATGATCAACTCATCA | 5346 | RDMINSS | 7013 | 162.984 |
| 368 | ACTAAGGGTAATAATCTGGTT | 5347 | TKGNNLV | 7014 | 162.899 |
| 369 | GGTTCTACGGTGTCGGCGCAG | 5348 | GSTVSAQ | 7015 | 162.631 |
| 370 | AGGGGTGATACTATGAATTAT | 5349 | RGDTMNY | 7016 | 162.425 |
| 371 | CATGCGGATGTGAATGCTGGG | 5350 | HADVNAG | 7017 | 161.99 |
| 372 | AGCGTTGTCAACACCAACATC | 5351 | SVVNTNI | 7018 | 161.9445 |
| 373 | TCTAATGTTCATGTTGTTAAT | 5352 | SNVHVVN | 7019 | 161.753 |
| 374 | TCGGTTGATAAGCCGCCGGGG | 5353 | SVDKPPG | 7020 | 161.487 |
| 375 | GACCGCACCTACTCAAACACA | 5354 | DRTYSNT | 7021 | 161.475 |
| 376 | TACTCCGGAGAACTAAACAAA | 5355 | YSGELNK | 7022 | 161.125 |
| 377 | TATGATAAGACTTTGAGTGTT | 5356 | YDKTLSV | 7023 | 160.90695 |
| 378 | CACACCGCCACCCTTAGCAGC | 5357 | HTATLSS | 7024 | 160.8605 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 379 | GCTCTGGAGAGGGCTCAGTAT | 5358 | ALERAQY | 7025 | 160.837 |
| 380 | GGTACGAGTGATAATTATAGG | 5359 | GTSDNYR | 7026 | 160.175 |
| 381 | CATGTGAATAGTAGGGATCTT | 5360 | HVNSRDL | 7027 | 160.127 |
| 382 | TCGTCAGACGTTACCAGACAA | 5361 | SSDVTRQ | 7028 | 160.07 |
| 383 | GCTCATCATATGACGACGGAG | 5362 | AHHMTTE | 7029 | 160.019 |
| 384 | GAGGTGTCTAGGGATGGTCTG | 5363 | EVSRDGL | 7030 | 159.7445 |
| 385 | GTGGGCCGTGACGCAGAAGCT | 5364 | VGRDAEA | 7031 | 159.58 |
| 386 | GCACACCAAAAAGACCTACGC | 5365 | AHQKDLR | 7032 | 159.3139 |
| 387 | AGTGTTCTGAGTAGTTCGACT | 5366 | SVLSSST | 7033 | 159.208 |
| 388 | CTGGGTACGCTGCTTAGTCAG | 5367 | LGTLLSQ | 7034 | 159.04 |
| 389 | TCACAAAAACCAATCGACGAC | 5368 | SQKPIDD | 7035 | 158.663 |
| 390 | GATAATGTGCATGGGCAGGTG | 5369 | DNVHGQV | 7036 | 158.321 |
| 391 | GGTTCGCACAACGGGCCGACA | 5370 | GSHNGPT | 7037 | 157.748 |
| 392 | ATCTCCGGTAGTAGCAGTCTA | 5371 | ISGSSSL | 7038 | 157.64 |
| 393 | GGTTTTCATATTAATGGTGAG | 5372 | GFHINGE | 7039 | 157.326 |
| 394 | ATGAGTGATGGGCATTCGAAG | 5373 | MSDGHSK | 7040 | 157.296 |
| 395 | ACTGTTGGTGGTAATCATCAT | 5374 | TVGGNHH | 7041 | 156.895 |
| 396 | AATGCTACTCCGCCGAATCAT | 5375 | NATPPNH | 7042 | 156.8609 |
| 397 | ACGGGTATGAATAGTAATAAG | 5376 | TGMNSNK | 7043 | 156.85 |
| 398 | ATCGAAGCCTACTCACGAGAC | 5377 | IEAYSRD | 7044 | 156.774 |
| 399 | CGCGACCGTCAAGACTCGGTA | 5378 | RDRQDSV | 7045 | 156.7165 |
| 400 | CACACGGTTCAAATACGCGAA | 5379 | HTVQIRE | 7046 | 156.6241 |
| 401 | ACTTTGACGCAGACTGGGATG | 5380 | TLTQTGM | 7047 | 156.5735 |
| 402 | ATTAATAATTTTAATACTCTG | 5381 | INNFNTL | 7048 | 156.48 |
| 403 | GTAGCCGCGGGACCAGAAGCG | 5382 | VAAGPEA | 7049 | 156.315 |
| 404 | GATGGTAAGAATAGTTATGCG | 5383 | DGKNSYA | 7050 | 156.294 |
| 405 | TCCAGGCAAGAAAACTTCTCC | 5384 | SRQENFS | 7051 | 156.182 |
| 406 | TCTAACAGCAGTGTTGCGGTA | 5385 | SNSSVAV | 7052 | 156.048 |
| 407 | GATCATAGTAAGCAGAGTTCG | 5386 | DHSKQSS | 7053 | 155.89425 |
| 408 | TTGAGTGGTGCTGGTAGTCAG | 5387 | LSGAGSQ | 7054 | 154.9295 |
| 409 | GGTTGGAGTAATAATGAGTTG | 5388 | GWSNNEL | 7055 | 154.4735 |
| 410 | CTAATACGAGGTTCCATGGAA | 5389 | LIRGSME | 7056 | 154.426 |
| 411 | AATACTTATACTGCTGGTAAG | 5390 | NTYTAGK | 7057 | 154.346 |
| 412 | ACTCGTGGCGACATGGAATTC | 5391 | TRGDMEF | 7058 | 154.246 |
| 413 | CTCATGTCAGGGAAAGAAAAC | 5392 | LMSGKEN | 7059 | 154.155 |
| 414 | AAGGATACTAATCAGCAGATT | 5393 | KDTNQQI | 7060 | 153.7595 |
| 415 | CACAACGTCGGCCTAGGACAC | 5394 | HNVGLGH | 7061 | 153.7 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 416 | CCTGATCAGCCTGGTCCTTCT | 5395 | PDQPGPS | 7062 | 153.51 |
| 417 | ATGCAAAGAGAAGCAGCCAAC | 5396 | MQREAAN | 7063 | 153.45 |
| 418 | GGGCAGCGTACGACGAATGAT | 5397 | GQRTTND | 7064 | 153.425 |
| 419 | AAACACACAGAAAACGGGACC | 5398 | KHTENGT | 7065 | 153.394 |
| 420 | TTAGACGTGACGAGAATGAGA | 5399 | LDVTRMR | 7066 | 153.086 |
| 421 | ACGTTGGATCGGAATCAGACT | 5400 | TLDRNQT | 7067 | 152.9552 |
| 422 | ATCAACGCCGGCAACTACCGA | 5401 | INAGNYR | 7068 | 152.8475 |
| 423 | GCCGTAGACCAATCACGTTTG | 5402 | AVDQSRL | 7069 | 152.8359 |
| 424 | GCTCTTGGGCATCAGGGGAAT | 5403 | ALGHQGN | 7070 | 152.467 |
| 425 | CTTCCGCGTCATGATCAGTAT | 5404 | LPRHDQY | 7071 | 152.412 |
| 426 | ATTTCTGGGTCGTCGTCTCTT | 5405 | ISGSSSL | 7072 | 152.2375 |
| 427 | TGGAATACGAATATGGCGATT | 5406 | WNTNMAI | 7073 | 151.8755 |
| 428 | ATGTCGGATCGTACTTCTGAT | 5407 | MSDRTSD | 7074 | 151.677 |
| 429 | ACAAGGGAATCAATGTCCATC | 5408 | TRESMSI | 7075 | 151.6105 |
| 430 | CAGCGGGGGGAGCTTCCTGCG | 5409 | QRGELPA | 7076 | 151.533 |
| 431 | TCGTCTGATCCTAAGGGGCAG | 5410 | SSDPKGQ | 7077 | 151.4265 |
| 432 | CCGAGTGATAGGACTACTTAT | 5411 | PSDRTTY | 7078 | 151.3695 |
| 433 | TCTTCTTCTGATAGTCCGCGT | 5412 | SSSDSPR | 7079 | 151.2845 |
| 434 | GTATTACACTCTGTATCAGCA | 5413 | VLHSVSA | 7080 | 151.217 |
| 435 | AGTATGCAATCATACACCATG | 5414 | SMQSYTM | 7081 | 151.1285 |
| 436 | TCTCTGCAACTCACAGCGGGT | 5415 | SLQLTAG | 7082 | 151.106 |
| 437 | AACAACGTAAACCCGTACTCG | 5416 | NNVNPYS | 7083 | 151.0935 |
| 438 | CTTGCGAATGGTATGACGGCT | 5417 | LANGMTA | 7084 | 150.9825 |
| 439 | GGAATCACAGGATCAACAGGA | 5418 | GITGSTG | 7085 | 150.979 |
| 440 | ATGCTTGTTCAGAATACTCCT | 5419 | MLVQNTP | 7086 | 150.943 |
| 441 | GATGCGAATGCGGGTACGAGG | 5420 | DANAGTR | 7087 | 150.871 |
| 442 | GAAACCGGAGCTATGACCTCT | 5421 | ETGAMTS | 7088 | 150.803 |
| 443 | ATACAAACTACTACAAAATGC | 5422 | IQTTTKC | 7089 | 150.692 |
| 444 | GCGCAGCAGAGTCTTCATGGT | 5423 | AQQSLHG | 7090 | 150.673 |
| 445 | ATTGATAGTACTTGGAATACG | 5424 | IDSTWNT | 7091 | 150.518 |
| 446 | ACCGAATCGCAAACCATGAGG | 5425 | TESQTMR | 7092 | 150.4394 |
| 447 | TTGATCCAAACGCAAGGCACG | 5426 | LIQTQGT | 7093 | 150.329 |
| 448 | ATAGTAAACATAACTCAATCG | 5427 | IVNITQS | 7094 | 150.305 |
| 449 | GTGGCGGTGTCTAATACGCCT | 5428 | VAVSNTP | 7095 | 150.03285 |
| 450 | GGTCATAGGGATTCGGGTGGT | 5429 | GHRDSGG | 7096 | 149.991 |
| 451 | CGGAATGAGAATCTTAATAAT | 5430 | RNENLNN | 7097 | 149.913 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 452 | GTCATGCAACGATCTGCACAA | 5431 | VMQRSAQ | 7098 | 149.77 |
| 453 | GTCTCGGGTCCGGTATCGGTC | 5432 | VSGPVSV | 7099 | 149.7645 |
| 454 | GGGGATATTCAGAGTCATAGT | 5433 | GDIQSHS | 7100 | 149.392 |
| 455 | GTTGAGAAGCCTCTGGAGACT | 5434 | VEKPLET | 7101 | 149.24 |
| 456 | GGTGTTCAGATGACTGCGGGG | 5435 | GVQMTAG | 7102 | 149.14805 |
| 457 | ACCACAAAAACGACATCTATG | 5436 | TTKTTSM | 7103 | 149.0935 |
| 458 | CCTGGGAATCCGTCTAGTAAT | 5437 | PGNPSSN | 7104 | 148.9075 |
| 459 | GCTTCGCGGCCTGCGGCTCAG | 5438 | ASRPAAQ | 7105 | 148.8831 |
| 460 | GTTCATGATCAGGGGGCTGGG | 5439 | VHDQGAG | 7106 | 148.829 |
| 461 | TCAGGTTCGGAATACCGTACC | 5440 | SGSEYRT | 7107 | 148.812 |
| 462 | TACGTGGACGACAACAGTCGC | 5441 | YVDDNSR | 7108 | 148.744 |
| 463 | ATGGCCGGTGACCAAGAACTC | 5442 | MAGDQEL | 7109 | 148.7 |
| 464 | CCTTTGCACAACATACCTCCT | 5443 | PLHNIPP | 7110 | 148.609 |
| 465 | AGTGGGATTGGTACTTATTCT | 5444 | SGIGTYS | 7111 | 148.357 |
| 466 | TCGAACGCAGACATCCTCGCC | 5445 | SNADILA | 7112 | 148.08 |
| 467 | AGTCACAACCAAGTAAACGTA | 5446 | SHNQVNV | 7113 | 147.981 |
| 468 | CAGCATTCTCCGAAGCCGGTT | 5447 | QHSPKPV | 7114 | 147.97 |
| 469 | TCCGCAAACAACATAGCCCCC | 5448 | SANNIAP | 7115 | 147.813 |
| 470 | GAAGAAACACGGACCAGAATG | 5449 | EETRTRM | 7116 | 147.667 |
| 471 | CTGTCTAATTCGATTACGCCT | 5450 | LSNSITP | 7117 | 147.594 |
| 472 | AGTGCTTTGAATAGTGTGGAT | 5451 | SALNSVD | 7118 | 147.326 |
| 473 | ACTAATCTTGCTGTTACGCTG | 5452 | TNLAVTL | 7119 | 147.1589 |
| 474 | CAGTCGACGCTGAATAGGCCT | 5453 | QSTLNRP | 7120 | 147.0302 |
| 475 | ATAGAACACATGCTTAGACCC | 5454 | IEHMLRP | 7121 | 146.9635 |
| 476 | CCGACTCCTAATGAGCATATG | 5455 | PTPNEHM | 7122 | 146.84 |
| 477 | ATTAATGAGATTGGTAGGATG | 5456 | INEIGRM | 7123 | 146.786 |
| 478 | AACAACGACAACGTCTACGTG | 5457 | NNDNVYV | 7124 | 146.764 |
| 479 | ATAGTCCACACCCCGCAAGTG | 5458 | IVHTPQV | 7125 | 146.309 |
| 480 | CATAAGAGTGAGAGTCATAAT | 5459 | HKSESHN | 7126 | 146.142 |
| 481 | TCATCGTCAGACTCACCCAGA | 5460 | SSSDSPR | 7127 | 146.067 |
| 482 | TACTCTACAGAAGCACGAGTC | 5461 | YSTEARV | 7128 | 145.9845 |
| 483 | ACCTCGGGTGACCGGTACACG | 5462 | TSGDRYT | 7129 | 145.963 |
| 484 | GAGAAGAATCTGACTAATGCT | 5463 | EKNLTNA | 7130 | 145.88775 |
| 485 | ACAAGGGACCAAAGGTCTACA | 5464 | TRDQRST | 7131 | 145.8855 |
| 486 | GCGACTGATAAGATGACTCCT | 5465 | ATDKMTP | 7132 | 145.881 |
| 487 | AATAGTTATACTGCTGGGAAG | 5466 | NSYTAGK | 7133 | 145.87565 |
| 488 | ACGCTGGATACTAAGGATCTT | 5467 | TLDTKDL | 7134 | 145.82 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 489 | GCATCCAACGGGCAAGTTAAC | 5468 | ASNGQVN | 7135 | 145.7395 |
| 490 | ACCTCAATATCGTCGCAAAGC | 5469 | TSISSQS | 7136 | 145.707 |
| 491 | GATAATAGTCCTGCTAATCAT | 5470 | DNSPANH | 7137 | 145.5712 |
| 492 | AACTCCAGGGAAATGGGTGTA | 5471 | NSREMGV | 7138 | 145.562 |
| 493 | ACCAGCGCGTCTGAAAACTGG | 5472 | TSASENW | 7139 | 145.56 |
| 494 | ACTGTAGGATCCTCATACGCT | 5473 | TVGSSYA | 7140 | 145.0453 |
| 495 | CAACAATCACAAAACTCTATA | 5474 | QQSQNSI | 7141 | 144.9825 |
| 496 | CTTCGGGATGGGATTGCTTCT | 5475 | LRDGIAS | 7142 | 144.9725 |
| 497 | GTGCAAAAAACGACGGCTTGG | 5476 | VQKTTAW | 7143 | 144.78 |
| 498 | ATGAGTACGGTTCTTCGGGAG | 5477 | MSTVLRE | 7144 | 144.5125 |
| 499 | AGTATGGATGCTCGGTTGACG | 5478 | SMDARLT | 7145 | 144.404 |
| 500 | GGCGCCCGTACAATCTTAGAC | 5479 | GARTILD | 7146 | 144.3975 |
| 501 | CACGAAAGCCACTACGTGTCA | 5480 | HESHYVS | 7147 | 144.2755 |
| 502 | CTTGAGGGTCAGAATAAGACG | 5481 | LEGQNKT | 7148 | 144.137 |
| 503 | CGGGACTTGAGACCCGTGACG | 5482 | RDLRPVT | 7149 | 143.788 |
| 504 | CAGATTTTGAATTATAGTGTG | 5483 | QILNYSV | 7150 | 143.741 |
| 505 | ATAAGTGTAGGTGTGTCCGTA | 5484 | ISVGVSV | 7151 | 143.727 |
| 506 | AAGGCGGGTGAGTATAGGGAT | 5485 | KAGEYRD | 7152 | 143.693 |
| 507 | CTTACTACGAATGGTATGCTG | 5486 | LTTNGML | 7153 | 143.66 |
| 508 | ACTAGTAATTATATGCATGAG | 5487 | TSNYMHE | 7154 | 143.642 |
| 509 | ACCCACAACTCTACAGGCCTT | 5488 | THNSTGL | 7155 | 143.502 |
| 510 | AATAATGTTGTTAGGGATGAT | 5489 | NNVVRDD | 7156 | 143.142 |
| 511 | AGTGGGACGTATGCTAGTCGT | 5490 | SGTYASR | 7157 | 143.123 |
| 512 | CTGTCTCACGCCATGGACCGG | 5491 | LSHAMDR | 7158 | 142.937 |
| 513 | AATTGGAATTCTGAGGGTACG | 5492 | NWNSEGT | 7159 | 142.7425 |
| 514 | AGTCTGCGTCCAACCCTACCT | 5493 | SLRPTLP | 7160 | 142.4292 |
| 515 | TACCAAACGGGAGACAAAGAC | 5494 | YQTGDKD | 7161 | 142.104 |
| 516 | CGCAGCGACAAAGGAACGTTG | 5495 | RSDKGTL | 7162 | 142.1004 |
| 517 | TCTACCATCGGCAACAGCACG | 5496 | STIGNST | 7163 | 142.0895 |
| 518 | GAAAACAACATGCAACACGGC | 5497 | ENNMQHG | 7164 | 142.037 |
| 519 | AAGTATACGGAGTCGAATGCG | 5498 | KYTESNA | 7165 | 142.0295 |
| 520 | CCAACAAACAACTTAAGTATG | 5499 | PTNNLSM | 7166 | 141.91 |
| 521 | TGCAAAAACAACTCAGAATGC | 5500 | CKNNSEC | 7167 | 141.874 |
| 522 | ACGGTTAATGCGGATGGGTCG | 5501 | TVNADGS | 7168 | 141.672 |
| 523 | TTTTCTGGTCAGGCGTTGGCT | 5502 | FSGQALA | 7169 | 141.6645 |
| 524 | AATCATATTAGGAATCCTATG | 5503 | NHIRNPM | 7170 | 141.628 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 525 | ATGGTGAATTCGGAGAATACT | 5504 | MVNSENT | 7171 | 141.624 |
| 526 | ACTGATGGGCCGCGTCTGGCT | 5505 | TDGPRLA | 7172 | 141.5814 |
| 527 | TTCAACGGGTACGTCATGGCA | 5506 | FNGYVMA | 7173 | 141.042 |
| 528 | AATGCGAATGGGCCTGTGAGT | 5507 | NANGPVS | 7174 | 141.0385 |
| 529 | AGTACGAGTCAGGAGAATAGG | 5508 | STSQENR | 7175 | 140.9233 |
| 530 | CAAGGGACTCTCTTGTCTCCA | 5509 | QGTLLSP | 7176 | 140.773 |
| 531 | CTAATCACAGCCACCACTAAC | 5510 | LITATTN | 7177 | 140.4315 |
| 532 | TCTGGCGTCTCGAAAGAACGG | 5511 | SGVSKER | 7178 | 140.3655 |
| 533 | TCTACTTCAATAGGAGTGGTA | 5512 | STSIGVV | 7179 | 140.351 |
| 534 | TCTCATGTGACTGTTACGGAT | 5513 | SHVTVTD | 7180 | 140.31 |
| 535 | TCTAATAATCTGAATCAGGAG | 5514 | SNNLNQE | 7181 | 140.282 |
| 536 | GCAAACCACGACAACATCGTG | 5515 | ANHDNIV | 7182 | 140.0405 |
| 537 | GACACGTCCTCCGGCAACAGG | 5516 | DTSSGNR | 7183 | 140.01 |
| 538 | GTGGTTCCTATGCCTACTACT | 5517 | VVPMPTT | 7184 | 139.945 |
| 539 | CTTACTAATAATTTTAAGGAT | 5518 | LTNNFKD | 7185 | 139.782 |
| 540 | TCTTCGCCTACTAAGGGTACT | 5519 | SSPTKGT | 7186 | 139.7594 |
| 541 | GATATTCCGTCTGATAATACG | 5520 | DIPSDNT | 7187 | 139.44 |
| 542 | TACACGGGATTCGAATTGAGA | 5521 | YTGFELR | 7188 | 139.43 |
| 543 | AACTCAGGTAACAACCCCATC | 5522 | NSGNNPI | 7189 | 139.4185 |
| 544 | ACGACCCGAAACGAACACTCG | 5523 | TTRNEHS | 7190 | 139.3175 |
| 545 | AATGTGGGTAATACTCTTGGG | 5524 | NVGNTLG | 7191 | 139.128 |
| 546 | TACCACACCCACCAAGTCGCA | 5525 | YHTHQVA | 7192 | 138.871 |
| 547 | GGTAGTGCGAGTAATAGTGGT | 5526 | GSASNSG | 7193 | 138.841 |
| 548 | GGGAAGAATCAGCCTACTCCG | 5527 | GKNQPTP | 7194 | 138.839 |
| 549 | TTCACCGCCACTTTAGGAACC | 5528 | FTATLGT | 7195 | 138.809 |
| 550 | ATGAACCAAATGGGCGGCCTG | 5529 | MNQMGGL | 7196 | 138.794 |
| 551 | AACGTGTCACTAACGCAAACG | 5530 | NVSLTQT | 7197 | 138.62365 |
| 552 | TCGTCTAGCAACACAAACGCT | 5531 | SSSNTNA | 7198 | 138.538 |
| 553 | ACTAATTCTAATCAGAGTTCG | 5532 | TNSNQSS | 7199 | 138.513 |
| 554 | ATAAGTCACGACCTTAAATAC | 5533 | ISHDLKY | 7200 | 138.4685 |
| 555 | GATTCGACGTATGTTTTGGCT | 5534 | DSTYVLA | 7201 | 138.402 |
| 556 | ATGAACACCGGCTCTTCGAGT | 5535 | MNTGSSS | 7202 | 138.35 |
| 557 | GCCGGAAACTACCAATCATCA | 5536 | AGNYQSS | 7203 | 138.2335 |
| 558 | ACGATTTATAATATGGGTCCG | 5537 | TIYNMGP | 7204 | 138.1385 |
| 559 | GTATCAACGACAACGGACCGG | 5538 | VSTTTDR | 7205 | 137.9925 |
| 560 | GGGGTGACTGTTAGGGAGCTT | 5539 | GVTVREL | 7206 | 137.96205 |
| 561 | GATATTACTAATCAGTCGTAT | 5540 | DITNQSY | 7207 | 137.802 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 562 | AATCAGTCGCTTACTATGGAT | 5541 | NQSLTMD | 7208 | 137.363 |
| 563 | ACGAATTATAATATTGGTCCG | 5542 | TNYNIGP | 7209 | 137.0645 |
| 564 | CGTGGTACGGAGGGGACGCCG | 5543 | RGTEGTP | 7210 | 137.0621 |
| 565 | CCCATAACACGGGAATCGGGA | 5544 | PITRESG | 7211 | 136.943 |
| 566 | ACCGGACAAGCGGGCGGATCG | 5545 | TGQAGGS | 7212 | 136.857 |
| 567 | ATGACTAAACACGACGCGACG | 5546 | MTKHDAT | 7213 | 136.624 |
| 568 | CCTATACCCCACGGTTCATCC | 5547 | PIPHGSS | 7214 | 136.299 |
| 569 | ACGACTGGGGGGACGGGGATG | 5548 | TTGGTGM | 7215 | 136.1295 |
| 570 | CTAACCGAATCTGTGAGAAAC | 5549 | LTESVRN | 7216 | 135.933 |
| 571 | AGTAGTAATCTGACTTTGTCT | 5550 | SSNLTLS | 7217 | 135.86 |
| 572 | TTGAATAATTCTGCGACTGTT | 5551 | LNNSATV | 7218 | 135.76 |
| 573 | GCATACGGATCGTCCGGAAGA | 5552 | AYGSSGR | 7219 | 135.5095 |
| 574 | GTTTCTTATGATAATGGGTCG | 5553 | VSYDNGS | 7220 | 135.48 |
| 575 | CCGAGTCAGAGTAGGTCGCTT | 5554 | PSQSRSL | 7221 | 135.38455 |
| 576 | GTCCTGGTTAACGTACACAAC | 5555 | VLVNVHN | 7222 | 135.346 |
| 577 | TTGATGACTGGTACTGCGTCG | 5556 | LMTGTAS | 7223 | 135.327 |
| 578 | GCTGCTGGTAATCCTACTCGT | 5557 | AAGNPTR | 7224 | 135.3067 |
| 579 | TCCGCGCAATCTTTCGTAGTT | 5558 | SAQSFVV | 7225 | 134.721 |
| 580 | CAAGACCAAACGAGCAACCGT | 5559 | QDQTSNR | 7226 | 134.721 |
| 581 | CAGTCGATTGGGCATCCGGTG | 5560 | QSIGHPV | 7227 | 134.625 |
| 582 | GCTGGGGTGCGTGAGTCGTTT | 5561 | AGVRESF | 7228 | 134.586 |
| 583 | AATACTAATTATGCGATGCAT | 5562 | NTNYAMH | 7229 | 134.493 |
| 584 | GAGCGGAGTACGCATAATGTT | 5563 | ERSTHNV | 7230 | 134.479 |
| 585 | ATGTCCGGATCCATGATATCA | 5564 | MSGSMIS | 7231 | 134.414 |
| 586 | TCTGGCCAAGGATTCTCGGCA | 5565 | SGQGFSA | 7232 | 134.3465 |
| 587 | ACATTCACTACTCTGGGCAAA | 5566 | TFTTLGK | 7233 | 134.2015 |
| 588 | GACGCAAACGCTGGCACAAGA | 5567 | DANAGTR | 7234 | 134.063 |
| 589 | AGGGATACGGCTAAGGGGGTG | 5568 | RDTAKGV | 7235 | 133.882 |
| 590 | GTGCGGTCTGGTAATAAGCCG | 5569 | VRSGNKP | 7236 | 133.87 |
| 591 | CCCCAATGGGGAACTGACCCG | 5570 | PQWGTDP | 7237 | 133.743 |
| 592 | GCCTTCCAAAACACCGGCGCA | 5571 | AFQNTGA | 7238 | 133.743 |
| 593 | GCGACGACTCAGCTGATGACT | 5572 | ATTQLMT | 7239 | 133.675 |
| 594 | ACGAACGCGAGCGAAGGCTCA | 5573 | TNASEGS | 7240 | 133.642 |
| 595 | ATGCTCACAGAAACCAAAGCA | 5574 | MLTETKA | 7241 | 133.57 |
| 596 | ACGAATAATTTGCTGGCTCAG | 5575 | TNNLLAQ | 7242 | 133.517 |
| 597 | GATGTTTTGCTTAAGAATTTT | 5576 | DVLLKNF | 7243 | 133.49 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 598 | TATACGCCTGGGCTTACTGAG | 5577 | YTPGLTE | 7244 | 133.356 |
| 599 | CGGCATGCTTCGGATGCTAAT | 5578 | RHASDAN | 7245 | 133.22 |
| 600 | AGTAAGGGTGATCAGCTTAAT | 5579 | SKGDQLN | 7246 | 133.1865 |
| 601 | GTGCTGGTTACTCAGAATCAT | 5580 | VLVTQNH | 7247 | 133.0645 |
| 602 | CGACAAGGCGACTTAAAAGAA | 5581 | RQGDLKE | 7248 | 132.97895 |
| 603 | ATTCAGTCGCAGTCGCAGTTG | 5582 | IQSQSQL | 7249 | 132.832 |
| 604 | AAAATAGAAAGCGGAACCATA | 5583 | KIESGTI | 7250 | 132.825 |
| 605 | ACAACTCTTAGCCAACAAAGC | 5584 | TTLSQQS | 7251 | 132.567 |
| 606 | TTTCAGTTGGCTAGTAATCCG | 5585 | FQLASNP | 7252 | 132.4465 |
| 607 | TGGATTTCTACTGAGATGAGG | 5586 | WISTEMR | 7253 | 132.356 |
| 608 | GCCATAACAATCACTCAAAAA | 5587 | AITITQK | 7254 | 132.1895 |
| 609 | GTTACTGGTGTTGATTATGCG | 5588 | VTGVDYA | 7255 | 131.7275 |
| 610 | ATAATAGCATCCTCTACCACG | 5589 | IIASSTT | 7256 | 131.506 |
| 611 | ATTTATACGAATAGTCATGTT | 5590 | IYTNSHV | 7257 | 131.43 |
| 612 | AACGACATCCCCACACGAGCC | 5591 | NDIPTRA | 7258 | 131.424 |
| 613 | GGCGTAACCAACGCTTCCAAA | 5592 | GVTNASK | 7259 | 131.404 |
| 614 | AGGGGTAACACTCTCGAAATG | 5593 | RGNTLEM | 7260 | 131.381 |
| 615 | GGTATTAATCATGTGGCGTCT | 5594 | GINHVAS | 7261 | 131.36 |
| 616 | TTCAACGAAACTGCCGGGCGA | 5595 | FNETAGR | 7262 | 131.2915 |
| 617 | GCCTCGCAATCAGAAAAAAAC | 5596 | ASQSEKN | 7263 | 131.243 |
| 618 | GAACTTAACGAAAGGAACCTC | 5597 | ELNERNL | 7264 | 131.06 |
| 619 | GGAGAACAAAGCCACAACCAA | 5598 | GEQSHNQ | 7265 | 130.951 |
| 620 | TTGACTAATGATAATAAGTTG | 5599 | LTNDNKL | 7266 | 130.846 |
| 621 | TCTTATGGGCAGGGTCTGGAG | 5600 | SYGQGLE | 7267 | 130.8108 |
| 622 | CACAGTGACATGGGCTCAAGC | 5601 | HSDMGSS | 7268 | 130.758 |
| 623 | GCGTTAAAATCCGACAGCGCC | 5602 | ALKSDSA | 7269 | 130.684 |
| 624 | ACGAATCTTTCTCCTAAGACG | 5603 | TNLSPKT | 7270 | 130.64725 |
| 625 | GCTGATACGAATATTATTGTG | 5604 | ADTNIIV | 7271 | 130.47 |
| 626 | AGTGAGGGTAGTTCGCGGTCG | 5605 | SEGSSRS | 7272 | 130.30865 |
| 627 | AACTCTAGTAACACTGGTTGG | 5606 | NSSNTGW | 7273 | 130.26 |
| 628 | GTAACGAACGAATCCCGCGCC | 5607 | VTNESRA | 7274 | 130.2145 |
| 629 | GGGCGGCACACATTAGCGGAC | 5608 | GRHTLAD | 7275 | 130.1035 |
| 630 | GCTGTTGTGAATGTTGCGCAG | 5609 | AVVNVAQ | 7276 | 130.094 |
| 631 | AAAAAACCACAACAGTGACTA | 5610 | KKPQQ*L | 7277 | 130.08 |
| 632 | GGCAACGCTTCCGGAAACCCA | 5611 | GNASGNP | 7278 | 129.97 |
| 633 | TTTGCGGCTGGGGCGCATGGT | 5612 | FAAGAHG | 7279 | 129.69 |
| 634 | GGAGGAAACCAAAACCTTACT | 5613 | GGNQNLT | 7280 | 129.6198 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 635 | CATACGCAGTCGACGGGTTAT | 5614 | HTQSTGY | 7281 | 129.541 |
| 636 | CTATTGGGAAACGCACCCACA | 5615 | LLGNAPT | 7282 | 129.534 |
| 637 | GAGAAGGGGAATAGTGGGGTT | 5616 | EKGNSGV | 7283 | 129.5155 |
| 638 | GGCACGGAACCGCGCACTGCA | 5617 | GTEPRTA | 7284 | 129.37 |
| 639 | ATGCATGCGCAGGAGTCTCGT | 5618 | MHAQESR | 7285 | 129.14615 |
| 640 | CTGATTTCGACTGGTAATAAT | 5619 | LISTGNN | 7286 | 129.021 |
| 641 | AAGAATAATAATTCTGATTCT | 5620 | KNNNSDS | 7287 | 128.767 |
| 642 | GGGACATTAGCCTCAATGTCC | 5621 | GTLASMS | 7288 | 128.734 |
| 643 | AGGATTGATACGTTGTTGGTG | 5622 | RIDTLLV | 7289 | 128.385 |
| 644 | ATTTCGGGGTCTCATTTGAAT | 5623 | ISGSHLN | 7290 | 128.3305 |
| 645 | ACGGTTGAGGGTTCTTATCCG | 5624 | TVEGSYP | 7291 | 128.288 |
| 646 | ACGGAGTATCTGGCTGGTCTG | 5625 | TEYLAGL | 7292 | 128.224 |
| 647 | TATCTGGAGGGTGCTCATCGT | 5626 | YLEGAHR | 7293 | 128.166 |
| 648 | TTATCCGCAACATCTACGATG | 5627 | LSATSTM | 7294 | 128.1455 |
| 649 | ATGCTTAGTCAGGTTCTGACG | 5628 | MLSQVLT | 7295 | 128.142 |
| 650 | GCCAGGAACGTAATGCTGGGG | 5629 | ARNVMLG | 7296 | 128.128 |
| 651 | CTTCATGGGAATTTTAGTCAG | 5630 | LHGNFSQ | 7297 | 128.112 |
| 652 | GGCCACGGAAGTGACTTGACC | 5631 | GHGSDLT | 7298 | 128.0576 |
| 653 | GGTGTGAATTATCATACTACG | 5632 | GVNYHTT | 7299 | 127.702 |
| 654 | TATCTGCAGACGGGTACTCTG | 5633 | YLQTGTL | 7300 | 127.624 |
| 655 | GTAAACGGGGGAAAACCAGTC | 5634 | VNGGKPV | 7301 | 127.5325 |
| 656 | GAAGTAGGTAAAACCACCCAC | 5635 | EVGKTTH | 7302 | 127.5065 |
| 657 | CGACCCCCGAACGAAAACAGA | 5636 | RPPNENR | 7303 | 127.49235 |
| 658 | GTGGATAAGAATCATCCTTTG | 5637 | VDKNHPL | 7304 | 127.431 |
| 659 | AGTAAGTCGACTGAGATTATG | 5638 | SKSTEIM | 7305 | 127.281 |
| 660 | ACCGCTCTTCTATCTAACTTA | 5639 | TALLSNL | 7306 | 127.228 |
| 661 | ATGCACACAAGTAGACCCCCA | 5640 | MHTSRPP | 7307 | 126.861 |
| 662 | ACTCCAACTAACGGGAACCCT | 5641 | TPTNGNP | 7308 | 126.785 |
| 663 | ACGACGTCTGTGGAGAAGACT | 5642 | TTSVEKT | 7309 | 126.7725 |
| 664 | CAATACGACGCCAGCCGACAA | 5643 | QYDASRQ | 7310 | 126.66 |
| 665 | TACAACGCCCACGAATCATTC | 5644 | YNAHESF | 7311 | 126.521 |
| 666 | GACAACCAACAAGCCCTAGCT | 5645 | DNQQALA | 7312 | 126.49 |
| 667 | ACGAAGAGTTTTAATGATCTT | 5646 | TKSFNDL | 7313 | 126.488 |
| 668 | TTAGCCGACTCAAACAGCAAA | 5647 | LADSNSK | 7314 | 126.48 |
| 669 | CCGAGTACTCATGGGTATGTT | 5648 | PSTHGYV | 7315 | 126.4775 |
| 670 | CAGGTTCAGGGGACTCTGGGG | 5649 | QVQGTLG | 7316 | 126.4394 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 671 | CTGACTGCTGTTGCGATTAGT | 5650 | LTAVAIS | 7317 | 126.235 |
| 672 | AGGTATGAGAGTACTAGTGCT | 5651 | RYESTSA | 7318 | 126.21 |
| 673 | GCGGATCATAATCATATTGCT | 5652 | ADHNHIA | 7319 | 126.21 |
| 674 | TGGAATGCTGAGAATAGTAAG | 5653 | WNAENSK | 7320 | 126.112 |
| 675 | AACTCTGTCGTAGGGAACATC | 5654 | NSVVGNI | 7321 | 126.111 |
| 676 | TTCGGAGCAACCACCACAGCA | 5655 | FGATTTA | 7322 | 126.048 |
| 677 | GCTTCAGGGTCTGAAATGCCT | 5656 | ASGSEMF | 7323 | 125.971 |
| 678 | GACGGAACAAAAAGCGGAATG | 5657 | DGTKSGM | 7324 | 125.871 |
| 679 | TACACCGCCGACAAAAAACAA | 5658 | YTADKKQ | 7325 | 125.562 |
| 680 | CCGATTGCTGAGAGGCCTTCT | 5659 | PIAERPS | 7326 | 125.558 |
| 681 | AGCAACTCGTACTTACTCAAC | 5660 | SNSYLLN | 7327 | 125.52 |
| 682 | ACGAGAGAATTGACAAAAAAC | 5661 | TRELTKN | 7328 | 125.47 |
| 683 | CTCGGAAACCACTACACACCC | 5662 | LGNHYTP | 7329 | 125.444 |
| 684 | TTGCTCCAATCCATAGTGGTA | 5663 | LLQSIVV | 7330 | 125.441 |
| 685 | ATGATGGCGAATAATATGCAG | 5664 | MMANNMQ | 7331 | 125.38 |
| 686 | GGCGCGGACACCTCGACCCGG | 5665 | GADTSTR | 7332 | 125.369 |
| 687 | GGGTTCGGGCACGTGCCCGAA | 5666 | GFGHVPE | 7333 | 125.324 |
| 688 | AACGTTATGCACTCTTCCTCC | 5667 | NVMHSSS | 7334 | 125.313 |
| 689 | TCTGCGTCGAAAGTGGAATAC | 5668 | SASKVEY | 7335 | 125.2945 |
| 690 | ATTTCGAGTTATGATGGTAAT | 5669 | ISSYDGN | 7336 | 125.273 |
| 691 | AAAAAAACGAAAACACTAACT | 5670 | KKTKTLT | 7337 | 125.26 |
| 692 | GGTACCATATTACCAAACCAA | 5671 | GTILPNQ | 7338 | 125.236 |
| 693 | TTAAACGTCGTACCAACACAA | 5672 | LNVVPTQ | 7339 | 125.09 |
| 694 | AGTAGTGTTACTTCGAGGGAG | 5673 | SSVTSRE | 7340 | 124.987 |
| 695 | CCCATCAACGTACTCACGACA | 5674 | PINVLTT | 7341 | 124.911 |
| 696 | GGGGATAAGGCGAGTTTGGCG | 5675 | GDKASLA | 7342 | 124.8255 |
| 697 | AGGATGTCGGAGAGTTCTGAT | 5676 | RMSESSD | 7343 | 124.5625 |
| 698 | AATCTTTTGACTTCGTCGCCT | 5677 | NLLTSSP | 7344 | 124.54 |
| 699 | TCGCGGCTATCACAAGACCCC | 5678 | SRLSQDP | 7345 | 124.3495 |
| 700 | TGGTCGAATGCTCAGAGTCCG | 5679 | WSNAQSP | 7346 | 124.231 |
| 701 | GGCAGACACCTTCAATCGGAC | 5680 | GRHLQSD | 7347 | 124.19 |
| 702 | ATGAGTCTCGCCTCCACCCAA | 5681 | MSLASTQ | 7348 | 124.092 |
| 703 | ATGAGTACGGTTCTTCGCGAG | 5682 | MSTVLRE | 7349 | 124.05 |
| 704 | TCTAAATCTGAAAACCTGCAA | 5683 | SKSENLQ | 7350 | 124.043 |
| 705 | TGGACGGAAGGGGGCTCAGGA | 5684 | WTEGGSG | 7351 | 124 |
| 706 | TCGACTACGGTTTGGACTGCT | 5685 | STTVWTA | 7352 | 123.99 |
| 707 | GTTAGTTTGGAGAGTCGGTTG | 5686 | VSLESRL | 7353 | 123.799 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 708 | TCTATGTATGGGCAGGCTGGG | 5687 | SMYGQAG | 7354 | 123.777 |
| 709 | ACTAATACGCAGAATAATCCG | 5688 | TNTQNNP | 7355 | 123.702 |
| 710 | GTCGGTGACAGGAACTTGGTC | 5689 | VGDRNLV | 7356 | 123.663 |
| 711 | CTCGCCCACAACTACTTAAGC | 5690 | LAHNYLS | 7357 | 123.6175 |
| 712 | TGGACAGCTAACCAAGGCTTA | 5691 | WTANQGL | 7358 | 123.566 |
| 713 | GTCTTCCGGGAAGGCATCGTG | 5692 | VFREGIV | 7359 | 123.54 |
| 714 | CAGGTGCAGCATGAGAGGGTG | 5693 | QVQHERV | 7360 | 123.5 |
| 715 | CAAATATTAAACTACTCAGTC | 5694 | QILNYSV | 7361 | 123.4 |
| 716 | AGTACGATTGGTAATTCTACT | 5695 | STIGNST | 7362 | 123.3029 |
| 717 | CCTATACACCACGGTTCATCC | 5696 | PIHHGSS | 7363 | 123.09 |
| 718 | ATTGCTACTAATGTGATTTAT | 5697 | IATNVIY | 7364 | 123.055 |
| 719 | CAAGGCGGTACAAACAACCCC | 5698 | QGGTNNP | 7365 | 123.037 |
| 720 | ACCCGTGGCAACGACATATCA | 5699 | TRGNDIS | 7366 | 123.023 |
| 721 | CAAACGCTCATAGTGGGGTCC | 5700 | QTLIVGS | 7367 | 123.007 |
| 722 | CGGGGTCTGCCTGATGTTAAT | 5701 | RGLPDVN | 7368 | 122.952 |
| 723 | CTTAATGTGAATACGCTTAAT | 5702 | LNVNTLN | 7369 | 122.896 |
| 724 | GGGACAAAAAGCTGGCCTGTC | 5703 | GTKSWPV | 7370 | 122.8432 |
| 725 | ACGCATCTTGTGAGTGATTCG | 5704 | THLVSDS | 7371 | 122.78 |
| 726 | TGGACGGGCGCACAACCTTCT | 5705 | WTGAQPS | 7372 | 122.73955 |
| 727 | TCTGCGATGCACACATTAGTC | 5706 | SAMHTLV | 7373 | 122.5735 |
| 728 | TCCCAACACCACACGCCACTG | 5707 | SQHHTPL | 7374 | 122.4691 |
| 729 | GATAATCGGATGGAGGCTACG | 5708 | DNRMEAT | 7375 | 122.416 |
| 730 | TTGGGAGGAACCCTGGGAATA | 5709 | LGGTLGI | 7376 | 122.38 |
| 731 | TTTCATAATGAGTCTTATGGG | 5710 | FHNESYG | 7377 | 122.36 |
| 732 | ATTCGGACTTCTGTGATTAAT | 5711 | IRTSVIN | 7378 | 122.333 |
| 733 | TATAATACTGTTGATCAGCGG | 5712 | YNTVDQR | 7379 | 122.2905 |
| 734 | GCGCACCAAACCGCCGGGCCA | 5713 | AHQTAGP | 7380 | 122.22 |
| 735 | CCTCCGGAAAGTGCCAGGGGC | 5714 | PPESARG | 7381 | 122.2044 |
| 736 | AATAATACTTTGAATATTTTG | 5715 | NNTLNIL | 7382 | 122.18 |
| 737 | GCTAGTTATAGTAGTATGGTG | 5716 | ASYSSMV | 7383 | 122.0975 |
| 738 | TCGGGTCAAAACGGTACATCA | 5717 | SGQNGTS | 7384 | 122.017 |
| 739 | TTGTCTAGTATGAGTACGGAT | 5718 | LSSMSTD | 7385 | 121.935 |
| 740 | GTCGCCTCGATGGTACACAAC | 5719 | VASMVHN | 7386 | 121.8215 |
| 741 | ACGCAATTGTCAGACGGCTGC | 5720 | TQLSDGC | 7387 | 121.81 |
| 742 | GCGATTGTGGATAGGGGGAGT | 5721 | AIVDRGS | 7388 | 121.757 |
| 743 | AACCGTCAAAGGGACTTCGAA | 5722 | NRQRDFE | 7389 | 121.734 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 744 | GCACACCAAAAAGACATACGC | 5723 | AHQKDIR | 7390 | 121.7 |
| 745 | TTCACCGAACGCGCACTCCAA | 5724 | FTERALQ | 7391 | 121.6915 |
| 746 | ATGCTGTCTCATGGTGCGCTT | 5725 | MLSHGAL | 7392 | 121.682 |
| 747 | TCCGTAACCAACGGAGCGGAA | 5726 | SVTNGAE | 7393 | 121.549 |
| 748 | ATCACCGCCGCGTCACCGCAA | 5727 | ITAASPQ | 7394 | 121.5325 |
| 749 | CAAAACACGCAACGATACTTG | 5728 | QNTQRYL | 7395 | 121.5036 |
| 750 | ACTGGCCAAGGATTCTCGGCA | 5729 | TGQGFSA | 7396 | 121.45 |
| 751 | AGTTTTGAGAAGAATGGTATT | 5730 | SFEKNGI | 7397 | 121.45 |
| 752 | CTCACGTCCCACTCTGCGGGC | 5731 | LTSHSAG | 7398 | 121.378 |
| 753 | TCTACAATCGGCAACAGCACG | 5732 | STIGNST | 7399 | 121.27 |
| 754 | GGTCTTAGTCGGAATGATGGT | 5733 | GLSRNDG | 7400 | 121.2415 |
| 755 | TCGACGACGCACCCTTCCGAA | 5734 | STTHPSE | 7401 | 121.238 |
| 756 | CCAAGTACGAACGAAAGCCGC | 5735 | PSTNESR | 7402 | 121.099 |
| 757 | GGTACGAAGGATATTCTGATT | 5736 | GTKDILI | 7403 | 121.039 |
| 758 | TCTACTATTAATATGCGTGCG | 5737 | STINMRA | 7404 | 120.929 |
| 759 | TATATTGCTGGGGGGGAGCAG | 5738 | YIAGGEQ | 7405 | 120.9 |
| 760 | TCCAGCGGCCAACCGCTCGTC | 5739 | SSGQPLV | 7406 | 120.7415 |
| 761 | GACAAACAACAAACCGGACAA | 5740 | DKQQTGQ | 7407 | 120.6775 |
| 762 | GGGCTAGGACAACCCCAACTC | 5741 | GLGQPQL | 7408 | 120.644 |
| 763 | AGTCCGCAGCATGGTGTTATT | 5742 | SPQHGVI | 7409 | 120.6145 |
| 764 | TATAGGGGTAGGGAGGATTGG | 5743 | YRGREDW | 7410 | 120.58 |
| 765 | GCGGGGGGTTTGCTGTCGCGG | 5744 | AGGLLSR | 7411 | 120.552 |
| 766 | CCGATACAACAAGCCTCATTG | 5745 | PIQQASL | 7412 | 120.375 |
| 767 | TGGAGCGCCGGCGAACGGGTG | 5746 | WSAGERV | 7413 | 120.3415 |
| 768 | AGGGGTGATGTTGCTACGACG | 5747 | RGDVATT | 7414 | 120.26 |
| 769 | TTAACGGGACAAAACGAATTC | 5748 | LTGQNEF | 7415 | 120.24 |
| 770 | ACGACGCCGCCTTTTTCTAAT | 5749 | TTPPFSN | 7416 | 120.2205 |
| 771 | ACGAGTATTGGTAGTGCTAAG | 5750 | TSIGSAK | 7417 | 120.195 |
| 772 | AATGTGCAGAATGTGCCTGGG | 5751 | NVQNVPG | 7418 | 120.16215 |
| 773 | TATACGGGTACTCTTGTTGTT | 5752 | YTGTLVV | 7419 | 120.047 |
| 774 | GGAACCCACGCCTCAGCATAC | 5753 | GTHASAY | 7420 | 119.959 |
| 775 | CTGGTTGTTTCGAATAGTCTG | 5754 | LVVSNSL | 7421 | 119.934 |
| 776 | ACGCATCTTGTGAGGGATTCG | 5755 | THLVRDS | 7422 | 119.7893 |
| 777 | AATCATGGTCGTGCTATTGAT | 5756 | NHGRAID | 7423 | 119.776 |
| 778 | CCCAAAACTCTAACTTCGACA | 5757 | PKTLTST | 7424 | 119.754 |
| 779 | TTCGGTATAGGGCACGGAACA | 5758 | FGIGHGT | 7425 | 119.734 |
| 780 | GCGCTTCCGTCTCGTGAGCGG | 5759 | ALPSRER | 7426 | 119.7235 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 781 | GCGACTAGGGGTGAGTCGTCT | 5760 | ATRGESS | 7427 | 119.715 |
| 782 | GGGACAACCGAAGTTAACAAA | 5761 | GTTEVNK | 7428 | 119.685 |
| 783 | ACCCACACCCTTGGGGGAACA | 5762 | THTLGGT | 7429 | 119.68 |
| 784 | GAAGCAGTAACAAGTAAATGG | 5763 | EAVTSKW | 7430 | 119.6575 |
| 785 | CACTACGGTAACAAAGACATA | 5764 | HYGNKDI | 7431 | 119.643 |
| 786 | ATTTCTACGCATACGATGACG | 5765 | ISTHTMT | 7432 | 119.64 |
| 787 | GATACGTATAATAGTAATACT | 5766 | DTYNSNT | 7433 | 119.6 |
| 788 | GTTTTTACTGGGCAGACGGAG | 5767 | VFTGQTE | 7434 | 119.544 |
| 789 | TCGGTCACCAGTGGAACACAA | 5768 | SVTSGTQ | 7435 | 119.502 |
| 790 | CATACGTATTCGCAGGCTGAT | 5769 | HTYSQAD | 7436 | 119.47455 |
| 791 | GTAGCGGGCTTAGTCGACATA | 5770 | VAGLVDI | 7437 | 119.41 |
| 792 | GACTCTACCAAAGCCATGCAA | 5771 | DSTKAMQ | 7438 | 119.403 |
| 793 | GAGGGGCATAATCGTGGTATT | 5772 | EGHNRGI | 7439 | 119.354 |
| 794 | GGGTTGCATGGGACGAGTAAT | 5773 | GLHGTSN | 7440 | 119.343 |
| 795 | CCGCTTTCTCTTCATAATAGT | 5774 | PLSLHNS | 7441 | 119.312 |
| 796 | GCGAGTGATAAGGGGGCGAAT | 5775 | ASDKGAN | 7442 | 119.249 |
| 797 | GTGCTGTTGCAGAATTCTCAT | 5776 | VLLQNSH | 7443 | 119.2225 |
| 798 | CTATACGACGGAAAACACGTC | 5777 | LYDGKHV | 7444 | 119.20995 |
| 799 | ACCCAAGGATCTAACACCACA | 5778 | TQGSNTT | 7445 | 119.08 |
| 800 | TTCCTCGACAAATACAACTAC | 5779 | FLDKYNY | 7446 | 119.058 |
| 801 | GACACCGGAATCAAAAACGTT | 5780 | DTGIKNV | 7447 | 119.05 |
| 802 | TCCGGAGCGGCACAAAACCCA | 5781 | SGAAQNP | 7448 | 119.019 |
| 803 | ACCCTCCACACCAAAGACCTA | 5782 | TLHTKDL | 7449 | 118.854 |
| 804 | GCTACTTACGTTGTCGGAACA | 5783 | ATYVVGT | 7450 | 118.84 |
| 805 | CTTGTGGGGACTTTGGTGTAT | 5784 | LVGTLVY | 7451 | 118.809 |
| 806 | TCTAATACGACTGTGCAGCTT | 5785 | SNTTVQL | 7452 | 118.76 |
| 807 | AAGGCTCAGATTAATCAGATG | 5786 | KAQINQM | 7453 | 118.727 |
| 808 | CGGAATGCTACTGTGACTGTT | 5787 | RNATVTV | 7454 | 118.655 |
| 809 | GCAACCAGAGTGGGCAACCAC | 5788 | ATRVGNH | 7455 | 118.599 |
| 810 | AGTTATCAGAATCCTCCGCCT | 5789 | SYQNPPP | 7456 | 118.512 |
| 811 | TTTGATAGTTATAATATTGTG | 5790 | FDSYNIV | 7457 | 118.51 |
| 812 | GCTACTCTTTCTCCGCATGCT | 5791 | ATLSPHA | 7458 | 118.497 |
| 813 | TGGGAGAGTCCGACTAATGCG | 5792 | WESPTNA | 7459 | 118.49 |
| 814 | ATCGAAAACGTAAACCACTTG | 5793 | IENVNHL | 7460 | 118.42 |
| 815 | TATCGGGCTTCGGATGTGGCG | 5794 | YRASDVA | 7461 | 118.372 |
| 816 | CATATGTCTTCTGTTGCGACT | 5795 | HMSSVAT | 7462 | 118.34 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 817 | ATCCAAAGAGACGTGGGCCAC | 5796 | IQRDVGH | 7463 | 118.2825 |
| 818 | GAGAGTGTTAGGGAGACTATT | 5797 | ESVRETI | 7464 | 118.25 |
| 819 | CAGGGGGGGAATAGTCGGTTT | 5798 | QGGNSRF | 7465 | 118.236 |
| 820 | GAAAAAGGCACACCAAGTAGC | 5799 | EKGTPSS | 7466 | 118.233 |
| 821 | CACGACAGCACAACCCGCCCA | 5800 | HDSTTRP | 7467 | 118.225 |
| 822 | TTACCAACAGGCGTCCTGCCC | 5801 | LPTGVLP | 7468 | 118.2065 |
| 823 | ACCCTAGGCTACCCAGACAAA | 5802 | TLGYPDK | 7469 | 118.1855 |
| 824 | GCTAACACCGTCACAGAACGA | 5803 | ANTVTER | 7470 | 118.17415 |
| 825 | CACGACAAATCTATCCAACCA | 5804 | HDKSIQP | 7471 | 118.16 |
| 826 | GGAGGAACAGCCCTTGGGAGC | 5805 | GGTALGS | 7472 | 118.123 |
| 827 | GGGGGTAACTACCACACCACT | 5806 | GGNYHTT | 7473 | 118.046 |
| 828 | ATCTCAGAAATGACTAGGTAC | 5807 | ISEMTRY | 7474 | 118.041 |
| 829 | GTTGAATCTAAATCCGAACCA | 5808 | VESKSEP | 7475 | 118.026 |
| 830 | GACCGTGCCCAAAACAACGAA | 5809 | DRAQNNE | 7476 | 118.006 |
| 831 | ACGGCGCAGACCGGCTGGGTT | 5810 | TAQTGWV | 7477 | 117.96 |
| 832 | GGGTTCGGGCACCTGCCCGAA | 5811 | GFGHLPE | 7478 | 117.86 |
| 833 | CCTATTACGGGTTTTAGTGTT | 5812 | PITGFSV | 7479 | 117.828 |
| 834 | GATAGGACGTATTCGAATACG | 5813 | DRTYSNT | 7480 | 117.7875 |
| 835 | ATGTCAAACGCCTCCTACATA | 5814 | MSNASYI | 7481 | 117.743 |
| 836 | GATAATAGTAGGCCTGAGGTG | 5815 | DNSRPEV | 7482 | 117.658 |
| 837 | TCAAGTTCCCAAACGGTTTTG | 5816 | SSSQTVL | 7483 | 117.655 |
| 838 | AGTAATCTTGATGGTACTATT | 5817 | SNLDGTI | 7484 | 117.643 |
| 839 | AGTAATATGCGTGAGGAGATT | 5818 | SNMREEI | 7485 | 117.629 |
| 840 | AGACTTACAGAACTGGTCATA | 5819 | RLTELVI | 7486 | 117.583 |
| 841 | CAGGTTAGTCTGGTGAAGTTG | 5820 | QVSLVKL | 7487 | 117.558 |
| 842 | GAAATACACACGACCACAGGC | 5821 | EIHTTTG | 7488 | 117.5505 |
| 843 | AGCAGGATAGAAAACAACAAC | 5822 | SRIENNN | 7489 | 117.5425 |
| 844 | GGAACAGGCAAAGAAGTTCGA | 5823 | GTGKEVR | 7490 | 117.521 |
| 845 | TGGCAGGATCATAATAAGGTG | 5824 | WQDHNKV | 7491 | 117.476 |
| 846 | TCGACAAACTCTATAGGCGCC | 5825 | STNSIGA | 7492 | 117.414 |
| 847 | TCCGAATTAATGGTCAGACCC | 5826 | SELMVRP | 7493 | 117.3623 |
| 848 | CCGCTTCAGAATAATAAGACG | 5827 | PLQNNKT | 7494 | 117.2175 |
| 849 | CCTTATGCGAATAGGCTTGAG | 5828 | PYANRLE | 7495 | 117.21145 |
| 850 | GGGACGGTTTCGCTTATTCCT | 5829 | GTVSLIP | 7496 | 117.175 |
| 851 | GATGTTTATCTTAAGAGTCCG | 5830 | DVYLKSP | 7497 | 117.1435 |
| 852 | TTGCCGGATAAGGGGCGGATT | 5831 | LPDKGRI | 7498 | 117.116 |
| 853 | TCGATAACGACCGTAGCGAAC | 5832 | SITTVAN | 7499 | 117.112 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 854 | CCGCTTCAATCCCAATCGGGA | 5833 | PLQSQSG | 7500 | 117.1045 |
| 855 | AATAATATGGGTCATGGTCAT | 5834 | NNMGHGH | 7501 | 117.0365 |
| 856 | AGCGGACAAAAAAACTCAGAA | 5835 | SGQKNSE | 7502 | 116.9665 |
| 857 | ACCGAAGCGGGCCGCCCCCAA | 5836 | TEAGRPQ | 7503 | 116.907 |
| 858 | ACCTTACACACGAAAGACTTG | 5837 | TLHTKDL | 7504 | 116.879 |
| 859 | CTTCGAGACCTAAACGGAGGA | 5838 | LRDLNGG | 7505 | 116.8691 |
| 860 | GTTTGTGTTACTACTTGTGCT | 5839 | VCVTTCA | 7506 | 116.861 |
| 861 | GTCACAGCTGCTCAACCCCAA | 5840 | VTAAQPQ | 7507 | 116.79 |
| 862 | GCGACTTTTAGTCATGCTGGT | 5841 | ATFSHAG | 7508 | 116.788 |
| 863 | ACTTATGCGCCTAGGTCGCCT | 5842 | TYAPRSP | 7509 | 116.75715 |
| 864 | ACGTCGGAGATGCGTACTGCT | 5843 | TSEMRTA | 7510 | 116.5885 |
| 865 | TACTCGACAACCATGCTTAAC | 5844 | YSTTMLN | 7511 | 116.584 |
| 866 | TCTTTCACGAACACAAACCCA | 5845 | SFTNTNP | 7512 | 116.5665 |
| 867 | AGTCCTCCTAGTACGTCGGGT | 5846 | SPPSTSG | 7513 | 116.551 |
| 868 | GTGACGACTGTTGATAGTGCT | 5847 | VTTVDSA | 7514 | 116.477 |
| 869 | GAGGCGCATAATCGTGTTATT | 5848 | EAHNRVI | 7515 | 116.461 |
| 870 | ATGGAGTTGACTTCTACTAGT | 5849 | MELTSTS | 7516 | 116.456 |
| 871 | CATTTGGTTACTAGTGGTATT | 5850 | HLVTSGI | 7517 | 116.45 |
| 872 | CAAACCATCACCTCACAAATG | 5851 | QTITSQM | 7518 | 116.431 |
| 873 | ACTGCGAATAGTACGTATGTG | 5852 | TANSTYV | 7519 | 116.329 |
| 874 | CTTATCCAATTATCGGGTCAA | 5853 | LIQLSGQ | 7520 | 116.317 |
| 875 | TCTTACGTTAGCGTCCCCGCC | 5854 | SYVSVPA | 7521 | 116.3005 |
| 876 | GTGCATGGGAATGCTCCGGCT | 5855 | VHGNAPA | 7522 | 116.2665 |
| 877 | GCCGGAAAAACCCACGCCGAC | 5856 | AGKTHAD | 7523 | 116.228 |
| 878 | ACATTCCACCAAGGGGTCAAA | 5857 | TFHQGVK | 7524 | 116.175 |
| 879 | TTAGGAAACAACCGGCCACTA | 5858 | LGNNRPL | 7525 | 116.17 |
| 880 | CTGCACCTCGTCCGGAGCTTC | 5859 | LHLVRSF | 7526 | 116.08 |
| 881 | TCCTACAGTACTTCAACACCG | 5860 | SYSTSTP | 7527 | 116.036 |
| 882 | ATATCGCAAGGCTCGAGCCTC | 5861 | ISQGSSL | 7528 | 116.025 |
| 883 | CTCCAACTGGCTACATCCCAC | 5862 | LQLATSH | 7529 | 116.0035 |
| 884 | GTGACTCAGCGGTTTGCTGAG | 5863 | VTQRFAE | 7530 | 115.952 |
| 885 | GCTATAGACTCCATCAAAATG | 5864 | AIDSIKM | 7531 | 115.9415 |
| 886 | GACGCACACACTTTCAGCCGG | 5865 | DAHTFSR | 7532 | 115.93 |
| 887 | CGTGGTTCAGACGGAGGATTG | 5866 | RGSDGGL | 7533 | 115.911 |
| 888 | TTAGCACAAGGCACGGACCGG | 5867 | LAQGTDR | 7534 | 115.884 |
| 889 | AAAAACAACAACTCAGACAGT | 5868 | KNNNSDS | 7535 | 115.7595 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 890 | GAAAACGAAAAACGAGAAAGC | 5869 | ENEKRES | 7536 | 115.741 |
| 891 | AACGAACAATTCGAAAAAGTC | 5870 | NEQFEKV | 7537 | 115.705 |
| 892 | ACACAAGTAGTCGCAAGAACA | 5871 | TQVVART | 7538 | 115.68045 |
| 893 | GGAGTAAACGTCACCAACAGC | 5872 | GVNVTNS | 7539 | 115.64 |
| 894 | GCCGACAAAGGATTCGGCCAC | 5873 | ADKGFGH | 7540 | 115.5886 |
| 895 | ACTCATAAGCAGGTGGATCTT | 5874 | THKQVDL | 7541 | 115.54825 |
| 896 | TCGGCTAACTTATACAAACAA | 5875 | SANLYKQ | 7542 | 115.544 |
| 897 | AAGCTGCATACTAAGGATCTT | 5876 | KLHTKDL | 7543 | 115.54 |
| 898 | GTGGTGGTTCACACTATCCCA | 5877 | VVVHTIP | 7544 | 115.52 |
| 899 | TCTACGTCTCAGGCTGTGCAG | 5878 | STSQAVQ | 7545 | 115.496 |
| 900 | CGTAACGGCTCCGCCCAAAGC | 5879 | RNGSAQS | 7546 | 115.465 |
| 901 | CATTATGGGAATAAGGATATT | 5880 | HYGNKDI | 7547 | 115.402 |
| 902 | AGCTTCTTGGTAGCCCACCCA | 5881 | SFLVAHP | 7548 | 115.4 |
| 903 | CAGCAGAATACGAGTTTGCCG | 5882 | QQNTSLP | 7549 | 115.39 |
| 904 | ATGCACGTCGACAAAACGAGT | 5883 | MHVDKTS | 7550 | 115.379 |
| 905 | AATAATGAGAATACGCGTAAT | 5884 | NNENTRN | 7551 | 115.363 |
| 906 | TCGATAAACAACATAGGCGCA | 5885 | SINNIGA | 7552 | 115.3425 |
| 907 | GCTACTATATCGGACCGAGCC | 5886 | ATISDRA | 7553 | 115.327 |
| 908 | TACTCAAACCTCGTACTTTCC | 5887 | YSNLVLS | 7554 | 115.285 |
| 909 | ATGATGAATGTGAGTGGTCAT | 5888 | MMNVSGH | 7555 | 115.2555 |
| 910 | GGGGAGACGCGGTCGACTGCT | 5889 | GETRSTA | 7556 | 115.18 |
| 911 | ACGAAGGGTTATAATGATCTT | 5890 | TKGYNDL | 7557 | 115.1635 |
| 912 | GCGTATAATATGTCGTCTGTT | 5891 | AYNMSSV | 7558 | 115.148 |
| 913 | GCAGACCCCGCTAAAGGCAAA | 5892 | ADPAKGK | 7559 | 115.1435 |
| 914 | TATATTTCGGCGCCTCCGATG | 5893 | YISAPPM | 7560 | 115.1145 |
| 915 | CGAAACAACCCATCGCACGAC | 5894 | RNNPSHD | 7561 | 115.069 |
| 916 | GGAACCTCCATAGACTACGTA | 5895 | GTSIDYV | 7562 | 115.053 |
| 917 | GGCACCGGGTACCCAAACCAA | 5896 | GTGYPNQ | 7563 | 115.038 |
| 918 | GATCATATGAATTTGAGGTCT | 5897 | DHMNLRS | 7564 | 114.9475 |
| 919 | ATTAATTCGTATTTGCATGAG | 5898 | INSYLHE | 7565 | 114.887 |
| 920 | TGGCAAATGGGGGCCGGGAGC | 5899 | WQMGAGS | 7566 | 114.833 |
| 921 | ATGGGTATCGGGTCATACAAA | 5900 | MGIGSYK | 7567 | 114.827 |
| 922 | CAAAACCACAACGAACTAAAA | 5901 | QNHNELK | 7568 | 114.749 |
| 923 | GATAAGTCTAATTATAGTATT | 5902 | DKSNYSI | 7569 | 114.736 |
| 924 | ACAACGAAACCGGTCGCGGAA | 5903 | TTKPVAE | 7570 | 114.7315 |
| 925 | GTGACTGTGAGTAATAGTCTG | 5904 | VTVSNSL | 7571 | 114.685 |
| 926 | ACGGCGTATCTGGATGGTCTG | 5905 | TAYLDGL | 7572 | 114.665 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 927 | AATTTGCAGACTGGTGTTCAG | 5906 | NLQTGVQ | 7573 | 114.65 |
| 928 | ACCGTCGCTCCCTACAGTAGC | 5907 | TVAPYSS | 7574 | 114.65 |
| 929 | GTTCAGATTTCTATGAATAAT | 5908 | VQISMNN | 7575 | 114.617 |
| 930 | TACATAGCAGGTGGTGAACAA | 5909 | YIAGGEQ | 7576 | 114.60015 |
| 931 | TTCATGGAAGTCATGAAAAAC | 5910 | FMEVMKN | 7577 | 114.547 |
| 932 | ACGACTGATAAGGGTATTAAT | 5911 | TTDKGIN | 7578 | 114.539 |
| 933 | TTGAGCTACAGCATCCAACAC | 5912 | LSYSIQH | 7579 | 114.53 |
| 934 | GCTTATAATGCTCGTCTGCCT | 5913 | AYNARLP | 7580 | 114.49305 |
| 935 | AACACCGGCACCACGAGTGTC | 5914 | NTGTTSV | 7581 | 114.475 |
| 936 | GTGCTGAGTACGGGGCTGCGG | 5915 | VLSTGLR | 7582 | 114.4165 |
| 937 | AACGACTCCTCGTCAATGTCC | 5916 | NDSSSMS | 7583 | 114.397 |
| 938 | CGCCAAGGCAGCTTGATGATA | 5917 | RQGSLMI | 7584 | 114.37 |
| 939 | ATCAGCACCGCATACATGTTG | 5918 | ISTAYML | 7585 | 114.36 |
| 940 | GGTACTATGAATATTGGTATT | 5919 | GTMNIGI | 7586 | 114.356 |
| 941 | CATAATAATAATTTGCTGAAT | 5920 | HNNNLLN | 7587 | 114.292 |
| 942 | CATTTTTCGCAGATTACTAAT | 5921 | HFSQITN | 7588 | 114.278 |
| 943 | GACCTGACCAGAGCTGCAATA | 5922 | DLTRAAI | 7589 | 114.256 |
| 944 | GTCGCTATGGGAGGCGGTCCC | 5923 | VAMGGGP | 7590 | 114.1845 |
| 945 | GCCTACGGTATCAGAGAAGTG | 5924 | AYGIREV | 7591 | 114.1465 |
| 946 | ACATCAGACGGTCTACTAAGT | 5925 | TSDGLLS | 7592 | 114.128 |
| 947 | ACGATGGCTACAAACTTAAGT | 5926 | TMATNLS | 7593 | 114.082 |
| 948 | AACAACGGCAACTCATCAAGG | 5927 | NNGNSSR | 7594 | 114.047 |
| 949 | ACGGAGAAGGCGAGTCCTCTG | 5928 | TEKASPL | 7595 | 114.031 |
| 950 | CTCAACCACACAATGCCCCTC | 5929 | LNHTMPL | 7596 | 114.027 |
| 951 | GATACGGCGAGTTATAATAAT | 5930 | DTASYNN | 7597 | 114 |
| 952 | AACATGACCAACGAACGGCTC | 5931 | NMTNERL | 7598 | 113.9675 |
| 953 | GTAGTCTCATCGGGCGGCTGG | 5932 | VVSSGGW | 7599 | 113.966 |
| 954 | GTGAATCAGAGTCCTGGGGCT | 5933 | VNQSPGA | 7600 | 113.85 |
| 955 | GATCATCATCCTCAGAGTCGT | 5934 | DHRPQSR | 7601 | 113.83 |
| 956 | CGATGGCAAGGACTGAGCGCG | 5935 | RWQGLSA | 7602 | 113.76 |
| 957 | GCGGTTACGACAAGCGTGAGG | 5936 | AVTTSVR | 7603 | 113.752 |
| 958 | TGGGGAGTCAGTAACTCAGCA | 5937 | WGVSNSA | 7604 | 113.7505 |
| 959 | GCGCATATGCATTCGGAGTTG | 5938 | AHMHSEL | 7605 | 113.74 |
| 960 | AATAATCTTACGAATTCGACG | 5939 | NNLTNST | 7606 | 113.736 |
| 961 | AGTAGTGGGGGTATGAAGGCG | 5940 | SSGGMKA | 7607 | 113.69 |
| 962 | GTTGGGTATGGGGAGCATGTT | 5941 | VGYGEHV | 7608 | 113.64 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 963 | ACCATAGTGTCCACTTCTTAC | 5942 | TIVSTSY | 7609 | 113.628 |
| 964 | CCCACCAGTCACCAAGAACCC | 5943 | PTSHQEP | 7610 | 113.62 |
| 965 | TCTAACCTTCGAAACACAATA | 5944 | SNLRNTI | 7611 | 113.58 |
| 966 | TCAAGACACGACGTCCGAAAC | 5945 | SRHDVRN | 7612 | 113.559 |
| 967 | CAGATGAATATTCATGATAAG | 5946 | QMNIHDK | 7613 | 113.543 |
| 968 | TGGGCTATGAATAATGTGCCG | 5947 | WAMNNVP | 7614 | 113.531 |
| 969 | GCGATGGATGGGTATAGGGTT | 5948 | AMDGYRV | 7615 | 113.462 |
| 970 | AAAGGGGGAAACCTCACCGCA | 5949 | KGGNLTA | 7616 | 113.4525 |
| 971 | ATTGGTAAGGATAGTGTTCCG | 5950 | IGKDSVP | 7617 | 113.448 |
| 972 | GTGCAGTTGACGCATAATGGG | 5951 | VQLTHNG | 7618 | 113.43 |
| 973 | GGCCTGAACCAGATCACATCG | 5952 | GLNQITS | 7619 | 113.4 |
| 974 | AGGGGTGATCCTTCTACGCCT | 5953 | RGDPSTP | 7620 | 113.4 |
| 975 | GTTCCCTCCGACCCCCACTGG | 5954 | VPSDPHW | 7621 | 113.35 |
| 976 | ACGTTAAGTTCCCAAGTCACA | 5955 | TLSSQVT | 7622 | 113.327 |
| 977 | AACCAAAGAGTTGAACAAAAA | 5956 | NQRVEQK | 7623 | 113.3075 |
| 978 | GTACTTCCAAGTCGGATCGCG | 5957 | VLPSRIA | 7624 | 113.3 |
| 979 | GGGCACTACGCTACAAACACA | 5958 | GHYATNT | 7625 | 113.212 |
| 980 | CCTTCGATTCCGTCGTTTTCG | 5959 | PSIPSFS | 7626 | 113.207 |
| 981 | ACTTATGAGTATCCGACTCGG | 5960 | TYEYPTR | 7627 | 113.19 |
| 982 | AAAGACCACATCCTCAGCCTC | 5961 | KDHILSL | 7628 | 113.1795 |
| 983 | GGCACAGGAGGTAACCGAGAA | 5962 | GTGGNRE | 7629 | 113.173 |
| 984 | AAGGGGGATGGTGCTTATGAG | 5963 | KGDGAYE | 7630 | 113.162 |
| 985 | TCTTCTTTCGGAAAAGACAAC | 5964 | SSFGKDN | 7631 | 113.1603 |
| 986 | ACAGTATCGTCATACGTACAA | 5965 | TVSSYVQ | 7632 | 113.0595 |
| 987 | AGGGCTCATGGGGATAATCAG | 5966 | RAHGDNQ | 7633 | 113.036 |
| 988 | TATCATGCTCATAGTAATGAG | 5967 | YHAHSNE | 7634 | 113.03 |
| 989 | GCAAACTTGCCCAGCGGTCAC | 5968 | ANLPSGH | 7635 | 113.03 |
| 990 | GCGAACCTCAACTTGACCAGT | 5969 | ANLNLTS | 7636 | 113.015 |
| 991 | AGGCTTAATGCGGGTGAGCAT | 5970 | RLNAGEH | 7637 | 113.0105 |
| 992 | TATGTTGATTATAGTAAGTCG | 5971 | YVDYSKS | 7638 | 112.9935 |
| 993 | GCTAATTCTGGGTTGCATAAT | 5972 | ANSGLHN | 7639 | 112.9695 |
| 994 | ACGAGTGGTGTGCTTACGCGG | 5973 | TSGVLTR | 7640 | 112.9485 |
| 995 | GGAAAACCAGCACAAGAATTC | 5974 | GKPAQEF | 7641 | 112.933 |
| 996 | GTGGGGACGCATTTGCATTCG | 5975 | VGTHLHS | 7642 | 112.918 |
| 997 | CCGATGAACAAAGACATACTG | 5976 | PMNKDIL | 7643 | 112.9116 |
| 998 | GACGCCCACCACTCAAGCAGC | 5977 | DAHHSSS | 7644 | 112.88 |
| 999 | ACTAACGCCATCTCTCAAACG | 5978 | TNAISQT | 7645 | 112.7997 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1000 | GTTTTGTCTGATAAGGCGTAT | 5979 | VLSDKAY | 7646 | 112.787 |
| 1001 | AACCTACTTGTCGACCAACGT | 5980 | NLLVDQR | 7647 | 112.78 |
| 1002 | ACTGGTCATCCGCCGGCGGCG | 5981 | TGHPPAA | 7648 | 112.7735 |
| 1003 | ATTAGTTCGGGGATTTTGTCG | 5982 | ISSGILS | 7649 | 112.7205 |
| 1004 | AATACGAATTTGTTGGGTTAT | 5983 | NTNLLGY | 7650 | 112.72 |
| 1005 | ACGCTATCGGTTACCCTGGGT | 5984 | TLSVTLG | 7651 | 112.71 |
| 1006 | CATACTGGTGTTCAGACTAAT | 5985 | HTGVQTN | 7652 | 112.704 |
| 1007 | GAGGTTAGTAATAATAATTAT | 5986 | EVSNNNY | 7653 | 112.69 |
| 1008 | CTGGCTAATATTTCGCTGTAT | 5987 | LANISLY | 7654 | 112.69 |
| 1009 | GTGGAGCATGTTGCTCATCAG | 5988 | VEHVAHQ | 7655 | 112.656 |
| 1010 | GTCGACAAAAGCGAAGCCGAC | 5989 | VDKSEAD | 7656 | 112.6 |
| 1011 | GGCTTCGCATTAACTGGCACC | 5990 | GFALTGT | 7657 | 112.564 |
| 1012 | TTGTTGACGGCTCCGCATAGG | 5991 | LLTAPHR | 7658 | 112.53 |
| 1013 | AATGCGGGGGCTCTTATGGGT | 5992 | NAGALMG | 7659 | 112.518 |
| 1014 | AGGACGCAAGCAGGGGACTCA | 5993 | RTQAGDS | 7660 | 112.483 |
| 1015 | AACACACACAGACAAGAATAC | 5994 | NTHRQEY | 7661 | 112.461 |
| 1016 | AACATAGCAGGCGGAGAACAA | 5995 | NIAGGEQ | 7662 | 112.442 |
| 1017 | GAGATTAATAATCGGACTGGT | 5996 | EINNRTG | 7663 | 112.43235 |
| 1018 | ACCGTTAACACAATGTACACG | 5997 | TVNTMYT | 7664 | 112.4 |
| 1019 | CCTATGAATGGTATTCTGTTG | 5998 | PMNGILL | 7665 | 112.388 |
| 1020 | AATCCTAGTTATGATCATCGG | 5999 | NPSYDHR | 7666 | 112.363 |
| 1021 | GCTGTTATTCTGAATCCTGTT | 6000 | AVILNPV | 7667 | 112.36 |
| 1022 | CTGTACGGGGGAGCACACCAA | 6001 | LYGGAHQ | 7668 | 112.3455 |
| 1023 | CAAGTCAACCAACCGAGAATA | 6002 | QVNQPRI | 7669 | 112.33 |
| 1024 | GCTGTTAGAACACCGGCAATG | 6003 | AVRTPAM | 7670 | 112.326 |
| 1025 | AGTTTGACGCCTAATAATCTT | 6004 | SLTPNNL | 7671 | 112.283 |
| 1026 | CTTGGGCAGGTTAATTCTACG | 6005 | LGQVNST | 7672 | 112.205 |
| 1027 | GCTAATTCTGCTACTAATCAG | 6006 | ANSATNQ | 7673 | 112.1605 |
| 1028 | TCCTTGACGGAAAAAGCGCCG | 6007 | SLTEKAP | 7674 | 112.15 |
| 1029 | CAATTCCACGGGACATCTGAA | 6008 | QFHGTSE | 7675 | 112.125 |
| 1030 | AAAAACGGCGCCATAGGAACA | 6009 | KNGAIGT | 7676 | 112.0867 |
| 1031 | GTGCTGGCGTCGACTGAGAAG | 6010 | VLASTEK | 7677 | 112.058 |
| 1032 | AGTAATATGAGTGAGGCGATT | 6011 | SNMSEAI | 7678 | 112.02 |
| 1033 | AACGCTAACGCCGGTGGAAAC | 6012 | NANAGGN | 7679 | 112.0148 |
| 1034 | CACTCTAACACACACTACGAA | 6013 | HSNTHYE | 7680 | 112.005 |
| 1035 | AGTGCTTTGATTAGTGTGGTT | 6014 | SALISVV | 7681 | 111.993 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1036 | GTGGCGACTCATTATAATGAG | 6015 | VATHYNE | 7682 | 111.971 |
| 1037 | AACCAAACGTTACAAGTAGAC | 6016 | NQTLQVD | 7683 | 111.97 |
| 1038 | AAAACACCCTCAGCTTCAGAA | 6017 | KTPSASE | 7684 | 111.957 |
| 1039 | GGTGAATCACGTACAAACATG | 6018 | GESRTNM | 7685 | 111.9393 |
| 1040 | CGGAATGAGCCGGTTAGTACT | 6019 | RNEPVST | 7686 | 111.912 |
| 1041 | GCAACACACGCCATGCGCCCA | 6020 | ATHAMRP | 7687 | 111.9005 |
| 1042 | TGGGAATCCCTCTCCAACGCA | 6021 | WESLSNA | 7688 | 111.885 |
| 1043 | CATAGTCCTCCTACGACTATG | 6022 | HSPPTTM | 7689 | 111.847 |
| 1044 | TCTACCATGAACACGATCACG | 6023 | STMNTIT | 7690 | 111.8162 |
| 1045 | AACATGGAACACACCATGGCG | 6024 | NMEHTMA | 7691 | 111.78965 |
| 1046 | CATAATACGGAGTCTAAGACT | 6025 | HNTESKT | 7692 | 111.778 |
| 1047 | CACAACTTAATGACCCAAATA | 6026 | HNLMTQI | 7693 | 111.77 |
| 1048 | AACCAAAACACCTACGAACTG | 6027 | NQNTYEL | 7694 | 111.756 |
| 1049 | TACGCCACTCTCGACACCATC | 6028 | YATLDTI | 7695 | 111.752 |
| 1050 | GTTCAGTTGGAGAATGCGAAT | 6029 | VQLENAN | 7696 | 111.7215 |
| 1051 | GGGCTCACAGGATACACAATG | 6030 | GLTGYTM | 7697 | 111.71 |
| 1052 | TTAGTACTTGACTCACGGAAC | 6031 | LVLDSRN | 7698 | 111.704 |
| 1053 | ATGTTGGTACAAAACACACCC | 6032 | MLVQNTP | 7699 | 111.702 |
| 1054 | CCTCATAATCAGGAGATGGGT | 6033 | PHNQEMG | 7700 | 111.6865 |
| 1055 | TCGTTGGGGGATGCGATGTTG | 6034 | SLGDAML | 7701 | 111.6776 |
| 1056 | CGCGCCGAAGGGAGCTCTGGC | 6035 | RAEGSSG | 7702 | 111.6645 |
| 1057 | AGTGAGGAGAGGACGCGTGCG | 6036 | SEERTRA | 7703 | 111.616 |
| 1058 | TCTAGTAAGGAGCGTACATCG | 6037 | SSKERTS | 7704 | 111.57 |
| 1059 | CCTGTTGTGAGGGATCGTTCT | 6038 | PVVRDRS | 7705 | 111.5643 |
| 1060 | AGGATGTCTGAGAGTTCGGAT | 6039 | RMSESSD | 7706 | 111.51 |
| 1061 | AACCAATCTATAAGCATGGAC | 6040 | NQSISMD | 7707 | 111.491 |
| 1062 | GTCGCTGTATCGAACACTCCA | 6041 | VAVSNTP | 7708 | 111.482 |
| 1063 | GGAGACATCTCAAGCAGAAAC | 6042 | GDISSRN | 7709 | 111.4603 |
| 1064 | GCTGCCGGAGCCGACTCTCCA | 6043 | AAGADSP | 7710 | 111.429 |
| 1065 | TTCGGCACATCGTACACAACC | 6044 | FGTSYTT | 7711 | 111.401 |
| 1066 | CGTGATACTAATACGGATAAG | 6045 | RDTNTDK | 7712 | 111.336 |
| 1067 | GGGTCTACGCCGGGGGCGAGT | 6046 | GSTPGAS | 7713 | 111.327 |
| 1068 | GGTACTAATCATGATTTTTCG | 6047 | GTNHDFS | 7714 | 111.302 |
| 1069 | AATGAGAGTACGAAGGAGAGT | 6048 | NESTKES | 7715 | 111.2845 |
| 1070 | GTGCATGTGACTAATGTGTTG | 6049 | VHVTNVL | 7716 | 111.2295 |
| 1071 | AGTACTACTAATGTTGCGTAT | 6050 | STTNVAY | 7717 | 111.2015 |
| 1072 | ATTACGTCGTTGAATGGGATG | 6051 | ITSLNGM | 7718 | 111.1615 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1073 | GAAGTACGGGGCAGCGTGCCA | 6052 | EVRGSVP | 7719 | 111.1435 |
| 1074 | GCACTTACCCGTATGCCTAAC | 6053 | ALTRMPN | 7720 | 111.1235 |
| 1075 | CTCAGTGTAGCCGACAGGCCA | 6054 | LSVADRP | 7721 | 111.06 |
| 1076 | GTTTCTACGGCGCAGAGGCAG | 6055 | VSTAQRQ | 7722 | 111.056 |
| 1077 | TTAAACGCAGAATACACCAAC | 6056 | LNAEYTN | 7723 | 111.02 |
| 1078 | AATGAGAAGCCGCAGTCGACG | 6057 | NEKPQST | 7724 | 111.009 |
| 1079 | TTGAATACGCTGATTGATAAG | 6058 | LNTLIDK | 7725 | 111.003 |
| 1080 | GTCACACACACACTGATCGAA | 6059 | VTHTLIE | 7726 | 110.987 |
| 1081 | GAGCAGAAGAAGACTGATCAT | 6060 | EQKKTDH | 7727 | 110.936 |
| 1082 | ACATCAGGCATGTACGACACG | 6061 | TSGMYDT | 7728 | 110.92 |
| 1083 | CCTGACGCAGCGCGTAGCCCG | 6062 | PDAARSP | 7729 | 110.916 |
| 1084 | TTGACGCAGGTTTATCATGAG | 6063 | LTQVYHE | 7730 | 110.91 |
| 1085 | AGAGAAATGAGCAGCCTATCT | 6064 | REMSSLS | 7731 | 110.891 |
| 1086 | ATGCCTTCGAAAGGCGAAGTA | 6065 | MPSKGEV | 7732 | 110.816 |
| 1087 | AATGAGCAGAATACGCCGAGT | 6066 | NEQNTPS | 7733 | 110.79 |
| 1088 | AAAAACTACGCAAGCACCGAC | 6067 | KNYASTD | 7734 | 110.7435 |
| 1089 | TGTATGGATGTTGGTAAGGCG | 6068 | CMDVGKA | 7735 | 110.711 |
| 1090 | GCTCTTCATAATCTGATGAAT | 6069 | ALHNLMN | 7736 | 110.711 |
| 1091 | CCTGACAGAGCGAACGACAAA | 6070 | PDRANDK | 7737 | 110.6835 |
| 1092 | ATTGCTCATGTGTCTACTAAT | 6071 | IAHVSTN | 7738 | 110.6805 |
| 1093 | AACGGTCCGACCGGATCCGCC | 6072 | NGPTGSA | 7739 | 110.6652 |
| 1094 | TCTACTCATCATGCTGATCGT | 6073 | STHHADR | 7740 | 110.629 |
| 1095 | GGTTCGCAGTATGGGCGGCAT | 6074 | GSQYGRH | 7741 | 110.629 |
| 1096 | ACCGGAACGGCTACACTCCCA | 6075 | TGTATLP | 7742 | 110.5825 |
| 1097 | AAAGCCCACGTTGTAGAAATA | 6076 | KAHVVEI | 7743 | 110.5795 |
| 1098 | ACTTCGCAGGGTAGGAGTCCT | 6077 | TSQGRSP | 7744 | 110.511 |
| 1099 | TTATCCTCCGAATCACCCAGG | 6078 | LSSESPR | 7745 | 110.5015 |
| 1100 | ACCGGGGTTCGAGAAACCATA | 6079 | TGVRETI | 7746 | 110.4575 |
| 1101 | ATGGATACTGAGCTTTATAGG | 6080 | MDTELYR | 7747 | 110.4475 |
| 1102 | ACACCTGAAGCGAGCGCTCGC | 6081 | TPEASAR | 7748 | 110.44 |
| 1103 | CACGACTTGAACCACGGAAAA | 6082 | HDLNHGK | 7749 | 110.428 |
| 1104 | CTTACTGGTCAGAATGCGATT | 6083 | LTGQNAI | 7750 | 110.416 |
| 1105 | ACCGTCGGATCGAACAGTATA | 6084 | TVGSNSI | 7751 | 110.411 |
| 1106 | CATACTGTGGGGGCTATGCAT | 6085 | HTVGAMH | 7752 | 110.41 |
| 1107 | GAACGAGTCAACGGGATGGCA | 6086 | ERVNGMA | 7753 | 110.405 |
| 1108 | TCCGAACCCCTTAGAGTTGGA | 6087 | SEPLRVG | 7754 | 110.3725 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1109 | GTCTCTAACGTCCTCTACAGC | 6088 | VSNVLYS | 7755 | 110.346 |
| 1110 | TTCTCCTCCGGAACAACCATA | 6089 | FSSGTTI | 7756 | 110.3 |
| 1111 | ACAAACCTAAGTCAATCGGCC | 6090 | TNLSQSA | 7757 | 110.24435 |
| 1112 | CCTAATACTGCTAGTAATTTT | 6091 | PNTASNF | 7758 | 110.2274 |
| 1113 | TGCGGCCTGAACTGCGGTAAA | 6092 | CGLNCGK | 7759 | 110.211 |
| 1114 | CCGACCGGAGGCTCACCACCA | 6093 | PTGGSPP | 7760 | 110.201 |
| 1115 | TACCTAGAATCCAACTACACC | 6094 | YLESNYT | 7761 | 110.18 |
| 1116 | ACATTAGAAACAACCCGCAGC | 6095 | TLETTRS | 7762 | 110.167 |
| 1117 | TCCGCTAACGAACACAACCAC | 6096 | SANEHNH | 7763 | 110.137 |
| 1118 | GCACGAGTGGACACCAACCAA | 6097 | ARVDTNQ | 7764 | 110.09 |
| 1119 | AACGTGGTGAAAAACAACACA | 6098 | NVVKNNT | 7765 | 110.077 |
| 1120 | GGTTCTTATTCTGATGGTAGT | 6099 | GSYSDGS | 7766 | 110.0355 |
| 1121 | CCCGGTAACGGACAAAGTCCG | 6100 | PGNGQSP | 7767 | 110.0275 |
| 1122 | TCGGGGGTAAACTTCGGAGTA | 6101 | SGVNFGV | 7768 | 109.998 |
| 1123 | CGAATCAACGCAGCAATCGAC | 6102 | RINAAID | 7769 | 109.99675 |
| 1124 | CAAGCTGGGAACGCGCCAAGG | 6103 | QAGNAPR | 7770 | 109.98825 |
| 1125 | CAGTCGGGGTCTCTGGTGCCG | 6104 | QSGSLVP | 7771 | 109.962 |
| 1126 | TTCTCAACGCAAGACATAAGC | 6105 | FSTQDIS | 7772 | 109.948 |
| 1127 | GTGAATCCGCATCCTGCGCAG | 6106 | VNPHPAQ | 7773 | 109.948 |
| 1128 | AAAGGCCACGCCTACGAAGCC | 6107 | KGHAYEA | 7774 | 109.897 |
| 1129 | GAAGACAGTATGAGATTCTCT | 6108 | EDSMRFS | 7775 | 109.874 |
| 1130 | GGTAGGAATGAGAGTCCGGAG | 6109 | GRNESPE | 7776 | 109.855 |
| 1131 | TCCGACGGATCGAAACTACTA | 6110 | SDGSKLL | 7777 | 109.8205 |
| 1132 | ACTCTCTCAGGCTACATGAGA | 6111 | TLSGYMR | 7778 | 109.808 |
| 1133 | GATATTCATAATCCGCGTACG | 6112 | DIHNPRT | 7779 | 109.789 |
| 1134 | TGGGCCAAAGACGTCAACGTC | 6113 | WAKDVNV | 7780 | 109.782 |
| 1135 | GCTGTGGGGCGGTCGGATGAT | 6114 | AVGRSDD | 7781 | 109.711 |
| 1136 | AAAGAAAAAACCACCCGCGAA | 6115 | KEKTTRE | 7782 | 109.697 |
| 1137 | CTGCTCCAATCGACCTACTTG | 6116 | LLQSTYL | 7783 | 109.672 |
| 1138 | AAGTCTAATTTGGAGGGTAAG | 6117 | KSNLEGK | 7784 | 109.6285 |
| 1139 | ACGAGGACGCCTTTTCTGGGG | 6118 | TRTPFLG | 7785 | 109.613 |
| 1140 | CAGTCGGATACGACTTCGATT | 6119 | QSDTTSI | 7786 | 109.605 |
| 1141 | GCGTGGTCTCAAGTCCTGACG | 6120 | AWSQVLT | 7787 | 109.587 |
| 1142 | ACTCAAGAACGACCACTAATC | 6121 | TQERPLI | 7788 | 109.56 |
| 1143 | GATGATAAGACTGGTCGGTAT | 6122 | DDKTGRY | 7789 | 109.549 |
| 1144 | TTTCCTTCGCATAATGGGGCG | 6123 | FPSHNGA | 7790 | 109.54 |
| 1145 | ATGCTGTCTCAAGTCTTAACA | 6124 | MLSQVLT | 7791 | 109.536 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1146 | TCTGTGACGACTAATCTGATG | 6125 | SVTTNLM | 7792 | 109.484 |
| 1147 | GAACACAACTCAAAAACTTAC | 6126 | EHNSKTY | 7793 | 109.4745 |
| 1148 | TATGCGCATCCTGTGACTCAT | 6127 | YAHPVTH | 7794 | 109.4635 |
| 1149 | CCTAATCCGTCTCCGAGGCAG | 6128 | PNPSPRQ | 7795 | 109.449 |
| 1150 | CATATGGGTTTGAATGAGCTT | 6129 | HMGLNEL | 7796 | 109.427 |
| 1151 | AACAGTTTGCAAGCAAGTGCA | 6130 | NSLQASA | 7797 | 109.402 |
| 1152 | GACCTCGGTACGGCTAGAACC | 6131 | DLGTART | 7798 | 109.388 |
| 1153 | TACGACAGCCGACTCTACGCG | 6132 | YDSRLYA | 7799 | 109.3853 |
| 1154 | CCGAAGCCTGGGACGGGGGAG | 6133 | PKPGTGE | 7800 | 109.3721 |
| 1155 | AGTCTGAATGGGGTGTTGGTT | 6134 | SLNGVLV | 7801 | 109.3685 |
| 1156 | CAGTCTAATTTGGTTATTAAT | 6135 | QSNLVIN | 7802 | 109.359 |
| 1157 | GCGTCTCCGGCGCAGACCGGC | 6136 | ASPAQTG | 7803 | 109.331 |
| 1158 | AACATGACCAACGAAAACGGA | 6137 | NMTNENG | 7804 | 109.324 |
| 1159 | TCACTTCGGACGGACGAATTC | 6138 | SLRTDEF | 7805 | 109.31815 |
| 1160 | ATATTGGACAACCACCGTTTC | 6139 | ILDNHRF | 7806 | 109.2685 |
| 1161 | TTGATTAATATGAGTCAGAAT | 6140 | LINMSQN | 7807 | 109.264 |
| 1162 | CCGCAAGACGTCCGCCAAACA | 6141 | PQDVRQT | 7808 | 109.2625 |
| 1163 | CCCTTCGTAGCGAACGAACCA | 6142 | PFVANEP | 7809 | 109.256 |
| 1164 | AATATTAATGATACTAAGAAT | 6143 | NINDTKN | 7810 | 109.253 |
| 1165 | AATTTTAGTAGTGGTGATGTT | 6144 | NFSSGDV | 7811 | 109.229 |
| 1166 | GAACGAAACGGACTAATAGAA | 6145 | ERNGLIE | 7812 | 109.215 |
| 1167 | AATTCTCATGTTCCTAATAAT | 6146 | NSHVPNN | 7813 | 109.2115 |
| 1168 | AACACAACCGGTAGCTCGGGC | 6147 | NTTGSSG | 7814 | 109.1925 |
| 1169 | TCAACCAGAAAAGAACACGAC | 6148 | STRKEHD | 7815 | 109.1875 |
| 1170 | GCTGCTAATCCTAGTACGGAG | 6149 | AANPSTE | 7816 | 109.1357 |
| 1171 | TCGGGTATGAATAGTAATAAG | 6150 | SGMNSNK | 7817 | 109.129 |
| 1172 | AAGACGCTTGATAATAATGCT | 6151 | KTLDNNA | 7818 | 109.09305 |
| 1173 | ACCGTAAAACAAACAAGTCCG | 6152 | TVKQTSP | 7819 | 109.0863 |
| 1174 | ATTTCTCAGGTGTCTTTTAAT | 6153 | ISQVSFN | 7820 | 109.082 |
| 1175 | TTAGAAGTAAACCTGCAAACG | 6154 | LEVNLQT | 7821 | 109.057 |
| 1176 | GAAATGCAAACCAAAAACGCC | 6155 | EMQTKNA | 7822 | 109.052 |
| 1177 | GCCGACAACAGAAACGACAAA | 6156 | ADNRNDK | 7823 | 109.008 |
| 1178 | GCGTATGATACGCTGAATAGT | 6157 | AYDTLNS | 7824 | 108.982 |
| 1179 | ACGATTCAGGATCATATTAAG | 6158 | TIQDHIK | 7825 | 108.942 |
| 1180 | GACCCCACTAAAGTTGGATCC | 6159 | DPTKVGS | 7826 | 108.939 |
| 1181 | TCCCTCCAACGAACCCCCGAC | 6160 | SLQRTPD | 7827 | 108.937 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1182 | GCAAACGACTCTGCCAAAACA | 6161 | ANDSAKT | 7828 | 108.9125 |
| 1183 | AAAAAAGTCGAACAAGAACCA | 6162 | KKVEQEP | 7829 | 108.907 |
| 1184 | GCAAGTCGGGACCTGGGACAA | 6163 | ASRDLGQ | 7830 | 108.906 |
| 1185 | TGGGAGAGTGATAAGTTTCGT | 6164 | WESDKFR | 7831 | 108.876 |
| 1186 | AACCGCGGAACAGAAGTTTAC | 6165 | NRGTEVY | 7832 | 108.8187 |
| 1187 | AATATTAGTAGTATTAATCAG | 6166 | NISSINQ | 7833 | 108.8155 |
| 1188 | GCCTCGAAAGGCTTCGGCCAC | 6167 | ASKGFGH | 7834 | 108.7886 |
| 1189 | CAGTCGCAGAATGTGACTCAG | 6168 | QSQNVTQ | 7835 | 108.7825 |
| 1190 | AACGGATACCAACTACAAATC | 6169 | NGYQLQI | 7836 | 108.779 |
| 1191 | TGTACTAATGCGTCGGATCTT | 6170 | CTNASDL | 7837 | 108.74 |
| 1192 | ACCGTCGCCTCGCCCAACACC | 6171 | TVASPNT | 7838 | 108.738 |
| 1193 | AATACTGCTCCGCCGAATCAT | 6172 | NTAPPNH | 7839 | 108.733 |
| 1194 | CTTTCTCAACAACGCGACTAC | 6173 | LSQQRDY | 7840 | 108.69245 |
| 1195 | TGGAATCAGAATGTGTCTCAT | 6174 | WNQNVSH | 7841 | 108.6785 |
| 1196 | ACAGGTAGTTCAGACAGATTA | 6175 | TGSSDRL | 7842 | 108.676 |
| 1197 | AACACAACGCCACCTAACCAC | 6176 | NTTPPNH | 7843 | 108.602 |
| 1198 | GTGGTCGACTCAACATACCCG | 6177 | VVDSTYP | 7844 | 108.592 |
| 1199 | ACGGATGCTACGGGGAGGCAT | 6178 | TDATGRH | 7845 | 108.5905 |
| 1200 | TTGTTTACTGCTGGGAGTACT | 6179 | LFTAGST | 7846 | 108.58 |
| 1201 | TTGCGTGATCAGACTAGTATG | 6180 | LRDQTSM | 7847 | 108.566 |
| 1202 | ATCGAAACGGACCGCCACCGG | 6181 | IETDRHR | 7848 | 108.531 |
| 1203 | AGTGGGCCTGAGAATACGTTG | 6182 | SGPENTL | 7849 | 108.526 |
| 1204 | GACAACCAAAACGCCGACAGG | 6183 | DNQNADR | 7850 | 108.486 |
| 1205 | CATGATGGTTATGTTCCTAAT | 6184 | HDGYVPN | 7851 | 108.469 |
| 1206 | CATATGTCTAGTTATTCGTCG | 6185 | HMSSYSS | 7852 | 108.436 |
| 1207 | AGTCGTCTGCAGACTCAGCAG | 6186 | SRLQTQQ | 7853 | 108.4358 |
| 1208 | TCATACACAGCAGGAAGACCC | 6187 | SYTAGRP | 7854 | 108.417 |
| 1209 | GTGCAGCAGAATAATATTAAT | 6188 | VQQNNIN | 7855 | 108.376 |
| 1210 | GATGCGAAGGCTCTTACGACT | 6189 | DAKALTT | 7856 | 108.368 |
| 1211 | AAGGATGAGCATCTTCATTAT | 6190 | KDEHLHY | 7857 | 108.358 |
| 1212 | CACGGTGACCGAACAGCTTTA | 6191 | HGDRTAL | 7858 | 108.327 |
| 1213 | AATTTTACTATTACGGAGGCG | 6192 | NFTITEA | 7859 | 108.32 |
| 1214 | GACACTCACATGAACAAACTG | 6193 | DTHMNKL | 7860 | 108.316 |
| 1215 | CAACCAGGAGCCCCCCAAACC | 6194 | QPGAPQT | 7861 | 108.312 |
| 1216 | GGGGAAGCACGCCGAGAAGCC | 6195 | GEARREA | 7862 | 108.302 |
| 1217 | AAGTCTCTTAGTAGTGATGAT | 6196 | KSLSSDD | 7863 | 108.2375 |
| 1218 | ATGAATACGACTTATAATGAG | 6197 | MNTTYNE | 7864 | 108.231 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1219 | GCGGCCGCACTAGAAACAATA | 6198 | AAALETI | 7865 | 108.223 |
| 1220 | AACGTCGCTCCCTACAGTAGC | 6199 | NVAPYSS | 7866 | 108.21595 |
| 1221 | TCTGCGGGTATGGTGAGTCTG | 6200 | SAGMVSL | 7867 | 108.2145 |
| 1222 | TGCGACTTGTCACAATCATGC | 6201 | CDLSQSC | 7868 | 108.133 |
| 1223 | GTTTTGATTACGATGAGTTCG | 6202 | VLITMSS | 7869 | 108.118 |
| 1224 | CAAGTTGGGGCTCTAATGGTT | 6203 | QVGALMV | 7870 | 108.037 |
| 1225 | CAACGTACCTCGGAAGCGCCA | 6204 | QRTSEAP | 7871 | 108.0315 |
| 1226 | TTGGGTAATGGTAGTTCTTTG | 6205 | LGNGSSL | 7872 | 108.0135 |
| 1227 | CCTAGTGTCCGTTTGCCCTTA | 6206 | PSVRLPL | 7873 | 108.007 |
| 1228 | GATTCTGCTCCGAGTACTATT | 6207 | DSAPSTI | 7874 | 108.003 |
| 1229 | AATTATAATGGGGTTAATGTG | 6208 | NYNGVNV | 7875 | 107.956 |
| 1230 | TCGGCTCATCAGACGCCGACG | 6209 | SAHQTPT | 7876 | 107.932 |
| 1231 | GATCATAGTAAGCAGATTTCG | 6210 | DHSKQIS | 7877 | 107.923 |
| 1232 | GCCGCCAGCTTGTCGCAAAGC | 6211 | AASLSQS | 7878 | 107.914 |
| 1233 | CACGCCGACGTTGGCATGAGC | 6212 | HADVGMS | 7879 | 107.888 |
| 1234 | CACGTGACAGTAACGTTAAAC | 6213 | HVTVTLN | 7880 | 107.8865 |
| 1235 | AATTCTACGCATATTAATTCG | 6214 | NSTHINS | 7881 | 107.8843 |
| 1236 | CTGGGGCTTGCTGGTCAGGTT | 6215 | LGLAGQV | 7882 | 107.884 |
| 1237 | AGCAGTCAAGCCCACGGCCCA | 6216 | SSQAHGP | 7883 | 107.872 |
| 1238 | GCTTTTAAGTCGGGTAGTATT | 6217 | AFKSGSI | 7884 | 107.866 |
| 1239 | CACTCCCCATCCCACGACTCG | 6218 | HSPSHDS | 7885 | 107.844 |
| 1240 | CCAAACGGCGAAAGTTCGCGA | 6219 | PNGESSR | 7886 | 107.8303 |
| 1241 | ATTCTTACGCCTTTGGATAAG | 6220 | ILTPLDK | 7887 | 107.825 |
| 1242 | TCCGCCTCTTACTCCAGGATG | 6221 | SASYSRM | 7888 | 107.815 |
| 1243 | GAGGCGTTGCATGATCGGAAT | 6222 | EALHDRN | 7889 | 107.793 |
| 1244 | GGTGAACAACACAACGCCCCC | 6223 | GEQHNAP | 7890 | 107.778 |
| 1245 | GGGAATATGGTTACGCCTAAT | 6224 | GNMVTPN | 7891 | 107.753 |
| 1246 | AACGCTCTCCTCAACGCACCT | 6225 | NALLNAP | 7892 | 107.742 |
| 1247 | GCAAGTGACCTACAAATGACG | 6226 | ASDLQMT | 7893 | 107.723 |
| 1248 | TCGTATGATATGCATACGAAT | 6227 | SYDMHTN | 7894 | 107.705 |
| 1249 | AATATGTCGCATAGTACTCTG | 6228 | NMSHSTL | 7895 | 107.6777 |
| 1250 | ACTGCCAACAACCACTCTCCG | 6229 | TANNHSP | 7896 | 107.671 |
| 1251 | CAAGCCCCGCCAACAGCACAA | 6230 | QAPPTAQ | 7897 | 107.668 |
| 1252 | AACTACCACGGAGACAACGTT | 6231 | NYHGDNV | 7898 | 107.637 |
| 1253 | AGGGATAGTACTATTAGTCGG | 6232 | RDSTISR | 7899 | 107.635 |
| 1254 | GTTTCTTCGCCTAATGGTACG | 6233 | VSSPNGT | 7900 | 107.6095 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1255 | TCCCGAATCACGGTGAACGCA | 6234 | SRITVNA | 7901 | 107.593 |
| 1256 | GTCGGAACAACCTCGAACGGC | 6235 | VGTTSNG | 7902 | 107.575 |
| 1257 | CATACGAATCAGATGCAGCCT | 6236 | HTNQMQP | 7903 | 107.5573 |
| 1258 | AAAAGCAACGCGGGATTCGGT | 6237 | KSNAGFG | 7904 | 107.5065 |
| 1259 | AAAGAAAGCCTCGAAGACGTC | 6238 | KESLEDV | 7905 | 107.49 |
| 1260 | GCGCAGGTTAATAATCATGAT | 6239 | AQVNNHD | 7906 | 107.489 |
| 1261 | AACGCTTCTACCTACATGGAC | 6240 | NASTYMD | 7907 | 107.479 |
| 1262 | ACGTCTGATACGAATGCTAGG | 6241 | TSDTNAR | 7908 | 107.4605 |
| 1263 | GAGAGTCGTATGCGTAGTATT | 6242 | ESRMRSI | 7909 | 107.451 |
| 1264 | CGTGTTGAAGACACCAACTCC | 6243 | RVEDTNS | 7910 | 107.416 |
| 1265 | GCCTCTAACCACCTACAAGCC | 6244 | ASNHLQA | 7911 | 107.3863 |
| 1266 | CGCTTACACGGCTCAGACTCG | 6245 | RLHGSDS | 7912 | 107.358 |
| 1267 | ACCGTCGAACAAATAAACTCG | 6246 | TVEQINS | 7913 | 107.349 |
| 1268 | AGGTCCGTACCATCACCACAC | 6247 | RSVPSPH | 7914 | 107.343 |
| 1269 | GAATACCTCGCCCTGGGACAC | 6248 | EYLALGH | 7915 | 107.336 |
| 1270 | AATACTAATAATCAGGAGCAG | 6249 | NTNNQEQ | 7916 | 107.332 |
| 1271 | AACTACGGTTCCGGACGAATC | 6250 | NYGSGRI | 7917 | 107.3205 |
| 1272 | CGCCACGGGGACACACCGATG | 6251 | RHGDTPM | 7918 | 107.303 |
| 1273 | AACGACACCATCGGCAGACCA | 6252 | NDTIGRP | 7919 | 107.2995 |
| 1274 | TATGGGGAGCGTGCTAGGACG | 6253 | YGERART | 7920 | 107.297 |
| 1275 | GTTCTTGGGATGCAGAGGTCT | 6254 | VLGMQRS | 7921 | 107.295 |
| 1276 | CTTCATTTTCATGCTTCGCAG | 6255 | LHFHASQ | 7922 | 107.281 |
| 1277 | ACCGACACGCTCAGCGAAAGA | 6256 | TDTLSER | 7923 | 107.247 |
| 1278 | GGGACAGGTACCGTTGGATGG | 6257 | GTGTVGW | 7924 | 107.203 |
| 1279 | ACAGAAAGCCCCAAACTACTA | 6258 | TESPKLL | 7925 | 107.2015 |
| 1280 | ACGATTAGGAGTGAGGGTTTT | 6259 | TIRSEGF | 7926 | 107.1495 |
| 1281 | GCGTCTAGTTATATTAATAAT | 6260 | ASSYINN | 7927 | 107.144 |
| 1282 | TTACACCTTGGGTTATCATCT | 6261 | LHLGLSS | 7928 | 107.1415 |
| 1283 | GTCACTGGCACTACCCCGGGA | 6262 | VTGTTPG | 7929 | 107.137 |
| 1284 | GTGACGTCGTCTGCTAGTGGT | 6263 | VTSSASG | 7930 | 107.0606 |
| 1285 | CAAATGCACCTACACATGCAA | 6264 | QMHLHMQ | 7931 | 107.057 |
| 1286 | GGTACCATGAGTCTATTAATG | 6265 | GTMSLLM | 7932 | 107.046 |
| 1287 | TGCGCATCAGAAGTTTGCCAA | 6266 | CASEVCQ | 7933 | 107.035 |
| 1288 | AATCTTGTGATGAGTGGGACG | 6267 | NLVMSGT | 7934 | 107.0225 |
| 1289 | CAATCACTCAAAGACGGCACT | 6268 | QSLKDGT | 7935 | 106.991 |
| 1290 | GCGTTGAATGGTTCTGGTATT | 6269 | ALNGSGI | 7936 | 106.976 |
| 1291 | AGACACGTCGTCCCCGACTCC | 6270 | RHVVPDS | 7937 | 106.9705 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1292 | CTGTATCATGATTCGCATCTT | 6271 | LYHDSHL | 7938 | 106.963 |
| 1293 | GGGAGTACGCCTATTACTTCT | 6272 | GSTPITS | 7939 | 106.957 |
| 1294 | CCCAACGACCAAATCAGCGGA | 6273 | PNDQISG | 7940 | 106.936 |
| 1295 | AGTGGAAAACAAGACAAATAC | 6274 | SGKQDKY | 7941 | 106.925 |
| 1296 | AGTGGGCATGCTTCTCAGGGT | 6275 | SGHASQG | 7942 | 106.8675 |
| 1297 | AAGATGGGGAGTATTGAGGTT | 6276 | KMGSIEV | 7943 | 106.864 |
| 1298 | TCAACTTTAGACCGAAGCGAA | 6277 | STLDRSE | 7944 | 106.8615 |
| 1299 | ACGGAGCTTAGTGAGTATACT | 6278 | TELSEYT | 7945 | 106.852 |
| 1300 | GCCAACGGAGGAGGATACCCC | 6279 | ANGGGYP | 7946 | 106.847 |
| 1301 | GTAACCGAATCTAACTCTCTA | 6280 | VTESNSL | 7947 | 106.83 |
| 1302 | CCAGTCTACGACCGCGACGTC | 6281 | PVYDRDV | 7948 | 106.812 |
| 1303 | GATAATAATAAGCATGGTACT | 6282 | DNNKHGT | 7949 | 106.806 |
| 1304 | ATCTACGAAACCGTAACCTTG | 6283 | IYETVTL | 7950 | 106.801 |
| 1305 | ACTCAGACTGGTCATGTTTCT | 6284 | TQTGHVS | 7951 | 106.7868 |
| 1306 | CAAGCCGACCTCAGGTACAAA | 6285 | QADLRYK | 7952 | 106.773 |
| 1307 | TGTAAGACGAATAATGCTGGT | 6286 | CKTNNAG | 7953 | 106.749 |
| 1308 | GCCGGTCACCAACAACTGGCC | 6287 | AGHQQLA | 7954 | 106.7459 |
| 1309 | GATAGGGATATGGAGGGTGTT | 6288 | DRDMEGV | 7955 | 106.742 |
| 1310 | GATCAGCCGGGGTATGTGCGT | 6289 | DQPGYVR | 7956 | 106.7387 |
| 1311 | GATGCTATGCTTGCTCATCCG | 6290 | DAMLAHP | 7957 | 106.735 |
| 1312 | GCCCTTAACCTGTACTCCAGC | 6291 | ALNLYSS | 7958 | 106.732 |
| 1313 | CTACTATCTAAAGGGGACTCC | 6292 | LLSKGDS | 7959 | 106.709 |
| 1314 | TCGAGTATTAGTCTGCGGTAT | 6293 | SSISLRY | 7960 | 106.645 |
| 1315 | GGGTCGAGCCAACACCACGAA | 6294 | GSSQHHE | 7961 | 106.62 |
| 1316 | TCGATTGGGTATTCGCCTCCG | 6295 | SIGYSPP | 7962 | 106.5773 |
| 1317 | CACTCCAACGCGACTACGATA | 6296 | HSNATTI | 7963 | 106.567 |
| 1318 | TCGGCACACGACGCAAGACTA | 6297 | SAHDARL | 7964 | 106.5665 |
| 1319 | GTTCACACCGCAGACACAATA | 6298 | VHTADTI | 7965 | 106.564 |
| 1320 | CGAGACGGCTCTACTAAAGTT | 6299 | RDGSTKV | 7966 | 106.55855 |
| 1321 | TTGCAGGAGTCTCTTCCTGGT | 6300 | LQESLPG | 7967 | 106.542 |
| 1322 | TTAGACTACACCCCTCAAAAC | 6301 | LDYTPQN | 7968 | 106.519 |
| 1323 | GGACCAAGTTCGCACATCGTT | 6302 | GPSSHIV | 7969 | 106.507 |
| 1324 | AGCGCCGACACCCGGTCCCCC | 6303 | SADTRSP | 7970 | 106.466 |
| 1325 | ATGATGAAGAGTGAGGAGAAT | 6304 | MMKSEEN | 7971 | 106.425 |
| 1326 | GGTATGACGAGTGAGTTGACG | 6305 | GMTSELT | 7972 | 106.417 |
| 1327 | GTAGACACCTACAGCGGTCTG | 6306 | VDTYSGL | 7973 | 106.415 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1328 | GGGATGAGGGATACGCCGCCG | 6307 | GMRDTPP | 7974 | 106.385 |
| 1329 | GAGCATGATGTGAGTACGCGT | 6308 | EHDVSTR | 7975 | 106.302 |
| 1330 | GAGGTGGTGAAGACTACTCAT | 6309 | EVVKTTH | 7976 | 106.269 |
| 1331 | GTTTACGACAACGTTTCTTCT | 6310 | VYDNVSS | 7977 | 106.268 |
| 1332 | CTCATGAAAGACATGGAATCC | 6311 | LMKDMES | 7978 | 106.2609 |
| 1333 | CCTCTTCATGTTGCTTCTCCT | 6312 | PLHVASP | 7979 | 106.239 |
| 1334 | GAAGTACGCGACCAAAAAACA | 6313 | EVRDQKT | 7980 | 106.2075 |
| 1335 | CCAACTCCCTACTACACCGCC | 6314 | PTPYYTA | 7981 | 106.124 |
| 1336 | AACAACTACGCCTACTCCGCT | 6315 | NNYAYSA | 7982 | 106.1085 |
| 1337 | CTTGTTGATACGGATAGGAAT | 6316 | LVDTDRN | 7983 | 106.108 |
| 1338 | TATCCGGCTGATCATCGGACT | 6317 | YPADHRT | 7984 | 106.088 |
| 1339 | TCTGCAACAACGAACCACGGA | 6318 | SATTNHG | 7985 | 106.066 |
| 1340 | CGTGATGATCAGCAGCTTGAT | 6319 | RDDQQLD | 7986 | 106.064 |
| 1341 | GGAGCGGGACAATCTCACGTG | 6320 | GAGQSHV | 7987 | 106.0351 |
| 1342 | GATAGGACTTATCATGAGGTG | 6321 | DRTYHEV | 7988 | 105.996 |
| 1343 | GATGGTAATAATACGACTTAT | 6322 | DGNNTTY | 7989 | 105.99 |
| 1344 | GTGCATATGGAGTCGTATGCG | 6323 | VHMESYA | 7990 | 105.983 |
| 1345 | TGGTACGAAACAATCAGCCCG | 6324 | WYETISP | 7991 | 105.959 |
| 1346 | CTGTTGGGGGCTCATCAGCCG | 6325 | LLGAHQP | 7992 | 105.9002 |
| 1347 | CACGTACCTAACACTGAAGCA | 6326 | HVPNTEA | 7993 | 105.893 |
| 1348 | AATTCTCAGAATCCTCAGGGT | 6327 | NSQNPQG | 7994 | 105.8895 |
| 1349 | CTACAAGACCGGGCAACGAAC | 6328 | LQDRATN | 7995 | 105.864 |
| 1350 | ATTGTGAATCAGCATTCGGAG | 6329 | IVNQHSE | 7996 | 105.832 |
| 1351 | TTTGAGCAGGGTAAGGTTGAG | 6330 | FEQGKVE | 7997 | 105.811 |
| 1352 | GTGGCGACGGGTGTGTTTGCT | 6331 | VATGVFA | 7998 | 105.808 |
| 1353 | GACAAAATACAAAACGAAACA | 6332 | DKIQNET | 7999 | 105.784 |
| 1354 | ACGGACAACCCGTCCTACAAA | 6333 | TDNPSYK | 8000 | 105.771 |
| 1355 | GGCGTGAACACAAAAATCGAA | 6334 | GVNTKIE | 8001 | 105.7665 |
| 1356 | GGCTCTCACAACGGCCCAGCC | 6335 | GSHNGPA | 8002 | 105.763 |
| 1357 | TCCAACATGGGCGTAGCCTCT | 6336 | SNMGVAS | 8003 | 105.76 |
| 1358 | AACACGGACACTAACGAAAAA | 6337 | NTDTNEK | 8004 | 105.759 |
| 1359 | TCTGCGCTTTTGCGGATGGAT | 6338 | SALLRMD | 8005 | 105.707 |
| 1360 | CCTCAACTAAGCGGCACAGCG | 6339 | PQLSGTA | 8006 | 105.6914 |
| 1361 | TCTATTGTTAATAATGGGGCT | 6340 | SIVNNGA | 8007 | 105.684 |
| 1362 | AGCCTAGACCACGCCCCTCTA | 6341 | SLDHAPL | 8008 | 105.661 |
| 1363 | GACCACTCGAAACAAAACTCT | 6342 | DHSKQNS | 8009 | 105.653 |
| 1364 | CACAGTGACATGGTCAGCGGC | 6343 | HSDMVSG | 8010 | 105.642 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1365 | CAGCATCGTGCGCAGGATGTG | 6344 | QHRAQDV | 8011 | 105.5608 |
| 1366 | GGTAGTACTAAGTCTGGGCAG | 6345 | GSTKSGQ | 8012 | 105.5509 |
| 1367 | ACAATGAGCGTAACTCTGGAA | 6346 | TMSVTLE | 8013 | 105.526 |
| 1368 | TATAATAATGGTGGGCATGTT | 6347 | YNNGGHV | 8014 | 105.516 |
| 1369 | GGTACTGCTGAGAATACGAGT | 6348 | GTAENTS | 8015 | 105.494 |
| 1370 | AATAGTTATGATGCGACGAGG | 6349 | NSYDATR | 8016 | 105.488 |
| 1371 | AGCGTCAACAACATGCGACTC | 6350 | SVNNMRL | 8017 | 105.4477 |
| 1372 | CTTAACTTACAATACACTCTG | 6351 | LNLQYTL | 8018 | 105.443 |
| 1373 | GAGGCGCAGACCGGCTGGGTT | 6352 | EAQTGWV | 8019 | 105.443 |
| 1374 | CCCGCTGAAGGAAACAACCGT | 6353 | PAEGNNR | 8020 | 105.442 |
| 1375 | TCTCTGGGTGGGAATCCGCCT | 6354 | SLGGNPP | 8021 | 105.4335 |
| 1376 | TATAATAGGGATAATGGTTCT | 6355 | YNRDNGS | 8022 | 105.4285 |
| 1377 | TTGACTGATCCTAAGGGGCAG | 6356 | LTDPKGQ | 8023 | 105.404 |
| 1378 | ACCCCAACAGGCACCAACAAA | 6357 | TPTGTNK | 8024 | 105.403 |
| 1379 | GTTCACGCTAACGCTACATTA | 6358 | VHANATL | 8025 | 105.38 |
| 1380 | CGCGAAATAGTGCACTCAAAC | 6359 | REIVHSN | 8026 | 105.376 |
| 1381 | TACGCCGTCGCGATAGGCACA | 6360 | YAVAIGT | 8027 | 105.366 |
| 1382 | AACACAACACCTCCCGACCAC | 6361 | NTTPPDH | 8028 | 105.348 |
| 1383 | GTTATTCAGTCTGATAATACG | 6362 | VIQSDNT | 8029 | 105.32 |
| 1384 | GTTCCGGCGCATTCTCGGGGT | 6363 | VPAHSRG | 8030 | 105.305 |
| 1385 | CAAAACAGTGACCTCGCCAGC | 6364 | QNSDLAS | 8031 | 105.296 |
| 1386 | CGCATCGTAGACACGTTGGGA | 6365 | RIVDTLG | 8032 | 105.2825 |
| 1387 | CACACTTACTCACAAGCAGAC | 6366 | HTYSQAD | 8033 | 105.267 |
| 1388 | ACGGCTCCATCCGTAGGGTCT | 6367 | TAPSVGS | 8034 | 105.259 |
| 1389 | AACGTGGGCACCGACAGAGAC | 6368 | NVGTDRD | 8035 | 105.231 |
| 1390 | GGGATTAATCGTACTAGTGAG | 6369 | GINRTSE | 8036 | 105.2145 |
| 1391 | GTAGAAACAGACAGCTTAATA | 6370 | VETDSLI | 8037 | 105.195 |
| 1392 | CACTCCGCAGCGGGTGACGGT | 6371 | HSAAGDG | 8038 | 105.195 |
| 1393 | GATGCTGGGATTAGTTCTTAT | 6372 | DAGISSY | 8039 | 105.102 |
| 1394 | TGCACCGCCACAAAATGCTCA | 6373 | CTATKCS | 8040 | 105.0959 |
| 1395 | CGCATAGACACTCTCCTAGTC | 6374 | RIDTLLV | 8041 | 105.089 |
| 1396 | GTATCACAATCACACGACGTG | 6375 | VSQSHDV | 8042 | 105.087 |
| 1397 | GCACTACCATCCCACTCCTCC | 6376 | ALPSHSS | 8043 | 105.059 |
| 1398 | GGGAAACCTGCGGAAGCGCCG | 6377 | GKPAEAP | 8044 | 105.055 |
| 1399 | TGGAATAGTCCGGGTGAGGCG | 6378 | WNSPGEA | 8045 | 105.053 |
| 1400 | AGGCTGGAGCGTCCGGATTAT | 6379 | RLERPDY | 8046 | 105.04 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1401 | ACGCGGGAGAGTCTGGTGGAT | 6380 | TRESLVD | 8047 | 105.022 |
| 1402 | AGACACGAAGGTCCGTACTCC | 6381 | RHEGPYS | 8048 | 105.002 |
| 1403 | GTTTTGTCTGATAAGGCGTTT | 6382 | VLSDKAF | 8049 | 104.981 |
| 1404 | ACTAGTGCGACTGATTCGATG | 6383 | TSATDSM | 8050 | 104.908 |
| 1405 | ACTGAGCCGCTTCCGATGTCT | 6384 | TEPLPMS | 8051 | 104.869 |
| 1406 | ATGCCTTACGTCGGGACAGTA | 6385 | MPYVGTV | 8052 | 104.838 |
| 1407 | CGTGATTATTCTCCTACTGAT | 6386 | RDYSPTD | 8053 | 104.836 |
| 1408 | CGGAATGGTGGTACTACGGAT | 6387 | RNGGTTD | 8054 | 104.7625 |
| 1409 | ATGATGGGCGCGACAACGAAA | 6388 | MMGATTK | 8055 | 104.7503 |
| 1410 | GCTGCCGTTGGCGGAGACACC | 6389 | AAVGGDT | 8056 | 104.742 |
| 1411 | CTTGTGAATAATGATGGGACT | 6390 | LVNNDGT | 8057 | 104.7255 |
| 1412 | AGTTCGACTCCGCAGGATACT | 6391 | SSTPQDT | 8058 | 104.713 |
| 1413 | AGTCTGCGGATGGAGAATAGT | 6392 | SLRMENS | 8059 | 104.7025 |
| 1414 | GTGCAGGGGCAGACCGGCTGG | 6393 | VQGQTGW | 8060 | 104.688 |
| 1415 | CTAGGTTTCACACCCCAACCG | 6394 | LGFTPQP | 8061 | 104.677 |
| 1416 | TCGGTTGCTAAGGATCAGACG | 6395 | SVAKDQT | 8062 | 104.675 |
| 1417 | CCGCGGCATGAGTTGAGTAAT | 6396 | PRHELSN | 8063 | 104.645 |
| 1418 | AAAATGGGATCGAACCCCGCA | 6397 | KMGSNPA | 8064 | 104.6241 |
| 1419 | GAGGCGACTCATGGTTCTTAT | 6398 | EATHGSY | 8065 | 104.613 |
| 1420 | CCTGAGGTTGCGTGTCCTGGG | 6399 | PEVACPG | 8066 | 104.595 |
| 1421 | GTGAATACGCGGGAGGTTACG | 6400 | VNTREVT | 8067 | 104.583 |
| 1422 | ACGGCTCGTGCGATTGATATG | 6401 | TARAIDM | 8068 | 104.551 |
| 1423 | ACCGACGGCGCCCTGGGTTAC | 6402 | TDGALGY | 8069 | 104.5325 |
| 1424 | GGGTCGCAATACGCGAACCGC | 6403 | GSQYANR | 8070 | 104.524 |
| 1425 | GAAATGGGTAACCAATACCCA | 6404 | EMGNQYP | 8071 | 104.453 |
| 1426 | CCGTCGACACTCGCTGAAACA | 6405 | PSTLAET | 8072 | 104.449 |
| 1427 | CGCATAGGCGTTGGAGCACCA | 6406 | RIGVGAP | 8073 | 104.4405 |
| 1428 | CTGAGTGTGAAGGAGGAGATT | 6407 | LSVKEEI | 8074 | 104.435 |
| 1429 | TATACTACTCATGAGAGTGGG | 6408 | YTTHESG | 8075 | 104.433 |
| 1430 | CTTACTGCTGTTCTGACTGTT | 6409 | LTAVLTV | 8076 | 104.424 |
| 1431 | CTGCAGACTTCTGTTGCTACT | 6410 | LQTSVAT | 8077 | 104.42 |
| 1432 | ACTGTGCGTTCGCCTCAGCCG | 6411 | TVRSPQP | 8078 | 104.391 |
| 1433 | CATCCTGATGGTACTCGGCCG | 6412 | HPDGTRP | 8079 | 104.375 |
| 1434 | GGAGTAACAATCGGTAGCAGG | 6413 | GVTIGSR | 8080 | 104.3732 |
| 1435 | ACATACGCCTCTACTGAAGCG | 6414 | TYASTEA | 8081 | 104.3675 |
| 1436 | AGGAGTAGTCCTGCGACGAAT | 6415 | RSSPATN | 8082 | 104.355 |
| 1437 | ATCGGGTCGCCGTTGGCCAAC | 6416 | IGSPLAN | 8083 | 104.35 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1438 | GCGTCGACTGAGTCTCATGTG | 6417 | ASTESHV | 8084 | 104.344 |
| 1439 | ATTGCGCAGAATGAGACGTAT | 6418 | IAQNETY | 8085 | 104.336 |
| 1440 | ATGGAGTCTAAGCCGTGGCAG | 6419 | MESKPWQ | 8086 | 104.307 |
| 1441 | TTAGAAAACCCAACACCAGCA | 6420 | LENPTPA | 8087 | 104.305 |
| 1442 | CCCAACCCCAGTCCAAGACAA | 6421 | PNPSPRQ | 8088 | 104.258 |
| 1443 | TCGACTAGTAATCCGCCTTAT | 6422 | STSNPPY | 8089 | 104.242 |
| 1444 | TATTTGACGGATACTCCTACT | 6423 | YLTDTPT | 8090 | 104.241 |
| 1445 | ATACGTGCATTGATGACGGAC | 6424 | IRALMTD | 8091 | 104.237 |
| 1446 | CCTATGGGTACGGATACGGTT | 6425 | PMGTDTV | 8092 | 104.221 |
| 1447 | ACGAGGACTCAGGGGACGTCT | 6426 | TRTQGTS | 8093 | 104.19625 |
| 1448 | TCTAATAATATGAATCAGGCG | 6427 | SNNMNQA | 8094 | 104.187 |
| 1449 | GAAGACTCTGTAAACCACATC | 6428 | EDSVNHI | 8095 | 104.185 |
| 1450 | TCTGTTGTGCCTACGGATAAG | 6429 | SVVPTDK | 8096 | 104.174 |
| 1451 | GTGCGCGGCGTTCAAGACGCC | 6430 | VRGVQDA | 8097 | 104.167 |
| 1452 | CATGATGTGACTGTGCGGAAT | 6431 | HDVTVRN | 8098 | 104.164 |
| 1453 | CATAATAATCATGCGGGTGAG | 6432 | HNNHAGE | 8099 | 104.153 |
| 1454 | GGTAATATGAATCATAGTATT | 6433 | GNMNHSI | 8100 | 104.15 |
| 1455 | GGTGTGCATACTCATACTGTT | 6434 | GVHTHTV | 8101 | 104.139 |
| 1456 | TTTTTGCCGCAGCTGGGGCAG | 6435 | FLPQLGQ | 8102 | 104.094 |
| 1457 | TTGGCCAACATGTCCGCACCA | 6436 | LANMSAP | 8103 | 104.093 |
| 1458 | GTTCGCAGAGACGAAACACCT | 6437 | VRRDETP | 8104 | 104.0585 |
| 1459 | TGCCGCGACAACGTCTTAGCT | 6438 | CRDNVLA | 8105 | 104.046 |
| 1460 | ATGTTGGCTTCTCGGGTGCCT | 6439 | MLASRVP | 8106 | 104.0205 |
| 1461 | GTCAGAACAGTCCTTCAACAA | 6440 | VRTVLQQ | 8107 | 104.017 |
| 1462 | TCGAATCAGAATGTGGATTGG | 6441 | SNQNVDW | 8108 | 104 |
| 1463 | ACTGAGGTTACGGGGGATAGT | 6442 | TEVTGDS | 8109 | 103.965 |
| 1464 | GAAAGTGCCACATCTCTAAAA | 6443 | ESATSLK | 8110 | 103.9355 |
| 1465 | AACCACCCCGCACCAAGCTCA | 6444 | NHPAPSS | 8111 | 103.9235 |
| 1466 | TACGGTAACGCGAACACCGTA | 6445 | YGNANTV | 8112 | 103.92115 |
| 1467 | CAAAACGACAAATCTGACAAC | 6446 | QNDKSDN | 8113 | 103.9165 |
| 1468 | AGTCAGGCTCAGATTCGTGTT | 6447 | SQAQIRV | 8114 | 103.915 |
| 1469 | TTTCAGCGTGATGTTGGTCAT | 6448 | FQRDVGH | 8115 | 103.8651 |
| 1470 | CTGATGAATCGTAATGCTCCT | 6449 | LMNRNAP | 8116 | 103.8648 |
| 1471 | GCGGGCAGTTCGCCATCACGC | 6450 | AGSSPSR | 8117 | 103.8635 |
| 1472 | TTATTCCACAGCCAAATGACC | 6451 | LFHSQMT | 8118 | 103.849 |
| 1473 | ATGATGTCTAACAGCCTCGCG | 6452 | MMSNSLA | 8119 | 103.8275 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1474 | GTTACCACCGTCCTCCAATCA | 6453 | VTTVLQS | 8120 | 103.818 |
| 1475 | GGTAGTCAGCGTGCTATGAAT | 6454 | GSQRAMN | 8121 | 103.8086 |
| 1476 | GCATCCGGCGCACGCTACGTC | 6455 | ASGARYV | 8122 | 103.7981 |
| 1477 | AAAAACTACGACAGTGACTCA | 6456 | KNYDSDS | 8123 | 103.794 |
| 1478 | GTGGGTTCTGGGGTTGGGGTT | 6457 | VGSGVGV | 8124 | 103.793 |
| 1479 | CGTTCTGACCTTACTGAAAGT | 6458 | RSDLTES | 8125 | 103.736 |
| 1480 | AGGGCGGAGTTTATTGATACG | 6459 | RAEFIDT | 8126 | 103.735 |
| 1481 | ACATCTGAAATGCGGACAGCC | 6460 | TSEMRTA | 8127 | 103.725 |
| 1482 | GAGTTGGATCATCTTTCGCAT | 6461 | ELDHLSH | 8128 | 103.714 |
| 1483 | ACACAAGCAGGTCTTGCGTCA | 6462 | TQAGLAS | 8129 | 103.696 |
| 1484 | GCGGCTCAGCATCATGATACG | 6463 | AAQHHDT | 8130 | 103.693 |
| 1485 | GGCGGCGCACACACTCGTGTA | 6464 | GGAHTRV | 8131 | 103.676 |
| 1486 | GCCTACGGTATACACGAAGTG | 6465 | AYGIHEV | 8132 | 103.653 |
| 1487 | GCGATGCTGCGTATGGAGCAG | 6466 | AMLRMEQ | 8133 | 103.652 |
| 1488 | ACGGATCGTTCGCGGCTGGGG | 6467 | TDRSRLG | 8134 | 103.622 |
| 1489 | GAGAGGGAGCCTCCTAAGAAT | 6468 | EREPPKN | 8135 | 103.621 |
| 1490 | GTTGTTAAGGAGATTAAGCTG | 6469 | VVKEIKL | 8136 | 103.6125 |
| 1491 | CACACCGGCCAAACACCATCA | 6470 | HTGQTPS | 8137 | 103.5945 |
| 1492 | GTGTCTCTGAGTTCGCCTCCG | 6471 | VSLSSPP | 8138 | 103.563 |
| 1493 | GGGGCAGGAAACCTGGGTACC | 6472 | GAGNLGT | 8139 | 103.5615 |
| 1494 | GCACGAGACGACACGATACAA | 6473 | ARDDTIQ | 8140 | 103.523 |
| 1495 | GGGACTTATACTAATATGCCG | 6474 | GTYTNMP | 8141 | 103.522 |
| 1496 | ATGCTGGGGGGTTTTGCGCAG | 6475 | MLGGFAQ | 8142 | 103.5051 |
| 1497 | CCATCCGAAATGAGGGCCGTA | 6476 | PSEMRAV | 8143 | 103.503 |
| 1498 | CGTATAAGCCCAGAAAACTCA | 6477 | RISPENS | 8144 | 103.497 |
| 1499 | AAGATGGGTGGTTCTCAGAGT | 6478 | KMGGSQS | 8145 | 103.477 |
| 1500 | GGTTTGATGGCGCATGTGACT | 6479 | GLMAHVT | 8146 | 103.464 |
| 1501 | TCACGTCAAACAGCGCTAACA | 6480 | SRQTALT | 8147 | 103.4599 |
| 1502 | AGTGATCTGAATCTTCCGCCG | 6481 | SDLNLPP | 8148 | 103.455 |
| 1503 | TATGTGTCTGATTATTTGCAT | 6482 | YVSDYLH | 8149 | 103.393 |
| 1504 | ACTAATGATAATAGTGATCGT | 6483 | TNDNSDR | 8150 | 103.374 |
| 1505 | TACTTAATGCACGACAGCGCA | 6484 | YLMHDSA | 8151 | 103.369 |
| 1506 | GGCTCTCGGAACGGACCCACA | 6485 | GSRNGPT | 8152 | 103.3096 |
| 1507 | AAAAACGGTGTTATAAACGAC | 6486 | KNGVIND | 8153 | 103.292 |
| 1508 | GAGTCTGTTGCTAATCTTAAG | 6487 | ESVANLK | 8154 | 103.162 |
| 1509 | GCATCGGACTCGACGACACCA | 6488 | ASDSTTP | 8155 | 103.149 |
| 1510 | CTGAACGTTAGTTCATCCAAA | 6489 | LNVSSSK | 8156 | 103.149 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1511 | GAGGCTAAGGGTTTTGGTCAT | 6490 | EAKGFGH | 8157 | 103.1228 |
| 1512 | GGTACGAGTGCGGAGAGTCGG | 6491 | GTSAESR | 8158 | 103.111 |
| 1513 | ATGCACAACCTACCCTCATAC | 6492 | MHNLPSY | 8159 | 103.10145 |
| 1514 | GTCTTCACAGAAATAGAATCG | 6493 | VFTEIES | 8160 | 103.101 |
| 1515 | ACTCAAACTTCTACCTGGACC | 6494 | TQTSTWT | 8161 | 103.094 |
| 1516 | CCTATGAATAAGGATATTTTG | 6495 | PMNKDIL | 8162 | 103.07 |
| 1517 | AAAGAATCTGAATACAGAGTT | 6496 | KESEYRV | 8163 | 103.07 |
| 1518 | TCGACGAATTCTGAGGCGGTT | 6497 | STNSEAV | 8164 | 103.068 |
| 1519 | GATACGGCGAATCGTTCGACT | 6498 | DTANRST | 8165 | 103.03715 |
| 1520 | CCTAAGGCTCCGCTTAATAAT | 6499 | PKAPLNN | 8166 | 103.032 |
| 1521 | TTAGCTACATACCCCTCCCAC | 6500 | LATYPSH | 8167 | 103.028 |
| 1522 | GCTACGGTTCAGTCGGTTGAT | 6501 | ATVQSVD | 8168 | 103.011 |
| 1523 | AATTCGATGGGTAATGGGGGT | 6502 | NSMGNGG | 8169 | 103.009 |
| 1524 | GATCATAGTGAGCAGAATTCG | 6503 | DHSEQNS | 8170 | 102.995 |
| 1525 | ACTTTTTTGCCTCAGCTTGGG | 6504 | TFLPQLG | 8171 | 102.994 |
| 1526 | GGGTTTACTAATACGAGTAAG | 6505 | GFTNTSK | 8172 | 102.9895 |
| 1527 | ACGATGAATTATAGTCATACT | 6506 | TMNYSHT | 8173 | 102.962 |
| 1528 | AGTATCGGATTCTCAGTAGGC | 6507 | SIGFSVG | 8174 | 102.9565 |
| 1529 | AGTGAGAATCGGGCTGGTAAT | 6508 | SENRAGN | 8175 | 102.945 |
| 1530 | AGTCTTAATCTGCATAGTGTG | 6509 | SLNLHSV | 8176 | 102.93 |
| 1531 | CATGAGAGTCATTATGTTAGT | 6510 | HESHYVS | 8177 | 102.921 |
| 1532 | AATGTTGTTAATGGGATGGAT | 6511 | NVVNGMD | 8178 | 102.908 |
| 1533 | CACTCCGACAAAGTCTCCTCA | 6512 | HSDKVSS | 8179 | 102.8992 |
| 1534 | AAATCTGTAGGCGACGGGAGA | 6513 | KSVGDGR | 8180 | 102.8979 |
| 1535 | AGGCAGGTTGAGCAGTCTGAT | 6514 | RQVEQSD | 8181 | 102.889 |
| 1536 | AGGGAGCTGGTGAATACGGAT | 6515 | RELVNTD | 8182 | 102.87 |
| 1537 | AACTACAGGGACATCACAATG | 6516 | NYRDITM | 8183 | 102.8605 |
| 1538 | GCCAGCCTTGACCGCCTTCCA | 6517 | ASLDRLP | 8184 | 102.857 |
| 1539 | AGACAACTTGCTTCTCTCCCA | 6518 | RQLASLP | 8185 | 102.846 |
| 1540 | GTCAGCAAAACCAAAGACTCG | 6519 | VSKTKDS | 8186 | 102.832 |
| 1541 | AACGTATACGAAGGGCACCGC | 6520 | NVYEGHR | 8187 | 102.815 |
| 1542 | CTAGAACAACTACGGGTCCCA | 6521 | LEQLRVP | 8188 | 102.815 |
| 1543 | ATGACCTACACATCCCCAACC | 6522 | MTYTSPT | 8189 | 102.807 |
| 1544 | AACTCCCACACCGACAGAGGA | 6523 | NSHTDRG | 8190 | 102.801 |
| 1545 | GTGGCTGGGGGGACTTCGGAG | 6524 | VAGGTSE | 8191 | 102.789 |
| 1546 | GTCGACGCACACAGGGCTAAC | 6525 | VDAHRAN | 8192 | 102.77 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1547 | CGGGCAGACATGACTCCCTTA | 6526 | RADMTPL | 8193 | 102.77 |
| 1548 | GGACACGAACAAACTGACGCA | 6527 | GHEQTDA | 8194 | 102.764 |
| 1549 | TACATCGCGGGAGGCGACCAA | 6528 | YIAGGDQ | 8195 | 102.75 |
| 1550 | TACGGCGACCTAACTACAGTC | 6529 | YGDLTTV | 8196 | 102.737 |
| 1551 | AGATTAGACCTGCAAGAACAC | 6530 | RLDLQEH | 8197 | 102.719 |
| 1552 | CACCTTAACCCGGCGGCCCAA | 6531 | HLNPAAQ | 8198 | 102.719 |
| 1553 | GGGGTTAACGAACAAACAAAC | 6532 | GVNEQTN | 8199 | 102.703 |
| 1554 | CGTCGGTTGAGTACGGATCTT | 6533 | RRLSTDL | 8200 | 102.702 |
| 1555 | GGATCCACAGGCCTACCCCCG | 6534 | GSTGLPP | 8201 | 102.7015 |
| 1556 | GACGACATGGTCAAAAACTCA | 6535 | DDMVKNS | 8202 | 102.6815 |
| 1557 | GTTATAGACCTAGTCACTCGC | 6536 | VIDLVTR | 8203 | 102.673 |
| 1558 | GGAGGCCTTACCAACGGTCTA | 6537 | GGLTNGL | 8204 | 102.67 |
| 1559 | CGTATGGAGGAGACTGCTTAT | 6538 | RMEETAY | 8205 | 102.6535 |
| 1560 | ACCGACATCTCCGGTTACGGA | 6539 | TDISGYG | 8206 | 102.642 |
| 1561 | CAGGTTAATCATAATACTAGT | 6540 | QVNHNTS | 8207 | 102.637 |
| 1562 | GCGACTACTGAGGATGTTCGT | 6541 | ATTEDVR | 8208 | 102.626 |
| 1563 | TGGAGCATCAAAAACCAAACA | 6542 | WSIKNQT | 8209 | 102.586 |
| 1564 | TCCCCTACCAGCAACACAATA | 6543 | SPTSNTI | 8210 | 102.584 |
| 1565 | ATGAAAAACTCTGGATTCGAC | 6544 | MKNSGFD | 8211 | 102.583 |
| 1566 | CTTGTTGCTGAGCGTTTGCCG | 6545 | LVAERLP | 8212 | 102.552 |
| 1567 | GGTGAAACTAACTTCCCAACT | 6546 | GETNFPT | 8213 | 102.532 |
| 1568 | AATGGTAAGCTGGGTACGACT | 6547 | NGKLGTT | 8214 | 102.52735 |
| 1569 | AACTTAGTAGCGTACACGAAA | 6548 | NLVAYTK | 8215 | 102.5245 |
| 1570 | TGGCAGCTTACGACGAGTCAT | 6549 | WQLTTSH | 8216 | 102.497 |
| 1571 | AGTTTGGACCTAGGAGGCAAC | 6550 | SLDLGGN | 8217 | 102.491 |
| 1572 | AACGAAAGCACCAAAGAATCT | 6551 | NESTKES | 8218 | 102.483 |
| 1573 | GGTTTTGATGGTAAGCAGCTT | 6552 | GFDGKQL | 8219 | 102.462 |
| 1574 | CATCTGTATATTTCGGCGGAT | 6553 | HLYISAD | 8220 | 102.442 |
| 1575 | TTACTTCCAAACAACACCCAC | 6554 | LLPNNTH | 8221 | 102.424 |
| 1576 | TCCGGAATGGCCGGCCTTTCC | 6555 | SGMAGLS | 8222 | 102.423 |
| 1577 | ATCACCTCACTCCCCGAAACC | 6556 | ITSLPET | 8223 | 102.414 |
| 1578 | GAGCTTAAGGAGAGTCAGAAG | 6557 | ELKESQK | 8224 | 102.408 |
| 1579 | AATATTGTGCAGGATTATCCG | 6558 | NIVQDYP | 8225 | 102.404 |
| 1580 | TCAGAAAACACCTCTGTACCC | 6559 | SENTSVP | 8226 | 102.388 |
| 1581 | GACCCCAACCAACCCAAAACA | 6560 | DPNQPKT | 8227 | 102.376 |
| 1582 | GCGGGTTTGGATGTGAATACG | 6561 | AGLDVNT | 8228 | 102.372 |
| 1583 | TCTCATGAGATGAATAATGGT | 6562 | SHEMNNG | 8229 | 102.366 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1584 | TCTTACGCCATAAACCAATCA | 6563 | SYAINQS | 8230 | 102.335 |
| 1585 | GGTCATCTGCCTGCGGCTAAG | 6564 | GHLPAAK | 8231 | 102.315 |
| 1586 | GAGTTGGGTAATAAGACGGCT | 6565 | ELGNKTA | 8232 | 102.311 |
| 1587 | CTTGAGTCTACTCGTAAGGCT | 6566 | LESTRKA | 8233 | 102.31 |
| 1588 | ACTCAAGGCAACTCTGAAGCA | 6567 | TQGNSEA | 8234 | 102.31 |
| 1589 | ATCTCTATAGACTCCGCTATG | 6568 | ISIDSAM | 8235 | 102.301 |
| 1590 | GAGTTTCAGAGGATTCGTGAG | 6569 | EFQRIRE | 8236 | 102.259 |
| 1591 | GCTAGTCTCTCCGCACCAGCC | 6570 | ASLSAPA | 8237 | 102.227 |
| 1592 | GACAGCCAAATCACAAGACTA | 6571 | DSQITRL | 8238 | 102.218 |
| 1593 | GGCCACGAAAACATGGGCGTG | 6572 | GHENMGV | 8239 | 102.215 |
| 1594 | ATGTCGGCGGGGCATCCTACG | 6573 | MSAGHPT | 8240 | 102.207 |
| 1595 | CACGCTCCAAGCGGCGCCATA | 6574 | HAPSGAI | 8241 | 102.2 |
| 1596 | ACGACTATTACTAATTCGGTT | 6575 | TTITNSV | 8242 | 102.187 |
| 1597 | CCTCAGCATCAGCATGAGCAT | 6576 | PQHQHEH | 8243 | 102.1805 |
| 1598 | CAATACTCGATGGACACGCGC | 6577 | QYSMDTR | 8244 | 102.173 |
| 1599 | CTTTATGAGGTTGGTACTCCT | 6578 | LYEVGTP | 8245 | 102.165 |
| 1600 | GGTGAGACTATGCGTCATAAT | 6579 | GETMRHN | 8246 | 102.119 |
| 1601 | ATGACAATAACCGTCGAACCG | 6580 | MTITVEP | 8247 | 102.096 |
| 1602 | GCGCAGCATCCTGAGCGTTCG | 6581 | AQHPERS | 8248 | 102.084 |
| 1603 | ACGCATGTTGCTAAGCCTGAT | 6582 | THVAKPD | 8249 | 102.082 |
| 1604 | ATGACTGCTAACTTGGTGGAA | 6583 | MTANLVE | 8250 | 102.076 |
| 1605 | AATAGGCAGCGGGATTTTGAG | 6584 | NRQRDFE | 8251 | 102.073 |
| 1606 | TCAAACAGCGCCGACGCGGGG | 6585 | SNSADAG | 8252 | 102.047 |
| 1607 | GGTGAGTATGGTGCGTCGGTT | 6586 | GEYGASV | 8253 | 102.037 |
| 1608 | GACGGCATGGTCAGGTCGACA | 6587 | DGMVRST | 8254 | 102.025 |
| 1609 | AATGGTCAGCTGCTGGCTAAT | 6588 | NGQLLAN | 8255 | 102.023 |
| 1610 | TCCGCGGGGATGACATTGGAC | 6589 | SAGMTLD | 8256 | 102.016 |
| 1611 | GATCATGTGCATCTGACTTAT | 6590 | DHVHLTY | 8257 | 102.008 |
| 1612 | ACGACACTAACGCAAACGGAC | 6591 | TTLTQTD | 8258 | 102.003 |
| 1613 | GTGCAGTTGGCTGATGGGCAT | 6592 | VQLADGH | 8259 | 102.003 |
| 1614 | ACTGACTCATCTGCAGACTCC | 6593 | TDSSADS | 8260 | 101.981 |
| 1615 | GCGATGAATGTGCGGAGTGAT | 6594 | AMNVRSD | 8261 | 101.9805 |
| 1616 | GGTGATATTTCTTATAGGGTT | 6595 | GDISYRV | 8262 | 101.977 |
| 1617 | ATGGGGTATGTTGATAGTCTG | 6596 | MGYVDSL | 8263 | 101.953 |
| 1618 | CTTTATTTGGCGGCGGCTTCG | 6597 | LYLAAAS | 8264 | 101.948 |
| 1619 | TCATCCCCAGACTCGTACAGA | 6598 | SSPDSYR | 8265 | 101.921 |

TABLE 3-continued

MHCK7/CK8 Combined Results mRNA Second Round of Capsid Variant Selection in C57BL6 mice-score capped at 100

| Variant ID for Table | Nucleotide Sequence | SEQ ID NO: | Amino Acid seq. | SEQ ID NO: | Sum of muscle mRNA score_capped at 100 |
|---|---|---|---|---|---|
| 1620 | AGTTATAATGTGGATCTGCAT | 6599 | SYNVDLH | 8266 | 101.892 |
| 1621 | CAACACACCGCCCACCCCATG | 6600 | QHTAHPM | 8267 | 101.892 |
| 1622 | GCAGTTATGGCTACACACCCC | 6601 | AVMATHP | 8268 | 101.87 |
| 1623 | ATTAGTCCGAGTGCTTCTAAT | 6602 | ISPSASN | 8269 | 101.855 |
| 1624 | ACTTTGGATAATAATCATTCT | 6603 | TLDNNHS | 8270 | 101.833 |
| 1625 | AGTGGGTCTTATGTGGCGACG | 6604 | SGSYVAT | 8271 | 101.806 |
| 1626 | ATGGCGGCTCCGCCGGAGCAT | 6605 | MAAPPEH | 8272 | 101.802 |
| 1627 | CAGACTGCGTCTGGTGATACT | 6606 | QTASGDT | 8273 | 101.7725 |
| 1628 | GAGTCTAAGACTGTGGTTATT | 6607 | ESKTVVI | 8274 | 101.7695 |
| 1629 | ACGGTATTACCACAATCAGAC | 6608 | TVLPQSD | 8275 | 101.744 |
| 1630 | CCATTAAACGCGAACGGCTCC | 6609 | PLNANGS | 8276 | 101.7415 |
| 1631 | CCCCTGAACACAGGATTAACC | 6610 | PLNTGLT | 8277 | 101.718 |
| 1632 | GCCATAACGATAATAGGCACT | 6611 | AITIIGT | 8278 | 101.711 |
| 1633 | AATCCTAGTGCGATTAGTTAT | 6612 | NPSAISY | 8279 | 101.687 |
| 1634 | ACAGAACACGAAAAATCCACT | 6613 | TEHEKST | 8280 | 101.66205 |
| 1635 | GCTGAGAGTCAGCTGGCGTCG | 6614 | AESQLAS | 8281 | 101.655 |
| 1636 | GTGCTTAAGGGTACGTTTCCG | 6615 | VLKGTFP | 8282 | 101.652 |
| 1637 | TCGTTCGCCGAAATAACGACT | 6616 | SFAEITT | 8283 | 101.651 |
| 1638 | CCGTTAAACGGCCGCGTAACC | 6617 | PLNGRVT | 8284 | 101.642 |
| 1639 | TCCGAACGCCCCCAATCGTCA | 6618 | SERPQSS | 8285 | 101.579 |
| 1640 | GCTCAGCTTCAGGATTCGGTG | 6619 | AQLQDSV | 8286 | 101.568 |
| 1641 | CCCAACCGTGTAACAGCACCC | 6620 | PNRVTAP | 8287 | 101.5542 |
| 1642 | GCGCTTATTGTTTCGAGTATG | 6621 | ALIVSSM | 8288 | 101.54 |
| 1643 | GCGCATGGTGCTTTTCCGGTT | 6622 | AHGAFPV | 8289 | 101.495 |
| 1644 | GAGGCTTATCAGACTGAGAAG | 6623 | EAYQTEK | 8290 | 101.49 |
| 1645 | GCTGCGGCTTCGCCTTTGGCT | 6624 | AAASPLA | 8291 | 101.484 |
| 1646 | CCCCAAGCCACTCTCAACAAC | 6625 | PQATLNN | 8292 | 101.432 |
| 1647 | ACGAGGGGTGATATGGAGTTT | 6626 | TRGDMEF | 8293 | 101.424 |
| 1648 | AGCAACCTAGGCGAAGCATCT | 6627 | SNLGEAS | 8294 | 101.423 |
| 1649 | GGAATCACCGGAAGCCCCGGC | 6628 | GITGSPG | 8295 | 101.42 |
| 1650 | GGGTTTGAGACGAGTAGTCCT | 6629 | GFETSSP | 8296 | 101.369 |
| 1651 | CCCGCGAGAAGCGACGCCCTT | 6630 | PARSDAL | 8297 | 101.359 |
| 1652 | CATGCTAATTATGTTGAGGTG | 6631 | HANYVEV | 8298 | 101.345 |
| 1653 | GTGACTCGTAGTACGAAGGAG | 6632 | VTRSTKE | 8299 | 101.32381 |
| 1654 | GATGTTGCGTTGAGGTCGAAT | 6633 | DVALRSN | 8300 | 101.254 |
| 1655 | GAGTCTGATTTGCGTCAGCGG | 6634 | ESDLRQR | 8301 | 101.225 |
| 1656 | CCGTTACTCGCAGCGAACCCG | 6635 | PLLAANP | 8302 | 101.207 |

TABLE 3-continued

| MHCK7/CK8 Combined Results mRNA Second Round of Capsid Variant Selection in C57BL6 mice-score capped at 100 | | | | | |
|---|---|---|---|---|---|
| Variant ID for Table | Nucleotide Sequence | SEQ ID NO: | Amino Acid seq. | SEQ ID NO: | Sum of muscle mRNA score_capped at 100 |
| 1657 | ATAAACGCCGCGCACAGGCCC | 6636 | INAAHRP | 8303 | 101.163 |
| 1658 | GCTCGGAGAGACGTAAACTCG | 6637 | ARRDVNS | 8304 | 101.15 |
| 1659 | AGTATGGATAAGGTGGAGAAG | 6638 | SMDKVEK | 8305 | 101.144 |
| 1660 | AACGTCAGCGCACGGGAAACA | 6639 | NVSARET | 8306 | 101.113 |
| 1661 | CTGACGACGGCTGGTATGTGG | 6640 | LTTAGMW | 8307 | 100.9605 |
| 1662 | GCGCGGGCAGAAGGGGTCTTC | 6641 | ARAEGVF | 8308 | 100.9325 |
| 1663 | CCGAGTGATCATATGCGGACT | 6642 | PSDHMRT | 8309 | 100.8849 |
| 1664 | AGTAGGACGGTTATTTTGTCG | 6643 | SRTVILS | 8310 | 100.8697 |
| 1665 | CAGAGTAATGCTGCTGAGGGT | 6644 | QSNAAEG | 8311 | 100.8152 |
| 1666 | TGGACCGAAACGGCCGCTCAC | 6645 | WTETAAH | 8312 | 100.7753 |
| 1667 | AAGGAGAATCAGCTTAGTAAG | 6646 | KENQLSK | 8313 | 100.7556 |

TABLE 4

| RGD Motifs from expression by a CK8 promoter | | |
|---|---|---|
| Rank | Sequence | SEQ ID NO: |
| 1 | RGDLSTP | 13 |
| 2 | RGDLNQY | 14 |
| 3 | RGDLTTP | 15 |
| 4 | RGDATEL | 16 |
| 5 | RGDQLYH | 17 |
| 6 | RGDLSTP | 18 |
| 7 | RGDVAAK | 19 |
| 8 | RGDLTTP | 20 |
| 9 | RGDLNQY | 21 |
| 10 | RGDTMSK | 22 |
| 11 | RGDVAAK | 23 |
| 12 | RGDTMSK | 24 |
| 13 | RGDATEL | 25 |

TABLE 5

| RGD Motifs from expression by MHCK7 promoter | | |
|---|---|---|
| Rank | Sequence | SEQ ID NO: |
| 1 | RGDLTTP | 26 |
| 2 | RGDLNQY | 27 |
| 3 | RGDLSTP | 28 |
| 4 | RGDQLYH | 29 |

TABLE 5-continued

| RGD Motifs from expression by MHCK7 promoter | | |
|---|---|---|
| Rank | Sequence | SEQ ID NO: |
| 5 | RGDTMSK | 30 |
| 6 | RGDATEL | 31 |
| 7 | RGDLSTP | 32 |
| 8 | RGDMINT | 33 |
| 9 | RGDLNQY | 34 |
| 10 | RGDTMSK | 35 |
| 11 | RGDLTTP | 36 |
| 12 | RGDLNDS | 37 |

TABLE 6

| RGD Motifs from expression by MHCK7 and CK8 combined. | | |
|---|---|---|
| Rank | Sequence | SEQ ID NO: |
| 1 | RGDLSTP | 38 |
| 2 | RGDLSTP | 39 |
| 3 | RGDLTTP | 40 |
| 4 | RGDLNQY | 41 |
| 5 | RGDQLYH | 42 |
| 6 | RGDATEL | 43 |
| 7 | RGDTMSK | 44 |
| 8 | RGDLNQY | 45 |

TABLE 6-continued

| RGD Motifs from expression by MHCK7 and CK8 combined. | | |
|---|---|---|
| Rank | Sequence | SEQ ID NO: |
| 9 | RGDLTTP | 46 |
| 10 | RGDMINT | 47 |
| 11 | RGDTMSK | 48 |
| 12 | RGDTMNY | 49 |
| 13 | RGDATEL | 50 |

In some embodiments, the n-mer motif is or includes an "RGD" motif. An "RGD" motif refers to n-mer motifs having the presence of the amino acids R, G, D and as the three consecutive amino acids in that order of the n-mer motif. In some embodiments, the RGD motif can have the general formula $X_m RGDX_n$, where m can be 0-4 amino acids, n can be 0-15 amino acids, and where X is any amino acid, where each amino acid present can each be independently selected from the others and can be selected from the group of any amino acid. It will be appreciated that when m=0 or n=0, that this means that there are no amino acids preceding the "RGD" in the RGD motif and/or there are no amino acids following the "RGD" in the RGD motif. In some embodiments, when m=0, RGD is the first three amino acids of the RGD motif. In some embodiments, when n=0, RGD is the last three amino acids of the RGD motif. In some embodiments, where m=0 and n=0, the RGD motif contains only the amino acids RGD. Exemplary RGD motifs are shown in e.g. Tables 1-6 and 8-9.

In some exemplary embodiments, the RGD motif is $X_1RGDX_2$ (SEQ ID NO: 9100), $X_1RGDX_2X_3$ (SEQ ID NO: 9101), $X_1RGDX_2X_3X_4$ (SEQ ID NO: 9102), $X_1RGDX_2X_3X_4X_5$ (SEQ ID NO: 9103), $X_1RGDX_2X_3X_4X_5X_6$ (SEQ ID NO: 9104), $X_1RGDX_2X_3X_4X_5X_6X_7$ (SEQ ID NO: 9105) $X_1RGDX_2X_3X_4X_5X_6X_7X_8$ (SEQ ID NO: 9106), $X_1RGDX_2X_3X_4X_5X_6X_7X_8X_9$ (SEQ ID NO: 9107), $X_1RGDX_2X_3X_4X_5X_6X_7X_8X_9X_{10}$ (SEQ ID NO: 9108), $X_1RGDX_2X_3X_4X_5X_6X_7X_8X_9X_{10}X_{11}$ (SEQ ID NO: 9109), or $X_1RGDX_2X_3X_4X_5X_6X_7X_8X_9X_{10}X_{11}X_{12}$ (SEQ ID NO: 9110).

In some exemplary embodiments, the RGD motif is $X_1X_2RGDX_3$ (SEQ ID NO: 9111), $X_1X_2RGDX_3X_4$ (SEQ ID NO: 9112), $X_1X_2RGDX_3X_4X_5$ (SEQ ID NO: 9113), $X_1X_2RGDX_3X_4X_5X_6$ (SEQ ID NO: 9114), $X_1X_2RGDX_3X_4X_5X_6X_7$ (SEQ ID NO: 9115), $X_1X_2RGDX_3X_4X_5X_6X_7X_8$ (SEQ ID NO: 9116), $X_1X_2RGDX_3X_4X_5X_6X_7X_8X_9$ (SEQ ID NO: 9117), $X_1X_2RGDX_3X_4X_5X_6X_7X_8X_9X_{10}$ (SEQ ID NO: 9118), $X_1X_2RGDX_3X_4X_5X_6X_7X_8X_9X_{10}X_{11}$ (SEQ ID NO: 9119), or $X_1X_2RGDX_3X_4X_5X_6X_7X_8X_9X_{10}X_{11}X_{12}$ (SEQ ID NO: 9120).

In some exemplary embodiments, the RGD motif is $X_1X_2X_3RGDX_4$ (SEQ ID NO: 9121), $X_1X_2X_3RGDX_4X_5$ (SEQ ID NO: 9122), $X_1X_2X_3RGDX_4X_5X_6$ (SEQ ID NO: 9123), $X_1X_2X_3RGDX_4X_5X_6X_7$ (SEQ ID NO: 9124), $X_1X_2X_3RGDX_4X_5X_6X_7X_8$ (SEQ ID NO: 9125), $X_1X_2X_3RGDX_4X_5X_6X_7X_8X_9$ (SEQ ID NO: 9126), $X_1X_2X_3RGDX_4X_5X_6X_7X_8X_9X_{10}$ (SEQ ID NO: 9127), $X_1X_2X_3RGDX_4X_5X_6X_7X_8X_9X_{10}X_{11}$ (SEQ ID NO: 9128), or $X_1X_2X_3RGDX_4X_5X_6X_7X_8X_9X_{10}X_{11}X_{12}$ (SEQ ID NO: 9129).

In some exemplary embodiments, the RGD motif is $X_1X_2X_3X_4RGDX_5$ (SEQ ID NO: 9130), $X_1X_2X_3X_4RGDX_5X_6$ (SEQ ID NO: 9131), $X_1X_2X_3X_4RGDX_5X_6X_7$ (SEQ ID NO: 9132), $X_1X_2X_3X_4RGDX_5X_6X_7X_8$ (SEQ ID NO: 9133), $X_1X_2X_3X_4RGDX_5X_6X_7X_8X_9$ (SEQ ID NO: 9134), $X_1X_2X_3X_4RGDX_5X_6X_7X_8X_9X_{10}$ (SEQ ID NO: 9135), $X_1X_2X_3X_4RGDX_5X_6X_7X_8X_9X_{10}X_{11}$ (SEQ ID NO: 9136), or $X_1X_2X_3X_4RGDX_5X_6X_7X_8X_9X_{10}X_{11}X_{12}$ (SEQ ID NO: 9137).

In some embodiments, the RGD motif has the amino acids RGD as the first three consecutive amino acids of the n-mer motif (i.e. m=0). In some exemplary embodiments, the n-mer can have a sequence of RGD or $RGDX_n$, where n can be 1-15 amino acids and X can be any amino acid, where each amino acid present can each be independently selected from the others and can be selected from the group of any amino acid. In some embodiments, the n-mer motif can be RGD (3-mer), $RGDX_1$ (4-mer), $RGDX_1X_2$ (5-mer) (SEQ ID NO: 2), $RGDX_1X_2X_3$ (6-mer) (SEQ ID NO: 3), $RGDX_1X_2X_3X_4$ (7 mer) (SEQ ID NO: 4), $RGDX_1X_2X_3X_4X_5$ (8 mer) (SEQ ID NO: 5), $RGDX_1X_2X_3X_4X_5X_6$ (9-mer) (SEQ ID NO: 6), $RGD_1X_2X_3X_4X_5X_6X_7$ (10-mer) (SEQ ID NO: 7), $RGD_1X_2X_3X_4X_5X_6X_7X_8$ (11-mer) (SEQ ID NO: 8), $RGDX_1X_2X_3X_4X_5X_6X_7X_8X_9$ (12-mer) (SEQ ID NO: 9), $RGDX_1X_2X_3X_4X_5X_6X_7X_8X_9X_{10}$ (13-mer) (SEQ ID NO: 10), (SEQ ID NO: 11), or $RGDX_1X_2X_3X_4X_5X_6X_7X_8X_9X_{10}X_{11}$ (14-mer) $RGDX_1X_2X_3X_4X_5X_6X_7X_8X_9X_{10}X_{11}X_{12}$ (15-mer) (SEQ ID NO: 12), where $X_1$, $X_2$, $X_3$, $X_4$, $X_5$, $X_6$, $X_7$, $X_8$, $X_9$, $X_{10}$, $X_{11}$, $X_{12}$ are each be independently selected from any amino acid. In some embodiments, $X_1$ is L, T, A, M, V, Q, or M. In some embodiments, $X_2$ is T, M, S, N, L, A, or I. In some embodiments, $X_3$ is T, E, N, O, S, Q, Y, A, or D. In some embodiments, $X_4$ is P, Y, K, L, H, T, or S. In some embodiments, n-mer motifs including the RGD motif is included in a muscle-specific engineered AAV capsids.

In some embodiments, the n-mer motif can be in any one of Tables 1-6. In some embodiments, the n-mer motif in any of Tables 1-6 and 8-9 can be included in a muscle specific engineered capsid.

In some embodiments, the n-mer motif can be in any one of Tables 4-6. In some embodiments, the n-mer motif in any of Tables 4-6 and 8-9 can be included in a muscle specific engineered capsid.

The muscle-specific targeting moiety can be coupled to or otherwise associated with a cargo. In some embodiments, one or more muscle-specific targeting moieties described herein is directly attached to the cargo. In some embodiments, one or more muscle-specific targeting moieties described herein is indirectly coupled to the cargo, such as via a linker molecule. In some embodiments, one or more one or more muscle-specific targeting moieties described herein is coupled to associated with a polypeptide or other particle that is coupled to, attached to, encapsulates, and/or contains a cargo.

Exemplary particles include, without limitation, viral particles (e.g. viral capsids, which is inclusive of bacteriophage capsids), polysomes, liposomes, nanoparticles, microparticles, exosomes, micelles, and the like. The term "nanoparticle" as used herein includes a nanoscale deposit of a homogenous or heterogeneous material. Nanoparticles may be regular or irregular in shape and may be formed from a plurality of co-deposited particles that form a composite nanoscale particle. Nanoparticles may be generally spherical in shape or have a composite shape formed from a plurality of co-deposited generally spherical particles. Exemplary shapes for the nanoparticles include, but are not limited to, spherical, rod, elliptical, cylindrical, disc, and the like. In some embodiments, the nanoparticles have a substantially spherical shape.

As used herein, the term "specific" when used in relation to described an interaction between two moieties, refers to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

In some embodiments, in addition to the one or more n-mer motifs the targeting moiety can include a polypeptide, a polynucleotide, a lipid, a polymer, a sugar, or a combination thereof.

Engineered Muscle Targeting Viral Capsids

In some embodiments, the muscle engineered muscle-specific targeting moiety is incorporated into a viral capsid protein, which can in turn be incorporated into an engineered viral capsid of an engineered virus particle, thus providing a muscle-specific virus particle. The muscle-specific engineered virus particle can be useful for delivering a cargo to muscle cells. In some embodiments, the targeting moiety is incorporated into a viral protein, such as a capsid protein, including but not limited to lentiviral, adenoviral, AAV, bacteriophage, retroviral proteins. In some embodiments, one or more n-mer motifs (such as an RGD or non-RGD n-mer motif) is located between two amino acids of the viral protein such that one or more of the one or more n-mer motifs are external (i.e. is presented on the surface of) to a viral capsid.

In some embodiments, the composition containing one or more of the muscle-specific targeting moieties described herein has increased muscle cell potency, muscle cell specificity, reduced immunogenicity, or any combination thereof.

Cargos include any molecule that is capable of being coupled to or associated with the muscle-specific targeting moieties described herein. Cargos include, without limitation, nucleotides, oligonucleotides, polynucleotides, amino acids, peptides, polypeptides, riboproteins, lipids, sugars, pharmaceutically active agents (e.g. drugs, imaging and other diagnostic agents, and the like), chemical compounds, and combinations thereof. In some embodiments, the cargo is or includes, DNA, RNA, amino acids, peptide(s), polypeptide(s), antibody(ies), aptamer(s), ribozyme(s), guide sequence(s) for ribozymes that inhibit translation or transcription of essential tumor proteins and genes, hormone(s), immunomodulator(s), antipyretic(s), anxiolytic(s), antipsychotic(s), analgesic(s), antispasmodic(s), anti-inflammatory (ries), anti-histamine(s), anti-infective(s), radiation sensitizer(s), chemotherapeutic(s), radioactive compound(s), imaging agent(s), genetic modifying agent(s), and combinations thereof.

In some embodiments, the cargo is capable of treating or preventing a muscle disease or disorder. In some embodiments, the muscle disease or disorder is (a) an auto immune disease; (b) a cancer; (c) a muscular dystrophy; (d) a neuro-muscular disease; (e) a sugar or glycogen storage disease; (f) an expanded repeat disease; (g) a dominant negative disease; (h) a cardiomyopathy; (i) a viral disease; (j) a progeroid disease; or (k) any combination thereof. In some embodiments, the expanded repeat disease is Huntington's disease, a Myotonic Dystrophy, or Facioscapulohumeral muscular dystrophy (FSHD). In some embodiments, the muscular dystrophy is Duchene muscular dystrophy, Becker Muscular dystrophy, a Limb-Girdle muscular dystrophy, an Emery Dreifuss muscular dystrophy, a myotonic dystrophy, or FSHD. In some embodiments, the myotonic dystrophy is Type 1 or Type 2. In some embodiments, the sugar or glycogen storage disease is a MPS type III disease or Pompe disease. In some embodiments, the MPS type III disease, is MPS Type IIIA, IIIB, IIIC, or IIID. In some embodiments, the neuro-muscular disease is Charcot-Marie-Tooth disease or Friedreich's Ataxia.

In some embodiments, the cargo is a morpholino, a peptide-linked morpholino, an antisense oligonucleotide, a PMO, a therapeutic transgene, a polynucleotide encoding a therapeutic polypeptide or peptide, a PPMO, one or more peptides, one or more polynucleotides encoding a CRISPR-Cas protein, a guide RNA, or both, a ribonucleoprotein, wherein the ribonucleoprotein comprises a CRISPR-Cas system molecule, a therapeutic transgene RNA, or other gene modifying or therapeutic RNA and/or protein, or any combination thereof.

In some embodiments, the cargo is capable of inducing exon skipping in a gene.

In some embodiments, the cargo is capable of inducing exon skipping in a dystrophin gene.

In some embodiments, the cargo is a mini- or micro-dystrophin gene. In some embodiments, the mini- or micro-dystrophin gene comprises spectrin-like repeats 1, 2, 3, 16, 17, and 24, and optionally an nNOS domain.

Engineered Muscle Targeting AAV Capsids and AAVs

In some embodiments, the engineered muscle-specific targeting moiety is incorporated an adeno-associated virus (AAV) capsid. Described herein are various embodiments of engineered AAV capsids that can be engineered to confer cell-specific tropism to an engineered AAV particle. The engineered capsids can be included in an engineered virus particle and can confer cell-specific tropism, reduced immunogenicity, or both to the engineered AAV particle. The engineered AAV capsids described herein can include one or more engineered AAV capsid proteins described herein. In some embodiments, the AAV capsid protein comprises one or more n-mer motifs. In some embodiments, one or more of the n-mer motifs contains or is an RGD motif or a non-RGD n-mer motif. Such motifs are defined and described in greater detail elsewhere herein. In some embodiments, one or more of the one or more n-mer motifs incorporated into one or more AAV capsid proteins can confer muscle specificity to an AAV virus particle having the engineered capsid with the n-mer motif(s).

The engineered AAV capsid and/or capsid proteins can be encoded by one or more engineered AAV capsid polynucleotides. In some embodiments, an engineered AAV capsid polynucleotide can include a 3' polyadenylation signal. The polyadenylation signal can be an SV40 polyadenylation signal.

The engineered AAV capsids can be variants of wild-type AAV capsids. In some embodiments, the wild-type AAV capsids can be composed of VP1, VP2, VP3 capsid proteins or a combination thereof. In other words, the engineered AAV capsids can include one or more variants of a wild-type VP1, wild-type VP2, and/or wild-type VP3 capsid proteins. In some embodiments, the serotype of the reference wild-type AAV capsid can be AAV1, AAV2, AAV3, AAV4, AAV5, AAV6, AAV7, AAV8, AAV rh.74, or AAV rh.10, or any combination thereof. In some embodiments, the serotype of the wild-type AAV capsid can be AAV-9. The engineered AAV capsids can have a different tropism than that of the reference wild-type AAV capsid.

The engineered AAV capsid can contain 1-60 engineered capsid proteins. In some embodiments, the engineered AAV capsids can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, to/or 60 engineered capsid proteins. In some embodiments, the engineered AAV capsid can contain 0-59 wild-type AAV capsid proteins. In some embodiments, the engineered AAV capsid can contain 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, to/or 59 wild-type AAV capsid proteins.

In some embodiments, the engineered AAV capsid protein has an n-mer amino acid motif, where n can be at least 3 amino acids. In some embodiments, n can be 3, 4, 5, 6, 7, 8, 9, 10, 11, 12, 13, 14, or 15 amino acids. In some embodiments, the engineered AAV capsid can have a 6-mer or 7-mer amino acid motif. In some embodiments, the n-mer amino acid motif is inserted between two amino acids in the wild-type viral protein (VP) (or capsid protein). In some embodiments, the n-mer motif can be inserted between two amino acids in a variable amino acid region in an AAV capsid protein. The core of each wild-type AAV viral protein contains an eight-stranded beta-barrel motif (betaB to betaI) and an alpha-helix (alphaA) that are conserved in autonomous parvovirus capsids (see e.g. DiMattia et al. 2012. J. Virol. 86 (12): 6947-6958). Structural variable regions (VRs) occur in the surface loops that connect the beta-strands, which cluster to produce local variations in the capsid surface. AAVs have 12 variable regions (also referred to as hypervariable regions) (see e.g. Weitzman and Linden. 2011. "Adeno-Associated Virus Biology." In Snyder, R. O., Moullier, P. (eds.) Totowa, NJ: Humana Press). In some embodiments, one or more n-mer motifs are inserted between two amino acids in one or more of the 12 variable regions in the wild-type AAV capsid proteins. In some embodiments, the one or more n-mer motifs are each inserted between two amino acids in VR-I, VR-II, VR-III, VR-IV, VR-V, VR-VI, VR-VII, VR-III, VR-IX, VR-X, VR-XI, VR-XII, or a combination thereof. In some embodiments, the n-mer is be inserted between two amino acids in the VR-III of a capsid protein. In some embodiments, the engineered capsid can have an n-mer inserted between any two contiguous amino acids between amino acids 262 and 269, between any two contiguous amino acids between amino acids 327 and 332, between any two contiguous amino acids between amino acids 382 and 386, between any two contiguous amino acids between amino acids 452 and 460, between any two contiguous amino acids between amino acids 488 and 505, between any two contiguous amino acids between amino acids 545 and 558, between any two contiguous amino acids between amino acids 581 and 593, between any two contiguous amino acids between amino acids 704 and 714 of an AAV9 viral protein. In some embodiments, the engineered capsid can have an n-mer inserted between amino acids 588 and 589 of an AAV9 viral protein. In some embodiments, the engineered capsid can have a 7-mer motif inserted between amino acids 588 and 589 of an AAV9 viral protein. SEQ ID NO: 1 is a reference AAV9 capsid sequence for at least referencing the insertion sites discussed above. It will be appreciated that n-mers can be inserted in analogous positions in AAV viral proteins of other serotypes. In some embodiments as previously discussed, the n-mer(s) can be inserted between any two contiguous amino acids within the AAV viral protein and in some embodiments the insertion is made in a variable region.

```
AAV9 capsid reference sequence.
                                        SEQ ID NO: 1
MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPFHSSYAHSQSLDRLMNPLIDQYLYYLSKT

INGSGQNQQTLKFSVAGPSNMAVQGRNYIPGPSYRQQRVSTTVTQNNNSE

FAWPGASSWALNGRNSLMNPGPAMASHKEGEDRFFPLSGSLIFGKQGTGR

DNVDADKVMITNEEEIKTTNPVATESYGQVATNHQSAQAQAQTGWVQNQG

ILPGMVWQDRDVYLQGPIWAKIPHTDGNFHPSPLMGGFGMKHPPPQILIK

NTPVPADPPTAFNKDKLNSFITQYSTGQVSVEIEWELQKENSKRWNPEIQ

YTSNYYKSNNVEFAVNTEGVYSEPRPIGTRYLTRNL
```

In some embodiments, the n-mer motif can be any amino acid motif as shown or encoded by a nucleic acid as shown in Tables 1-3. In some embodiments, insertion of the n-mer motif in an AAV capsid can result in cell, tissue, organ, specific engineered AAV capsids. In some embodiments, the engineered capsid has a specificity (or tropism) for muscle cells. In some embodiments, the engineered capsid can have a specificity for bone tissue and/or cells, lung tissue and/or cells, liver tissues and/or cells, bladder tissue and/or cells, kidney tissue and/or cells, cardiac tissue and/or cells, skeletal muscle tissue and/or cells, smooth muscle and/or cells, neuronal tissue and/or cells, intestinal tissue and/or cells, pancreases tissue and/or cells, adrenal gland tissue and/or cells, brain tissue and/or cells, tendon tissues or cells, skin tissues and/or cells, spleen tissue and/or cells, eye tissue and/or cells, blood cells, synovial fluid cells, immune cells (including specificity for particular types of immune cells), and combinations thereof.

In some embodiments, the AAV capsids are muscle-specific. In some embodiments, muscle-specificity of the engineered AAV capsid is conferred by a muscle specific n-mer motif incorporated in the engineered AAV capsid. While not intending to be bound by theory, it is believed that the n-mer motif confers a 3D structure to or within a domain or region of the engineered AAV capsid such that the interaction of an engineered AAV containing said engineered AAV capsid has increased or improved interactions (e.g. increased affinity) with a cell surface receptor and/or other molecule on the surface of a muscle cell. In some embodiments, the cell surface receptor is AAV receptor (AAVR). In some embodiments, the cell surface receptor is a muscle cell specific AAV receptor. In some embodiments, a muscle specific engineered AAV containing the muscle-specific capsid can have an increased transduction rate, efficiency, amount, or a combination thereof in a muscle cell as compared to other cells types and/or other AAVs that do not contain a muscle-specific engineered AAV capsid as described herein.

Methods of Generating Muscle Specific Targeting Moieties

Figure 6:
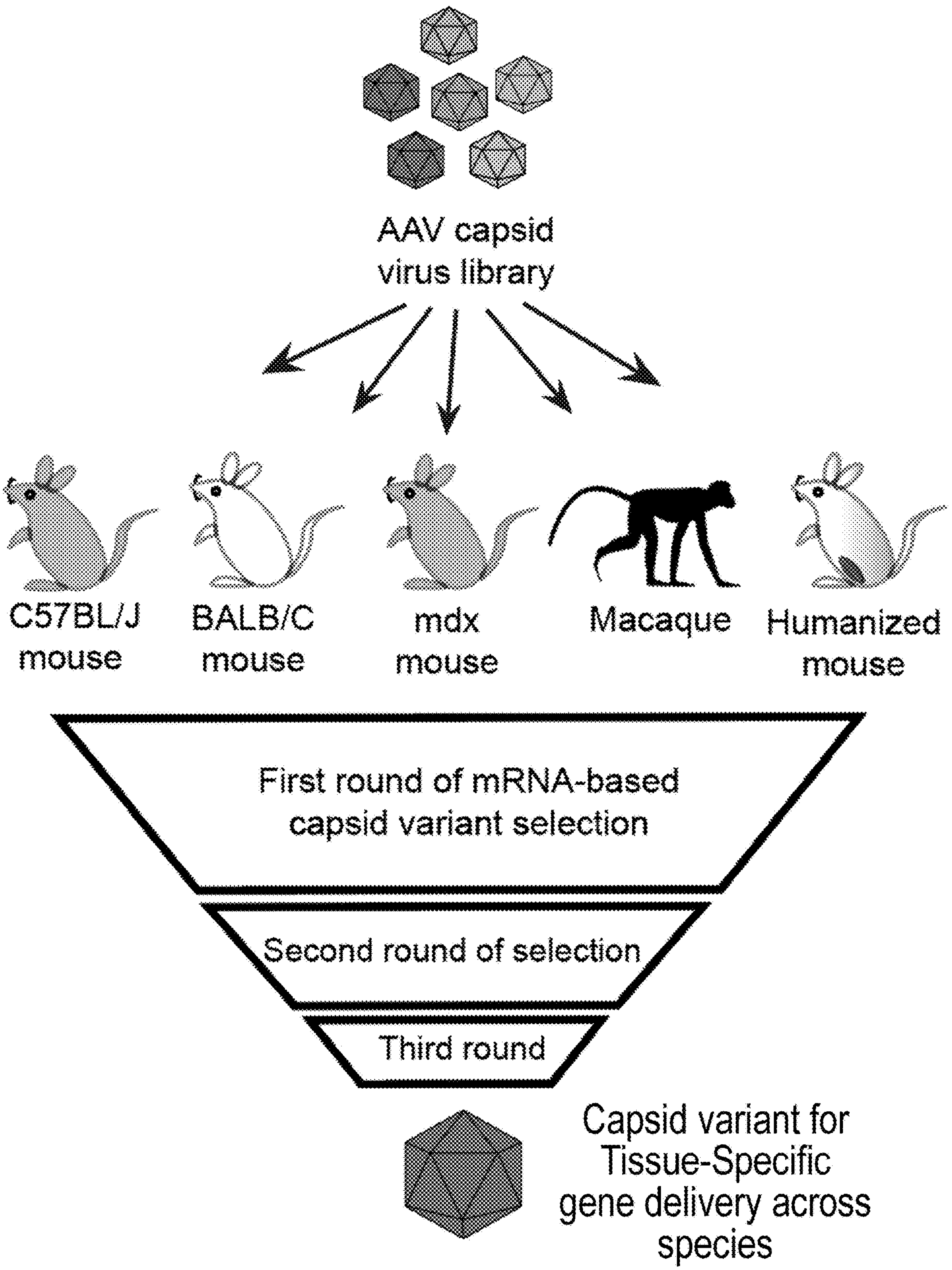
FIG. 6 shows a schematic demonstrating embodiments of a method of producing and selecting capsid variants for tissue-specific gene delivery across species.
Figure 7:
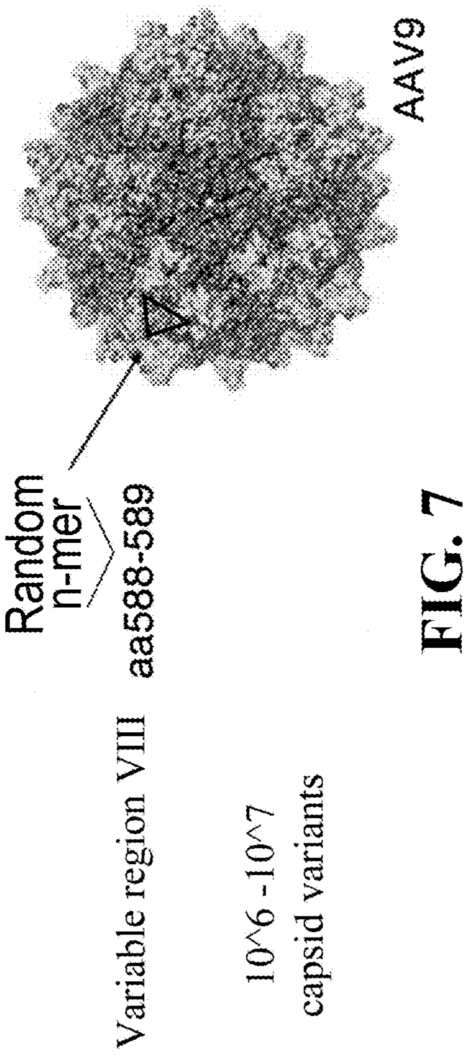
FIG. 7 shows a schematic demonstrating embodiments of generating an AAV capsid variant library, particularly insertion of a random n-mer (n=3-15 amino acids) into a wild-type AAV, e.g. AAV9.
Figure 8:
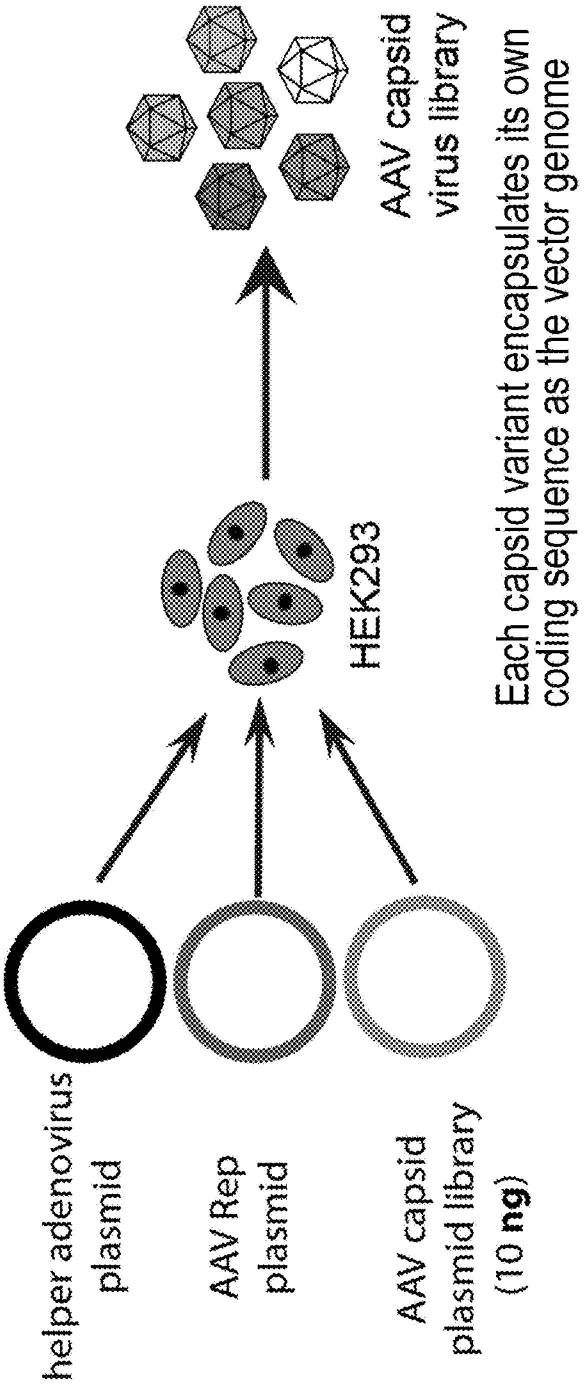
FIG. 8 shows a schematic demonstrating embodiments of generating an AAV capsid variant library, particularly variant AAV particle production. Each capsid variant encapsulates its own coding sequence as the vector genome.

Also provided herein are methods of generating engineered AAV capsids. The engineered AAV capsid variants can be variants of wild-type AAV capsids. FIGS. 6-8 can illustrate various embodiments of methods capable of generating engineered AAV capsids described herein. Generally, an AAV capsid library can be generated by expressing engineered capsid vectors each containing an engineered AAV capsid polynucleotide previously described in an appropriate AAV producer cell line. See e.g. FIG. 8. It will be appreciated that although FIG. 8 shows a helper-dependent method of AAV particle production, it will be appreciated that this can be done via a helper-free method as well. This can generate an AAV capsid library that can contain one more desired cell-specific engineered AAV capsid variant. As shown in FIG. 6 the AAV capsid library can be administered to various non-human animals for a first round of mRNA-based selection. As shown in FIG. 1, the transduction process by AAVs and related vectors can result in the production of an mRNA molecule that is reflective of the genome of the virus that transduced the cell. As is at least demonstrated in the Examples herein, mRNA based-selection can be more specific and effective to determine a virus particle capable of functionally transducing a cell because it is based on the functional product produced as opposed to just detecting the presence of a virus particle in the cell by measuring the presence of viral DNA.

After first-round administration, one or more engineered AAV virus particles having a desired capsid variant can then be used to form a filtered AAV capsid library. Desirable AAV virus particles can be identified by measuring the mRNA expression of the capsid variants and determining which variants are highly expressed in the desired cell type(s) as compared to non-desired cells type(s). Those that are highly expressed in the desired cell, tissue, and/or organ type are the desired AAV capsid variant particles. In some embodiments, the AAV capsid variant encoding polynucleotide is under control of a tissue-specific promoter that has selective activity in the desired cell, tissue, or organ.

The engineered AAV capsid variant particles identified from the first round can then be administered to various non-human animals. In some embodiments, the animals used in the second round of selection and identification are not the same as those animals used for first round selection and identification. Similar to round 1, after administration the top expressing variants in the desired cell, tissue, and/or organ type(s) can be identified by measuring viral mRNA expression in the cells. The top variants identified after round two can then be optionally barcoded and optionally pooled. In some embodiments, top variants from the second round can then be administered to a non-human primate to identify the top cell-specific variant(s), particularly if the end use for the top variant is in humans. Administration at each round can be systemic.

In some embodiments, the method of generating an AAV capsid variant can include the steps of: (a) expressing a vector system described herein that contains an engineered AAV capsid polynucleotide in a cell to produce engineered AAV virus particle capsid variants; (b) harvesting the engineered AAV virus particle capsid variants produced in step (a); (c) administering engineered AAV virus particle capsid variants to one or more first subjects, wherein the engineered AAV virus particle capsid variants are produced by expressing an engineered AAV capsid variant vector or system thereof in a cell and harvesting the engineered AAV virus particle capsid variants produced by the cell; and (d) identifying one or more engineered AAV capsid variants produced at a significantly high level by one or more specific cells or specific cell types in the one or more first subjects. In this context, "significantly high" can refer to a titer that can range from between about $2\times10^{11}$ to about $6\times10^{12}$ vector genomes per 15 cm dish.

The method can further include the steps of: (e) administering some or all engineered AAV virus particle capsid variants identified in step (d) to one or more second subjects; and (f) identifying one or more engineered AAV virus particle capsid variants produced at a significantly high level in one or more specific cells or specific cell types in the one or more second subjects. The cell in step (a) can be a prokaryotic cell or a eukaryotic cell. In some embodiments, the administration in step (c), step (e), or both is systemic. In some embodiments, one or more first subjects, one or more second subjects, or both, are non-human mammals. In some embodiments, one or more first subjects, one or more second subjects, or both, are each independently selected from the group consisting of: a wild-type non-human mammal, a humanized non-human mammal, a disease-specific non-human mammal model, and a non-human primate.

Other methods and details of developing muscle-specific targeting moieties are described in, for example, U.S. Provisional Application Ser. Nos. 62/899,453, 62/916,207, 63/018,454, 63/055,252, and 62/916,221 and International Application No. PCT/US20/50534.

Engineered Muscle-Specific Targeting Moiety Encoding Polynucleotides, Vectors, and Vector Systems Described herein are polynucleotides that encode the one or more muscle-specific engineered targeting moieties and vectors and/or vector systems thereof. In some embodiments, the encoding polynucleotides, vectors, and/or vector systems can be used to express and/or produce the engineered muscle-specific targeting moieties, couple the engineered muscle-specific targeting moiety to one or more other polypeptides, and/or produce particles, such as viral particles that optionally contain a cargo, that include one or more engineered muscle-specific targeting moieties described herein. The term "engineered muscle-specific targeting moiety polynucleotide" as used herein refers to a polynucleotide that encodes an engineered muscle-specific targeting moiety. As used herein, the term "encode" refers to principle that DNA can be transcribed into RNA, which can then be translated into amino acid sequences that can form proteins. Thus, polynucleotides said to encode a subsequent polynucleotide (such as an RNA species) or proteins can also be referred to as encoding polynucleotides and refer to DNA molecules that are subsequently transcribed and/or translated as well as RNA molecules that are translated.

Also provided herein are vectors and vector systems that can contain one or more of the engineered muscle-specific targeting moiety polynucleotides (including, but not limited to, engineered AAV capsid polynucleotides) described herein. As used in this context, engineered AAV capsid polynucleotides refers to any one or more of the polynucleotides described herein capable of encoding an engineered AAV capsid as described elsewhere herein and/or polynucleotide(s) capable of encoding one or more engineered AAV capsid proteins described elsewhere herein. Further, where the vector includes an engineered muscle-specific targeting moiety polynucleotide (including, but not limited to, an engineered AAV capsid polynucleotide) described herein, the vector can also be referred to and considered an engineered vector or system thereof although not specifically noted as such. In embodiments, the vector can contain one or more polynucleotides encoding one or more elements of an engineered viral capsid, such as an AAV capsid, described herein. The vectors and systems thereof can be useful in producing bacterial, fungal, yeast, plant cells, animal cells, and transgenic animals that can express a muscle-specific targeting moiety or composition containing a muscle-specific targeting moiety described herein. In some embodiments, the vectors and systems thereof can be useful in producing bacterial cells, fungal cells, yeast cells, plant cells, animal cells, or transgenic organisms (e.g. plants, animals) that can express the one or more components of the engineered AAV capsid described herein. Within the scope of this disclosure are vectors containing one or more of the polynucleotide sequences described herein. One or more of the polynucleotides that are part of the engineered AAV capsid and system thereof described herein can be included in a vector or vector system.

The vectors and/or vector systems can be used, for example, to express one or more of the engineered muscle-specific targeting moiety polynucleotides (including, but not limited to, engineered AAV capsid polynucleotides) in a cell, such as a producer cell, to produce engineered viral particles containing an engineered viral capsid (e.g. an AAV containing an engineered AAV capsid) described elsewhere herein. Other uses for the vectors and vector systems described herein are also within the scope of this disclosure. In general, and throughout this specification, the term is a tool that allows or facilitates the transfer of an entity from one environment to another. In some contexts which will be appreciated by those of ordinary skill in the art, "vector" can be a term of art to refer to a nucleic acid molecule capable of transporting another nucleic acid to which it has been linked. A vector can be a replicon, such as a plasmid, phage, or cosmid, into which another DNA segment may be inserted so as to bring about the replication of the inserted segment. Generally, a vector is capable of replication when associated with the proper control elements.

Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can be composed of a nucleic acid (e.g. a polynucleotide) of the invention in a form suitable for expression of the nucleic acid in a host cell, which means that the recombinant expression vectors include one or more regulatory elements, which can be selected on the basis of the host cells to be used for expression, that is operatively-linked to the nucleic acid sequence to be expressed. Within a recombinant expression vector, "operably linked" and "operatively-linked" are used interchangeably herein and further defined elsewhere herein. In the context of a vector, the term "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Advantageous vectors include adeno-associated viruses, and types of such vectors can also be selected for targeting particular types of cells, such as those engineered AAV vectors containing an engineered AAV capsid polynucleotide with a desired cell-specific tropism, such as a muscle-specific tropism. These and other embodiments of the vectors and vector systems are described elsewhere herein.

In some embodiments, the vector can be a bicistronic vector. In some embodiments, a bicistronic vector can be used for expressing one or more engineered muscle-specific targeting moiety polynucleotides (including, but not limited to, engineered AAV capsid polynucleotides) system described herein. In some embodiments, expression of an engineered muscle-specific targeting moiety polynucleotides (including, but not limited to, engineered AAV capsid polynucleotides) described herein can be driven by the suitable constitutive or tissue specific promoter. Such embodiments can be advantageous for generating muscle-specific targeting moieties, which are described in greater detail elsewhere herein. Where the element of the engineered AAV capsid system is an RNA, its expression can be driven by a Pol III promoter, such as a U6 promoter. In some embodiments, the two are combined.

Cell-Based Vector Amplification and Expression

Vectors can be designed for expression of one or more engineered muscle-specific targeting moiety polynucleotides (including, but not limited to, engineered AAV capsid polynucleotides) or a system including one or more engineered muscle-specific targeting moiety polynucleotides (including, but not limited to, engineered AAV capsid polynucleotides) or product thereof described herein (e.g. nucleic acid transcripts, proteins, enzymes, and combinations thereof) in a suitable host cell. In some embodiments, the suitable host cell is a prokaryotic cell. Suitable host cells include, but are not limited to, bacterial cells, yeast cells, insect cells, and mammalian cells. The vectors can be viral-based or non-viral based. In some embodiments, the suitable host cell is a eukaryotic cell. In some embodiments, the suitable host cell is a suitable bacterial cell. Suitable bacterial cells include, but are not limited to, bacterial cells from the bacteria of the species *Escherichia coli*. Many suitable strains of *E. coli* are known in the art for expression of vectors. These include, but are not limited to Pir1, Stb12, Stb13, Stb14, TOP10, XL1 Blue, and XL10 Gold. In some embodiments, the host cell is a suitable insect cell. Suitable insect cells include those from *Spodoptera frugiperda*. Suitable strains of *S. frugiperda* cells include, but are not limited to, Sf9 and Sf21. In some embodiments, the host cell is a suitable yeast cell. In some embodiments, the yeast cell can be from *Saccharomyces cerevisiae*. In some embodiments, the host cell is a suitable mammalian cell. Many types of mammalian cells have been developed to express vectors. Suitable mammalian cells include, but are not limited to, HEK293, Chinese Hamster Ovary Cells (CHOs), mouse myeloma cells, HeLa, U2OS, A549, HT1080, CAD, P19, NIH 3T3, L929, N2a, MCF-7, Y79, SO-Rb50, HepG G2, DIKX-X11, J558L, Baby hamster kidney cells (BHK), and chicken embryo fibroblasts (CEFs). Suitable host cells are discussed further in Goeddel, GENE EXPRESSION TECHNOLOGY: METHODS IN ENZYMOLOGY 185, Academic Press, San Diego, Calif. (1990).

In some embodiments, the vector can be a yeast expression vector. Examples of vectors for expression in yeast *Saccharomyces cerevisiae* include pYepSecl (Baldari, et al., 1987. EMBO J. 6:229-234), pMFa (Kuijan and Herskowitz, 1982. Cell 30:933-943), pJRY88 (Schultz et al., 1987. Gene 54:113-123), pYES2 (Invitrogen Corporation, San Diego, Calif.), and picZ (In Vitrogen Corp, San Diego, Calif.). As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in Yeast Protocols, 2nd edition, Xiao, W., ed. (Humana Press, New York, 2007) and Buckholz, R. G. and Gleeson, M. A. (1991) Biotechnology (NY) 9 (11): 1067-72. Yeast vectors can contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2μ plasmids, yeast integrative plasmids, yeast replicative plasmids, shuttle vectors, and episomal plasmids.

In some embodiments, the vector is a baculovirus vector or expression vector and can be suitable for expression of polynucleotides and/or proteins in insect cells. Baculovirus vectors available for expression of proteins in cultured insect cells (e.g., SF9 cells) include the pAc series (Smith, et al., 1983. Mol. Cell. Biol. 3:2156-2165) and the pVL series (Lucklow and Summers, 1989. Virology 170:31-39). rAAV (recombinant Adeno-associated viral) vectors are preferably produced in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

In some embodiments, the vector is a mammalian expression vector. In some embodiments, the mammalian expression vector is capable of expressing one or more polynucleotides and/or polypeptides in a mammalian cell. Examples of mammalian expression vectors include, but are not limited to, pCDM8 (Seed, 1987. Nature 329:840) and pMT2PC (Kaufman, et al., 1987. EMBO J. 6:187-195). The mammalian expression vector can include one or more suitable regulatory elements capable of controlling expression of the one or more polynucleotides and/or proteins in the mammalian cell. For example, commonly used promoters are derived from polyoma, adenovirus 2, cytomegalovirus, simian virus 40, and others disclosed herein and known in the art. More detail on suitable regulatory elements are described elsewhere herein.

For other suitable expression vectors and vector systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1:268-277), lymphoid-specific promoters (Calame and Eaton, 1988. *Adv. Immunol.* 43:235-275), in particular promoters of T cell receptors (Winoto and Baltimore, 1989. *EMBO*) *J.* 8:729-733) and immunoglobulins (Baneiji, et al., 1983. *Cell* 33:729-740; Queen and Baltimore, 1983. *Cell* 33:741-748), neuron-specific promoters (e.g., the neurofilament promoter; Byrne and Ruddle, 1989. *Proc. Natl. Acad. Sci. USA* 86:5473-5477), pancreas-specific promoters (Edlund, et al., 1985. *Science* 230:912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249:374-379) and the α-fetoprotein promoter (Campes and Tilghman, 1989. *Genes Dev.* 3:537-546). With regards to these prokaryotic and eukaryotic vectors, mention is made of U.S. Pat. No. 6,750,059, the contents of which are incorporated by reference herein in their entirety. Other embodiments can utilize viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element can be operably linked to or coupled to one or more engineered muscle-specific targeting moiety polynucleotides (including, but not limited to, engineered AAV capsid polynucleotides) and/or one or more elements of a system comprising one or more engineered muscle-specific targeting moiety polynucleotides (including, but not limited to, engineered AAV capsid polynucleotides) or product thereof so as to drive expression of the one or more elements of the engineered muscle-specific targeting moiety polynucleotides (including, but not limited to, engineered AAV capsid polynucleotides) or system thereof described herein.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism.

In some embodiments, the vector can be a fusion vector or fusion expression vector. In some embodiments, fusion vectors add a number of amino acids to a protein encoded therein, such as to the amino terminus, carboxy terminus, or both of a recombinant protein. Such fusion vectors can serve one or more purposes, such as: (i) to increase expression of recombinant protein; (ii) to increase the solubility of the recombinant protein; and (iii) to aid in the purification of the recombinant protein by acting as a ligand in affinity purification. In some embodiments, expression of polynucleotides (such as non-coding polynucleotides) and proteins in prokaryotes can be carried out in *Escherichia coli* with vectors containing constitutive or inducible promoters directing the expression of either fusion or non-fusion polynucleotides and/or proteins. In some embodiments, the fusion expression vector can include a proteolytic cleavage site, which can be introduced at the junction of the fusion vector backbone or other fusion moiety and the recombinant polynucleotide or protein to enable separation of the recombinant polynucleotide or protein from the fusion vector backbone or other fusion moiety subsequent to purification of the fusion polynucleotide or protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, one or more vectors driving expression of one or more engineered muscle-specific targeting moiety polynucleotides (including, but not limited to, engineered AAV capsid polynucleotides), vector, and/or vector system thereof described herein are introduced into a host cell such that expression of one or more the engineered muscle-specific targeting moiety polynucleotides (including, but not limited to, engineered AAV capsid polynucleotides), vectors, and/or vector systems described herein direct formation of an engineered muscle-specific targeting moiety and/or compositions or engineered muscle-specific delivery systems that include one or more engineered muscle-specific targeting moieties described herein. In some embodiments, the engineered muscle-specific delivery system is a viral particle such as an engineered AAV particle that contains an engineered capsid that contains one or more engineered muscle-specific targeting moieties described elsewhere herein. For example, different elements of an engineered muscle-specific delivery system can each be operably linked to separate regulatory elements on the same or separate vectors. RNA(s) of different elements of the engineered muscle-specific delivery system described herein that can include one or more engineered muscle-specific targeting moiety can be delivered to an animal or mammal or cell thereof to produce an animal or mammal or cell thereof that constitutively, inducibly, or conditionally expresses different elements of the engineered muscle-specific delivery system described herein or contains one or more cells that incorporates and/or expresses one or more elements of the engineered muscle-specific delivery system described herein.

In some embodiments, two or more of the elements expressed from the same or different regulatory element(s) can be combined in a single vector along with one or more additional vectors providing any components of the system not included in the first vector. Engineered muscle-specific delivery system polynucleotides (including but not limited to engineered muscle-specific targeting moiety polynucleotides) that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding one or more engineered muscle-specific targeting moiety polynucleotides, embedded within one or more intron sequences (e.g., each in a different intron, two or more in at least one intron, or all in a single intron). In some embodiments, two or more engineered muscle-specific targeting moiety polynucleotides can be operably linked to and expressed from the same promoter.

Vector Features

The vectors can include additional features that can confer one or more functionalities to the vector, the polynucleotide to be delivered, a virus particle produced there from, or polypeptide expressed thereof. Such features include, but are not limited to, regulatory elements, selectable markers, molecular identifiers (e.g. molecular barcodes), stabilizing elements, and the like. It will be appreciated by those skilled in the art that the design of the expression vector and additional features included can depend on such factors as the choice of the host cell to be transformed, the level of expression desired, etc.

Regulatory Elements

In embodiments, the polynucleotides and/or vectors thereof described herein (such as the engineered muscle-specific targeting moiety polynucleotides of the present invention) can include one or more regulatory elements that can be operatively linked to the polynucleotide. The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter can direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8 (1), p. 466-472, 1988); SV40 enhancer; and the intron sequence between exons 2 and 3 of rabbit β-globin (Proc. Natl. Acad. Sci. USA., Vol. 78 (3), p. 1527-31, 1981).

In some embodiments, the regulatory sequence can be a regulatory sequence described in U.S. Pat. No. 7,776,321, U.S. Pat. Pub. No. 2011/0027239, and PCT publication WO 2011/028929, the contents of which are incorporated by reference herein in their entirety. In some embodiments, the vector can contain a minimal promoter. In some embodiments, the minimal promoter is the Mecp2 promoter, tRNA promoter, or U6. In a further embodiment, the minimal promoter is tissue specific. In some embodiments, the length of the vector polynucleotide the minimal promoters and polynucleotide sequences is less than 4.4 Kb.

To express a polynucleotide, the vector can include one or more transcriptional and/or translational initiation regulatory sequences, e.g. promoters, that direct the transcription of the gene and/or translation of the encoded protein in a cell. In some embodiments a constitutive promoter may be employed. Suitable constitutive promoters for mammalian cells are generally known in the art and include, but are not limited to SV40, CAG, CMV, EF-1α, β-actin, RSV, and PGK. Suitable constitutive promoters for bacterial cells, yeast cells, and fungal cells are generally known in the art, such as a T-7 promoter for bacterial expression and an alcohol dehydrogenase promoter for expression in yeast.

In some embodiments, the regulatory element can be a regulated promoter. "Regulated promoter" refers to promoters that direct gene expression not constitutively, but in a temporally- and/or spatially-regulated manner, and includes tissue-specific, tissue-preferred and inducible promoters. In some embodiments, the regulated promoter is a tissue specific promoter as previously discussed elsewhere herein. Regulated promoters include conditional promoters and inducible promoters. In some embodiments, conditional promoters can be employed to direct expression of a polynucleotide in a specific cell type, under certain environmental conditions, and/or during a specific state of development. Suitable tissue specific promoters can include, but are not limited to, liver specific promoters (e.g. APOA2, SERPIN A1 (hAAT), CYP3A4, and MIR122), pancreatic cell promoters (e.g. INS, IRS2, Pdx1, Alx3, Ppy), cardiac specific promoters (e.g. Myh6 (alpha MHC), MYL2 (MLC-2v), TNI3 (cTn1), NPPA (ANF), Slc8a1 (Ncx1)), central nervous system cell promoters (SYN1, GFAP, INA, NES, MOBP, MBP, TH, FOXA2 (HNF3 beta)), skin cell specific promoters (e.g. FLG, K14, TGM3), immune cell specific promoters, (e.g. ITGAM, CD43 promoter, CD14 promoter, CD45 promoter, CD68 promoter), urogenital cell specific promoters (e.g. Pbsn, Upk2, Sbp, Fer114), endothelial cell specific promoters (e.g. ENG), pluripotent and embryonic germ layer cell specific promoters (e.g. Oct4, NANOG, Synthetic Oct4, T brachyury, NES, SOX17, FOXA2, MIR122), and muscle cell specific promoter (e.g. Desmin). Other tissue and/or cell specific promoters are discussed elsewhere herein and can be generally known in the art and are within the scope of this disclosure.

Inducible/conditional promoters can be positively inducible/conditional promoters (e.g. a promoter that activates transcription of the polynucleotide upon appropriate interaction with an activated activator, or an inducer (compound, environmental condition, or other stimulus) or a negative/conditional inducible promoter (e.g. a promoter that is repressed (e.g. bound by a repressor) until the repressor condition of the promotor is removed (e.g. inducer binds a repressor bound to the promoter stimulating release of the promoter by the repressor or removal of a chemical repressor from the promoter environment). The inducer can be a compound, environmental condition, or other stimulus. Thus, inducible/conditional promoters can be responsive to any suitable stimuli such as chemical, biological, or other molecular agents, temperature, light, and/or pH. Suitable inducible/conditional promoters include, but are not limited to, Tet-On, Tet-Off, Lac promoter, pBad, AlcA, LexA, Hsp70 promoter, Hsp90 promoter, pDawn, XVE/OlexA, GVG, and pOp/LhGR.

Where expression in a plant cell is desired, the components of the engineered AAV capsid system described herein are typically placed under control of a plant promoter, i.e. a promoter operable in plant cells. The use of different types of promoters is envisaged. In some embodiments, inclusion of a engineered AAV capsid system vector in a plant can be for AAV vector production purposes.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. Different promoters may direct the expression of a gene in different tissues or cell types, or at different stages of development, or in response to different environmental conditions. In particular embodiments, one or more of the engineered AAV capsid system components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the engineered AAV capsid system are found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Examples of promoters that are inducible and that can allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc.), or light inducible systems (Phytochrome, LOV domains, or cryptochrome), such as a Light Inducible Transcriptional Effector (LITE) that direct changes in transcriptional activity in a sequence-specific manner. The components of a light inducible system may include one or more elements of the engineered muscle-specific delivery system described herein, a light-responsive cytochrome heterodimer (e.g. from *Arabidopsis thaliana*), and a transcriptional activation/repression domain. In some embodiments, the vector can include one or more of the inducible DNA binding proteins provided in PCT publication WO 2014/018423 and US Publications, 2015/0291966, 2017/0166903, 2019/0203212, which describe e.g. embodiments of inducible DNA binding proteins and methods of use and can be adapted for use with the present invention.

In some embodiments, transient or inducible expression can be achieved by including, for example, chemical-regulated promotors, i.e. whereby the application of an exogenous chemical induces gene expression. Modulation of gene expression can also be obtained by including a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) Plant Cell Physiol 38:568-77), the maize GST promoter (GST-11-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

In some embodiments, the vector or system thereof can include one or more elements capable of translocating and/or expressing an engineered muscle-specific targeting moiety polynucleotide to/in a specific cell component or organelle. Such organelles can include, but are not limited to, nucleus, ribosome, endoplasmic reticulum, golgi apparatus, chloroplast, mitochondria, vacuole, lysosome, cytoskeleton, plasma membrane, cell wall, peroxisome, centrioles, etc.

Selectable Markers and Tags

One or more of the engineered muscle-specific targeting moiety polynucleotides can be operably linked, fused to, or otherwise modified to include a polynucleotide that encodes or is a selectable marker or tag, which can be a polynucleotide or polypeptide. In some embodiments, the polynucleotide encoding a polypeptide selectable marker is incorporated in the engineered muscle-specific delivery system polynucleotide such that the selectable marker polynucleotide, when translated, is inserted between two amino acids between the N- and C-terminus of the engineered muscle-specific targeting moiety polypeptide (including but not limited to an engineered AAV capsid polypeptide) or at the N- and/or C-terminus of the engineered muscle-specific targeting moiety polypeptide (including but not limited to an engineered AAV capsid polypeptide). In some embodiments, the selectable marker or tag is a polynucleotide barcode or unique molecular identifier (UMI).

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a single cell, a viral vector, labeling ligand (e.g., an aptamer), protein, shRNA, sgRNA or cDNA such that multiple species can be sequenced together.

Barcoding may be performed based on any of the compositions or methods disclosed in patent publication WO 2014047561 A1, compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In preferred embodiments, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The UMI may also be used to determine the number of transcripts that gave rise to an amplified product, or in the case of target barcodes as described herein, the number of binding events. In preferred embodiments, the amplification is by PCR or multiple displacement amplification (MDA).

It will be appreciated that the polynucleotide encoding such selectable markers or tags can be incorporated into a polynucleotide encoding one or more components of the engineered muscle-specific delivery system described herein in an appropriate manner to allow expression of the selectable marker or tag. Such techniques and methods are described elsewhere herein and will be instantly appreciated by one of ordinary skill in the art in view of this disclosure. Many such selectable markers and tags are generally known in the art and are intended to be within the scope of this disclosure.

Suitable selectable markers and tags include, but are not limited to, affinity tags, such as chitin binding protein (CBP), maltose binding protein (MBP), glutathione-S-transferase (GST), poly(His) tag; solubilization tags such as thioredoxin (TRX) and poly (NANP), MBP, and GST; chromatography tags such as those consisting of polyanionic amino acids, such as FLAG-tag; epitope tags such as V5-tag, Myc-tag, HA-tag and NE-tag; protein tags that can allow specific enzymatic modification (such as biotinylation by biotin ligase) or chemical modification (such as reaction with FLASH-EDT2 for fluorescence imaging), DNA and/or RNA segments that contain restriction enzyme or other enzyme cleavage sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipient cell (e.g., tRNA genes, auxotrophic markers); DNA and/or RNA segments that encode products which can be readily identified (e.g., phenotypic markers such as β-galactosidase, GUS; fluorescent proteins such as green fluorescent protein (GFP), cyan (CFP), yellow (YFP), red (RFP), luciferase, and cell surface proteins); polynucleotides that can generate one or more new primer sites for PCR (e.g., the juxtaposition of two DNA sequences not previously juxtaposed), DNA sequences not acted upon or acted upon by a restriction endonuclease or other DNA modifying enzyme, chemical, etc.; epitope tags (e.g. GFP, FLAG- and His-tags), and, DNA sequences that make a molecular barcode or unique molecular identifier (UMI), DNA sequences required for a specific modification (e.g., methylation) that allows its identification. Other suitable markers will be appreciated by those of skill in the art.

Selectable markers and tags can be operably linked to one or more components of the engineered AAV capsid system described herein via suitable linker, such as a glycine or glycine serine linkers as short as GS or GG up to $(GGGGG)_3$ (SEQ ID NO: 51) or $(GGGGS)_3$ (SEQ ID NO: 56). Other suitable linkers are described elsewhere herein.

The vector or vector system can include one or more polynucleotides encoding one or more engineered muscle-specific targeting moiety(ies) described elsewhere herein. In some embodiments, the targeting moiety encoding polynucleotides can be included in the vector or vector system, such as a viral vector system, such that they are expressed within and/or on the virus particle(s) produced such that the virus particles can be targeted to specific cells, tissues, organs, etc. In some embodiments, one or more engineered muscle-specific targeting moiety encoding polynucleotides are included in the vector or vector system such that the engineered muscle-specific targeting moiety polynucleotide (s) and/or products expressed therefrom include the targeting moiety and can be targeted to specific cells, tissues, organs, etc., such as muscle cells, muscle tissue, or muscle containing organs (e.g. heart). In some embodiments, such as non-viral carriers, the targeting moiety can be attached to the carrier (e.g. polymer, lipid, inorganic molecule etc.) and can be capable of targeting the carrier and any attached or associated engineered muscle-specific targeting moiety polynucleotide(s) to specific cells, tissues, organs, etc., such as such as muscle cells, muscle tissue, or muscle containing organs (e.g. heart).

Cell-Free Vector and Polynucleotide Expression

In some embodiments, the polynucleotide encoding one or more features of the engineered muscle-specific delivery system containing one or more engineered muscle-specific targeting moieties described herein is expressed from a vector or suitable polynucleotide in a cell-free in vitro system. In other words, the polynucleotide can be transcribed and optionally translated in vitro. In vitro transcription/translation systems and appropriate vectors are generally known in the art and commercially available. Generally, in vitro transcription and in vitro translation systems replicate the processes of RNA and protein synthesis, respectively, outside of the cellular environment. Vectors and suitable polynucleotides for in vitro transcription can include T7, SP6, T3, promoter regulatory sequences that can be recognized and acted upon by an appropriate polymerase to transcribe the polynucleotide or vector.

In vitro translation can be stand-alone (e.g. translation of a purified polyribonucleotide) or linked/coupled to transcription. In some embodiments, the cell-free (or in vitro) translation system can include extracts from rabbit reticulocytes, wheat germ, and/or *E. coli*. The extracts can include various macromolecular components that are needed for translation of exogenous RNA (e.g. 70S or 80S ribosomes, tRNAs, aminoacyl-tRNA, synthetases, initiation, elongation factors, termination factors, etc.). Other components can be included or added during the translation reaction, including but not limited to, amino acids, energy sources (ATP, GTP), energy regenerating systems (creatine phosphate and creatine phosphokinase (eukaryotic systems)) (phosphoenol pyruvate and pyruvate kinase for bacterial systems), and other co-factors (Mg2+, K+, etc.). As previously mentioned, in vitro translation can be based on RNA or DNA starting material. Some translation systems can utilize an RNA template as starting material (e.g. reticulocyte lysates and wheat germ extracts). Some translation systems can utilize a DNA template as a starting material (e.g. *E. coli*-based systems). In these systems, transcription and translation are coupled and DNA is first transcribed into RNA, which is subsequently translated. Suitable standard and coupled cell-free translation systems are generally known in the art and are commercially available.

Codon Optimization of Vector Polynucleotides

As described elsewhere herein, the polynucleotide encoding one or more embodiments of the engineered muscle-specific delivery system described herein is codon optimized. In some embodiments, one or more polynucleotides contained in a vector ("vector polynucleotides") described herein that are in addition to an optionally codon optimized polynucleotide encoding embodiments of the engineered muscle-specific delivery system described herein described herein can be codon optimized. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at www.yeastgenome.org/community/codon_usage.shtml, or *Codon selection in yeast*, Bennetzen and Hall, J Biol Chem. 1982 Mar. 25; 257 (6): 3026-31. As to codon usage in plants including algae, reference is made to *Codon usage in higher plants, green algae, and cyanobacteria*, Campbell and Gowri, Plant Physiol. 1990 January; 92 (1): 1-11; as well as *Codon usage in plant genes*, Murray et al, Nucleic Acids Res. 1989 Jan. 25; 17 (2): 477-98; or *Selection on the codon bias of*

*chloroplast and cyanelle genes in different plant and algal lineages*, Morton B R, J Mol Evol. 1998 April; 46 (4): 449-59.

The vector polynucleotide can be codon optimized for expression in a specific cell-type, tissue type, organ type, and/or subject type. In some embodiments, a codon optimized sequence is a sequence optimized for expression in a eukaryote, e.g., humans (i.e. being optimized for expression in a human or human cell), or for another eukaryote, such as another animal (e.g. a mammal or avian) as is described elsewhere herein. Such codon optimized sequences are within the ambit of the ordinary skilled artisan in view of the description herein. In some embodiments, the polynucleotide is codon optimized for a specific cell type. Such cell types can include, but are not limited to, epithelial cells (including skin cells, cells lining the gastrointestinal tract, cells lining other hollow organs), nerve cells (nerves, brain cells, spinal column cells, nerve support cells (e.g. astrocytes, glial cells, Schwann cells etc.), muscle cells (e.g. cardiac muscle, smooth muscle cells, and skeletal muscle cells), connective tissue cells (fat and other soft tissue padding cells, bone cells, tendon cells, cartilage cells), blood cells, stem cells and other progenitor cells, immune system cells, germ cells, and combinations thereof. Such codon optimized sequences are within the ambit of the ordinary skilled artisan in view of the description herein. In some embodiments, the polynucleotide is codon optimized for a specific tissue type. Such tissue types can include, but are not limited to, muscle tissue, connective tissue, connective tissue, nervous tissue, and epithelial tissue. Such codon optimized sequences are within the ambit of the ordinary skilled artisan in view of the description herein. In some embodiments, the polynucleotide is codon optimized for a specific organ. Such organs include, but are not limited to, muscles, skin, intestines, liver, spleen, brain, lungs, stomach, heart, kidneys, gallbladder, pancreas, bladder, thyroid, bone, blood vessels, blood, and combinations thereof. Such codon optimized sequences are within the ambit of the ordinary skilled artisan in view of the description herein.

In some embodiments, a vector polynucleotide is codon optimized for expression in particular cells, such as prokaryotic or eukaryotic cells. The eukaryotic cells may be those of or derived from a particular organism, such as a plant or a mammal, including but not limited to human, or non-human eukaryote or animal or mammal as discussed herein, e.g., mouse, rat, rabbit, dog, livestock, or non-human mammal or primate.

Non-Viral Vectors

In some embodiments, the vector is a non-viral vector or carrier. In some embodiments, non-viral vectors can have the advantage(s) of reduced toxicity and/or immunogenicity and/or increased biosafety as compared to viral vectors. The terms of art "Non-viral vectors and carriers" and as used herein in this context refers to molecules and/or compositions that are not based on one or more component of a virus or virus genome (excluding any nucleotide to be delivered and/or expressed by the non-viral vector) that can be capable of attaching to, incorporating, coupling, and/or otherwise interacting with an engineered muscle-specific targeting moiety polynucleotide of the present invention and can be capable of ferrying the polynucleotide to a cell and/or expressing the polynucleotide. It will be appreciated that this does not exclude the inclusion of a virus-based polynucleotide that is to be delivered. For example, if a gRNA to be delivered is directed against a virus component and it is inserted or otherwise coupled to an otherwise non-viral vector or carrier, this would not make said vector a "viral vector". Non-viral vectors and carriers include naked polynucleotides, chemical-based carriers, polynucleotide (non-viral) based vectors, and particle-based carriers. It will be appreciated that the term "vector" as used in the context of non-viral vectors and carriers refers to polynucleotide vectors and "carriers" used in this context refers to a non-nucleic acid or polynucleotide molecule or composition that be attached to or otherwise interact with a polynucleotide to be delivered, such as an engineered muscle-specific targeting moiety polynucleotide of the present invention.

Naked Polynucleotides

In some embodiments, one or more engineered muscle specific targeting moiety polynucleotides described elsewhere herein can be included in a naked polynucleotide. The term of art "naked polynucleotide" as used herein refers to polynucleotides that are not associated with another molecule (e.g. proteins, lipids, and/or other molecules) that can often help protect it from environmental factors and/or degradation. As used herein, associated with includes, but is not limited to, linked to, adhered to, adsorbed to, enclosed in, enclosed in or within, mixed with, and the like. Naked polynucleotides that include one or more of the engineered muscle specific targeting moiety polynucleotides described herein can be delivered directly to a host cell and optionally expressed therein. The naked polynucleotides can have any suitable two- and three-dimensional configurations. By way of non-limiting examples, naked polynucleotides can be single-stranded molecules, double stranded molecules, circular molecules (e.g. plasmids and artificial chromosomes), molecules that contain portions that are single stranded and portions that are double stranded (e.g. ribozymes), and the like. In some embodiments, the naked polynucleotide contains only the engineered muscle specific targeting moiety polynucleotide(s) of the present invention. In some embodiments, the naked polynucleotide can contain other nucleic acids and/or polynucleotides in addition to the engineered muscle specific targeting moiety polynucleotide(s) of the present invention. The naked polynucleotides can include one or more elements of a transposon system. Transposons and system thereof are described in greater detail elsewhere herein.

Non-Viral Polynucleotide Vectors

In some embodiments, one or more of the engineered muscle specific targeting moiety polynucleotides can be included in a non-viral polynucleotide vector. Suitable non-viral polynucleotide vectors include, but are not limited to, transposon vectors and vector systems, plasmids, bacterial artificial chromosomes, yeast artificial chromosomes, AR (antibiotic resistance)-free plasmids and miniplasmids, circular covalently closed vectors (e.g. minicircles, minivectors, miniknots), linear covalently closed vectors ("dumbbell shaped"), MIDGE (minimalistic immunologically defined gene expression) vectors, MiLV (micro-linear vector) vectors, Ministrings, mini-intronic plasmids, PSK systems (post-segregationally killing systems), ORT (operator repressor titration) plasmids, and the like. See e.g. Hardee et al. 2017. Genes. 8 (2): 65.

In some embodiments, the non-viral polynucleotide vector can have a conditional origin of replication. In some embodiments, the non-viral polynucleotide vector can be an ORT plasmid. In some embodiments, the non-viral polynucleotide vector can have a minimalistic immunologically defined gene expression. In some embodiments, the non-viral polynucleotide vector can have one or more post-segregationally killing system genes. In some embodiments, the non-viral polynucleotide vector is AR-free. In some embodiments, the non-viral polynucleotide vector is a minivector. In some embodiments, the non-viral polynucleotide vector includes a nuclear localization signal. In some embodiments, the non-viral polynucleotide vector can include one or more CpG motifs. In some embodiments, the non-viral polynucleotide vectors can include one or more scaffold/matrix attachment regions (S/MARs). See e.g. Mirkovitch et al. 1984. Cell. 39:223-232, Wong et al. 2015. Adv. Genet. 89:113-152, whose techniques and vectors can be adapted for use in the present invention. S/MARs are AT-rich sequences that play a role in the spatial organization of chromosomes through DNA loop base attachment to the nuclear matrix. S/MARs are often found close to regulatory elements such as promoters, enhancers, and origins of DNA replication. Inclusion of one or S/MARs can facilitate a once-per-cell-cycle replication to maintain the non-viral polynucleotide vector as an episome in daughter cells. In embodiments, the S/MAR sequence is located downstream of an actively transcribed polynucleotide (e.g. one or more engineered muscle specific targeting moiety polynucleotides of the present invention) included in the non-viral polynucleotide vector. In some embodiments, the S/MAR can be a S/MAR from the beta-interferon gene cluster. See e.g. Verghese et al. 2014. Nucleic Acid Res. 42: e53; Xu et al. 2016. Sci. China Life Sci. 59:1024-1033; Jin et al. 2016. 8:702-711; Koirala et al. 2014. Adv. Exp. Med. Biol. 801: 703-709; and Nehlsen et al. 2006. Gene Ther. Mol. Biol. 10:233-244, whose techniques and vectors can be adapted for use in the present invention.

In some embodiments, the non-viral vector is a transposon vector or system thereof. As used herein, "transposon" (also referred to as transposable element) refers to a polynucleotide sequence that is capable of moving form location in a genome to another. There are several classes of transposons. Transposons include retrotransposons and DNA transposons. Retrotransposons require the transcription of the polynucleotide that is moved (or transposed) in order to transpose the polynucleotide to a new genome or polynucleotide. DNA transposons are those that do not require reverse transcription of the polynucleotide that is moved (or transposed) in order to transpose the polynucleotide to a new genome or polynucleotide. In some embodiments, the non-viral polynucleotide vector can be a retrotransposon vector. In some embodiments, the retrotransposon vector includes long terminal repeats. In some embodiments, the retrotransposon vector does not include long terminal repeats. In some embodiments, the non-viral polynucleotide vector can be a DNA transposon vector. DNA transposon vectors can include a polynucleotide sequence encoding a transposase. In some embodiments, the transposon vector is configured as a non-autonomous transposon vector, meaning that the transposition does not occur spontaneously on its own. In some of these embodiments, the transposon vector lacks one or more polynucleotide sequences encoding proteins required for transposition. In some embodiments, the non-autonomous transposon vectors lack one or more Ac elements.

In some embodiments, a non-viral polynucleotide transposon vector system can include a first polynucleotide vector that contains the engineered muscle specific targeting moiety polynucleotide(s) of the present invention flanked on the 5' and 3' ends by transposon terminal inverted repeats (TIRs) and a second polynucleotide vector that includes a polynucleotide capable of encoding a transposase coupled to a promoter to drive expression of the transposase. When both are expressed in the same cell the transposase can be expressed from the second vector and can transpose the material between the TIRs on the first vector (e.g. the engineered muscle specific targeting moiety polynucleotide (s) of the present invention) and integrate it into one or more positions in the host cell's genome. In some embodiments, the transposon vector or system thereof can be configured as a gene trap. In some embodiments, the TIRs can be configured to flank a strong splice acceptor site followed by a reporter and/or other gene (e.g. one or more of the engineered muscle specific targeting moiety polynucleotide(s) of the present invention) and a strong poly A tail. When transposition occurs while using this vector or system thereof, the transposon can insert into an intron of a gene and the inserted reporter or other gene can provoke a mis-splicing process and as a result it in activates the trapped gene.

Any suitable transposon system can be used. Suitable transposon and systems thereof can include, Sleeping Beauty transposon system (Tcl/mariner superfamily) (see e.g. Ivics et al. 1997. Cell. 91 (4): 501-510), piggyBac (piggyBac superfamily) (see e.g. Li et al. 2013 110 (25): E2279-E2287 and Yusa et al. 2011. PNAS. 108 (4): 1531-1536), Tol2 (superfamily hAT), Frog Prince (Tcl/mariner superfamily) (see e.g. Miskey et al. 2003 Nucleic Acid Res. 31 (23): 6873-6881) and variants thereof.

Viral Vectors

In some embodiments, the vector is a viral vector. The term of art "viral vector" and as used herein in this context refers to polynucleotide based vectors that contain one or more elements from or based upon one or more elements of a virus that can be capable of expressing and packaging a polynucleotide, such as an engineered muscle specific targeting moiety polynucleotide of the present invention, into a virus particle and producing said virus particle when used alone or with one or more other viral vectors (such as in a viral vector system). Viral vectors and systems thereof can be used for producing viral particles for delivery of and/or expression of one or more components of the engineered muscle-specific system described herein. The viral vector can be part of a viral vector system involving multiple vectors. In some embodiments, systems incorporating multiple viral vectors can increase the safety of these systems. Suitable viral vectors can include adenoviral-based vectors, adeno associated vectors, helper-dependent adenoviral (HdAd) vectors, hybrid adenoviral vectors, and the like. Other embodiments of viral vectors and viral particles produce therefrom are described elsewhere herein. In some embodiments, the viral vectors are configured to produce replication incompetent viral particles for improved safety of these systems.

Adenoviral Vectors, Helper-Dependent Adenoviral Vectors, and Hybrid Adenoviral Vectors In some embodiments, the vector can be an adenoviral vector. Accordingly, the present invention is applicable to a virus within the family Adenoviridae, such as Atadenovirus, e.g., Ovine atadenovirus D, Aviadenovirus, e.g., Fowl aviadenovirus A, Ichtadenovirus, e.g., Sturgeon ichtadenovirus A, Mastadenovirus (which includes adenoviruses such as all human adenoviruses), e.g., Human mastadenovirus C, and Siadenovirus, e.g., Frog siadenovirus A. Thus, a virus of within the family Adenoviridae is contemplated as within the invention with discussion herein as to adenovirus applicable to other family members. In some embodiments, the adenoviral vector can include elements such that the virus particle produced using the vector or system thereof can be serotype 2, 5, or 9. In some embodiments, the polynucleotide to be delivered via the adenoviral particle can be up to about 8 kb. Thus, in some embodiments, an adenoviral vector can include a DNA polynucleotide to be delivered that can range in size from about 0.001 kb to about 8 kb. Adenoviral vectors have been used successfully in several contexts (see e.g. Teramato et al. 2000. Lancet. 355:1911-1912; Lai et al. 2002. DNA Cell. Biol. 21:895-913; Flotte et al., 1996. Hum. Gene. Ther. 7:1145-1159; and Kay et al. 2000. Nat. Genet. 24:257-261. The engineered muscle specific targeting moiety(ies) can be included in an adenoviral vector to produce adenoviral particles containing said engineered AAV capsids containing the engineered muscle specific targeting moiety(ies).

In some embodiments, the vector can be a helper-dependent adenoviral vector or system thereof. These are also referred to in the field as "gutless" or "gutted" vectors and are a modified generation of adenoviral vectors (see e.g. Thrasher et al. 2006. Nature. 443: E5-7). In embodiments of the helper-dependent adenoviral vector system, one vector (the helper) can contain all the viral genes required for replication but contains a conditional gene defect in the packaging domain. The second vector of the system can contain only the ends of the viral genome, one or more engineered AAV capsid polynucleotides, and the native packaging recognition signal, which can allow selective packaged release from the cells (see e.g. Cideciyan et al. 2009. N Engl J Med. 361:725-727). Helper-dependent Adenoviral vector systems have been successful for gene delivery in several contexts (see e.g. Simonelli et al. 2010. J Am Soc Gene Ther. 18:643-650; Cideciyan et al. 2009. N Engl J Med. 361:725-727; Crane et al. 2012. Gene Ther. 19 (4): 443-452; Alba et al. 2005. Gene Ther. 12:18-S27; Croyle et al. 2005. Gene Ther. 12:579-587; Amalfitano et al. 1998. J. Virol. 72:926-933; and Morral et al. 1999. PNAS. 96:12816-12821). The techniques and vectors described in these publications can be adapted for inclusion of the engineered AAV capsid polynucleotides described herein. In some embodiments, the viral particle containing an engineered muscle specific targeting moiety or encoding polynucleotide is produced from a helper-dependent adenoviral vector or system thereof can be up to about 38 kb. Thus, in some embodiments, an adenoviral vector can range in size from about 0.001 kb to about 37 kb (see e.g. Rosewell et al. 2011. J. Genet. Syndr. Gene Ther. Suppl. 5:001).

In some embodiments, the vector is a hybrid-adenoviral vector or system thereof. Hybrid adenoviral vectors are composed of the high transduction efficiency of a gene-deleted adenoviral vector and the long-term genome-integrating potential of adeno-associated, retroviruses, lentivirus, and transposon based-gene transfer. In some embodiments, such hybrid vector systems can result in stable transduction and limited integration site. See e.g. Balague et al. 2000. Blood. 95:820-828; Morral et al. 1998. Hum. Gene Ther. 9:2709-2716; Kubo and Mitani. 2003. J. Virol. 77 (5): 2964-2971; Zhang et al. 2013. PloS One. 8 (10) e76771; and Cooney et al. 2015. Mol. Ther. 23 (4): 667-674), whose techniques and vectors described therein can be modified and adapted for use in the engineered AAV muscle-specific delivery system of the present invention. In some embodiments, a hybrid-adenoviral vector can include one or more features of a retrovirus and/or an adeno-associated virus. In some embodiments, the hybrid-adenoviral vector can include one or more features of a spuma retrovirus or foamy virus (FV). See e.g. Ehrhardt et al. 2007. Mol. Ther. 15:146-156 and Liu et al. 2007. Mol. Ther. 15:1834-1841, whose techniques and vectors described therein can be modified and adapted for use in the engineered AAV capsid system of the present invention. Advantages of using one or more features from the FVs in the hybrid-adenoviral vector or system thereof can include the ability of the viral particles produced therefrom to infect a broad range of cells, a large packaging capacity as compared to other retroviruses, and the ability to persist in quiescent (non-dividing) cells. See also e.g. Ehrhardt et al. 2007. Mol. Ther. 156:146-156 and Shuji et al. 2011. Mol. Ther. 19:76-82, whose techniques and vectors described therein can be modified and adapted for use in the engineered AAV capsid system of the present invention.

Adeno Associated Vectors

In an embodiment, the engineered vector or system thereof can be an adeno-associated vector (AAV). See, e.g., West et al., Virology 160:38-47 (1987); U.S. Pat. No. 4,797,368; WO 93/24641; Kotin, Human Gene Therapy 5:793-801 (1994); and Muzyczka, J. Clin. Invest. 94:1351 (1994). Although similar to adenoviral vectors in some of their features, AAVs have some deficiency in their replication and/or pathogenicity and thus can be safer that adenoviral vectors. In some embodiments the AAV can integrate into a specific site on chromosome 19 of a human cell with no observable side effects. In some embodiments, the capacity of the AAV vector, system thereof, and/or AAV particles can be up to about 4.7 kb. The AAV vector or system thereof can include one or more engineered capsid polynucleotides described herein.

The AAV vector or system thereof can include one or more regulatory molecules. In some embodiments the regulatory molecules can be promoters, enhancers, repressors and the like, which are described in greater detail elsewhere herein. In some embodiments, the AAV vector or system thereof can include one or more polynucleotides that can encode one or more regulatory proteins. In some embodiments, the one or more regulatory proteins can be selected from Rep78, Rep68, Rep52, Rep40, variants thereof, and combinations thereof. In some embodiments, the promoter can be a tissue specific promoter as previously discussed. In some embodiments, the tissue specific promoter can drive expression of an engineered capsid AAV capsid polynucleotide described herein. This can be advantageous such as for determining muscle-specific targeting moieties as previously described and as set forth in 62/899,453, 62/916,207, 63/018,454, 63/055,252, and 62/916,221 and International Application No. PCT/US20/50534.

The AAV vector or system thereof can include one or more polynucleotides that can encode one or more capsid proteins, such as the engineered AAV capsid proteins described elsewhere herein. The engineered capsid proteins can be capable of assembling into a protein shell (an engineered capsid) of the AAV virus particle. The engineered capsid can have a cell-, tissue,—and/or organ-specific tropism. In some embodiments, the AAV capsid protein can include one or more engineered muscle-specific targeting moieties described elsewhere herein. In some embodiments, one or more muscle-specific targeting moieties included in the AAV capsid includes an RGD motif as described in greater detail elsewhere herein.

In some embodiments, the AAV vector or system thereof can include one or more adenovirus helper factors or polynucleotides that can encode one or more adenovirus helper factors. Such adenovirus helper factors can include, but are not limited, E1A, E1B, E2A, E4ORF6, and VA RNAs. In some embodiments, a producing host cell line expresses one or more of the adenovirus helper factors.

The AAV vector or system thereof can be configured to produce AAV particles having a specific serotype. In some embodiments, the serotype can be AAV1, AAV2, AAV3, AAV4, AAV5, AAV6, AAV7, AAV8, AAV9, AAV rh.74, AAV rh.10, or any combination thereof. In some embodiments, the AAV can be AAV1, AAV-2, AAV-5, AAV-9 or any combination thereof. One can select the AAV of the AAV with regard to the cells to be targeted; e.g., one can select AAV serotypes 1, 2, 5, 9 or a hybrid capsid AAV-1, AAV-2, AAV-5, AAV-9 or any combination thereof for targeting brain and/or neuronal cells; and one can select AAV-4 for targeting cardiac tissue; and one can select AAV-8 for delivery to the liver. Thus, in some embodiments, an AAV vector or system thereof capable of producing AAV particles capable of targeting the brain and/or neuronal cells can be configured to generate AAV particles having serotypes 1, 2, 5 or a hybrid capsid AAV-1, AAV-2, AAV-5 or any combination thereof. In some embodiments, an AAV vector or system thereof capable of producing AAV particles capable of targeting cardiac tissue can be configured to generate an AAV particle having an AAV-4 serotype. In some embodiments, an AAV vector or system thereof capable of producing AAV particles capable of targeting the liver can be configured to generate an AAV having an AAV-8 serotype. See also Srivastava. 2017. Curr. Opin. Virol. 21:75-80.

It will be appreciated that while the different serotypes can provide some level of cell, tissue, and/or organ specificity, each serotype still is multi-tropic and thus can result in tissue-toxicity if using that serotype to target a tissue that the serotype is less efficient in transducing. Thus, in addition to achieving some tissue targeting capacity via selecting an AAV of a particular serotype, it will be appreciated that the tropism of the AAV serotype can be modified by an engineered AAV capsid described herein. As described elsewhere herein, variants of wild-type AAV of any serotype can be generated via a method described herein and determined to have a particular cell-specific tropism, which can be the same or different as that of the reference wild-type AAV serotype. In some embodiments, the cell, tissue, and/or specificity of the wild-type serotype can be enhanced (e.g. made more selective or specific for a particular cell type that the serotype is already biased towards). For example, wild-type AAV-9 is biased towards muscle and brain in humans (see e.g. Srivastava. 2017. Curr. Opin. Virol. 21:75-80.) By including an engineered AAV capsid and/or capsid protein variant of wild-type AAV-9 as described herein, the bias for e.g. brain can be reduced or eliminated and/or the muscle septicity increased such that the brain specificity appears reduced in comparison, thus enhancing the specificity for the muscle as compared to the wild-type AAV-9. As previously mentioned, inclusion of an engineered capsid and/or capsid protein variant of a wild-type AAV serotype can have a different tropism than the wild-type reference AAV serotype.

For example, an engineered AAV capsid and/or capsid protein variant of AAV-9 can have specificity for a tissue other than muscle or brain in humans.

In some embodiments, the AAV vector is a hybrid AAV vector or system thereof. Hybrid AAVs are AAVs that include genomes with elements from one serotype that are packaged into a capsid derived from at least one different serotype. For example, if it is the rAAV2/5 that is to be produced, and if the production method is based on the helper-free, transient transfection method discussed above, the 1st plasmid and the 3rd plasmid (the adeno helper plasmid) will be the same as discussed for rAAV2 production. However, the 2nd plasmid, the pRepCap will be different. In this plasmid, called pRep2/Cap5, the Rep gene is still derived from AAV2, while the Cap gene is derived from AAV5. The production scheme is the same as the above-mentioned approach for AAV2 production. The resulting rAAV is called rAAV2/5, in which the genome is based on recombinant AAV2, while the capsid is based on AAV5. It is assumed the cell or tissue-tropism displayed by this AAV2/5 hybrid virus should be the same as that of AAV5. It will be appreciated that wild-type hybrid AAV particles suffer the same specificity issues as with the non-hybrid wild-type serotypes previously discussed.

Advantages achieved by the wild-type based hybrid AAV systems can be combined with the increased and customizable cell-specificity that can be achieved with the engineered AAV capsids can be combined by generating a hybrid AAV that can include an engineered AAV capsid described elsewhere herein. It will be appreciated that hybrid AAVs can contain an engineered AAV capsid containing a genome with elements from a different serotype than the reference wild-type serotype that the engineered AAV capsid is a variant of. For example, a hybrid AAV can be produced that includes an engineered AAV capsid that is a variant of an AAV-9 serotype that is used to package a genome that contains components (e.g. rep elements) from an AAV-2 serotype. As with wild-type based hybrid AAVs previously discussed, the tropism of the resulting AAV particle will be that of the engineered AAV capsid.

A tabulation of certain wild-type AAV serotypes as to these cells can be found in Grimm, D. et al, J. Virol. 82:5887-5911 (2008) reproduced below as Table 7. Further tropism details can be found in Srivastava. 2017. Curr. Opin. Virol. 21:75-80 as previously discussed.

TABLE 7

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

In some embodiments, the AAV vector or system thereof is AAV rh.74 or AAV rh.10.

In some embodiments, the AAV vector or system thereof is configured as a "gutless" vector, similar to that described in connection with a retroviral vector. In some embodiments, the "gutless" AAV vector or system thereof can have the cis-acting viral DNA elements involved in genome amplification and packaging in linkage with the heterologous sequences of interest (e.g. the engineered AAV capsid polynucleotide(s)).

Retroviral and Lentiviral Vectors

In some embodiments, the engineered muscle-specific delivery system or component thereof is or is incorporated into a retroviral or lentiviral vector. Retroviral vectors can be composed of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Suitable retroviral vectors for the CRISPR-Cas systems can include those based upon murine leukemia virus (MuLV), gibbon ape leukemia virus (GaLV), Simian immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). Selection of a retroviral gene transfer system may therefore depend on the target tissue.

The tropism of a retrovirus can be altered by incorporating foreign envelope proteins, expanding the potential target population of target cells. Lentiviral vectors are retroviral vectors that are able to transduce or infect non-dividing cells and are described in greater detail elsewhere herein. A retrovirus can also be engineered to allow for conditional expression of the inserted transgene, such that only certain cell types are infected by the lentivirus. In some embodiments where the end product is a muscle-specific viral particle, the tropism is defined at least in part by the presence of a muscle-specific targeting moiety described herein, such as incorporated within a capsid protein and/or capsid of the retrovirus or lentivirus particles.

Lentiviruses are complex retroviruses that have the ability to infect and express their genes in both mitotic and postmitotic cells. Advantages of using a lentiviral approach can include the ability to transduce or infect non-dividing cells and their ability to typically produce high viral titers, which can increase efficiency or efficacy of production and delivery. Suitable lentiviral vectors include, but are not limited to, human immunodeficiency virus (HIV)-based lentiviral vectors, feline immunodeficiency virus (FIV)-based lentiviral vectors, simian immunodeficiency virus (SIV)-based lentiviral vectors, Moloney Murine Leukaemia Virus (Mo-MLV), Visna-maedi virus (VMV)-based lentiviral vector, caprine arthritis-encephalitis virus (CAEV)-based lentiviral vector, bovine immune deficiency virus (BIV)-based lentiviral vector, and Equine infectious anemia (EIA V)-based lentiviral vector. In some embodiments, an HIV-based lentiviral vector system can be used. In some embodiments, a FIV-based lentiviral vector system can be used.

In some embodiments, the lentiviral vector is an EIAV-based lentiviral vector or vector system. EIA V vectors have been used to mediate expression, packaging, and/or delivery in other contexts, such as for ocular gene therapy (see, e.g., Balagaan, J Gene Med 2006; 8:275-285). In another embodiment, RetinoStat®, (see, e.g., Binley et al., HUMAN GENE THERAPY 23:980-991 (September 2012)), which describes RetinoStat®, an equine infectious anemia virus-based lentiviral gene therapy vector that expresses angiostatic proteins endostatin and angiostatin that is delivered via a subretinal injection for the treatment of the wet form of age-related macular degeneration. Any of these vectors described in these publications can be modified for the elements of the engineered muscle-specific delivery system described herein.

In some embodiments, the lentiviral vector or vector system thereof can be a first-generation lentiviral vector or vector system thereof. First-generation lentiviral vectors can contain a large portion of the lentivirus genome, including the gag and pol genes, other additional viral proteins (e.g. VSV-G) and other accessory genes (e.g. vif, vprm vpu, nef, and combinations thereof), regulatory genes (e.g. tat and/or rev) as well as the gene of interest between the LTRs. First generation lentiviral vectors can result in the production of virus particles that can be capable of replication in vivo, which may not be appropriate for some instances or applications.

In some embodiments, the lentiviral vector or vector system thereof can be a second-generation lentiviral vector or vector system thereof. Second-generation lentiviral vectors do not contain one or more accessory virulence factors and do not contain all components necessary for virus particle production on the same lentiviral vector. This can result in the production of a replication-incompetent virus particle and thus increase the safety of these systems over first-generation lentiviral vectors. In some embodiments, the second-generation vector lacks one or more accessory virulence factors (e.g. vif, vprm, vpu, nef, and combinations thereof). Unlike the first-generation lentiviral vectors, no single second generation lentiviral vector includes all features necessary to express and package a polynucleotide into a virus particle. In some embodiments, the envelope and packaging components are split between two different vectors with the gag, pol, rev, and tat genes being contained on one vector and the envelope protein (e.g. VSV-G) are contained on a second vector. The gene of interest, its promoter, and LTRs can be included on a third vector that can be used in conjunction with the other two vectors (packaging and envelope vectors) to generate a replication-incompetent virus particle.

In some embodiments, the lentiviral vector or vector system thereof can be a third-generation lentiviral vector or vector system thereof. Third-generation lentiviral vectors and vector systems thereof have increased safety over first- and second-generation lentiviral vectors and systems thereof because, for example, the various components of the viral genome are split between two or more different vectors but used together in vitro to make virus particles, they can lack the tat gene (when a constitutively active promoter is included upstream of the LTRs), and they can include one or more deletions in the 3'LTR to create self-inactivating (SIN) vectors having disrupted promoter/enhancer activity of the LTR. In some embodiments, a third-generation lentiviral vector system can include (i) a vector plasmid that contains the polynucleotide of interest and upstream promoter that are flanked by the 5' and 3' LTRs, which can optionally include one or more deletions present in one or both of the LTRs to render the vector self-inactivating; (ii) a "packaging vector(s)" that can contain one or more genes involved in packaging a polynucleotide into a virus particle that is produced by the system (e.g. gag, pol, and rev) and upstream regulatory sequences (e.g. promoter(s)) to drive expression of the features present on the packaging vector, and (iii) an "envelope vector" that contains one or more envelope protein genes and upstream promoters. In certain embodiments, the third-generation lentiviral vector system can include at least two packaging vectors, with the gag-pol being present on a different vector than the rev gene.

In some embodiments, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) can be used/and or adapted to the CRISPR-Cas system of the present invention.

In some embodiments, the pseudotype and infectivity or tropism of a lentivirus particle can be tuned by altering the type of envelope protein(s) included in the lentiviral vector or system thereof. As used herein, an "envelope protein" or "outer protein" means a protein exposed at the surface of a viral particle that is not a capsid protein. For example, envelope or outer proteins typically comprise proteins embedded in the envelope of the virus. In some embodiments, a lentiviral vector or vector system thereof can include a VSV-G envelope protein. VSV-G mediates viral attachment to an LDL receptor (LDLR) or an LDLR family member present on a host cell, which triggers endocytosis of the viral particle by the host cell. Because LDLR is expressed by a wide variety of cells, viral particles expressing the VSV-G envelope protein can infect or transduce a wide variety of cell types. Other suitable envelope proteins can be incorporated based on the host cell that a user desires to be infected by a virus particle produced from a lentiviral vector or system thereof described herein and can include, but are not limited to, feline endogenous virus envelope protein (RD114) (see e.g. Hanawa et al. Molec. Ther. 2002 5 (3) 242-251), modified Sindbis virus envelope proteins (see e.g. Morizono et al. 2010. J. Virol. 84 (14) 6923-6934; Morizono et al. 2001. J. Virol. 75:8016-8020; Morizono et al. 2009. J. Gene Med. 11:549-558; Morizono et al. 2006 Virology 355:71-81; Morizono et al J. Gene Med. 11:655-663, Morizono et al. 2005 Nat. Med. 11:346-352), baboon retroviral envelope protein (see e.g. Girard-Gagnepain et al. 2014. Blood. 124:1221-1231); Tupaia paramyxovirus glycoproteins (see e.g. Enkirch T. et al., 2013. Gene Ther. 20:16-23); measles virus glycoproteins (see e.g. Funke et al. 2008. Molec. Ther. 16 (8): 1427-1436), rabies virus envelope proteins, MLV envelope proteins, Ebola envelope proteins, baculovirus envelope proteins, filovirus envelope proteins, hepatitis E1 and E2 envelope proteins, gp41 and gp120 of HIV, hemagglutinin, neuraminidase, M2 proteins of influenza virus, and combinations thereof.

In some embodiments, the tropism of the resulting lentiviral particle can be tuned by incorporating cell targeting peptides into a lentiviral vector such that the cell targeting peptides are expressed on the surface of the resulting lentiviral particle. In some embodiments, a lentiviral vector can contain an envelope protein that is fused to a cell targeting protein (see e.g. Buchholz et al. 2015. Trends Biotechnol. 33:777-790; Bender et al. 2016. PLOS Pathog. 12 (e1005461); and Friedrich et al. 2013. Mol. Ther. 2013. 21:849-859.

In some embodiments, a split-intein-mediated approach to target lentiviral particles to a specific cell type can be used (see e.g. Chamoun-Emaneulli et al. 2015. Biotechnol. Bioeng. 112:2611-2617, Ramirez et al. 2013. Protein. Eng. Des. Sel. 26:215-233. In these embodiments, a lentiviral vector can contain one half of a splicing-deficient variant of the naturally split intein from *Nostoc punctiforme* fused to a cell targeting peptide and the same or different lentiviral vector can contain the other half of the split intein fused to an envelope protein, such as a binding-deficient, fusion-competent virus envelope protein. This can result in production of a virus particle from the lentiviral vector or vector system that includes a split intein that can function as a molecular Velcro linker to link the cell-binding protein to the pseudotyped lentivirus particle. This approach can be advantageous for use where surface-incompatibilities can restrict the use of, e.g., cell targeting peptides.

In some embodiments, a covalent-bond-forming protein-peptide pair can be incorporated into one or more of the lentiviral vectors described herein to conjugate a cell targeting peptide to the virus particle (see e.g. Kasaraneni et al. 2018. Sci. Reports (8) No. 10990). In some embodiments, a lentiviral vector can include an N-terminal PDZ domain of InaD protein (PDZ1) and its pentapeptide ligand (TEFCA) from NorpA, which can conjugate the cell targeting peptide to the virus particle via a covalent bond (e.g. a disulfide bond). In some embodiments, the PDZ1 protein can be fused to an envelope protein, which can optionally be binding deficient and/or fusion competent virus envelope protein and included in a lentiviral vector. In some embodiments, the TEFCA can be fused to a cell targeting peptide and the TEFCA-CPT fusion construct can be incorporated into the same or a different lentiviral vector as the PDZ1-envenlope protein construct. During virus production, specific interaction between the PDZ1 and TEFCA facilitates producing virus particles covalently functionalized with the cell targeting peptide and thus capable of targeting a specific cell-type based upon a specific interaction between the cell targeting peptide and cells expressing its binding partner. This approach can be advantageous for use where surface-incompatibilities can restrict the use of, e.g., cell targeting peptides.

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015. Any of these systems or a variant thereof can be used to deliver an engineered muscle-specific polynucleotide to a cell and/or incorporate a muscle-specific targeting moiety described herein for muscle-specific delivery to a cell.

In some embodiments, a lentiviral vector system can include one or more transfer plasmids. Transfer plasmids can be generated from various other vector backbones and can include one or more features that can work with other retroviral and/or lentiviral vectors in the system that can, for example, improve safety of the vector and/or vector system, increase virial titers, and/or increase or otherwise enhance expression of the desired insert to be expressed and/or packaged into the viral particle. Suitable features that can be included in a transfer plasmid can include, but are not limited to, 5'LTR, 3'LTR, SIN/LTR, origin of replication (Ori), selectable marker genes (e.g. antibiotic resistance genes), Psi (ψ), RRE (rev response element), cPPT (central polypurine tract), promoters, WPRE (woodchuck hepatitis posttranscriptional regulatory element), SV40 polyadenylation signal, pUC origin, SV40 origin, F1 origin, and combinations thereof.

In another embodiment, Cocal vesiculovirus envelope pseudotyped retroviral or lentiviral vector particles are contemplated (see, e.g., US Patent Publication No. 20120164118 assigned to the Fred Hutchinson Cancer Research Center). Cocal virus is in the Vesiculovirus genus and is a causative agent of vesicular stomatitis in mammals. Cocal virus was originally isolated from mites in Trinidad (Jonkers et al., Am. J. Vet. Res. 25:236-242 (1964)), and infections have been identified in Trinidad, Brazil, and Argentina from insects, cattle, and horses. Many of the vesiculoviruses that infect mammals have been isolated from naturally infected arthropods, suggesting that they are vector-borne. Antibodies to vesiculoviruses are common among people living in rural areas where the viruses are endemic and laboratory-acquired; infections in humans usually result in influenza-like symptoms. The Cocal virus envelope glycoprotein shares 71.5% identity at the amino acid level with VSV-G Indiana, and phylogenetic comparison of the envelope gene of vesiculoviruses shows that Cocal virus is serologically distinct from, but most closely related to, VSV-G Indiana strains among the vesiculoviruses. Jonkers et al., Am. J. Vet. Res. 25:236-242 (1964) and Travassos da Rosa et al., Am. J. Tropical Med. & Hygiene 33:999-1006 (1984). The Cocal vesiculovirus envelope pseudotyped retroviral vector particles may include for example, lentiviral, alpharetroviral, betaretroviral, gammaretroviral, deltaretroviral, and epsilonretroviral vector particles that may comprise retroviral Gag, Pol, and/or one or more accessory protein(s) and a Cocal vesiculovirus envelope protein. In certain embodiments of these embodiments, the Gag, Pol, and accessory proteins are lentiviral and/or gammaretroviral. In some embodiments, a retroviral vector can contain encoding polypeptides for one or more Cocal vesiculovirus envelope proteins such that the resulting viral or pseudoviral particles are Cocal vesiculovirus envelope pseudotyped.

Herpes Simplex Viral Vectors

In some embodiments, the vector can be a Herpes Simplex Viral (HSV)-based vector or system thereof. HSV systems can include the disabled infections single copy (DISC) viruses, which are composed of a glycoprotein H defective mutant HSV genome. When the defective HSV is propagated in complementing cells, virus particles can be generated that are capable of infecting subsequent cells permanently replicating their own genome but are not capable of producing more infectious particles. See e.g. 2009. Trobridge. Exp. Opin. Biol. Ther. 9:1427-1436, whose techniques and vectors described therein can be modified and adapted for use in the CRISPR-Cas system of the present invention. In some embodiments where an HSV vector or system thereof is utilized, the host cell can be a complementing cell. In some embodiments, HSV vector or system thereof can be capable of producing virus particles capable of delivering a polynucleotide cargo of up to 150 kb. Thus, in some embodiment the engineered muscle-specific targeting moiety polynucleotide(s) included in the HSV-based viral vector or system thereof can sum from about 0.001 to about 150 kb. HSV-based vectors and systems thereof have been successfully used in several contexts including various models of neurologic disorders. See e.g. Cockrell et al. 2007. Mol. Biotechnol. 36:184-204; Kafri T. 2004. Mol. Biol. 246:367-390; Balaggan and Ali. 2012. Gene Ther. 19:145-153; Wong et al. 2006. Hum. Gen. Ther. 2002. 17:1-9; Azzouz et al. J. Neurosci. 22L10302-10312; and Betchen and Kaplitt. 2003. Curr. Opin. Neurol. 16:487-493. Any of these systems or a variant thereof can be used to deliver an engineered muscle-specific polynucleotide to a cell and/or incorporate a muscle-specific targeting moiety described herein for muscle-specific delivery to a cell.

Poxvirus Vectors

In some embodiments, the vector can be a poxvirus vector or system thereof. In some embodiments, the poxvirus vector can result in cytoplasmic expression of one or more cargos that can be packaged by such virus of the present invention. In some embodiments, the capacity of a poxvirus vector or system thereof can be about 25 kb or more. In some embodiments, a poxvirus vector or system thereof can include one or more engineered muscle-specific targeting moiety polynucleotides and/or muscle-specific targeting moieties, engineered capsid proteins, and/or capsids described herein.

Viral Vectors for Delivery to Plants

The systems and compositions may be delivered to plant cells using viral vehicles. Plant cells can be engineered to express compositions (such as proteins) that can contain muscle-specific targeting moiety(ies) that can be subsequently harvested and used as appropriate, such as a therapy for humans or non-human animals. In particular embodiments, the compositions and systems may be introduced in the plant cells using a plant viral vector (e.g., as described in Scholthof et al. 1996, Annu Rev Phytopathol. 1996; 34:299-323). Such viral vector may be a vector from a DNA virus, e.g., geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). The viral vector may be a vector from an RNA virus, e.g., tobravirus (e.g., tobacco rattle virus, tobacco mosaic virus), potexvirus (e.g., potato virus X), or hordeivirus (e.g., barley stripe mosaic virus). The replicating genomes of plant viruses may be non-integrative vectors.

Vector Construction

The vectors described herein can be constructed using any suitable process or technique. In some embodiments, one or more suitable recombination and/or cloning methods or techniques can be used to the vector(s) described herein. Suitable recombination and/or cloning techniques and/or methods can include, but not limited to, those described in U.S. Application publication No. US 2004-0171156 A1. Other suitable methods and techniques are described elsewhere herein.

Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Any of the techniques and/or methods can be used and/or adapted for constructing an AAV or other vector described herein. AAV vectors are discussed elsewhere herein.

In some embodiments, the vector can have one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors.

Delivery vehicles, vectors, particles, nanoparticles, formulations and components thereof for expression of one or more elements of an engineered AAV capsid system described herein are as used in the foregoing documents, such as WO 2014/093622 (PCT/US2013/074667) and are discussed in greater detail herein.

Virus Particle Production from Viral Vectors

AAV Particle Production

There are two main strategies for producing AAV particles from AAV vectors and systems thereof, such as those described herein, which depend on how the adenovirus helper factors are provided (helper v. helper free). In some embodiments, a method of producing AAV particles from AAV vectors and systems thereof can include adenovirus infection into cell lines that stably harbor AAV replication and capsid encoding polynucleotides along with AAV vector containing the polynucleotide to be packaged and delivered by the resulting AAV particle (e.g. the engineered AAV capsid polynucleotide(s)). In some embodiments, a method of producing AAV particles from AAV vectors and systems thereof can be a "helper free" method, which includes co-transfection of an appropriate producing cell line with three vectors (e.g. plasmid vectors): (1) an AAV vector that contains a polynucleotide of interest (e.g. the engineered AAV capsid polynucleotide(s)) between 2 ITRs; (2) a vector that carries the AAV Rep-Cap encoding polynucleotides; and (helper polynucleotides. One of skill in the art will appreciate various methods and variations thereof that are both helper and -helper free and as well as the different advantages of each system.

The engineered AAV vectors and systems thereof described herein can be produced by any of these methods.

Retroviral Production

In some embodiments, one or more viral vectors and/or system thereof can be delivered to a suitable cell line for production of virus particles containing the polynucleotide or other payload to be delivered to a host cell. Suitable host cells for virus production from viral vectors and systems thereof described herein are known in the art and are commercially available. For example, suitable host cells include HEK 293 cells and its variants (HEK 293T and HEK 293TN cells). In some embodiments, the suitable host cell for virus production from viral vectors and systems thereof described herein can stably express one or more genes involved in packaging (e.g. pol, gag, and/or VSV-G) and/or other supporting genes.

In some embodiments, after delivery of one or more viral vectors to the suitable host cells for or virus production from viral vectors and systems thereof, the cells are incubated for an appropriate length of time to allow for viral gene expression from the vectors, packaging of the polynucleotide or other cargo to be delivered (e.g. an CRISPR-Cas system polynucleotide), and virus particle assembly, and secretion of mature virus particles into the culture media. Various other methods and techniques are generally known to those of ordinary skill in the art.

Mature virus particles can be collected from the culture media by a suitable method. In some embodiments, this can involve centrifugation to concentrate the virus. The titer of the composition containing the collected virus particles can be obtained using a suitable method. Such methods can include transducing a suitable cell line (e.g. NIH 3T3 cells) and determining transduction efficiency, infectivity in that cell line by a suitable method. Suitable methods include PCR-based methods, flow cytometry, and antibiotic selection-based methods. Various other methods and techniques are generally known to those of ordinary skill in the art. The concentration of virus particle can be adjusted as needed. In some embodiments, the resulting composition containing virus particles can contain $1\times10^{1}$-$1\times10^{20}$ particles/mL.

Lentiviruses may be prepared from any lentiviral vector or vector system described herein. In one example embodiment, after cloning pCasES10 (which contains a lentiviral transfer plasmid backbone), HEK293FT at low passage (p=5) can be seeded in a T-75 flask to 50% confluence the day before transfection in DMEM with 10% fetal bovine serum and without antibiotics. After 20 hours, the media can be changed to OptiMEM (serum-free) media and transfection of the lentiviral vectors can done 4 hours later. Cells can be transfected with 10 μg of lentiviral transfer plasmid (pCasES10) and the appropriate packaging plasmids (e.g., 5 μg of pMD2.G (VSV-g pseudotype), and 7.5 μg of psPAX2 (gag/pol/rev/tat)). Transfection can be carried out in 4 mL OptiMEM with a cationic lipid delivery agent (50 uL Lipofectamine 2000 and 100 ul Plus reagent). After 6 hours, the media can be changed to antibiotic-free DMEM with 10% fetal bovine serum. These methods can use serum during cell culture, but serum-free methods are preferred.

Following transfection and allowing the producing cells (also referred to as packaging cells) to package and produce virus particles with packaged cargo, the lentiviral particles can be purified. In an exemplary embodiment, virus-containing supernatants can be harvested after 48 hours. Collected virus-containing supernatants can first be cleared of debris and filtered through a 0.45 um low protein binding (PVDF) filter. They can then be spun in an ultracentrifuge for 2 hours at 24,000 rpm. The resulting virus-containing pellets can be resuspended in 50 ul of DMEM overnight at 4 degrees C. They can be then aliquoted and used immediately or immediately frozen at −80 degrees C. for storage.

Vector and Virus Particle Delivery

A vector (including non-viral carriers) described herein can be introduced into host cells to thereby produce transcripts, proteins, or peptides, including fusion proteins or peptides encoded by nucleic acids as described herein (e.g., engineered AAV capsid system transcripts, proteins, enzymes, mutant forms thereof, fusion proteins thereof, etc.), and virus particles (such as from viral vectors and systems thereof).

One or more engineered AAV capsid polynucleotides can be delivered using adeno associated virus (AAV), adenovirus or other plasmid or viral vector types as previously described, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus.

For plasmid delivery, the route of administration, formulation and dose can be as in U.S. Pat. No. 5,846,946 and as in clinical studies involving plasmids. In some embodiments, doses can be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into or otherwise delivered to the tissue or cell of interest.

In terms of in vivo delivery, AAV is advantageous over other viral vectors for a couple of reasons such as low toxicity (this may be due to the purification method not requiring ultra-centrifugation of cell particles that can activate the immune response) and a low probability of causing insertional mutagenesis because it doesn't integrate into the host genome.

The vector(s) and virus particles described herein can be delivered in to a host cell in vitro, in vivo, and/or ex vivo. Delivery can occur by any suitable method including, but not limited to, physical methods, chemical methods, and biological methods. Physical delivery methods are those methods that employ physical force to counteract the membrane barrier of the cells to facilitate intracellular delivery of the vector. Suitable physical methods include, but are not limited to, needles (e.g. injections), ballistic polynucleotides (e.g. particle bombardment, micro projectile gene transfer, and gene gun), electroporation, sonoporation, photoporation, magnetofection, hydroporation, and mechanical massage. Chemical methods are those methods that employ a chemical to elicit a change in the cells membrane permeability or other characteristic(s) to facilitate entry of the vector into the cell. For example, the environmental pH can be altered which can elicit a change in the permeability of the cell membrane. Biological methods are those that rely and capitalize on the host cell's biological processes or biological characteristics to facilitate transport of the vector (with or without a carrier) into a cell. For example, the vector and/or its carrier can stimulate an endocytosis or similar process in the cell to facilitate uptake of the vector into the cell.

Delivery of engineered AAV capsid system components (e.g. polynucleotides encoding engineered AAV capsid and/or capsid proteins) to cells via particles. The term "particle" as used herein, refers to any suitable sized particles for delivery of the engineered AAV capsid system components described herein. Suitable sizes include macro-, micro-, and nano-sized particles. In some embodiments, any of the engineered AAV capsid system components (e.g. polypeptides, polynucleotides, vectors and combinations thereof described herein) can be attached to, coupled to, integrated with, otherwise associated with one or more particles or component thereof as described herein. The particles described herein can then be administered to a cell or organism by an appropriate route and/or technique. In some embodiments, particle delivery can be selected and be advantageous for delivery of the polynucleotide or vector components. It will be appreciated that in embodiments, particle delivery can also be advantageous for other engineered capsid system molecules and formulations described elsewhere herein.

Engineered Virus Particles

Also described herein are engineered virus particles (also referred to herein as "engineered viral particles") that can contain an engineered muscle-specific capsid (e.g. a capsid containing one or more engineered capsid polypeptides having one or more engineered muscle-specific targeting moieties as described in detail elsewhere herein). Also described herein are virus particles containing, as cargo, one or more engineered muscle-specific targeting moiety polynucleotides described elsewhere herein.

It will be appreciated that the engineered viral particles can be lentiviral-based, retroviral-based, poxvirus-based, herpesvirus-based, adenovirus-based particles, helper adenovirus-based particles, AAV-based particles, or hybrid adenovirus-based particles that contain at least one engineered capsid protein as previously described. An engineered viral capsid is one that contains one or more engineered capsid proteins that contain one or more muscle-specific targeting moieties as are described elsewhere herein. In some embodiments, the engineered viral capsid is an engineered AAV capsids.

In some embodiments, the engineered AAV particles can include 1-60 engineered AAV capsid proteins described herein. In some embodiments, the engineered AAV particles can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 engineered capsid proteins. In some embodiments, the engineered AAV particles can contain 0-59 wild-type AAV capsid proteins. In some embodiments, the engineered AAV particles can contain 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 wild-type AAV capsid proteins. The engineered AAV particles can thus include one or more n-mer motifs as is previously described. In some embodiments, the n-mer is an RGD motif.

The engineered virus particles can each include one or more cargo polynucleotides. Cargo polynucleotides are discussed in greater detail elsewhere herein. Methods of making the engineered AAV particles from viral and non-viral vectors are described elsewhere herein. Formulations containing the engineered virus particles are described elsewhere herein.

Engineered Non-Vector Delivery Vehicles

In some embodiments, the muscle-specific targeting moiety is incorporated in a non-vector delivery vehicle. In some embodiments, the muscle specific targeting moiety is operably coupled or otherwise attached to the non-vector delivery vehicle. As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects. In some embodiments, the muscle-specific targeting moiety is incorporated into a composition (such as a protein or polynucleotide) that is operably coupled to or is otherwise attached to the non-vector delivery vehicle. In some embodiments, the engineered muscle-specific targeting moiety is operatively coupled or otherwise attached such that the muscle specific targeting moiety is on a surface of the non-vector delivery vehicle. The delivery vehicles may comprise non-viral vehicles. In general, methods and vehicles capable of delivering nucleic acids and/or proteins may be used for delivering the systems compositions herein. Examples of non-viral vehicles include lipid nanoparticles, cell-penetrating peptides (CPPs), DNA nanoclews, metal nanoparticles, streptolysin O, multifunctional envelope-type nanodevices (MENDs), lipid-coated mesoporous silica particles, and other inorganic nanoparticles.

Lipid Particles

The delivery vehicles may comprise lipid particles, e.g., lipid nanoparticles (LNPs) and liposomes. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, International Patent Publication Nos. WO 91/17424 and WO 91/16024. The preparation of lipid: nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722

(1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946, 787).

Lipid Nanoparticles (LNPs)

LNPs may encapsulate nucleic acids within cationic lipid particles (e.g., liposomes) and may be delivered to cells with relative ease. In some examples, lipid nanoparticles do not contain any viral components, which helps minimize safety and immunogenicity concerns. Lipid particles may be used for in vitro, ex vivo, and in vivo deliveries. Lipid particles may be used for various scales of cell populations.

In some embodiments, LNPs may be used for delivering DNA molecules (e.g., those comprising coding sequences of Cas and/or gRNA) and/or RNA molecules (e.g., mRNA of Cas, gRNAs). In certain cases, LNPs may be use for delivering RNP complexes of Cas/gRNA.

Components in LNPs may comprise cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-O-[2"-(methoxypoly-ethyleneglycol 2000) succinoyl]-1,2-dimyristoyl-sn-glycol (PEG-S-DMG), R-3-[(ro-methoxy-poly(ethylene glycol) 2000) carbamoyl]-1,2-dimyristyloxlpropyl-3-amine (PEG-C-DOMG, and any combination thereof. Preparation of LNPs and encapsulation may be adapted from Rosin et al, Molecular Therapy, vol. 19, no. 12, pages 1286-220 Dec. 2011).

In some embodiments, an LNP delivery vehicle can be used to deliver a virus particle containing a CRISPR-Cas system and/or component(s) thereof. In some embodiments, the virus particle(s) can be adsorbed to the lipid particle, such as through electrostatic interactions, and/or can be attached to the liposomes via a linker.

In some embodiments, the LNP contains a nucleic acid, wherein the charge ratio of nucleic acid backbone phosphates to cationic lipid nitrogen atoms is about 1:1.5-7 or about 1:4.

In some embodiments, the LNP also includes a shielding compound, which is removable from the lipid composition under in vivo conditions. In some embodiments, the shielding compound is a biologically inert compound. In some embodiments, the shielding compound does not carry any charge on its surface or on the molecule as such. In some embodiments, the shielding compounds are polyethylene glycols (PEGs), hydroxyethylglucose (HEG) based polymers, polyhydroxyethyl starch (polyHES) and polypropylene. In some embodiments, the PEG, HEG, polyHES, and a polypropylene weight between about 500 to 10,000 Da or between about 2000 to 5000 Da. In some embodiments, the shielding compound is PEG2000 or PEG5000.

In some embodiments, the LNP can include one or more helper lipids. In some embodiments, the helper lipid can be a phosphor lipid or a steroid. In some embodiments, the helper lipid is between about 20 mol % to 80 mol % of the total lipid content of the composition. In some embodiments, the helper lipid component is between about 35 mol % to 65 mol % of the total lipid content of the LNP. In some embodiments, the LNP includes lipids at 50 mol % and the helper lipid at 50 mol % of the total lipid content of the LNP.

Other non-limiting, exemplary LNP delivery vehicles are described in U.S. Patent Publication Nos. US20160174546, US20140301951, US20150105538, US20150250725, Wang et al., J. Control Release, 2017 Jan. 31. pii: S0168-3659 (17) 30038-X. doi: 10.1016/j.jconrel.2017.01.037. [Epub ahead of print]; Altinoğlu et al., Biomater Sci., 4 (12): 1773-80, Nov. 15, 2016; Wang et al., PNAS, 113 (11): 2868-73 Mar. 15, 2016; Wang et al., PloS One, 10 (11): e0141860. doi: 10.1371/journal.pone.0141860. eCollection 2015 Nov. 3, 2015; Takeda et al., Neural Regen Res. 10 (5): 689-90, May 2015; Wang et al., Adv. Healthc Mater., 3 (9): 1398-403, September 2014; and Wang et al., Agnew Chem Int Ed Engl., 53 (11): 2893-8, Mar. 10, 2014; James E. Dahlman and Carmen Barnes et al. Nature Nanotechnology (2014) published online 11 May 2014, doi: 10.1038/nnano.2014.84; Coelho et al., N Engl J Med 2013; 369:819-29; Aleku et al., *Cancer Res.,* 68 (23): 9788-98 (Dec. 1, 2008), Strumberg et al., *Int. J. Clin. Pharmacol. Ther.,* 50 (1): 76-8 (January 2012), Schultheis et al., *J. Clin. Oncol.,* 32 (36): 4141-48 (Dec. 20, 2014), and Fehring et al., *Mol. Ther.,* 22 (4): 811-20 (Apr. 22, 2014); Novobrantseva, Molecular Therapy-Nucleic Acids (2012) 1, e4; doi: 10.1038/mtna.2011.3; WO2012135025; US20140348900; US20140328759; US 20140308304; WO 2005/105152; WO 2006/069782; WO 2007/121947; US 2015/082080; US 20120251618; U.S. Pat. Nos. 7,982,027; 7,799,565; 8,058,069; 8,283,333; 7,901, 708; 7,745,651; 7,803,397; 8,101,741; 8,188,263; 7,915, 399; 8,236,943 and 7,838,658 and European Pat. Nos 1766035; 1519714; 1781593 and 1664316.

Liposomes

In some embodiments, a lipid particle may be liposome. Liposomes are spherical vesicle structures composed of a uni- or multilamellar lipid bilayer surrounding internal aqueous compartments and a relatively impermeable outer lipophilic phospholipid bilayer. In some embodiments, liposomes are biocompatible, nontoxic, can deliver both hydrophilic and lipophilic drug molecules, protect their cargo from degradation by plasma enzymes, and transport their load across biological membranes and the blood brain barrier (BBB).

Liposomes can be made from several different types of lipids, e.g., phospholipids. A liposome may comprise natural phospholipids and lipids such as 1,2-distearoyl-sn-glycero-3-phosphatidyl choline (DSPC), sphingomyelin, egg phosphatidylcholines, monosialoganglioside, or any combination thereof.

Several other additives may be added to liposomes in order to modify their structure and properties. For instance, liposomes may further comprise cholesterol, sphingomyelin, and/or 1,2-dioleoyl-sn-glycero-3-phosphoethanolamine (DOPE), e.g., to increase stability and/or to prevent the leakage of the liposomal inner cargo.

In some embodiments, a liposome delivery vehicle can be used to deliver a virus particle containing a CRISPR-Cas system and/or component(s) thereof. In some embodiments, the virus particle(s) can be adsorbed to the liposome, such as through electrostatic interactions, and/or can be attached to the liposomes via a linker.

In some embodiments, the liposome can be a Trojan Horse liposome (also known in the art as Molecular Trojan Horses), see e.g. cshprotocols.cshlp.org/content/2010/4/pdb.prot5407.long, the teachings of which can be applied and/or adapted to generated and/or deliver the CRISPR-Cas systems described herein.

Other non-limiting, exemplary liposomes can be those as set forth in Wang et al., ACS Synthetic Biology, 1, 403-07 (2012); Wang et al., PNAS, 113 (11) 2868-2873 (2016); Spuch and Navarro, Journal of Drug Delivery, vol. 2011, Article ID 469679, 12 pages, 2011. doi: 10.1155/2011/469679; WO 2008/042973; U.S. Pat. No. 8,071,082; WO 2014/186366; 20160257951; US20160129120; US20160244761; 20120251618; WO2013/093648; Lipofectin (a combination of DOTMA and DOPE), Lipofectase, LIPOFECTAMINE® (e.g., LIPOFECTAMINE® 2000, LIPOFECTAMINE® 3000, LIPOFECTAMINE® RNAIMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif.).

Stable Nucleic-Acid-Lipid Particles (SNALPs)

In some embodiments, the lipid particles may be stable nucleic acid lipid particles (SNALPs). SNALPs may comprise an ionizable lipid (DLinDMA) (e.g., cationic at low pH), a neutral helper lipid, cholesterol, a diffusible polyethylene glycol (PEG)-lipid, or any combination thereof. In some examples, SNALPs may comprise synthetic cholesterol, dipalmitoylphosphatidylcholine, 3-N-[(w-methoxy polyethylene glycol) 2000) carbamoyl]-1,2-dimyristoyloxypropylamine, and cationic 1,2-dilinoleyloxy-3-N, Ndimethylaminopropane. In some examples, SNALPs may comprise synthetic cholesterol, 1,2-distearoyl-sn-glycero-3-phosphocholine, PEG-CDMA, and 1,2-dilinoleyloxy-3-(N;N-dimethyl)aminopropane (DLinDMAo).

Other non-limiting, exemplary SNALPs that can be used to deliver the CRISPR-Cas systems described herein can be any such SNALPs as described in Morrissey et al., Nature Biotechnology, Vol. 23, No. 8, August 2005, Zimmerman et al., Nature Letters, Vol. 441, 4 May 2006; Geisbert et al., Lancet 2010; 375:1896-905; Judge, J. Clin. Invest. 119:661-673 (2009); and Semple et al., Nature Biotechnology, Volume 28 Number 2 Feb. 2010, pp. 172-177.

Other Lipids

The lipid particles may also comprise one or more other types of lipids, e.g., cationic lipids, such as amino lipid 2,2-dilinoleyl-4-dimethylaminoethyl-[1,3]-dioxolane (DLin-KC2-DMA), DLin-KC2-DMA4, C12-200 and colipids distearoylphosphatidyl choline, cholesterol, and PEG-DMG.

In some embodiments, the delivery vehicle can be or include a lipidoid, such as any of those set forth in, for example, US20110293703.

In some embodiments, the delivery vehicle can be or include an amino lipid, such as any of those set forth in, for example, Jayaraman, Angew. Chem. Int. Ed. 2012, 51, 8529-8533.

In some embodiments, the delivery vehicle can be or include a lipid envelope, such as any of those set forth in, for example, Korman et al., 2011. Nat. Biotech. 29:154-157.

Lipoplexes/Polyplexes

In some embodiments, the delivery vehicles comprise lipoplexes and/or polyplexes. Lipoplexes may bind to negatively charged cell membrane and induce endocytosis into the cells. Examples of lipoplexes may be complexes comprising lipid(s) and non-lipid components. Examples of lipoplexes and polyplexes include FuGENE-6 reagent, a non-liposomal solution containing lipids and other components, zwitterionic amino lipids (ZALs), Ca2p (e.g., forming DNA/$Ca^{2+}$ microcomplexes), polyethenimine (PEI) (e.g., branched PEI), and poly(L-lysine) (PLL).

Sugar-Based Particles

In some embodiments, the delivery vehicle can be a sugar-based particle. In some embodiments, the sugar-based particles can be or include GalNAc, such as any of those described in WO2014118272; US20020150626; Nair, J K et al., 2014, Journal of the American Chemical Society 136 (49), 16958-16961; Østergaard et al., Bioconjugate Chem., 2015, 26 (8), pp 1451-1455.

Cell Penetrating Peptides

In some embodiments, the delivery vehicles comprise cell penetrating peptides (CPPs). CPPs are short peptides that facilitate cellular uptake of various molecular cargo (e.g., from nanosized particles to small chemical molecules and large fragments of DNA).

CPPs may be of different sizes, amino acid sequences, and charges. In some examples, CPPs can translocate the plasma membrane and facilitate the delivery of various molecular cargoes to the cytoplasm or an organelle. CPPs may be introduced into cells via different mechanisms, e.g., direct penetration in the membrane, endocytosis-mediated entry, and translocation through the formation of a transitory structure.

CPPs may have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. Another type of CPPs is the trans-activating transcriptional activator (Tat) from Human Immunodeficiency Virus 1 (HIV-1). Examples of CPPs include to Penetratin, Tat (48-60), Transportan, and (R-AhX-R4) (Ahx refers to aminohexanoyl), Kaposi fibroblast growth factor (FGF) signal peptide sequence, integrin β3 signal peptide sequence, polyarginine peptide Args sequence, Guanine rich-molecular transporters, and sweet arrow peptide. Examples of CPPs and related applications also include those described in U.S. Pat. No. 8,372,951.

CPPs can be used for in vitro and ex vivo work quite readily, and extensive optimization for each cargo and cell type is usually required. In some examples, CPPs may be covalently attached to the Cas protein directly, which is then complexed with the gRNA and delivered to cells. In some examples, separate delivery of CPP-Cas and CPP-gRNA to multiple cells may be performed. CPP may also be used to delivery RNPs.

CPPs may be used to deliver the compositions and systems to plants. In some examples, CPPs may be used to deliver the components to plant protoplasts, which are then regenerated to plant cells and further to plants.

DNA Nanoclews

In some embodiments, the delivery vehicles comprise DNA nanoclews. A DNA nanoclew refers to a sphere-like structure of DNA (e.g., with a shape of a ball of yarn). The nanoclew may be synthesized by rolling circle amplification with palindromic sequences that aide in the self-assembly of the structure. The sphere may then be loaded with a payload. An example of DNA nanoclew is described in Sun W et al, J Am Chem Soc. 2014 Oct. 22; 136 (42): 14722-5; and Sun W et al, Angew Chem Int Ed Engl. 2015 Oct. 5; 54 (41): 12029-33. DNA nanoclew may have a palindromic sequences to be partially complementary to the gRNA within the Cas: gRNA ribonucleoprotein complex. A DNA nanoclew may be coated, e.g., coated with PEI to induce endosomal escape.

Metal Nanoparticles

In some embodiments, the delivery vehicles comprise gold nanoparticles (also referred to AuNPs or colloidal gold). Gold nanoparticles may form complex with cargos, e.g., Cas: gRNA RNP. Gold nanoparticles may be coated, e.g., coated in a silicate and an endosomal disruptive polymer, PAsp (DET). Examples of gold nanoparticles include AuraSense Therapeutics' Spherical Nucleic Acid (SNA™)

constructs, and those described in Mout R, et al. (2017). ACS Nano 11:2452-8; Lee K, et al. (2017). Nat Biomed Eng 1:889-901. Other metal nanoparticles can also be complexed with cargo(s). Such metal particles include, tungsten, palladium, rhodium, platinum, and iridium particles. Other non-limiting, exemplary metal nanoparticles are described in US20100129793.

iTOP

In some embodiments, the delivery vehicles comprise iTOP. iTOP refers to a combination of small molecules drives the highly efficient intracellular delivery of native proteins, independent of any transduction peptide. iTOP may be used for induced transduction by osmocytosis and propanebetaine, using NaCl-mediated hyperosmolality together with a transduction compound (propanebetaine) to trigger macropinocytotic uptake into cells of extracellular macromolecules. Examples of iTOP methods and reagents include those described in D'Astolfo D S, Pagliero R J, Pras A, et al. (2015). Cell 161:674-690.

Polymer-Based Particles

In some embodiments, the delivery vehicles may comprise polymer-based particles (e.g., nanoparticles). In some embodiments, the polymer-based particles may mimic a viral mechanism of membrane fusion. The polymer-based particles may be a synthetic copy of Influenza virus machinery and form transfection complexes with various types of nucleic acids ((siRNA, miRNA, plasmid DNA or shRNA, mRNA) that cells take up via the endocytosis pathway, a process that involves the formation of an acidic compartment. The low pH in late endosomes acts as a chemical switch that renders the particle surface hydrophobic and facilitates membrane crossing. Once in the cytosol, the particle releases its payload for cellular action. This Active Endosome Escape technology is safe and maximizes transfection efficiency as it is using a natural uptake pathway. In some embodiments, the polymer-based particles may comprise alkylated and carboxyalkylated branched polyethylenimine. In some examples, the polymer-based particles are VIROMER, e.g., VIROMER RNAi, VIROMER RED, VIROMER mRNA, VIROMER CRISPR. Example methods of delivering the systems and compositions herein include those described in Bawage S S et al., Synthetic mRNA expressed Cas13a mitigates RNA virus infections, www.biorxiv.org/content/10.1101/370460v1.full doi: doi.org/10.1101/370460, Viromer® RED, a powerful tool for transfection of keratinocytes. doi: 10.13140/RG.2.2.16993.61281, Viromer® Transfection-Factbook 2018: technology, product overview, users' data, doi: 10.13140/RG.2.2.23912.16642. Other exemplary and non-limiting polymeric particles are described in US20170079916, US20160367686, US 20110212179, US20130302401, U.S. Pat. Nos. 6,007,845, 5,855,913, 5,985,309, 5,543,158, WO2012135025, US20130252281, US20130245107, US20130244279; US20050019923, 20080267903.

Streptolysin O (SLO)

The delivery vehicles may be streptolysin O (SLO). SLO is a toxin produced by Group A streptococci that works by creating pores in mammalian cell membranes. SLO may act in a reversible manner, which allows for the delivery of proteins (e.g., up to 100 kDa) to the cytosol of cells without compromising overall viability. Examples of SLO include those described in Sierig G, et al. (2003). Infect Immun 71:446-55; Walev I, et al. (2001). Proc Natl Acad Sci USA 98:3185-90; Teng K W, et al. (2017). Elife 6: e25460.

Multifunctional Envelope-Type Nanodevice (MEND)

The delivery vehicles may comprise multifunctional envelope-type nanodevice (MENDs). MENDs may comprise condensed plasmid DNA, a PLL core, and a lipid film shell. A MEND may further comprise cell-penetrating peptide (e.g., stearyl octaarginine). The cell penetrating peptide may be in the lipid shell. The lipid envelope may be modified with one or more functional components, e.g., one or more of: polyethylene glycol (e.g., to increase vascular circulation time), ligands for targeting of specific tissues/cells, additional cell-penetrating peptides (e.g., for greater cellular delivery), lipids to enhance endosomal escape, and nuclear delivery tags. In some examples, the MEND may be a tetra-lamellar MEND (T-MEND), which may target the cellular nucleus and mitochondria. In certain examples, a MEND may be a PEG-peptide-DOPE-conjugated MEND (PPD-MEND), which may target bladder cancer cells. Examples of MENDs include those described in Kogure K, et al. (2004). J Control Release 98:317-23; Nakamura T, et al. (2012). Acc Chem Res 45:1113-21.

Cargo Polynucleotides

The engineered muscle-specific delivery system polynucleotides, viral capsid polynucleotides, other AAV polynucleotide(s), and/or vector polynucleotides, virus particles, and/or non-vector delivery vehicles can contain one or more cargo polynucleotides. In some embodiments, the one or more cargo polynucleotides are operably linked to the engineered muscle-specific delivery system polynucleotides(s) and is, in some embodiments, be part of the engineered viral genome of an engineered viral system of the present invention. The cargo polynucleotides can be packaged into an engineered virus particle, which can be delivered to, e.g., a cell. In some embodiments, the cargo polynucleotide can be capable of modifying a polynucleotide (e.g. gene or transcript) of a cell to which it is delivered. In some embodiments, the cargo is a polynucleotide that encodes a replacement polypeptide to correct for a defective polypeptide. As used herein, "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA. Polynucleotide, gene, transcript, etc. modification includes all genetic engineering techniques including, but not limited to, gene editing as well as conventional recombinational gene modification techniques (e.g. whole or partial gene insertion, deletion, and mutagenesis (e.g. insertional and deletional mutagenesis) techniques.

In some embodiments, the cargo molecule is a polynucleotide that is or can encode a vaccine. In some embodiments, the vaccine can stimulate an immune response against a cancer. In some embodiments, the vaccine can stimulate an immune response against colorectal or pancreatic cancer. In some embodiments, the vaccine can create an unstable environment for hCG-producing cells, such as hCG producing cancer cells.

In some embodiments the cargo is a polynucleotide that itself or a product thereof can be effective to treat a muscle disease or a symptom thereof.

Gene Modification Cargo Polynucleotides

In some embodiments, the cargo molecule can be a polynucleotide or polypeptide that can alone or when delivered as part of a system, whether or not delivered with other components of the system, operate to modify the genome, epigenome, and/or transcriptome of a cell to which it is delivered. Such systems include, but are not limited to, CRISPR-Cas systems. Other gene modification systems, e.g. TALENs, Zinc Finger nucleases, Cre-Lox, morpholinos, etc. are other non-limiting examples of gene modification systems whose one or more components can be delivered by the engineered AAV particles described herein.

In some embodiments, the cargo molecule is a gene editing system or component thereof. In some embodiments, the cargo molecule is a CRISPR-Cas system molecule or a component thereof. In some embodiments, the cargo molecule is a polynucleotide that encodes one or more components of a gene modification system (such as a CRISPR-Cas system). In some embodiments, the cargo molecule is a gRNA.

In some embodiments, the cargo molecule can be a polynucleotide or polypeptide that can alone or when delivered as part of a system, whether or not delivered with other components of the system, operate to modify the genome, epigenome, and/or transcriptome of a cell to which it is delivered, is such that it treats or prevents a disease, a disorder, or a symptom thereof of a muscle or skeletal disorder, a neurologic disease or disorder, and/or viruses (such as single stranded RNA viruses). In some embodiments, the cargo molecule, whether or not delivered with other components of the system, operate to modify the genome, epigenome, and/or transcriptome of a cell to which it is delivered, is such that it treats or prevents, a progeroid disease (e.g. progeroid laminopathy) a glycogen storage disease an immune disorder (such as an autoimmune disease), a cancer, Duchenne muscular dystrophy (DMD), 6 Limb-girdle muscular dystrophy diseases (LGMD), Charcot-Marie-Tooth (CMT), MPS IIIA, Pompe disease, or other CNS-related diseases such as Huntington's and other expanded repeat diseases.

In some embodiments, the cargo molecule, whether or not delivered with other components of the system, operate to modify the genome, epigenome, and/or transcriptome of a cell to which it is delivered, is such that can modify the GAA gene, such as any of those described in US Pat. App. Pub. 20190284555, the contents of which are incorporated by reference as if expressed in their entirety herein and can be adapted for use with the present invention.

In some embodiments, the cargo molecule includes an oligonucleotide coupled to a MHCK7, CK8, or other muscle specific promoter.

In some embodiments, the cargo molecule is a micro-dystrophin oligonucleotide that contains only selected regions of the dystrophin gene optimized for protein functionality. In some embodiments, the selected regions include spectrin-like repeats 1, 2, 3, and 24. See e.g. Harper S Q, Hauser M A, DelloRusso C, et al. Modular flexibility of dystrophin: implications for gene therapy of Duchenne muscular dystrophy. Nat Med. 2002; 8 (3): 253-261. In some embodiments, the micro-dystrophin oligonucleotide is that is delivered by the rAAV agent known as AAVrh74.MHCK7 microdystrophin gene or SRP-9001, which is subject to the clinical trials NCT03375164 and NCT03769116. This microdystrophin gene construct includes NT-H1-R1-R2-R3-H2-R24-H4-CR-CT. In some embodiments, the microdystrophin gene includes ABD-H1-R1-R2-R3-H2-R24-H4-CR-CT. In some embodiments, the microdystrophin gene includes H stands for hinge region. England S B, et al. Nature. 1990; 343 (6254): 180-182; Wells D J, et al. Hum Mol Genet. 1995; 4 (8): 1245-1250, Salva M Z, et al. Mol Ther. 2007; 15 (2): 320-329; Mendell J R, et al. Neurosci Lett. 2012; 527 (2): 90-99; Rodino-Klapac L R, et al. Hum Mol Genet. 2013; 22 (24): 4929-4937; Velazquez V M, et al. Mol Ther Methods Clin Dev. 2017; 4:159-168; Harper S Q, et al. Nat Med. 2002; 8 (3): 253-261; Nelson D M, et al. Hum Mol Genet. 2018; 27 (12): 2090-2100. In some embodiments, the selected regions at least include spectrin-like repeats 2 and 3. In some embodiments, the micro-dystrophin gene contains a nNOS domain. In some embodiments, the nNOS domain is composed of spectrin-like repeats 16 and/or 17. In some embodiments, the micro-dystrophin gene includes spectrin-like repeats 16 and 17. In some embodiments, the nNOS domain is composed of spectrin-like repeats R1, R16, R17, R23, and R24. In some embodiments, the micro-dystrophin gene is coupled to a muscle specific promoter. In some embodiments, the micro-dystrophin oligonucleotide is coupled to a MHCK7, CK8, SNP18, SP0033, SP0051, SP0173, tmCK, or another muscle specific promoter.

In some embodiments, the cargo microdystrophin includes an ABD (actin binding domain), one or more hinge regions (e.g. H1, H2, H3, H4), and one or more spectrin-like repeats (e.g. R1, R1' R2, R3, R16, R17, R20, R21, R22, R23, R24, R24' and optionally a dystroglycan binding domain (DBD). In some embodiments, the microdystrophin is composed of ABD-H1-R1-R16-R17-R23-R24-H4-DBD. In some embodiments, the microdystrophin is composed ABD-H1-R1-R2-R3-H2-R24-H4-CR. In some embodiments, the microdystrophin gene includes ABD-H1-R1-R2-R3-H2-R24-H4-CR-CT. In some embodiments, the microdystrophin gene includes ABD-H1-R1'-R24'-H4-CR-CT.

In some embodiments, the cargo molecule is a polynucleotide that can encode a microdystrophin gene, where the microdystrophin gene contains spectrin-like repeats, R1, R16, R17, R23 and R24. In some embodiments, the micro-dystrophin gene contains hinge region (H) 4 and/or H1. In some embodiments, the microdystrophin gene contains the N-terminal actin binding domain. In some embodiments, the microdystrophin gene contains the C-terminal dystroglycan binding domain of the human full-length dystrophin protein. The micro-dystrophin gene can contain an nNOS domain. In some embodiments, the nNOS domain is composed of spectrin-like repeats 16 and/or 17. In some embodiments, the micro-dystrophin gene includes spectrin-like repeats 16 and 17. The microdystrophin gene can be as described in WO2019118806A1 and WO2016/115543, which are incorporated by reference as if expressed in their entirety herein and can be adapted for use with the present invention. In some embodiments, the cargo polynucleotide can encode a 5-repeat microdystrophin protein that contains, from N- to C-terminus, the N-terminal actin binding domain, Hinge region 1 (H1), spectrin-like repeats R1, R16, R17, R23, and R24, Hinge region 4 (H4), and the C-terminal dystroglycan binding domain of the human full-length dystrophin protein. The protein sequence of this 5-repeat microdystrophin and the related dystrophin minigene are described in WO2016/115543. In some embodiments, the cargo polynucleotide can correspond to a microdystrophin gene that is part of the agent known as SGT001 as currently in clinical trial having the identifier number NCT03368742.

In some embodiments, the cargo molecule is a minidys gene or vector. In some embodiments, the minidys gene or vector can be composed of ABD-H1-R1-R2-R3-R16-R17-H3-R20-R21; ABD-H1-R1-R2-R3-R16-R17-H3-R20-R21-R22-R23-R24-H4-CR; or H3-R20-R21-R22-R23-R24-H4-CR-CT.

In some embodiments, the cargo molecule is an SCGB cDNA. In some embodiments, the SGCB cDNA is coupled to a MHCK7, CK8 promoter, SNP18 promoter, SP0033 promoter, SP0051, SP0173 promoter, tmCK promoter or another muscle specific promoter. In some embodiments, the cargo molecule is a beta-sarcoglycan cDNA, an alpha-sarcoglycan cDNA, a dysferlin cDNA, a gamma-sarcoglycan cDNA, a Calpin-3 cDNA, a SGSH cDNA (e.g., LYS-SAF302), a neurotropin 3 cDNA, an anoctamin-5 cDNA, or any combination thereof.

In some embodiments, the cargo molecule, whether or not delivered with other components of the system, operate to modify the genome, epigenome, and/or transcriptome of a cell to which it is delivered, is such that treat, prevent, and/or modify a gene or gene product associated with an expanded repeat disease, such as Huntington's disease, such as those described in U.S. Pat. App. Pub. 20190100755, U.S. patent Ser. No. 10/066,228, the contents of which are incorporated by reference as if expressed in their entirety herein and can be adapted for use with the present invention.

In some embodiments, the cargo molecule is an antisense oligomer or RNA molecule, such as those described in U.S. Pat. App. Pub. US20160251398, US20150267202, US20190015440, US20140287983, US20180216111, WO/2017/062835, US20190177723, US20170051278, US20180271893, WO/2016/14965, U.S. patent Ser. No. 10/076,536, WO/2018/00580, WO/2018/11866, WO/2019/059973, the contents of which are incorporated by reference as if expressed in their entirety herein and can be adapted for use with the present invention.

In some embodiments, the cargo molecule, whether or not delivered with other components of the system, operate to modify the genome, epigenome, and/or transcriptome of a cell to which it is delivered, is such that it treats or prevents a single stranded RNA virus, such influenza, West Nile Virus, SARS, Hepatitis C, dengue fever, Ebola, Marburg, and/or Calicivirus. In some embodiments the cargo molecule can be an antisense antiviral compound, such as any of those described in U.S. Pat. No. 8,703,735B2, the contents of which are incorporated by reference as if expressed in their entirety herein and can be adapted for use with the present invention.

Additional, exemplary genetic and gene associated diseases and genes capable of being modified by a cargo molecule described herein are listed elsewhere herein, see e.g. Tables A-B.

In some embodiments, the cargo molecule can add or modify a GALGT2 gene. Instead of acting to resupply missing dystrophin, GALGT2 gene therapy fortifies the structural integrity of muscle in ways that compensate for the absence of dystrophin, by increasing expression of proteins not mutated or lost in the disease. GALGT2 offers the potential to treat DMD irrespective of specific dystrophin mutation, as well as having utility in other muscular dystrophies.

In some embodiments, the cargo molecule is a morpholino, such as in US20180161359, US20190054113 the contents of which are incorporated by reference as if expressed in their entirety herein and can be adapted for use with the present invention. In some embodiments, the morpholino is a morpholino oligomer (PMO) or a peptide linked morpholino PPMO. PMO based platforms can be used to treat genetic diseases by altering mRNA transcription. PMOs are synthetic chemical structures modeled after the natural framework of RNA. While PMOs have the same nucleic acid bases found in RNA, they are bound to six-sided morpholine rings instead of five-sided ribose rings. In addition, the morpholine rings are connected to each other by phosphorodiamidate linkages instead of the phosphodiester linkages found in RNA. PMOs and PPMOs can be used for exon skipping and translation suppression.

In some embodiments, the cargo molecule can be a peptide-oligomer, conjugate as described in e.g. WO2017106304A1, the contents of which are incorporated by reference as if expressed in their entirety herein and can be adapted for use with the present invention.

In some embodiments, the morpholino is the morpholino found in Eteplirsen, which can be effective to target Exon 51 of the dystrophin mRNA. In some embodiments, the cargo molecule can generate exon skipping in the context of DMD, such as those described in e.g. US20140315977A1, US2018010581, the contents of which are incorporated by reference as if expressed in their entirety herein and can be adapted for use with the present invention.

Exon Skipping

In some embodiments, the nucleotide sequences may encode nucleic acids capable of inducing exon skipping. Such encoded nucleic acids may be antisense oligonucleotides or antisense nucleotide systems. As used herein, the term "exon skipping" refers to the modification of pre-mRNA splicing by the targeting of splice donor and/or acceptor sites within a pre-mRNA with one or more complementary antisense oligonucleotide(s) (AONs). By blocking access of a spliceosome to one or more splice donor or acceptor site, an AON may prevent a splicing reaction thereby causing the deletion of one or more exons from a fully-processed mRNA. Exon skipping may be achieved in the nucleus during the maturation process of pre-mRNAs. In some examples, exon skipping may include the masking of key sequences involved in the splicing of targeted exons by using antisense oligonucleotides (AON) that are complementary to splice donor sequences within a pre-mRNA.

In some embodiments, the nucleotide sequences encode antisense oligonucleotides or antisense nucleotide systems capable of inducing exon skipping in dystrophin mRNA. For example, a non-sense or frameshift mutation within exon x of a dystrophin gene yields a carboxy-terminally truncated, non-functional dystrophin protein. The expression of that mature mRNA transcript may yield a functional dystrophin protein that is deleted in the amino acids encoded by exon x but that includes dystrophin amino acids both N-terminal and C-terminal to those deleted amino acids.

The nucleotide sequences may encode antisense oligonucleotides or antisense nucleotide systems capable of inducing exon skipping at exon 1, 2, 3, 4, 5, 6, 7, 8, 10, 11, 12, 13, 14, 15, 16, 17, 18, 19, 20, 21, 22, 23, 24, 25, 26, 27, 28, 29, 30, 31, 32, 33, 34, 45, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or any combination thereof. In some embodiments, nucleotide sequences may encode antisense oligonucleotides or antisense nucleotide systems capable of inducing exon skipping at exon 43, 44, 50, 51, 52, 55, or any combination thereof.

CRISPR-Cas System Cargo Molecules

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

Class 1 Systems

The methods, systems, and tools provided herein may be designed for use with Class 1 CRISPR proteins. In certain example embodiments, the Class 1 system may be Type I, Type III or Type IV Cas proteins as described in Makarova et al. "Evolutionary classification of CRISPR-Cas systems: a burst of class 2 and derived variants" Nature Reviews Microbiology, 18:67-81 (February 2020), incorporated in its entirety herein by reference, and particularly as described in FIG. 1, p. 326. The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g. Cas1, Cas2, RNA nuclease), and/or one or more accessory proteins (e.g. Cas 4, DNA nuclease), CRISPR associated Rossman fold (CARF) domain containing proteins, and/or RNA transcriptase. Although Class 1 systems have limited sequence similarity, Class 1 system proteins can be identified by their similar architectures, including one or more Repeat Associated Mysterious Protein (RAMP) family subunits, e.g. Cas 5, Cas6, Cas7. RAMP proteins are characterized by having one or more RNA recognition motif domains. Large subunits (for example cas8 or cas10) and small subunits (for example, cas11) are also typical of Class 1 systems. See, e.g., FIGS. 1 and 2. Koonin E V, Makarova K S. 2019 Origins and evolution of CRISPR-Cas systems. Phil. Trans. R. Soc. B 374:20180087, DOI: 10.1098/rstb.2018.0087. In one aspect, Class 1 systems are characterized by the signature protein Cas3. The Cascade in particular Class1 proteins can comprise a dedicated complex of multiple Cas proteins that binds pre-crRNA and recruits an additional Cas protein, for example Cas6 or Cas5, which is the nuclease directly responsible for processing pre-crRNA. In one aspect, the Type I CRISPR protein comprises an effector complex comprises one or more Cas5 subunits and two or more Cas7 subunits. Class 1 subtypes include Type I-A, I-B, I-C, I-U, I-D, I-E, and I-F, Type IV-A and IV-B, and Type III-A, III-D, III-C, and III-B. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas. 1709035114; see also, Makarova et al, the CRISPR Journal, v. 1, n5, FIG. 5.

Class 2 Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1 (V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the RuvC-like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), Cas12d (CasY), Cas12e (CasX), Cas14, and/or Cas@.

In some embodiments, the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Cas Molecules

In some embodiments, the cargo molecule can be or include a Cas polypeptide and/or a polynucleotide that can encode a Cas polypeptide or a fragment thereof. Any Cas molecule can be a cargo molecule. In some embodiments, the cargo molecule is Class I CRISPR-Cas system Cas polypeptide. In some embodiments, the cargo molecule is a Class II CRISPR-Cas system Cas polypeptide. In some embodiments, the Cas polypeptide is a Type I Cas polypeptides. In some embodiments, the Cas polypeptide is a Type II Cas polypeptides. In some embodiments, the Cas polypeptides is a Type III Cas polypeptide. In some embodiments, the Cas polypeptides is a Type IV Cas polypeptide. In some embodiments, the Cas polypeptides is a Type V Cas polypeptide. In some embodiments, the Cas polypeptides is a Type VI Cas polypeptide. In some embodiments, the Cas polypeptides is a Type VII Cas polypeptide. Non-limiting examples of Cas proteins include Cas1, Cas1B, Cas2, Cas3, Cas4, Cas5, Cas6, Cas7, Cas8, Cas9 (also known as Csn1 and Csx12), Cas10, Cas 12, Cas 12a, Cas 13a, Cas 13b, Cas 13c, Cas 13d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. Other suitable Cas proteins or encoding polynucleotides that can be included as cargo are described elsewhere herein such as with discussion related to CRISPR-Cas systems.

Specialized Cas-Based Systems

In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (International Patent Publication No. WO 2014/204725, Ran et al. Cell. 2013 Sep. 12; 154 (6): 1380-1389), Cas12 (Liu et al. Nature Communications, 8, 2095 (2017), and Cas13 (International Patent Publication Nos. WO 2019/005884 and WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Patent Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33 (2): 139-142 and International Patent Publication WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein, "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are generally known: cytosine base editors (CBEs) and adenine base editors (ABEs). CBEs convert a C·G base pair into a T. A base pair (Komor et al. 2016. Nature. 533:420-424; Nishida et al. 2016. Science. 353; and Li et al. Nat. Biotech. 36:324-327) and ABEs convert an A·T base pair to a G·C base pair. Collectively, CBEs and ABEs can mediate all four possible transition mutations (C to T, A to G, T to C, and G to A). Rees and Liu. 2018. Nat. Rev. Genet. 19 (12): 770-788, particularly at FIGS. 1*b*, 2*a*-2*c*, 3*a*-3*f*, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19 (12): 770-788. Base editors also generally do not need a DNA donor template and/or rely on homology-directed repair. Komor et al. 2016. Nature. 533:420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471.

Other Example Type V base editing systems are described in International Patent Publication Nos. WO 2018/213708, WO 2018/213726, and International Patent Applications No. PCT/US2018/067207, PCT/US2018/067225, and PCT/US2018/067307, each of which is incorporated herein by reference.

In certain example embodiments, the base editing system may be an RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA base editor may be used to delete or introduce a post-translation modification site in the expressed mRNA. In contrast to DNA base editors, whose edits are permanent in the modified cell, RNA base editors can provide edits where finer, temporal control may be needed, for example in modulating a particular immune response. Example Type VI RNA-base editing systems are described in Cox et al. 2017. Science 358:1019-1027, International Patent Publication Nos. WO 2019/005884, WO 2019/005886, and WO 2019/071048, and International Patent Application Nos. PCT/US20018/05179 and PCT/US2018/067207, which are incorporated herein by reference. An example FnCas9 system that may be adapted for RNA base editing purposes is described in International Patent Publication No. WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system. See e.g. Anzalone et al. 2019. Nature. 576:149-157. Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion and combinations thereof. Generally, a prime editing system, as exemplified by PE1, PE2, and PE3 (Id.), can include a reverse transcriptase fused or otherwise coupled or associated with an RNA-programmable nickase and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRISPR-Cas systems along with few byproducts and greater or similar efficiency as compared to traditional CRISPR-Cas systems.

In some embodiments, the prime editing guide molecule can specify both the target polynucleotide information (e.g., sequence) and contain a new polynucleotide cargo that replaces target polynucleotides. To initiate transfer from the guide molecule to the target polynucleotide, the PE system can nick the target polynucleotide at a target side to expose a 3'hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576:149-157, particularly at FIGS. 1*b*, 1*c*, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PEI system or variant thereof, a PE2 system or variant thereof, or a PE3 (e.g. PE3, PE3b) system. See e.g., Anzalone et al. 2019. Nature. 576:149-157, particularly at pgs. 2-3, FIGS. 2*a*, 3*a*-3*f*, 4*a*-4*b*, Extended data FIGS. 3*a*-3*b*, and 4.

The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576:149-157, particularly at pg. 3, FIG. 2*a*-2*b*, and Extended Data FIGS. 5*a-c*.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Sequences

In some embodiments, the cargo is or includes one or more guide molecules for a CRISPR-Cas system. The terms guide molecule, guide sequence and guide polynucleotide refer to polynucleotides capable of guiding Cas to a target genomic locus and are used interchangeably as in foregoing cited documents such as International Patent Publication No. WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36 (4) 702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide, may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106 (1): 23-24; and PA Carr and GM Church, 2009, Nature Biotechnology 27 (12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it being advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in International Patent Application No. PCT US2019/045582, specifically paragraphs [0178]-[0333], which is incorporated herein by reference.

Target Sequences, PAMs, and PESs

Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16 (4): 504-517. Table 10 (from Gleditzsch et al. 2019) below shows several Cas polypeptides and the PAM sequence they recognize.

TABLE 10

Example PAM Sequences

| Cas Protein | PAM Sequence |
|---|---|
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein His A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561): 481-5. doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155 (Pt. 3): 733-740; Atschul et al. 1990. J. Mol. Biol. 215:403-410; Biswass et al. 2013 RNA Biol. 10:817-827; and Grissa et al. 2007. Nucleic Acid Res. 35: W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016. Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs)

instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16 (4): 504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16 (4): 504-517.

Overall Type VI CRISPR-Cas systems appear to have less restrictive rules for substrate (e.g., target sequence) recognition than those that target DNA (e.g., Type V and type II).

Sequences Related to Nucleus Targeting and Transportation

In some embodiments, one or more components (e.g., the Cas protein and/or deaminase) in the composition for engineering cells may comprise one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used in the methods of the present disclosure to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO: 52) or PKKKRKVEAS (SEQ ID NO: 53); the NLS from nucleoplasmin (e.g., the nucleoplasmin bipartite NLS with the sequence KRPAATKKAGQAKKKK (SEQ ID NO: 54)); the c-myc NLS having the amino acid sequence PAAKRVKLD (SEQ ID NO: 55) or RQRRNELKRSP (SEQ ID NO: 57); the hRNPAI M9 NLS having the sequence NQSSNFGPMKGGNFGGRSSGPYGGGGQYFAK-PRNQGGY (SEQ ID NO: 58); the sequence RMRIZFKNKGKDTAELRRRR VEVSVELRKAKKD-EQILKRRNV (SEQ ID NO: 59) of the IBB domain from importin-alpha; the sequences VSRKRPRP (SEQ ID NO: 9088) and PPKKARED (SEQ ID NO: 9089) of the myoma T protein; the sequence PQPKKKPL (SEQ ID NO: 9090) of human p53; the sequence SALIKKKKKMAP (SEQ ID NO: 9091) of mouse c-abl IV; the sequences DRLRR (SEQ ID NO: 9092) and PKQKKRK (SEQ ID NO: 9093) of the influenza virus NS1; the sequence RKLKKKIKKL (SEQ ID NO: 9094) of the Hepatitis virus delta antigen; the sequence REKKKFLKRR (SEQ ID NO: 9095) of the mouse Mx1 protein; the sequence KRKGDEVDGVDEVAKKKSKK (SEQ ID NO: 9096) of the human poly(ADP-ribose) polymerase; and the sequence RKCLQAGMNLEARKTKK (SEQ ID NO: 9097) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting), as compared to a control not exposed to the CRISPR-Cas protein and deaminase protein, or exposed to a CRISPR-Cas and/or deaminase protein lacking the one or more NLSs.

The CRISPR-Cas and/or nucleotide deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments, the CRISPR-Cas protein and the deaminase protein are delivered to the cell or expressed within the cell as separate proteins. In these embodiments, each of the CRISPR-Cas and deaminase protein can be provided with one or more NLSs as described herein. In certain embodiments, the CRISPR-Cas and deaminase proteins are delivered to the cell or expressed with the cell as a fusion protein. In these embodiments one or both of the CRISPR-Cas and deaminase protein is provided with one or more NLSs. Where the nucleotide deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the nucleotide deaminase and the CRISPR-Cas protein.

In certain embodiments, guides of the disclosure comprise specific binding sites (e.g. aptamers) for adapter proteins, which may be linked to or fused to a nucleotide deaminase or catalytic domain thereof. When such a guide forms a CRISPR complex (e.g., CRISPR-Cas protein binding to guide and target), the adapter proteins bind and the nucleotide deaminase or catalytic domain thereof associated with the adapter protein is positioned in a spatial orientation which is advantageous for the attributed function to be effective.

The skilled person will understand that modifications to the guide which allow for binding of the adapter+nucleotide deaminase, but not proper positioning of the adapter+nucleotide deaminase (e.g. due to steric hindrance within the three-dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and in some cases at both the tetra loop and stem loop 2.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of component. Alternatively, or additionally, the NES or NLS may be at the N terminus of component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Templates

In some embodiments, the composition for engineering cells comprise a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas protein mediated cleavage event. In an embodiment, the template nucleic acid may include a sequence that corresponds to both, a first site on the target sequence that is cleaved in a first Cas protein mediated event, and a second site on the target sequence that is cleaved in a second Cas protein mediated event.

In certain embodiments, the template nucleic acid can include a sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include a sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include a sequence which, when integrated, results in decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include a sequence which results in a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 110+/−20, 120+/−20, 130+/−20, 140+/−20, 150+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Suzuki et al. describe in vivo genome editing via CRISPR/Cas9 mediated homology-independent targeted integration (2016, Nature 540:144-149), which is incorporated by reference herein and can be adapted for use with the present invention.

TALE Nucleases

In some embodiments, a TALE nuclease or TALE nuclease system can be used to modify a polynucleotide. In some embodiments, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-$(X_{12}X_{13})$-$X_{14-33}$ or $_{34}$ or $_{35}$, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$-$(X_{12}X_{13})$-$X_{14-33}$ or $_{34}$ or $_{35})_z$, where in an advantageous embodiment, z is at least 5 to 40. In a further advantageous embodiment, z is at least 10 to 26.

The TALE monomers can have a nucleotide binding affinity that is determined by the identity of the amino acids in its RVD. For example, polypeptide monomers with an RVD of NI can preferentially bind to adenine (A), monomers with an RVD of NG can preferentially bind to thymine (T), monomers with an RVD of HD can preferentially bind to cytosine (C) and monomers with an RVD of NN can preferentially bind to both adenine (A) and guanine (G). In some embodiments, monomers with an RVD of IG can preferentially bind to T. Thus, the number and order of the polypeptide monomer repeats in the nucleic acid binding domain of a TALE determines its nucleic acid target specificity. In some embodiments, monomers with an RVD of NS can recognize all four base pairs and can bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011).

The polypeptides used in methods of the invention can be isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In some embodiments, polypeptide monomers having RVDs RN, NN, NK, SN, NH, KN, HN, NQ, HH, RG, KH, RH and SS can preferentially bind to guanine. In some embodiments, polypeptide monomers having RVDs RN, NK, NQ, HH, KH, RH, SS and SN can preferentially bind to guanine and can thus allow the generation of TALE polypeptides with high binding specificity for guanine containing target nucleic acid sequences. In some embodiments, polypeptide monomers having RVDs HH, KH, NH, NK, NQ, RH, RN and SS can preferentially bind to guanine and thereby allow the generation of TALE polypeptides with high binding specificity for guanine containing target nucleic acid sequences. In some embodiments, the RVDs that have high binding specificity for guanine are RN, NH RH and KH. Furthermore, polypeptide monomers having an RVD of NV can preferentially bind to adenine and guanine. In some embodiments, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full-length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 9098)

```
M D P I R S R T P S P A R E L L S G P Q P D G V Q
P T A D R G V S P P A G G P L D G L P A R R T M S
R T R L P S P P A P S P A F S A D S F S D L L R Q
F D P S L F N T S L F D S L P P F G A H H T E A A
T G E W D E V Q S G L R A A D A P P P T M R V A V
T A A R P P R A K P A P R R R A A Q P S D A S P A
A Q V D L R T L G Y S Q Q Q Q E K I K P K V R S T
V A Q H H E A L V G H G F T H A H I V A L S Q H P
A A L G T V A V K Y Q D M I A A L P E A T H E A I
V G V G K Q W S G A R A L E A L L T V A G E L R G
P P L Q L D T G Q L L K I A K R G G V T A V E A V
H A W R N A L T G A P L N
```

An exemplary amino acid sequence of a C-terminal capping region is:

(SEQ ID NO: 9099)

```
R P A L E S I V A Q L S R P D P A L A A L T N D H
L V A L A C L G G R P A L D A V K K G L P H A P A
L I K R T N R R I P E R T S H R V A D H A Q V V R
V L G F F Q C H S H P A Q A F D D A M T Q F G M S
R H G L L Q L F R R V G V T E L E A R S G T L P P
A S Q R W D R I L Q A S G M K R A K P S P T S T Q
T P D Q A S L H A F A D S L E R D L D A P S P M H
E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies can be generated by any of a number of computer programs known in the art, which include but are not limited to BLAST or FASTA. Suitable computer programs for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments, the effector domain is an enhancer of transcription (i.e., an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Meganucleases

In some embodiments, a meganuclease or system thereof can be used to modify a polynucleotide. Meganucleases, which are endodeoxyribonucleases characterized by a large recognition site (double-stranded DNA sequences of 12 to 40 base pairs). Exemplary methods for using meganucleases can be found in U.S. Pat. Nos. 8,163,514, 8,133,697, 8,021,867, 8,119,361, 8,119,381, 8,124,369, and 8,129,134, which are specifically incorporated herein by reference.

RNAi

In certain embodiments, the genetic modifying agent is RNAi (e.g., shRNA). As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated herein by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Engineered Cells and Organisms

Described herein are engineered cells that can include one or more of the engineered muscle-specific targeting moiety polynucleotides, polypeptides, vectors, and/or vector systems. In some embodiments, one or more of the engineered muscle-specific targeting moiety polynucleotides can be expressed in the engineered cells. In some embodiments, the engineered cells can be capable of producing engineered muscle-specific viral capsid proteins and/or engineered muscle-specific viral particles that are described elsewhere herein. Also described herein are modified or engineered organisms that can include one or more engineered cells described herein. The engineered cells can be engineered to express a cargo molecule (e.g. a cargo polynucleotide) dependently or independently of an engineered muscle-specific viral capsid polynucleotide as described elsewhere herein.

A wide variety of animals, plants, algae, fungi, yeast, etc. and animal, plant, algae, fungus, yeast cell or tissue systems may be engineered to express one or more nucleic acid constructs of the engineered muscle-specific delivery system described herein using various transformation methods mentioned elsewhere herein. This can produce organisms that can produce engineered muscle-specific targeting moiety or composition thereof, such as for production purposes, engineered muscle-specific viral capsid design and/or generation, and/or model organisms. In some embodiments, the polynucleotide(s) encoding one or more components of the engineered viral capsid system described herein can be stably or transiently incorporated into one or more cells of a plant, animal, algae, fungus, and/or yeast or tissue system. In some embodiments, one or more of engineered viral capsid system polynucleotides are genomically incorporated into one or more cells of a plant, animal, algae, fungus, and/or yeast or tissue system. Further embodiments of the modified organisms and systems are described elsewhere herein. In some embodiments, one or more components of the engineered viral capsid system described herein are expressed in one or more cells of the plant, animal, algae, fungus, yeast, or tissue systems.

Engineered Cells

Described herein are various embodiments of engineered cells that can include one or more of the engineered muscle-specific targeting moiety, composition thereof, and/or delivery system thereof polynucleotides, polypeptides, vectors, and/or vector systems described elsewhere herein. In some embodiments, the cells can express one or more of the engineered muscle-specific targeting moiety polynucleotides and can produce one or more engineered muscle-specific viral particles, which are described in greater detail herein. Such cells are also referred to herein as "producer cells". It will be appreciated that these engineered cells are different from "modified cells" described elsewhere herein in that the modified cells are not necessarily producer cells (i.e. they do not make engineered muscle-specific delivery particles (i.e. particles that can deliver a cargo to a cell in a muscle-specific manner guided by a muscle-specific targeting moiety described herein) unless they include one or more of the engineered viral capsid polynucleotides, engineered viral capsid vectors or other vectors described herein that render the cells capable of producing an engineered virus particle or are modified to produce compositions (such as proteins) that include one or more engineered muscle-specific targeting moieties.

Modified cells can be recipient cells of a cargo delivered by a delivery vehicle (e.g. viral, vector, or non-vector delivery vehicle) that includes one or more engineered muscle-specific targeting moieties, and can, in some embodiments, be modified by the delivery vehicle and/or a cargo polynucleotide delivered to the recipient cell. Modified cells are discussed in greater detail elsewhere herein. The term modification can be used in connection with modification of a cell that is not dependent on being a recipient cell. For example, isolated cells can be modified prior to receiving an engineered delivery vehicle described herein.

In an embodiment, the invention provides a non-human eukaryotic organism; for example, a multicellular eukaryotic organism, including a eukaryotic host cell containing one or more components of an engineered muscle-specific delivery system described herein according to any of the described embodiments. In other embodiments, the invention provides a eukaryotic organism; preferably a multicellular eukaryotic organism, comprising a eukaryotic host cell containing one or more components of an engineered delivery system described herein according to any of the described embodiments. In some embodiments, the organism is a host of AAV.

In particular embodiments, the plants, algae, fungi, yeast, etc., cells or parts obtained are transgenic plants, comprising an exogenous DNA sequence incorporated into the genome of all or part of the cells.

The engineered cell can be a prokaryotic cell. The prokaryotic cell can be bacterial cell. The prokaryotic cell can be an archaea cell. The bacterial cell can be any suitable bacterial cell. Suitable bacterial cells can be from the genus *Escherichia, Bacillus, Lactobacillus, Rhodococcus, Rhodobacter, Synechococcus, Synechocystis, Pseudomonas, Pseudoalteromonas, Stenotrophomonas*, and *Streptomyces* Suitable bacterial cells include, but are not limited to *Escherichia coli* cells, *Caulobacter crescentus* cells, *Rhodobacter sphaeroides* cells, *Psedoaltermonas haloplanktis* cells. Suitable strains of bacterial include, but are not limited to BL21 (DE3), DL21 (DE3)-pLysS, BL21 Star-pLysS, BL21-SI, BL21-AI, Tuner, Tuner pLysS, Origami, Origami B pLysS, Rosetta, Rosetta pLysS, Rosetta-gami-pLysS, BL21 CodonPlus, AD494, BL2trxB, HMS174, NovaBlue (DE3), BLR, C41 (DE3), C43 (DE3), Lemo21 (DE3), Shuffle T7, ArcticExpress and Artic Express (DE3).

The engineered cell can be a eukaryotic cell. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments the engineered cell can be a cell line. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, CIR, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO—IR, CHO-K1, CHO-K2, CHO-T, CHO Dhfr-/-, COR-L23, COR-L23/CPR, COR-L23/5010, COR-L23/R23, COS-7, COV-434, CML TI, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, $X_{63}$, YAC-1, YAR, and transgenic varieties thereof. Cell lines are available from a variety of sources known to those with skill in the art (see, e.g., the American Type Culture Collection (ATCC) (Manassas, Va.)).

In some embodiments, the engineered or modified cell is a muscle cell (e.g. cardiac muscle, skeletal muscle, and/or smooth muscle), bone cell, blood cell, immune cell (including but not limited to B cells, macrophages, T-cells, CAR-T cells, and the like), kidney cells, bladder cells, lung cells, heart cells, liver cells, brain cells, neurons, skin cells, stomach cells, neuronal support cells, intestinal cells, epithelial cells, endothelial cells, stem or other progenitor cells, adrenal gland cells, cartilage cells, and combinations thereof.

In some embodiments, the engineered cell can be a fungus cell. As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell.

As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerevisiae, Kluyveromyces marxianus*, or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis*, a.k.a. *Pichia kudriavzevii* and *Candida acidothermophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains can include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, inactivation, activation, or modification of meiosis, cytokinesis, or DNA replication). A polyploid cell may refer to a cell whose entire genome is polyploid, or it may refer to a cell that is polyploid in a particular genomic locus of interest.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

In some embodiments, the engineered cell is a cell obtained from a subject. In some embodiments, the subject is a healthy or non-diseased subject. In some embodiments, the subject is a subject with a desired physiological and/or biological characteristic such that when a engineered AAV capsid particle is produced it can package one or more cargo polynucleotides that can be related to the desired physiological and/or biological characteristic and/or capable of modifying the desired physiological and/or biological characteristic. Thus, the cargo polynucleotides of the produced engineered AAV capsid particle can be capable of transferring the desired characteristic to a recipient cell. In some embodiments, the cargo polynucleotides are capable of modifying a polynucleotide of the engineered cell such that the engineered cell has a desired physiological and/or biological characteristic.

In some embodiments, a cell transfected with one or more vectors described herein is used to establish a new cell line comprising one or more vector-derived sequences.

The engineered cells can be used to produce engineered AAV capsid polynucleotides, vectors, and/or particles. In some embodiments, the engineered AAV capsid polynucleotides, vectors, and/or particles are produced, harvested, and/or delivered to a subject in need thereof. In some embodiments, the engineered cells are delivered to a subject. Other uses for the engineered cells are described elsewhere herein. In some embodiments, the engineered cells can be included in formulations and/or kits described elsewhere herein.

The engineered cells can be stored short-term or long-term for use at a later time. Suitable storage methods are generally known in the art. Further, methods of restoring the stored cells for use (such as thawing, reconstitution, and otherwise stimulating metabolism in the engineered cell after storage) at a later time are also generally known in the art.

Formulations

The compositions, polynucleotides, polypeptides, particles, cells, vector systems and combinations thereof described herein can be contained in a formulation, such as a pharmaceutical formulation. In some embodiments, the formulations can be used to generate polypeptides and other particles that include one or more muscle-specific targeting moieties described herein. In some embodiments, the formulations can be delivered to a subject in need thereof. In some embodiments, the engineered muscle-specific targeting moieties, compositions thereof, delivery systems thereof, engineered cells, engineered viral particles, and/or combinations thereof described herein can be included in a formulation that can be delivered to a subject or a cell. In some embodiments, the formulation is a pharmaceutical formulation. One or more of the polypeptides, polynucleotides, vectors, cells, and combinations thereof described herein can be provided to a subject in need thereof or a cell alone or as an active ingredient, such as in a pharmaceutical formulation. As such, also described herein are pharmaceutical formulations containing an amount of one or more of the polypeptides, polynucleotides, vectors, cells, or combinations thereof described herein. In some embodiments, the pharmaceutical formulation can contain an effective amount of the one or more of the polypeptides, polynucleotides, vectors, cells, and combinations thereof described herein. The pharmaceutical formulations described herein can be administered to a subject in need thereof or a cell.

In some embodiments, the amount of the one or more of the polypeptides, polynucleotides, vectors, cells, virus particles, nanoparticles, other delivery particles, and combinations thereof described herein contained in the pharmaceutical formulation can range from about 1 μg/kg to about 10 mg/kg based upon the bodyweight of the subject in need thereof or average bodyweight of the specific patient population to which the pharmaceutical formulation can be administered. The amount of the one or more of the polypeptides, polynucleotides, vectors, cells, and combinations thereof described herein in the pharmaceutical formulation can range from about 1 μg to about 10 g or from about 10 nL to about 10 ml. In embodiments where the pharmaceutical formulation contains one or more cells, the amount can range from about 1 cell to $1\times10^2$, $1\times10^3$, $1\times10^4$, $1\times10^5$, $1\times10^6$, $1\times10^7$, $1\times10^8$, $1\times10^9$, $1\times10^{10}$ or more cells. In embodiments where the pharmaceutical formulation contains one or more cells, the amount can range from about 1 cell to $1\times10^2$, $1\times10^3$, $1\times10^4$, $1\times10^5$, $1\times10^6$, $1\times10^7$, $1\times10^8$, $1\times10^9$, $1\times10^{10}$ or more cells per nL, μL, mL, or L.

In embodiments, were engineered AAV capsid particles are included in the formulation, the formulation can contain 1 to $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, or $1\times10^{20}$ transducing units (TU)/mL of the engineered AAV capsid particles. In some embodiments, the formulation can be 0.1 to 100 mL in volume and can contain 1 to $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, or $1\times10^{20}$ transducing units (TU)/mL of the engineered viral particles.

Pharmaceutically Acceptable Carriers and Auxiliary Ingredients and Agents

In embodiments, the pharmaceutical formulation containing an amount of one or more of the polypeptides, polynucleotides, vectors, cells, virus particles, nanoparticles, other delivery particles, and combinations thereof described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to an amount of one or more of the polypeptides, polynucleotides, vectors, cells, viral particles, nanoparticles, other delivery particles, and combinations thereof described herein, the pharmaceutical formulation can also include an effective amount of an auxiliary active agent, including but not limited to, polynucleotides, amino acids, peptides, polypeptides, antibodies, aptamers, ribozymes, hormones, immunomodulators, antipyretics, anxiolytics, antipsychotics, analgesics, antispasmodics, anti-inflammatoires, anti-histamines, anti-infectives, chemotherapeutics, and combinations thereof.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eicosanoids (e.g. arachidonic acid, lipoxins, and prostaglandins), and steroid hormones (e.g. estradiol, testosterone, tetrahydro testosterone Cortisol). Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-K, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylate, and sodium salicylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotonergic antidepressants (e.g. selective serotonin reuptake inhibitors, tricyclic antidepressants, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromperidol, droperidol, haloperidol, moperone, pipaperone, timiperone, fluspirilene, penfluridol, pimozide, acepromazine, chlorpromazine, cyamemazine, dixyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzapine, paliperidone, perospirone, quetiapine, remoxipride, risperidone, sertindole, trimipramine, ziprasidone, zotepine, alstonie, bifeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, nonsteroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupirtine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papaverine, cyclobenzaprine, carisoprodol, orphenadrine, tizanidine, metaxalone, methocarbamol, chlorzoxazone, baclofen, dantrolene, baclofen, tizanidine, and dantrolene. Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, H1-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocetirizine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g. cimetidine, famotidine, lafutidine, nizatidine, ranitidine, and roxatidine), tritoqualine, catechin, cromoglicate, nedocromil, and p2-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, albendazole, thiabendazole, oxamniquine), antifungals (e.g. azole antifungals (e.g. itraconazole, fluconazole, parconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proguanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, abacavir/lamivudine/zidovudine, lamivudine/zidovudine, emtricitabine/tenofovir, emtricitabine/lopinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delavirdine, nevirapine, entecavir, lamivudine, adefovir, sofosbuvir, didanosine, tenofovir, abacavir, zidovudine, stavudine, emtricitabine, zalcitabine, telbivudine, simeprevir, boceprevir, telaprevir, lopinavir/ritonavir, boceprevir, darunavir, ritonavir, tipranavir, atazanavir, nelfinavir, amprenavir, indinavir, saquinavir, ribavirin, valacyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, cefazoline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, ceftizoxime, and ceftazidime), glycopeptide antibiotics (e.g. vancomycin, dalbavancin, oritavancin, and telavancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erythromycin, azithromycin, clarithromycin, dirithromycin, and troleandomycin), linezolid, sulfamethoxazole/trimethoprim, rifaximin, chloramphenicol, Fosfomycin, metronidazole, aztreonam, bacitracin, penicillin (amoxicillin, ampicillin, piperacillin, bacampicillin, carbenicillin, ticarcillin, amoxicillin/clavulanate, ampicillin/sulbactam, piperacillin/tazobactam, clavulanate/ticarcillin, penicillin, procaine penicillin, oxacillin, dicloxacillin, and nafcillin), quinolones (e.g. lomefloxacin, norfloxacin, ofloxacin, gatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfisoxazole), tetracyclines (e.g. doxycycline, demeclocycline, minocycline, doxycycline/salicylic acid, doxycycline/omega-3 polyunsaturated fatty acids, and tetracycline), and urinary anti-infectives (e.g. nitrofurantoin, methenamine, Fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, Cytoxan, cyclophosphamide, decitabine, dexamethasone, docetaxel, hydroxyurea, dacarbazine, leuprolide, epirubicin, oxaliplatin, asparaginase, estramustine, cetuximab, vismodegib, asparginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylate, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, adotrastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octreotide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, arsenic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

In embodiments where there is an auxiliary active agent contained in the pharmaceutical formulation in addition to the one or more of the polypeptides, polynucleotides, vectors, cells, virus particles, nanoparticles, other delivery particles, and combinations thereof described herein, amount, such as an effective amount, of the auxiliary active agent will vary depending on the auxiliary active agent. In some embodiments, the amount of the auxiliary active agent ranges from 0.001 micrograms to about 1 milligram. In other embodiments, the amount of the auxiliary active agent ranges from about 0.01 IU to about 1000 IU. In further embodiments, the amount of the auxiliary active agent ranges from 0.001 mL to about 1 mL. In yet other embodiments, the amount of the auxiliary active agent ranges from about 1% w/w to about 50% w/w of the total pharmaceutical formulation. In additional embodiments, the amount of the auxiliary active agent ranges from about 1% v/v to about 50% v/v of the total pharmaceutical formulation. In still other embodiments, the amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravitreal, intracerebral, gingival, subgingival, intracerebroventricular, and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of the targeted effector fusion protein and/or complex thereof or composition containing the one or more of the polypeptides, polynucleotides, vectors, cells, and combinations thereof described herein. The oral dosage form can be administered to a subject in need thereof.

Where appropriate, the dosage forms described herein can be microencapsulated.

The dosage form can also be prepared to prolong or sustain the release of any ingredient. In some embodiments, the one or more of the polypeptides, polynucleotides, vectors, cells, and combinations thereof described herein can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Weiterstadt, Germany), zein, shellac, and polysaccharides.

Coatings may be formed with a different ratio of water-soluble polymer, water insoluble polymers, and/or pH dependent polymers, with or without water insoluble/water soluble non-polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the one or more of the polypeptides, polynucleotides, vectors, cells, and combinations thereof described herein can be formulated with a paraffinic or water-miscible ointment base. In some embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the one or more of the polypeptides, polynucleotides, vectors, cells, and combinations thereof described herein is contained in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient (e.g. the one or more of the polypeptides, polynucleotides, vectors, cells, and combinations thereof described herein and/or auxiliary active agent), which may be generated by various types of metered dose pressurized aerosols, nebulizers, or insufflators.

In some embodiments, the dosage forms can be aerosol formulations suitable for administration by inhalation. In some of these embodiments, the aerosol formulation can contain a solution or fine suspension of the one or more of the polypeptides, polynucleotides, vectors, cells, and combinations thereof described herein and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of one or more of the polypeptides, polynucleotides, vectors, cells, and combinations thereof described herein. In further embodiments, the aerosol formulation can also contain co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulation. In addition to the one or more of the polypeptides, polynucleotides, vectors, cells, and combinations thereof described herein, an auxiliary active ingredient, and/or pharmaceutically acceptable salt thereof, such a dosage form can contain a powder base such as lactose, glucose, trehalose, mannitol, and/or starch. In some of these embodiments, the one or more of the polypeptides, polynucleotides, vectors, cells, and combinations thereof described herein is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol dosage forms can be arranged so that each metered dose of aerosol contains a predetermined amount of an active ingredient, such as the one or more of the one or more of the polypeptides, polynucleotides, vectors, cells, and combinations thereof described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraperitoneal, subcutaneous, intramuscular, intradermal, intraosseous, epidural, intracardiac, intraarticular, intracavernous, gingival, subgingival, intrathecal, intravitreal, intracerebral, and intracerebroventricular) can include aqueous and/or non-aqueous sterile injection solutions, which can contain anti-oxidants, buffers, bacteriostatic, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or nonaqueous sterile solutions that can optionally be adapted for injection, and which can optionally contain anti-oxidants, buffers, bacteriostats, solutes that render the composition isotonic with the eye or fluid contained therein or around the eye of the subject, and aqueous and nonaqueous sterile suspensions, which can include suspending agents and thickening agents.

For some embodiments, the dosage form contains a predetermined amount of the one or more of the polypeptides, polynucleotides, vectors, cells, and combinations thereof described herein per unit dose. In some embodiments, the predetermined amount of the such unit doses may therefore be administered once or more than once a day. Such pharmaceutical formulations may be prepared by any of the methods well known in the art.

Kits

Also described herein are kits that contain one or more of the one or more of the compositions, polypeptides, polynucleotides, vectors, cells, viral particles, other delivery vehicles, or other components described herein and combinations thereof and pharmaceutical formulations described herein. In embodiments, one or more of the polypeptides, polynucleotides, vectors, cells, and combinations thereof described herein can be presented as a combination kit. As used herein, the terms "combination kit" or "kit of parts" refers to the compounds, or formulations and additional components that are used to package, screen, test, sell, market, deliver, and/or administer the combination of elements or a single element, such as the active ingredient, contained therein. Such additional components include but are not limited to, packaging, syringes, blister packages, bottles, and the like. The combination kit can contain one or more of the components (e.g. one or more of the one or more of the polypeptides, polynucleotides, vectors, cells, and combinations thereof) or formulation thereof can be provided in a single formulation (e.g. a liquid, lyophilized powder, etc.), or in separate formulations. The separate components or formulations can be contained in a single package or in separate packages within the kit. The kit can also include instructions in a tangible medium of expression that can contain information and/or directions regarding the content of the components and/or formulations contained therein, safety information regarding the content of the components(s) and/or formulation(s) contained therein, information regarding the amounts, dosages, indications for use, screening methods, component design recommendations and/or information, recommended treatment regimen(s) for the components(s) and/or formulations contained therein. As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory drive or CD-ROM or on a server that can be accessed by a user via, e.g. a web interface.

In one embodiment, the invention provides a kit comprising one or more of the components described herein. In some embodiments, the kit comprises a vector system and instructions for using the kit. In some embodiments, the vector system includes a regulatory element operably linked to one or more engineered polynucleotides, such as those containing a muscle-specific targeting moiety and/or composition thereof, as described elsewhere herein and, optionally, a cargo molecule, which can optionally be operably linked to a regulatory element. The one or more engineered delivery system polynucleotides can be included on the same or different vectors as the cargo molecule in embodiments containing a cargo molecule within the kit.

In some embodiments, the kit comprises a vector system and instructions for using the kit. In some embodiments, the vector system comprises (a) a first regulatory element operably linked to a direct repeat sequence and one or more insertion sites for inserting one or more guide sequences up- or downstream (whichever applicable) of the direct repeat sequence, wherein when expressed, the guide sequence directs sequence-specific binding of a Cas9 CRISPR complex to a target sequence in a eukaryotic cell, wherein the Cas9 CRISPR complex comprises a Cas9 enzyme complexed with the guide sequence that is hybridized to the target sequence; and/or (b) a second regulatory element operably linked to an enzyme-coding sequence encoding said Cas9 enzyme comprising a nuclear localization sequence. Where applicable, a tracr sequence may also be provided. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the Cas9 enzyme comprises one or more nuclear localization sequences of sufficient strength to drive accumulation of said CRISPR enzyme in a detectable amount in the nucleus of a eukaryotic cell. In some embodiments, the CRISPR enzyme is a type V or VI CRISPR system enzyme. In some embodiments, the CRISPR enzyme is a Cas9 enzyme. In some embodiments, the Cas9 enzyme is derived from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens*, or *Porphyromonas macacae* Cas9 (e.g., modified to have or be associated with at least one DD), and may include further alteration or mutation of the Cas9, and can be a chimeric Cas9. In some embodiments, the DD-CRISPR enzyme is codon-optimized for expression in a eukaryotic cell. In some embodiments, the DD-CRISPR enzyme directs cleavage of one or two strands at the location of the target sequence. In some embodiments, the DD-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 16, 17, 18, 19, 20, 25 nucleotides, or between 16-30, or between 16-25, or between 16-20 nucleotides in length.

Methods of Use

General Discussion

The compositions including one or more of the muscle-specific targeting moieties, engineered muscle-specific delivery system, engineered viral capsids and particles, polynucleotides, polypeptides, vector(s), engineered cells of the present invention can be used generally to package and/or deliver one or more cargos to a recipient cell. In some embodiments, delivery is done in cell-specific manner based upon the specificity of the targeting moiety, such as in a muscle specific manner. In some embodiments, this is conferred by the tropism of the engineered viral capsid, which can be influenced at least in part by the inclusion of one or more RGD and/ord n-mer motifs described elsewhere herein. In some embodiments, the tropism is muscle specific. In some embodiments, compositions including one or more of the muscle-specific targeting moieties, engineered viral capsids and viral particles, can be administered to a subject or a cell, tissue, and/or organ and facilitate the transfer and/or integration of the cargo to the recipient cell. In other embodiments, engineered cells capable of producing compositions, such as polypeptides and other particles (e.g. engineered AAV capsids and viral particles), containing one or more of the muscle-specific targeting moieties can be generated from the polynucleotides, vectors, and vector systems etc., described herein. This includes without limitation, the engineered AAV capsid system molecules (e.g. polynucleotides, vectors, and vector systems, etc.). In some embodiments, the polynucleotides, vectors, and vector systems etc., described herein capable of generating the compositions, such as polypeptides and other particles (e.g. engineered AAV capsids and viral particles), containing one or more of the muscle-specific targeting moieties can be delivered to a cell or tissue, in vivo, ex vivo, or in vitro. In some embodiments, when delivered to a subject, the composition can transform a subject's cell in vivo or ex vivo to produce an engineered cell that can be capable of making a composition described herein that contains one or more of the muscle-specific targeting moieties described herein, including but not limited to the engineered AAV capsid particles, which can be released from the engineered cell and deliver cargo molecule(s) to a recipient cell in vivo or produce personalized engineered compositions (e.g. AAV capsid particles) for reintroduction into the subject from which the recipient cell was obtained.

In some embodiments, an engineered cell can be delivered to a subject, where it can release produced compositions of the present invention (including but not limited to engineered AAV capsid particles) such that they can then deliver a cargo (e.g. a cargo polynucleotide(s)) to a recipient cell. These general processes can be used in a variety of ways to treat and/or prevent disease or a symptom thereof in a subject, generate model cells, generate modified organisms, provide cell selection and screening assays, in bioproduction, and in other various applications.

In some embodiments, the compositions, such as polypeptides and other particles (e.g. engineered AAV capsids and viral particles), containing one or more of the muscle-specific targeting moieties) can be delivered to a subject or a cell, tissue, and/or organ. In this way they can be used to deliver any cargo they may contain or are associated with to a muscle cell.

In some embodiments, the engineered AAV capsid polynucleotides, vectors, and systems thereof can be used to generate engineered AAV capsid variant libraries that can be mined for variants with a desired cell-specificity. The description provided herein as supported by the various Examples can demonstrate that one having a desired cell-specificity in mind could utilize the present invention as described herein to obtain a capsid with the desired cell-specificity.

The subject invention may be used as part of a research program wherein there is transmission of results or data. A computer system (or digital device) may be used to receive, transmit, display and/or store results, analyze the data and/or results, and/or produce a report of the results and/or data and/or analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers). In some embodiments, the computer system comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users. A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution. Accordingly, the invention comprehends performing any method herein-discussed and storing and/or transmitting data and/or results therefrom and/or analysis thereof, as well as products from performing any method herein-discussed, including intermediates.

Therapeutics

In some embodiments, the compositions containing one or more of the muscle-specific targeting moieties described herein, including, but not limited to the engineered AAV capsids, engineered viral particles, engineered cells, and/or formulations thereof described herein can be delivered to a subject in need thereof as a therapy for one or more diseases. In some embodiments, the disease to be treated is a genetic- or epigenetic-based disease. In some embodiments, the disease to be treated is not a genetic- or epigenetic-based disease. In some embodiments, one the compositions containing one or more of the muscle-specific targeting moieties described herein, including, but not limited to, the engineered viral capsids, viral particles, engineered cells, and/or formulations thereof described herein can be delivered to a subject in need thereof as a treatment or prevention (or as a part of a treatment or prevention) of a disease. It will be appreciated that the specific disease to be treated and/or prevented by delivery of a composition, formulation, cell and the like of the present invention, can be dependent on the cargo coupled to, attached to, contained in, or otherwise associated with the composition, formulation, cell and the like of the present invention.

Genetic diseases that can be treated are discussed in greater detail elsewhere herein (see e.g. discussion on Gene-modification based-therapies below). Other diseases include but are not limited to any of the following: cancer, Acubetivacter infections, actinomycosis, African sleeping sickness, AIDS/HIV, amoebiasis, Anaplasmosis, Angiostrongyliasis, Anisakiasis, Anthrax, *Arcanobacterium haemolyticum* infection, Argentine hemorrhagic fever, Ascariasis, Aspergillosis, Astrovirus infection, Babesiosis, Bacterial meningitis, Bacterial pneumonia, Bacterial vaginosis, Bacteroides infection, balantidiasis, Bartonellosis, *Baylisascaris* infection, BK virus infection, Black *Piedra, Blastocystis*, Blastomycosis, Bolivian hemorrhagic fever, Botulism, Brazilian hemorrhagic fever, brucellosis, Bubonic plague, *Burkholderia* infection, buruli ulcer, calicivirus invention, campylobacteriosis, Candidiasis, Capillariasis, Carrion's disease, Cat-scratch disease, cellulitis, Chagas Disease, Chancroid, Chickenpox, Chikungunya, *Chlamydia, Chlamydia pneumoniae*, Cholera, Chromoblastomycosis, Chytridiomycosis, Clonorchiasis, *Clostridium difficile* colitis, Coccidioidomycosis, Colorado tick fever, rhinovirus/coronavirus infection (common cold), Creutzfeldt-Jakob disease, Crimean-congo hemorrhagic fever, Cryptococcosis, Cryptosporidiosis, Cutaneous larva migrans (CLM), cyclosporiasis, cysticercosis, cytomegalovirus infection, Dengue fever, Desmodesmus infection, Dientamoebiasis, Diphtheria, Diphyllobothriasis, Dracunculiasis, Ebola, Echinococcosis, Ehrlichiosis, Enterobiasis, *Enterococcus* infection, Enterovirus infection, Epidemic typhus, Erythema Infectiosum, Exanthem subitum, Fascioliasis, Fasciolopsiasis, fatal familial insomnia, filariasis, *Clostridium perfringens* infection, *Fusobacterium* infection, Gas gangrene (clostridial myonecrosis), Geotrichosis, Gerstmann-Straussler-Scheinker syndrome, Giardiasis, Glanders, Gnathostomiasis, Gonorrhea, Granuloma inguinales, Group A streptococcal infection, Group B streptococcal infection, *Haemophilus influenzae* infection, Hand, foot, and mouth disease, hanta virus pulmonary syndrome, heartland virus disease, *Helicobacter pylori* infection, hemorrhagic fever with renal syndrome, Hendra virus infection, Hepatitis (all groups A, B, C, D, E), herpes simplex, histoplasmosis, hookworm infection, human bocavirus infection, human ewingii ehrlichiosis, Human granulocytic anaplasmosis, human metapneumovirus infection, human monocytic ehrlichiosis, human papilloma virus, Hymenolepiasis, Epstein-Barr infection, mononucleosis, influenza, isosporiasis, Kawasaki disease, Kingella kingae infection, Kuru, Lassa fever, Legionellosis (Legionnaire's disease and Potomac Fever), Leishmaniasis, Leprosy, Leptospirosis, Listeriosis, Lyme disease, lymphatic filariasis, lymphocytic choriomeningitis, Malaria, Marburg hemorrhagic fever, measles, Middle East respiratory syndrome, Melioidosis, meningitis, Meningococcal disease, Metagonimiasis, Microsporidiosis, Molluscum contagiosum, Monkeypox, Mumps, Murine typhus, *Mycoplasma* pneumonia, *Mycoplasma genitalium* infection, Mycetoma, Myiasis, Conjunctivitis, Nipah virus infection, Norovirus, Variant Creutzfeldt-Jakob disease, Nocardiosis, Onchocerciasis, Opisthorchiasis, Paracoccidioidomycosis, Paragonimiasis, Pasteurellosis, Pediculosis capitis, Pediculosis corporis, Pediculosis pubis, pelvic inflammatory disease, pertussis, plague, pneumococcal infection, *pneumocystis* pneumonia, pneumonia, poliomyelitis, *prevotella* infection, primary amoebic meningoencephalitis, progressive multifocal leukoencephalopathy, Psittacosis, Q fever, rabies, relapsing fever, respiratory syncytial virus infection, rhinovirus infection, rickettsial infection, Rickettsialpox, Rift Valley Fever, Rocky Mountain Spotted Fever, Rotavirus infection, Rubella, *Salmonellosis*, SARS, Scabies, Scarlet fever, Schistosomiasis, Sepsis, Shigellosis, Shingles, Smallpox, Sporotrichosis, Staphylococcal infection (including MRSA), strongyloidiasis, subacute sclerosing panencephalitis, Syphilis, Taeniasis, tetanus, *Trichophyton* species infection, Toxocariasis, Toxoplasmosis, Trachoma, Trichinosis, Trichuriasis, Tuberculosis, Tularemia, Typhoid Fever, Typhus Fever, *Ureaplasma urealyticum* infection, Valley fever, Venezuelan equine encephalitis, Venezuelan hemorrhagic fever, *Vibrio* species infection, Viral pneumonia, West Nile Fever, White *Piedra, Yersinia pseudotuberculosis*, Yersiniosis, Yellow fever, Zeaspora, Zika fever, Zygomycosis and combinations thereof.

Other diseases and disorders that can be treated using embodiments of the present invention include, but are not limited to, endocrine diseases (e.g. Type I and Type II diabetes, gestational diabetes, hypoglycemia. Glucagonoma, Goiter, Hyperthyroidism, hypothyroidism, thyroiditis, thyroid cancer, thyroid hormone resistance, parathyroid gland disorders, Osteoporosis, osteitis deformans, rickets, osteomalacia, hypopituitarism, pituitary tumors, etc.), skin conditions of infections and non-infectious origin, eye diseases of infectious or non-infectious origin, gastrointestinal disorders of infectious or non-infectious origin, cardiovascular diseases of infectious or non-infectious origin, brain and neuron diseases of infectious or non-infectious origin, nervous system diseases of infectious or non-infectious origin, muscle diseases of infectious or non-infectious origin, bone diseases of infectious or non-infectious origin, reproductive system diseases of infectious or non-infectious origin, renal system diseases of infectious or non-infectious origin, blood diseases of infectious or non-infectious origin, lymphatic system diseases of infectious or non-infectious origin, immune system diseases of infectious or non-infectious origin, mental-illness of infectious or non-infectious origin and the like.

In some embodiments, the disease to be treated is a muscle or muscle related disease or disorder, such as a genetic muscle disease or disorder.

Other diseases and disorders will be appreciated by those of skill in the art.

Adoptive Cell Therapies

Generally speaking, adoptive cell transfer involves the transfer of cells (autologous, allogeneic, and/or xenogeneic) to a subject. The cells may or may not be modified and/or otherwise manipulated prior to delivery to the subject.

In some embodiments, an engineered cell as described herein can be included in an adoptive cell transfer therapy. In some embodiments, an engineered cell as described herein can be delivered to a subject in need thereof. In some embodiments, the cell can be isolated from a subject, manipulated in vitro such that it contains and/or is capable of generating a composition of the present invention containing a muscle-specific targeting moiety described elsewhere herein (including but not limited to an engineered viral particle) described herein to produce an engineered cell and delivered back to the subject in an autologous manner or to a different subject in an allogeneic or xenogeneic manner. The cell isolated, manipulated, and/or delivered can be a eukaryotic cell. The cell isolated, manipulated, and/or delivered can be a stem cell. The cell isolated, manipulated, and/or delivered can be a differentiated cell. The cell isolated, manipulated, and/or delivered can be an immune cell, a blood cell, an endocrine cell, a renal cell, an exocrine cell, a nervous system cell, a vascular cell, a muscle cell, a urinary system cell, a bone cell, a soft tissue cell, a cardiac cell, a neuron, or an integumentary system cell. Other specific cell types will instantly be appreciated by one of ordinary skill in the art.

In some embodiments, the isolated cell can be manipulated such that it becomes an engineered cell as described elsewhere herein (e.g. contain and/or express one or more engineered delivery system molecules or vectors described elsewhere herein). Methods of making such engineered cells are described in greater detail elsewhere herein.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can be or involve the administration of $10^4$-$10^9$ cells per kg body weight including all integer values of cell numbers within those ranges. In some embodiments, $10^5$ to $10^6$ cells/kg are delivered Dosing in adoptive cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tissue. In some embodiments, the tissue can be a tumor.

To guard against possible adverse reactions, engineered cells can be equipped with a transgenic safety switch, in the form of a transgene that renders the cells vulnerable to exposure to a specific signal. For example, the herpes simplex viral thymidine kinase (TK) gene may be used in this way, for example by introduction into the engineered cell similar to that discussed in Greco, et al., improving the safety of cell therapy with the TK-suicide gene. Front. Pharmacol. 2015; 6:95. In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28 (6): 1107-15 (2010)).

Methods of modifying isolated cells to obtain the engineered cells with the desired properties are described elsewhere herein. In some embodiments, the methods can include genome modification, including, but not limited to, genome editing using a CRISPR-Cas system to modify the cell. This can be in addition to introduction of an e.g., engineered AAV capsid system molecule describe elsewhere herein.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112 (12): 4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic cells, such as engineered cells described herein. Therefore, to effectively use an adoptive immunotherapy approach in these conditions, the introduced cells would need to be resistant to the immunosuppressive treatment. Thus, in a particular embodiment, the present invention further comprises a step of modifying the engineered cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to engineered cells for adoptive cell therapy by inactivating the target of the immunosuppressive agent in engineered cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44 (2): 356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

International Patent Publication No. WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In some embodiments, the gene locus involved in the expression of PD-1 or CTLA-4 genes is targeted. In some embodiments, combinations of genes are targeted, such as but not limited to PD-1 and TIGIT.

In some embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic or other modification of the engineered cells (such as engineered T cells (e.g. the isolated cell is a T cell), the engineered cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. The engineered cells can be expanded in vitro or in vivo.

In some embodiments, the method comprises editing the engineered cells ex vivo by a suitable gene modification method described elsewhere herein (e.g. gene editing via a CRISPR-Cas system) to eliminate potential alloreactive TCRs or other receptors to allow allogeneic adoptive transfer. In some embodiments, T cells are edited ex vivo by a CRISPR-Cas system or other suitable genome modification technique to knock-out or knock-down an endogenous gene encoding a TCR (e.g., an αβ TCR) or other relevant receptor to avoid graft-versus-host-disease (GVHD). In some embodiments, where the engineered cells are T cells, the engineered cells are edited ex vivo by CRISPR or other appropriate gene modification method to mutate the TRAC locus. In some embodiments, T cells are edited ex vivo via a CRISPR-Cas system using one or more guide sequences targeting the first exon of TRAC. See Liu et al., Cell Research 27:154-157 (2017). In some embodiments, the first exon of TRAC is modified using another appropriate gene modification method. In some embodiments, the method comprises use of CRISPR or other appropriate method to knock-in an exogenous gene encoding a CAR or a TCR into the TRAC locus, while simultaneously knocking-out the endogenous TCR (e.g., with a donor sequence encoding a self-cleaving P2A peptide following the CAR cDNA). See Eyquem et al., Nature 543:113-117 (2017). In some embodiments, the exogenous gene comprises a promoter-less CAR-encoding or TCR-encoding sequence which is inserted operably downstream of an endogenous TCR promoter.

In some embodiments, the method comprises editing the engineered cell, e.g. engineered T cells, ex vivo via a CRISPR-Cas system to knock-out or knock-down an endogenous gene encoding an HLA-I protein to minimize immunogenicity of the edited cells, e.g. engineered T cells. In some embodiments, engineered T cells can be edited ex vivo via a CRISPR-Cas system to mutate the beta-2 microglobulin (B2M) locus. In some embodiments, engineered cell, e.g. engineered T cells, are edited ex vivo via a CRISPR-Cas system using one or more guide sequences targeting the first exon of B2M. The first exon of B2M can also be modified using another appropriate modification method. See Liu et al., Cell Research 27:154-157 (2017). The first exon of B2M can also be modified using another appropriate modification method, which will be appreciated by those of ordinary skill in the art. In some embodiments, the method comprises use a CRISPR-Cas system to knock-in an exogenous gene encoding a CAR or a TCR into the B2M locus, while simultaneously knocking-out the endogenous B2M (e.g., with a donor sequence encoding a self-cleaving P2A peptide following the CAR cDNA). See Eyquem et al., Nature 543:113-117 (2017). This can also be accomplished using another appropriate modification method, which will be appreciated by those of ordinary skill in the art. In some embodiments, the exogenous gene comprises a promoter-less CAR-encoding or TCR-encoding sequence which is inserted operably downstream of an endogenous B2M promoter.

In some embodiments, the method comprises editing the engineered cell, e.g. engineered T cells, ex vivo via a CRISPR-Cas system to knock-out or knock-down an endogenous gene encoding an antigen targeted by an exogenous CAR or TCR. This can also be accomplished using another appropriate modification method, which will be appreciated by those of ordinary skill in the art. In some embodiments, the engineered cells, such as engineered T cells, are edited ex vivo via a CRISPR-Cas system to knock-out or knock-down the expression of a tumor antigen selected from human telomerase reverse transcriptase (hTERT), survivin, mouse double minute 2 homolog (MDM2), cytochrome P450 1B 1 (CYPIB), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (DI) (see WO2016/011210). This can also be accomplished using another appropriate modification method, which will be appreciated by those of ordinary skill in the art. In some embodiments, the engineered cells, such as engineered T cells are edited ex vivo via a CRISPR-Cas system to knock-out or knock-down the expression of an antigen selected from B cell maturation antigen (BCMA), transmembrane activator and CAML Interactor (TACI), or B-cell activating factor receptor (BAFF-R), CD38, CD138, CS-1, CD33, CD26, CD30, CD53, CD92, CD100, CD148, CD150, CD200, CD261, CD262, or CD362 (see WO2017/011804). This can also be accomplished using another appropriate modification method, which will be appreciated by those of ordinary skill in the art.

Gene Drives

The present invention also contemplates use of the compositions containing a muscle-specific targeting moiety described elsewhere herein, formulations thereof, cells thereof, vector systems, and the like to generate a gene drive via delivery of one or more cargo polynucleotides or production of a composition containing a muscle-specific targeting moiety described elsewhere herein (including but not limited to engineered AAV capsid particles) with one or more cargo polynucleotides capable of producing a gene drive. In some embodiments, the gene drive can be a Cas-mediated RNA-guided gene drive e.g. Cas- to provide RNA-guided gene drives, for example in systems analogous to gene drives described in International Patent Publication WO 2015/105928. Systems of this kind may for example provide methods for altering eukaryotic germline cells, by introducing into the germline cell a nucleic acid sequence encoding an RNA-guided DNA nuclease and one or more guide RNAs. The guide RNAs may be designed to be complementary to one or more target locations on genomic DNA of the germline cell. The nucleic acid sequence encoding the RNA guided DNA nuclease and the nucleic acid sequence encoding the guide RNAs may be provided on constructs between flanking sequences, with promoters arranged such that the germline cell may express the RNA guided DNA nuclease and the guide RNAs, together with any desired cargo-encoding sequences that are also situated between the flanking sequences. The flanking sequences will typically include a sequence which is identical to a corresponding sequence on a selected target chromosome, so that the flanking sequences work with the components encoded by the construct to facilitate insertion of the foreign nucleic acid construct sequences into genomic DNA at a target cut site by mechanisms such as homologous recombination, to render the germline cell homozygous for the foreign nucleic acid sequence. In this way, gene-drive systems are capable of introgressing desired cargo genes throughout a breeding population (Gantz et al., 2015, Highly efficient Cas9-mediated gene drive for population modification of the malaria vector mosquito *Anopheles stephensi*, PNAS 2015, published ahead of print Nov. 23, 2015, doi: 10.1073/pnas.1521077112; Esvelt et al., 2014, Concerning RNA-guided gene drives for the alteration of wild populations eLife 2014; 3: e03401). In select embodiments, target sequences may be selected which have few potential off-target sites in a genome. Targeting multiple sites within a target locus, using multiple guide RNAs, may increase the cutting frequency and hinder the evolution of drive resistant alleles. Truncated guide RNAs may reduce off-target cutting. Paired nickases may be used instead of a single nuclease, to further increase specificity. Gene drive constructs (such as gene drive engineered delivery system constructs) may include cargo sequences encoding transcriptional regulators, for example to activate homologous recombination genes and/or repress non-homologous end-joining. Target sites may be chosen within an essential gene, so that non-homologous end-joining events may cause lethality rather than creating a drive-resistant allele. The gene drive constructs can be engineered to function in a range of hosts at a range of temperatures (Cho et al. 2013, Rapid and Tunable Control of Protein Stability in *Caenorhabditis elegans* Using a Small Molecule, PLOS ONE 8 (8): e72393. doi: 10.1371/journal.pone.0072393).

Transplantation and Xenotransplantation

The compositions containing a muscle-specific targeting moiety described elsewhere herein, formulations thereof, cells thereof, vector systems, and the like, can be used to deliver cargo polynucleotides and/or otherwise be involved in modifying tissues for transplantation between two different persons (transplantation) or between species (xenotransplantation). Such techniques for generation of transgenic animals is described elsewhere herein. Interspecies transplantation techniques are generally known in the art. For example, RNA-guided DNA nucleases can be delivered using via engineered viral particles or other delivery vehicles, polynucleotides, vectors, and/or engineered cells of the present invention described herein and can be used to knockout, knockdown or disrupt selected genes in an organ for transplant (e.g. ex vivo (e.g. after harvest but before transplantation) or in vivo (in donor or recipient)), animal, such as a transgenic pig (such as the human heme oxygenase-1 transgenic pig line), for example by disrupting expression of genes that encode epitopes recognized by the human immune system, i.e. xenoantigen genes. Candidate porcine genes for disruption may for example include a (1,3)-galactosyltransferase and cytidine monophosphate-N-acetylneuraminic acid hydroxylase genes (see International Patent Publication WO 2014/066505). In addition, genes encoding endogenous retroviruses may be disrupted, for example the genes encoding all porcine endogenous retroviruses (see Yang et al., 2015, Genome-wide inactivation of porcine endogenous retroviruses (PERVs), Science 27 Nov. 2015: Vol. 350 no. 6264 pp. 1101-1104). In addition, RNA-guided DNA nucleases may be used to target a site for integration of additional genes in xenotransplant donor animals, such as a human CD55 gene to improve protection against hyperacute rejection.

Where it is interspecies transplantation (such as human to human) the composition compositions containing a muscle-specific targeting moiety described elsewhere herein, or composition containing a muscle-specific targeting moiety (e.g. an engineered AAV capsid system molecule, vectors, engineered cells, and/or engineered delivery particles described herein), can be used to deliver cargo polynucleotides and/or otherwise be involved to modify the tissue to be transplanted. In some embodiments, the modification can include modifying one or more HLA antigens or other tissue type determinants, such that the immunogenic profile is more similar or identical to the recipient's immunogenic profile than to the donor's so as to reduce the occurrence of rejection by the recipient. Relevant tissue type determinants are known in the art (such as those used to determine organ matching) and techniques to determine the immunogenic profile (which is made up of the expression signature of the tissue type determinants) are generally known in the art.

In some embodiments, the donor (such as before harvest) or recipient (after transplantation) can receive one or more of the compositions containing a muscle-specific targeting moiety described elsewhere herein, formulations thereof, cells thereof, vector systems, engineered muscle-specific delivery system molecules, vectors, engineered cells, and/or engineered delivery particles described herein that are capable of modifying the immunogenic profile of the transplanted cells, tissue, and/or organ. In some embodiments, the transplanted cells, tissue, and/or organ can be harvested from the donor and the compositions containing a muscle-specific targeting moiety described elsewhere herein, formulations thereof, cells thereof, vector systems, engineered muscle-specific delivery system molecules, vectors, engineered cells, and/or engineered delivery particles described herein capable of modifying the harvested cells, tissue, and/or organ to be, for example, less immunogenic or be modified to have some specific characteristic when transplanted in the recipient can be delivered to the harvested cells, tissue, and/or organ ex vivo. After delivery the cells, tissue, and/or organs can be transplanted into the donor.

Gene Modification and Treatment of Diseases with Genetic or Epigenetic Aspects

The engineered muscle-specific delivery system molecules, vectors, engineered cells, and/or engineered delivery particles described herein containing a muscle-specific targeting moiety can be used to modify genes or other polynucleotides and/or treat diseases with genetic and/or epigenetic aspects. As described elsewhere herein the cargo molecule can be a polynucleotide that can be delivered to a cell and, in some embodiments, be integrated into the genome of the cell. In some embodiments, the cargo molecule(s) can be one or more CRISPR-Cas system components. In some embodiments, the CRISPR-Cas components, when delivered by a composition or formulation thereof of the present invention, such as an engineered muscle-specific viral particle or other engineered delivery vehicle described herein, can be optionally expressed in the recipient cell and act to modify the genome of the recipient cell in a sequence specific manner. In some embodiments, the cargo molecules that can be packaged and delivered by the engineered viral particles or other engineered delivery vehicles and/or compositions described herein can facilitate/mediate genome modification via a method that is not dependent on CRISPR-Cas. Such non-CRISPR-Cas genome modification systems will instantly be appreciated by those of ordinary skill in the art and are also, at least in part, described elsewhere herein. In some embodiments, modification is at a specific target sequence. In other embodiments, modification is at locations that appear to be random throughout the genome.

Examples of disease-associated genes and polynucleotides and disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Any of these can be appropriate to be treated by one or more of the methods described herein. In some embodiments, the disease is a muscle disease or disorder, neuro-muscular disease or disorder, or a cardiomyopathy. In some embodiments, the disease or disorder selected from any one or more of the following:

(a) an auto immune disease;
(b) a cancer;
(c) a muscular dystrophy;
(d) a neuro-muscular disease;
(e) a sugar or glycogen storage disease;
(f) an expanded repeat disease;
(g) a dominant negative disease;
(h) a cardiomyopathy;
(i) a viral disease;
(j) a progeroid disease; or
(k) any combination thereof.

In some embodiments, the expanded repeat disease is Huntington's disease, a Myotonic Dystrophy, or Facioscapulohumeral muscular dystrophy (FSHD). In some embodiments, the muscular dystrophy is Duchene muscular dystrophy, Becker Muscular dystrophy, a Limb-Girdle muscular dystrophy, an Emery Dreifuss muscular dystrophy, a myotonic dystrophy, or FSHD. In some embodiments, the myotonic dystrophy is Type 1 or Type 2. In some embodiments, the LGMD is subtype 2A, 2B, 2C, 2D, 2E, or 2L. In some embodiments, the cardiomyopathy is dilated cardiomyopathy, hypertrophic cardiomyopathy, DMD-associated cardiomyopathy, or Dannon disease. In some embodiments, the sugar or glycogen storage disease is a MPS type III disease or Pompe disease. In some embodiments, the MPS type III disease, is MPS Type IIIA, IIIB, IIIC, or IIID. In some embodiments, the neuro-muscular disease is Charcot-Marie-Tooth disease or Friedreich's Ataxia.

More specifically, mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a CRISPR complex of the present invention. Examples of disease-associated and/or cell function-associated genes and polynucleotides are listed in Tables A and B.

TABLE A

Exemplary Genetic and Other Diseases and Associated Genes

| Disease Name | Primary Tissues or System Affected | Additional Tissues/ Systems Affected | Genes |
|---|---|---|---|
| Achondroplasia | Bone and Muscle | | fibroblast growth factor receptor 3 (FGFR3) |
| Achromatopsia | eye | | CNGA3, CNGB3, GNAT2, PDE6C, PDE6H, ACHM2, ACHM3, |
| Acute Renal Injury | kidney | | NFkappaB, AATF, p85alpha, FAS, Apoptosis cascade elements (e.g. FASR, Caspase 2, 3, 4, 6, 7, 8, 9, 10, AKT, TNF alpha, IGF1, IGF1R, RIPK1), p53 |
| Age Related Macular Degeneration | eye | | Abcr; CCL2; CC2; CP (ceruloplasmin); Timp3; cathepsinD; VLDLR, CCR2 |
| AIDS | Immune System | | KIR3DL1, NKAT3, NKB1, AMB11, KIR3DS1, IFNG, CXCL12, SDF1 |

TABLE A-continued

| Exemplary Genetic and Other Diseases and Associated Genes | | | |
|---|---|---|---|
| Disease Name | Primary Tissues or System Affected | Additional Tissues/ Systems Affected | Genes |
| Albinism (including oculocutaneous albinism (types 1-7) and ocular albinism) | Skin, hair, eyes, | | TYR, OCA2, TYRP1, and SLC45A2, SLC24A5 and C10orf11 |
| Alkaptonuria | Metabolism of amino acids | Tissues/organs where homogentisic acid accumulates, particularly cartilage (joints), heart valves, kidneys | HGD |
| alpha-1 antitrypsin deficiency (AATD or A1AD) | Lung | Liver, skin, vascular system, kidneys, GI | SERPINA1, those set forth in WO2017165862, PiZ allele |
| ALS | CNS | | SOD1; ALS2; ALS3; ALS5; ALS7; STEX; FUS; TARDBP; VEGF (VEGF-a; VEGF-b; VEGF-c); DPP6; NEFH, PTGS1, SLC1A2, TNFRSF10B, PRPH, HSP90AA1, CRIA2, IFNG, AMPA2 S100B, FGF2, AOX1, CS, TXN, RAPHJ1, MAP3K5, NBEAL1, GPX1, ICA1L, RAC1, MAPT, ITPR2, ALS2CR4, GLS, ALS2CR8, CNTFR, ALS2CR11, FOLH1, FAM117B, P4HB, CNTF, SQSTM1, STRADB, NAIP, NLR, YWHAQ, SLC33A1, TRAK2, SCA1, NIF3L1, NIF3, PARD3B, COX8A, CDK15, HECW1, HECT, C2, WW 15, NOS1, MET, SOD2, HSPB1, NEFL, CTSB, ANG, HSPA8, RNase A, VAPB, VAMP, SNCA, alpha HGF, CAT, ACTB, NEFM, TH, BCL2, FAS, CASP3, CLU, SMN1, G6PD, BAX, HSF1, RNF19A, JUN, ALS2CR12, HSPA5, MAPK14, APEX1, TXNRD1, NOS2, TIMP1, CASP9, XIAP, GLG1, EPO, VEGFA, ELN, GDNF, NFE2L2, SLC6A3, HSPA4, APOE, PSMB8, DCTN2, TIMP3, KIFAP3, SLC1A1, SMN2, CCNC, STUB1, ALS2, PRDX6, SYP, CABIN1, CASP1, GART, CDK5, ATXN3, RTN4, C1QB, VEGFC, HTT, PARK7, XDH, GFAP, MAP2, CYCS, FCGR3B, CCS, UBL5, MMP9m SLC18A3, TRPM7, HSPB2, AKT1, DEERL1, CCL2, NGRN, GSR, TPPP3, APAF1, BTBD10, GLUD1, CXCR4, S:C1A3, FLT1, PON1, AR, LIF, ERBB3, :GA:S1, CD44, TP53, TLR3, GRIA1, GAPDH, AMPA, GRIK1, DES, CHAT, FLT4, CHMP2B, BAG1, CHRNA4, GSS, BAK1, KDR, GSTP1, OGG1, IL6 |
| Alzheimer's Disease | Brain | | E1; CHIP; UCH; UBB; Tau; LRP; PICALM; CLU; PS1; SORL1; CR1; VLDLR; UBA1; UBA3; CHIP28; AQP1; UCHL1; UCHL3; APP, AAA, CVAP, AD1, APOE, AD2, DCP1, ACE1, MPO, PACIP1, PAXIP1L, PTIP, A2M, BLMH, BMH, PSEN1, AD3, ALAS2, ABCA1, BIN1, BDNF, BTNL8, C1ORF49, CDH4, CHRNB2, CKLFSF2, CLEC4E, CR1L, CSF3R, CST3, CYP2C, DAPK1, ESR1, FCAR, FCGR3B, FFA2, FGA, GAB2, GALP, GAPDHS, GMPB, HP, HTR7, IDE, IF127, IFI6, IFIT2, IL1RN, IL-1RA, IL8RA, IL8RB, JAG1, KCNJ15, |

TABLE A-continued

| Exemplary Genetic and Other Diseases and Associated Genes | | | |
|---|---|---|---|
| Disease Name | Primary Tissues or System Affected | Additional Tissues/ Systems Affected | Genes |
| | | | LRP6, MAPT, MARK4, MPHOSPH1, MTHFR, NBN, NCSTN, NIACR2, NMNAT3, NTM, ORM1, P2RY13, PBEF1, PCK1, PICALM, PLAU, PLXNC1, PRNP, PSEN1, PSEN2, PTPRA, RALGPS2, RGSL2, SELENBP1, SLC25A37, SORL1, Mitoferrin-1, TF, TFAM, TNF, TNFRSF10C, UBE1C |
| Amyloidosis | | | APOA1, APP, AAA, CVAP, AD1, GSN, FGA, LYZ, TTR, PALB |
| Amyloid neuropathy | | | TTR, PALB |
| Anemia | Blood | | CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT |
| Angelman Syndrome | Nervous system, brain | | UBE3A |
| Attention Deficit Hyperactivity Disorder (ADHD) | Brain | | PTCHD1 |
| Autoimmune lymphoproliferative syndrome | Immune system | | TNFRSF6, APT1, FAS, CD95, ALPS1A |
| Autism, Autism spectrum disorders (ASDs), including Asperger's and a general diagnostic category called Pervasive Developmental Disorders (PDDs) | Brain | | PTCHD1; Mecp2; BZRAP1; MDGA2; Sema5A; Neurexin 1; GLO1, RTT, PPMX, MRX16, RX79, NLGN3, NLGN4, KIAA1260, AUTSX2, FMRI, FMR2; FXR1; FXR2; MGLUR5, ATP10C, CDH10, GRM6, MGLUR6, CDH9, CNTN4, NLGN2, CNTNAP2, SEMA5A, DHCR7, NLGN4X, NLGN4Y, DPP6, NLGN5, EN2, NRCAM, MDGA2, NRXN1, FMR2, AFF2, FOXP2, OR4M2, OXTR, FXR1, FXR2, PAH, GABRA1, PTEN, GABRA5, PTPRZ1, GABRB3, GABRG1, HIRIP3, SEZ6L2, HOXA1, SHANK3, IL6, SHBZRAP1, LAMB1, SLC6A4, SERT, MAPK3, TAS2R1, MAZ, TSC1, MDGA2, TSC2, MECP2, UBE3A, WNT2, see also 20110023145 |
| autosomal dominant polycystic kidney disease (ADPKD) - (includes diseases such as von Hippel-Lindau disease and tubreous sclerosis complex disease) | kidney | liver | PKD1, PKD2 |
| Autosomal Recessive Polycystic Kidney Disease (ARPKD) | kidney | liver | PKDH1 |
| Ataxia-Telangiectasia (a.k.a Louis Bar syndrome) | Nervous system, immune system | various | ATM |
| B-Cell Non-Hodgkin Lymphoma | | | BCL7A, BCL7 |
| Bardet-Biedl syndrome | Eye, musculoskeletal system, kidney, reproductive organs | Liver, ear, gastrointestinal system, brain | ARL6, BBS1, BBS2, BBS4, BBS5, BBS7, BBS9, BBS10, BBS12, CEP290, INPP5E, LZTFL1, MKKS, MKS1, SDCCAG8, TRIM32, TTC8 |
| Bare Lymphocyte Syndrome | blood | | TAPBP, TPSN, TAP2, ABCB3, PSF2, RING11, MHC2TA, C2TA, RFX5, RFXAP, RFX5 |
| Barter's Syndrome (types I, II, III, IVA and B, and V) | kidney | | SLC12A1 (type I), KCNJ1 (type II), CLCNKB (type III), BSND (type IV A), or both the CLCNKA CLCNKB genes (type IV B), CASR (type V). |
| Becker muscular dystrophy | Muscle | | DMD, BMD, MYF6 |
| Best Disease (Vitelliform Macular Dystrophy type 2) | eye | | VMD2 |

TABLE A-continued

Exemplary Genetic and Other Diseases and Associated Genes

| Disease Name | Primary Tissues or System Affected | Additional Tissues/ Systems Affected | Genes |
|---|---|---|---|
| Bleeding Disorders | blood | | TBXA2R, P2RX1, P2X1 |
| Blue Cone Monochromacy | eye | | OPN1LW, OPN1MW, and LCR |
| Breast Cancer | Breast tissue | | BRCA1, BRCA2, COX-2 |
| Bruton's Disease (aka X-linked Agammglobulinemia) | Immune system, specifically B cells | | BTK |
| Cancers (e.g., lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma | Various | | FAS, BID, CTLA4, PDCD1, CBLB, PTPN6, TRAC, TRBC, those described in WO2015048577 |
| Cardiovascular Diseases | heart | Vascular system | IL1B, XDH, TP53, PTGS, MB, IL4, ANGPT1, ABCGu8, CTSK, PTGIR, KCNJ11, INS, CRP, PDGFRB, CCNA2, PDGFB, KCNJ5, KCNN3, CAPN10, ADRA2B, ABCG5, PRDX2, CPAN5, PARP14, MEX3C, ACE, RNF, IL6, TNF, STN, SERPINE1, ALB, ADIPOQ, APOB, APOE, LEP, MTHFR, APOA1, EDN1, NPPB, NOS3, PPARG, PLAT, PTGS2, CETP, AGTR1, HMGCR, IGF1, SELE, REN, PPARA, PON1, KNG1, CCL2, LPL, VWF, F2, ICAM1, TGFB, NPPA, IL10, EPO, SOD1, VCAM1, IFNG, LPA, MPO, ESR1, MAPK, HP, F3, CST3, COG2, MMP9, SERPINC1, F8, HMOX1, APOC3, IL8, PROL1, CBS, NOS2, TLR4, SELP, ABCA1, AGT, LDLR, GPT, VEGFA, NR3C2, IL18, NOS1, NR3C1, FGB, HGF, ILIA, AKT1, LIPC, HSPD1, MAPK14, SPP1, ITGB3, CAT, UTS2, THBD, F10, CP, TNFRSF11B, EGFR, MMP2, PLG, NPY, RHOD, MAPK8, MYC, FN1, CMA1, PLAU, GNB3, ADRB2, SOD2, F5, VDR, ALOX5, HLA-DRB1, PARP1, CD40LG, PON2, AGER, IRS1, PTGS1, ECE1, F7, IRMN, EPHX2, IGFBP1, MAPK10, FAS, ABCB1, JUN, IGFBP3, CD14, PDE5A, AGTR2, CD40, LCAT, CCR5, MMP1, TIMP1, ADM, DYT10, STAT3, MMP3, ELN, USF1, CFH, HSPA4, MMP12, MME, F2R, SELL, CTSB, ANXA5, ADRB1, CYBA, FGA, GGT1, LIPG, HIF1A, CXCR4, PROC, SCARB1, CD79A, PLTP, ADD1, FGG, SAA1, KCNH2, DPP4, NPR1, VTN, KIAA0101, FOS, TLR2, PPIG, IL1R1, AR, CYP1A1, SERPINA1, MTR, RBP4, APOA4, CDKN2A, FGF2, EDNRB, ITGA2, VLA-2, CABIN1, SHBG, HMGB1, HSP90B2P, CYP3A4, GJA1, CAV1, ESR2, LTA, GDF15, BDNF, CYP2D6, NGF, SP1, TGIF1, SRC, EGF, PIK3CG, HLA-A, KCNQ1, CNR1, FBN1, CHKA, BEST1, |

TABLE A-continued

| Exemplary Genetic and Other Diseases and Associated Genes | | | |
|---|---|---|---|
| Disease Name | Primary Tissues or System Affected | Additional Tissues/ Systems Affected | Genes |
| | | | CTNNB1, IL2, CD36, PRKAB1, TPO, ALDH7A1, CX3CR1, TH, F9, CH1, TF, HFE, IL17A, PTEN, GSTM1, DMD, GATA4, F13A1, TTR, FABP4, PON3, APOC1, INSR, TNFRSF1B, HTR2A, CSF3, CYP2C9, TXN, CYP11B2, PTH, CSF2, KDR, PLA2G2A, THBS1, GCG, RHOA, ALDH2, TCF7L2, NFE2L2, NOTCH1, UGT1A1, IFNA1, PPARD, SIRT1, GNHR1, PAPPA, ARR3, NPPC, AHSP, PTK2, IL13, MTOR, ITGB2, GSTT1, IL6ST, CPB2, CYP1A2, HNF4A, SLC64A, PLA2G6, TNFSF11, SLC8A1, F2RL1, AKR1A1, ALDH9A1, BGLAP, MTTP, MTRR, SULT1A3, RAGE, C4B, P2RY12, RNLS, CREB1, POMC, RAC1, LMNA, CD59, SCM5A, CYP1B1, MIF, MMP13, TIMP2, CYP19A1, CUP21A2, PTPN22, MYH14, MBL2, SELPLG, AOC3, CTSL1, PCNA, IGF2, ITGB1, CAST, CXCL12, IGHE, KCNE1, TFRC, COL1A1, COL1A2, IL2RB, PLA2G10, ANGPT2, PROCR, NOX4, HAMP, PTPN11, SLCA1, IL2RA, CCL5, IRF1, CF:AR, CA:CA, EIF4E, GSTP1, JAK2, CYP3A5, HSPG2, CCL3, MYD88, VIP, SOAT1, ADRBK1, NR4A2, MMP8, NPR2, GCH1, EPRS, PPARGC1A, F12, PECAM1, CCL4, CERPINA34, CASR, FABP2, TTF2, PROS1, CTF1, SGCB, YME1L1, CAMP, ZC3H12A, AKR1B1, MMP7, AHR, CSF1, HDAC9, CTGF, KCNMA1, UGT1A, PRKCA, COMT, S100B, EGR1, PRL, IL15, DRD4, CAMK2G, SLC22A2, CCL11, PGF, THPO, GP6, TACR1, NTS, HNF1A, SST, KCDN1, LOC646627, TBXAS1, CUP2J2, TBXA2R, ADH1C, ALOX12, AHSG, BHMT, GJA4, SLC25A4, ACLY, ALOX5AP, NUMA1, CYP27B1, CYSLTR2, SOD3, LTC4S, UCN, GHRL, APOC2, CLEC4A, KBTBD10, TNC, TYMS, SHC1, LRP1, SOCS3, ADH1B, KLK3, HSD11B1, VKORC1, SERPINB2, TNS1, RNF19A, EPOR, ITGAM, PITX2, MAPK7, FCGR3A, LEEPR, ENG, GPX1, GOT2, HRH1, NR112, CRH, HTR1A, VDAC1, HPSE, SFTPD, TAP2, RMF123, PTK2Bm NTRK2, IL6R, ACHE, GLP1R, GHR, GSR, NQO1, NR5A1, GJB2, SLC9A1, MAOA, PCSK9, FCGR2A, SERPINF1, EDN3, UCP2, TFAP2A, C4BPA, SERPINF2, TYMP, ALPP, CXCR2, SLC3A3, ABCG2, ADA, JAK3, HSPA1A, FASN, FGF1, F11, ATP7A, CR1, GFPA, ROCK1, MECP2, MYLK, BCHE, LIPE, ADORA1, WRN, CXCR3, CD81, SMAD7, LAMC2, MAP3K5, CHGA, IAPP, RHO, ENPP1, PTHLH, NRG1, VEGFC, ENPEP, CEBPB, NAGLU,. F2RL3, CX3CL1, BDKRB1, ADAMTS13, ELANE, ENPP2, CISH, GAST, MYOC, ATP1A2, NF1, GJB1, MEF2A, VCL, BMPR2, TUBB, CDC42, KRT18, HSF1, MYB, |

TABLE A-continued

Exemplary Genetic and Other Diseases and Associated Genes

| Disease Name | Primary Tissues or System Affected | Additional Tissues/ Systems Affected | Genes |
|---|---|---|---|
| | | | PRKAA2, ROCK2, TFP1, PRKG1, BMP2, CTNND1, CTH, CTSS, VAV2, NPY2R, IGFBP2, CD28, GSTA1, PPIA, APOH, S100A8, IL11, ALOX15, FBLN1, NR1H3, SCD, GIP, CHGB, PRKCB, SRD5A1,HSD11B2, CALCRL, GALNT2, ANGPTL4, KCNN4, PIK3C2A, HBEGF, CYP7A1, HLA-DRB5, BNIP3, GCKR, S100A12, PADI4, HSPA14, CXCR1, H19, KRTAP19-3, IDDM2, RAC2, YRY1, CLOCK, NGFR, DBH, CHRNA4, CACNA1C, PRKAG2, CHAT, PTGDS, NR1H2, TEK, VEGFB, MEF2C, MAPKAPK2, TNFRSF11A, HSPA9, CYSLTR1, MATIA, OPRL1, IMPA1, CLCN2, DLD, PSMA6, PSMB8, CHI3L1, ALDH1B1, PARP2,STAR, LBP, ABCC6, RGS2, EFNB2, GJB6, APOA2, AMPD1, DYSF, FDFT1, EMD2, CCR6, GJB3, IL1RL1, ENTPD1, BBS4, CELSR2, F11R, RAPGEF3, HYAL1, ZNF259, ATOX1, ATF6, KHK, SAT1, GGH, TIMP4, SLC4A4, PDE2A, PDE3B, FADS1, FADS2, TMSB4X, TXNIP, LIMS1, RHOB, LY96, FOXO1, PNPLA2,TRH, GJC1, S:C17A5, FTO, GJD2, PRSC1, CASP12, GPBAR1, PXK, IL33, TRIB1, PBX4, NUPR1, 15-SEP, CILP2, TERC, GGT2, MTCO1, UOX, AVP, ANGPLT3 |
| Cataract | eye | | CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1 |
| CDKL-5 Deficiencies or Mediated Diseases | Brain, CNS | | CDKL5 |
| Charcot-Marie-Tooth (CMT) disease (Types 1, 2, 3, 4,) | Nervous system | Muscles (dystrophy) | PMP22 (CMT1A and E), MPZ (CMT1B), LITAF (CMT1C), EGR2 (CMT1D), NEFL (CMT1F), GJB1 (CMT1X), MFN2 (CMT2A), KIF1B (CMT2A2B), RAB7A (CMT2B), TRPV4 (CMT2C), GARS (CMT2D), NEFL (CMT2E), GAPD1 (CMT2K), HSPB8 (CMT2L), DYNC1H1, CMT20), LRSAM1 (CMT2P), IGHMBP2 (CMT2S), MORC2 (CMT2Z), GDAP1 (CMT4A), MTMR2 or SBF2/MTMR13 (CMT4B), SH3TC2 (CMT4C), NDRG1 (CMT4D), PRX (CMT4F), FIG4 (CMT4J), NT-3 |
| Chédiak-Higashi Syndrome | Immune system | Skin, hair, eyes, neurons | LYST |
| Choroidermia | | | CHM, REP1, |
| Chorioretinal atrophy | eye | | PRDM13, RGR, TEAD1 |
| Chronic Granulomatous Disease | Immune system | | CYBA, CYBB, NCF1, NCF2, NCF4 |
| Chronic Mucocutaneous Candidiasis | Immune system | | AIRE, CARD9, CLEC7A IL12B, IL12B1, IL1F, IL17RA, IL17RC, RORC, STAT1, STAT3, TRAF31P2 |
| Cirrhosis | liver | | KRT18, KRT8, CIRH1A, NAIC, TEX292, KIAA1988 |

TABLE A-continued

| Exemplary Genetic and Other Diseases and Associated Genes | | | |
|---|---|---|---|
| Disease Name | Primary Tissues or System Affected | Additional Tissues/ Systems Affected | Genes |
| Colon cancer (Familial adenomatous polyposis (FAP) and hereditary nonpolyposis colon cancer (HNPCC)) | Gastrointestinal | | FAP: APC HNPCC: MSH2, MLH1, PMS2, SH6, PMS1 |
| Combined Immunodeficiency | Immune System | | IL2RG, SCIDX1, SCIDX, IMD4); HIV-1 (CCL5, SCYA5, D17S136E, TCP228 |
| Cone(-rod) dystrophy | eye | | AIPL1, CRX, GUA1A, GUCY2D, PITPM3, PROM1, PRPH2, RIMS1, SEMA4A, ABCA4, ADAM9, ATF6, C21ORF2, C8ORF37, CACNA2D4, CDHR1, CERKL, CNGA3, CNGB3, CNNM4, CNAT2, IFT81, KCNV2, PDE6C, PDE6H, POC1B, RAX2, RDH5, RPGRIP1, TTLL5, RetCG1, GUCY2E |
| Congenital Stationary Night Blindness | eye | | CABP4, CACNA1F, CACNA2D4, GNAT1, CPR179, GRK1, GRM6, LRIT3, NYX, PDE6B, RDH5, RHO, RLBP1, RPE65, SAG, SLC24A1, TRPM1, |
| Congenital Fructose Intolerance | Metabolism | | ALDOB |
| Cori's Disease (Glycogen Storage Disease Type III) | Various-wherever glycogen accumulates, particularly liver, heart, skeletal muscle | | AGL |
| Corneal clouding and dystrophy | eye | | APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD |
| Cornea plana congenital | | | KERA, CNA2 |
| Cri du chat Syndrome, also known as 5p syndrome and cat cry syndrome | | | Deletions involving only band 5p15.2 to the entire short arm of chromosome 5, e.g. CTNND2, TERT, |
| Cystic Fibrosis (CF) | Lungs and respiratory system | Pancreas, liver, digestive system, reproductive system, exocrine, glands, | CTFR, ABCC7, CF, MRP7, SCNN1A, those described in WO2015157070 |
| Diabetic nephropathy | kidney | | Gremlin, 12/15- lipoxygenase, TIM44, |
| Dent Disease (Types 1 and 2) | Kidney | | Type 1: CLCN5, Type 2: ORCL |
| Dentatorubro-Pallidoluysian Atrophy (DRPLA) (aka Haw River and Naito-Oyanagi Disease) | CNS, brain, muscle | | Atrophin-1 and Atn1 |
| Down Syndrome | various | | Chromosome 21 trisomy |
| Drug Addiction | Brain | | Prkce; Drd2; Drd4; ABAT; GRIA2; Grm5; Grin1; Htr1b; Grin2a; Drd3; Pdyn; Gria1 |
| Duane syndrome (Types 1, 2, and 3, including subgroups A, B and C). Other names for this condition include: Duane's Retraction Syndrome (or DR syndrome), Eye Retraction Syndrome, Retraction Syndrome, Congenital retraction syndrome and Stilling-Turk-Duane Syndrome | eye | | CHN1, indels on chromosomes 4 and 8 |
| Duchenne muscular dystrophy (DMD) | muscle | Cardiovascular, respiratory | DMD, BMD, dystrophin gene, intron flanking exon 51 of DMD gene, exon 51 mutations in DMD gene, see also WO2013163628 and US Pat. Pub. 20130145487 |

TABLE A-continued

Exemplary Genetic and Other Diseases and Associated Genes

| Disease Name | Primary Tissues or System Affected | Additional Tissues/ Systems Affected | Genes |
|---|---|---|---|
| Edward's Syndrome (Trisomy 18) | | | Complete or partial trisomy of chromosome 18 |
| Ehlers-Danlos Syndrome (Types I-VI) | Various depending on type: including musculoskeletal, eye, vasculature, immune, and skin | | COL5A1, COL5A2, COL1A1, COL3A1, TNXB, PLOD1, COL1A2, FKBP14 and ADAMTS2 |
| Emery-Dreifuss muscular dystrophy | muscle | | LMNA, LMN1, EMD2, FPLD, CMD1A, HGPS, LGMD1B, LMNA, LMN1, EMD2, FPLD, CMD1A |
| Enhanced S-Cone Syndrome | eye | | NR2E3, NRL |
| Fabry's Disease | Various - including skin, eyes, and gastrointestinal system, kidney, heart, brain, nervous system | | GLA |
| Facioscapulohumeral muscular dystrophy | muscles | | FSHMD1A, FSHD1A, FRG1, |
| Factor H and Factor H-like 1 | blood | | HF1, CFH, HUS |
| Factor V Leiden thrombophilia and Factor V deficiency | blood | | Factor V (F5) |
| Factor V and Factor VII deficiency | blood | | MCFD2 |
| Factor VII deficiency | blood | | F7 |
| Factor X deficiency | blood | | F10 |
| Factor XI deficiency | blood | | F11 |
| Factor XII deficiency | blood | | F12, HAF |
| Factor XIIIA deficiency | blood | | F13A1, F13A |
| Factor XIIIB deficiency | blood | | F13B |
| Familial Hypercholestereolemia | Cardiovascular system | | APOB, LDLR, PCSK9 |
| Familial Mediterranean Fever (FMF) also called recurrent polyserositis or familial paroxysmal polyserositis | Various- organs/tissues with serous or synovial membranes, skin, joints | Heart, kidney, brain/CNS, reproductive organs | MEFV |
| Fanconi Anemia | Various - blood (anemia), immune system, cognitive, kidneys, eyes, musculoskeletal | | FANCA, FACA, FA1, FA, FAA, FAAP95, FAAP90, FLJ34064, FANCC, FANCG, RAD51, BRCA1, BRCA2, BRIP1, BACH1, FANCJ, FANCB, FANCD1, FANCD2, FANCD, FAD, FANCE, FACE, FANCF, FANCI, ERCC4, FANCL, FANCM, PALB2, RAD51C, SLX4, UBE2T, FANCB, XRCC9, PHF9, KIAA1596 |
| Fanconi Syndrome Types I (Childhood onset) and II (Adult Onset) | kidneys | | FRTS1, GATM |
| Fragile X syndrome and related disorders | brain | | FMR1, FMR2; FXR1; FXR2; mGLUR5 |
| Fragile XE Mental Retardation (aka Martin Bell syndrome) | Brain, nervous system | | FMR1 |
| Friedreich Ataxia (FRDA) | Brain, nervous system | heart | FXN/X25 |
| Fuchs endothelial corneal dystrophy | Eye | | TCF4; COL8A2 |
| Galactosemia | Carbohydrate metabolism disorder | Various-where galactose accumulates - liver, brain, eyes | GALT, GALK1, and GALE |
| Gastrointestinal Epithelial Cancer, GI cancer | | | CISH |
| Gaucher Disease (Types 1, 2, and 3, as well as other unusual forms that may not fit into these types) | Fat metabolism disorder | Various-liver, spleen, blood, CNS, skeletal system | GBA |

TABLE A-continued

| Disease Name | Primary Tissues or System Affected | Additional Tissues/ Systems Affected | Genes |
|---|---|---|---|
| Exemplary Genetic and Other Diseases and Associated Genes | | | |
| Griscelli syndrome | | | |
| Glaucoma | eye | | MYOC, TIGR, GLC1A, JOAG, GPOA, OPTN, GLC1E, FIP2, HYPL, NRP, CYP1B1, GLC3A, OPA1, NTG, NPG, CYP1B1, GLC3A, those described in WO2015153780 |
| Glomerulo sclerosis | kidney | | CC chemokine ligand 2 |
| Glycogen Storage Diseases Types I-VI -See also Cori's Disease, Pompe's Disease, McArdle's disease, Hers Disease, and Von Gierke's disease | Metabolism Diseases | | SLC2A2, GLUT2, G6PC, G6PT, G6PT1, GAA, LAMP2, LAMPB, AGL, GDE, GBE1, GYS2, PYGL, PFKM, see also Cori's Disease, Pompe's Disease, McArdle's disease, Hers Disease, and Von Gierke's disease |
| RBC Glycolytic enzyme deficiency | blood | | any mutations in a gene for an enzyme in the glycolysis pathway including mutations in genes for hexokinases I and II, glucokinase, phosphoglucose isomerase, phosphofructokinase, aldolase Bm triosephosphate isomerease, glyceraldehydee-3-phosphate dehydrogenase, phosphoglycerokinase, phosphoglycerate mutase, enolase I, pyruvate kinase |
| Hartnup's disease | Malabsorption disease | Various- brain, gastrointestinal, skin, | SLC6A19 |
| Hearing Loss | ear | | NOX3, Hes5, BDNF, |
| Hemochromatosis (HH) | Iron absorption regulation disease | Various-wherever iron accumulates, liver, heart, pancreas, joints, pituitary gland | HFE and H63D |
| Hemophagocytic lymphohistiocytosis disorders | blood | | PRF1, HPLH2, UNC13D, MUNC13-4, HPLH3, HLH3, FHL3 |
| Hemorrhagic disorders | blood | | PI, ATT, F5 |
| Hers disease (Glycogen storage disease Type VI) | liver | muscle | PYGL |
| Hereditary angioedema (HAE) | | | kalikrein B1 |
| Hereditary Hemorrhagic Telangiectasia (Osler-Weber-Rendu Syndrome) | Skin and mucous membranes | | ACVRL1, ENG and SMAD4 |
| Hereditary Spherocytosis | blood | | NK1, EPB42, SLC4A1, SPTA1, and SPTB |
| Hereditary Persistence of Fetal Hemoglobin | blood | | HBG1, HBG2, BCL11A, promoter region of HBG 1 and/or 2 (in the CCAAT box) |
| Hemophilia (hemophilia A (Classic) a B (aka Christmas disease) and C) | blood | | A: FVIII, F8C, HEMA<br>B: FVIX, HEMB, FIX<br>C: F9, F11 |
| Hepatic adenoma | liver | | TCF1, HNF1A, MODY3 |
| Hepatic failure, early onset, and neurologic disorder | liver | | SCOD1, SCO1 |
| Hepatic lipase deficiency | liver | | LIPC |
| Hepatoblastoma, cancer and carcinomas | liver | | CTNNB1, PDGFRL, PDGRL, PRLTS, AXIN1, AXIN, CTNNB1, TP53, P53, LFS1, IGF2R, MPRI, MET, CASP8, MCH5 |
| Hermansky-Pudlak syndrome | Skin, eyes, blood, lung, kidneys, intestine | | HPS1, HPS3, HPS4, HPS5, HPS6, HPS7, DTNBP1, BLOC1, BLOC1S2, BLOC3 |
| HIV susceptibility or infection | Immune system | | IL10, CSIF, CMKBR2, CCR2, CMKBR5, CCCKR5 (CCR5), those in WO2015148670A1 |

TABLE A-continued

Exemplary Genetic and Other Diseases and Associated Genes

| Disease Name | Primary Tissues or System Affected | Additional Tissues/ Systems Affected | Genes |
|---|---|---|---|
| Holoprosencephaly (HPE) (Alobar, Semilobar, and Lobar) | brain | | ACVRL1, ENG, SMAD4 |
| Homocystinuria | Metabolic disease | Various- connective tissue, muscles, CNS, cardiovascular system | CBS, MTHFR, MTR, MTRR, and MMADHC |
| HPV | | | HPV16 and HPV18 E6/E7 |
| HSV1, HSV2, and related keratitis | eye | | HSV1 genes (immediate early and late HSV-1 genes (UL1, 1.5, 5, 6, 8, 9, 12, 15, 16, 18, 19, 22, 23, 26, 26.5, 27, 28, 29, 30, 31, 32, 33, 34, 35, 36, 37, 38, 42, 48, 49.5, 50, 52, 54, S6, RL2, RS1, those described in WO2015153789, WO2015153791 |
| Hunter's Syndrome (aka Mucopolysaccharidosis type II) | Lysosomal storage disease | Various- liver, spleen, eye, joint, heart, brain, skeletal | IDS |
| Huntington's disease (HD) and HD-like disorders | Brain, nervous system | | HD, HTT, IT15, PRNP, PRIP, JPH3, JP3, HDL2, TBP, SCA17, PRKCE; IGF1; EP300; RCOR1; PRKCZ; HDAC4; and TGM2, and those described in WO2013130824, WO2015089354 |
| Hurler's Syndrome (aka mucopolysaccharidosis type I H, MPS IH) | Lysosomal storage disease | Various- liver, spleen, eye, joint, heart, brain, skeletal | IDUA, α-L-iduronidase |
| Hurler-Scheie syndrome (aka mucopolysaccharidosis type I H-S, MPS I H-S) | Lysosomal storage disease | Various- liver, spleen, eye, joint, heart, brain, skeletal | IDUA, α-L-iduronidase |
| hyaluronidase deficiency (aka MPS IX) | Soft and connective tissues | | HYAL1 |
| Hyper IgM syndrome | Immune system | | CD40L |
| Hyper- tension caused renal damage | kidney | | Mineral corticoid receptor |
| Immunodeficiencies | Immune System | | CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI |
| Inborn errors of metabolism: including urea cycle disorders, organic acidemias), fatty acid oxidation defects, amino acidopathies, carbohydrate disorders, mitochondrial disorders | Metabolism diseases, liver | Various organs and cells | See also: Carbohydrate metabolism disorders (e.g. galactosemia), Amino acid Metabolism disorders (e.g. phenylketonuria), Fatty acid metabolism (e.g. MCAD deficiency), Urea Cycle disorders (e.g. Citrullinemia), Organic acidemias (e.g. Maple Syrup Urine disease), Mitochondrial disorders (e.g. MELAS), peroxisomal disorders (e.g. Zellweger syndrome) |
| Inflammation | Various | | IL-10; IL-1 (IL-1a; IL-1b); IL-13; IL-17 (IL-17a (CTLA8); IL-17b; IL-17c; IL-17d; IL-17f); Il-23; Cx3cr1; ptpn22; TNFa; NOD2/CARD15 for IBD; IL-6; IL-12 (IL-12a; IL-12b); CTLA4; Cx3cl1 |
| Inflammatory Bowel Diseases (e.g. Ulcerative Colitis and Chron's Disease) | Gastrointestinal | Joints, skin | NOD2, IRGM, LRRK2, ATG5, ATG16L1, IRGM, GATM, ECM1, CDH1, LAMB1, HNF4A, GNA12, IL10, CARD9/15. CCR6, IL2RA, MST1, TNFSF15, REL, STAT3, IL23R, IL12B, FUT2 |

TABLE A-continued

| Exemplary Genetic and Other Diseases and Associated Genes | | | |
|---|---|---|---|
| Disease Name | Primary Tissues or System Affected | Additional Tissues/ Systems Affected | Genes |
| Interstitial renal fibrosis | kidney | | TGF-β type II receptor |
| Job's Syndrome (aka Hyper IgE Syndrome) | Immune System | | STAT3, DOCK8 |
| Juvenile Retinoschisis | eye | | RS1, XLRS1 |
| Kabuki Syndrome 1 | | | MLL4, KMT2D |
| Kennedy Disease (aka Spinobulbar Muscular Atrophy) | Muscles, brain, nervous system | | SBMA/SMAX1/AR |
| Klinefelter syndrome | Various- particularly those involved in development of male characteristics | | Extra X chromosome in males |
| Lafora Disease | Brain, CNS | | EMP2A and EMP2B |
| Leber Congenital Amaurosis | eye | | CRB1, RP12, CORD2, CRD, CRX, IMPDH1, OTX2, AIPL1, CABP4, CCT2, CEP290, CLUAP1, CRB1, CRX, DTHD1, GDF6, GUCY2D, IFT140, IQCB1, KCNJ13, LCA5, LRAT, NMNAT1, PRPH2, RD3, RDH12, RPE65, RP20, RPGRIP1, SPATA7, TULP1, LCA1, LCA4, GUC2D, CORD6, LCA3, |
| Lesch-Nyhan Syndrome | Metabolism disease | Various - joints, cognitive, brain, nervous system | HPRT1 |
| Leukocyte deficiencies and disorders | blood | | ITGB2, CD18, LCAMB, LAD, EIF2B1, EIF2BA, EIF2B2, EIF2B3, EIF2B5, LVWM, CACH, CLE, EIF2B4 |
| Leukemia | Blood | | TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN |
| Limb-girdle muscular dystrophy diseases | muscle | | LGMD |
| Lowe syndrome | brain, eyes, kidneys | | OCRL |
| Lupus glomerulo- nephritis | kidney | | MAPK1 |
| Machado-Joseph's Disease (also known as Spinocerebellar ataxia Type 3) | Brain, CNS, muscle | | ATX3 |
| Macular degeneration | eye | | ABC4, CBC1, CHM1, APOE, C1QTNF5, C2, C3, CCL2, CCR2, CD36, CFB, CFH, CFHR1, CFHR3, CNGB3, CP, CRP, CST3, CTSD, CX3CR1, ELOVL4, ERCC6, FBLN5, FBLN6, FSCN2, HMCN1, HIRAI, IL6, IL8, PLEKHA1, PROM1, PRPH2, RPGR, SERPING1, TCOF1, TIMP3, TLR3 |

TABLE A-continued

| Disease Name | Primary Tissues or System Affected | Additional Tissues/ Systems Affected | Genes |
|---|---|---|---|
| Exemplary Genetic and Other Diseases and Associated Genes | | | |
| Macular Dystrophy | eye | | BEST1, C1QTNF5, CTNNA1, EFEMP1, ELOVL4, FSCN2, GUCA1B, HMCN1, IMPG1, OTX2, PRDM13, PROM1, PRPH2, RP1L1, TIMP3, ABCA4, CFH, DRAM2, IMG1, MFSD8, ADMD, STGD2, STGD3, RDS, RP7, PRPH, AVMD, AOFMD, VMD2 |
| Malattia Leventinesse | eye | | EFEMP1, FBLN3 |
| Maple Syrup Urine Disease | Metabolism disease | | BCKDHA, BCKDHB, and DBT |
| Marfan syndrome | Connective tissue | Musculoskeletal | FBN1 |
| Maroteaux-Lamy Syndrome (aka MPS VI) | Musculoskeletal system, nervous system | Liver, spleen | ARSB |
| McArdle's Disease (Glycogen Storage Disease Type V) | Glycogen storage disease | muscle | PYGM |
| Medullary cystic kidney disease | kidney | | UMOD, HNFJ, FJHN, MCKD2, ADMCKD2 |
| Metachromatic leukodystrophy | Lysosomal storage disease | Nervous system | ARSA |
| Methylmalonic acidemia (MMA) | Metabolism disease | | MMAA, MMAB, MUT, MMACHC, MMADHC, LMBRD1 |
| Morquio Syndrome (aka MPS IV A and B) | Connective tissue, skin, bone, eyes | heart | GALNS |
| Mucopolysaccharidosis diseases (Types I H/S, I H, II, III A B and C, I S, IVA and B, IX, VII, and VI) | Lysosomal storage disease - affects various organs/tissues | | See also Hurler/Scheie syndrome, Hurler disease, Sanfillipo syndrome, Scheie syndrome, Morquio syndrome, hyaluronidase deficiency, Sly syndrome, and Maroteaux-Lamy syndrome |
| Muscular Atrophy | muscle | | VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1 |
| Muscular dystrophy | muscle | | FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1 |
| Myotonic dystrophy (Type 1 and Type 2) | Muscles | Eyes, heart, endocrine | CNBP (Type 2) and DMPK (Type 1) |
| Neoplasia | | | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |

TABLE A-continued

| Exemplary Genetic and Other Diseases and Associated Genes | | | |
|---|---|---|---|
| Disease Name | Primary Tissues or System Affected | Additional Tissues/ Systems Affected | Genes |
| Neurofibromatosis (NF) (NF1, formerly Recklinghausen's NF, and NF2) | brain, spinal cord, nerves, and skin | | NF1, NF2 |
| Niemann-Pick Lipidosis (Types A, B, and C) | Lysosomal Storage Disease | Various- where sphingomyelin accumulates, particularly spleen, liver, blood, CNS | Types A and B: SMPD1; Type C: NPC1 or NPC2 |
| Noonan Syndrome | Various - musculoskeletal, heart, eyes, reproductive organs, blood | | PTPN11, SOS1, RAF1 and KRAS |
| Norrie Disease or X-linked Familial Exudative Vitreoretinopathy | eye | | NDP |
| North Carolina Macular Dystrophy | eye | | MCDR1 |
| Osteogenesis imperfecta (OI) (Types I, II, III, IV, V, VI, VII) | bones, musculoskeletal | | COL1A1, COL1A2, CRTAP, P3H |
| Osteopetrosis | bones | | LRP5, BMND1, LRP7, LR3, OPPG, VBCH2, CLCN7, CLC7, OPTA2, OSTM1, GL, TCIRG1, TIRC7, OC116, OPTB1 |
| Patau's Syndrome (Trisomy 13) | Brain, heart, skeletal system | | Additional copy of chromosome 13 |
| Parkinson's disease (PD) | Brain, nervous system | | SNCA (PARK1), UCHL1 (PARK 5), and LRRK2 (PARK8), (PARK3), PARK2, PARK4, PARK7 (PARK7), PINK1 (PARK6); x-Synuclein, DJ-1, Parkin, NR4A2, NURR1, NOT, TINUR, SNCAIP, TBP, SCA17, NCAP, PRKN, PDJ, DBH, NDUFV2 |
| Pattern Dystrophy of the RPE | eye | | RDS/peripherin |
| Phenylketonuria (PKU) | Metabolism disorder | Various due to build-up of phenylalanine, phenyl ketones in tissues and CNS | PAH, PKU1, QDPR, DHPR, PTS |
| Polycystic kidney and hepatic disease | Kidney, liver | | FCYT, PKHD1, ARPKD, PKD1, PKD2, PKD4, PKDTS, PRKCSH, G19P1, PCLD, SEC63 |
| Pompe's Disease | Glycogen storage disease | Various - heart, liver, spleen | GAA |
| Porphyria (actually refers to a group of different diseases all having a specific heme production process abnormality) | Various- wherever heme precursors accumulate | | ALAD, ALAS2, CPOX, FECH, HMBS, PPOX, UROD, or UROS |
| posterior polymorphous corneal dystrophy | eyes | | TCF4; COL8A2 |
| Primary Hyperoxaluria (e.g. type 1) | Various - eyes, heart, kidneys, skeletal system | | LDHA (lactate dehydrogenase A) and hydroxyacid oxidase 1 (HAO1) |
| Primary Open Angle Glaucoma (POAG) | eyes | | MYOC |
| Primary sclerosing cholangitis | Liver, gallbladder | | TCF4; COL8A2 |
| Progeria (also called Hutchinson-Gilford progeria syndrome) | All | | LMNA |
| Prader-Willi Syndrome | Musculoskeletal system, brain, reproductive and endocrine system | | Deletion of region of short arm of chromosome 15, including UBE3A |

TABLE A-continued

Exemplary Genetic and Other Diseases and Associated Genes

| Disease Name | Primary Tissues or System Affected | Additional Tissues/ Systems Affected | Genes |
|---|---|---|---|
| Prostate Cancer | prostate | | HOXB13, MSMB, GPRC6A, TP53 |
| Pyruvate Dehydrogenase Deficiency | Brain, nervous system | | PDHA1 |
| Kidney/Renal carcinoma | kidney | | RLIP76, VEGF |
| Rett Syndrome | Brain | | MECP2, RTT, PPMX, MRX16, MRX79, CDKL5, STK9, MECP2, RTT, PPMX, MRX16, MRX79, x-Synuclein, DJ-1 |
| Retinitis pigmentosa (RP) | eye | | ADIPOR1, ABCA4, AGBL5, ARHGEF18, ARL2BP, ARL3, ARL6, BEST1, BBS1, BBS2, C2ORF71, C8ORF37, CA4, CERKL, CLRN1, CNGA1, CMGB1, CRB1, CRX, CYP4V2, DHDDS, DHX38, EMC1, EYS, FAM161A, FSCN2, GPR125, GUCA1B, HK1, HPRPF3, HGSNAT, IDH3B, IMPDH1, IMPG2, IFT140, IFT172, KLHL7, KIAA1549, KIZ, LRAT, MAK, MERTK, MVK, NEK2, NUROD1, NR2E3, NRL, OFD1, PDE6A, PDE6B, PDE6G, POMGNT1, PRCD, PROM1, PRPF3, PRPF4, PRPF6, PRPF8, PRPF31, PRPH2, RPB3, RDH12, REEP6, RP39, RGR, RHO, RLBP1, ROM1, RP1, RP1L1, RPY, RP2, RP9, RPE65, RPGR, SAMD11, SAG, SEMA4A, SLC7A14, SNRNP200, SPP2, SPATA7, TRNT1, TOPORS, TTC8, TULP1, USH2A, ZFN408, ZNF513, see also 20120204282 |
| Scheie syndrome (also known as mucopolysaccharidosis type I S(MPS I-S)) | Various- liver, spleen, eye, joint, heart, brain, skeletal | | IDUA, α-L-iduronidase |
| Schizophrenia | Brain | | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b; 5-HTT (Slc6a4); COMT; DRD (Drd1a); SLC6A3; DAOA; DTNBP1; Dao (Dao1); TCF4; COL8A2 |
| Secretase Related Disorders | Various | | APH-1 (alpha and beta); PSEN1; NCSTN; PEN-2; Nos1, Parp1, Nat1, Nat2, CTSB, APP, APH1B, PSEN2, PSENEN, BACE1, ITM2B, CTSD, NOTCH1, TNF, INS, DYT10, ADAM17, APOE, ACE, STN, TP53, IL6, NGFR, IL1B, ACHE, CTNNB1, IGF1, IFNG, NRG1, CASP3, MAPK1, CDH1, APBB1, HMGCR, CREB1, PTGS2, HES1, CAT, TGFB1, ENO2, ERBB4, TRAPPC10, MAOB, NGF, MMP12, JAG1, CD40LG, PPARG, FGF2, LRP1, NOTCH4, MAPK8, PREP, NOTCH3, PRNP, CTSG, EGF, REN, CD44, SELP, GHR, ADCYAP1, INSR, GFAP, MMP3, MAPK10, SP1, MYC, CTSE, PPARA, JUN, TIMP1, IL5, IL1A, MMP9, HTR4, HSPG2, KRAS, CYCS, SMG1, IL1R1, PROK1, MAPK3, NTRK1, IL13, MME, TKT, CXCR2, CHRM1, ATXN1, PAWR, NOTCJ2, M6PR, CYP46A1, CSNK1D, MAPK14, PRG2, PRKCA, L1 CAM, CD40, NR1I2, JAG2, CTNND1, CMA1, SORT1, DLK1, THEM4, JUP, CD46, CCL11, CAV3, RNASE3, HSPA8, CASP9, CYP3A4, CCR3, TFAP2A, |

TABLE A-continued

| Exemplary Genetic and Other Diseases and Associated Genes | | | |
|---|---|---|---|
| Disease Name | Primary Tissues or System Affected | Additional Tissues/ Systems Affected | Genes |
| | | | SCP2, CDK4, JOF1A, TCF7L2, B3GALTL, MDM2, RELA, CASP7, IDE, FANP4, CASK, ADCYAP1R1, ATF4, PDGFA, C21ORF33, SCG5, RMF123, NKFB1, ERBB2, CAV1, MMP7, TGFA, RXRA, STX1A, PSMC4, P2RY2, TNFRSF21, DLG1, NUMBL, SPN, PLSCR1, UBQLN2, UBQLN1, PCSK7, SPON1, SILV, QPCT, HESS, GCC1 |
| Selective IgA Deficiency | Immune system | | Type 1: MSH5; Type 2: TNFRSF13B |
| Severe Combined Immunodeficiency (SCID) and SCID-X1, and ADA-SCID | Immune system | | JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4, those identified in US Pat. App. Pub. 20110225664, 20110091441, 20100229252, 20090271881 and 20090222937; |
| Sickle cell disease | blood | | HBB, BCL11A, BCL11Ae, cis-regulatory elements of the B-globin locus, HBG ½ promoter, HBG distal CCAAT box region between −92 and −130 of the HBG Transcription Start Site, those described in WO2015148863, WO 2013/126794, US Pat. Pub. 20110182867 |
| Sly Syndrome (aka MPS VII) | | | GUSB |
| Spinocerebellar Ataxias (SCA types 1, 2, 3, 6, 7, 8, 12 and 17) | | | ATXN1, ATXN2, ATX3 |
| Sorsby Fundus Dystrophy | eye | | TIMP3 |
| Stargardt disease | eye | | ABCR, ELOVL4, ABCA4, PROM1 |
| Tay-Sachs Disease | Lysosomal Storage disease | Various - CNS, brain, eye | HEX-A |
| Thalassemia (Alpha, Beta, Delta) | blood | | HBA1, HBA2 (Alpha), HBB (Beta), HBB and HBD (delta), LCRB, BCL11A, BCL11Ae, cis-regulatory elements of the B-globin locus, HBG ½ promoter, those described in WO2015148860, US Pat. Pub. 20110182867, 2015/148860 |
| Thymic Aplasia (DiGeorge Syndrome; 22q11.2 deletion syndrome) | Immune system, thymus | | deletion of 30 to 40 genes in the middle of chromosome 22 at a location known as 22q11.2, including TBX1, DGCR8 |
| Transthyretin amyloidosis (ATTR) | liver | | TTR (transthyretin) |
| trimethylaminuria | Metabolism disease | | FMO3 |
| Trinucleotide Repeat Disorders (generally) | Various | | HTT; SBMA/SMAX1/AR; FXN/X25 ATX3; ATXN1; ATXN2; DMPK; Atrophin-1 and Atn1 (DRPLA Dx); CBP (Creb-BP - global instability); VLDLR; Atxn7; Atxn10; FEN1, TNRC6A, PABPN1, JPH3, MED15, ATXN1, ATXN3, TBP, CACNA1A, ATXN80S, PPP2R2B, ATXN7, TNRC6B, TNRC6C, CELF3, MAB21L1, MSH2, TMEM185A, SIX5, CNPY3, RAXE, GNB2, RPL14, ATXN8, ISR, TTR, EP400, GIGYF2, OGG1, STC1, CNDP1, C10ORF2, MAML3, DKC1, PAXIP1, CASK, MAPT, SP1, POLG, AFF2, THBS1, TP53, ESR1, CGGBP1, ABT1, KLK3, PRNP, JUN, KCNN3, BAX, FRAXA, KBTBD10, MBNL1, RAD51, NCOA3, ERDA1, TSC1, COMP, GGLC, RRAD, MSH3, DRD2, CD44, CTCF, CCND1, CLSPN, MEF2A, PTPRU, GAPDH, TRIM22, WT1, AHR, GPX1, TPMT, NDP, ARX, |

TABLE A-continued

| Exemplary Genetic and Other Diseases and Associated Genes | | | |
|---|---|---|---|
| Disease Name | Primary Tissues or System Affected | Additional Tissues/ Systems Affected | Genes |
| | | | TYR, EGR1, UNG, NUMBL, FABP2, EN2, CRYGC, SRP14, CRYGB, PDCD1, HOXA1, ATXN2L, PMS2, GLA, CBL, FTH1, IL12RB2, OTX2, HOXA5, POLG2, DLX2, AHRR, MANF, RMEM158, see also 20110016540 |
| Turner's Syndrome (XO) | Various - reproductive organs, and sex characteristics, vasculature | | Monosomy X |
| Tuberous Sclerosis | CNS, heart, kidneys | | TSC1, TSC2 |
| Usher syndrome (Types I, II, and III) | Ears, eyes | | ABHD12, CDH23, CIB2, CLRN1, DFNB31, GPR98, HARS, MYO7A, PCDH15, USH1C, USH1G, USH2A, USH11A, those described in WO2015134812A1 |
| Velocardiofacial syndrome (aka 22q11.2 deletion syndrome, DiGeorge syndrome, conotruncal anomaly face syndrome (CTAF), autosomal dominant Opitz G/BB syndrome or Cayler cardiofacial syndrome) | Various - skeletal, heart, kidney, immune system, brain | | Many genes are deleted, COM, TBX1, and other are associated with symptoms |
| Von Gierke's Disease (Glycogen Storage Disease type I) | Glycogen Storage disease | Various - liver, kidney | G6PC and SLC37A4 |
| Von Hippel-Lindau Syndrome | Various - cell growth regulation disorder | CNS, Kidney, Eye, visceral organs | VHL |
| Von Willebrand Disease (Types I, II and III) | blood | | VWF |
| Wilson Disease | Various - Copper Storage Disease | Liver, brains, eyes, other tissues where copper builds up | ATP7B |
| Wiskott-Aldrich Syndrome | Immune System | | WAS |
| Xeroderma Pigmentosum | Skin | Nervous system | POLH |
| XXX Syndrome | Endocrine, brain | | X chromosome trisomy |

TABLE B

| Exemplary Genes controlling Cellular Functions | |
|---|---|
| CELLULAR FUNCTION | GENES |
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; |

TABLE B-continued

Exemplary Genes controlling Cellular Functions

| CELLULAR FUNCTION | GENES |
| --- | --- |
| | PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |

TABLE B-continued

Exemplary Genes controlling Cellular Functions

| CELLULAR FUNCTION | GENES |
|---|---|
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; |

TABLE B-continued

Exemplary Genes controlling Cellular Functions

| CELLULAR FUNCTION | GENES |
|---|---|
| | KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |

TABLE B-continued

| Exemplary Genes controlling Cellular Functions | |
|---|---|
| CELLULAR FUNCTION | GENES |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARMI; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |

TABLE B-continued

| Exemplary Genes controlling Cellular Functions | |
|---|---|
| CELLULAR FUNCTION | GENES |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLDI; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |

TABLE B-continued

| Exemplary Genes controlling Cellular Functions | |
|---|---|
| CELLULAR FUNCTION | GENES |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |

TABLE B-continued

| Exemplary Genes controlling Cellular Functions | |
|---|---|
| CELLULAR FUNCTION | GENES |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

Thus, also described herein are methods of inducing one or more mutations in a eukaryotic or prokaryotic cell (in vitro, i.e. in an isolated eukaryotic cell) as herein discussed comprising delivering to cell a vector as described herein. The mutation(s) can include the introduction, deletion, or substitution of one or more nucleotides at a target sequence of cell(s). In some embodiments, the mutations can include the introduction, deletion, or substitution of 1-75 nucleotides at each target sequence of said cell(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence. The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s). The mutations can include the introduction, deletion, or substitution of 20, 21, 22, 23, 24, 25, 26, 27, 28, 29, 30, 35, 40, 45, 50, or 75 nucleotides at each target sequence of said cell(s). The mutations can include the introduction, deletion, or substitution of 40, 45, 50, 75, 100, 200, 300, 400 or 500 nucleotides at each target sequence of said cell(s). The mutations can include the introduction, deletion, or substitution of 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, or 9900 to 10000 nucleotides at each target sequence of said cell(s).

In some embodiments, the modifications can include the introduction, deletion, or substitution of nucleotides at each target sequence of said cell(s) via nucleic acid components (e.g. guide(s) RNA(s) or sgRNA(s)), such as those mediated by a CRISPR-Cas system.

In some embodiments, the modifications can include the introduction, deletion, or substitution of nucleotides at a target or random sequence of said cell(s) via a non CRISPR-Cas system or technique. Such techniques are discussed elsewhere herein, such as where engineered cells and methods of generating the engineered cells and organisms are discussed.

For minimization of toxicity and off-target effect when using a CRISPR-Cas system, it may be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example *S. pyogenes* Cas9-like with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, a tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to a guide sequence.

In one embodiment, the invention provides a method of modifying a target polynucleotide in a eukaryotic cell. In some embodiments, the method includes delivering an engineered cell described herein and/or an engineered AAV capsid particle described herein having a CRISPR-Cas molecule as a cargo molecule to a subject and/or cell. The CRISPR-Cas system molecule(s) delivered can complex to bind to the target polynucleotide, e.g., to effect cleavage of said target polynucleotide, thereby modifying the target polynucleotide, wherein the CRISPR complex comprises a CRISPR enzyme complexed with a guide sequence hybridized to a target sequence within said target polynucleotide, wherein said guide sequence can be linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein one or more vectors comprise the CRISPR enzyme and one or more vectors drive expression of one or more of: the guide sequence linked to the tracr mate sequence, and the tracr sequence. In some embodiments, said CRISPR enzyme drive expression of one or more of: the guide sequence linked to the tracr mate sequence, and the tracr sequence. In some embodiments such CRISPR enzyme are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject. In some embodiments, the isolated cells can be returned to the subject after delivery of one or more engineered viral particles or other engineered delivery vehicles to the isolated cell. In some embodiments, the isolated cells can be returned to the subject after delivering one or more molecules of the engineered delivery system described herein to the isolated cell, thus making the isolated cells engineered cells as previously described.

Screening and Cell Selection

The engineered muscle-specific delivery system vectors, engineered cells, engineered viral particles, and/or engineered muscle-specific delivery systems described herein can be used in a screening assay and/or cell selection assay. The engineered delivery system vectors, engineered cells, and/or engineered viral particles, and/or other engineered delivery system of the present invention can be delivered to a subject and/or cell. In some embodiments, the cell is a eukaryotic cell. The cell can be in vitro, ex vivo, in situ, or in vivo. The engineered delivery system molecules, delivery vehicles, vectors, engineered cells, and/or engineered viral particles described herein can introduce an exogenous molecule or compound to subject or cell to which they are delivered. The presence of an exogenous molecule or compound can be detected which can allow for identification of a cell and/or attribute thereof. In some embodiments, the delivered molecules or particles can impart a gene or other nucleotide modification (e.g. mutations, gene or polynucleotide insertion and/or deletion, etc.). In some embodiments the nucleotide modification can be detected in a cell by sequencing. In some embodiments, the nucleotide modification can result in a physiological and/or biological modification to the cell that results in a detectable phenotypic change in the cell, which can allow for detection, identification, and/or selection of the cell. In some embodiments, the phenotypic change can be cell death, such as embodiments where binding of a CRISPR complex to a target polynucleotide results in cell death. Embodiments of the invention allow for selection of specific cells without requiring a selection marker or a two-step process that may include a counter-selection system. The cell(s) may be prokaryotic or eukaryotic cells.

In one embodiment the invention provides for a method of selecting one or more cell(s) by introducing one or more mutations in a gene in the one or more cell(s), the method comprising: introducing one or more vectors, which can include one or more engineered delivery system molecules or vectors described elsewhere herein, into the cell(s), wherein the one or more vectors can include a CRISPR enzyme and/or drive expression of one or more of: a guide sequence linked to a tracr mate sequence, a tracr sequence, and an editing template; or other polynucleotide to be inserted into the cell and/or genome thereof; wherein, for example that which is being expressed is within and expressed in vivo by the CRISPR enzyme and/or the editing template, when included, comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, wherein binding of the CRISPR complex to the target polynucleotide induces cell death, thereby allowing one or more cell(s) in which one or more mutations have been introduced to be selected. In a preferred embodiment, the CRISPR enzyme is a Cas protein. In another embodiment of the invention the cell to be selected may be a eukaryotic cell.

The screening methods involving the engineered AAV capsid system molecules, vectors, engineered cells, and/or engineered AAV capsid particles, including but not limited to those that deliver one more CRISPR-Cas system molecules to cell, can be used in detection methods such as fluorescence in situ hybridization (FISH). In some embodiments, one or more components of an engineered CRISPR-Cas system that includes a catalytically inactive Cas protein, can be delivered by an engineered delivery system molecule (such as an engineered virus particle or other engineered delivery vehicle), engineered cell, or other composition including an engineered muscle-specific targeting moiety described elsewhere herein to a cell and used in a FISH method. The CRISPR-Cas system can include an inactivated Cas protein (dCas) (e.g. a dCas9), which lacks the ability to produce DNA double-strand breaks may be fused with a marker, such as fluorescent protein, such as the enhanced green fluorescent protein (eEGFP) and co-expressed with small guide RNAs to target pericentric, centric and teleomeric repeats in vivo. The dCas system can be used to visualize both repetitive sequences and individual genes in the human genome. Such new applications of labelled dCas, dCas CRISPR-Cas systems, engineered AAV delivery system molecules, engineered cells, and/or engineered delivery particles (viral or non-viral) can be used in imaging cells and studying the functional nuclear architecture, especially in cases with a small nucleus volume or complex 3-D structures. (Chen B, Gilbert L A, Cimini B A, Schnitzbauer J, Zhang W, Li G W, Park J, Blackburn E H, Weissman J S, Qi L S, Huang B. 2013. Dynamic imaging of genomic loci in living human cells by an optimized CRISPR/Cas system.

Cell 155 (7): 1479-91. doi: 10.1016/j.cell.2013.12.001., the teachings of which can be applied and/or adapted to the CRISPR systems described herein. A similar approach involving a polynucleotide fused to a marker (e.g. a fluorescent marker) can be delivered to a cell via an engineered AAV capsid system molecule, vector, engineered cell, and/or engineered AAV capsid particle described herein and integrated into the genome of the cell and/or otherwise interact with a region of the genome of a cell for FISH analysis.

Similar approaches for studying other cell organelles and other cell structures can be accomplished by delivering to the cell (e.g. via an engineered delivery AAV capsid molecule, engineered cell, and/or engineered AAV capsid particle described herein) one or more molecules fused to a marker (such as a fluorescent marker), wherein the molecules fused to the marker are capable of targeting one or more cell structures. By analyzing the presence of the markers, one can identify and/or image specific cell structures.

In some embodiments, the engineered muscle-specific delivery system molecules can be used in a screening assay inside or outside of a cell. In some embodiments, the screening assay can include delivering a CRISPR-Cas cargo molecule(s) via an engineered muscle-specific delivery particle of the present invention.

Use of the present system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again. Other screening assays are discussed elsewhere herein.

In an embodiment, the invention provides a cell from or of an in vitro method of delivery, wherein the method comprises contacting the delivery system with a cell, optionally a eukaryotic cell, whereby there is delivery into the cell of constituents of the delivery system, and optionally obtaining data or results from the contacting, and transmitting the data or results.

In an embodiment, the invention provides a cell from or of an in vitro method of delivery, wherein the method comprises contacting the delivery system with a cell, optionally a eukaryotic cell, whereby there is delivery into the cell of constituents of the delivery system, and optionally obtaining data or results from the contacting, and transmitting the data or results; and wherein the cell product is altered compared to the cell not contacted with the delivery system, for example altered from that which would have been wild type of the cell but for the contacting. In an embodiment, the cell product is non-human or animal. In some embodiments, the cell product is human.

In some embodiments, a host cell is transiently or non-transiently transfected with one or more vectors described herein. In some embodiments, a cell is transfected as it naturally occurs in a subject optionally to be reintroduced therein. In some embodiments, a cell that is transfected is taken from a subject. In some embodiments, the cell obtained from or is derived from cells taken from a subject, such as a cell line. Delivery mechanisms and techniques of the engineered muscle-specific delivery system and particles thereof that are described elsewhere herein.

In some embodiments it is envisaged to introduce the engineered muscle-specific delivery system molecule(s)) directly to the host cell. For instance, the engineered muscle-specific delivery system molecule(s) can be delivered together with one or more cargo molecules that are packaged into an engineered muscle-specific viral particle or contained in or coupled to a non-viral engineered muscle-specific delivery particle.

In some embodiments, the invention provides a method of expressing an engineered delivery molecule and cargo molecule to be packaged in an engineered viral particle (such as an engineered muscle-specific AAV particle) in a cell that can include the step of introducing the vector according any of the vector delivery systems disclosed herein.

The invention is further described in the following examples, which do not limit the scope of the invention described in the claims.

EXAMPLES

Figure 2:
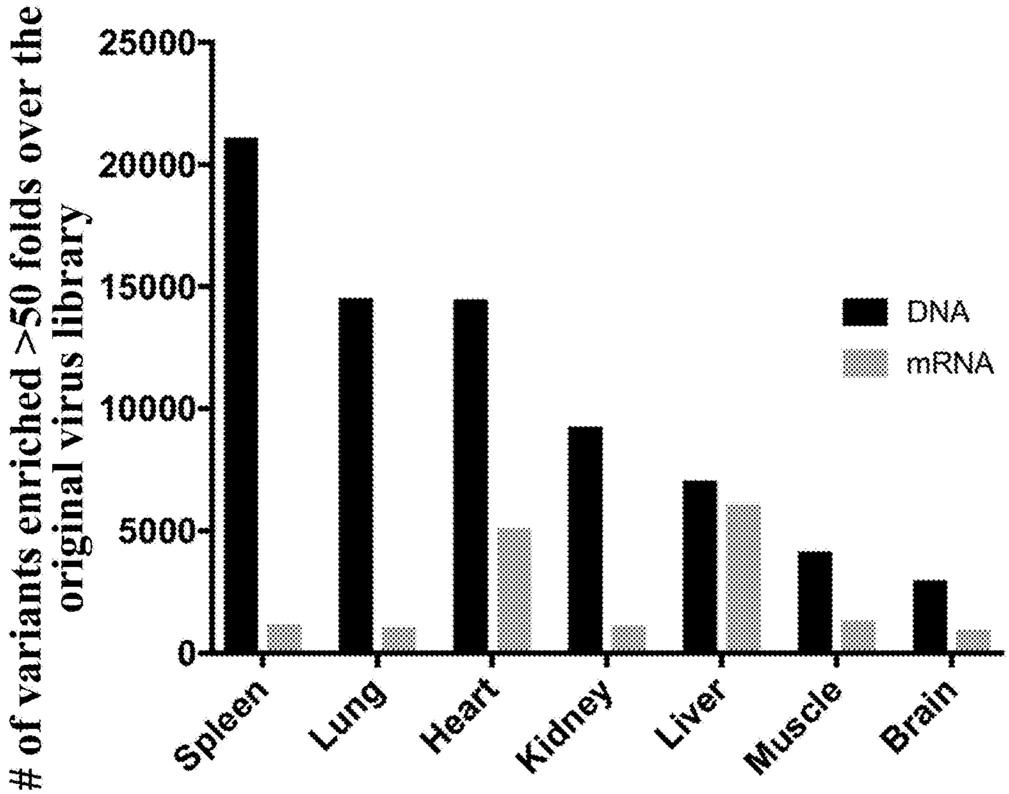
FIG. 2 shows a graph that can demonstrate that mRNA-based selection of AAV variants can be more stringent than DNA-based selection. The virus library was expressed under the control of a CMV promoter.

Example 1—mRNA Based Detection Methods are More Stringent for Selection of AAV Variants FIG. 1 demonstrates the adeno-associated virus (AAV) transduction mechanism, which results in production of mRNA. As is demonstrated in FIG. 1, functional transduction of a cell by an AAV particle can result in the production of an mRNA strand. Non-functional transduction would not produce such a product despite the viral genome being detectable using a DNA-based assay. Thus, mRNA-based detection assays to detect transduction by e.g. an AAV can be more stringent and provide feedback as to the functionality of a virus particle that is able to functionally transduce a cell. FIG. 2 shows a graph that can demonstrate that mRNA-based selection of AAV variants can be more stringent than DNA-based selection. The virus library was expressed under the control of a CMV promoter.

Figure 3A:
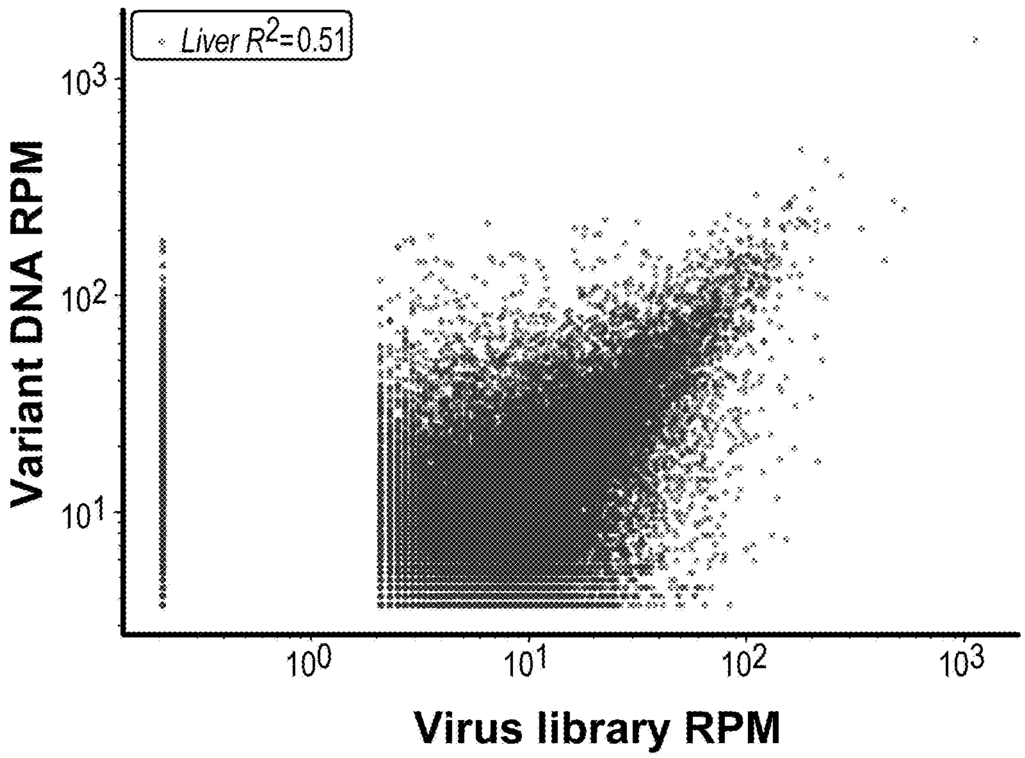
FIGS. 3A-3B show graphs that can demonstrate a correlation between the virus library and vector genome DNA (FIG. 3A) and mRNA (FIG. 3B) in the liver.
Figure 3B:
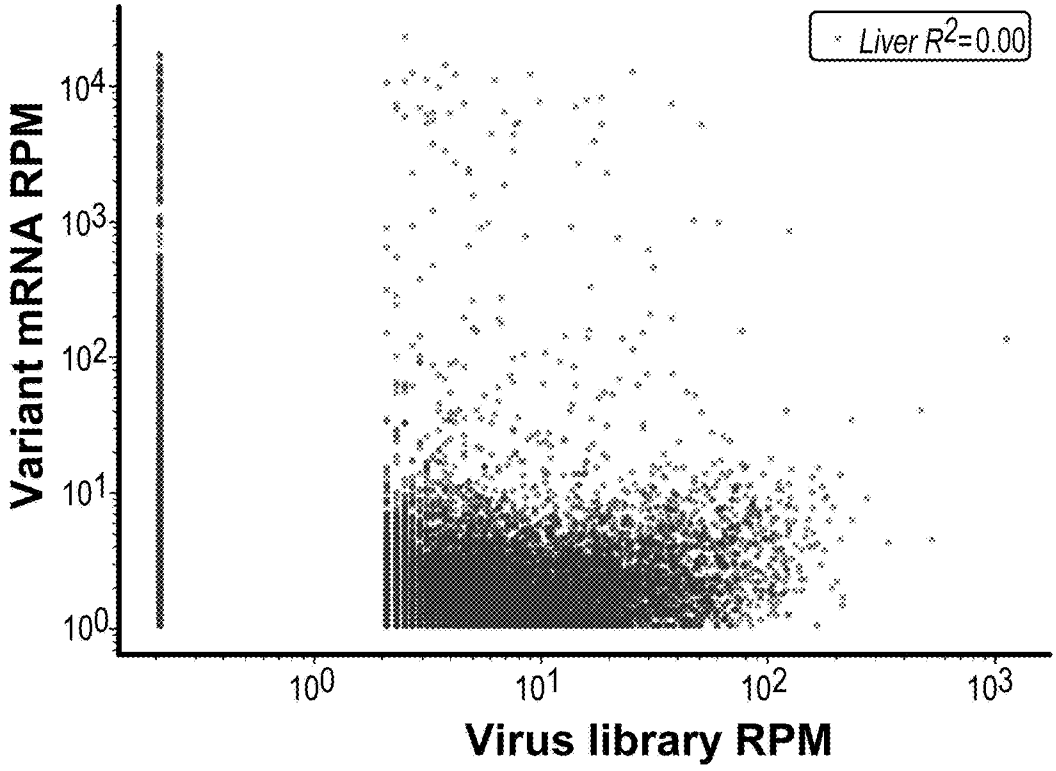
Figure 4A:
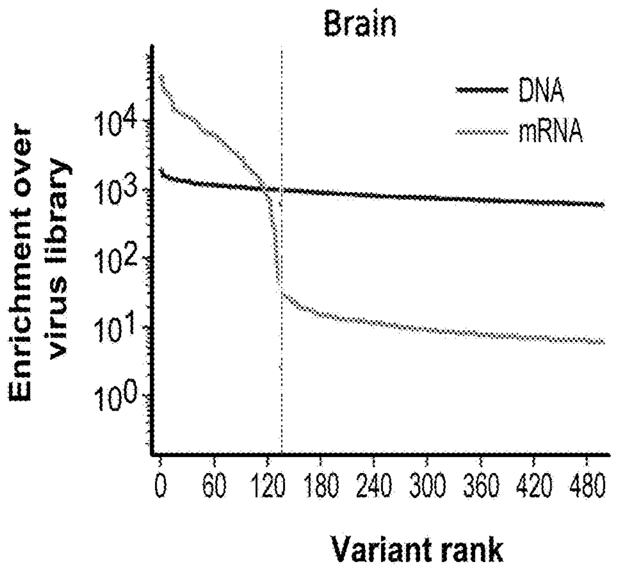
FIGS. 4A-4F show graphs that can demonstrate capsid variants present at the DNA level and expressed at the mRNA level identified in different tissues. For this experiment, the virus library was expressed under the control of a CMV promoter.
Figure 4B:
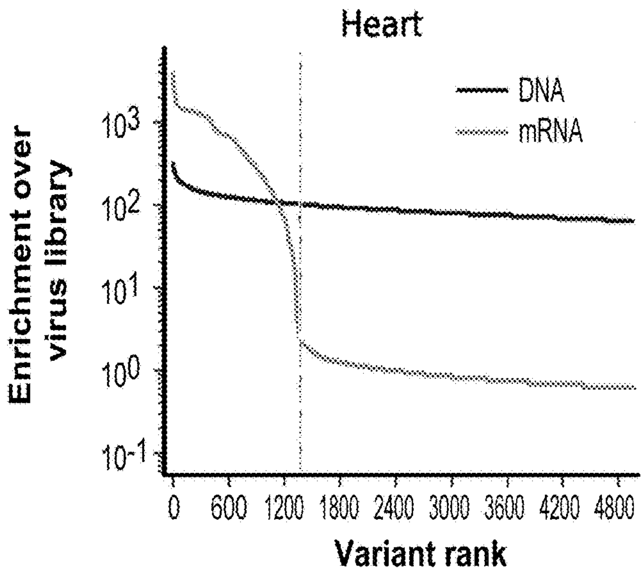
Figure 4C:
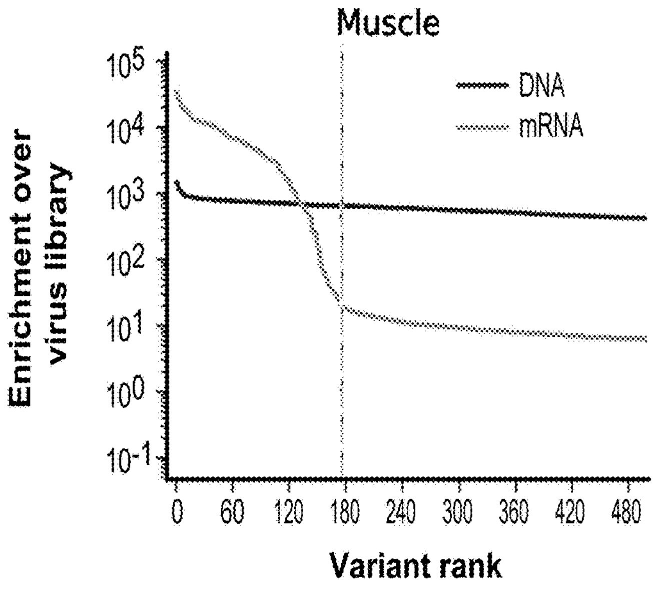
Figure 4D:
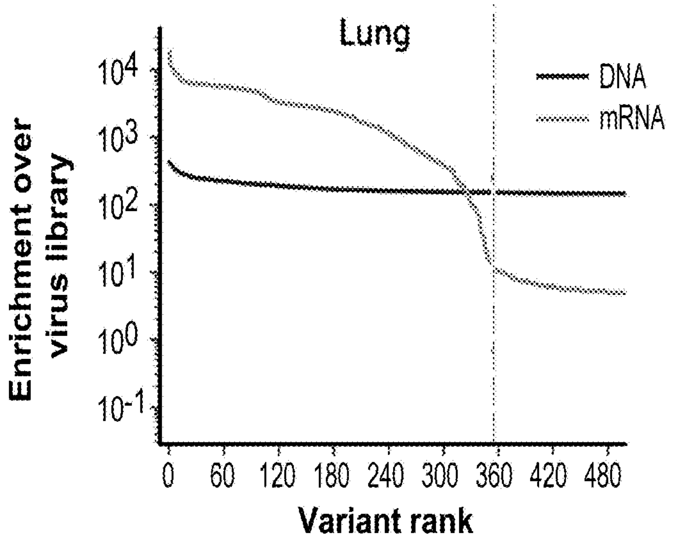
Figure 4E:
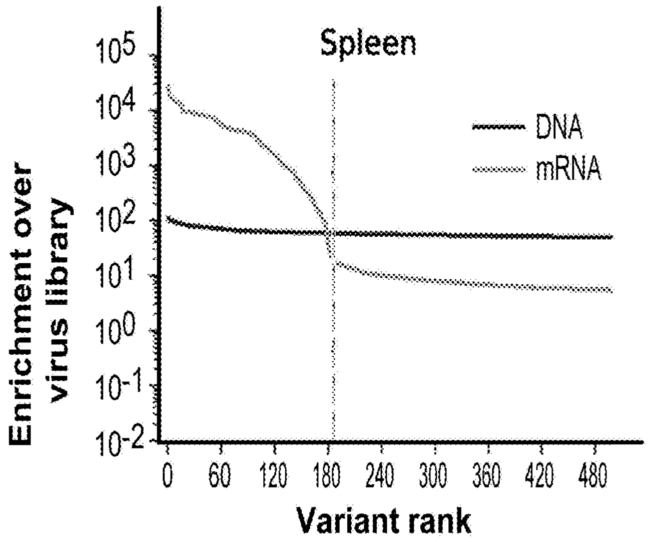
Figure 4F:
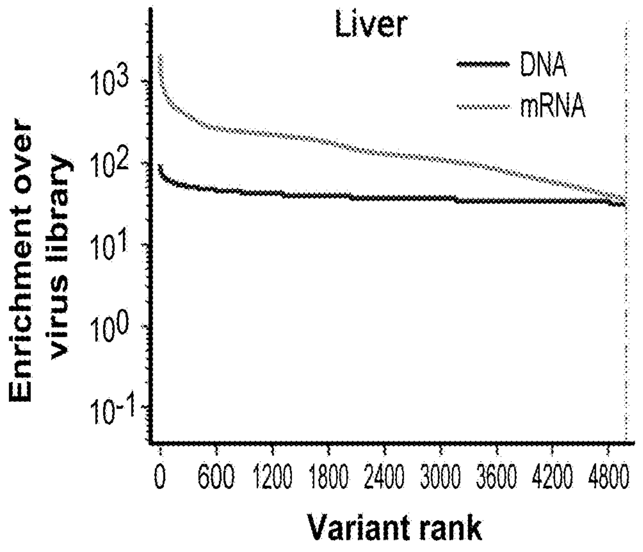

Example 2—mRNA Based Detection Methods can be Used to Detect AAV Capsid Variants from a Capsid Variant Library FIGS. 3A-3B show graphs that can demonstrate a correlation between the virus library and vector genome DNA (FIG. 3A) and mRNA (FIG. 3B) in the liver. FIGS. 4A-4F show graphs that can demonstrate capsid variants expressed at the mRNA level identified in different tissues.

Example 3—Capsid mRNA Expression can be Driven by Tissue Specific Promoters

Figure 5A:
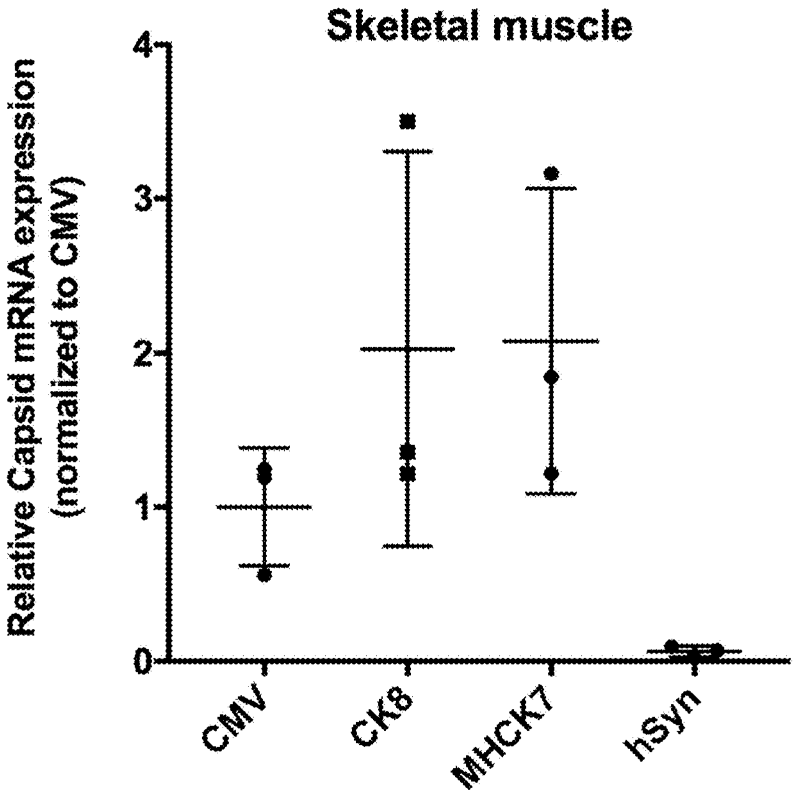
FIGS. 5A-5C show graphs that can demonstrate capsid mRNA expression in different tissues under the control of cell-type specific promoters (as noted on x-axis). CMV was included as an exemplary constitutive promoter. CK8 is a muscle-specific promoter. MHCK7 is a muscle-specific promoter. hSyn is a neuron specific promoter. Expression levels from the cell type-specific promoters have been normalized based on expression levels from the constitutive CMV promoter in each tissue.
Figure 5B:
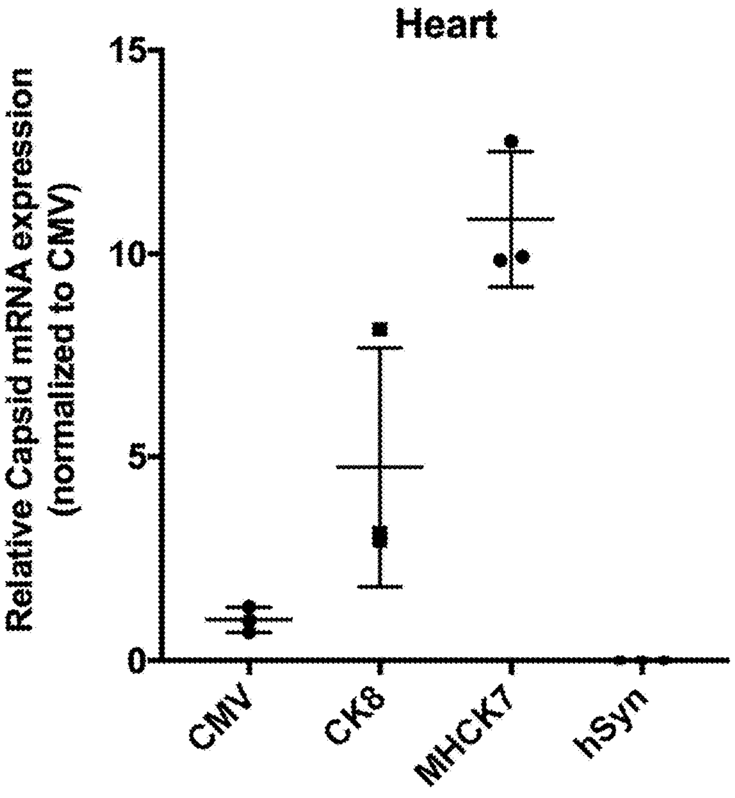
Figure 5C:
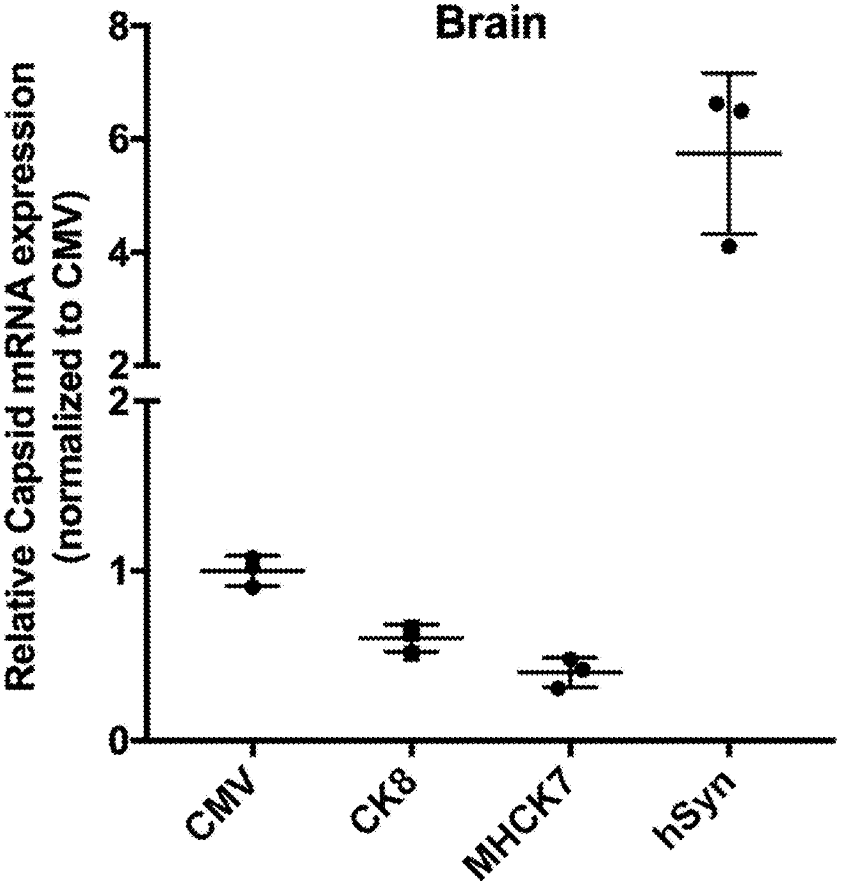

FIGS. 5A-5C show graphs that can demonstrate capsid mRNA expression in different tissues under the control of cell-type specific promoters (as noted on x-axis). CMV was included as an exemplary constitutive promoter. CK8 is a muscle-specific promoter. MHCK7 is a muscle-specific promoter. hSyn is a neuron specific promoter.

Figure 9:
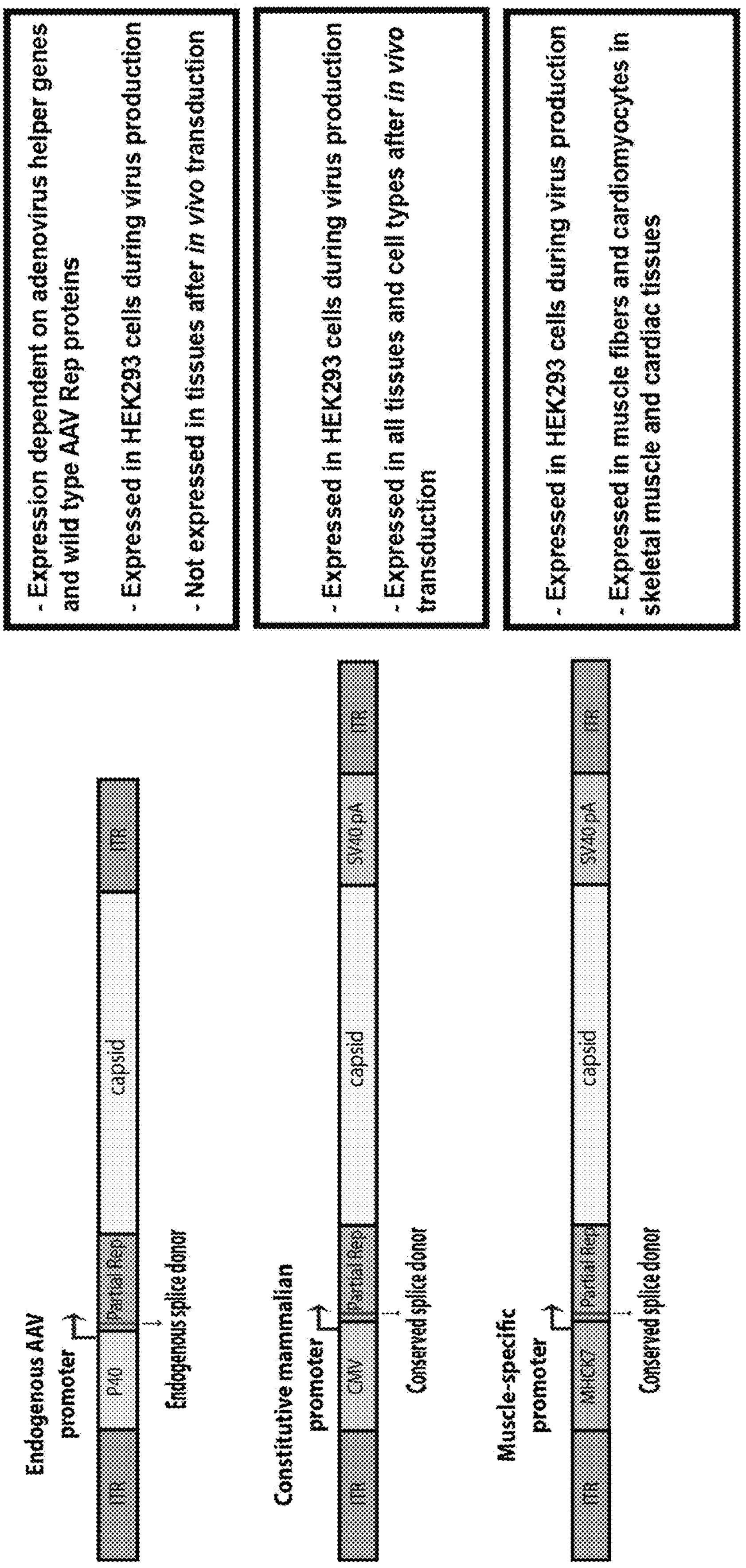
FIG. 9 shows schematic vector maps of representative AAV capsid plasmid library vectors (see e.g.

Example 4—Capsid Variant Library Generation, Variant Screening, and Variant Identification Generally, an AAV capsid library can be generated by expressing engineered capsid vectors each containing an engineered AAV capsid polynucleotide previously described in an appropriate AAV producer cell line. See e.g. FIG. 8. This can generate an AAV capsid library that can contain one more desired cell-specific engineered AAV capsid variant. FIG. 7 shows a schematic demonstrating embodiments of generating an AAV capsid variant library, particularly insertion of a random n-mer (n=3-15 amino acids) into a wild-type AAV, e.g. AAV9. In this example, random 7-mers were inserted between aa588-589 of variable region VIII of AAV9 viral protein and used to form the viral genome containing vectors with one variant per vector. As shown in FIG. 8, the capsid variant vector library was used to generate AAV particles where each capsid variant encapsulated its coding sequence as the vector genome. FIG. 9 shows vector maps of representative AAV capsid plasmid library vectors (see e.g. FIG. 8) that can be used in an AAV vector system to generate an AAV capsid variant library. The library can be generated with the capsid variant polynucleotide under the control of a tissue specific promoter or constitutive promoter. The library was also made with capsid variant polynucleotide that included a polyadenylation signal.

As shown in FIG. 6 the AAV capsid library can be administered to various non-human animals for a first round of mRNA-based selection. As shown in FIG. 1, the transduction process by AAVs and related vectors can result in the production of an mRNA molecule that is reflective of the genome of the virus that transduced the cell. As is at least demonstrated in the Examples herein, mRNA based-selection can be more specific and effective to determine a virus particle capable of functionally transducing a cell because it is based on the functional product produced as opposed to just detecting the presence of a virus particle in the cell by measuring the presence of viral DNA.

After first-round administration, one or more engineered AAV virus particles having a desired capsid variant can then be used to form a filtered AAV capsid library. Desirable AAV virus particles can be identified by measuring the mRNA expression of the capsid variants and determining which variants are highly expressed in the desired cell type(s) as compared to non-desired cells type(s). Those that are highly expressed in the desired cell, tissue, and/or organ type are the desired AAV capsid variant particles. In some embodiments, the AAV capsid variant encoding polynucleotide is under control of a tissue-specific promoter that has selective activity in the desired cell, tissue, or organ.

The engineered AAV capsid variant particles identified from the first round can then be administered to various non-human animals. In some embodiments, the animals used in the second round of selection and identification are not the same as those animals used for first round selection and identification. Similar to round 1, after administration the top expressing variants in the desired cell, tissue, and/or organ type(s) can be identified by measuring viral mRNA expression in the cells. The top variants identified after round two can then be optionally barcoded and optionally pooled. In some embodiments, top variants from the second round can then be administered to a non-human primate to identify the top cell-specific variant(s), particularly if the end use for the top variant is in humans. Administration at each round can be systemic.

Figure 10:
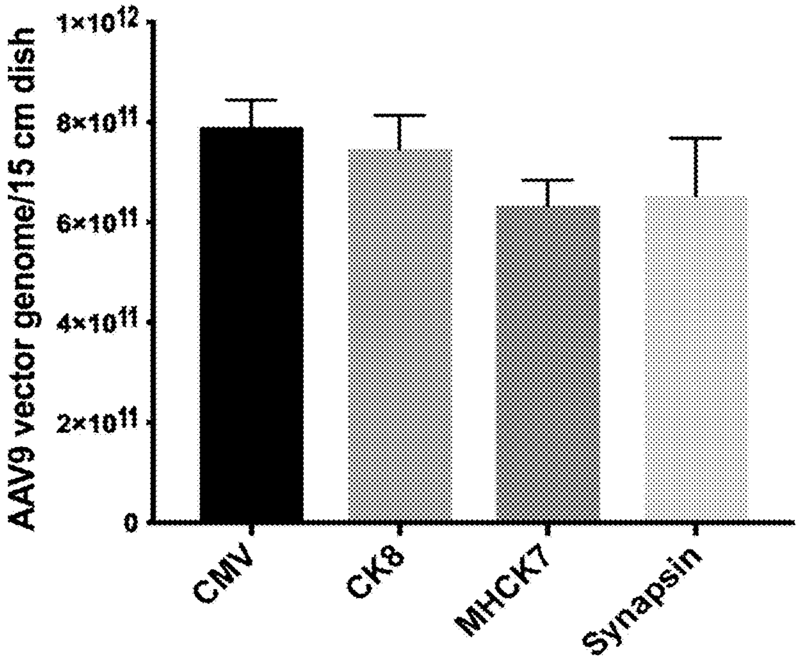
FIG. 10 shows a graph that can demonstrate the viral titer (calculated as AAV9 vector genome/15 cm dish) produced by constructs containing different constitutive and cell-type specific mammalian promoters.
Figure 11A:
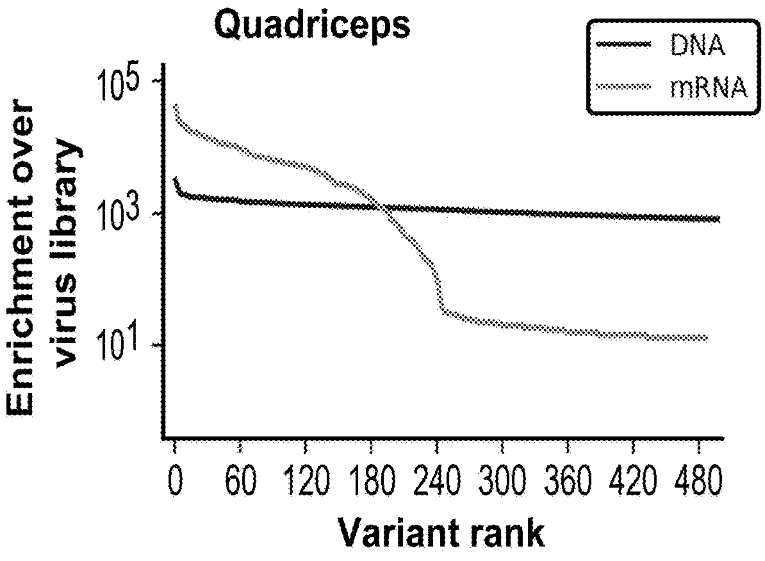
FIGS. 11A-11F show graphs that can demonstrate the results obtained after the first round of selection in C57BL/6 mice using a capsid library expressed under the control of the MHCK7 muscle-specific promoter.
Figure 11B:
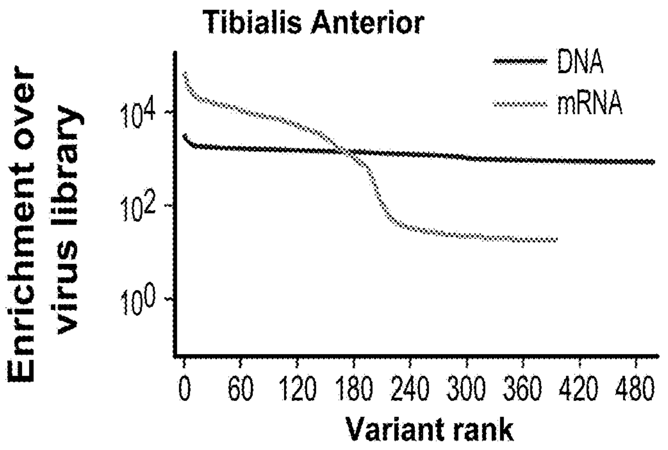
Figure 11C:
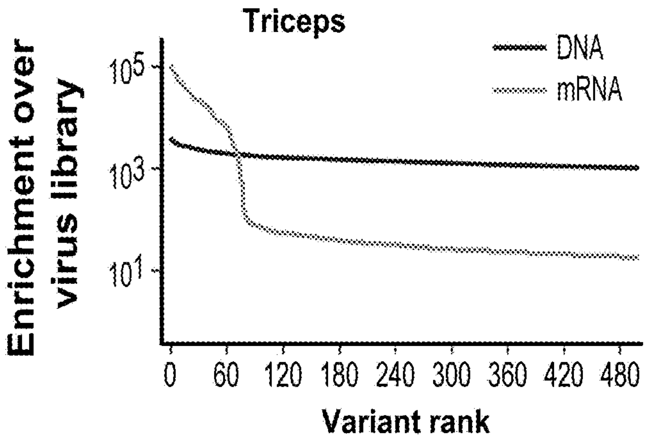
Figure 11D:
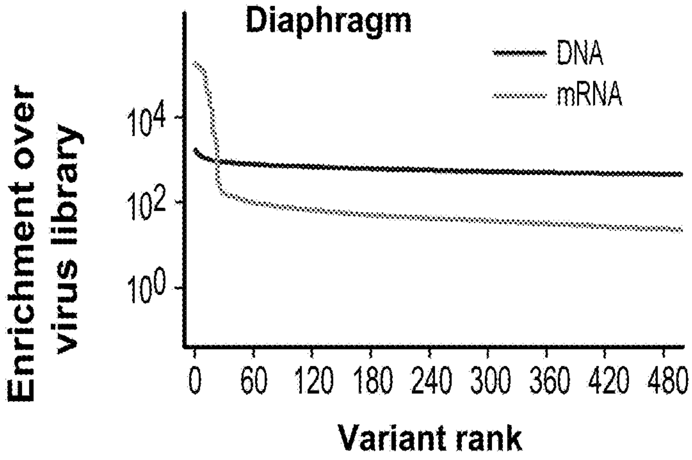
Figure 11E:
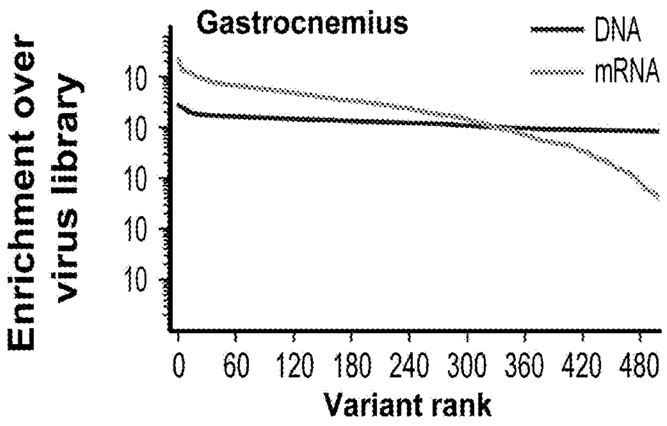
Figure 11F:
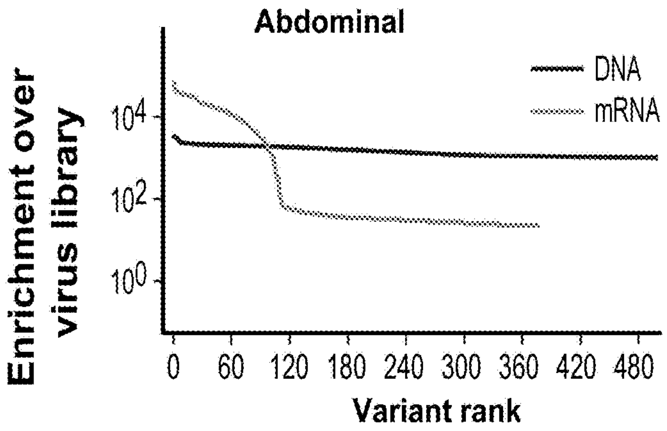
Figure 12A:
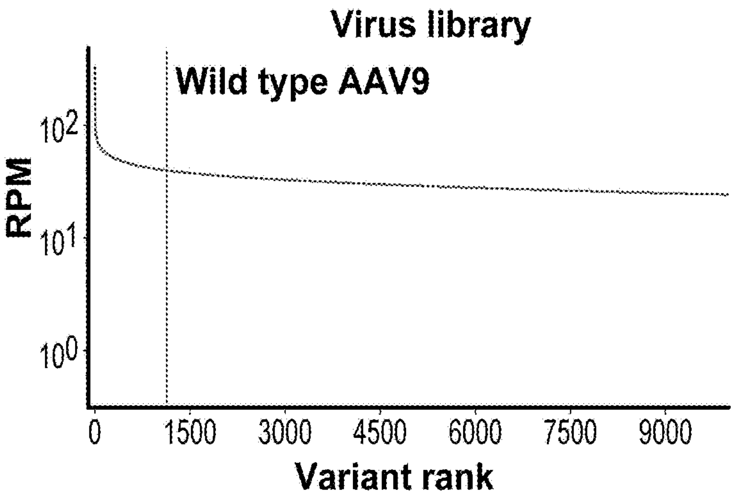
FIGS. 12A-12D show graphs that can demonstrate the results obtained after the second round of selection in C57BL/6 mice using a capsid library expressed under the control of the MHCK7 muscle-specific promoter.
Figure 12B:
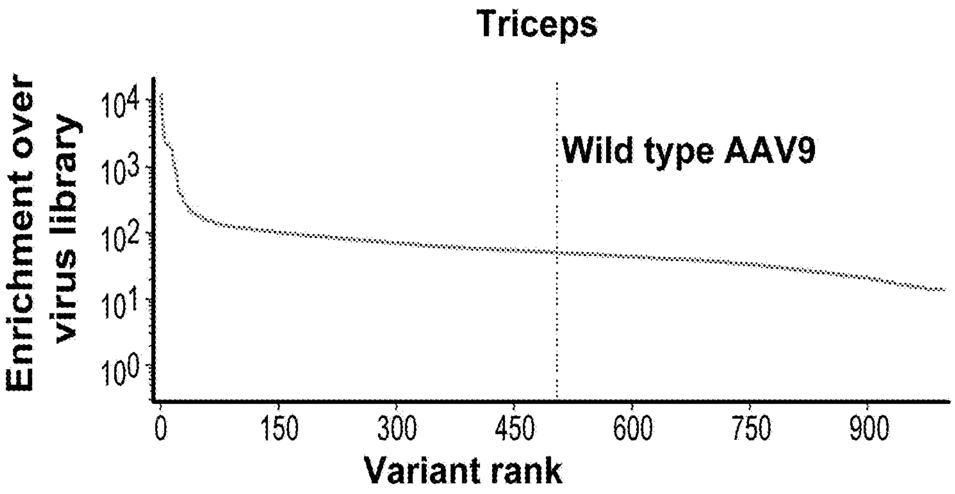
Figure 12C:
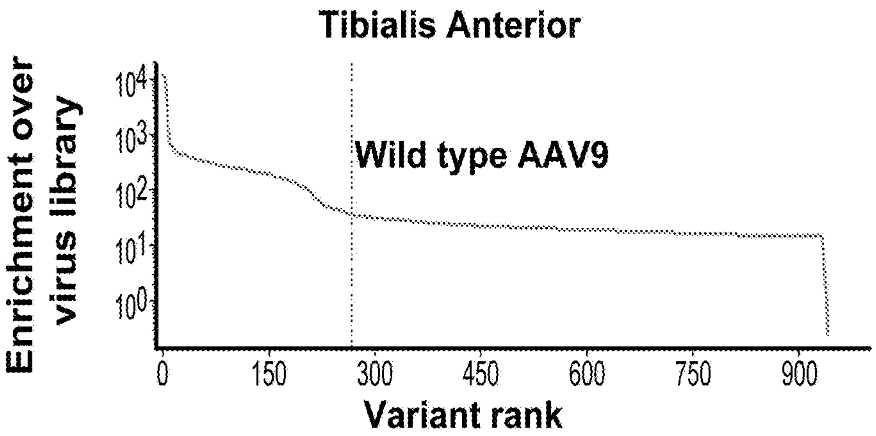
Figure 12D:
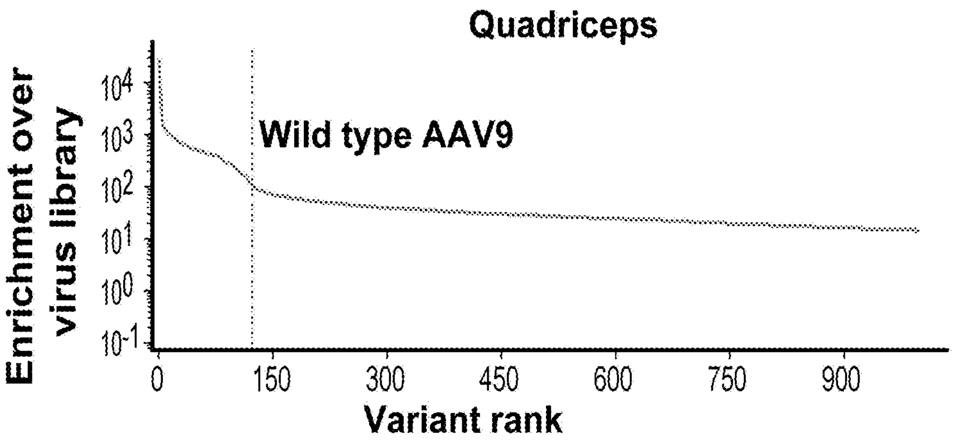

FIG. 10 shows a graph that can demonstrate the viral titer (calculated as AAV9 vector genome/15 cm dish) produced by libraries generated using different promoters. As demonstrated in FIG. 10, virus titer was not affected significantly be the use of different promoters.

FIGS. 11A-11F show graphs that can demonstrate the results obtained after the first round of selection in C57BL/6 mice using a capsid library expressed under the control of the MHCK7 muscle-specific promoter.

FIGS. 12A-12D show graphs that can demonstrate the results obtained after the second round of selection in C57BL/6 mice.

Figure 13A:
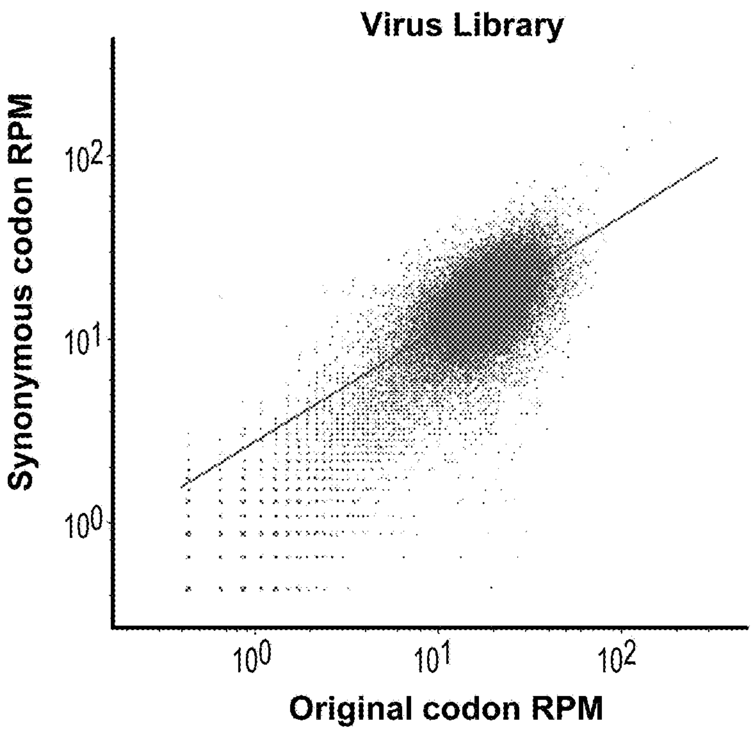
FIGS. 13A-13B shows graphs that can demonstrate a correlation between the abundance of variants encoded by synonymous codons.
Figure 13B:
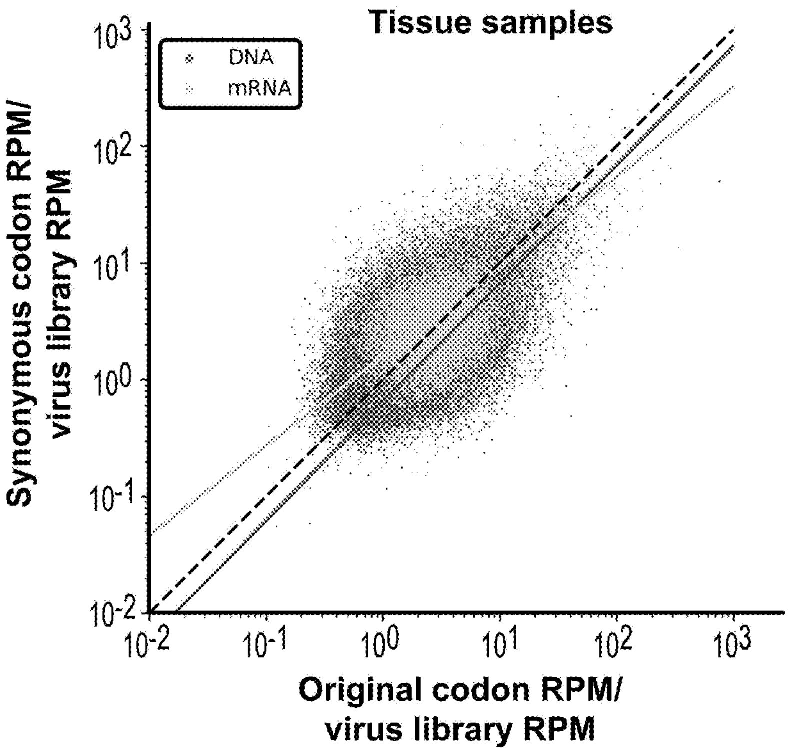

FIGS. 13A-13B shows graphs that can demonstrate a correlation between the abundance of variants encoded by synonymous codons. This graph can demonstrate that there is little to no codon bias in both the virus library and the functional virus particles.

Figure 14:
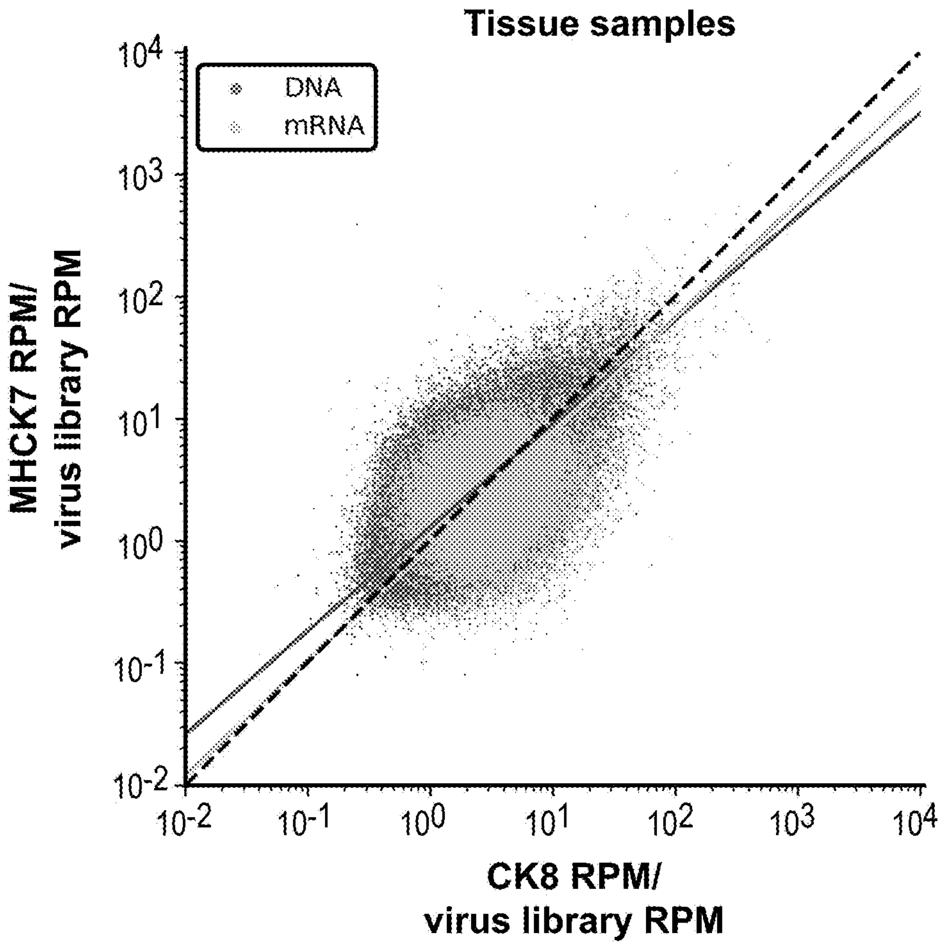
FIG. 14 shows a graph that can demonstrate a correlation between the abundance of the same variants expressed under the control of two different muscle specific promoters (MHCK7 and CK8).

FIG. 14 shows a graph that can demonstrate a correlation between the abundance of the same variants expressed under the control of two different muscle specific promoters (MHCK7 and CK8). This graph can demonstrate that there is little effect of which tissue-specific promoter is used to generate the capsid variant library, at least for muscle cells.

Example 5—Muscle-Tropic rAAV Capsids

Figure 15:
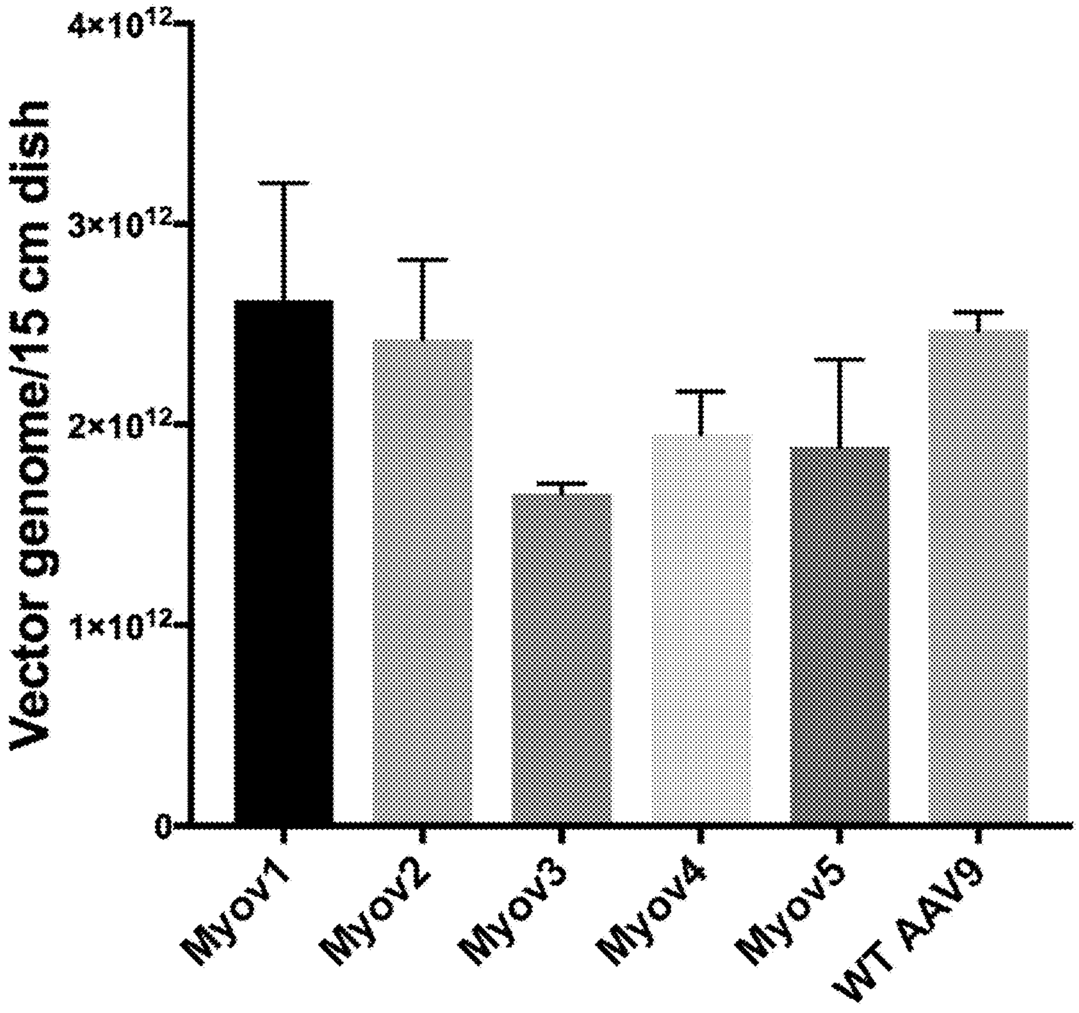
FIG. 15 shows a graph that can demonstrate muscle-tropic capsid variants that produce rAAV with similar titers to wild-type AAV9 capsid.

FIG. 15 shows a graph that can demonstrate muscle-tropic capsid variants that produce rAAV with similar titers to wild-type AAV9 capsid.

Figure 16:
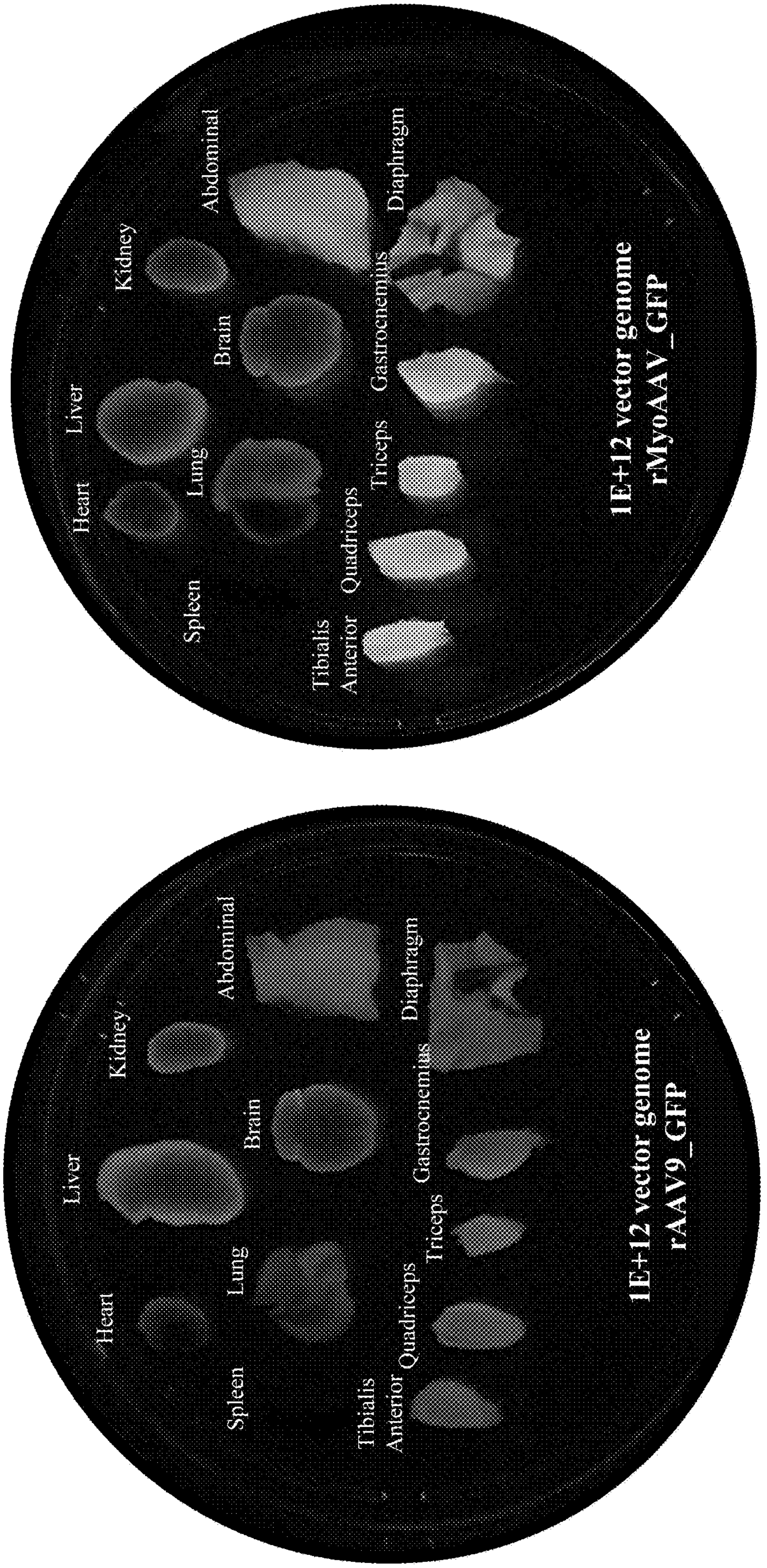
FIG. 16 shows images that can demonstrate a comparison of mouse tissue transduction between rAAV9-GFP and rMyoAAV-GFP.

FIG. 16 shows images that can demonstrate a comparison of mouse tissue transduction between rAAV9-GFP and rMyoAAV-GFP.

Figure 17:
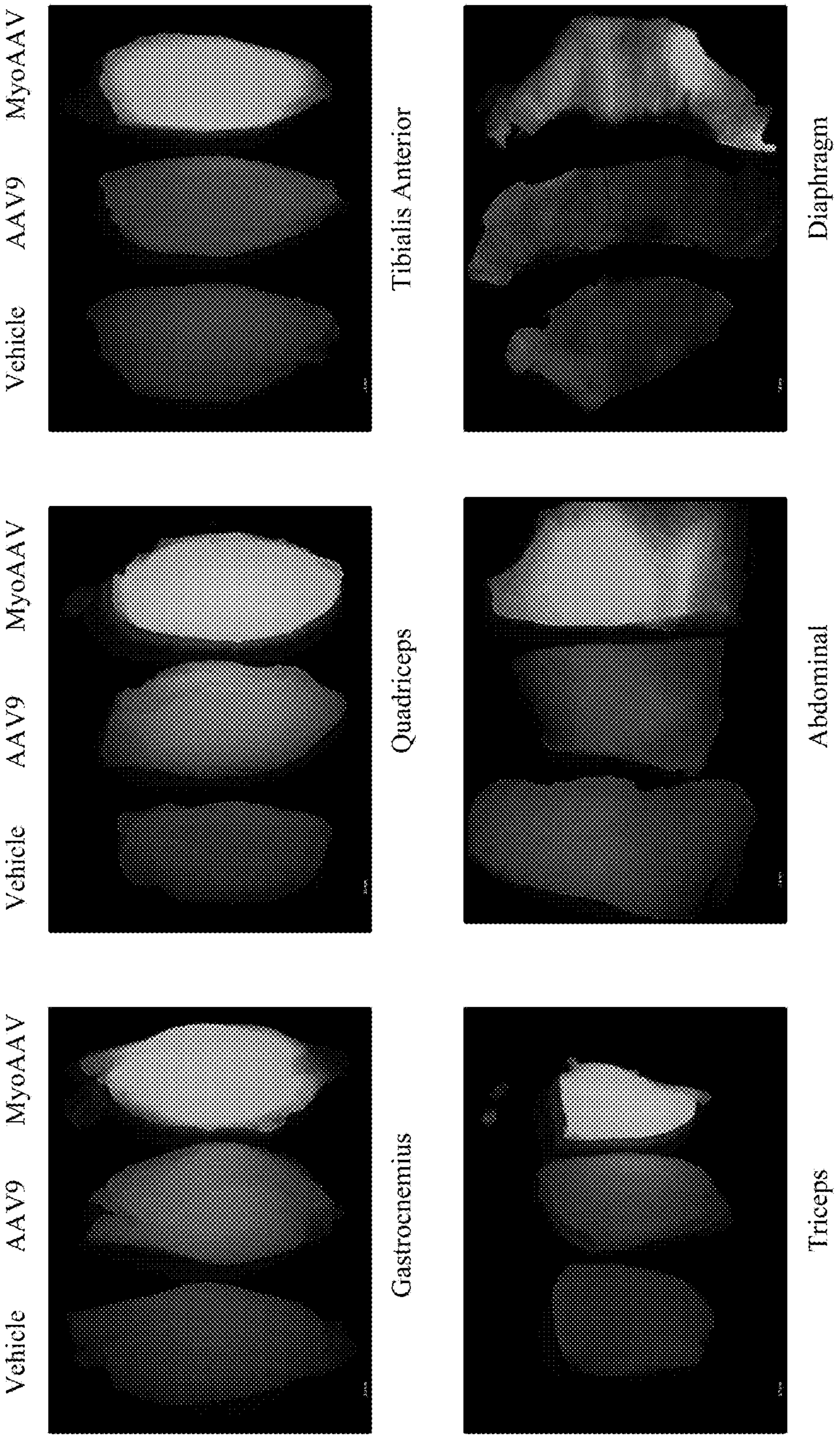
FIG. 17 shows a panel of images that can demonstrate a comparison of mouse tissue transduction between rAAV9-GFP and rMyoAAV-G.

FIG. 17 shows a panel of images that can demonstrate a comparison of mouse tissue transduction between rAAV9-GFP and rMyoAAV-GFP.

Figure 18:
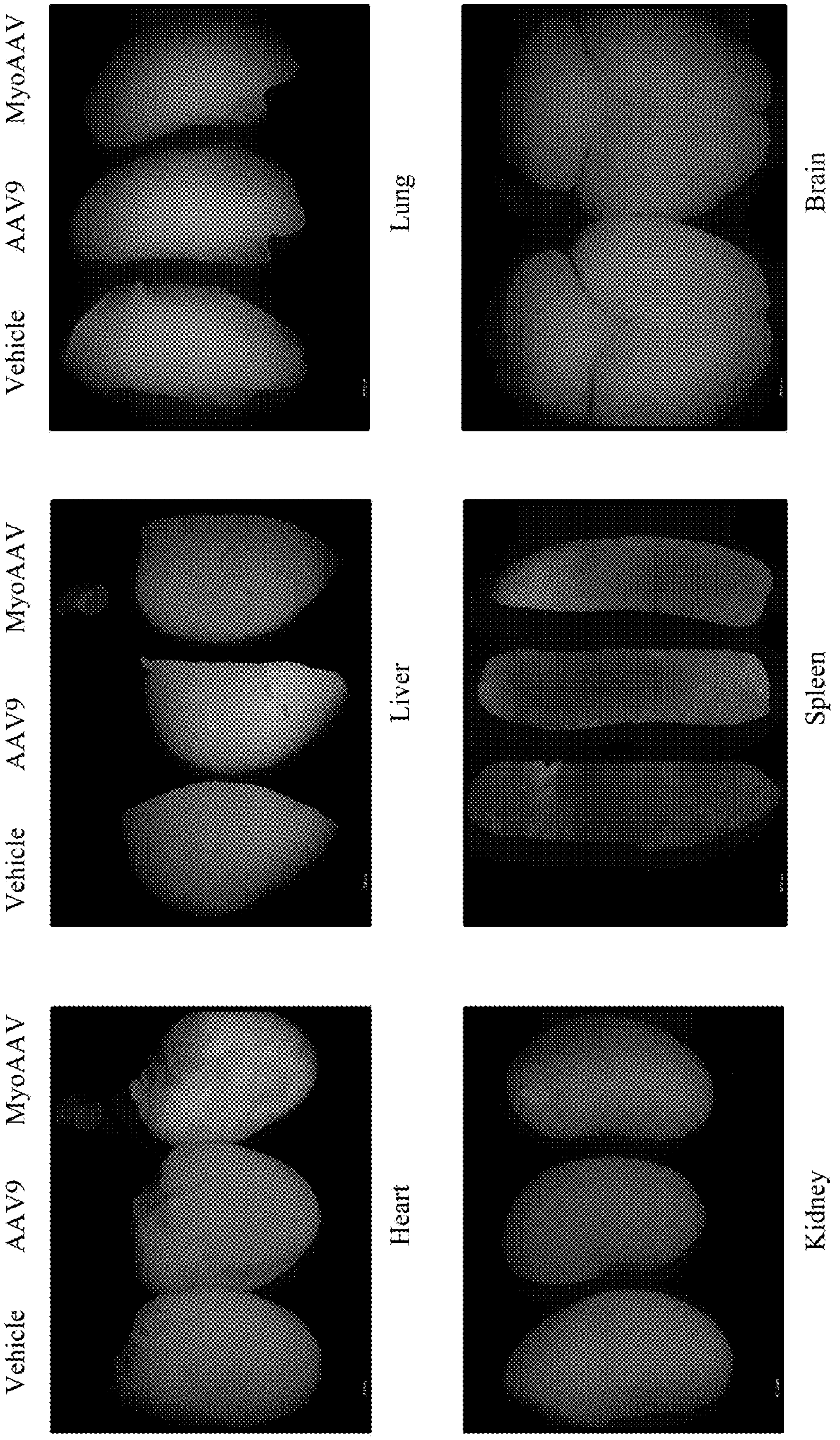
FIG. 18 shows a panel of images that can demonstrate a comparison of mouse tissue transduction between rAAV9-GFP and rMyoAAV-GF.

FIG. 18 shows a panel of images that can demonstrate a comparison of mouse tissue transduction between rAAV9-GFP and rMyoAAV-GFP.

Figure 19:
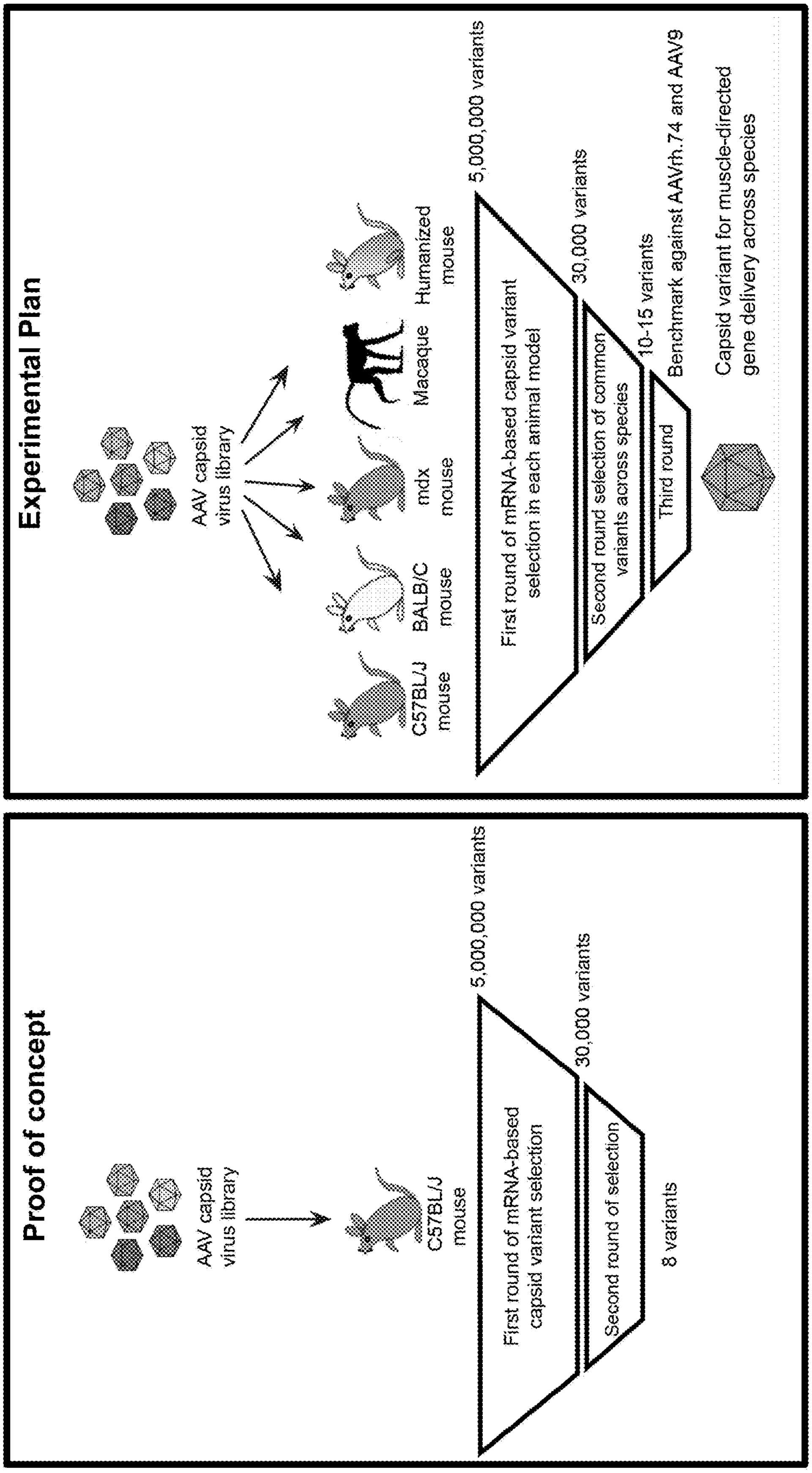
FIG. 19 shows a schematic of selection of potent capsid variants for muscle-directed gene delivery across species.

FIG. 19 shows a schematic of selection of potent capsid variants for muscle-directed gene delivery across species.

FIGS. 20A-20C show tables that can demonstrate selection in different strains of mice identifies the same variants as the top muscle-tropic hits.

Example 6—Comparison of MyoAAV and AAV9 and AAV8

As previously discussed, FIG. 17 can demonstrate a comparison of mouse tissue transduction between rAAV9-GFP and rMyoAAV-GFP.

Figure 21:
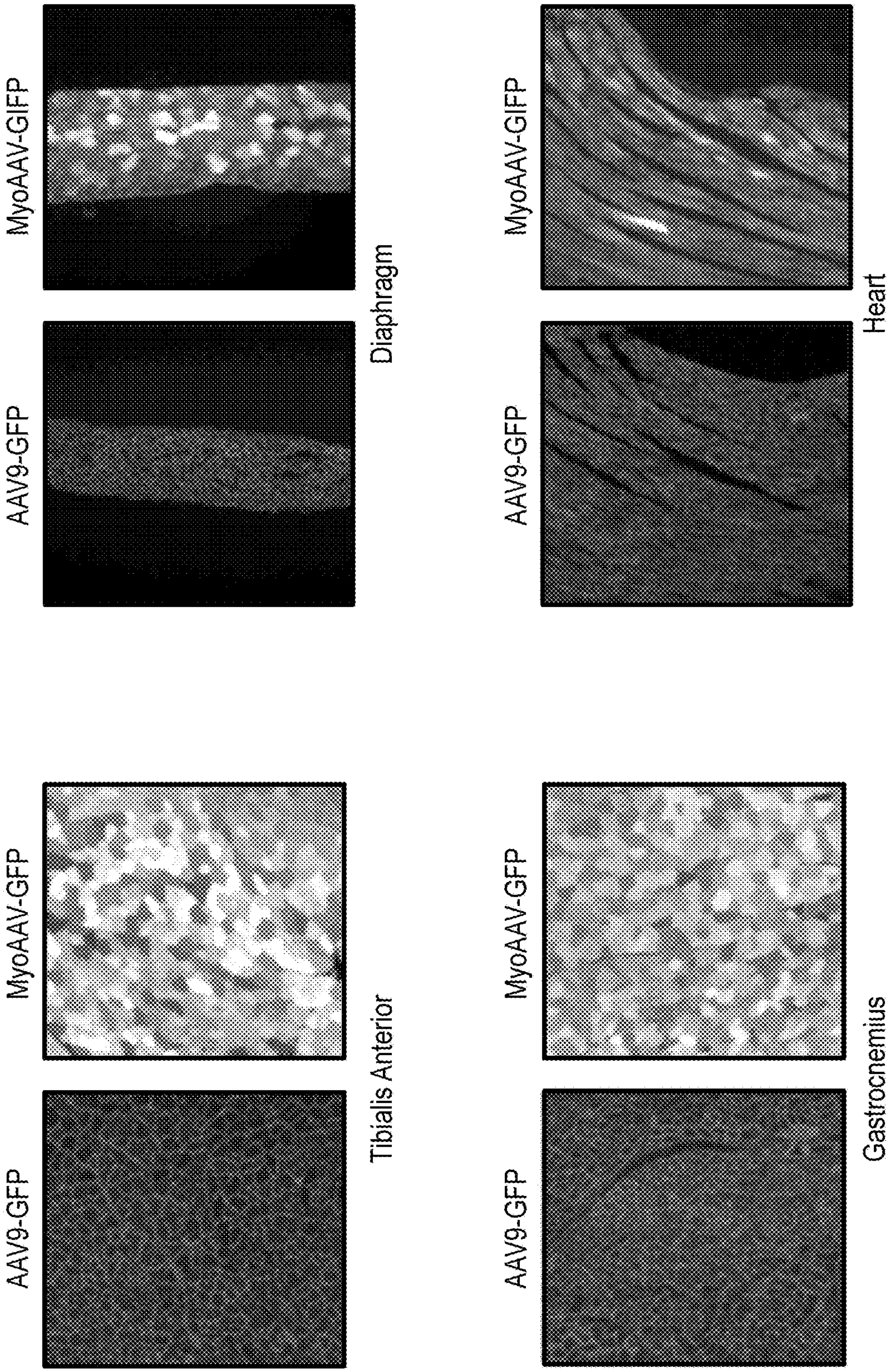
FIG. 21 shows images that can demonstrate a comparison of mouse muscle transduction between rAAV9-GFP and rMyoAAV-GFP.

FIG. 21 shows images that can demonstrate a comparison of mouse muscle transduction between rAAV9-GFP and rMyoAAV-GFP.

Figure 22:
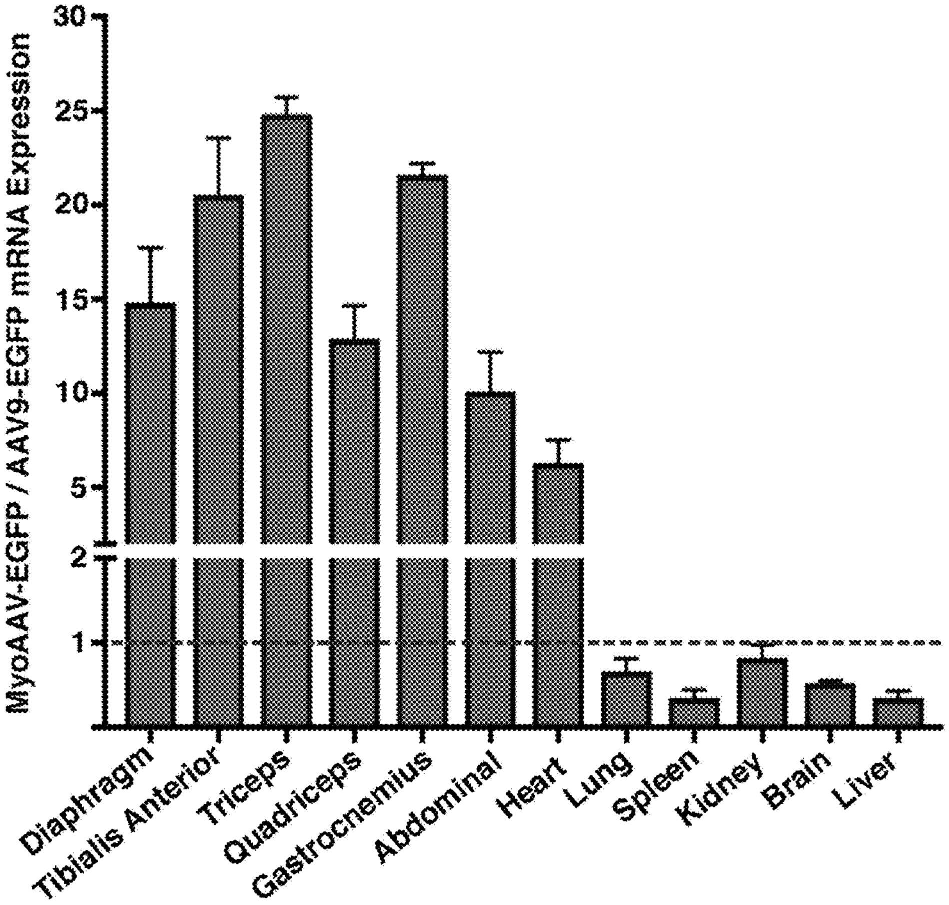
FIG. 22 shows graphs that can demonstrate a comparison of mouse tissue transduction between rAAV9-GFP and rMyoAAV-GFP.

FIG. 22 shows graphs that can demonstrate a comparison of mouse tissue transduction between rAAV9-GFP and rMyoAAV-GFP.

Figure 23:
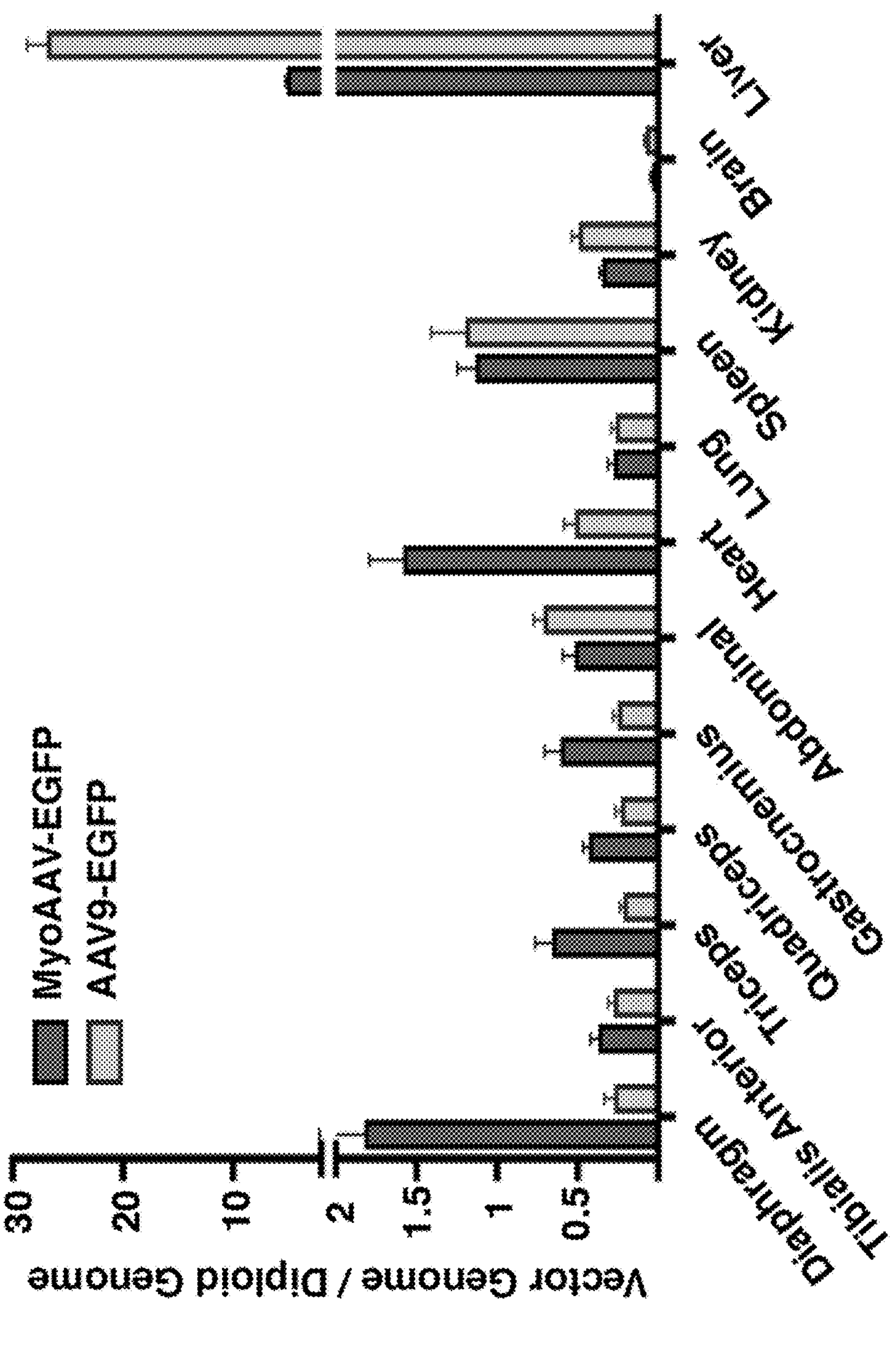
FIG. 23 shows graphs that can demonstrate a comparison of vector genome biodistribution between rAAV9-GFP and rMyoAAV-GFP.

FIG. 23 shows graphs that can demonstrate a comparison of vector genome biodistribution between rAAV9-GFP and rMyoAAV-GFP.

Figure 24A:
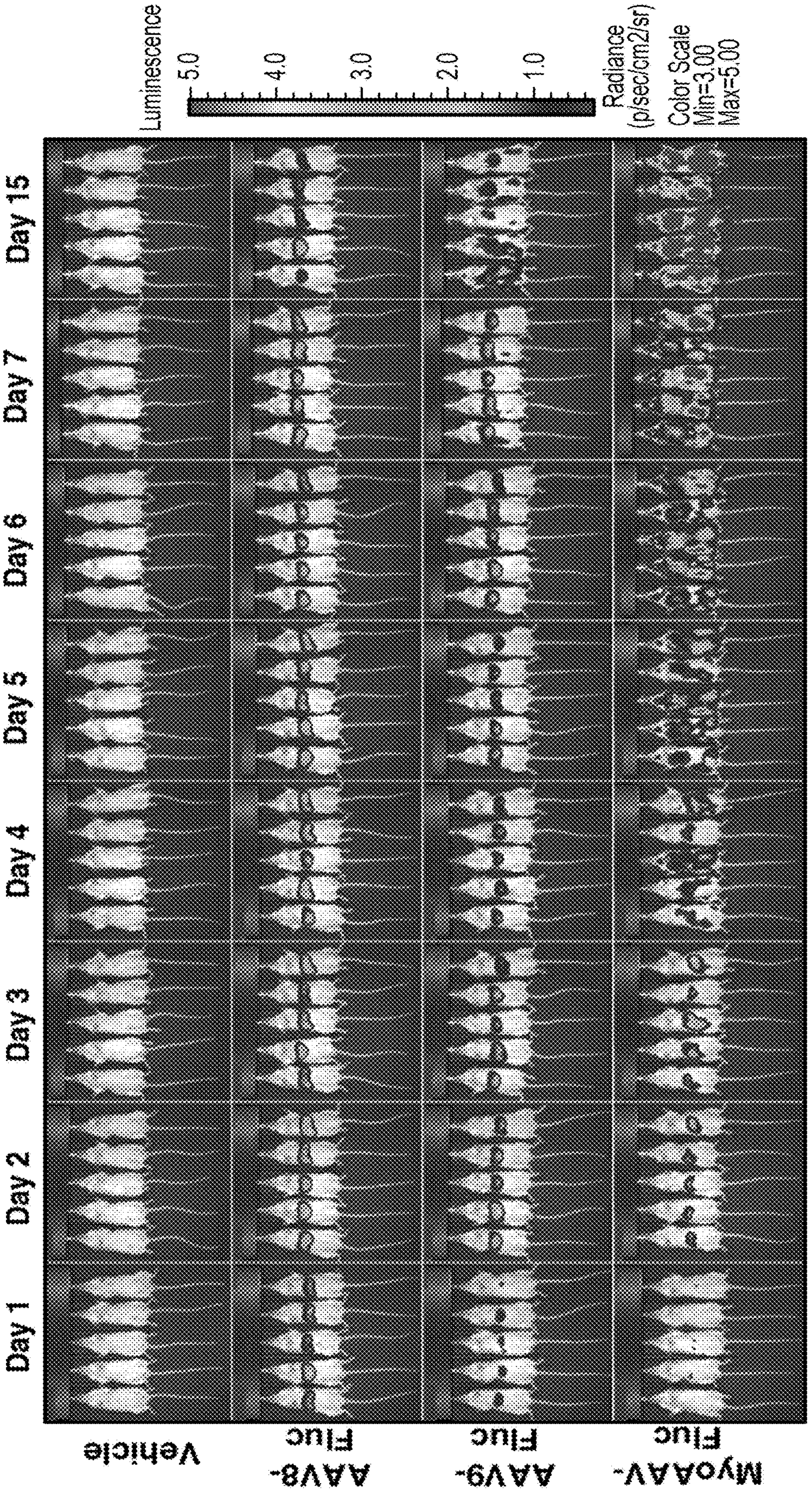
FIGS. 24A-24B show images that can demonstrate faster kinetics of in vivo gene expression in muscle by MyoAAV as compared to AAV9 and AAV8.
Figure 24B:
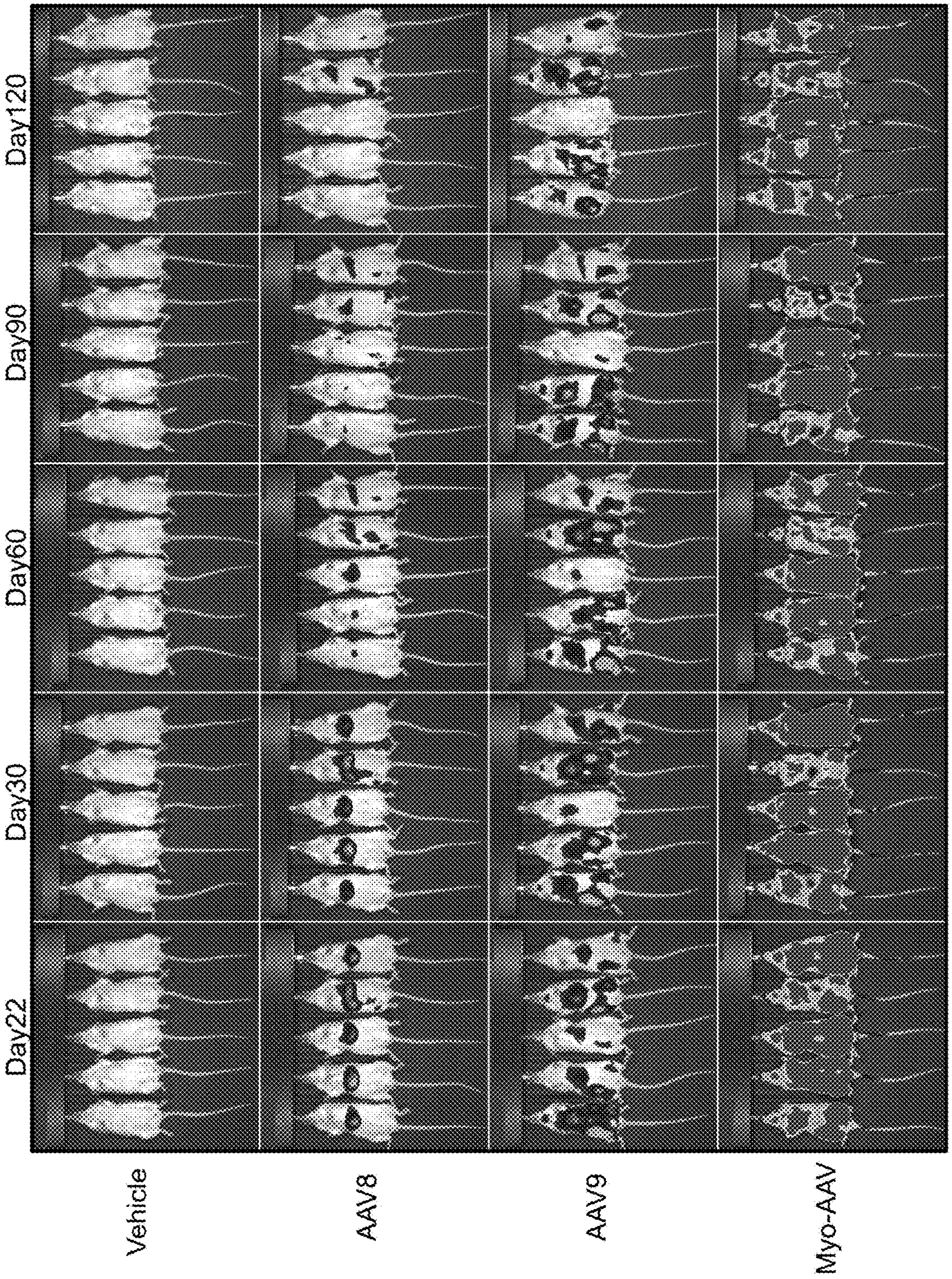

FIGS. 24A-24B show images that can demonstrate faster kinetics of in vivo gene expression in muscle by MyoAAV as compared to AAV9 and AAV8.

Figure 25:
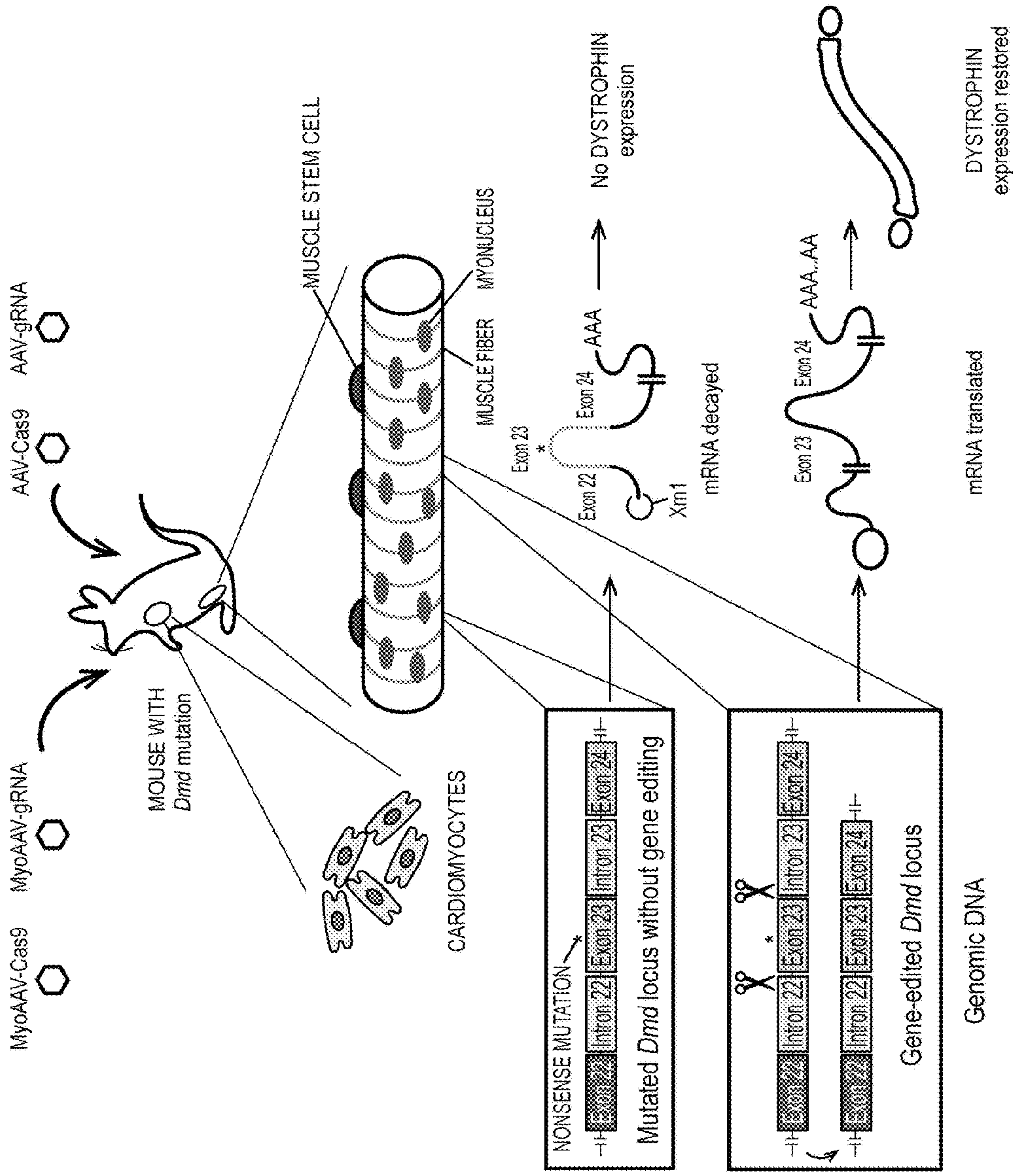
FIG. 25 can demonstrate a mechanism of correction of a DMD mutation in model mdx mice by MyoAAV-CRISPR as compared to AAV9-CRISPR.

FIG. 25 can demonstrate a mechanism of correction of a DMD mutation in model mdx mice by MyoAAV-CRISPR or AAV9-CRISPR.

Figure 26A:
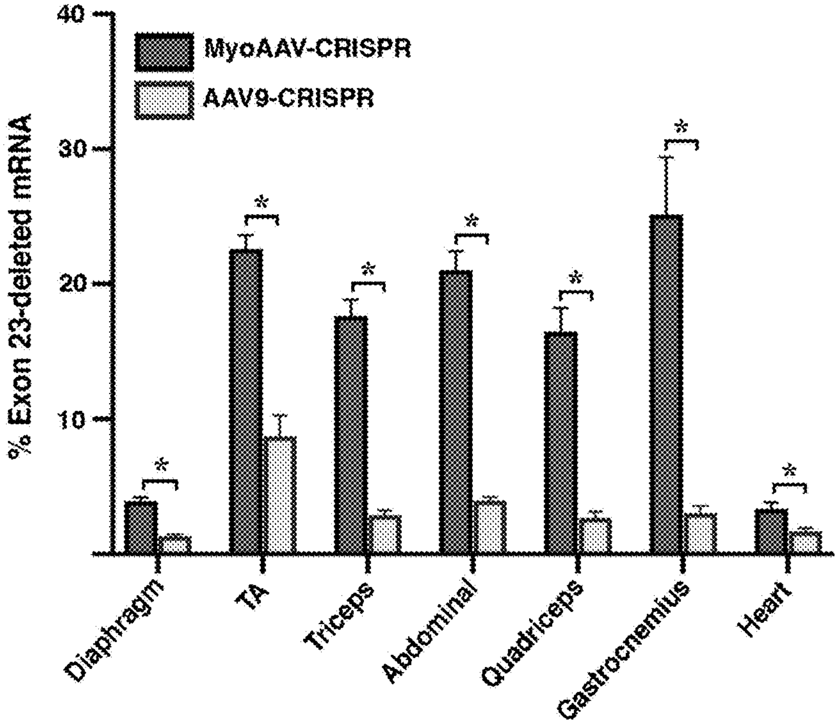
FIGS. 26A-26C can demonstrate correction of a DMD mutation in model mdx mice with MyoAAV-CRISPR as compared to AAV9-CRISPR.
Figure 26B:
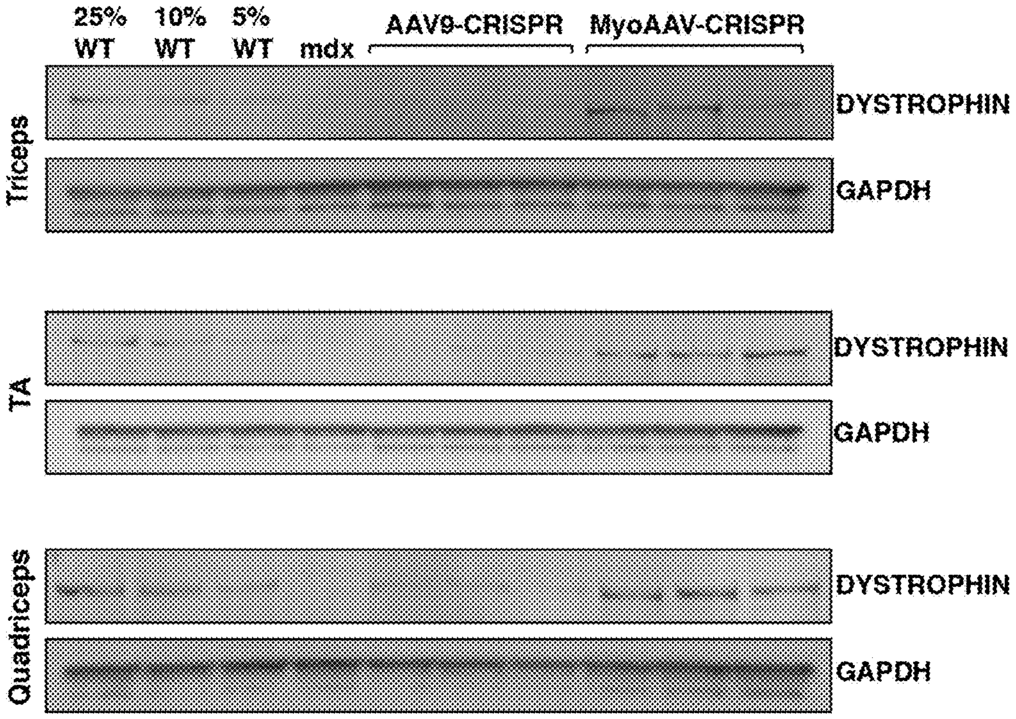
Figure 26C:
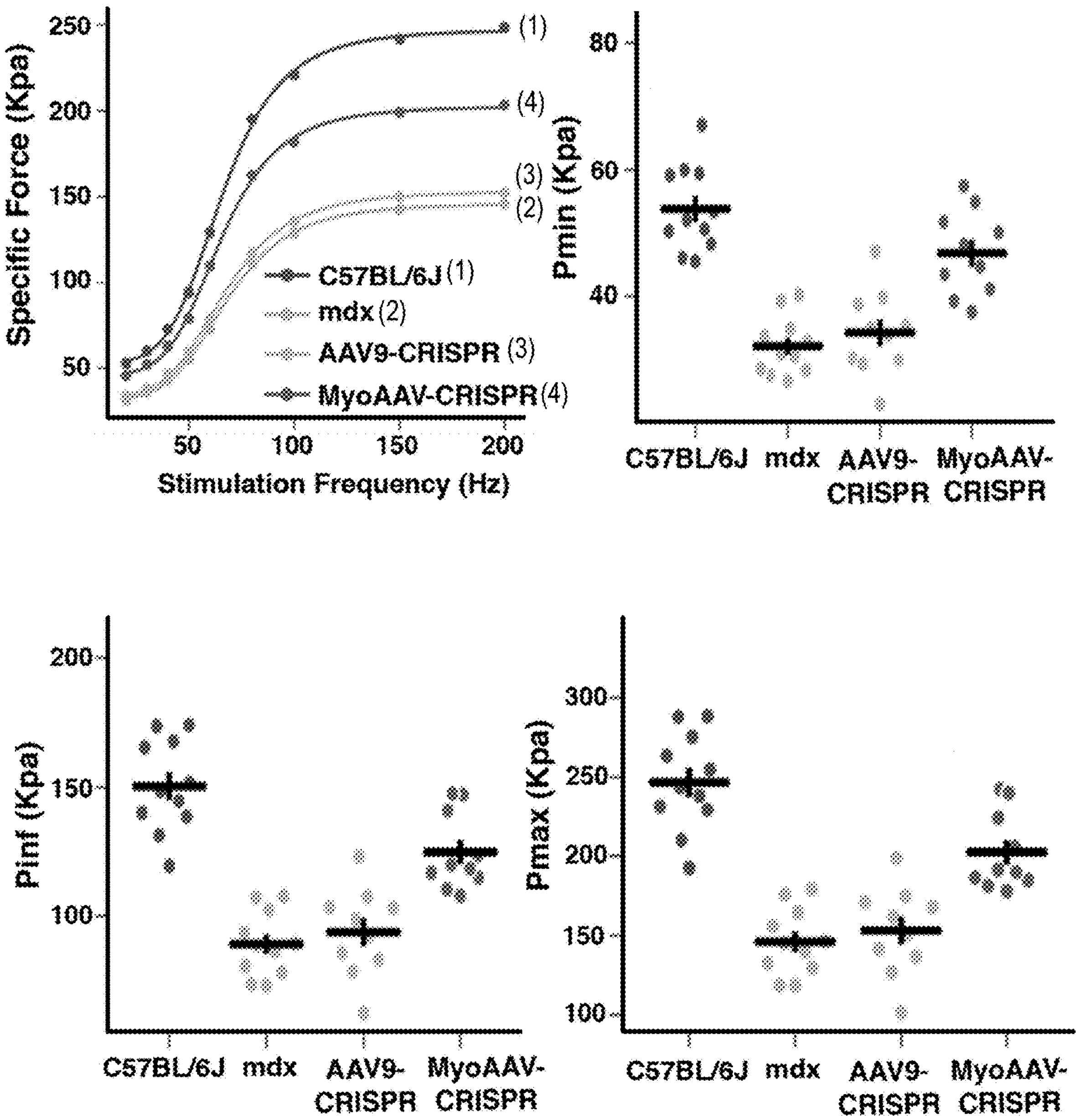

FIGS. 26A-26C can demonstrate correction of a DMD mutation in model mdx mice with MyoAAV-CRISPR as compared to AAV9-CRISPR.

Figure 27:
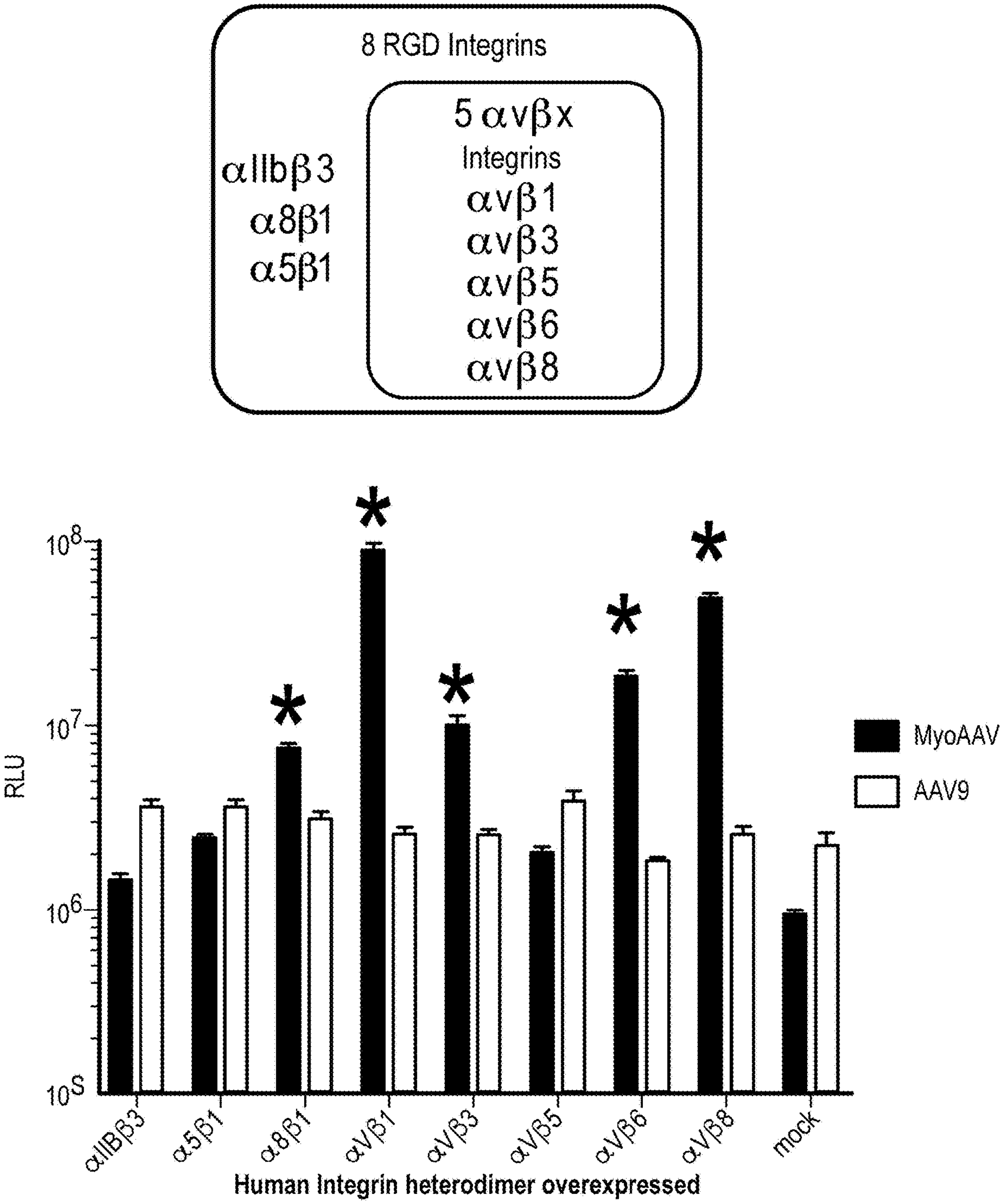
FIG. 27 can demonstrate that MyoAAV uses integrin heterodimers as the receptor to enter cells.

FIG. 27 can demonstrate that MyoAAV uses integrin heterodimers as the receptor to enter cells.

Figure 28:
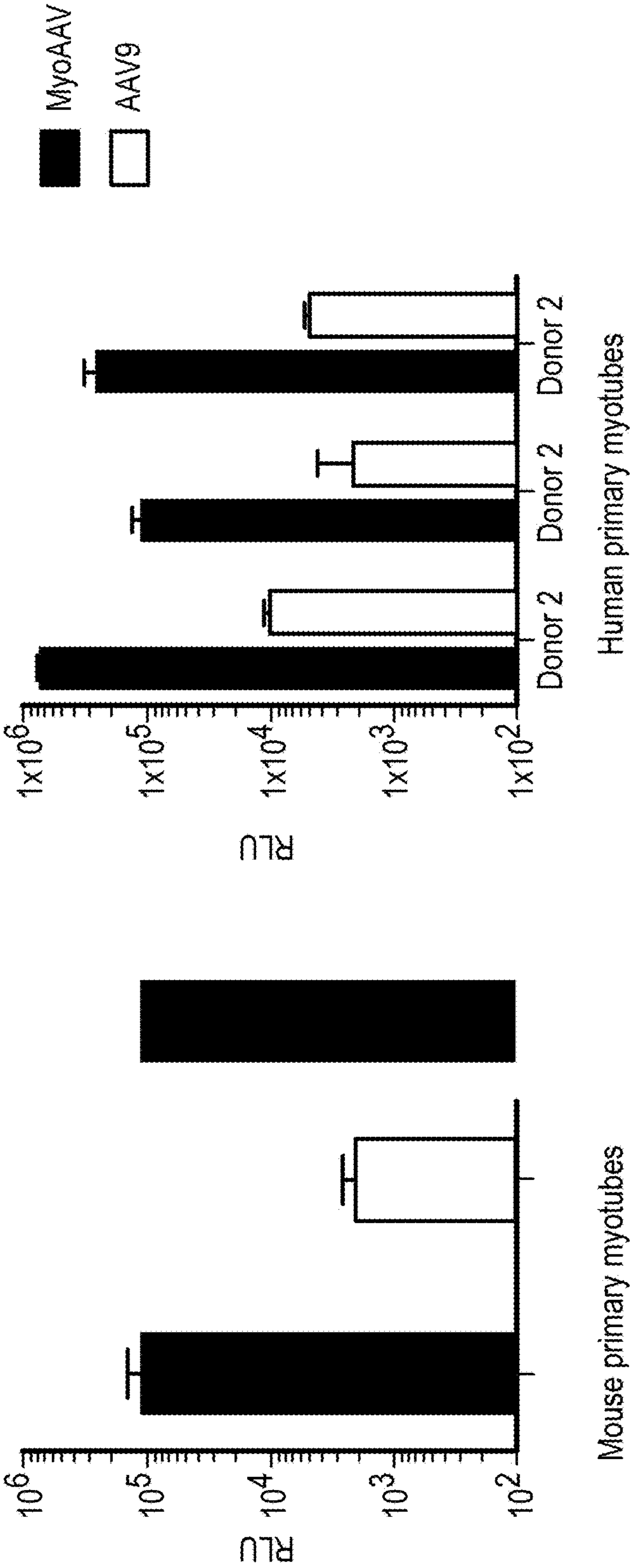
FIG. 28 shows graphs that can demonstrate that myoAAV can transduce both mouse and human primary myotubes 50-100 times more effectively than AAV9.

FIG. 28 shows graphs that can demonstrate that myoAAV can transduce both mouse and human primary myotubes more effectively than AAV9.

Figure 29A:
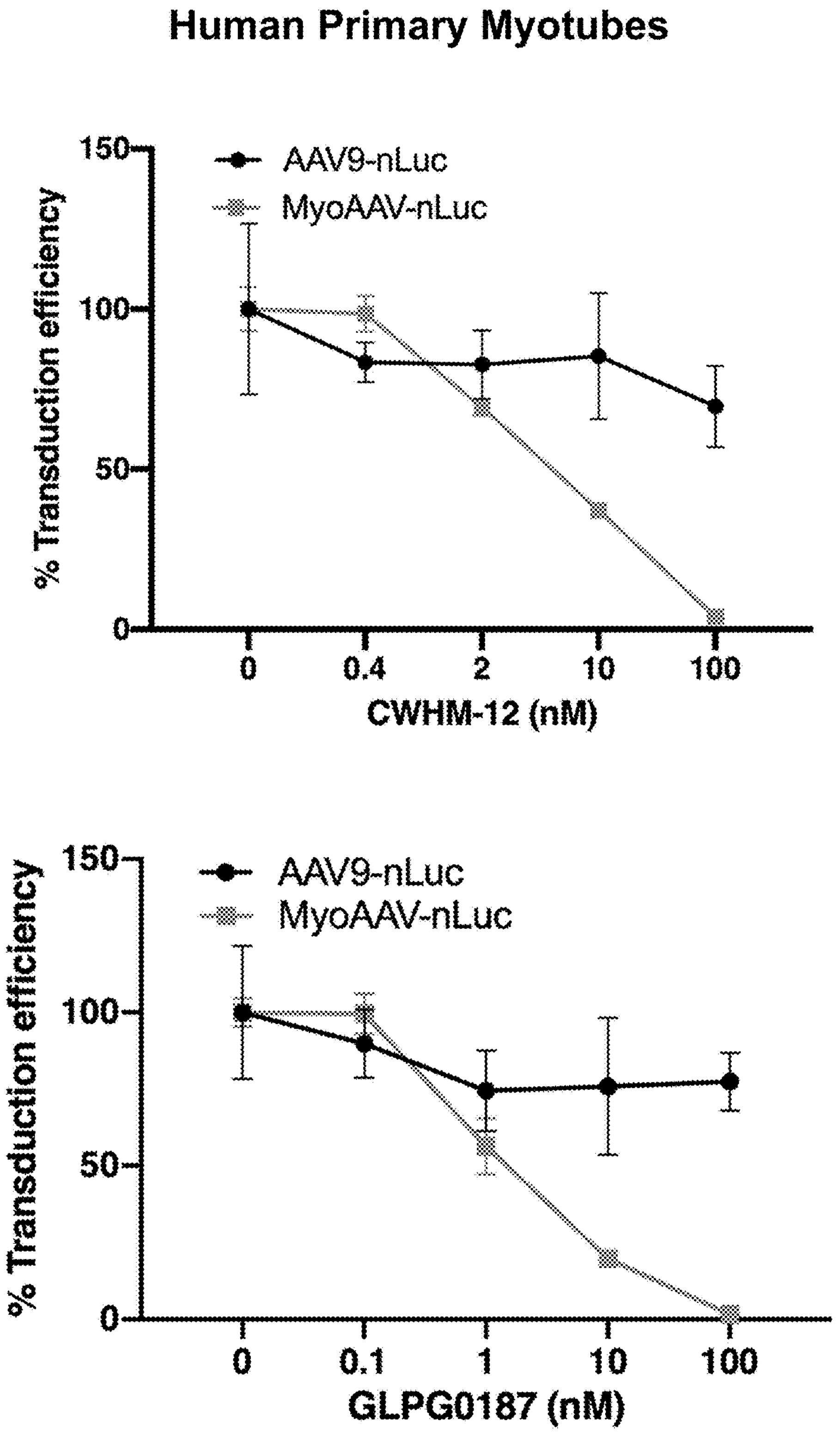
FIGS. 29A-29B can demonstrate that integrin alpha V small molecule inhibitors suppress transduction of human primary myotubes by MyoAAV.
Figure 29B:
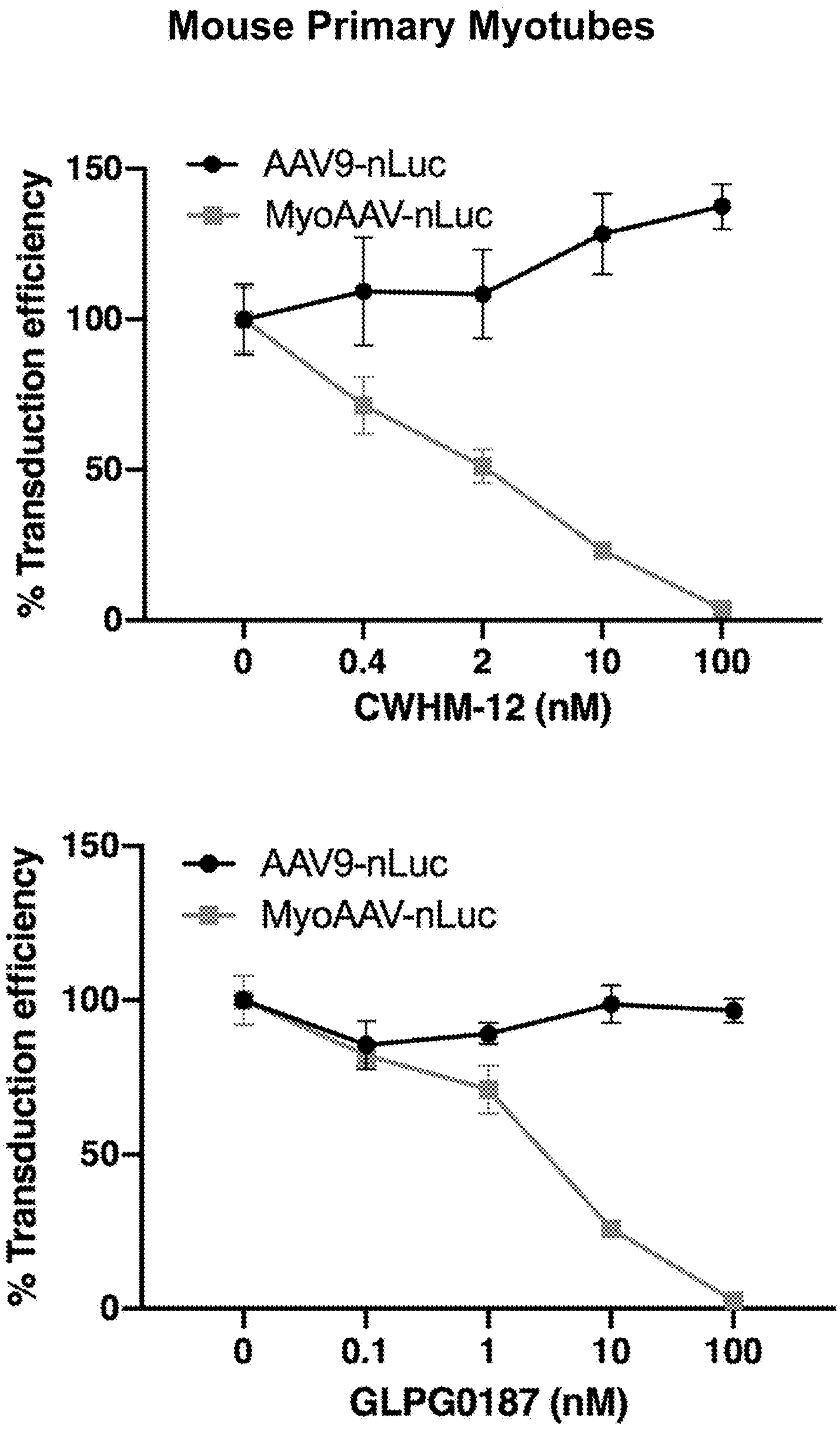

FIGS. 29A-29B can demonstrate that integrin alpha V small molecule inhibitors suppress transduction of human and mouse primary myotubes by MyoAAV.

Example 7—Top n-Mer Motifs in Non-Human Primates

Muscle specific AAV capsids were developed using a muscle specific promoter and the resulting capsid libraries were screened in non-human primates as described elsewhere herein and/or in U.S. Provisional Application Ser. Nos. 62/899,453, 62/916,207, 63/018,454, 63/055,252, and 62/916,221 and International Application No. PCT/US20/50534. Tables 8 and 9 show the top hits of muscle specific n-mer motifs and their encoding sequence in rank order within each table.

TABLE 8

| N-Mer Motif | SEQ ID NO: | Encoding Sequence | score | SEQ ID NO: |
|---|---|---|---|---|
| RGDYHAI | 8314 | AGGGGCGACTACCACGCCATC | 4178 | 8503 |
| RGDYASL | 8315 | CGGGGCGACTACGCAAGCCTG | 3851 | 8504 |
| RGDYVGL | 8316 | CGGGGTGATTATGTGGGGCTG | 3686 | 8505 |
| RGDLRPT | 8317 | CGTGGGGATCTTAGGCCGACG | 3610 | 8506 |
| RGDHVSL | 8318 | CGTGGGGATCATGTGTCTTTG | 3050 | 8507 |
| DVRSLHG | 8319 | GACGTTAGATCCCTTCACGGC | 2985 | 8508 |
| RGDYHAI | 8320 | CGTGGTGATTATCATGCTATT | 2944 | 8509 |
| RGDYGGL | 8321 | CGTGGTGATTATGGTGGGCTG | 2816 | 8510 |
| RGDHGVL | 8322 | CGGGGTGATCATGGGGTTCTT | 2692 | 8511 |
| RGDYREL | 8323 | AGAGGAGACTACCGGGAACTC | 2690 | 8512 |
| VSRGDVP | 8324 | GTTAGTCGGGGTGATGTGCCT | 2675 | 8513 |
| RGDYVGL | 8325 | CGCGGGGACTACGTAGGTTTA | 2666 | 8514 |
| RGDYSGL | 8326 | CGGGGTGATTATTCGGGGTTG | 2642 | 8515 |
| RGDLTVT | 8327 | AGGGGGGACCTGACAGTCACG | 2604 | 8516 |
| RGDHASW | 8328 | CGTGGTGATCATGCTTCTTGG | 2603 | 8517 |
| RGDLVGY | 8329 | AGGGGGGATCTTGTGGGGTAT | 2543 | 8518 |
| RGDGAAM | 8330 | CGTGGGGATGGTGCGGCGATG | 2439 | 8519 |
| VSAARSL | 8331 | GTGAGTGCGGCGCGTTCTCTG | 2437 | 8520 |
| LTAQYVT | 8332 | TTGACTGCTCAGTATGTGACG | 2430 | 8521 |
| RGDHGVL | 8333 | CGCGGAGACCACGGTGTATTA | 2429 | 8522 |
| VGNRFSP | 8334 | GTTGGGAATAGGTTTTCGCCG | 2410 | 8523 |
| TGVHTRV | 8335 | ACGGGTGTTCATACGAGGGTG | 2405 | 8524 |
| VRTGDAS | 8336 | GTGCGTACTGGTGATGCGTCG | 2401 | 8525 |
| MVVRGGV | 8337 | ATGGTGGTGCGTGGGGGTGTT | 2393 | 8526 |
| RGDRESH | 8338 | CGCGGAGACCGAGAAAGCCAC | 2370 | 8527 |
| RGDYSGL | 8339 | CGTGGCGACTACTCTGGTCTA | 2306 | 8528 |
| RGDLSSV | 8340 | CGGGGTGATCTTTCGAGTGTT | 2292 | 8529 |
| LLGQRAA | 8341 | CTGCTTGGTCAGAGGGCTGCT | 2269 | 8530 |
| GKGTVPS | 8342 | GGGAAGGGGACTGTGCCGAGT | 2262 | 8531 |
| SSIGVKI | 8343 | TCGTCGATTGGTGTGAAGATT | 2256 | 8532 |
| ANKGLGT | 8344 | GCAAACAAAGGCCTGGGCACG | 2246 | 8533 |
| RGDHASW | 8345 | CGGGGGGATCATGCTTCTTGG | 2245 | 8534 |
| RGDRLVI | 8346 | AGAGGAGACAGGCTGGTCATC | 2219 | 8535 |

TABLE 8-continued

| N-Mer Motif | SEQ ID NO: | Encoding Sequence | score | SEQ ID NO: |
|---|---|---|---|---|
| GQGHRGD | 8347 | GGACAAGGCCACCGGGGAGAC | 2215 | 8536 |
| ERTRAGE | 8348 | GAGAGGACTCGGGCGGGTGAG | 2209 | 8537 |
| RGDLSGT | 8349 | AGGGGCGACCTGTCTGGCACC | 2203 | 8538 |
| RGDYREM | 8350 | CGGGGGGATTATCGTGAGATG | 2201 | 8539 |
| RGDLAHN | 8351 | AGGGGTGATCTTGCGCATAAT | 2183 | 8540 |
| GFSGRTV | 8352 | GGGTTTAGTGGGAGGACGGTG | 2183 | 8541 |
| VMRAGAT | 8353 | GTTATGCGAGCAGGTGCGACG | 2173 | 8542 |
| EGGIYRV | 8354 | GAAGGAGGAATCTACCGTGTT | 2168 | 8543 |
| RGDYREL | 8355 | CGTGGTGATTATCGTGAGTTG | 2168 | 8544 |
| QSVSIKS | 8356 | CAGAGTGTGTCTATTAAGTCT | 2167 | 8545 |
| RGDLVHV | 8357 | CGAGGAGACTTGGTCCACGTC | 2161 | 8546 |
| YRGDIRV | 8358 | TACCGTGGTGACATACGGGTG | 2156 | 8547 |
| RGDASTW | 8359 | CGTGGGGACGCCAGTACCTGG | 2148 | 8548 |
| RGDYGGI | 8360 | CGTGGGGATTATGGTGGTATT | 2146 | 8549 |
| VGTRGDT | 8361 | GTGGGTACGCGGGGGGATACG | 2146 | 8550 |
| RGDLTTV | 8362 | CGGGGGGATCTGACGACTGTT | 2133 | 8551 |
| RGDMRPV | 8363 | CGTGGTGATATGCGTCCGGTT | 2126 | 8552 |
| AAGRLTT | 8364 | GCTGCTGGTAGGCTTACGACG | 2125 | 8553 |
| NAGRSTL | 8365 | AACGCAGGGCGCTCTACCTTA | 2108 | 8554 |
| ERDRISG | 8366 | GAGCGGGATCGGATTTCGGGT | 2091 | 8555 |
| RGDLTTT | 8367 | CGGGGTGACCTGACAACCACG | 2082 | 8556 |
| TTGLRLA | 8368 | ACGACTGGGCTTCGTCTGGCT | 2082 | 8557 |
| RGDHSGW | 8369 | CGTGGTGATCATAGTGGTTGG | 2080 | 8558 |
| SGGTYLA | 8370 | AGCGGGGGAACGTACCTTGCC | 2078 | 8559 |
| AVVRGGP | 8371 | GCTGTTGTGCGGGGTGGTCCT | 2064 | 8560 |
| IVRGLSD | 8372 | ATTGTGAGGGGTCTGAGTGAT | 2054 | 8561 |
| RGDTMRL | 8373 | CGCGGAGACACGATGAGACTG | 2054 | 8562 |
| TRVPVSG | 8374 | ACGCGAGTACCGGTGAGCGGG | 2052 | 8563 |
| RTYDSNV | 8375 | CGAACGTACGACTCAAACGTA | 2052 | 8564 |
| RGDRMGV | 8376 | CGGGGTGATCGTATGGGTGTG | 2043 | 8565 |
| QLNAYSG | 8377 | CAGTTGAATGCGTATAGTGGG | 2042 | 8566 |
| SLGITSG | 8378 | TCATTGGGTATAACCTCGGGC | 2040 | 8567 |
| TAAVRTY | 8379 | ACGGCTGCGGTGCGTACGTAT | 2031 | 8568 |
| RGDLTTT | 8380 | CGTGGGGATCTTACTACGACT | 2031 | 8569 |
| RGDYATF | 8381 | CGGGGTGATTATGCTACTTTT | 2028 | 8570 |
| RGDIVGL | 8382 | AGGGGTGACATAGTGGGCCTC | 2027 | 8571 |
| GSRGDLS | 8383 | GGTAGTCGTGGCGACTTATCG | 2027 | 8572 |
| RGDVTHI | 8384 | AGAGGAGACGTTACGCACATC | 2024 | 8573 |

TABLE 8-continued

| N-Mer Motif | SEQ ID NO: | Encoding Sequence | score | SEQ ID NO: |
|---|---|---|---|---|
| IGGTRVQ | 8385 | ATTGGTGGGACTCGGGTGCAG | 2023 | 8574 |
| ENHTHRA | 8386 | GAGAATCATACTCATAGGGCT | 2023 | 8575 |
| RGDLTYA | 8387 | CGTGGTGATCTGACGTATGCT | 2022 | 8576 |
| LLHESRV | 8388 | TTGTTGCATGAGTCGCGGGTT | 2021 | 8577 |
| RGDVSGI | 8389 | CGTGGTGATGTTAGTGGGATT | 2018 | 8578 |
| LNSAMRT | 8390 | CTGAATTCTGCGATGCGTACT | 2015 | 8579 |
| RGDYATL | 8391 | AGGGGGGACTACGCCACACTG | 2010 | 8580 |
| SANVVRG | 8392 | TCTGCGAATGTTGTGAGGGGG | 2010 | 8581 |
| VAGQRSV | 8393 | GTTGCTGGGCAGCGTTCTGTT | 2008 | 8582 |
| RGDREHF | 8394 | CGTGGTGATAGGGAGCATTTT | 2007 | 8583 |
| RGDYVTI | 8395 | CGCGGAGACTACGTTACAATA | 1999 | 8584 |
| RLVSTAP | 8396 | CGTCTTGTTTCGACTGCTCCG | 1998 | 8585 |
| HQSFHGA | 8397 | CACCAATCATTCCACGGCGCA | 1996 | 8586 |
| VRGDSRF | 8398 | GTAAGGGGCGACAGCAGATTC | 1991 | 8587 |
| RGDFGGV | 8399 | AGGGGTGACTTCGGAGGTGTC | 1990 | 8588 |
| LVRTTVS | 8400 | CTTGTCAGAACTACAGTGTCC | 1989 | 8589 |
| RGDYVSV | 8401 | CGTGGGGATTATGTGTCTGTG | 1989 | 8590 |
| RGDYASL | 8402 | AGGGGTGATTATGCGTCTCTT | 1983 | 8591 |
| IVRDGRL | 8403 | ATCGTCCGAGACGGAAGACTT | 1978 | 8592 |
| LTHGMIG | 8404 | CTGACGCATGGTATGATTGGT | 1973 | 8593 |
| RGDVRVI | 8405 | CGAGGCGACGTTCGGGTCATA | 1964 | 8594 |
| KAQPSSS | 8406 | AAGGCTCAGCCGTCTTCGTCT | 1964 | 8595 |
| GMRGASV | 8407 | GGGATGAGGGGTGCTTCGGTG | 1961 | 8596 |
| AAGRVGT | 8408 | GCTGCGGGTAGGGTTGGGACG | 1955 | 8597 |
| QMGRVQV | 8409 | CAGATGGGTCGGGTTCAGGTG | 1954 | 8598 |
| LMSRGDT | 8410 | TTGATGTCGCGGGGTGATACT | 1953 | 8599 |
| VHSRGDM | 8411 | GTCCACTCTCGCGGAGACATG | 1952 | 8600 |
| RGDLVTV | 8412 | CGGGGGGATCTGGTTACGGTT | 1952 | 8601 |
| RNYGDHS | 8413 | AGAAACTACGGCGACCACTCG | 1951 | 8602 |
| RGDYSQI | 8414 | AGAGGCGACTACAGCCAAATA | 1950 | 8603 |
| RGDLANS | 8415 | AGGGGTGATTTGGCTAATTCT | 1945 | 8604 |
| RSSHLDV | 8416 | CGTTCCAGTCACCTTGACGTT | 1940 | 8605 |
| RSGTVGL | 8417 | CGCTCCGGGACCGTTGGACTG | 1939 | 8606 |
| IGARGDT | 8418 | ATAGGAGCGAGGGGGGACACG | 1938 | 8607 |
| SNAVPGT | 8419 | TCGAATGCGGTTCCTGGTACT | 1935 | 8608 |
| LDARGHL | 8420 | TTGGATGCTAGGGGGCATCTG | 1930 | 8609 |
| TSVSVKY | 8421 | ACTTCTGTGTCGGTGAAGTAT | 1928 | 8610 |
| TRVMGAT | 8422 | ACGCGGGTGATGGGGGCGACT | 1920 | 8611 |
| RGGTGVN | 8423 | CGAGGCGGGACTGGAGTAAAC | 1919 | 8612 |
| VASRTSV | 8424 | GTGGCTAGTCGTACGTCTGTT | 1918 | 8613 |
| RGDRLQI | 8425 | CGTGGTGATCGGCTTCAGATT | 1917 | 8614 |
| RGDYERL | 8426 | CGCGGTGACTACGAACGACTA | 1916 | 8615 |
| LAAKALV | 8427 | CTTGCGGCTAAGGCTCTGGTT | 1915 | 8616 |
| LGTTSAS | 8428 | CTGGGGACGACTTCTGCGTCG | 1914 | 8617 |
| RGDHGTI | 8429 | CGTGGGGATCATGGGACGATT | 1914 | 8618 |
| GLRVVQA | 8430 | GGACTCCGAGTAGTCCAAGCC | 1913 | 8619 |
| RQTVGMG | 8431 | CGTCAGACTGTGGGGATGGGT | 1909 | 8620 |
| RGDLLTN | 8432 | AGGGGGGATCTGTTGACGAAT | 1905 | 8621 |
| YGHGMVG | 8433 | TACGGACACGGCATGGTCGGG | 1904 | 8622 |
| VVAALRG | 8434 | GTTGTTGCTGCTCTTCGGGGT | 1904 | 8623 |
| QLSRSGT | 8435 | CAGTTGTCGAGGAGTGGTACG | 1902 | 8624 |
| GLSRTGV | 8436 | GGTCTTTCGAGGACGGGGGTG | 1902 | 8625 |
| MGGGRLT | 8437 | ATGGGTGGTGGTCGTCTTACT | 1896 | 8626 |
| RGDLVMV | 8438 | AGAGGCGACTTAGTGATGGTG | 1896 | 8627 |
| RGDVVGL | 8439 | AGGGGTGACGTCGTAGGCCTG | 1888 | 8628 |
| VTKVGVL | 8440 | GTGACGAAGGTTGGGGTGCTG | 1887 | 8629 |
| RTSYPEA | 8441 | CGCACCTCATACCCTGAAGCC | 1887 | 8630 |
| ESRATMS | 8442 | GAATCGCGGGCAACGATGTCT | 1885 | 8631 |
| SRVGVGA | 8443 | AGTCGGGTGGGTGTTGGTGCG | 1883 | 8632 |
| RGDYVTM | 8444 | CGAGGCGACTACGTGACTATG | 1880 | 8633 |
| RAQGPQA | 8445 | AGGGCTCAGGGTCCTCAGGCG | 1878 | 8634 |
| VTSHAMA | 8446 | GTCACATCCCACGCCATGGCC | 1877 | 8635 |
| RGDLGGV | 8447 | CGAGGGGACTTAGGCGGCGTC | 1873 | 8636 |
| SIRGELG | 8448 | AGTATTCGTGGTGAGCTGGGT | 1867 | 8637 |
| RGDGSAL | 8449 | CGTGGTGATGGGAGTGCTCTT | 1863 | 8638 |
| SRSGIAI | 8450 | TCTAGGAGTGGTATTGCGATT | 1860 | 8639 |
| QAGTLGY | 8451 | CAGGCGGGGACGCTTGGGTAT | 1860 | 8640 |
| RGDLTTA | 8452 | AGGGGTGATCTTACGACTGCG | 1859 | 8641 |
| LGHRGDV | 8453 | CTTGGTCATCGGGGTGATGTT | 1859 | 8642 |
| RGDLTIT | 8454 | AGAGGCGACCTGACCATCACA | 1856 | 8643 |
| RGDLRVP | 8455 | CGTGGGGATCTTCGGGTGCCT | 1856 | 8644 |
| NSDHRIL | 8456 | AACTCGGACCACCGCATACTC | 1852 | 8645 |
| RGDYHSF | 8457 | CGTGGAGACTACCACTCATTC | 1851 | 8646 |
| GTGRYVS | 8458 | GGGACAGGTCGATACGTGAGC | 1851 | 8647 |
| PLLRSGT | 8459 | CCGTTGTTGAGGAGTGGGACG | 1849 | 8648 |
| RGDVVSW | 8460 | CGTGGAGACGTCGTAAGTTGG | 1849 | 8649 |

TABLE 8-continued

| N-Mer Motif | SEQ ID NO: | Encoding Sequence | score | SEQ ID NO: |
|---|---|---|---|---|
| VMRVGHA | 8461 | GTGATGCGTGTGGGGCATGCT | 1848 | 8650 |
| RGDLVSV | 8462 | AGGGGGGATCTGGTGTCTGTT | 1847 | 8651 |
| RGDLTGV | 8463 | CGGGGTGATTTGACGGGGGTG | 1845 | 8652 |
| VSSTKMA | 8464 | GTGTCGTCTACGAAGATGGCT | 1844 | 8653 |
| RGDHTQW | 8465 | CGCGGAGACCACACGCAATGG | 1843 | 8654 |
| VVRGVTD | 8466 | GTAGTTAGAGGTGTGACCGAC | 1842 | 8655 |
| VQVAVQR | 8467 | GTTCAGGTTGCGGTGCAGAGG | 1838 | 8656 |
| RTVTAVE | 8468 | CGTACTGTGACGGCGGTGGAG | 1838 | 8657 |
| RTQLGMA | 8469 | CGAACTCAATTAGGAATGGCG | 1835 | 8658 |
| GGSVRGS | 8470 | GGGGGTTCGGTGAGGGGTTCG | 1835 | 8659 |
| RGDHSSL | 8471 | AGGGGGGATCATTCTAGTCTG | 1834 | 8660 |
| LAGTSGA | 8472 | CTTGCTGGGACTAGTGGGGCG | 1831 | 8661 |
| LRTGTLS | 8473 | CTTAGGACTGGGACTTTGAGT | 1830 | 8662 |
| WKAQVQA | 8474 | TGGAAAGCCCAAGTTCAAGCT | 1827 | 8663 |
| NSTALRG | 8475 | AATTCTACGGCTCTTCGTGGG | 1825 | 8664 |
| DGGRMAY | 8476 | GACGGTGGGCGAATGGCTTAC | 1825 | 8665 |
| TRTPSPA | 8477 | ACAAGAACACCTTCTCCCGCT | 1824 | 8666 |
| STVARGD | 8478 | TCAACGGTCGCAAGGGGGGAC | 1823 | 8667 |
| RAGTAMS | 8479 | AGGGCTGGCACGGCCATGAGT | 1822 | 8668 |
| RGDRESH | 8480 | AGGGGGGATCGTGAGAGTCAT | 1820 | 8669 |
| LSRSGEL | 8481 | CTGAGTCGGAGTGGTGAGCTG | 1819 | 8670 |
| TAGRVQV | 8482 | ACTGCTGGGCGTGTTCAGGTG | 1813 | 8671 |
| VTTRGDV | 8483 | GTGACGACTCGTGGTGATGTG | 1809 | 8672 |
| VMRAGTS | 8484 | GTTATGCGTGCGGGGACTAGT | 1809 | 8673 |
| LSRSGDL | 8485 | TTGTCTCGGAGTGGTGATCTT | 1808 | 8674 |
| GYGHDRS | 8486 | GGTTATGGTCATGATCGGAGT | 1807 | 8675 |
| HAYKTSP | 8487 | CATGCTTATAAGACGTCTCCT | 1804 | 8676 |
| SPGKSGG | 8488 | AGTCCGGGTAAGTCTGGGGGT | 1802 | 8677 |
| SAGKTVV | 8489 | TCGGCGGGGAAGACGGTTGTT | 1799 | 8678 |
| VRGQQND | 8490 | GTGAGGGGGCAGCAGAATGAT | 1799 | 8679 |
| AVTRGGF | 8491 | GCTGTGACTAGGGGTGGTTTT | 1796 | 8680 |
| RGDLYTP | 8492 | AGGGGTGATCTTTATACGCCG | 1796 | 8681 |
| RAGTAIT | 8493 | CGTGCGGGTACTGCTATTACT | 1796 | 8682 |
| SLVRAAA | 8494 | TCGTTGGTTCGTGCTGCTGCT | 1795 | 8683 |
| VVRGDVG | 8495 | GTCGTCCGAGGCGACGTCGGC | 1793 | 8684 |
| RGDLSGT | 8496 | CGTGGTGATCTTTCGGGTACG | 1792 | 8685 |
| RYGATGT | 8497 | AGGTATGGTGCTACGGGGACT | 1787 | 8686 |
| PGLRGVA | 8498 | CCTGGTCTGAGGGGGGTTGCG | 1782 | 8687 |
| IPMRGQM | 8499 | ATTCCGATGAGGGGTCAGATG | 1781 | 8688 |
| SAGRSQG | 8500 | AGTGCTGGTCGTAGTCAGGGG | 1779 | 8689 |
| VRGVGTA | 8501 | GTTCGGGGGGTTGGTACGGCT | 1778 | 8690 |
| RGDYVSV | 8502 | CGGGGAGACTACGTCAGTGTC | 1777 | 8691 |

TABLE 9

| Rank | N-mer motif | SEQ ID NO: | Encoding sequence | SEQ ID NO: |
|---|---|---|---|---|
| 1 | RGDYVGL | 8692 | CGGGGTGATTATGTGGGGCTG | 8890 |
| 2 | RGDYSSV | 8693 | CGGGGTGATTATTCGAGTGTT | 8891 |
| 3 | RGDYSGL | 8694 | CGGGGTGATTATTCGGGGTTG | 8892 |
| 4 | RGDHERL | 8695 | CGTGGTGATCATGAGCGTTTG | 8893 |
| 5 | RGDLTVT | 8696 | AGGGGGGACCTGACAGTCACG | 8894 |
| 6 | RGDYHAI | 8697 | AGGGGCGACTACCACGCCATC | 8895 |
| 7 | RGDYREL | 8698 | AGAGGAGACTACCGGGAACTC | 8896 |
| 8 | RGDHGVL | 8699 | CGGGGTGATCATGGGGTTCTT | 8897 |
| 9 | RGDHASW | 8700 | CGTGGTGATCATGCTTCTTGG | 8898 |
| 10 | RGDYSGL | 8701 | CGTGGCGACTACTCTGGTCTA | 8899 |
| 11 | RGDAMHL | 8702 | CGTGGGGATGCGATGCATCTG | 8900 |
| 12 | RGDHVSL | 8703 | CGTGGGGATCATGTGTCTTTG | 8901 |
| 13 | RGDHGQL | 8704 | CGGGGGGATCATGGGCAGTTG | 8902 |
| 14 | RGDYGGL | 8705 | CGTGGTGATTATGGTGGGCTG | 8903 |
| 15 | RGDYVTM | 8706 | CGAGGCGACTACGTGACTATG | 8904 |
| 16 | RGDHSTW | 8707 | CGCGGGGACCACTCTACCTGG | 8905 |
| 17 | RGDLSGT | 8708 | AGGGGCGACCTGTCTGGCACC | 8906 |
| 18 | RGDYREM | 8709 | CGGGGGGATTATCGTGAGATG | 8907 |
| 19 | RGDTERL | 8710 | AGAGGGGACACCGAAAGATTG | 8908 |
| 20 | RGDHSTW | 8711 | CGGGGTGATCATAGTACTTGG | 8909 |
| 21 | RGDLSGT | 8712 | CGTGGTGATCTTTCGGGTACG | 8910 |
| 22 | RGDHASW | 8713 | CGGGGGGATCATGCTTCTTGG | 8911 |
| 23 | RGDLSSV | 8714 | CGGGGTGATCTTTCGAGTGTT | 8912 |
| 24 | RGDTVVL | 8715 | CGAGGAGACACGGTGGTCCTA | 8913 |
| 25 | RGDAAGL | 8716 | CGTGGGGACGCGGCTGGGTTG | 8914 |
| 26 | RGDGATL | 8717 | CGGGGTGATGGTGCGACTCTG | 8915 |
| 27 | RGDYASL | 8718 | AGGGGTGATTATGCGTCTCTT | 8916 |
| 28 | MTARNPM | 8719 | ATGACTGCTCGGAATCCGATG | 8917 |
| 29 | YVVGSRS | 8720 | TATGTGGTGGGGAGTAGGAGT | 8918 |
| 30 | YAVGSRS | 8721 | TATGCGGTGGGGAGTAGGAGT | 8919 |

TABLE 9-continued

| Rank | N-mer motif | SEQ ID NO: | Encoding sequence | SEQ ID NO: |
|---|---|---|---|---|
| 31 | RGDYVGL | 8722 | CGCGGGGACTACGTAGGTTTA | 8920 |
| 32 | RGDLTTT | 8723 | CGGGGTGACCTGACAACCACG | 8921 |
| 33 | RGDYERL | 8724 | CGCGGTGACTACGAACGACTA | 8922 |
| 34 | RGDYREL | 8725 | CGTGGTGATTATCGTGAGTTG | 8923 |
| 35 | RGDHGVL | 8726 | CGCGGAGACCACGGTGTATTA | 8924 |
| 36 | RGDYHAI | 8727 | CGTGGTGATTATCATGCTATT | 8925 |
| 37 | RGDHTQW | 8728 | CGCGGAGACCACACGCAATGG | 8926 |
| 38 | RGDLLGT | 8729 | CGGGGTGATTTGTTGGGGACT | 8927 |
| 39 | RGDLTGV | 8730 | CGGGGTGATTTGACGGGGGTG | 8928 |
| 40 | RGDSYTL | 8731 | CGTGGCGACTCCTACACCTTG | 8929 |
| 41 | RGDYGTV | 8732 | CGCGGAGACTACGGAACGGTC | 8930 |
| 42 | RGDVVGL | 8733 | AGGGGTGACGTCGTAGGCCTG | 8931 |
| 43 | RGDTERL | 8734 | CGGGGTGATACTGAGCGTCTG | 8932 |
| 44 | RGDHSSL | 8735 | CGCGGCGACCACTCCTCATTG | 8933 |
| 45 | RGDHGQL | 8736 | AGGGGCGACCACGGTCAACTT | 8934 |
| 46 | RGDVTGM | 8737 | CGTGGCGACGTAACTGGAATG | 8935 |
| 47 | RGDYGGL | 8738 | CGCGGCGACTACGGGGGCTTA | 8936 |
| 48 | RGDYAGH | 8739 | CGTGGGGATTATGCGGGGCAT | 8937 |
| 49 | RGDIVGL | 8740 | AGGGGTGACATAGTGGGCCTC | 8938 |
| 50 | RGDLVGY | 8741 | AGGGGGGATCTTGTGGGGTAT | 8939 |
| 51 | RGDGAHL | 8742 | CGTGGTGATGGTGCTCATCTG | 8940 |
| 52 | RGDQVVV | 8743 | CGTGGTGATCAGGTTGTGGTT | 8941 |
| 53 | RGDTMGM | 8744 | CGTGGGGATACGATGGGTATG | 8942 |
| 54 | RGDLLGT | 8745 | CGTGGGGATTTGTTGGGGACT | 8943 |
| 55 | RGDLSGN | 8746 | CGTGGGGATCTTTCTGGTAAT | 8944 |
| 56 | FNVSTRT | 8747 | TTCAACGTAAGTACGAGAACA | 8945 |
| 57 | RGDRTVI | 8748 | CGTGGTGATCGTACTGTGATT | 8946 |
| 58 | RGDVSGI | 8749 | CGTGGTGATGTTAGTGGGATT | 8947 |
| 59 | RGDYASL | 8750 | CGGGGCGACTACGCAAGCCTG | 8948 |
| 60 | RGDQALI | 8751 | CGTGGTGATCAGGCGCTTATT | 8949 |
| 61 | RGDRDSW | 8752 | CGTGGTGATCGTGATTCGTGG | 8950 |
| 62 | RGDREGL | 8753 | CGTGGTGATCGTGAGGGTCTT | 8951 |
| 63 | RGDYVSV | 8754 | CGGGGAGACTACGTCAGTGTC | 8952 |
| 64 | RGDTMRL | 8755 | CGCGGAGACACGATGAGACTG | 8953 |
| 65 | RGDYAHT | 8756 | AGGGGTGACTACGCTCACACG | 8954 |
| 66 | RGDTEKL | 8757 | CGGGGTGATACGGAGAAGTTG | 8955 |
| 67 | RGDQWQV | 8758 | AGGGGGGATCAGTGGCAGGTG | 8956 |
| 68 | RGDILNV | 8759 | CGGGGTGATATTCTGAATGTG | 8957 |
| 69 | RGDREQV | 8760 | CGTGGTGATCGTGAGCAGGTT | 8958 |
| 70 | RGDNWQM | 8761 | CGAGGCGACAACTGGCAAATG | 8959 |
| 71 | RGDYGGM | 8762 | AGGGGGGATTATGGTGGGATG | 8960 |
| 72 | RGDLDGR | 8763 | CGTGGTGATCTGGATGGGCGG | 8961 |
| 73 | RGDHERL | 8764 | AGAGGGGACCACGAACGGCTT | 8962 |
| 74 | RGDLGVV | 8765 | AGGGGTGATCTGGGTGTGGTG | 8963 |
| 75 | RGDRESH | 8766 | CGCGGAGACCGAGAAAGCCAC | 8964 |
| 76 | RGDAATM | 8767 | CGGGGGGATGCTGCGACGATG | 8965 |
| 77 | RGDLGGV | 8768 | CGTGGTGATTTGGGTGGGGTG | 8966 |
| 78 | RGDAGQL | 8769 | CGGGGTGATGCGGGGCAGCTT | 8967 |
| 79 | RGDRGEI | 8770 | CGGGGGGATCGTGGTGAGATT | 8968 |
| 80 | RGDVVSW | 8771 | CGTGGAGACGTCGTAAGTTGG | 8969 |
| 81 | MTARSPM | 8772 | ATGACTGCTCGGAGTCCGATG | 8970 |
| 82 | TIRDGRL | 8773 | ACGATCCGTGACGGCAGGTTG | 8971 |
| 83 | RGDIVGL | 8774 | CGTGGGGATATTGTTGGTCTG | 8972 |
| 84 | RGDYQAV | 8775 | CGCGGTGACTACCAAGCAGTG | 8973 |
| 85 | RGDGAHM | 8776 | CGTGGTGATGGGGCGCATATG | 8974 |
| 86 | RGDAASI | 8777 | CGGGGTGATGCTGCTTCGATT | 8975 |
| 87 | RGDNSQW | 8778 | CGTGGGGATAATTCTCAGTGG | 8976 |
| 88 | RGDHSGL | 8779 | AGAGGCGACCACTCGGGCCTC | 8977 |
| 89 | RGDMGGT | 8780 | CGAGGCGACATGGGAGGCACC | 8978 |
| 90 | RGDLTGV | 8781 | AGGGGAGACCTCACAGGTGTA | 8979 |
| 91 | RGDVSGY | 8782 | CGGGGTGATGTGTCTGGTTAT | 8980 |
| 92 | RGDLTTT | 8783 | CGTGGGGATCTTACTACGACT | 8981 |
| 93 | RGDYGTV | 8784 | AGGGGTGATTATGGGACTGTT | 8982 |
| 94 | RGDTMGM | 8785 | CGCGGTGACACCATGGGCATG | 8983 |
| 95 | RGDYSSV | 8786 | CGTGGGGATTATTCGTCTGTG | 8984 |
| 96 | RGDYGGM | 8787 | CGGGGTGACTACGGCGGTATG | 8985 |
| 97 | RGDYVSV | 8788 | CGTGGGGATTATGTGTCTGTG | 8986 |
| 98 | RGDVTGL | 8789 | CGTGGAGACGTGACCGGACTG | 8987 |
| 99 | RGDLLTN | 8790 | CGAGGTGACCTTCTCACAAAC | 8988 |
| 100 | RGDHSGW | 8791 | CGTGGTGATCATAGTGGTTGG | 8989 |
| 101 | VSRGDVP | 8792 | GTTAGTCGGGGTGATGTGCCT | 8990 |
| 102 | RGDVSGM | 8793 | CGTGGTGATGTGAGTGGGATG | 8991 |
| 103 | RGDRVGM | 8794 | CGGGGAGACCGCGTGGGCATG | 8992 |
| 104 | RGDGGVL | 8795 | CGTGGGGATGGTGGTGTGCTT | 8993 |
| 105 | RGDYVTI | 8796 | AGGGGTGATTATGTGACGATT | 8994 |
| 106 | RGDIAGV | 8797 | CGGGGTGATATTGCTGGTGTT | 8995 |
| 107 | RGDREQV | 8798 | CGCGGAGACAGAGAACAAGTG | 8996 |

TABLE 9-continued

| Rank | N-mer motif | SEQ ID NO: | Encoding sequence | SEQ ID NO: |
|---|---|---|---|---|
| 108 | RGDLDNK | 8799 | CGTGGGGATTTGGATAATAAG | 8997 |
| 109 | RGDLTSV | 8800 | CGTGGTGATCTGACGTCTGTT | 8998 |
| 110 | FNVSVRN | 8801 | TTCAACGTAAGTGTTCGCAAC | 8999 |
| 111 | RGDLVHT | 8802 | CGTGGTGATCTGGTTCATACT | 9000 |
| 112 | RGDHGVI | 8803 | AGGGGTGACCACGGTGTGATA | 9001 |
| 113 | RGDAREM | 8804 | CGTGGTGATGCTCGTGAGATG | 9002 |
| 114 | RGDQASY | 8805 | CGTGGTGATCAGGCGTCTTAT | 9003 |
| 115 | RGDHSSL | 8806 | AGGGGGGATCATTCTAGTCTG | 9004 |
| 116 | RGDVRVI | 8807 | CGAGGCGACGTTCGGGTCATA | 9005 |
| 117 | TVGRGDT | 8808 | ACGGTTGGTCGTGGTGATACG | 9006 |
| 118 | RGDHGSL | 8809 | CGAGGCGACCACGGTTCACTG | 9007 |
| 119 | RGDFERT | 8810 | CGAGGGGACTTCGAACGAACC | 9008 |
| 120 | RGDHSGL | 8811 | CGTGGTGATCATAGTGGGCTT | 9009 |
| 121 | RGDMSTV | 8812 | AGAGGCGACATGTCTACGGTG | 9010 |
| 122 | RGDYATL | 8813 | CGGGGTGATTATGCTACGCTT | 9011 |
| 123 | LPGVGHA | 8814 | CTGCCTGGTGTGGGTCATGCT | 9012 |
| 124 | RGDALHL | 8815 | AGGGGCGACGCGCTCCACCTT | 9013 |
| 125 | SGGTYLA | 8816 | AGCGGGGGAACGTACCTTGCC | 9014 |
| 126 | RGDVVHL | 8817 | AGGGGTGATGTTGTGCATCTG | 9015 |
| 127 | RGDQVQL | 8818 | CGGGGTGATCAGGTGCAGCTG | 9016 |
| 128 | SSIGVKI | 8819 | TCGTCGATTGGTGTGAAGATT | 9017 |
| 129 | RGDHMSL | 8820 | CGCGGCGACCACATGTCTCTA | 9018 |
| 130 | RGDMSTV | 8821 | AGGGGGGATATGAGTACTGTT | 9019 |
| 131 | VMRAGAT | 8822 | GTTATGCGAGCAGGTGCGACG | 9020 |
| 132 | RGDVVGL | 8823 | CGGGGGGATGTTGTTGGGCTT | 9021 |
| 133 | RGDTVVL | 8824 | CGTGGTGATACTGTTGTGTTG | 9022 |
| 134 | GTKVGVL | 8825 | GGGACGAAGGTTGGTGTGCTG | 9023 |
| 135 | TGVHTRV | 8826 | ACAGGAGTGCACACCCGGGTT | 9024 |
| 136 | RGDAGVL | 8827 | CGTGGTGATGCTGGGGTTCTT | 9025 |
| 137 | RGDLSTT | 8828 | CGTGGTGATCTTTCGACTACT | 9026 |
| 138 | RGDRLQI | 8829 | CGTGGTGATCGGCTTCAGATT | 9027 |
| 139 | RGDAVTL | 8830 | CGTGGGGATGCGGTGACTTTG | 9028 |
| 140 | RGDMVSV | 8831 | CGGGGGGATATGGTTAGTGTG | 9029 |
| 141 | RGDRENL | 8832 | CGTGGGGATAGGGAGAATCTT | 9030 |
| 142 | RGDGAAM | 8833 | CGTGGGGATGGTGCGGCGATG | 9031 |
| 143 | RGDLTRT | 8834 | CGGGGGGATCTTACTAGGACG | 9032 |
| 144 | RGDYGGI | 8835 | CGTGGGGATTATGGTGGTATT | 9033 |
| 145 | RGDMEPR | 8836 | CGGGGTGATATGGAGCCTCGT | 9034 |
| 146 | RGDTAVQ | 8837 | CGTGGGGATACGGCGGTTCAG | 9035 |

TABLE 9-continued

| Rank | N-mer motif | SEQ ID NO: | Encoding sequence | SEQ ID NO: |
|---|---|---|---|---|
| 147 | AVTRGGV | 8838 | GCTGTGACTAGGGGTGGTGTT | 9036 |
| 148 | VSAARSL | 8839 | GTGAGTGCGGCGCGTTCTCTG | 9037 |
| 149 | GRLPQQT | 8840 | GGTCGGCTTCCTCAGCAGACT | 9038 |
| 150 | RGDLVGY | 8841 | CGAGGCGACTTGGTTGGTTAC | 9039 |
| 151 | RGDLVTV | 8842 | CGGGGGGATCTGGTTACGGTT | 9040 |
| 152 | RGDYVVH | 8843 | CGCGGGGACTACGTCGTTCAC | 9041 |
| 153 | RGDAARL | 8844 | CGCGGCGACGCTGCACGACTA | 9042 |
| 154 | RGDYTGV | 8845 | AGGGGTGACTACACAGGCGTC | 9043 |
| 155 | RGDLGGT | 8846 | AGGGGTGATCTTGGGGGTACG | 9044 |
| 156 | RGDTVYL | 8847 | CGGGGTGATACGGTGTATCTG | 9045 |
| 157 | RGDLMGS | 8848 | CGGGGGGATCTTATGGGGAGT | 9046 |
| 158 | LGRGDVS | 8849 | TTGGGTCGGGGTGATGTGTCG | 9047 |
| 159 | TAGRVQV | 8850 | ACTGCTGGGCGTGTTCAGGTG | 9048 |
| 160 | VVVRGGV | 8851 | GTGGTGGTGCGTGGTGGGGTT | 9049 |
| 161 | RGDHTNI | 8852 | AGAGGGGACCACACTAACATC | 9050 |
| 162 | RGDLVGI | 8853 | AGGGGCGACTTAGTAGGAATC | 9051 |
| 163 | RGDLSPV | 8854 | AGAGGAGACTTGTCCCCGGTG | 9052 |
| 164 | RGDLSGV | 8855 | CGGGGTGATTTGTCGGGGGTT | 9053 |
| 165 | YGIAARS | 8856 | TACGGCATCGCAGCAAGATCT | 9054 |
| 166 | RGDREGL | 8857 | CGGGGGGACCGAGAAGGGCTA | 9055 |
| 167 | RGDLHST | 8858 | CGTGGTGATTTGCATTCGACG | 9056 |
| 168 | RGDATGW | 8859 | CGGGGTGATGCGACGGGTTGG | 9057 |
| 169 | RGDQSHV | 8860 | CGAGGCGACCAAAGCCACGTA | 9058 |
| 170 | DKRVGTP | 8861 | GATAAGAGGGTTGGGACTCCT | 9059 |
| 171 | RGDLVVT | 8862 | AGAGGCGACCTGGTCGTAACT | 9060 |
| 172 | RGDFGGV | 8863 | AGGGGTGACTTCGGAGGTGTC | 9061 |
| 173 | RGDLSNT | 8864 | CGTGGAGACCTCAGCAACACA | 9062 |
| 174 | HRGQAVD | 8865 | CATCGGGGTCAGGCGGTGGAT | 9063 |
| 175 | SMVRSGT | 8866 | AGTATGGTTCGTTCGGGGACG | 9064 |
| 176 | TSVSVKY | 8867 | ACTTCTGTGTCGGTGAAGTAT | 9065 |
| 177 | RGDYSQI | 8868 | AGAGGCGACTACAGCCAAATA | 9066 |
| 178 | RGDISGV | 8869 | CGGGGTGATATTTCGGGGGTT | 9067 |
| 179 | RGDVAGV | 8870 | CGGGGTGATGTGGCGGGGGTT | 9068 |
| 180 | RGDQVTI | 8871 | AGGGGTGATCAGGTTACTATT | 9069 |
| 181 | RGDRLVI | 8872 | AGAGGAGACAGGCTGGTCATC | 9070 |
| 182 | PLLRSGT | 8873 | CCGTTGTTGAGGAGTGGGACG | 9071 |
| 183 | RGDFGSV | 8874 | CGGGGTGATTTTGGTAGTGTG | 9072 |
| 184 | RGDVAYV | 8875 | CGGGGTGATGTTGCTTATGTG | 9073 |

TABLE 9-continued

| Rank | N-mer motif | SEQ ID NO: | Encoding sequence | SEQ ID NO: |
|---|---|---|---|---|
| 185 | ARMGTGV | 8876 | GCTCGTATGGGTACGGGTGTG | 9074 |
| 186 | VMRVGHA | 8877 | GTGATGCGTGTGGGGCATGCT | 9075 |
| 187 | ARVQSSP | 8878 | GCTCGTGTTCAGAGTTCGCCT | 9076 |
| 188 | RGDGGIL | 8879 | CGGGGTGATGGGGGGATTCTT | 9077 |
| 189 | RSDLGAL | 8880 | AGGTCTGATCTTGGGGCTTTG | 9078 |
| 190 | SYSRSAV | 8881 | TCGTATTCGCGGAGTGCGGTT | 9079 |
| 191 | RGDVLLV | 8882 | AGGGGGGATGTTCTTCTGGTG | 9080 |
| 192 | TGVHTRV | 8883 | ACGGGTGTTCATACGAGGGTG | 9081 |
| 193 | TVGNLRG | 8884 | ACTGTGGGGAATTTGCGTGGT | 9082 |
| 194 | TVVGQGY | 8885 | ACTGTCGTCGGACAAGGTTAC | 9083 |
| 195 | RGDGGAL | 8886 | CGTGGTGATGGTGGTGCTCTG | 9084 |
| 196 | NSYHAGA | 8887 | AACAGCTACCACGCTGGGGCC | 9085 |
| 197 | RGDLTVT | 8888 | CGGGGTGATTTGACTGTGACT | 9086 |
| 198 | RGDVHGF | 8889 | CGGGGAGACGTCCACGGCTTC | 9087 |

Muscle specific AAV capsids were developed using expression from two different muscle specific promoters and the resulting capsid libraries for each promoter were screened in non-human primates as described elsewhere herein and/or in U.S. Provisional Application Ser. Nos. 62/899,453, 62/916,207, 63/018,454, 63/055,252, and 62/916,221 and International Application No. PCT/US20/50534.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

SEQUENCE LISTING

The patent contains a lengthy sequence listing. A copy of the sequence listing is available in electronic form from the USPTO web site (https://seqdata.uspto.gov/docdetail?docId=US12767957B2). An electronic copy of the sequence listing will also be available from the USPTO upon request and payment of the fee set forth in 37 CFR 1.19(b)(3).

What is claimed is:

1. A composition comprising an adeno-associated virus (AAV) which comprises a targeting moiety effective to target a muscle cell and a polynucleotide encoding a cargo, wherein the targeting moiety comprises a viral capsid protein comprising a motif; which comprises XmRGDXn, wherein X is any amino acid, m is 1 or 2, and n is 4, and wherein the motif is (a) inserted between any two amino acids of the viral capsid protein, (b) replaces one or more native viral capsid protein amino acids, or both (a) and (b).

2. The composition of claim 1, wherein the motif is 8 amino acids in length.

3. The composition of claim 1, wherein the motif is 9 amino acids in length.

4. The composition of claim 1, wherein the motif is located at the N or C terminal of any amino acid in variable region VIII (VR-VIII).

5. The composition of claim 1, wherein the motif is located at the N or C terminal of any amino acid in amino acids 581 to 593 corresponding to the wild type AAV9 capsid protein.

6. The composition of claim 1, wherein the motif is located at the N or C terminal of any amino acid in variable region (VR-IV).

7. The composition of claim 1, wherein the motif is located at the N or C terminal of any amino acid in amino acids 452 and 460 corresponding to the wild type AAV9 capsid protein.

8. The composition of claim 1, wherein the viral capsid protein comprises an AAVRh74 capsid protein with one, two, or three amino acid substitution, insertion, or deletion.

9. The composition of claim 4, wherein the viral capsid protein comprises an AAVRh74 capsid protein with one, two, or three amino acid substitution, insertion, or deletion.

10. The composition of claim 9, wherein the amino acid sequence of the AAVRh74 capsid protein is different from the amino acid sequence of the wild type AAV9 capsid protein by 9 amino acids.

11. The composition of claim 9, wherein the amino acid sequence of the AAVRh74 capsid protein is different from the amino acid sequence of the wild type AAV9 capsid protein by 10 amino acids.

12. The composition of claim 1, wherein the viral capsid protein comprises an AAV9 capsid protein with one, two, or three amino acid substitution, insertion or deletion.

13. The composition of claim 6, wherein the viral capsid protein comprises an AAV9 capsid protein with one, two, or three additional amino acid substitution, insertion or deletion.

14. The composition of claim 13, wherein the amino acid sequence of the viral capsid protein is different from the amino acid sequence of the wild type AAV9 capsid protein by 9 amino acids.

15. The composition of claim 13, wherein the amino acid sequence of the viral capsid protein is different from the amino acid sequence of the wild type AAV9 capsid protein by 10 amino acids.

16. The composition of claim 1, wherein the cargo comprises a micro-dystrophin protein.

17. The composition of claim 16, wherein the cargo polynucleotide is operably linked to a promoter.

18. The composition of claim 17, wherein the promoter comprises a muscle-specific promoter.

19. The composition of claim 18, wherein the muscle-specific promoter comprises a MHCK7 promoter.

20. A method of targeting a muscle cell in a subject in need thereof having a muscular dystrophy comprising administering the composition of claim 1 to the subject, wherein the cargo is expressed in the muscle cell.

21. A method of targeting a muscle cell in a subject in need thereof having a muscular dystrophy comprising administering the composition of claim 2 to the subject, wherein the cargo is expressed in the muscle cell.

22. A method of targeting a muscle cell in a subject in need thereof having a muscular dystrophy comprising administering the composition of claim 3 to the subject, wherein the cargo is expressed in the muscle cell.

23. A method of targeting a muscle cell in a subject in need thereof having a muscular dystrophy comprising administering the composition of claim 13 to the subject, wherein the cargo is expressed in the muscle cell.

24. A method of targeting a muscle cell in a subject in need thereof having a muscular dystrophy comprising administering the composition of claim 14 to the subject, wherein the cargo is expressed in the muscle cell.

25. The method of claim 20, wherein the composition is capable of transducing the muscle cell more effectively than a composition comprising an AAV without the motif.

26. The method of claim 25, wherein the composition is capable of transducing the muscle cells by at least 50 times more effectively than the composition comprising an AAV without the motif.

27. The method of claim 25, wherein the composition is capable of transducing the muscle cells by about 50 to 100 times more effectively than the composition comprising an AAV without the motif.

28. The method of claim 20, wherein the composition is capable of inducing faster kinetics of in vivo gene expression in the muscle cell compared to a composition comprising an AAV without the motif.

29. The method of claim 20, wherein the composition is capable of expressing a micro-dystrophin protein in the muscle cell.

* * * * *